US012202844B2

(12) United States Patent
Brubaker et al.

(10) Patent No.: US 12,202,844 B2
(45) Date of Patent: Jan. 21, 2025

(54) MAP4K1 INHIBITORS

(71) Applicant: Blueprint Medicines Corporation, Cambridge, MA (US)

(72) Inventors: Jason D. Brubaker, Cambridge, MA (US); Joshua T. Close, Cambridge, MA (US); Thomas A. Dineen, Cambridge, MA (US); Chandrasekhar V. Miduturu, Cambridge, MA (US); Emanuele Perola, Cambridge, MA (US)

(73) Assignee: Blueprint Medicines Corporation, Cambridge, MA (US)

( * ) Notice: Subject to any disclaimer, the term of this patent is extended or adjusted under 35 U.S.C. 154(b) by 0 days.

(21) Appl. No.: 17/864,106

(22) Filed: Jul. 13, 2022

(65) Prior Publication Data

US 2023/0112729 A1 Apr. 13, 2023

Related U.S. Application Data

(60) Provisional application No. 63/221,825, filed on Jul. 14, 2021.

(51) Int. Cl.
*C07D 519/00* (2006.01)
*A61P 35/00* (2006.01)
*C07D 491/052* (2006.01)

(52) U.S. Cl.
CPC ............ *C07D 519/00* (2013.01); *A61P 35/00* (2018.01); *C07D 491/052* (2013.01)

(58) Field of Classification Search
CPC .......................... C07D 519/00; C07D 491/052
See application file for complete search history.

(56) References Cited

U.S. PATENT DOCUMENTS

| | | | |
|---|---|---|---|
| 8,785,454 | B2 | 7/2014 | Ren et al. |
| 10,947,201 | B2 | 3/2021 | Qian et al. |
| 11,534,441 | B2 | 12/2022 | Brubaker et al. |
| 12,042,495 | B2 | 7/2024 | Brubaker et al. |
| 2007/0087988 | A1 | 4/2007 | Sawasdikosol et al. |
| 2008/0306093 | A1 | 12/2008 | Servant et al. |
| 2013/0225596 | A1 | 8/2013 | Kai et al. |
| 2018/0072718 | A1 | 3/2018 | Liu et al. |
| 2018/0282328 | A1 | 10/2018 | Chan et al. |
| 2024/0199648 | A1 | 6/2024 | Brubaker et al. |

FOREIGN PATENT DOCUMENTS

| | | | |
|---|---|---|---|
| WO | 2006/029879 | A2 | 3/2006 |
| WO | 2006/105021 | A2 | 10/2006 |
| WO | 2006/122150 | A1 | 11/2006 |
| WO | 2007/005874 | A2 | 1/2007 |
| WO | 2007/075598 | A2 | 7/2007 |
| WO | 2007/125405 | A2 | 11/2007 |
| WO | 2008/036642 | A2 | 3/2008 |
| WO | 2008/036653 | A2 | 3/2008 |
| WO | 2008/132601 | A1 | 11/2008 |
| WO | 2009/009116 | A2 | 1/2009 |
| WO | 2009/044273 | A2 | 4/2009 |
| WO | 2009/073620 | A2 | 6/2009 |
| WO | 2009/103966 | A1 | 8/2009 |
| WO | 2009/132238 | A2 | 10/2009 |
| WO | 2010/019570 | A2 | 2/2010 |
| WO | 2010/077634 | A1 | 7/2010 |
| WO | 2011/028683 | A1 | 3/2011 |
| WO | 2011/056652 | A1 | 5/2011 |
| WO | 2011/109400 | A2 | 9/2011 |
| WO | 2012/020742 | A1 | 2/2012 |
| WO | 2012/032433 | A1 | 3/2012 |
| WO | 2012/142237 | A1 | 10/2012 |
| WO | 2012/145493 | A1 | 10/2012 |
| WO | 2013/079174 | A1 | 6/2013 |

(Continued)

OTHER PUBLICATIONS

Degnan et al., Discovery of Orally Active Isofuranones as Potent, Selective Inhibitors of Hematopoetic Progenitor Kinase 1. ACS Med Chem Lett. Feb. 19, 2021;12(3):443-450, pre-publication edition.

(Continued)

*Primary Examiner* — Susanna Moore

(74) *Attorney, Agent, or Firm* — McCarter & English, LLP; Steven G. Davis; Xin Zhang

(57) ABSTRACT

One embodiment of the disclosure is a compound represented by Formula I or a pharmaceutically acceptable salt thereof. The variables in Formula I are defined herein.

I

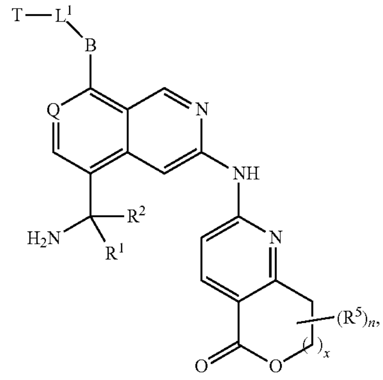

Compounds of Formula I are MAP4K1 inhibitors, which can be used to treat a diseases or disorders in a subject that benefits from control of MAP4K1 activity.

30 Claims, No Drawings

Specification includes a Sequence Listing.

(56) References Cited

FOREIGN PATENT DOCUMENTS

| | | | |
|---|---|---|---|
| WO | 2013/083991 | A1 | 6/2013 |
| WO | 2014/008218 | A1 | 1/2014 |
| WO | 2015/009812 | A2 | 1/2015 |
| WO | 2016/061280 | A1 | 4/2016 |
| WO | 2016/133935 | A1 | 8/2016 |
| WO | 2018/102366 | A1 | 6/2018 |
| WO | 2019/014513 | A1 | 1/2019 |
| WO | 2020/023551 | A1 | 1/2020 |
| WO | 2021/000935 | A1 | 1/2021 |
| WO | 2021/004547 | A1 | 1/2021 |
| WO | 2021/133809 | A1 | 7/2021 |
| WO | 2021/146370 | A1 | 7/2021 |
| WO | 2022/192145 | A1 | 9/2022 |

OTHER PUBLICATIONS

You et al., Enhanced antitumor immunity by a novel small molecule HPK1 inhibitor. J Immunother Cancer. Jan. 2021;9(1):e001402, 19 pages.

International Search Report and Written Opinion for Application No. PCT/US2022/073697, dated Nov. 24, 2022, 13 pages.

Copending U.S. Appl. No. 17/968,439, filed Oct. 18, 2022.

Alzabin et al., Hematopoietic progenitor kinase 1 is a critical component of prostaglandin E2-mediated suppression of the anti-tumor immune response. Cancer Immunol Immunother. Mar. 2010;59(3):419-29.

Alzabin et al., Hematopoietic progenitor kinase 1 is a negative regulator of dendritic cell activation. J Immunol. May 15, 2009;182(10):6187-94.

Hernandez et al., The Kinase Activity of Hematopoietic Progenitor Kinase 1 Is Essential for the Regulation of T Cell Function. Cell Rep. Oct. 2, 2018;25(1):80-94.

Hu et al., Human HPK1, a novel human hematopoietic progenitor kinase that activates the JNK/SAPK kinase cascade. Genes Dev. Sep. 15, 1996;10(18):2251-64.

Ikegami et al., The expression of prostaglandin E receptors EP2 and EP4 and their different regulation by lipopolysaccharide in C3H/HeN peritoneal macrophages. J Immunol. Apr. 1, 2001;166(7):4689-96.

Kiefer et al., HPK1, a hematopoietic protein kinase activating the SAPK/JNK pathway. EMBO J. Dec. 16, 1996;15(24):7013-25.

Lim et al., An HPK1 inhibitor CMPD0431 is a novel immuno-oncology agent that induces anti-tumor effects. Cancer Res. 79(Suppl. 13):Abstract 4150, 4 pages, (2019).

Liou et al., HPK1 is activated by lymphocyte antigen receptors and negatively regulates AP-1. Immunity. Apr. 2000;12(4):399-408.

Liu et al., Critical role of kinase activity of hematopoietic progenitor kinase 1 in anti-tumor immune surveillance. PLoS One. Mar. 26, 2019;14(3):e0212670, 18 pages.

Shui et al., Hematopoietic progenitor kinase 1 negatively regulates T cell receptor signaling and T cell-mediated immune responses. Nat Immunol. Jan. 2007;8(1):84-91.

Wang et al., Activation of the hematopoietic progenitor kinase-1 (HPK1)-dependent, stress-activated c-Jun N-terminal kinase (JNK) pathway by transforming growth factor beta (TGF-beta)-activated kinase (TAK1), a kinase mediator of TGF beta signal transduction. J Biol Chem. Sep. 5, 1997;272(36):22771-5.

Wang et al., Down-regulation of B cell receptor signaling by hematopoietic progenitor kinase 1 (HPK1)-mediated phosphorylation and ubiquitination of activated B cell linker protein (BLNK). J Biol Chem. Mar. 30, 2012;287(14):11037-48.

Zhou et al., Hematopoietic progenitor kinase 1 is a component of transforming growth factor beta-induced c-Jun N-terminal kinase signaling cascade. J Biol Chem. May 7, 1999;274(19):13133-8.

MAP4K1 INHIBITORS

CROSS-REFERENCE TO RELATED APPLICATIONS

This application claims priority to U.S. Provisional Application No. 63/221,825, filed on Jul. 14, 2021.

REFERENCE TO ELECTRONIC SEQUENCE LISTING

The application contains a Sequence Listing which has been submitted electronically in .XML format and is hereby incorporated by reference in its entirety. Said .XML copy, created on Aug. 2, 2024, is named "131608-81302.xml" and is 4,804 bytes in size. The sequence listing contained in this .XML file is part of the specification and is hereby incorporated by reference herein in its entirety.

FIELD

This application is directed to MAP4K1 inhibitors and methods for their use, such as to control the activity of MAP4K1 in a subject.

BACKGROUND

MAP4K1, also known as hematopoietic progenitor kinase 1 (HPKl), was originally cloned from hematopoietic progenitor cells (Hu, M. C., et al., Genes Dev, 1996. 10(18): p. 2251-64). MAP4K1 is of particular interest as a target, because it is predominantly expressed in hematopoietic cells such as T cells, B cells, macrophages, dendritic cells, neutrophils, and mast cells (Hu, M. C., et al, Genes Dev, 1996. 10(18): p. 2251-64; Kiefer, F., et al, EMBO J, 1996. 15(24): p. 7013-25). MAP4K1 kinase activity has been shown to be induced upon activation of T cell receptors (TCR) (Liou, J., et al., Immunity, 2000. 12(4): p. 399-408), B cell receptors (BCR) (Liou, J., et al., Immunity, 2000. 12(4): p. 399-408), transforming growth factor receptor (TGF-R) (Wang, W., et al, J Biol Chem, 1997. 272(36): p. 22771-5; Zhou, G., et al, J Biol Chem, 1999. 274(19): p. 13133-8), or $G_s$-coupled $PGE_2$ receptors (EP2 and EP4) (Ikegami, R, et al, J Immunol, 2001. 166(7): p. 4689-96). As such, MAP4K1 regulates diverse functions of various immune cells.

MAP4K1 is important in regulating the functions of various immune cells and it has been implicated in autoimmune diseases and anti-tumor immunity (Shui, J. W., et al, Nat Immunol, 2007. 8(1): p. 84-91; Wang, X., et al, J Biol Chem, 2012. 287(14): p. 11037-48). Those observations suggested that attenuation of MAP4K1 activity may contribute to autoimmunity in patients. Furthermore, MAP4K1 may also control anti-tumor immunity via T cell-dependent mechanisms. In the PGE2-producing Lewis lung carcinoma tumor model, the tumors developed more slowly in MAP4K1 knockout mice as compared to wild-type mice (see US 2007/0087988). In addition, it was shown that adoptive transfer of MAP4K1 deficient T cells was more effective in controlling tumor growth and metastasis than wild-type T cells (Alzabin, S., et al., Cancer Immunol Immunother, 2010. 59(3): p. 419-29). Similarly, bone marrow derived dendritic cells (BMDCs) from MAP4K1 knockout mice were more efficient to mount a T cell response to eradicate Lewis lung carcinoma as compared to wild-type BMDCs (Alzabin, S., et al., J Immunol, 2009. 182(10): p. 6187-94). Data obtained from MAP4K1 kinase dead mice demonstrated that MAP4K1 kinase activity is critical in conferring suppressive functions of MAP4K1 in a wide range of immune cells including CD4+, CD8+, DC, NK to T regulatory cells (Tregs) and inactivation of kinase domain was sufficient to elicit robust anti-tumor immune responses. Liu et al., PLoS ONE 14(3):e0212670 https://doi.org/10.1371/journal.pone.0212670. Moreover, loss of MAP4K1 kinase function suppresses tumor growth in preclinical tumor models and therapeutic co-blockade of MAP4K1 kinase and PD-L1 enhances anti-tumor responses. Hernandez S. et al., Cell Reports 2018 25: p. 80-94. Recently presented results show tumor growth inhibition in a CT-26 syngeneic mouse model using a small molecule MAP4K1 inhibitor (Seungmook, L., Cancer research.AACR Journal, 2019, Abstract 4150). These data have validated MAP4K1 as a novel drug target for enhancing antitumor immunity.

Accordingly, there is a need for new compounds that modulate MAP4K1 activity for the treatment of MAP4K1-dependent diseases or disorders such as cancer, viral infection, and other diseases and disorders. Of particular importance is the need for new compounds that selectively modulate MAP4K1 activity.

SUMMARY

Provided herein are compounds, or pharmaceutically acceptable salts thereof, and compositions which inhibit MAP4K1, thereby enhancing an immune response in a subject. For example, the $IC_{50}$ values for inhibition of MAP4K1 provided in Table 3 demonstrate that these compounds are potent inhibitors of MAP4K1. Also disclosed are methods of using the compounds and compositions described herein for treating cancer and viral infection.

A first embodiment of the disclosure is a compound represented by Formula I:

I

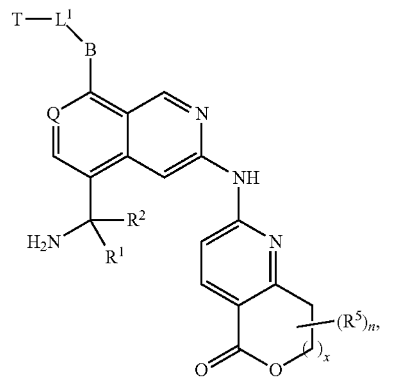

or a pharmaceutically acceptable salt thereof, wherein:

T is selected from

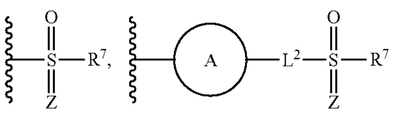

and 4-5 membered heterocycle containing

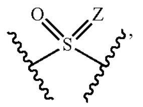

wherein said heterocycle is optionally substituted with 1-2 $R^6$;

Z is absent, O or NH;

Ring A is $C_{4-6}$ cycloalkyl or 4-6 membered heterocycle containing nitrogen, wherein said cycloalkyl or heterocycle is optionally substituted with 1-2 $R^6$;

$L^1$ is selected from bond and $C_1$-$C_3$ alkylene, wherein said alkylene is optionally substituted with 1-2 $R^{11}$;

$L^2$ is selected from bond and $C_1$-$C_3$ alkylene;

B is O or NH;

Q is N or CH;

x is 0, 1, or 2;

n is 0, 1, 2, 3, or 4;

$R^1$ and $R^2$ are each independently selected from hydrogen, $C_{1-6}$ alkyl, $C_{3-6}$ cycloalkyl, and 4 to 6-membered heterocycle, wherein said alkyl is optionally substituted with 1-2 $R^3$;

each $R^3$ is independently selected from halogen, hydroxyl and $OR^4$;

each $R^4$ is independently selected from $C_{1-3}$ alkyl, $CF_3$, $CH_2F$, and $CHF_2$;

each $R^5$ is independently selected from $C_{1-2}$ alkyl, $CF_3$, $CH_2F$, and $CHF_2$, or two $R^5$ attached to the same carbon atom taken together with the carbon atom to which they attach form $C_{3-5}$ cycloalkyl; or two $R^5$ attached to two adjacent carbon atoms taken together with the two adjacent carbon atoms to which they attach form $C_{4-6}$ cycloalkyl;

each $R^6$ is independently selected from $CH_3$, methoxy, $CF_3$, $CH_2F$, and $CHF_2$;

$R^7$ is selected from $C_{1-3}$ alkyl, $C_{3-6}$ cycloalkyl, $OC_{1-4}$ alkyl, $NR^9R^{10}$, and 3-5 membered heterocycle containing nitrogen or oxygen, wherein said alkyl, cycloalkyl, or heterocycle is optionally substituted with 1-3 $R^8$;

each $R^8$ is independently selected from halogen, $C_{1-3}$ alkyl, hydroxyl and $OC_{1-3}$ alkyl, wherein said alkyl is optionally substituted with 1-3 $R^{12}$;

$R^9$ is selected from $C_{1-2}$ alkyl;

$R^{10}$ is selected from $C_{1-2}$ alkyl;

each $R^{11}$ is independently selected from halogen, methoxy, $C_{1-2}$ alkyl, $CH_2F$, $CHF_2$ and $CF_3$, or two $R^{11}$ taken together with the two adjacent carbon atoms to which they attach form cyclopropyl; and each $R^{12}$ is halogen.

Another embodiment of the disclosure is a pharmaceutical composition comprising a pharmaceutically acceptable carrier or excipient and a compound disclosed herein or a pharmaceutically acceptable salt thereof.

Another embodiment of the disclosure is a method of inhibiting MAP4K1 in a subject in need thereof, comprising contacting MAP4K1 with an effective amount of the compound disclosed herein or a pharmaceutically acceptable salt thereof or a pharmaceutical composition comprising a compound disclosed herein or a pharmaceutically acceptable salt thereof.

Another embodiment of the disclosure is a method of treating a MAP4K1-dependent disorder or disease (e.g., treating a cancer) in a subject in need thereof, comprising administering to the subject an effective amount of a compound disclosed herein or a pharmaceutically acceptable salt thereof or a pharmaceutical composition comprising the compound(s).

Another embodiment of the disclosure is the use of a compound disclosed herein or a pharmaceutically acceptable salt thereof or a pharmaceutical composition comprising the compound(s), for the preparation of a medicament for treating a MAP4K1-dependent disorder or disease (e.g., treating a cancer) in a subject in need thereof.

Another embodiment of the disclosure is a compound disclosed herein or a pharmaceutically acceptable salt thereof or a pharmaceutical composition comprising the compound(s), for use in treating a MAP4K1-dependent disorder or disease (e.g., treating a cancer) in a subject in need thereof.

DETAILED DESCRIPTION

The disclosed compounds or pharmaceutically acceptable salts thereof are MAP4K1 inhibitors, which can be used for treating a MAP4K1-dependent disorder or disease. Such diseases or disorders include cancer and viral infection.

COMPOUND EMBODIMENTS

Example Embodiments Include:

First Embodiment: A Compound Represented by Formula I

I

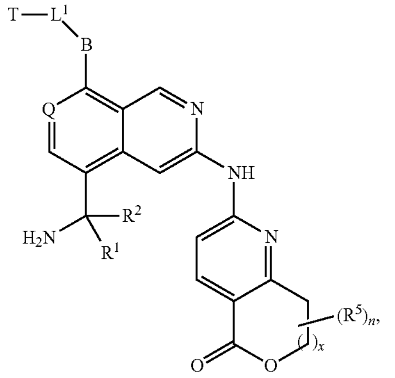

or a pharmaceutically acceptable salt thereof. The variables in Formula I are described in the summary above.

Second Embodiment: A Compound Represented by Formula II

II

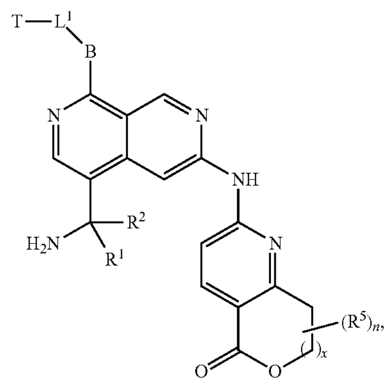

or a pharmaceutically acceptable salt thereof, wherein the definitions for the other variables in Formula II are as defined in the first embodiment.

Third Embodiment: A Compound Represented by Formula III

III

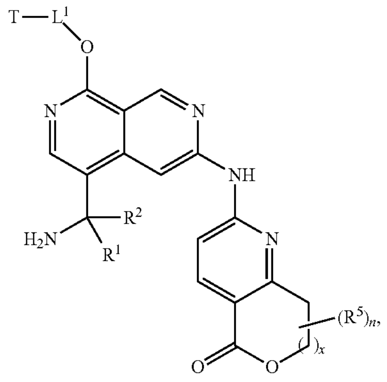

or a pharmaceutically acceptable salt thereof, wherein the definitions for the other variables in Formula III are as defined in the first embodiment.

Fourth Embodiment: A Compound is Represented by Formula IV

IV

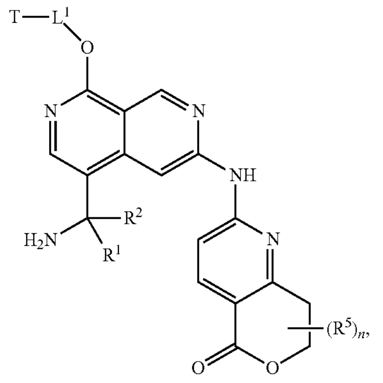

or a pharmaceutically acceptable salt thereof, wherein the definitions for the other variables in Formula IV are as defined in the first embodiment.

Fifth Embodiment: A Compound Represented by Formula V

V

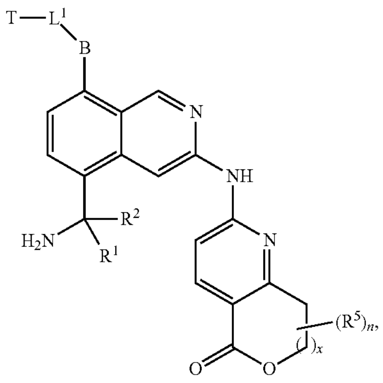

or a pharmaceutically acceptable salt thereof, wherein the definitions for the other variables in Formula V are as defined in the first embodiment.

Sixth Embodiment: A Compound Represented by Formula VI

VI

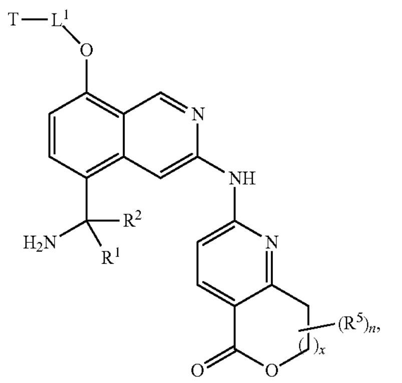

or a pharmaceutically acceptable salt thereof, wherein the definitions for the other variables in Formula VI are as defined in the first embodiment.

Seventh Embodiment: A Compound Represented by Formula VII

VII

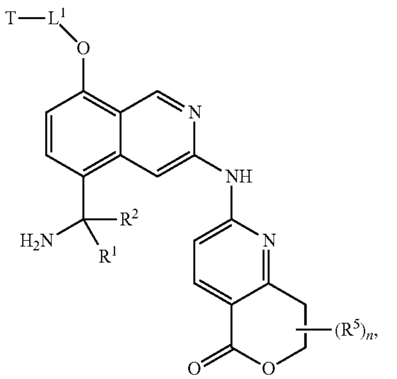

or a pharmaceutically acceptable salt thereof, wherein the definitions for the other variables in Formula VII are as defined in the first embodiment.

Eighth embodiment: a compound represented by Formulae I, II, III, IV, V, VI or VII, or a pharmaceutically acceptable salt thereof, wherein $L^1$ is bond; T is

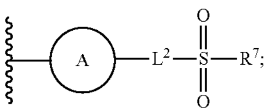

and $L^2$ is a bond or methylene, wherein the definitions for the other variables in Formulae I, II, III, IV, V, VI and VII are as defined in the first embodiment.

Ninth embodiment: a compound represented by Formulae I, II, III, IV, V, VI or VII, or a pharmaceutically acceptable salt thereof, wherein Ring A is selected from azetidinylene, cyclobutylene, cyclopentylene and pyrrolidinylene, and said azetidinylene, cyclobutylene, cyclopentylene and pyrrolidinylene is optionally substituted with 1-2 $R^6$, wherein the definitions for the other variables in Formulae I, II, III, IV, V, VI and VII are as defined in the first and/or eighth embodiments.

Tenth embodiment: a compound represented by Formulae I, II, III, IV, V, VI or VII, or a pharmaceutically acceptable salt thereof, wherein Ring A is cyclobutylene optionally substituted with 1-2 $R^6$, and the definitions for the other variables in Formulae I, II, III, IV, V, VI and VII are as defined in the first and/or eighth embodiments.

Eleventh embodiment: a compound represented by Formulae I, II, III, IV, V, VI or VII, or a pharmaceutically acceptable salt thereof, wherein $L^1$ is $C_1$-$C_3$ alkylene optionally substituted with 1-2 $R^{11}$; and T is

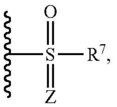

wherein the definitions for the other variables in Formulae I, II, III, IV, V, VI and VII are as defined in the first embodiment.

Twelfth embodiment: a compound represented by Formulae I, II, III, IV, V, VI or VII, or a pharmaceutically acceptable salt thereof, wherein $L^1$ is propylene optionally substituted with 1-2 $R^{11}$, and the definitions for the other variables in Formulae I, II, III, IV, V, VI and VII are as defined in the first and/or eleventh embodiments.

Thirteenth embodiment: a compound represented by Formulae I, II, III, IV, V, VI or VII, or a pharmaceutically acceptable salt thereof, wherein $L^1$ is selected from Formula L-1, L-2, L-3, L-4, L-5, L-6 and L-7:

L-1

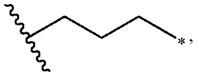

L-2

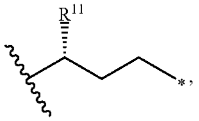

L-3

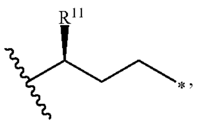

L-4

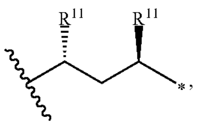

L-5

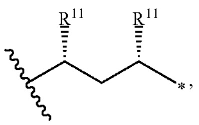

-continued

L-6

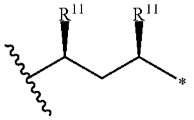

and

L-7

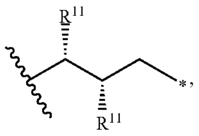

, wherein ⌇ represents a bond to B, and —* represents a bond to T, and wherein the definitions for the other variables in Formulae I, II, III, IV, V, VI and VII are as defined in the first, eleventh and/or twelfth embodiments.

Fourteenth embodiment: a compound represented by Formulae I, II, III, IV, V, VI or VII, or a pharmaceutically acceptable salt thereof, wherein Z is O, and the definitions for the other variables in Formulae I, II, III, IV, V, VI and VII are as defined in the first, eleventh, twelfth and/or thirteenth embodiments.

Fifteenth embodiment: a compound represented by Formulae I, II, III, IV, V, VI or VII, or a pharmaceutically acceptable salt thereof, wherein Z is NH, and the definitions for the other variables in Formulae I, II, III, IV, V, VI and VII are as defined in the first, eleventh, twelfth and/or thirteenth embodiments.

Sixteenth embodiment: a compound represented by Formulae I, II, III, IV, V, VI or VII, or a pharmaceutically acceptable salt thereof, wherein Z is absent, and the definitions for the other variables in Formulae I, II, III, IV, V, VI and VII are as defined in the first, eleventh, twelfth and/or thirteenth embodiments.

Seventeenth embodiment: a compound represented by Formulae I, II, III, IV, V, VI or VII, or a pharmaceutically acceptable salt thereof, wherein T is 4-5 membered heterocycle containing sulfone, and said heterocycle is optionally substituted with 1-2 $R^6$; and $L^1$ is selected from bond, methylene and ethylene, and wherein the definitions for the other variables in Formulae I, II, III, IV, V, VI and VII are as defined in the first embodiment.

Eighteenth embodiment: a compound represented by Formulae I, II, III, IV, V, VI or VII, or a pharmaceutically acceptable salt thereof, wherein T is 4-membered heterocycle containing sulfone, wherein said heterocycle is optionally substituted with 1-2 $R^6$, and wherein the definitions for the other variables in Formulae I, II, III, IV, V, VI and VII are as defined in the first and/or seventeenth embodiments.

Nineteenth embodiment: a compound represented by Formulae I, II, III, IV, V, VI or VII, or a pharmaceutically acceptable salt thereof, wherein $R^1$ and $R^2$ are each independently selected from hydrogen, $C_{1-6}$ alkyl, and $C_{3-6}$ cycloalkyl, wherein said alkyl is optionally substituted with $OR^3$; each $R^3$ is independently selected from halogen, hydroxyl and $OR^4$; and each $R^4$ is independently selected from $C_{1-3}$ alkyl, and wherein the definitions for the other variables in Formulae I, II, III, IV, V, VI and VII are as defined in the first, eighth, ninth, tenth, eleventh, twelfth, thirteen, fourteenth, fifteenth, sixteenth, seventeenth and/or eighteenth embodiments.

Twentieth embodiment: a compound represented by Formulae I, II, III, IV, V, VI or VII, or a pharmaceutically acceptable salt thereof, wherein $R^1$ and $R^2$ are each independently selected from hydrogen, $CH_3$, $CH_2CH_3$, $CH_2CH_2CH_3$, $CH_2$—$OCH_3$ and cyclopropyl, and wherein the definitions for the other variables in Formulae I, II, III, IV, V, VI and VII are as defined in the first, eighth, ninth, tenth, eleventh, twelfth, thirteen, fourteenth, fifteenth, sixteenth, seventeenth and/or eighteenth embodiments. In alternative embodiments, for a compound represented by Formulae I, II, III, IV, V, VI or VII, or a pharmaceutically acceptable salt thereof: $R^1$ and $R^2$ are each $CH_3$; or $R^1$ is hydrogen and $R^2$ is $CH_2CH_3$; or $R^1$ is $CH_3$ and $R^2$ is $CH_2CH_3$; or $R^1$ is $CH_3$ and $R^2$ is $CH_2$—$OCH_3$; or $R^1$ is hydrogen and $R^2$ is $CH_2CH_2CH_3$; or $R^1$ is $CH_3$ and $R^2$ is $CH_2CH_2CH_3$; or $R^1$ is hydrogen and $R^2$ is cyclopropyl; or $R^1$ is $CH_3$ and $R^2$ is cyclopropyl, and wherein the definitions for the other variables in Formulae I, II, III, IV, V, VI and VII are as defined in the first, eighth, ninth, tenth, eleventh, twelfth, thirteen, fourteenth, fifteenth, sixteenth, seventeenth and/or eighteenth embodiments.

Twenty-first embodiment: a compound represented by Formulae I, II, III, IV, V, VI or VII, or a pharmaceutically acceptable salt thereof, wherein $R^5$ is $CH_3$, or two $R^5$ attached to the same carbon atom taken together with the carbon atom to which they attach form cyclopropyl; and n is 1, 2, 3 or 4, and wherein the definitions for the other variables in Formulae I, II, III, IV, V, VI and VII are as defined in the first, eighth, ninth, tenth, eleventh, twelfth, thirteen, fourteenth, fifteenth, sixteenth, seventeenth, eighteenth, nineteenth and/or twentieth embodiments. In alternative embodiments: for a compound represented by Formulae I, II, III, IV, V, VI or VII, or a pharmaceutically acceptable salt thereof: n is 0; or n is 1 and $R^5$ is $CH_3$; or n is 2 and each $R^5$ is $CH_3$; or n is 3 and each $R^5$ is $CH_3$; or n is 3, two $R^5$ attached to the same carbon atom taken together with the carbon atom to which they attach form cyclopropyl, and one $R^5$ is $CH_3$; or n is 4, two $R^5$ attached to the same carbon atom taken together with the carbon atom to which they attach form cyclopropyl, and two $R^5$ are $CH_3$, and wherein the definitions for the other variables in Formulae I, II, III, IV, V, VI and VII are as defined in the first, eighth, ninth, tenth, eleventh, twelfth, thirteen, fourteenth, fifteenth, sixteenth, seventeenth, eighteenth, nineteenth and/or twentieth embodiments.

Twenty second embodiment: a compound represented by Formulae I, II, III, IV, V, VI or VII, or a pharmaceutically acceptable salt thereof, wherein each $R^6$ is $CH_3$, and wherein the definitions for the other variables in Formulae I, II, III, IV, V, VI and VII are as defined in the first, eighth, ninth, tenth, seventeenth, eighteenth, nineteenth, twentieth and/or twenty first embodiments.

Twenty third embodiment: a compound represented by Formulae I, II, III, IV, V, VI or VII, or a pharmaceutically acceptable salt thereof, wherein $R^7$ is selected from $C_{1-3}$ alkyl, $CH_2F$, $CHF_2$, $CF_3$, $C_{3-6}$ cycloalkyl and $NR^9R^{10}$; $R^9$ is selected from $C_{1-2}$ alkyl; and $R^{10}$ is selected from $C_{1-2}$ alkyl, and wherein the definitions for the other variables in Formulae I, II, III, IV, V, VI and VII are as defined in the first, eighth, ninth, tenth, eleventh, twelfth, thirteen, fourteenth, fifteenth, sixteenth, nineteenth, twentieth, twenty first and/or twenty second embodiments.

Twenty fourth embodiment: a compound represented by Formulae I, II, III, IV, V, VI or VII, or a pharmaceutically acceptable salt thereof, wherein $R^7$ is selected from $CH_3$, $CF_3$, $CH_2CH_3$, $CH(CH_3)_2$, cyclopropyl and $N(CH_3)_2$, and wherein the definitions for the other variables in Formulae I, II, III, IV, V, VI and VII are as defined in the first, eighth, ninth, tenth, eleventh, twelfth, thirteen, fourteenth, fifteenth, sixteenth, nineteenth, twentieth, twenty first and/or twenty second embodiments.

Twenty fifth embodiment: a compound represented by Formulae I, II, III, IV, V, VI or VII, or a pharmaceutically acceptable salt thereof, wherein each $R^{11}$ is independently selected from $CH_3$, $CF_3$ and $CH_2CH_3$, and wherein the definitions for the other variables in Formulae I, II, III, IV, V, VI and VII are as defined in the first, eighth, ninth, tenth, eleventh, twelfth, thirteen, fourteenth, fifteenth, sixteenth, seventeenth, eighteenth, nineteenth, twentieth, twenty first, twenty second, twenty third and/or twenty fourth embodiments.

Twenty sixth embodiment: a compound represented by Formulae I, II, III, IV, V, VI or VII, or a pharmaceutically acceptable salt thereof, wherein each $R^{11}$ is $CH_3$, and wherein the definitions for the other variables in Formulae I, II, III, IV, V, VI and VII are as defined in the first, eighth, ninth, tenth, eleventh, twelfth, thirteen, fourteenth, fifteenth, sixteenth, seventeenth, eighteenth, nineteenth, twentieth, twenty first, twenty second, twenty third and/or twenty fourth embodiments.

In alternative embodiments, for a compound represented by Formulae I, II or V, or a pharmaceutically acceptable salt thereof, B is NH, and wherein the definitions for the other variables in Formulae I, II and V are as defined in the first, eighth, ninth, tenth, eleventh, twelfth, thirteen, fourteenth, fifteenth, sixteenth, seventeenth, eighteenth, nineteenth, twentieth, twenty first, twenty second, twenty third, twenty fourth, twenty fifth and/or twenty sixth embodiments.

The disclosure also includes the compounds depicted in Table 1 and prepared in the Exemplification, in both the neutral form and pharmaceutically acceptable salts thereof. The synthetic protocol used to prepare compounds in Table 1 is listed in the last column of Table 1 and full details for each synthetic protocol are described in Schemes 1 and 2 and in the General Synthetic Methods and Intermediates section.

TABLE 1

| Cpd. # | Structure | LCMS (M + 1) | NMR | Synthetic Protocol |
|---|---|---|---|---|
| 1 | 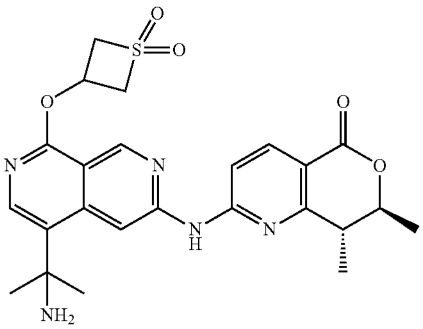 [SMILES: C[C@@H]1OC(=O)c2ccc(Nc3cc4c(C(C)(C)N)cnc(OC5CS(=O)(=O)C5)c4cn3)nc2[C@H]1C] | 498 | $^1$H-NMR (400 MHz, 6d-DMSO): δ ppm 10.73 (s, 1H), 9.47 (s, 1H), 9.40 (s, 1H), 8.18 (s, 1H), 8.09 (d, J = 8.8 Hz, 1H), 7.38 (d, J = 8.8 Hz, 1H), 5.72-5.66 (m, 1H), 4.83 (dd, J = 7.6, 15.6 Hz, 2H), 4.61 (q, J = 6.0 Hz, 1H), 4.48 (dd, J = 3.2, 15.6 Hz, 2H), 3.03-2.96 (m, 1H), 1.66 (d, J = 2.0 Hz, 6H), 1.44 (d, J = 7.2 Hz, 3H), 1.38 (d, J = 6.4 Hz, 3H). | Scheme 1, Intermediate 1 and Intermediate 21 |
| 2 | 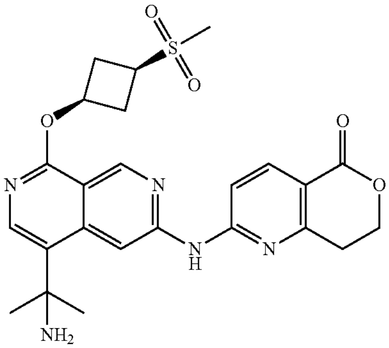 [SMILES: CC(C)(N)c1cnc(O[C@H]2C[C@@H](S(C)(=O)=O)C2)c2cnc(Nc3ccc4c(n3)CCOC4=O)cc12] | 597 | $^1$H-NMR (400 MHz, CD3OD): δ ppm 9.40 (s, 1H), 9.33 (s, 1H), 8.19-8.09 (m, 2H), 7.15 (d, J = 8.4 Hz, 1H), 5.45-5.37 (m, 1H), 4.66-4.62 (m, 2H), 3.88-3.77 (m, 1H), 3.24-3.18 (m, 2H), 3.00-2.95 (m, 2H), 2.93 (s, 3H), 2.72-2.62 (m, 2H), 1.81 (s, 6H). | Scheme 1, Intermediate 7 and Intermediate 22 |
| 3 | 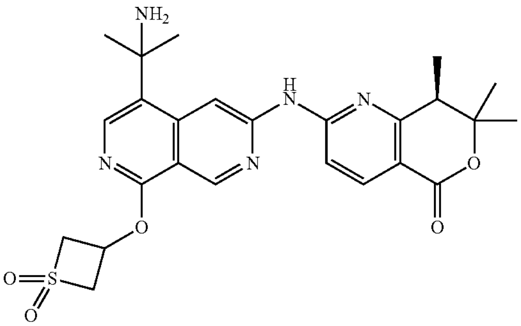 [SMILES: C[C@@H]1c2nc(Nc3cc4c(C(C)(C)N)cnc(OC5CS(=O)(=O)C5)c4cn3)ccc2C(=O)OC1(C)C] | 512 | $^1$H-NMR (400 MHz, CD3OD): δ ppm 9.45 (s, 1H), 9.39 (s, 1H), 8.19 (s, 1H), 8.15 (d, J = 8.8 Hz, 1H), 7.24 (d, J = 8.8 Hz, 1H), 5.79-5.75 (m, 1H), 4.80 (dd, J = 8.0 Hz, J = 3.6 Hz, 2H), 4.42 (dd, J = 8.0 Hz, J = 3.6 Hz, 2H), 3.07-3.02 (m, 1H), 1.84 (d, J = 8.0 Hz, 6H), 1.55 (s, 3H), 1.46 (s, 3H), 1.41 (d, J = 7.6 Hz, 3H). | Scheme 1, Intermediate 3 and Intermediate 21 |

TABLE 1-continued

| Cpd. # | Structure | LCMS (M + 1) | NMR | Synthetic Protocol |
|---|---|---|---|---|
| 4 | 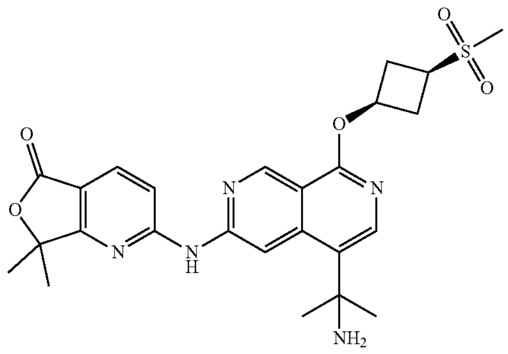 | 512 | $^1$H-NMR (400 MHz, 6d-DMSO): δ ppm 10.99 (s, 1H), 9.68 (s, 1H), 9.34 (s, 1H), 8.19 (s, 1H), 8.03 (d, J = 8.4 Hz, 1H), 7.34 (d, J = 8.4 Hz, 1H), 5.43-5.29 (m, 1H), 3.91-3.77 (m, 1H), 2.95 (s, 3H), 2.90-2.80 (m, 2H), 2.11-1.98 (m, 2H), 1.69 (s, 12H). | Scheme 1, Intermediate 6 and Intermediate 22 |
| 5 | 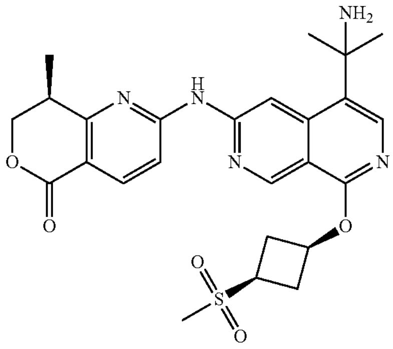 [SMILES: C[C@@H]1COC(=O)c2ccc(Nc3cc4c(C(C)(C)N)cnc(O[C@H]5C[C@@H](S(C)(=O)=O)C5)c4cn3)nc21] or 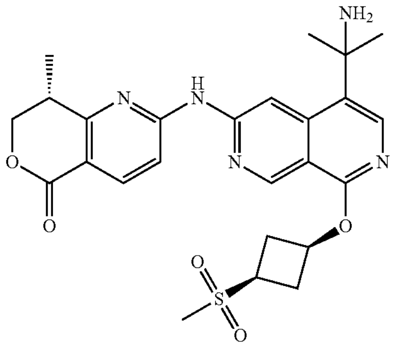 [SMILES: C[C@H]1COC(=O)c2ccc(Nc3cc4c(C(C)(C)N)cnc(O[C@H]5C[C@@H](S(C)(=O)=O)C5)c4cn3)nc21] | 512 | $^1$H-NMR (400 MHz, CD3OD): δ ppm 9.41 (s, 1H), 9.24 (s, 1H), 8.17 (d, J = 8.8 Hz, 1H), 8.05 (s, 1H), 7.26 (d, J = 8.8 Hz, 1H), 5.57-5.32 (m, 1H), 4.75-4.66 (m, 1H), 4.43 (dd, J = 2.8, 11.4 Hz, 1H), 3.83 (t, J = 8.4 Hz, 1H), 3.23-3.11 (m, 1H), 3.03-2.95 (m, 2H), 2.93 (s, 3H), 2.77-2.61 (m, 2H), 1.95 (d, J = 7.4 Hz, 6H), 1.49 (d, J = 7.2 Hz, 3H). | Scheme 1, Intermediate 8 and Intermediate 22 2nd eluting isomer from chiral HPLC Column: Chiralpak IC-3 50 × 4.6 mm I.D., 3 um; Mobile phase: A2 = Heptane (0.05% DEA); B1 = IPA + ACN (0.05% DEA); Gradient elution: 40% IPA + ACN (0.05% DEA) |
| 6 | 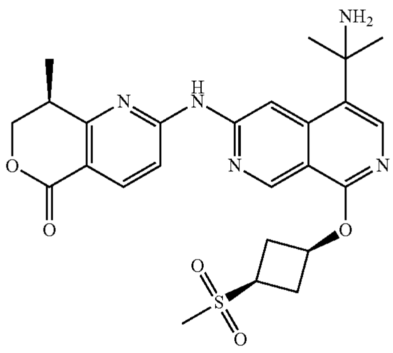 [SMILES: C[C@@H]1COC(=O)c2ccc(Nc3cc4c(C(C)(C)N)cnc(O[C@H]5C[C@@H](S(C)(=O)=O)C5)c4cn3)nc21] or | 512 | $^1$H-NMR (400 MHz, $CD_3OD$): δ ppm 9.39 (s, 1H), 9.28 (s, 1H), 8.16 (d, J = 8.8 Hz, 1H), 8.10 (s, 1H), 7.25 (d, J = 8.4 Hz, 1H), 5.44 (q, J = 7.2 Hz, 1H), 4.70 (dd, J = 3.6, 11.6 Hz, 1H), 4.43 (dd, J = 2.6, 11.4 Hz, 1H), 3.83 (t, J = 8.4 Hz, 1H), 3.24-3.11 (m, 1H), 3.01-2.95 (m, 2H), 2.93 (s, 3H), 2.75-2.65 (m, 2H), 1.89 (d, J = 7.0 Hz, 6H), 1.49 (d, J = 7.2 Hz, 3H). | Scheme 1, Intermediate 8 and Intermediate 22 1st eluting isomer from chiral HPLC Column: Daicel Chiralpak IC(250 mm*30 mm, 10 um); Mobile phase: 35% Hexane-IPA (0.1% NH3) in $CO_2$) |

TABLE 1-continued

| Cpd. # | Structure | LCMS (M + 1) | NMR | Synthetic Protocol |
|---|---|---|---|---|
| | 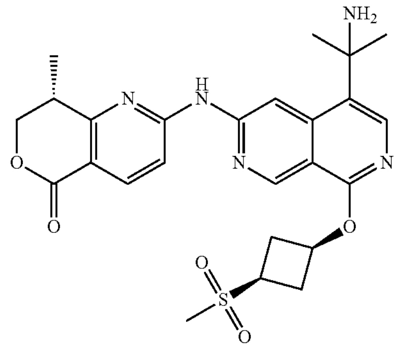 [SMILES: C[C@H]1COC(=O)c2ccc(Nc3cc4c(C(C)(C)N)cnc(O[C@H]5C[C@@H](S(C)(=O)=O)C5)c4cn3)nc21] | | | |
| 7 | 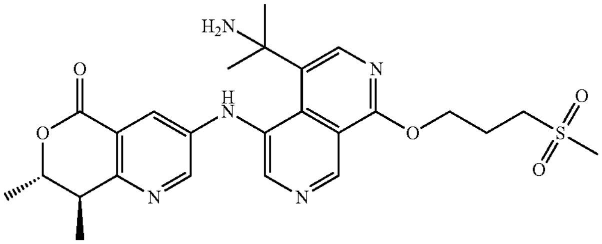 | 514 | $^1$H-NMR (400 MHz, $CD_3OD$): δ ppm 9.47 (s, 1H), 8.94 (s, 1H), 8.46 (s, 1H), 8.17 (d, J = 8.8 Hz, 1H), 8.04-7.92 (m, 1H), 7.39 (d, J = 8.8 Hz, 1H), 4.75-4.64 (m, 3H), 3.45-3.37 (m, 2H), 3.04 (s, 3H), 3.02-2.98 (m, 1H), 2.49-2.38 (m, 2H), 2.02 (d, J = 6.8 Hz, 6H), 1.51 (d, J = 6.8 Hz, 3H), 1.46 (d, J = 6.0 Hz, 3H). | Scheme 1, Intermediate 1 and Intermediate 23 |
| 8 | 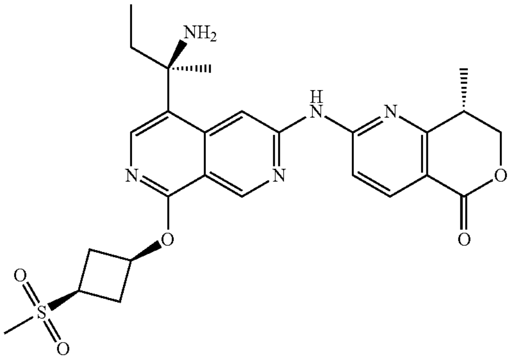 [SMILES: CC[C@@](C)(N)c1cnc(O[C@H]2C[C@@H](S(C)(=O)=O)C2)c2cnc(Nc3ccc4c(n3)[C@H](C)COC4=O)cc12] or 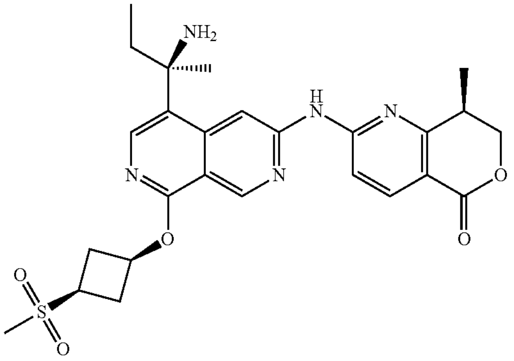 [SMILES: CC[C@@](C)(N)c1cnc(O[C@H]2C[C@@H](S(C)(=O)=O)C2)c2cnc(Nc3ccc4c(n3)[C@@H](C)COC4=O)cc12] | 526 | $^1$H-NMR (400 MHz, $CD_3OD$): δ ppm 9.37 (s, 1H), 9.21 (s, 1H), 8.13 (d, J = 8.6 Hz, 1H), 8.05 (s, 1H), 7.23 (d, J = 8.6 Hz, 1H), 5.44 (t, J = 12 Hz, 1H), 4.70 (dd, J = 3.6, 11.2 Hz, 1H), 4.43 (dd, J = 3.2, 11.2 Hz, 1H), 3.90-3.74 (m, 1H), 3.16 (td, J = 3.6, 7.2 Hz, 1H), 3.02-2.96 (m, 2H), 2.93 (s, 3H), 2.74-2.65 (m, 2H), 2.55 (qd, J = 7.3, 14.6 Hz, 1H), 2.24 (qd, J = 7.4, 14.6 Hz, 1H), 1.89-1.81 (m, 3H), 1.47 (d, J = 7.2 Hz, 3H), 0.77 (t, J = 7.4 Hz, 3H). | Scheme 1, Intermediate 8 and Intermediate 24 2nd eluting isomer from SFC Column: Daicel Chiralpak AD-H (250 mm* 30 mm, 5 um); Mobile phase: [0.1% $NH_3H_2O$ IPA]; B %: 40%-40% |

TABLE 1-continued

| Cpd. # | Structure | LCMS (M + 1) | NMR | Synthetic Protocol |
|---|---|---|---|---|
| 9 | 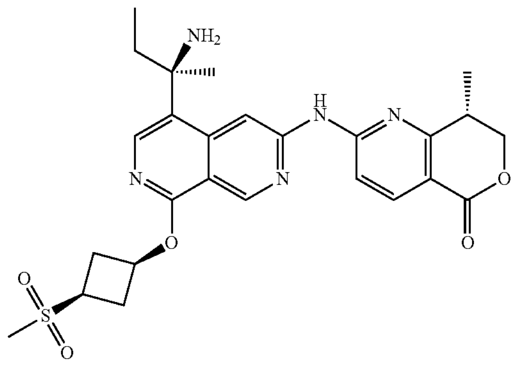 [SMILES: CC[C@@](C)(N)c1cnc(O[C@H]2C[C@@H](S(C)(=O)=O)C2)c2cnc(Nc3ccc4c(n3)[C@H](C)COC4=O)cc12] or 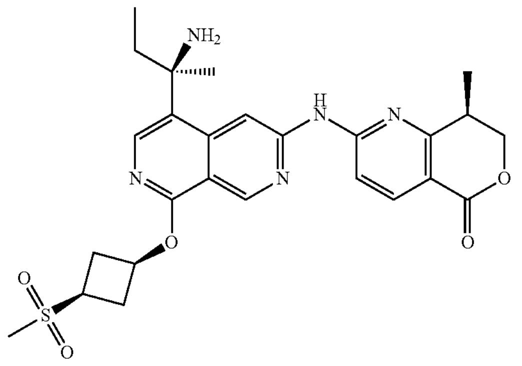 [SMILES: CC[C@@](C)(N)c1cnc(O[C@H]2C[C@@H](S(C)(=O)=O)C2)c2cnc(Nc3ccc4c(n3)[C@@H](C)COC4=O)cc12] | 526 | $^1$H-NMR (400 MHz, $CD_3OD$): δ ppm 9.39 (s, 1H), 9.22-9.14 (m, 1H), 8.15 (d, J = 8.6 Hz, 1H), 8.02 (s, 1H), 7.25 (d, J = 8.8 Hz, 1H), 5.45 (t, 7=7.2 Hz, 1H), 4.70 (dd, J = 3.6, 11.2 Hz, 1H), 4.43 (dd, J= 2.9, 11.3Hz, 1H), 3.83 (q, J = 8.4 Hz, 1H), 3.19-3.10 (m, 1H), 3.03-2.95 (m, 2H), 2.93 (s, 3H), 2.77-2.64 (m, 2H), 2.63-2.54 (m, 1H), 2.22 (qd, J = 7.2, 14.6 Hz, 1H), 1.92 (s, 3H), 1.48 (d, J = 7.2 Hz, 3H), 0.79 (t, J = 7.4 Hz, 3H). | Scheme 1, Intermediate 8 and Intermediate 24 1st eluting isomer from SFC Column: Daicel Chiralpak AD-H (250mm*30 mm, 5 um); Mobile phase: [0.1% $NH_3H_2O$ IPAJ; B %: 40%-40% |
| 10 | 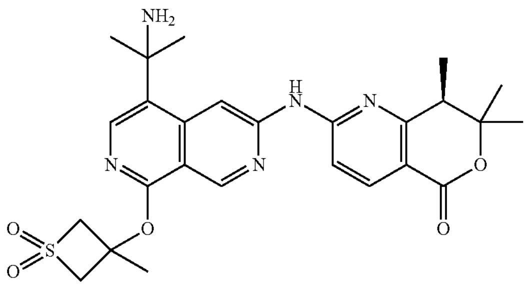 [SMILES: C[C@@H]1c2nc(Nc3cc4c(C(C)(C)N)cnc(OC5(C)CS(=O)(=O)C5)c4cn3)ccc2C(=O)OC1(C)C] | 526 | $^1$H NMR (400 MHz, MeOD-d4) δ ppm 9.39 (d, J = 9.2 Hz, 2H), 8.22 (s, 1H), 8.14 (d, J = 8.8 Hz, 1H), 7.22 (d, J = 8.8 Hz, 1H), 4.81-4.77 (m, 2H), 4.55-4.48 (m, 2H), 3.05 (q, J = 7.2 Hz, 1H), 2.10 (s, 3H), 1.80 (d, J = 7.6 Hz, 6H), 1.54 (s, 3H), 1.45 (s, 3H), 1.40 (d, J = 7.2 Hz, 3H). | Scheme 1, Intermediate 3 and Intermediate 25 |
| 11 | 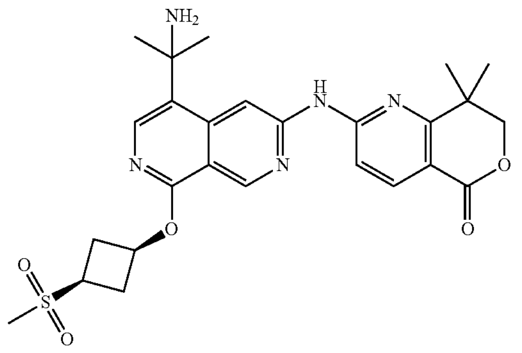 [SMILES: CC(C)(N)c1cnc(O[C@H]2C[C@@H](S(C)(=O)=O)C2)c2cnc(Nc3ccc4c(n3)C(C)(C)COC4=O)cc12] | 526 | $^1$H NMR (400 MHz, MeOD): δ ppm 9.40 (s, 1H), 8.76 (s, 1H), 8.17 (s, 1H), 7.49 (d, J = 8.8 Hz, 1H), 7.50 (J = 8.8 Hz, 1H), 5.45-5.41 (m, 1H), 4.32 (s, 2H), 3.82-3.80 (m, 1H), 3.02-2.95 (m, 2H), 2.93 (s, 3H), 2.69-2.66 (m, 2H), 1.78 (s, 6H), 1.47 (s, 6H). | Scheme 1, Intermediate 14 and Intermediate 22 |

TABLE 1-continued

| Cpd. # | Structure | LCMS (M + 1) | NMR | Synthetic Protocol |
|---|---|---|---|---|
| 12 | 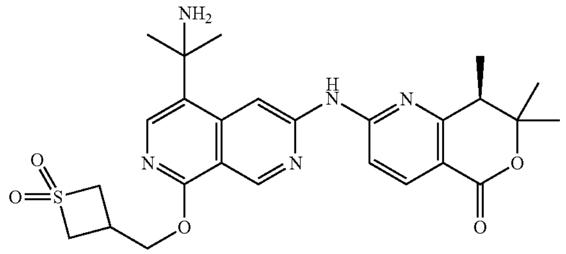 [SMILES: C[C@@H]1c2nc(Nc3cc4c(C(C)(C)N)cnc(OCC5CS(=O)(=O)C5)c4cn3)ccc2C(=O)OC1(C)C] | 526 | $^1$H-NMR (400 MHz, $CDCl_3$): δ ppm 9.39 (s, 2H), 8.23 (d, J = 8.8 Hz, 1H), 8.14 (s, 1H), 8.03 (s, 1H), 7.18 (d, J = 8.8 Hz, 1H), 4.74 (d, J = 6.4 Hz, 2H), 4.39-4.33 (m, 2H), 4.21-4.16 (m, 2H), 3.22-3.17 (m, 1H), 3.02-2.96 (m, 1H), 1.77 (s, 6H), 1.51 (s, 3H), 1.48 (s, 3H), 1.43 (d, J = 7.2 Hz, 3H). | Scheme 1, Intermediate 3 and Intermediate 26 |
| 13 | 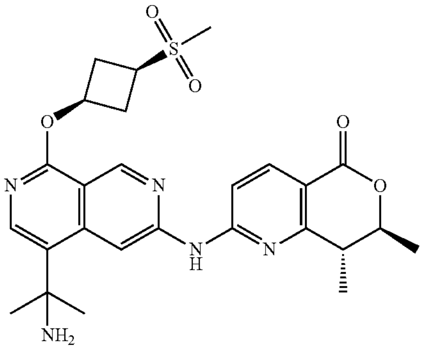 [SMILES: C[C@@H]1OC(=O)c2ccc(Nc3cc4c(C(C)(C)N)cnc(O[C@H]5C[C@@H](S(C)(=O)=O)C5)c4cn3)nc2[C@H]1C] | 526 | $^1$H-NMR (400 MHz, 6d-DMSO): δ ppm 10.69 (s, 1H), 9.44 (s, 1H), 9.32 (s, 1H), 8.15 (s, 1H), 8.08 (d, J = 8.8 Hz, 1H), 7.37 (d, J = 8.8 Hz, 1H), 5.39-5.32 (m, 1H), 4.64-4.57 (m, 1H), 3.89-3.79 (m, 1H), 3.52-3.42 (m, 1H), 3.28 (s, 1H), 3.03-2.97 (m, 1H), 2.94 (s, 3H), 2.90-2.79 (m, 2H), 2.08-1.93 (m, 2H), 1.65 (d, J = 2.0 Hz, 6H), 1.44 (d, J = 7.2 Hz, 3H), 1.38 (d, J = 6.4 Hz, 3H). | Scheme 1, Intermediate 1 and Intermediate 22 |
| 14 | 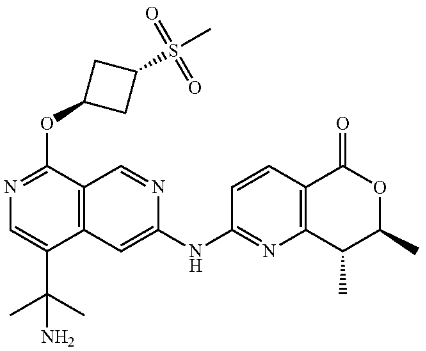 [SMILES: C[C@@H]1OC(=O)c2ccc(Nc3cc4c(C(C)(C)N)cnc(O[C@H]5C[C@H](S(C)(=O)=O)C5)c4cn3)nc2[C@H]1C] | 526 | $^1$H-NMR (400 MHz, 6d-DMSO): 10.7 (s, 1H), 9.45-9.34 (m, 2H), 8.29 (s, 1H), 8.16 (s, 1H), 8.10 (d, J = 8.8 Hz, 1H), 8.09-8.08 (m, 1H), 7.40 (d, J = 8.8 Hz, 1H), 5.52 (m, 1H), 4.62 (m, 1H), 4.11-3.98 (m, 2H), 3.03 (s, 3H), 3.01-2.89 (m, 3H), 2.77-2.66 (m, 2H), 1.68 (m, 6H), 1.45 (d, J = 7.2 Hz, 3H), 1.39 (d, J = 6.4 Hz, 3H). | Scheme 1, Intermediate 1 and Intermediate 27 |
| 15 | 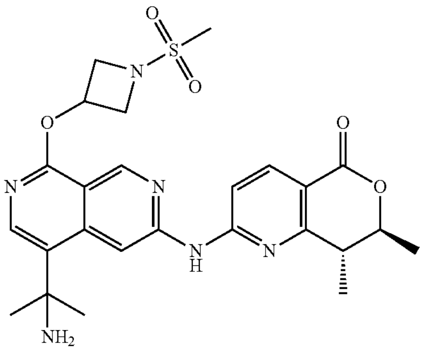 [SMILES: C[C@@H]1OC(=O)c2ccc(Nc3cc4c(C(C)(C)N)cnc(OC5CN(S(C)(=O)=O)C5)c4cn3)nc2[C@H]1C] | 527 | $^1$H-NMR (400 MHz, $CD_3OD$): δ ppm 9.48 (s, 1H), 9.03 (s, 1H), 8.17 (d, J = 8.8 Hz, 1H), 8.04 (s, 1H), 7.38 (d, J = 8.8 Hz, 1H), 5.70-5.57 (m, 1H), 4.72-4.61 (m, 1H), 4.45 (dd, J = 6.8, 10.0 Hz, 2H), 4.19 (dd, J = 4.8, 9.6 Hz, 2H), 3.05 (s, 3H), 3.04-2.98 (m, 1H), 1.98 (d, J = 6.6 Hz, 6H), 1.53 (d, J = 7.2 Hz, 3H), 1.48 (d, J = 6.4 Hz, 3H). | Scheme 1, Intermediate 1 and Intermediate 20 |

TABLE 1-continued

| Cpd. # | Structure | LCMS (M + 1) | NMR | Synthetic Protocol |
|---|---|---|---|---|
| 16 | 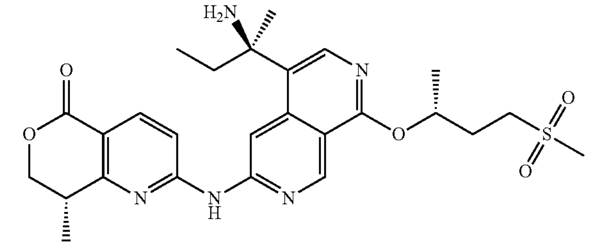 [SMILES: CC[C@@](C)(N)c1cnc(O[C@H](C)CCS(C)(=O)=O)c2cnc(Nc3ccc4c(n3)[C@H](C)COC4=O)cc12]<br>or<br>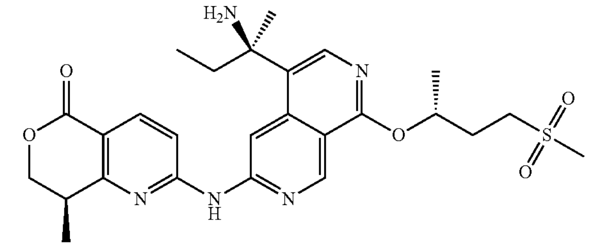 [SMILES: CC[C@@](C)(N)c1cnc(O[C@H](C)CCS(C)(=O)=O)c2cnc(Nc3ccc4c(n3)[C@@H](C)COC4=O)cc12] | 528 | $^1$H-NMR (400 MHz, $CD_3OD$): δ ppm 9.42 (s, 1H), 9.19 (s, 1H), 8.56 (s, 1H), 8.20-8.12 (m, 1H), 8.06 (s, 1H), 7.30-7.24 (m, 1H), 5.75-5.61 (m, 1H), 4.75-4.68 (m, 1H), 4.48-4.40 (m. 1H), 3.44-3.34 (m, 2H), 3.22-3.11 (m, 1H), 3.03 (s, 3H), 2.69-2.55 (m, 1H), 2.44-2.33 (m, 2H), 2.33-2.22 (m, 1H), 1.94 (s, 3H), 1.56-1.51 (m, 3H), 1.50-1.46 (m, 3H), 0.86-0.77 (m, 3H). | Scheme 1, Intermediate 8 and Intermediate 31 2nd eluting isomer from chiral HPLC Column: Phenomenex Ge mini-NX C18 75*30 mm *3 um; Mobile phase: [water (0.225% FA)-ACN]; B%: 10%-40%) |
| 17 | 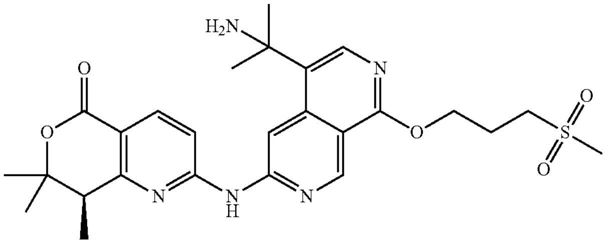 | 528 | $^1$H-NMR (400 MHz, $CD_3OD$): δ ppm 9.41 (s, 1H), 9.34 (s, 1H), 8.17 (s, 1H), 8.13 (d, J = 8.8 Hz, 1H), 7.22 (d, J = 8.8 Hz, 1H), 4.67 (t, J = 6.2 Hz, 2H), 3.46-3.37 (m, 2H), 3.10-2.98 (m, 4H), 2.51-2.34 (m, 2H), 1.82 (d, J = 7.6 Hz, 6H), 1.54 (s, 3H), 1.45 (s, 3H), 1.40 (d, J = 16 Hz, 3H). | Scheme 1, Intermediate 3 and Intermediate 23 |
| 18 | 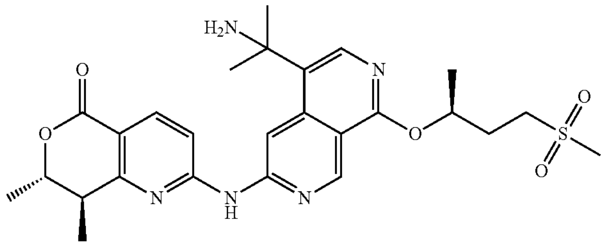<br>or<br>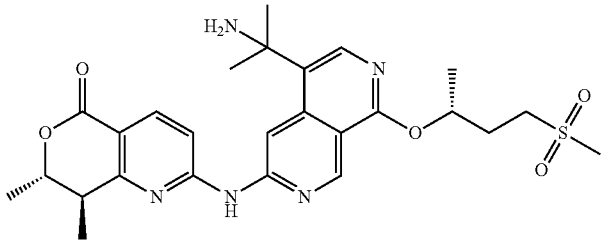 | 528 | $^1$H-NMR (400 MHz, 6d-DMSO): δ ppm 10.64 (s, 1H), 9.38 (s, 1H), 9.35 (s, 1H), 8.18 (s, 1H), 8.08 (d, J = 8.8 Hz, 1H), 7.42 (d, J = 8.4 Hz, 1H), 5.54-5.50 (m, 1H), 4.60 (m, 1H), 3.31 (s, 2H), 3.02-2.93 (m, 4 H), 2.23-2.19 (m, 2H), 2.00 (s, 2H), 1.66 (d, J = 2.0 Hz, 6H), 1.44 (m, 6H), 1.39 (d, J = 6.4 Hz, 3H). | Scheme 1, Intermediate 1 and Intermediate 29 |

TABLE 1-continued

| Cpd. # | Structure | LCMS (M + 1) | NMR | Synthetic Protocol |
|---|---|---|---|---|
| 19 | 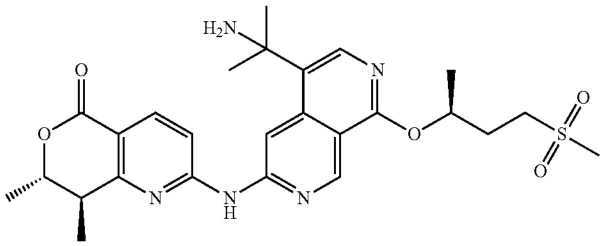<br>or<br>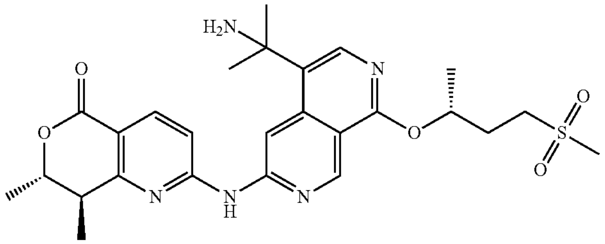 | 528 | $^1$H-NMR (400 MHz, 6d-DMSO): δ ppm 10.64 (s, 1H), 9.36-9.22 (m, 2H), 8.17 (s, 1H), 8.09 (d, J = 8.8 Hz, 1H), 7.43 (d, J = 8.8 Hz, 1H), 5.54-5.49 (m, 1H), 4.60 (m, 1H), 3.32-3.23 (m, 3H), 3.02 (s, 3H), 2.20-2.10 (m, 2H), 2.01 (s, 2H), 1.66 (s, 6H), 1.42-1.45 (m, 6H), 1.38 (d, J = 6.4 Hz, 3H). | Scheme 1, Intermediate 1 and Intermediate 28 |
| 20 | 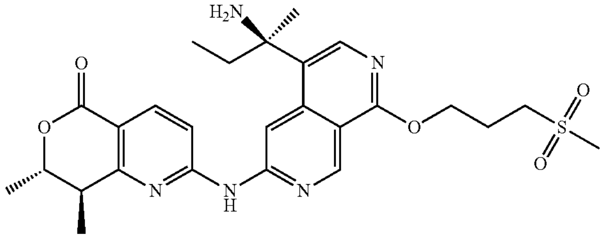 | 528 | $^1$H-NMR (400 MHz, $CD_3OD$): δ ppm 9.47 (s, 1H), 8.94 (s, 1H), 8.17 (d, J = 8.8 Hz, 1H), 8.00 (s, 1H), 7.38 (d, J = 8.8 Hz, 1H), 4.71 (t, J = 6.2 Hz, 2H), 4.68-4.62 (m, 1H), 3.46-3.37 (m, 2H), 3.04 (s, 3H), 3.02-2.95 (m, 1H), 2.62 (m, 1H), 2.51-2.39 (m, 2H), 2.30 (m, 1H), 1.95 (s, 3H), 1.48 (m, 6H), 0.82 (t, J = 7.6 Hz, 3H). | Scheme 1, Intermediate 1 and Intermediate 100 |
| 21 | 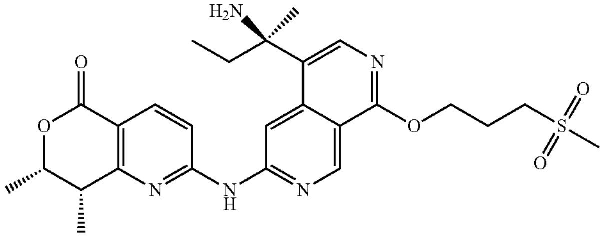<br>or<br>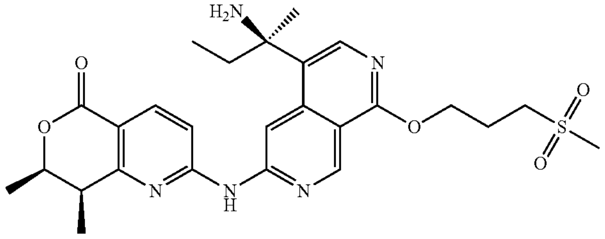 | 528 | $^1$H-NMR (400 MHz, $CD_3OD$): δ ppm 9.44 (s, 1H), 9.32 (s, 1H), 8.51 (s, 1H), 8.15 (d, J = 8.8 Hz, 1H), 8.04 (s, 1H), 7.19 (d, J = 8.8 Hz, 1H), 4.91 (m, 1H), 4.70 (t, J = 6.2 Hz, 2H), 3.45-3.37 (m, 2H), 3.04 (s, 3H), 3.02-2.95 (m, 1H), 2.66-2.55 (m, 1H), 2.48-2.39 (m, 2H), 2.30 (m, 1H), 1.91 (s, 3H), 1.52 (d, J = 6.4 Hz, 3H), 1.32 (d, J = 7.2 Hz, 3H), 0.81 (t, J = 7.4 Hz, 3H). | Scheme 1, Intermediate 93 and Intermediate 100 |
| 22 | 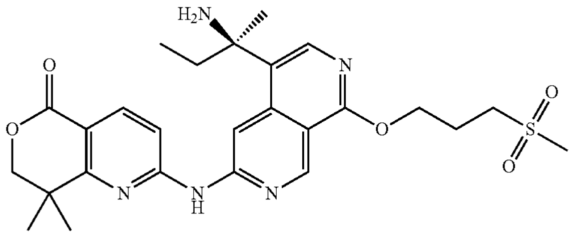 [SMILES: CC[C@@](C)(N)c1cnc(OCCCS(C)(=O)=O)c2cnc(Nc3ccc4c(n3)C(C)(C)COC4=O)cc12] | 528 | $^1$H NMR (400MHz, $CD_3OD$): δ ppm 9.50-9.47 (m, 1H), 8.60-8.50 (m, 1H), 8.35-7.99 (m, 2H), 7.60-7.50 (m, 1H), 4.70-4.62 (m, 2H), 4.40-4.30 (m, 2H), 3.50-3.40 (m, 2H), 3.05-2.95 (m, 3H), 2.55-2.40 (m, 3H), 2.25-2.05 (m, 1H), 1.90-1.78 (m, 3H), 1.52-1.40 (m, 6H), 0.77-0.72 (m, 3H). | Scheme 1, Intermediate 14 and Intermediate 100 |

TABLE 1-continued

| Cpd. # | Structure | LCMS (M + 1) | NMR | Synthetic Protocol |
|---|---|---|---|---|
| 23 | 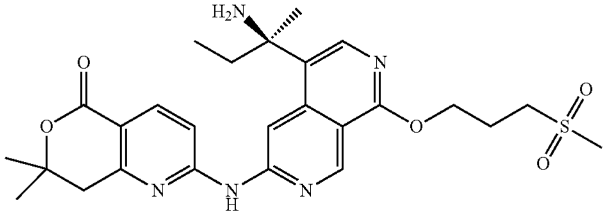 | 528 | $^1$H-NMR (400 MHz, $CD_3OD$): δ ppm 10.68 (s, 1H), 9.42 (s, 1H), 9.38 (s, 1H), 8.35 (s, 1H), 8.16 (s, 1H), 8.08 (d, J = 8.8 Hz, 1H), 7.35 (d, J = 8.8 Hz, 1H), 4.57 (t, J = 6.2 Hz, 2H), 3.43 (s, 2H), 3.15 (s, 2H), 3.04 (s, 3H), 2.35-2.21 (m, 2H), 2.18-1.98 (m, 2H), 1.63 (s, 3H), 1.45 (s, 6H), 0.66 (t, J = 7.4 Hz, 3H). | Scheme 1, Intermediate 5 and Intermediate 100 |
| 24 | 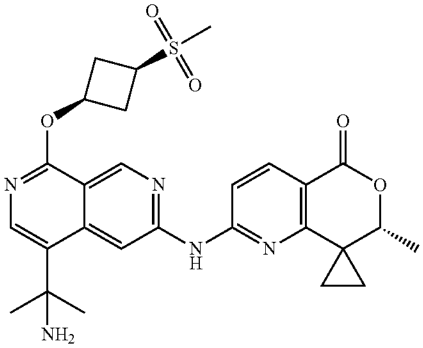 [SMILES: C[C@H]1OC(=O)c2ccc(Nc3cc4c(C(C)(C)N)cnc(O[C@H]5C[C@@H](S(C)(=O)=O)C5)c4cn3)nc2C12CC2]<br>or<br>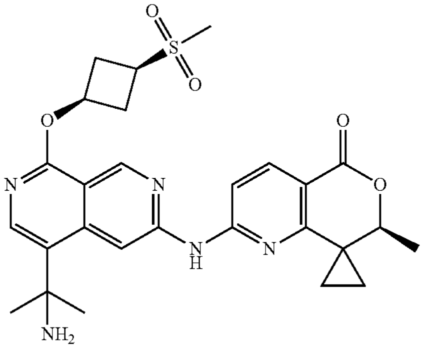 [SMILES: C[C@@H]1OC(=O)c2ccc(Nc3cc4c(C(C)(C)N)cnc(O[C@H]5C[C@@H](S(C)(=O)=O)C5)c4cn3)nc2C12CC2] | 538 | $^1$H NMR (400 MHz, CD3OD): δ ppm 9.43 (s, 1 H), 8.36 (s, 1 H), 8.18 (d, J = 8.8 Hz, 1 H), 8.04 (s, 1 H), 7.59 (d, J = 8.8 Hz, 1 H), 5.50-5.35 (m, 1 H), 4.74-4.58 (m, 1 H), 3.91-3.72 (m, 1 H), 3.02-2.95 (m, 2 H), 2.93 (s, 3 H), 2.74-2.64 (m, 2 H), 1.88 (s, 6 H), 1.63-1.47 (m, 2 H), 1.41-1.35 (m, 3 H), 1.29-1.23 (m, 2 H). | Scheme 1, Intermediate 12 and Intermediate 100 |
| 25 | 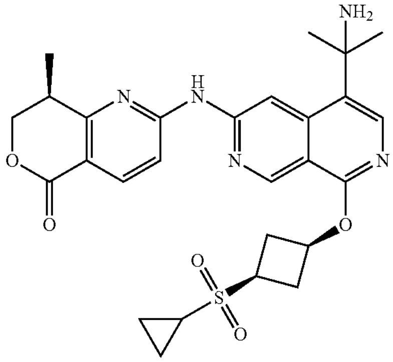 [SMILES: C[C@@H]1COC(=O)c2ccc(Nc3cc4c(C(C)(C)N)cnc(O[C@H]5C[C@@H](S(=O)(=O)C6CC6)C5)c4cn3)nc21]<br>or | 538 | $^1$H-NMR (400 MHz, $CD_3OD$): δ ppm 9.38 (s, 1H), 9.25 (s, 1H), 8.14 (d, J = 8.8 Hz, 1H), 8.10 (s, 1H), 7.23 (d, J = 8.8 Hz, 1H), 5.48-5.40 (m, 1H), 4.72-4.65 (m, 1H), 4.45-4.40 (m, 1H), 3.90-3.82 (m, 1H), 3.20-3.10 (m, 1H), 3.05-2.91 (m, 2H), 2.75-2.62 (m, 2H), 2.60-2.52 (m, 1H), 1.89 (d, J = 7.2 Hz, 6H), 1.48 (d, J = 7.2 Hz, 3H), 1.14-1.07 (m, 4H). | Scheme 1, Intermediate 8 and Intermediate 32 2nd eluting isomer from chiral HPLC Column: Shim-pack C18 150 * 25 * 10 um; Mobile phase: [water (0.225% FA)-ACN]; B %: 12%-42%) |

TABLE 1-continued

| Cpd. # | Structure | LCMS (M + 1) | NMR | Synthetic Protocol |
|---|---|---|---|---|
| | 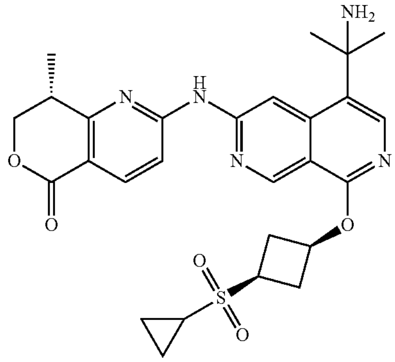 [SMILES: C[C@H]1COC(=O)c2ccc(Nc3cc4c(C(C)(C)N)cnc(O[C@H]5C[C@@H](S(=O)(=O)C6CC6)C5)c4cn3)nc21] | | | |
| 26 | 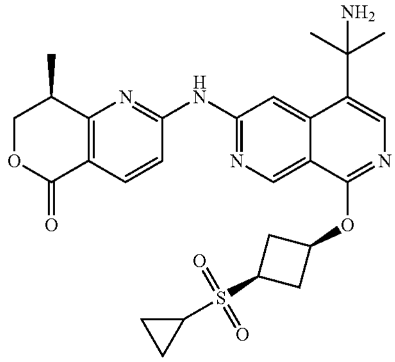 [SMILES: C[C@@H]1COC(=O)c2ccc(Nc3cc4c(C(C)(C)N)cnc(O[C@H]5C[C@@H](S(=O)(=O)C6CC6)C5)c4cn3)nc21]<br>or<br>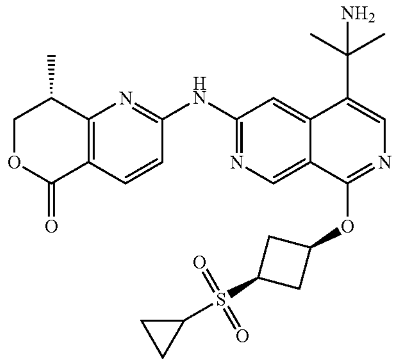 [SMILES: C[C@H]1COC(=O)c2ccc(Nc3cc4c(C(C)(C)N)cnc(O[C@H]5C[C@@H](S(=O)(=O)C6CC6)C5)c4cn3)nc21] | 538 | $^{1}$H-NMR (400 MHz, $CD_3OD$): δ ppm 9.40 (s, 1H), 9.25 (s, 1H), 8.15 (d, J = 8.8 Hz, 1H), 8.08 (s, 1H), 7.25 (d, J = 8.8 Hz, 1H), 5.45-5.40 (m, 1H), 4.72-4.65 (m, 1H), 4.45-4.40 (m, 1H), 3.93-3.89 (m, 1H), 3.25-3.12 (m, 1H), 3.00-2.91 (m, 2H), 2.75-2.63 (m, 2H), 2.60-2.52 (m, 1H), 1.91 (d, J = 7.2 Hz, 6H), 1.48 (d, J = 7.2 Hz, 3H), 1.14-1.07 (m, 4H). | Scheme 1, Intermediate 8 and Intermediate 32 1st eluting isomer from chiral HPLC Column: Shim-pack C18 150 * 25 * 10 um; Mobile phase: [water (0.225% FA)-ACN]; B %: 12%-42%) |
| 27 | 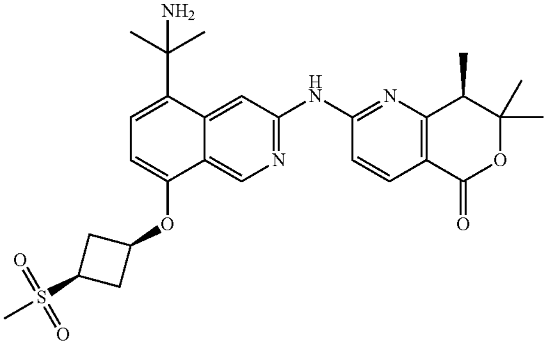 | 539 | $^{1}$H-NMR (400 MHz, CD3OD): δ ppm 9.34 (s, 1H), 9.19 (s, 1H), 8.13 (d, J = 8.8 Hz, 1H), 8.02 (s, 1H), 7.23 (d, J = 8.8 Hz, 1H), 4.68-4.64 (m, 1H), 3.91-3.74 (m, 1H), 3.06-2.98 (m, 1H), 2.92 (s, 3H), 2.89-2.80 (m, 2H), 2.66 (s, 1H), 2.59-2.49 (m, 2H), 1.83 (d, J = 8.4 Hz, 6H), 1.54 (s, 3H), 1.44 (s, 3H), 1.41-1.37 (m, 3H). | Scheme 1, Intermediate 3 and Intermediate 35 |

TABLE 1-continued

| Cpd. # | Structure | LCMS (M + 1) | NMR | Synthetic Protocol |
| --- | --- | --- | --- | --- |
| 28 | 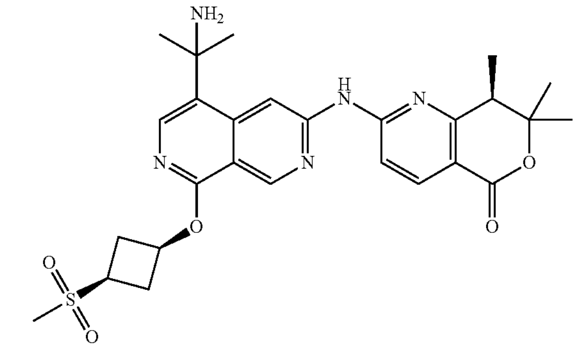 | 539 | $^1$H-NMR (400 MHz, $CD_3OD$): δ ppm 9.34 (s, 1H), 9.19 (s, 1H), 8.13 (d, J = 8.8 Hz, 1H), 8.02 (s, 1H), 7.23 (d, J = 8.8 Hz, 1H), 4.68-4.64 (m, 1H), 3.91-3.74 (m, 1H), 3.06-2.98 (m, 1H), 2.92 (s, 3H), 2.89-2.80 (m, 2H), 2.66 (s, 1H), 2.59-2.49 (m, 2H), 1.83 (d, J = 8.4 Hz, 6H), 1.54 (s, 3H), 1.44 (s, 3H), 1.41-1.37 (m, 3H). | Scheme 1, Intermediate 3 and Intermediate 36 |
| 29 | 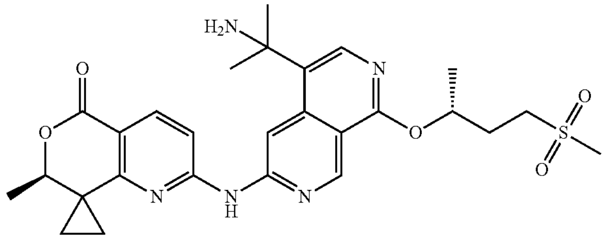<br>or<br>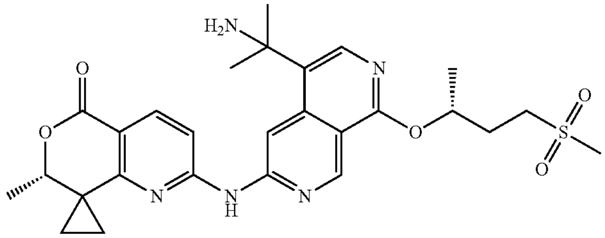 | 540 | $^1$H-NMR (400 MHz, $CD_3OD$): δ ppm 9.39 (s, 1H), 8.53 (s, 1H), 8.17 (s, 1H), 8.14 (d, J = 8.8 Hz, 1H), 7.50 (d, J = 8.8 Hz, 1H), 5.67-5.55 (m, 1H), 4.67-4.57 (m, 1H), 3.41-3.32 (m, 2H), 3.00 (s, 3H), 2.40-2.26 (m, 2H), 1.75 (s, 6H), 1.68-1.61 (m, 1H), 1.57-1.53 (m, 1H), 1.50 (d, J = 6.4 Hz, 3H), 1.37 (d, J = 6.4 Hz, 3H), 1.27-1.16 (m. 2H). | Scheme 1, Intermediate 12 and Intermediate 55 |
| 30 | 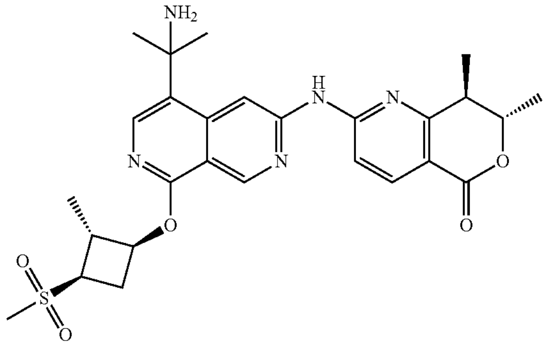<br>or | 540 | $^1$H-NMR (400 MHz, $CD_3OD$): δ ppm 9.42 (s, 1H), 9.02 (s, 1H), 8.17 (d, J = 8.8 Hz, 1H), 8.04 (s, 1H), 7.36 (d, J = 8.8 Hz, 1H), 5.20-5.16 (m, 1H), 4.72-4.64 (m, 1H), 3.50-3.40 (m, 1H), 3.09-2.89 (m, 6H), 2.49-2.41 (m, 1H), 1.96 (d, J = 6.0 Hz, 6H), 1.53-1.43 (m, 9H). | Scheme 1, Intermediate 1 and Intermediate 39 |

TABLE 1-continued
| Cpd. # | Structure | LCMS (M + 1) | NMR | Synthetic Protocol |
|---|---|---|---|---|
| | 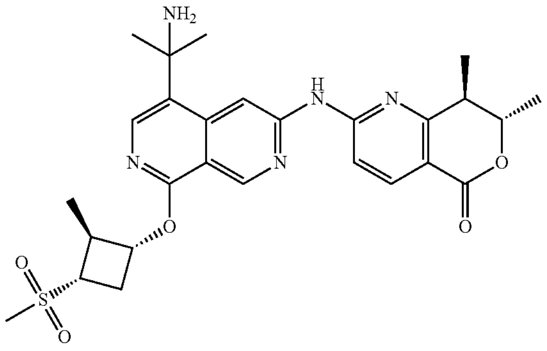 | | | |
| 31 | 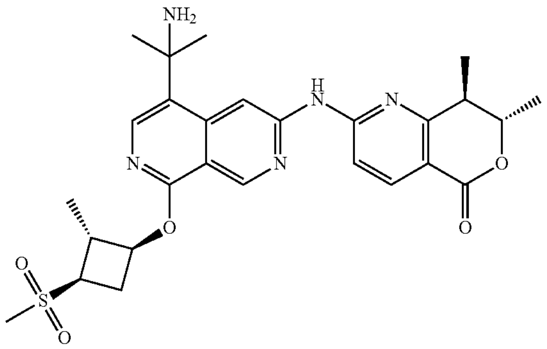 or 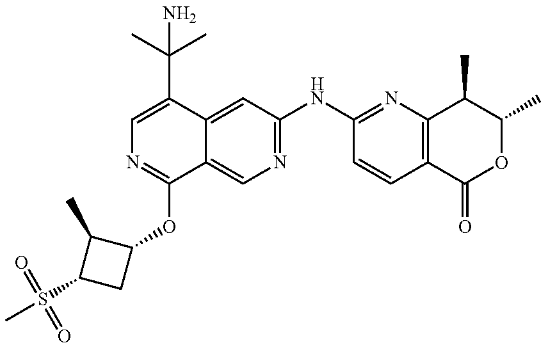 | 540 | $^1$H-NMR (400 MHz, $CD_3OD$): δ ppm 9.38 (s, 1H), 9.06 (s, 1H), 8.14 (d, J = 8.8 Hz, 1H), 8.10 (s, 1H), 7.33 (d, J = 8.8 Hz, 1H), 5.18-5.12 (m, 1H), 4.72-4.64 (m, 1H), 3.48-3.39 (m, 1H), 3.08-2.88 (m, 6H), 2.49-2.36 (m, 1H), 1.88 (d, J = 6.0 Hz, 6H), 1.52-1.41 (m, 9H). | Scheme 1, Intermediate 1 and Intermediate 40 |
| 32 | 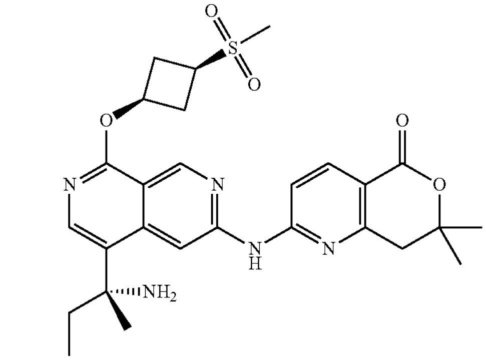 [SMILES: CC[C@@](C)(N)c1cnc(O[C@H]2C[C@@H](S(C)(=O)=O)C2)c2cnc(Nc3ccc4c(n3)CC(C)(C)OC4=O)cc12] | 540 | $^1$H-NMR (400 MHz, $CD_3OD$): δ ppm 9.38 (s, 1H), 9.25 (s, 1H), 8.54 (br s, 1H), 8.14 (d, J = 8.8 Hz, 1H), 8.04 (s, 1H), 7.21 (d, J = 8.6 Hz, 1H), 5.45 (q, J = 7.2 Hz, 1H), 3.83 (q, J = 8.4 Hz, 1H), 3.20 (s, 2H), 3.03-2.95 (m, 2H), 2.93 (s, 3H), 2.75-2.65 (m, 2H), 2.51 (br dd, J = 7.3, 14.4 Hz, 1H), 2.27 (qd, J = 7.2, 14.4 Hz, 1H), 1.88 (s, 3H), 1.53 (s, 6H), 0.80 (br t, J = 7.2 Hz, 3H). | Scheme 1, Intermediate 5 and Intermediate 24 |

TABLE 1-continued

| Cpd. # | Structure | LCMS (M + 1) | NMR | Synthetic Protocol |
|---|---|---|---|---|
| 33 | 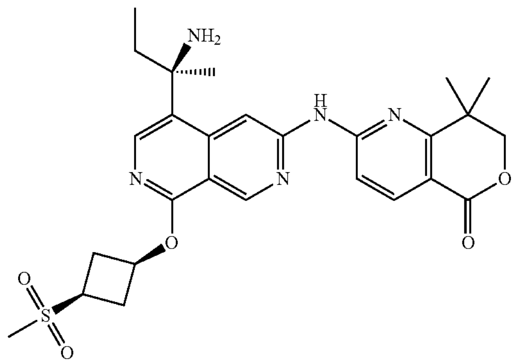 [SMILES: CC[C@@](C)(N)c1cnc(O[C@H]2C[C@@H](S(C)(=O)=O)C2)c2cnc(Nc3ccc4c(n3)C(C)(C)COC4=O)cc12] | 540 | $^1$H-NMR (400 MHz, $CD_3OD$): δ ppm 9.41 (s, 1H), 8.53 (s, 1H), 8.15 (d, J = 8.8 Hz, 1H), 8.06 (s, 1H), 7.58 (d, J = 8.6 Hz, 1H), 5.45 (t, J = 7.2 Hz, 1H), 4.31 (s, 2H), 3.83 (br t, J = 8.4 Hz, 1H), 3.03-2.96 (m, 2H), 2.94 (s, 3H), 2.76-2.64 (m, 2H), 2.49 (br dd, J = 7.4, 14.4 Hz, 1H), 2.17 (qd, J = 7.2, 14.4 Hz, 1H), 1.83 (s, 3H), 1.45 (s, 6H), 0.77 (t, J = 7.4 Hz, 3H). | Scheme 1, Intermediate 14 and Intermediate 24 |
| 34 | 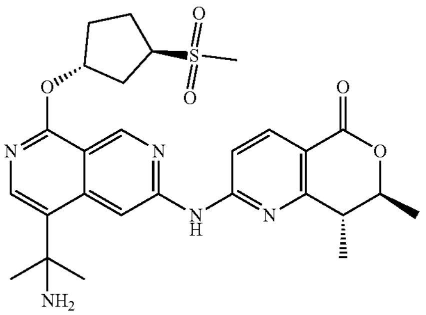 [SMILES: C[C@@H]1OC(=O)c2ccc(Nc3cc4c(C(C)(C)N)cnc(O[C@@H]5CC[C@@H](S(C)(=O)=O)C5)c4cn3)nc2[C@H]1C] or 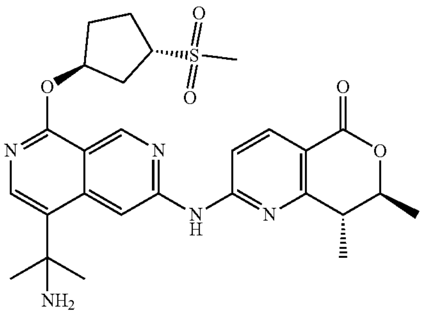 [SMILES: C[C@@H]1OC(=O)c2ccc(Nc3cc4c(C(C)(C)N)cnc(O[C@H]5CC[C@H](S(C)(=O)=O)C5)c4cn3)nc2[C@H]1C] | 540 | $^1$H-NMR (400 MHz, $CD_3OD$): δ ppm 9.34 (s, 1H), 9.19 (s, 1H), 8.20 (s, 1H), 8.13 (d, J = 8.8 Hz, 1H), 7.30 (d, J = 8.8 Hz, 1H), 5.80 (s, 1H), 4.67-4.64 (m, 1H), 3.99-3.95 (m, 1H), 3.02-3.00 (m, 1H), 2.98 (s, 3H), 2.49-2.45 (m, 2H), 2.27-2.22 (m, 4H), 1.77 (d, J = 4.8 Hz, 6H), 1.51 (d, J = 6.4 Hz, 3H), 1.45 (d, J = 6.4 Hz, 3H). | Scheme 1, Intermediate 1 and Intermediate 42 2nd eluting isomer from chiral SFC Column: DAICEL CHIRALPAK AD(250 mm* 30mm, 10 um); Mobile phase: [0.1% NH3H2O IPA]; B %: 40%-40%) |
| 35 | 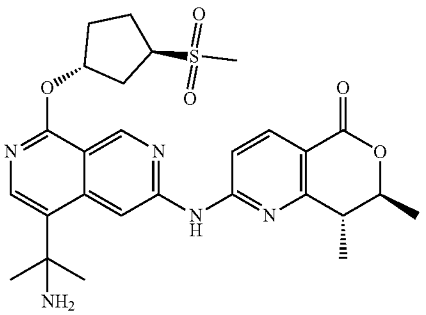 [SMILES: C[C@@H]1OC(=O)c2ccc(Nc3cc4c(C(C)(C)N)cnc(O[C@@H]5CC[C@@H](S(C)(=O)=O)C5)c4cn3)nc2[C@H]1C] or | 540 | $^1$H-NMR (400 MHz, $CD_3OD$): δ ppm 9.39 (s, 1H), 9.04 (s, 1H), 8.51 (s, 1H), 8.17 (d, J = 8.8 Hz, 1H), 8.07 (s, 1H), 7.34 (d, J = 8.8 Hz, 1H), 5.82 (s, 1H), 4.70-4.60 (m, 1H), 4.02-3.92 (m, 1H), 3.04-3.00 (m, 1H), 2.98 (s, 3H), 2.50-2.47 (m, 2H), 2.40-2.15 (m, 4H), 1.91 (d, J = 6.8 Hz, 6H), 1.51 (d, J = 7.2 Hz, 3H), 1.45 (d, J = 6.8 Hz, 3H). | Scheme 1, Intermediate 1 and Intermediate 42 1st eluting isomer from chiral SFC Column: DAICEL CHIRALPAK AD(250 mm* 30mm, 10 um); Mobile phase: [0.1% NH3H2O IPA]; B %: 40%-40%) |

TABLE 1-continued
| Cpd. # | Structure | LCMS (M + 1) | NMR | Synthetic Protocol |
|---|---|---|---|---|
| | 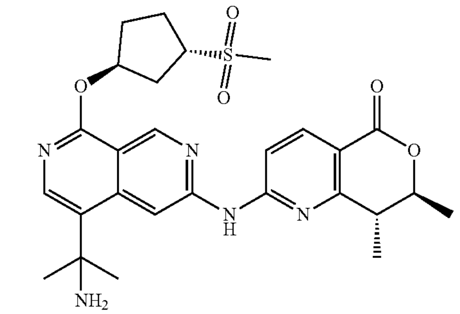 [SMILES: C[C@@H]1OC(=O)c2ccc(Nc3cc4c(C(C)(C)N)cnc(O[C@H]5CC[C@H](S(C)(=O)=O)C5)c4cn3)nc2[C@H]1C] | | | |
| 36 | 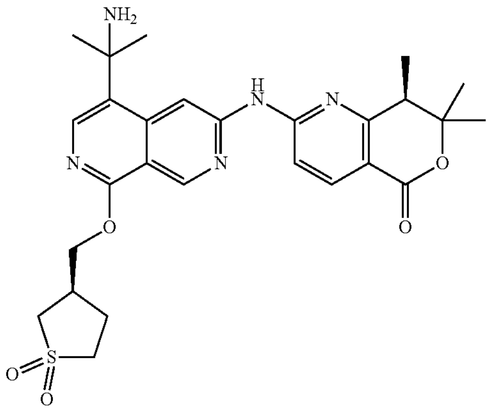 [SMILES: C[C@@H]1c2nc(Nc3cc4c(C(C)(C)N)cnc(OC[C@H]5CCS(=O)(=O)C5)c4cn3)ccc2C(=O)OC1(C)C] or 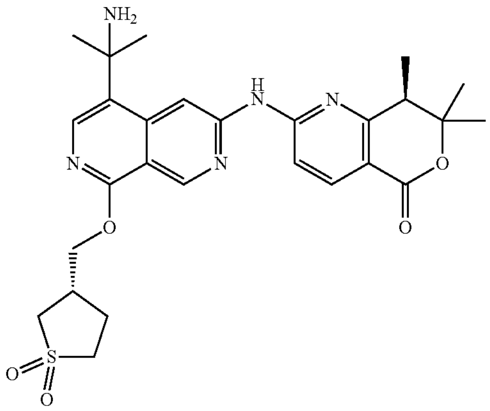 [SMILES: C[C@@H]1c2nc(Nc3cc4c(C(C)(C)N)cnc(OC[C@@H]5CCS(=O)(=O)C5)c4cn3)ccc2C(=O)OC1(C)C] | 540 | $^1$H-NMR (400 MHz, $CD_3OD$): δ ppm 9.43 (s, 1H), 9.40 (s, 1H), 8.21 (s, 1H), 8.15 (d, J = 8.8 Hz, 1H), 7.24 (d, J = 8.8 Hz, 1H), 4.67-4.61 (m, 2H), 3.48-3.41 (m, 1H), 3.31-3.27 (m, 1H), 3.24-3.18 (m, 1H), 3.17-3.12 (m, 2H), 3.08-3.03 (m, 1H), 2.58-2.47 (m, 1H), 2.27-2.15 (m, 1H), 1.82 (d, J = 7.2 Hz, 6H), 1.56 (s, 3H), 1.47 (s, 3H), 1.42 (d, J = 7.2 Hz, 3H). | Scheme 1, Intermediate 3 and Intermediate 43 2nd eluting isomer from chiral SFC Column: Phenomenex-Cellulose-2(250 mm*30 mm, 10 um); Mobile phase: [0.1% NH3H2O MEOH]; B %: 50%-50%) |

TABLE 1-continued

| Cpd. # | Structure | LCMS (M + 1) | NMR | Synthetic Protocol |
| --- | --- | --- | --- | --- |
| 37 | 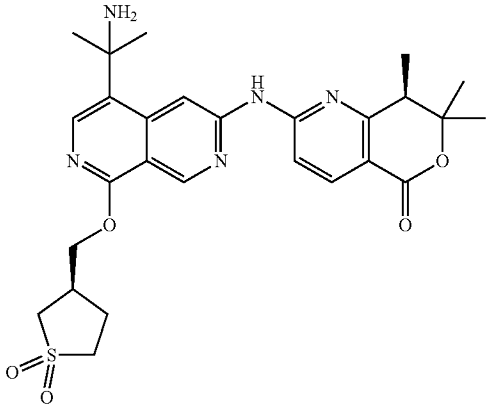 [SMILES: C[C@@H]1c2nc(Nc3cc4c(C(C)(C)N)cnc(OC[C@H]5CCS(=O)(=O)C5)c4cn3)ccc2C(=O)OC1(C)C] or 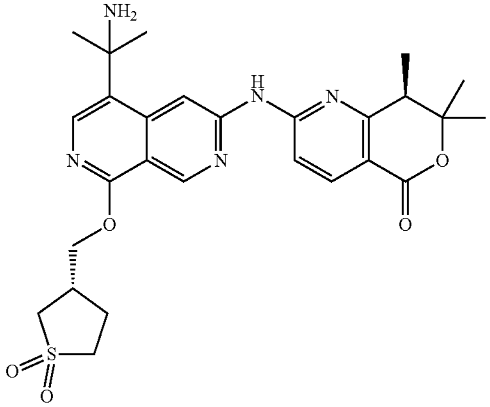 [SMILES: C[C@@H]1c2nc(Nc3cc4c(C(C)(C)N)cnc(OC[C@@H]5CCS(=O)(=O)C5)c4cn3)ccc2C(=O)OC1(C)C] | 540 | $^1$H-NMR (400 MHz, $CD_3OD$): δ ppm 9.43 (s, 1H), 9.40 (s, 1H), 8.21 (s, 1H), 8.15 (d, J = 8.8 Hz, 1H), 7.24 (d, J = 8.8 Hz, 1H), 4.68-4.59 (m, 2H), 3.46-3.38 (m, 1H), 3.32-3.27 (m, 1H), 3.24-3.17 (m, 1H), 3.17-3.10 (m, 2H), 3.09-3.03 (m, 1H), 2.57-2.48 (m, 1H), 2.27-2.15 (m, 1H), 1.82 (d, J = 7.2 Hz, 6H), 1.56 (s, 3H), 1.47 (s, 3H), 1.42 (d, J = 7.2 Hz, 3H). | Scheme 1, Intermediate 3 and Intermediate 43 1st eluting isomer from chiral SFC Column: Phenomenex-Cellulose-2(250 mm*30 mm, 10 um); Mobile phase: [0.1% NH3H2O MEOH]; B %: 50%-50%) |
| 38 | 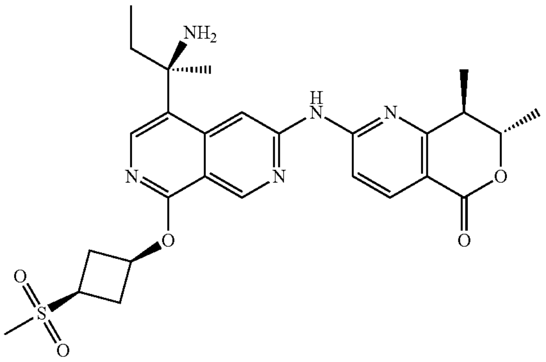 | 540 | $^1$H-NMR (400 MHz, $CD_3OD$): δ ppm 9.39 (s, 1H), 9.08 (d, J = 7.6 Hz, 1H), 8.15 (d, J = 8.8 Hz, 1H), 8.07 (s, 1H), 7.32 (d, J = 8.4 Hz, 1H), 5.48-5.41 (m, 1H), 4.70-4.64 (m, 1H), 3.87-3.79 (m, 1H), 3.03-2.95 (m, 3H), 2.93 (s, 3H), 2.72-2.66 (m, 2H), 2.52-2.46 (m, 1H), 2.26-2.15 (m, 1H), 1.83 (d, J = 12.8 Hz, 3H), 1.51-1.49 (m, 3H), 1.47-1.45 (m, 3H), 0.78-0.75 (m, 3H). | Scheme 1, Intermediate 1 and Intermediate 24 |
| 39 | 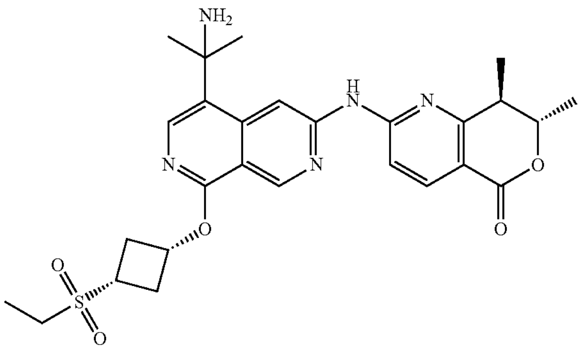 [SMILES: CCS(=O)(=O)[C@H]1C[C@@H](Oc2ncc(C(C)(C)N)c3cc(Nc4ccc5c(n4)[C@@H](C)[C@H](C)OC5=O)ncc23)C1] | 540 | $^1$H-NMR (400 MHz, d6-DMSO): δ ppm 10.70 (s, 1H), 9.42 (s, 1H), 9.32 (s, 1H), 8.14 (s, 1H), 8.08 (d, J = 8.63 Hz, 1H) 7.37 (d, J = 8.8 Hz, 1H), 5.42-5.30 (m, 1H), 4.67-4.49 (m, 1H), 3.99-3.77 (m, 1H), 3.10-3.04 (m, 2H), 3.02-2.95 (m, 1H), 2.89-2.82 (m, 2H), 2.57-2.53 (m, 1H), 1.65 (d, J = 2.4 Hz, 6H), 1.44 (d, J = 7.2 Hz, 3H), 1.37 (d, J = 6.4 Hz, 3H), 1.21 (t, J = 7.4 Hz, 3H). | Scheme 1, Intermediate 1 and Intermediate 44 |

TABLE 1-continued

| Cpd. # | Structure | LCMS (M + 1) | NMR | Synthetic Protocol |
|---|---|---|---|---|
| 40 | 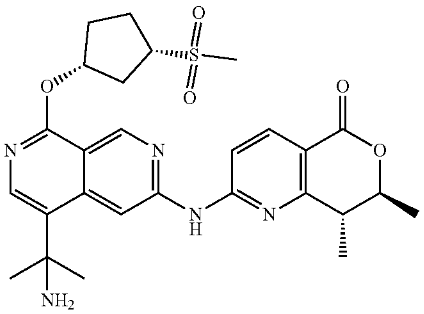 [SMILES: C[C@@H]1OC(=O)c2ccc(Nc3cc4c(C(C)(C)N)cnc(O[C@@H]5CC[C@H](S(C)(=O)=O)C5)c4cn3)nc2[C@H]1C]<br>or<br>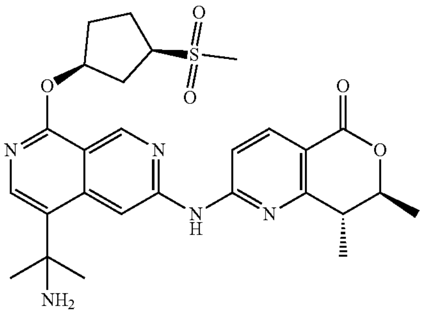 [SMILES: C[C@@H]1OC(=O)c2ccc(Nc3cc4c(C(C)(C)N)cnc(O[C@H]5CC[C@@H](S(C)(=O)=O)C5)c4cn3)nc2[C@H]1C] | 540 | $^{1}$H-NMR (400 MHz, $CD_3OD$): δ ppm 9.31 (s, 1H), 9.07 (s, 1H), 8.09 (s, 1H), 8.04 (d, J = 8.4 Hz, 1H), 7.21 (d, J = 8.8 Hz, 1H), 5.62-5.06 (m, 1H), 4.60-4.50 (m, 1H), 3.75-3.70 (m, 1H), 3.00-2.95 (m, 1H), 2.87 (s, 3H), 2.60-2.50 (m, 1H), 2.40-2.30 (m, 2H), 2.35-2.20 (m, 2H), 2.20-1.90 (m, 1H), 1.70 (d, J = 4.4 Hz, 6H), 1.41 (d, J = 7.2 Hz, 3H), 1.36 (d, J = 6.8 Hz, 3H). | Scheme 1, Intermediate 1 and Intermediate 41, 2nd eluting isomer from Chiral SFC Column: DAICEL CHIRALPAK AD(250 mm* 30 mm, 10 um); Mobile phase: [0.1% NH3H2O MEOH]; B %: 50%-50%) |
| 41 | 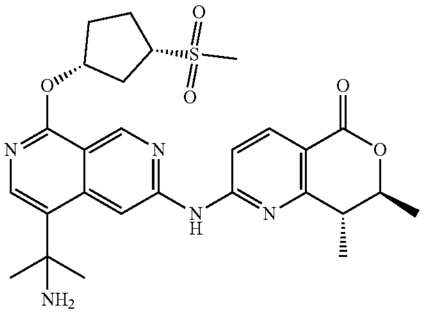 [SMILES: C[C@@H]1OC(=O)c2ccc(Nc3cc4c(C(C)(C)N)cnc(O[C@@H]5CC[C@H](S(C)(=O)=O)C5)c4cn3)nc2[C@H]1C]<br>or<br>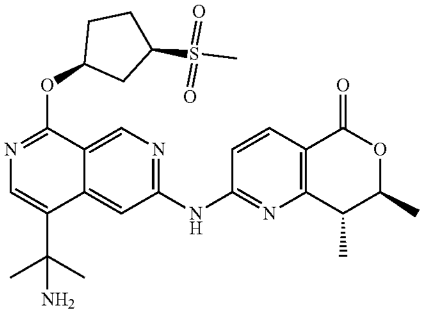 [SMILES: C[C@@H]1OC(=O)c2ccc(Nc3cc4c(C(C)(C)N)cnc(O[C@H]5CC[C@@H](S(C)(=O)=O)C5)c4cn3)nc2[C@H]1C] | 540 | $^{1}$H-NMR (400 MHz, $CD_3OD$): δ ppm 9.31 (s, 1H), 9.07 (s, 1H), 8.09 (s, 1H), 8.04 (d, J = 8.4 Hz, 1H), 7.21 (d, J = 8.8 Hz, 1H), 5.62-5.06 (m, 1H), 4.60-4.50 (m, 1H), 3.75-3.70 (m, 1H), 3.00-2.95 (m, 1H), 2.87 (s, 3H), 2.60-2.50 (m, 1H), 2.40-2.30 (m, 2H), 2.35-2.20 (m, 2H), 2.20-1.90 (m, 1H), 1.70 (d, J = 4.4 Hz, 6H), 1.41 (d, J = 7.2 Hz, 3H), 1.36 (d, J = 6.8 Hz, 3H). | Scheme 1, Intermediate 1 and Intermediate 41, 1st eluting isomer from Chiral SFC Column: DAICEL CHIRALPAK AD(250 mm* 30 mm, 10 um); Mobile phase: [0.1% NH3H2O MEOH]; B %: 50%-50%) |

TABLE 1-continued

| Cpd. # | Structure | LCMS (M + 1) | NMR | Synthetic Protocol |
|---|---|---|---|---|
| 42 | 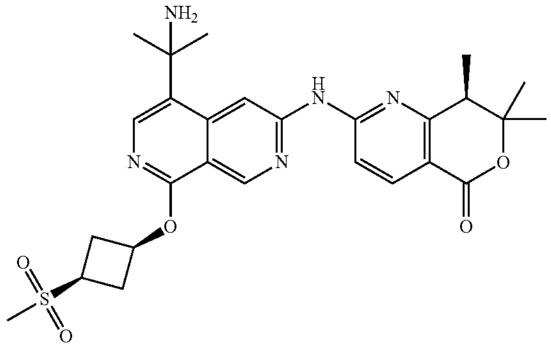 | 540 | $^1$H-NMR (400 MHz, $CD_3OD$): δ ppm 9.39 (s, 1H), 9.21 (s, 1H), 8.54 (s, 1H), 8.14 (d, J = 8.8 Hz, 1H), 8.07-8.03 (m, 1H), 7.25 (d, J = 8.8 Hz, 1H), 5.51-5.36 (m, 1H), 3.92-3.75 (m, 1H), 3.05-2.95 (m, 3H), 2.93 (s, 3H), 2.76-2.63 (m, 2H), 1.94 (d, J = 11.2 Hz, 6H), 1.53 (s, 3H), 1.45 (s, 3H), 1.40 (d, J = 7.2 Hz, 3H). | Scheme 1, Intermediate 3 and Intermediate 22 |
| 43 | 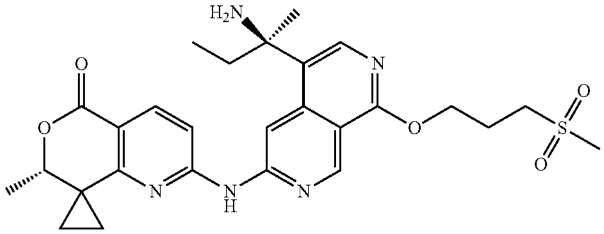 or 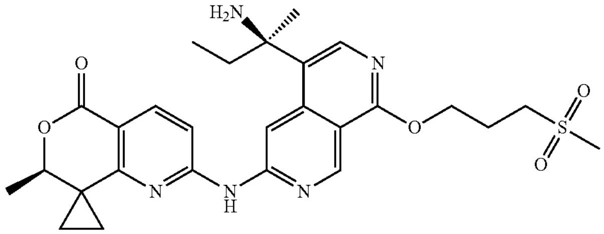 | 540 | $^1$H-NMR (400 MHz, $CD_3OD$): δ ppm 9.47 (s, 1H), 8.52 (s, 1H), 8.26 (s, 1H), 8.17 (d, J = 8.8 Hz, 1H), 8.02 (s, 1H), 7.64 (d, J = 8.8 Hz, 1H), 4.69 (t, J = 6.2 Hz, 2H), 4.67-4.61 (m, 1H), 3.46-3.38 (m, 2H), 3.04 (s, 3H), 2.51-2.39 (m, 3H), 2.20 (m, 1H), 1.85 (s, 3H), 1.64-1.56 (m, 1H), 1.53-1.44 (m, 1H), 1.38 (d, J = 6.4 Hz, 3H), 1.28-1.17 (m, 2H), 0.80 (t, J = 7.4 Hz, 3H). | Scheme 1, Intermediate 12 and Intermediate 100 |
| 44 | 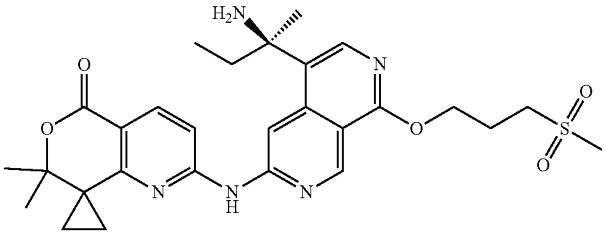 | 554 | $^1$H-NMR (400 MHz, $CD_3OD$): δ ppm 9.49 (s, 1H), 8.50 (s, 1H), 8.18 (d, J = 8.8 Hz, 1H), 8.14 (s, 1H), 7.98 (s, 1H),7.71 (d, J = 8.4 Hz, 1H), 4.70 (t, J = 6.0 Hz, 2H), 3.46-3.38 (m, 2H), 3.04 (s, 3H), 2.57-2.38 (m, 3H), 2.28-2.16 (m, 1H), 1.89 (s, 3H), 1.52 (s, 2H), 1.42 (s, 6H), 1.29 (s, 2H), 0.81 (t, J = 7.0 Hz, 3H). | Scheme 1, Intermediate 15 and Intermediate 100 |
| 45 | 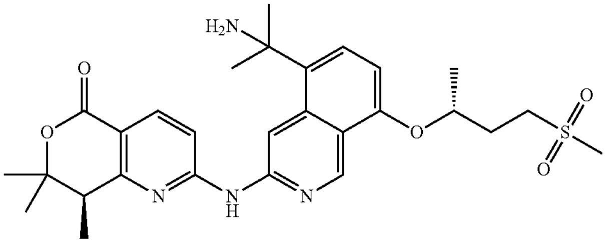 or | 541 | $^1$H-NMR (400 MHz, $CD_3OD$): δ ppm 9.38 (s, 2H), 8.08 (d, J = 8.4 Hz, 1H), 7.73 (d, J = 8.0 Hz, 1H), 7.14 (d, J = 8.8 Hz, 1H), 6.87 (d, J = 8.8 Hz, 1H), 4.95-4.90 (m, 2H), 3.45-3.35 (m, 1H), 3.06-3.01 (m, 1H), 3.00 (s, 3H), 2.40-2.28 (m, 2H), 1.82 (d, J = 8.0 Hz, 6H), 1.54 (s, 3H), 1.48 (d, J = 6.0 Hz, 3H), 1.44 (s, 3H), 1.37 (d, J = 7.2 Hz, 3H). | Scheme 1, Intermediate 3 and Intermediate 34 2nd eluting isomer from chiral SFC Column: Chiralpak AD-3 50 × 4.6 mm I.D., 3 um; Mobile phase |

TABLE 1-continued

| Cpd. # | Structure | LCMS (M + 1) | NMR | Synthetic Protocol |
|---|---|---|---|---|
| | 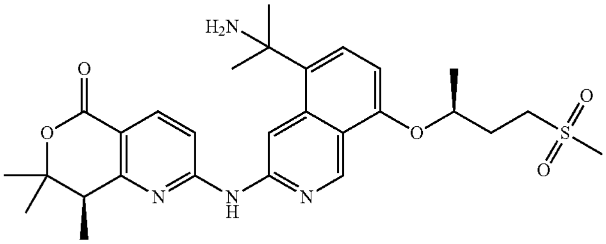 | | | 40% IPA (0.05% DEA) in CO2 |
| 46 | 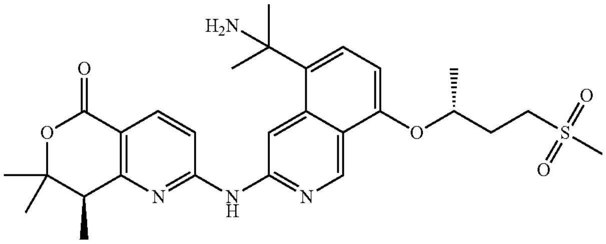 or 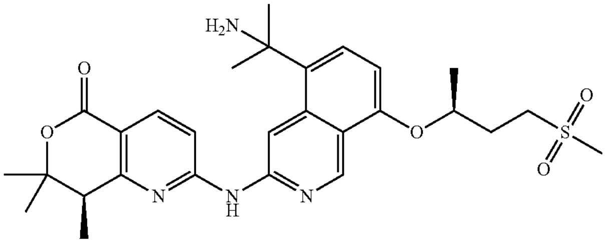 | 541.2 | $^1$H-NMR (400 MHz, $CD_3OD$): δ ppm 9.40 (s, 2H), 8.07 (d, J = 8.8 Hz, 1H), 7.73 (d, J = 8.0 Hz, 1H), 7.14 (d, J = 8.8 Hz, 1H), 6.87 (d, J = 8.4 Hz, 1H), 4.95-4.90 (m, 2H), 3.45-3.35 (m, 1H), 3.06-3.01 (m, 1H), 3.00 (s, 3H), 2.36-2.29 (m, 2H), 1.82 (d, J = 9.8 Hz, 6H), 1.54 (s, 3H), 1.48 (d, J = 6.0 Hz, 3H), 1.44 (s, 3H), 1.37 (d, J = 7.2 Hz, 3H). | Scheme 1, Intermediate 3 and Intermediate 34 1st eluting isomer from chiral SFC Column: Chiralpak AD-3 50 × 4.6 mm I.D., 3 um; Mobile phase 40% IPA (0.05% DEA) in CO2 |
| 47 | 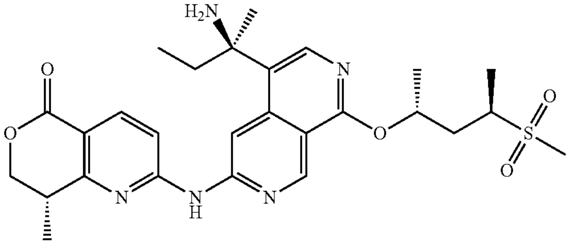 [SMILES: CC[C@@](C)(N)c1cnc(O[C@H](C)C[C@@H](C)S(C)(=O)=O)c2cnc(Nc3ccc4c(n3)[C@H](C)COC4=O)cc12] Or 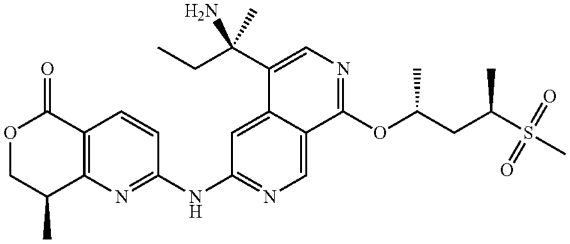 [SMILES: CC[C@@](C)(N)c1cnc(O[C@H](C)C[C@@H](C)S(C)(=O)=O)c2cnc(Nc3ccc4c(n3)[C@@H](C)COC4=O)cc12] | 542 | $^1$H-NMR (400 MHz, $CD_3OD$): δ ppm 9.44 (s, 1H), 9.13 (s, 1H), 8.17 (d, J = 8.8 Hz, 1H), 7.98 (s, 1H), 7.30 (d, J = 8.4 Hz, 1H), 5.76-5.71 (m, 1H), 4.74-4.70 (m, 1H), 4.47-4.43 (m, 1H), 3.41-3.36 (m, 1H), 3.19-3.15 (m, 1H), 2.94 (s, 3H), 2.79-2.74 (m, 1H), 2.46-2.36 (m, 2H), 2.22-2.11 (m, 1H), 2.04 (s, 3H), 1.52-1.47 (m, 9H), 0.86-0.82 (m, 3H). | Scheme 1, Intermediate 8 and Intermediate 53 2nd eluting isomer from chiral SFC Column: DAICEL CHIRALCEL OJ-H (250 mm* 30 mm, 5 um); Mobile phase: [0.1% NH3H2O MEOH]; B %: 20%-20%) |

TABLE 1-continued

| Cpd. # | Structure | LCMS (M + 1) | NMR | Synthetic Protocol |
|---|---|---|---|---|
| 48 | 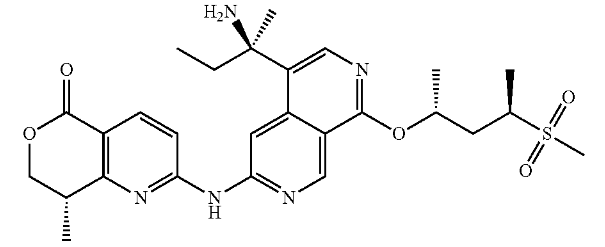 [SMILES: CC[C@@](C)(N)c1cnc(O[C@H](C)C[C@@H](C)S(C)(=O)=O)c2cnc(Nc3ccc4c(n3)[C@H](C)COC4=O)cc12]<br>or<br>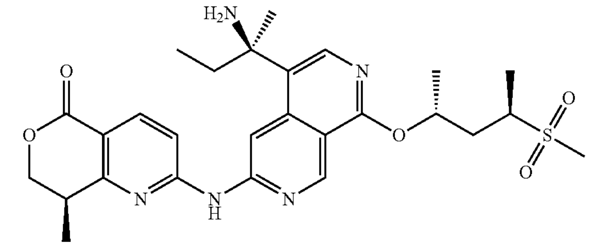 [SMILES: CC[C@@](C)(N)c1cnc(O[C@H](C)C[C@@H](C)S(C)(=O)=O)c2cnc(Nc3ccc4c(n3)[C@@H](C)COC4=O)cc12] | 542 | $^1$H-NMR (400 MHz, $CD_3OD$): δ ppm 9.38 (s, 1H), 9.26 (s, 1H), 8.16-8.14 (m, 2H), 7.23 (d, J = 8.8 Hz, 1H), 5.72-5.67 (m, 1H), 4.71-4.68 (m, 1H), 4.45-4.41 (m, 1H), 3.39-3.34 (m, 1H), 3.18-3.14 (m, 1H), 2.93 (s, 3H), 2.54-2.39 (m, 2H), 2.19-2.09 (m, 2H), 1.81 (s, 3H), 1.51-1.48 (m, 9H), 0.77-0.73 (m, 3H). | Scheme 1, Intermediate 8 and Intermediate 53 1st eluting isomer from chiral SFC Column: DAICEL CHIRALCEL OJ-H (250 mm* 30 mm, 5 um); Mobile phase: [0.1% NH3H2O MEOH]; B %: 20%-20% |
| 49 | 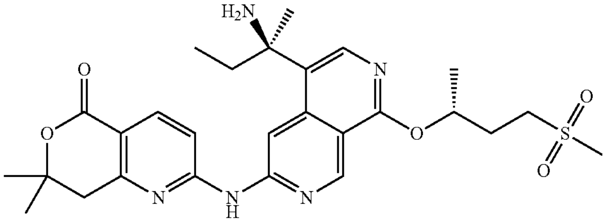 | 542 | $^1$H-NMR (400 MHz, $CD_3OD$): δ ppm 9.39 (s, 1H), 9.25 (s, 1H), 8.13 (d, J = 8.8 Hz, 1H), 8.07 (s, 1H), 7.20 (d, J = 8.8 Hz, 1H), 5.68-5.59 (m, 1H), 3.43-3.32 (m, 2H), 3.19 (s, 2H), 3.01 (s, 3H), 2.55-2.44 (m, 1H), 2.40-2.30 (m, 2H), 2.30-2.21 (m, 1H), 1.86 (s, 3H), 1.55-1.48 (m, 9H), 0.79 (t, J = 7.4 Hz, 3H). | Scheme 1, Intermediate 5 and Intermediate 31 |
| 50 | 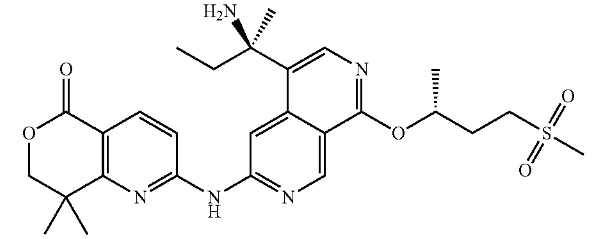 [SMILES: CC[C@@](C)(N)c1cnc(O[C@H](C)CCS(C)(=O)=O)c2cnc(Nc3ccc4c(n3)C(C)(C)COC4=O)cc12] | 542 | $^1$H-NMR (400 MHz, $CD_3OD$): δ ppm 9.46 (s, 1H), 8.44 (s, 1H), 8.17 (d, J = 8.8 Hz, 1H), 8.02 (s, 1H), 7.63 (d, J = 8.8 Hz, 1H), 5.69-5.60 (m, 1H), 4.38-4.25 (m, 2H), 3.43-3.32 (m, 2H), 3.01 (s, 3H), 2.64-2.52 (m, 1H), 2.41-2.29 (m, 2H), 2.26-2.16 (m, 1H), 1.89 (s, 3H), 1.52 (d, J = 6.2 Hz, 3H), 1.45 (s, 6H), 0.79 (t, J = 7.4 Hz, 3H). | Scheme 1, Intermediate 14 and Intermediate 31 |
| 51 | 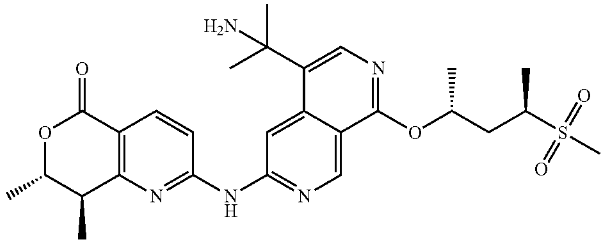 | 542 | $^1$H-NMR (400 MHz, $CD_3OD$): δ ppm 9.43 (s, 1H), 8.99 (s, 1H), 8.52 (s, 1H), 8.18 (d, J = 8.8 Hz, 1H), 8.04 (s, 1H), 7.38 (d, J = 8.4 Hz, 1H), 5.74-5.71 (m, 1H), 4.70-4.64 (m, 1H), 3.40-3.35 (m, 1H), 3.05-3.01 (m, 1H), 2.94 (s, 3H), 2.46-2.35 (m, 1H), 2.20-2.11 (m, 1H), 1.99 (d, J = 5.2 Hz, 6H), 1.52-1.46 (m, 12H). | Scheme 1, Intermediate 1 and Intermediate 52 |
| 52 | 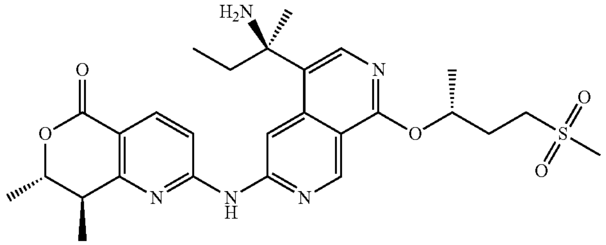 | 542 | $^1$H-NMR (400 MHz, $CD_3OD$): δ ppm 9.40 (s, 1H), 9.14 (s, 1H), 8.20-8.11 (m, 2H), 7.31 (d, J = 8.8 Hz, 1H), 5.71-5.53 (m, 1H), 4.73-4.63 (m, 1H), 3.42-3.32 (m, 2H), 3.07-2.97 (m, 4H), 2.50-2.39 (m, 1H), 2.37-2.29 (m, 2H), 2.24-2.11 (m, 1H), 1.78 (s, 3H), 1.54-1.48 (m, 6H), 1.46 (d, J = 6.8 Hz, 3H), 0.75 (t, J = 7.4 Hz, 3H). | Scheme 1, Intermediate 1 and Intermediate 31 |

TABLE 1-continued

| Cpd. # | Structure | LCMS (M + 1) | NMR | Synthetic Protocol |
| --- | --- | --- | --- | --- |
| 53 | 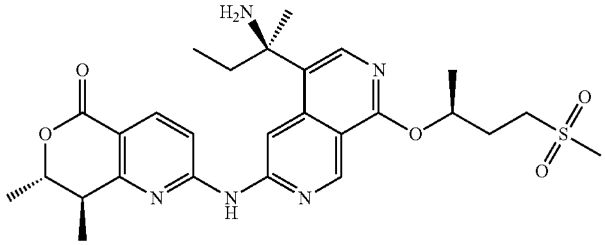 | 542 | $^1$H-NMR (400 MHz, $CD_3OD$): δ ppm 9.41 (s, 1H), 9.09 (s, 1H), 8.15 (d, J = 8.8 Hz, 1H), 8.10 (s, 1H), 7.32 (d, J = 8.8 Hz, 1H), 5.68-5.58 (m, 1H), 4.75-4.63 (m, 1H), 3.41-3.32 (m, 2H), 3.04-2.98 (m, 4H), 2.53-2.42 (m, 1H), 2.39-2.29 (m. 2H), 2.27-2.15 (m, 1H), 1.82 (s, 3H), 1.50 (t, J = 6.6 Hz, 6H), 1.46 (d, J = 6.8 Hz, 3H), 0.77 (t, J = 7.4 Hz, 3H). | Scheme 1, Intermediate 1 and Intermediate 54 |
| 54 | 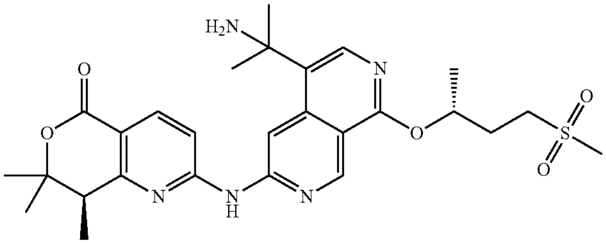<br>or<br>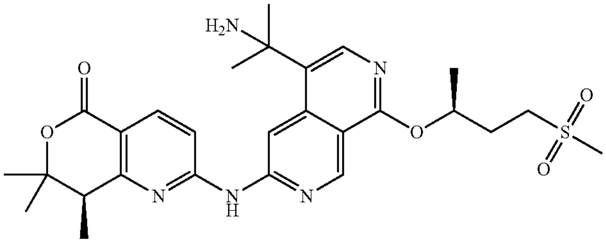 | 542 | $^1$H-NMR (400 MHz, $CD_3OD$): δ ppm 9.44 (s, 1H), 9.23 (s, 1H), 8.17 (d, J = 8.8 Hz, 1H), 8.10 (s, 1H), 7.28 (d, J = 8.8 Hz, 1H), 5.69-5.65 (m, 1H), 3.40-3.34 (m, 2H), 3.07-3.04 (m, 1H), 3.02 (s, 3H), 2.38-2.33 (m, 2H), 2.06-1.97 (s, 6H), 1.56 (s, 3H), 1.54 (s, 3H), 1.47 (s, 3H), 1.43 (d, J = 7.2 Hz, 3H). | Scheme 1, Intermediate 3 and Intermediate 28 |
| 55 | 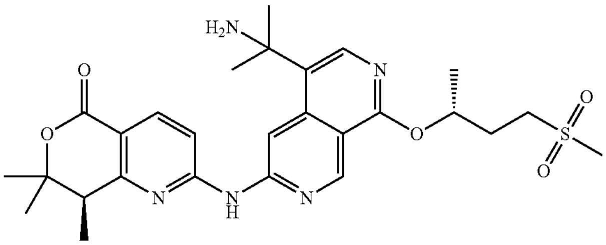<br>or<br>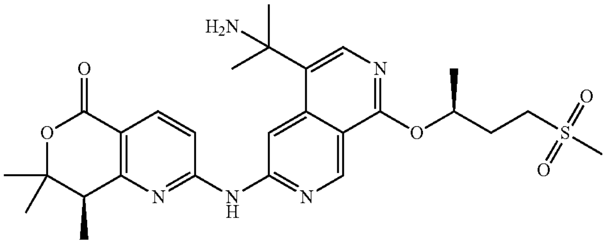 | 542 | $^1$H-NMR (400 MHz, $CD_3OD$): δ ppm 9.41 (m, 1H), 9.38 (s, 1H), 8.22 (s, 1H), 8.15 (d, J = 8.8 Hz, 1H), 7.24 (d, J = 8.80 Hz, 1H), 5.67-5.60 (m, 1H), 3.39-3.35 (m, 2H), 3.07 (m, 1H), 3.02 (s, 3H), 2.38-2.34 (m, 2H), 1.82 (d, J = 6.8 Hz, 6H), 1.56 (s, 3H), 1.52 (d, J = 6.4 Hz, 3H), 1.47 (s, 3H), 1.42 (d, J = 7.6 Hz, 3H). | Scheme 1, Intermediate 3 and Intermediate 29 |

TABLE 1-continued

| Cpd. # | Structure | LCMS (M + 1) | NMR | Synthetic Protocol |
|---|---|---|---|---|
| 56 | 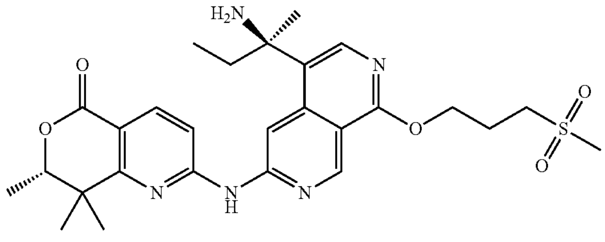 or 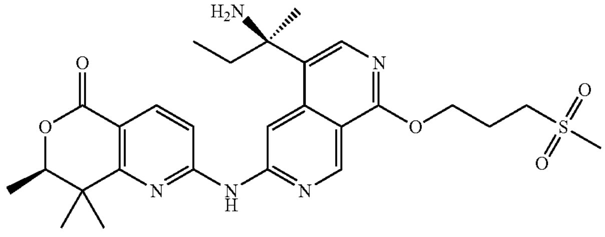 | 542 | $^1$H-NMR (400 MHz, $CD_3OD$): δ ppm 9.50 (s, 1H), 8.31 (s, 1H), 8.18 (d, J = 8.8 Hz, 1H), 7.97 (s, 1H), 7.72 (d, J = 8.8 Hz, 1H), 4.71 (t, J = 6.0 Hz, 2H), 4.65-4.55 (m, 1H), 3.43 (t, J = 6.0 Hz, 2H), 3.05 (s, 3H), 2.70-2.60 (m, 1H), 2.50-2.40 (m, 2H), 2.30-2.20 (m, 1H), 1.95 (s, 3H), 1.55-1.45 (m, 6H), 1.30 (s, 3H), 0.85-0.78 (m, 3H). | Scheme 1, Intermediate 97 and Intermediate 100 |
| 57 | 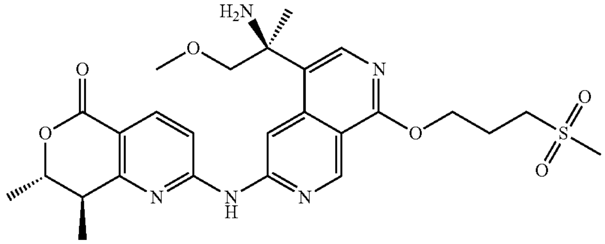 | 544 | $^1$H-NMR (400 MHz, $CD_3OD$): δ ppm 9.43 (s, 1H), 9.05 (s, 1H), 8.15 (d, J = 8.8 Hz, 1H), 8.07 (s, 1H), 7.35 (d, J = 8.8 Hz, 1H), 4.71-4.65 (m, 3H), 4.00-3.99 (m, 2H), 3.44-3.38 (m, 5H), 3.04-3.00 (m, 4H), 2.47-2.40 (m, 2H), 1.87 (s, 3H), 1.51-1.42 (m, 6H). | Scheme 1, Intermediate 1 and Intermediate 99 |
| 58 | 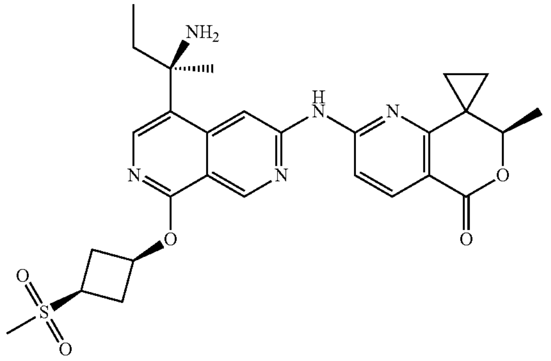 or 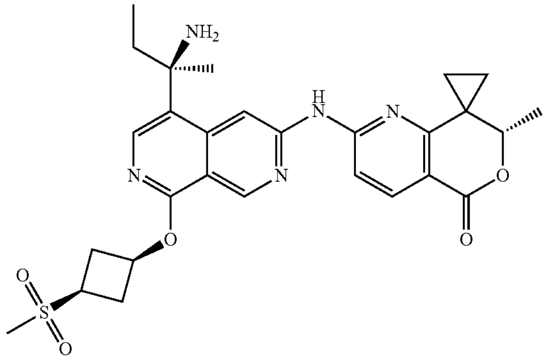 | 552 | $^1$H-NMR (400 MHz, CD3OD): δ ppm 9.39 (s, 1 H), 8.39 (s, 1 H), 8.15 (d, J = 8.4 Hz, 1 H), 8.08 (s, 1 H), 7.56 (d, J = 8.8 Hz, 1 H), 5.47-5.38 (m, 1 H), 4.66-4.60 (m , 1 H), 3.72-3.95 (m, 1 H), 3.01-2.95 (m, 2 H), 2.93 (s, 3 H), 2.73-2.64 (m, 2 H), 2.40-2.29 (m, 1 H), 2.16-2.06 (m, 1 H), 1.75 (s, 3 H), 1.65-1.47 (m, 2 H), 1.37 (d, J = 6.60 Hz, 3 H), 1.25-1.17 (m, 2 H), 0.77-0.71 (m, 3 H). | Scheme 1, Intermediate 12 and Intermediate 24 |

TABLE 1-continued

| Cpd. # | Structure | LCMS (M + 1) | NMR | Synthetic Protocol |
| --- | --- | --- | --- | --- |
| 59 | 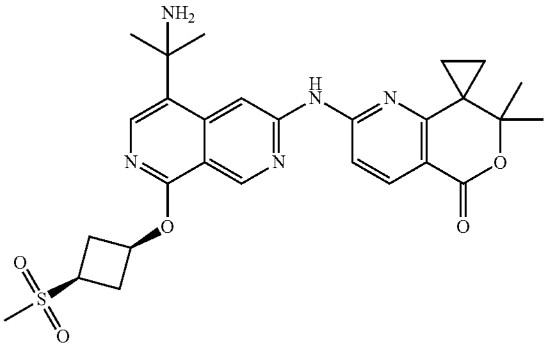 | 552 | $^1$H-NMR (400 MHz, CD3OD): δ ppm 9.41 (s, 1 H), 8.37 (s, 1 H), 8.16 (d, J = 8.8 Hz, 1 H), 8.08 (s, 1 H), 7.59 (d, J = 8.8 Hz, 1 H), 5.5-5.36 (m, 1 H), 3.90-3.75 (m, 1 H), 3.01-2.95 (m, 2 H), 2.93 (s, 3 H), 2.75-2.60 (m, 2 H), 1.83 (s, 6 H), 1.58-1.53 (m, 2 H), 1.42 (s, 6 H), 1.31-1.28 (m, 2 H). | Scheme 1, Intermediate 15 and Intermediate 22 |
| 60 | 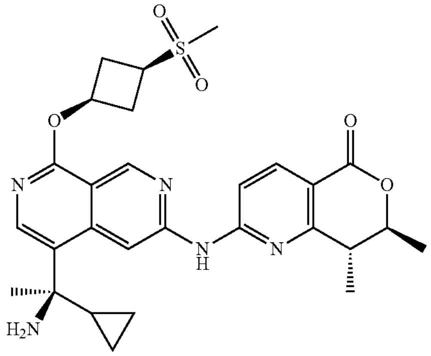 [SMILES: C[C@@H]1OC(=O)c2ccc(Nc3cc4c([C@](C)(N)C5CC5)cnc(O[C@H]5C[C@@H](S(C)(=O)=O)C5)c4cn3)nc2[C@H]1C] or 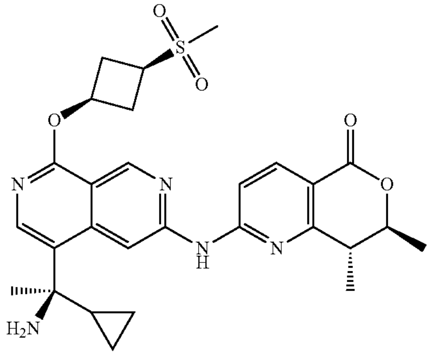 [SMILES: C[C@@H]1OC(=O)c2ccc(Nc3cc4c([C@](C)(N)C5CC5)cnc(O[C@H]5C[C@@H](S(C)(=O)=O)C5)c4cn3)nc2[C@H]1C] | 552 | $^1$H-NMR (400 MHz, 6d-DMSO): δ ppm 10.67 (s, 1H), 9.54 (s, 1H), 9.32 (s, 1H), 8.31 (s, 1H), 8.08 (d, J = 8.8 Hz, 1H), 7.38 (d, J = 8.8 Hz, 1H), 5.42-5.31 (m, 1H), 4.64-4.56 (m, 1H), 3.90-3.80 (m, 1H), 3.00-2.92 (m, 4H), 2.89-2.82 (m, 2H), 2.56-2.53 (m, 1H), 1.61-1.52 (m, 5H), 1.44 (d, J = 7.2 Hz, 3H), 1.37 (d, J = 6.0 Hz, 3H), 0.61-0.54 (m, 1H), 0.48-0.37 (m, 3H). | Scheme 1, Intermediate 1 and Intermediate 56 |
| 61 | 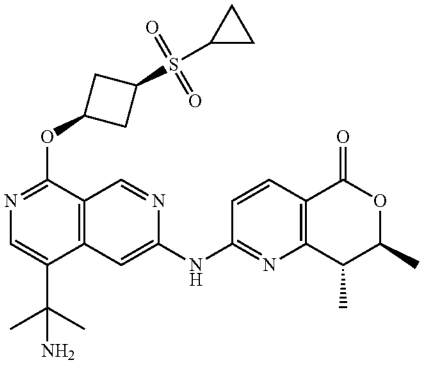 | 552 | $^1$H-NMR (400 MHz, $CD_3OD$): δ ppm 9.38 (s, 1H), 9.14 (s, 1H), 8.16-8.12 (m, 2H), 7.31 (d, J = 8.8 Hz, 1H), 5.49-5.39 (m, 1H), 4.67-4.60 (m, 1H), 3.88-3.84 (m, 1H), 3.05-2.95 (m, 3H), 2.80-2.64 (m, 2H), 2.60-2.50 (m, 1H), 1.83 (d, J = 5.2 Hz, 6H), 1.55-1.43 (m, 6H), 1.14-1.07 (m, 4H). | Scheme 1, Intermediate 1 and Intermediate 32 |

TABLE 1-continued

| Cpd. # | Structure | LCMS (M + 1) | NMR | Synthetic Protocol |
|---|---|---|---|---|
| 62 | 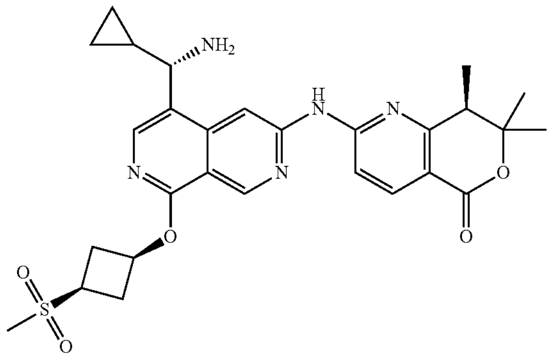 or 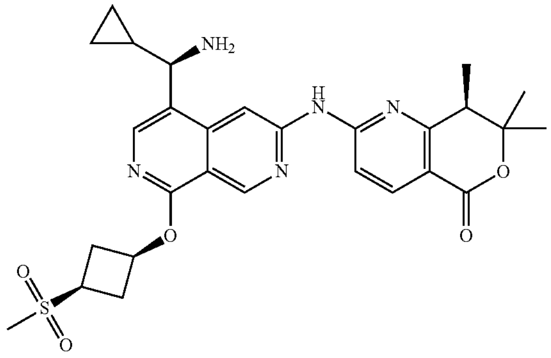 | 552 | $^{1}$H-NMR (400 MHz, $CD_3OD$): δ ppm 9.39-9.23 (m, 1H), 8.97-8.83 (m, 1H), 8.20 (s, 1H), 8.15-8.07 (m, 1H), 7.19 (d, J = 8.8 Hz, 1H), 5.61-5.27 (m, 2H), 3.83 (d, J = 6.4 Hz, 2H), 3.67-3.56 (m, 1H), 3.22-3.11 (m, 1H), 2.93 (s, 4H), 2.68 (d, J = 5.2 Hz, 2H), 1.54-1.43 (m, 9 H), 0.73-0.34 (m, 4 H). | Scheme 2, Intermediate 3 and Intermediate 58 Pcnultamite intermediate was 2nd eluting isomer from prep-HPLC Column: Phenomenex Gemini-NX C18 75*30 mm* 3 μm; Mobile phase: [water (0.05% ammonia hydroxide v/v)-ACN]; B %: 26%-56%, 10 min |
| 63 | 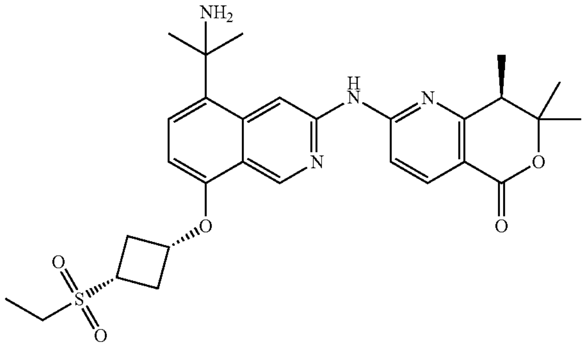 | 553 | $^{1}$H-NMR (400 MHz, $CD_3OD$): δ ppm 9.42 (s, 1H), 9.33 (s, 1H), 8.10 (d, J = 8.8 Hz, 1H), 7.61 (d, J = 8.4 Hz, 1H), 7.17 (d, J = 8.8 Hz, 1H), 6.73 (d, J = 8.4 Hz, 1H), 5.01 (d, J = 6.8 Hz, 1H), 3.87-3.78 (m, 1H), 3.07 (q, J = 7.2 Hz, 2H), 3.04-2.96 (m, 3H), 2.74-2.64 (m, 2H), 1.93 (d, J = 10.4 Hz, 6H), 1.54 (s, 3H), 1.45 (s, 3H), 1.39 (d, J = 7.2 Hz, 3H), 1.36 (t, J = 7.6 Hz, 3H). | Scheme 1, Intermediate 3 and Intermediate 59 |
| 64 | 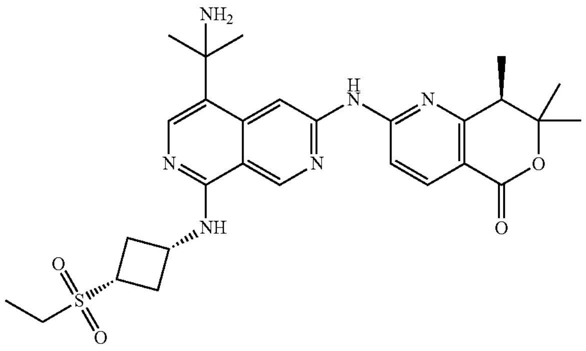 [SMILES: CCS(=O)(=O)[C@H]1C[C@@H](Nc2ncc(C(C)(C)N)c3cc(Nc4ccc5c(n4)[C@@H](C)C(C)(C)OC5=O)ncc23)C1] | 553 | $^{1}$H-NMR (400 MHz, $CD_3OD$): δ ppm 9.37 (s, 1H), 9.01 (s, 1H), 8.51 (s, 1H), 8.13 (d, J = 8.8 Hz, 1H), 7.88 (s, 1H), 7.26 (d, J = 8.8 Hz, 1H), 4.74-5.62 (m, 1H), 3.85-3.81 (m, 1H), 3.06-2.96 (m, 3H), 2.81-2.78 (m, 2H), 2.59-2.51 (m, 2H), 1.94 (d, J= 11.2 Hz, 6H), 1.52 (s, 3H), 1.43 (s, 3H), 1.38 (d, J = 7.2 Hz, 3H), 1.34 (t, J = 7.6 Hz, 3H). | Scheme 1, Intermediate 3 and Intermediate 60 |

TABLE 1-continued

| Cpd. # | Structure | LCMS (M + 1) | NMR | Synthetic Protocol |
|---|---|---|---|---|
| 65 | 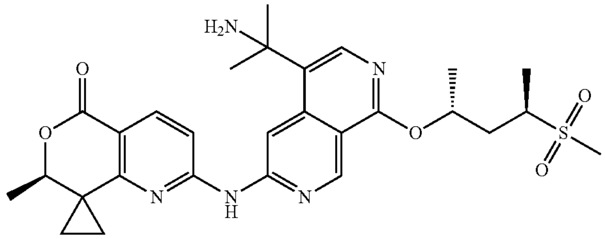 or 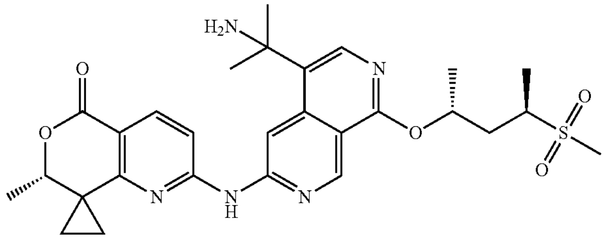 | 554 | $^1$H-NMR (400 MHz, $CD_3OD$): δ6 ppm 9.40 (s, 1H), 8.47 (s, 1H), 8.15 (d, J = 8.4 Hz, 1H), 8.13 (s, 1H), 7.54 (d, J = 8.4 Hz, 1H), 5.74-5.65 (m, 1H), 4.68-4.60 (m, 1H), 3.41-3.33 (m, 1H), 2.93 (s, 3H), 2.45-2.37 (m, 1H), 2.17-2.08 (m, 1H), 1.80 (s, 6H), 1.68-1.61 (m, 1H), 1.54-1.52 (m, 1H), 1.51-1.47 (m, 6H), 1.38 (d, J = 6.4 Hz, 3H), 1.26-1.18 (m, 2H). | Scheme 1, Intermediate 12 and Intermediate 52 |
| 66 | 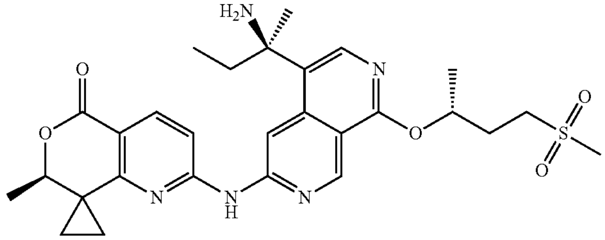 or 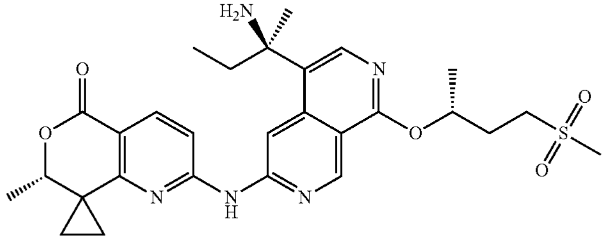 | 554 | $^1$H-NMR (400 MHz, $CD_3OD$): δ ppm 9.41 (s, 1H), 8.44 (s, 1H), 8.16 (d, J = 8.8 Hz, 1H), 8.12 (s, 1H), 7.56 (d, J = 8.8 Hz, 1H), 5.67-5.57 (m, 1H), 4.67-4.59 m, 1H), 3.41-3.32 (m, 2H), 3.00 (s, 3H), 2.40-2.24 (m, 3H), 2.16-2.03 (m, 1H), 1.73 (s, 3H), 1.69-1.62 (m, 1H), 1.51 (d, J = 6.0 Hz, 4H), 1.38 (d, J = 6.4 Hz, 3H), 1.27-1.14 (m, 2H), 0.74 (t, J = 7.4 Hz, 3H). | Scheme 1, Intermediate 12 and Intermediate 31 |
| 67 | 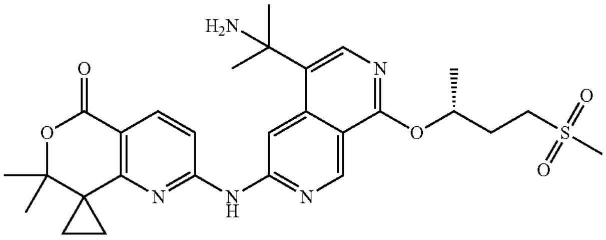 | 554 | $^1$H-NMR (400 MHz, $CD_3OD$): δ ppm 9.66 (s, 1H), 8.77 (s, 1H), 8.45 (s, 1H), 8.40 (d. J = 8.4 Hz, 1H), 7.78 (d, J = 8.8 Hz, 1H), 5.93-5.86 (m, 1H), 3.72-3.63 (m, 2H), 3.63-3.58 (m, 2H), 2.68-2.57 (m, 2H), 2.02 (s, 6H), 1.87-1.82 (m, 3H), 1.80-1.78 (d, 3H), 1.69 (s, 6H), 1.57-1.53 (m, 2H). | Scheme 1, Intermediate 15 and Intermediate 55 |

TABLE 1-continued

| Cpd. # | Structure | LCMS (M + 1) | NMR | Synthetic Protocol |
|---|---|---|---|---|
| 68 | 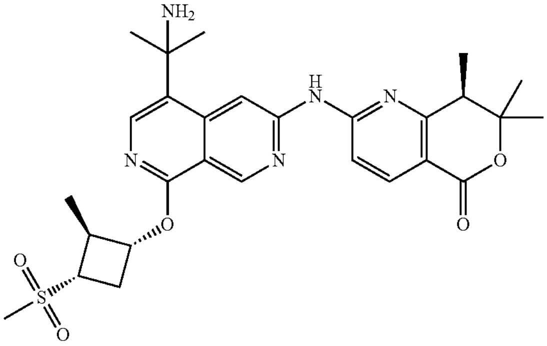 or 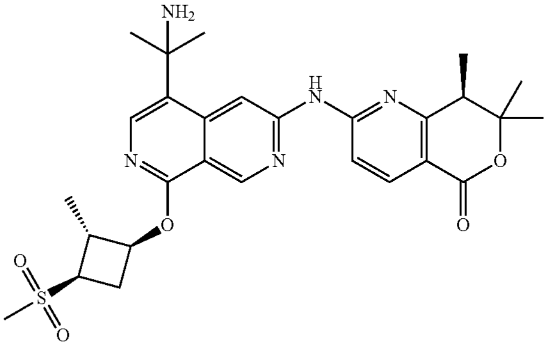 | 554 | $^1$H-NMR (400 MHz, $CD_3OD$): δ ppm 9.40 (s, 1H), 9.26 (s, 1H), 8.14 (d, J = 8.8 Hz, 1H), 8.10 (s, 1H), 7.25 (d, J = 8.8 Hz, 1H), 5.20-5.10 (m, 1H), 3.48-3.40 (m, 1H), 3.10-2.90 (m, 6H), 2.48-2.40 (m, 1H), 1.90 (d, J = 9.2 Hz, 6H), 1.54 (s, 3H), 1.46-1.38 (m, 9H). | Scheme 1, Intermediate 3 and Intermediate 38 2nd eluting isomer from chiral SFC Column: Daicel Chiralpak AD (250 mm*30 mm, 10 um); Mobile phase: [0.1% NH3H2O IPA]; B %: 40%-40% |
| 69 | 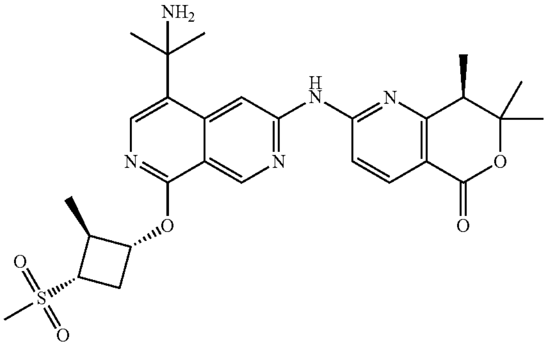 or 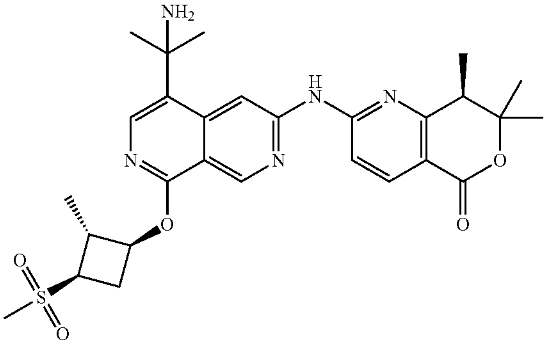 | 554 | $^1$H-NMR (400 MHz, $CD_3OD$): δ ppm 9.42 (s, 1H), 9.20 (s, 1H), 8.15 (d, J = 8.8 Hz, 1H), 8.05 (s, 1H), 7.27 (d, J = 8.8 Hz, 1H), 5.20-5.13 (m, 1H), 3.45-3.40 (m, 1H), 3.10-2.90 (m, 6H), 2.50-2.40 (m, 1H), 1.95 (d, J = 11.2 Hz, 6H), 1.53 (s, 3H), 1.45-1.35 (m, 9H). | Scheme 1, Intermediate 3 and Intermediate 38 1st eluting isomer from chiral SFC Column: Daicel Chiralpak AD (250 mm*30 mm, 10 um); Mobile phase: [0.1% NH3H2O IPA]; B %: 40%-40% |

TABLE 1-continued

| Cpd. # | Structure | LCMS (M + 1) | NMR | Synthetic Protocol |
|---|---|---|---|---|
| 70 | 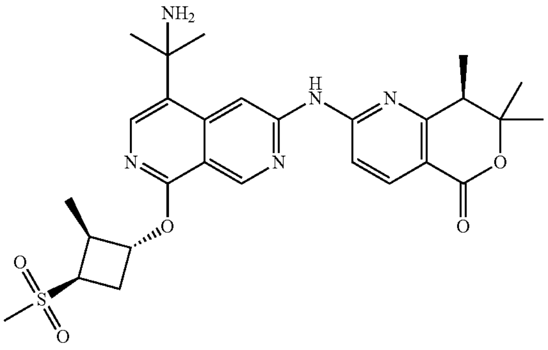<br>or<br>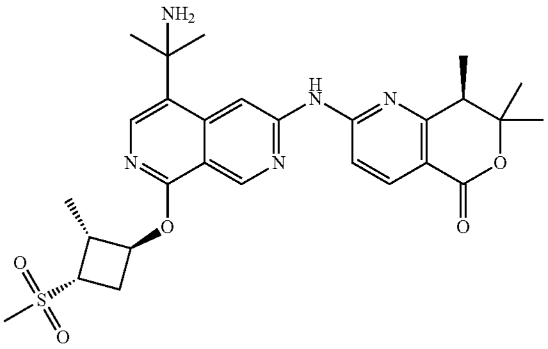 | 554 | $^1$H-NMR (400 MHz, $CD_3OD$): δ ppm 9.38 (s, 1H), 9.31 (s, 1H), 8.14-8.10 (m, 2H), 7.23 (d, J = 8.4 Hz, 1H), 5.52-5.45 (m, 1H), 3.97-3.92 (m, 1H), 3.27-3.25 (m, 1H), 3.05-2.95 (m, 5H), 2.62-2.54 (m, 1H), 1.85 (d, J = 8.4 Hz, 6H), 1.56-1.53 (m, 6H), 1.45-1.38 (m, 6H). | Scheme 1, Intermediate 3 and Intermediate 37 2nd eluting isomer from chiral SFC Column: Daicel Chiralpak AD (250 mm * 30 mm, 10 um); Mobile phase: [0.1% $NH_3H_2O$_ETOH] |
| 71 | 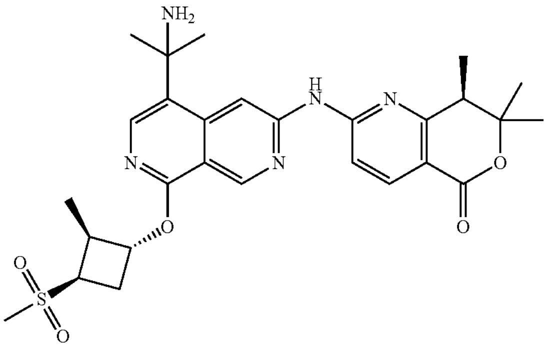<br>or<br>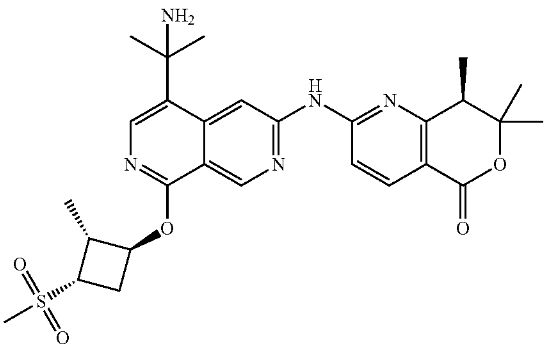 | 554 | $^1$H-NMR (400 MHz, $CD_3OD$): δ ppm 9.38 (s, 1H), 9.31 (s, 1H), 8.14-8.10 (m, 2H), 7.23 (d, J = 8.4 Hz, 1H), 5.52-5.45 (m, 1H), 3.97-3.92 (m, 1H), 3.27-3.25 (m, 1H), 3.05-2.95 (m, 5H), 2.62-2.54 (m, 1H), 1.85 (d, J = 8.4 Hz, 6H), 1.56-1.53 (m, 6H), 1.45-1.38 (m, 6H). | Scheme 1, Intermediate 3 and Intermediate 37 1st eluting isomer from chiral SFC Column: Daicel Chiralpak AD (250 mm * 30 mm, 10 um); Mobile phase: [0.1% $NH_3H_2O$_ETOH] |

TABLE 1-continued

| Cpd. # | Structure | LCMS (M + 1) | NMR | Synthetic Protocol |
|---|---|---|---|---|
| 72 | 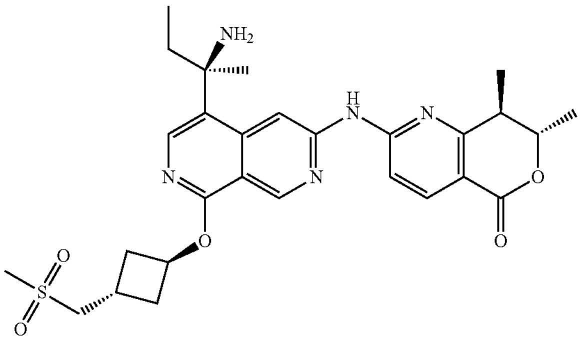 | 554 | $^1$H-NMR (400 MHz, $CDCl_3$): δ ppm 9.42 (s, 1H), 9.21 (s, 1H), 8.24 (d, J = 9.6 Hz, 1H), 8.08 (s, 1H), 7.89 (s, 1H), 5.60-5.50 (m, 1H), 4.59-4.52 (m, 1H), 3.31 (d, J = 7.6 Hz, 2H), 3.19-3.11 (m, 1H), 3.04-2.97 (m, 1H), 2.93 (s, 3H), 2.76-2.64 (m, 2H), 2.64-2.56 (m, 2H), 2.23-2.13 (m, 1H), 2.09-2.01 (m, 1H), 1.69 (s, 3H), 1.61 (s, 3H,), 1.52 (s, 3H), 0.83-0.70 (m, 3H). | Scheme 1, Intermediate 1 and Intermediate 49 |
| 73 | 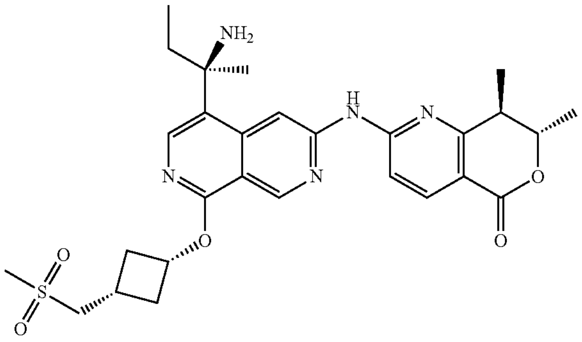 | 554 | $^1$H-NMR (400 MHz, 6d-DMSO): δ ppm 10.7 (s, 1H), 9.33 (s, 1H), 9.31 (s, 1H), 8.14 (s, 1H), 8.08 (d, J = 8.4 Hz, 1H), 7.38 (d, J = 8.4 Hz, 1H), 5.33-5.24 (m, 1H), 4.69-4.48 (m, 1H), 3.37 (s, 2H), 3.02-2.96 (m, 1H), 2.94 (s, 3H), 2.82-2.74 (m, 2H), 2.55-2.51 (m, 1H), 2.47 (s, 1H), 2.21-1.98 (m, 5H), 1.59 (s, 3H), 1.42 (d, J = 12 Hz, 3H), 1.37 (d, J = 6.4 Hz, 3H), 0.66-0.60 (m, 3H). | Scheme 1, Intermediate 1 and Intermediate 48 |
| 74 | 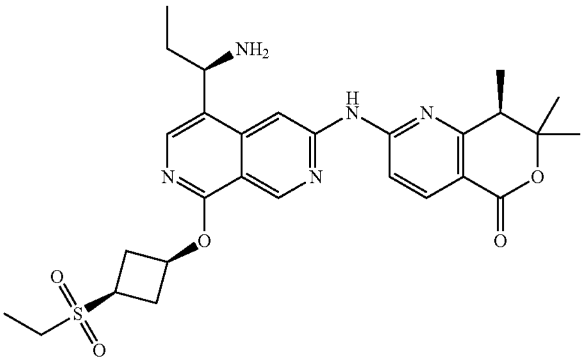 [SMILES: CC[C@@H](N)c1cnc(O[C@H]2C[C@@H](S(=O)(=O)CC)C2)c2cnc(Nc3ccc4c(n3)[C@@H](C)C(C)(C)OC4=O)cc12] or 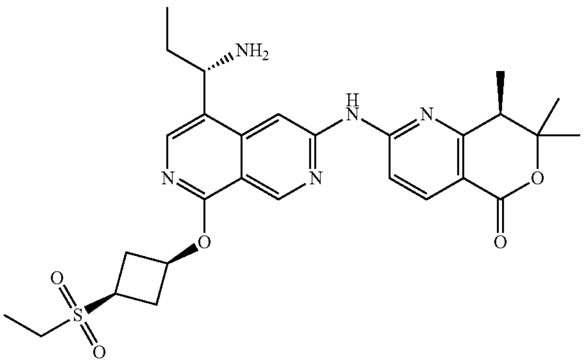 [SMILES: CC[C@H](N)c1cnc(O[C@H]2C[C@@H](S(=O)(=O)CC)C2)c2cnc(Nc3ccc4c(n3)[C@@H](C)C(C)(C)OC4=O)cc12] | 554 | $^1$H-NMR (400 MHz, $CD_3OD$): δ ppm 9.38 (s, 1H), 8.73 (s, 1H), 8.20 (s, 1H), 8.13 (d, J = 8.7 Hz, 1H), 7.31 (d, J = 8.7 Hz, 1H), 5.47 (br t, J = 7.3 Hz, 1H), 4.73 (br t, J = 7.0 Hz, 1H), 3.89-3.75 (m, 1H), 3.19 (q, J = 7.1 Hz, 1H), 3.07 (q, J = 7.5 Hz, 2H), 2.97 (td, J = 7.4, 12.0 Hz, 2H), 2.76-2.64 (m, 2H), 2.17 (quin, J = 7.2 Hz, 2H), 1.57-1.49 (m, 6H), 1.43 (s, 3H), 1.36 (t, J = 7.5 Hz, 3H), 1.04 (t, J =7.4 Hz, 3H) | Scheme 2, Intermediate 3 and Intermediate 46 penultimate intermediate was first eluting isomer from by prep-HPLC Column: Phenomenex Luna C18 75*30 mm* 3 um; Mobile phase: [water(0.05% HCl)-ACN]; B %: 42%-62%) |

TABLE 1-continued

| Cpd. # | Structure | LCMS (M + 1) | NMR | Synthetic Protocol |
|---|---|---|---|---|
| 75 | 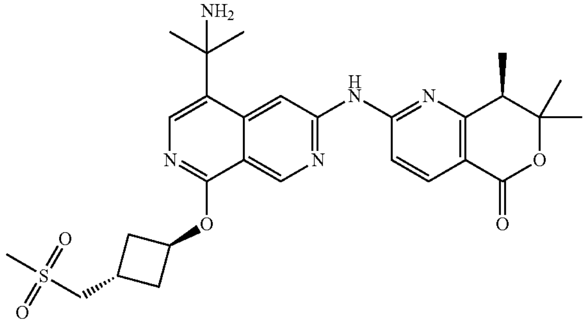 | 554 | $^1$H-NMR (400 MHz, $CD_3OD$): δ ppm 9.40 (s, 1H), 9.37 (s, 1H), 8.18-8.10 (m, 2H), 7.21 (d, J = 8.8 Hz, 1H), 5.57-5.49 (m, 1H), 3.43 (d, J = 7.6 Hz, 2H), 3.13-3.01 (m, 2H), 2.97 (s, 3H), 2.64-2.56 (m, 4H), 1.79 (d, J = 7.6 Hz, 6H), 1.54 (s, 3H), 1.45 (s, 3H), 1.40 (d, J = 7.2 Hz, 3H). | Scheme 1, Intermediate 3 and Intermediate 47 1st eluting isomer from chiral SFC Column: DAICEL CHIRALPAK ID (250 mm × 30 mm, 10 μm); Mobile phase: [0.1% NH3H2O ETOH]; B %: 60%-60%) |
| 76 | 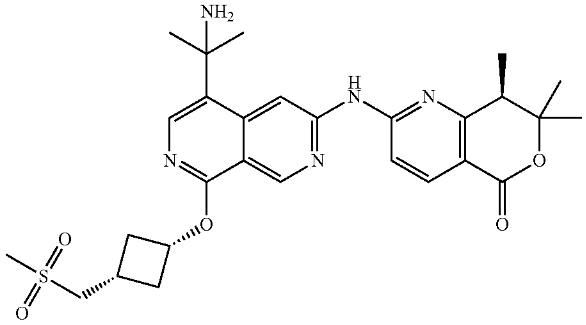 | 554 | $^1$H-NMR (400 MHz, $CD_3OD$): δ ppm 9.46-9.29 (m, 2H), 8.24-8.08 (m, 2H), 7.29-7.13 (m, 1H), 5.45-5.30 (m, 1H), 3.37 (d, J = 6.8 Hz, 2H), 3.10-3.00 (m, 1H), 2.96 (s, 3H), 2.94-2.84 (m, 2H), 2.68-2.54 (m, 1H), 2.25-2.11 (m, 2H), 1.79 (d, J = 5.6 Hz, 6H), 1.54 (s, 3H), 1.45 (s, 3H), 1.39 (d, J = 5.6 Hz, 3H). | Scheme 1, Intermediate 3 and Intermediate 47 2nd eluting isomer from chiral SFC Column: DAICEL CHIRALPAK ID (250 mm × 30 mm, 10 μm); Mobile phase: 10.1% NH3 H2O ETOH]; B %: 60%-60%) |
| 77 | 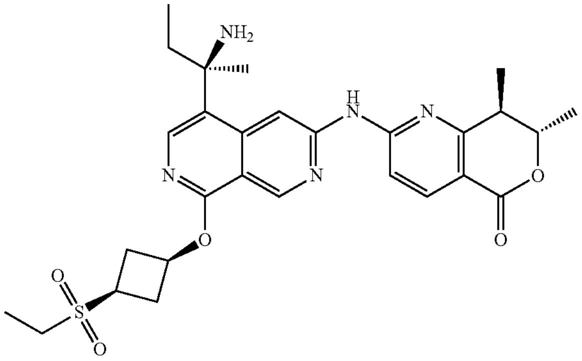 [SMILES: CC[C@@](C)(N)c1cnc(O[C@H]2C[C@@H](S(=O)(=O)CC)C2)c2cnc(Nc3ccc4c(n3)[C@@H](C)[C@H](C)OC4=O)cc12] | 554 | $^1$H-NMR (400 MHz, $CD_3OD$): δ ppm 9.35 (s, 1H), 9.16 (d, J = 10.8 Hz, 1H), 8.16-8.11 (m, 2H), 7.30-7.27 (m, 1H), 5.47-5.40 (m, 1H), 4.69-4.63 (m, 1H), 3.87-3.78 (m, 1H), 3.09-3.06 (m, 2H), 3.02-2.93 (m, 3H), 2.73-2.65 (m, 2H), 2.41-2.31 (m, 1H), 2.19-2.04 (m, 1H), 1.73 (s, 3H), 1.51-1.45 (m, 6H), 1.37-1.34 (m, 3H), 0.74-0.70 (m, 3H). | Scheme 1, Intermediate 1 and Intermediate 45 |
| 78 | 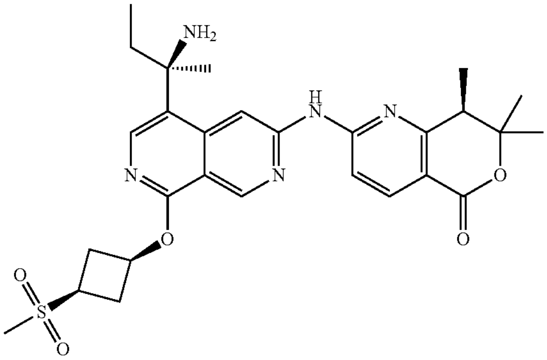 | 554 | $^1$H-NMR (400 MHz, $CD_3OD$): δ ppm 9.37 (s, 1H), 9.28 (d, J = 15.6 Hz, 1H), 8.31 (d, J = 8.4 Hz, 1H), 8.09 (s, 1H), 7.22 (d, J = 8.8 Hz, 1H), 5.48-5.40 (m, 1H), 3.87-3.79 (m, 1H), 3.04-2.95 (m, 3H), 2.93 (s, 3H), 2.73-2.65 (m, 2H), 2.50-2.41 (m, 1H), 2.28-2.16 (m, 1H), 1.81 (d, J = 8.4 Hz, 3H), 1.54 (s, 3H), 1.45 (s, 3H), 1.40-1.38 (m, 3H), 0.78-0.74 (m, 3H). | Scheme 1, Intermediate 3 and Intermediate 24 |

TABLE 1-continued

| Cpd. # | Structure | LCMS (M + 1) | NMR | Synthetic Protocol |
|---|---|---|---|---|
| 79 | 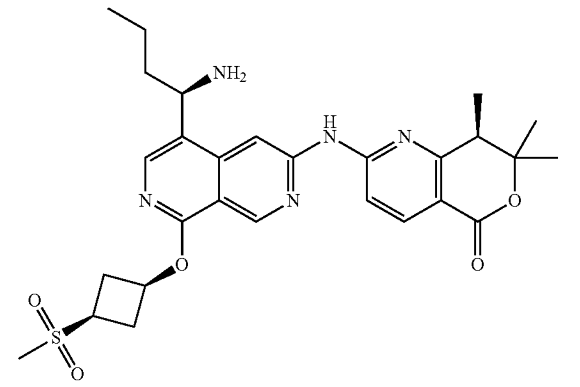 or 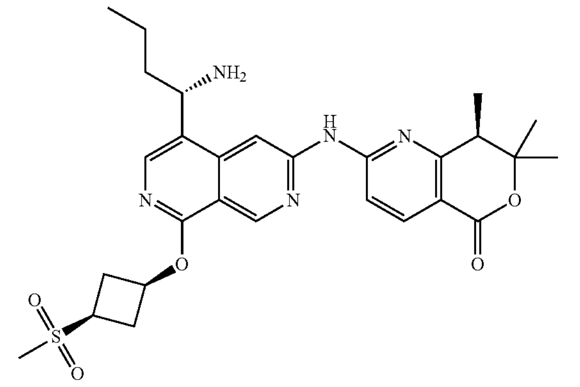 | 554 | $^1$H-NMR (400 MHz, $CD_3OD$): δ ppm 9.33 (s, 1H), 8.85 (s, 1H), 8.21-8.04 (m, 2H), 7.23 (d, J = 8.8 Hz, 1H), 5.47-5.39 (m, 1H), 4.52-4.46 (m, 1H), 3.90-3.73 (m, 1H), 3.18-3.1 (m, 1H), 2.96 (s, 2H), 2.93 (s, 3H), 2.74-2.62 (m, 2H), 2.02-1.81 (m, 2H), 1.52-1.48 (m, 6H), 1.45 (s, 3H), 1.44-1.27 (m, 2H), 0.99-0.93 (m, 3H). | Scheme 2, Intermediate 3 and Intermediate 61 |
| 80 | 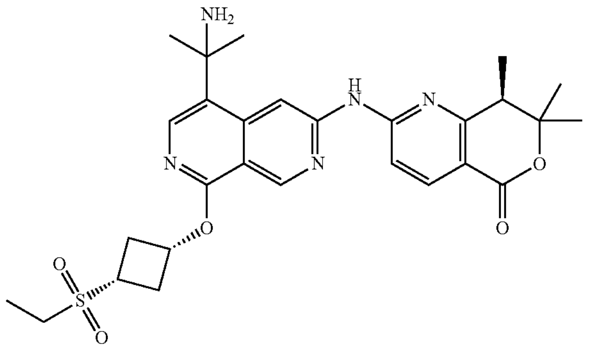 [SMILES: CCS(=O)(=O)[C@H]1C[C@@H](Oc2ncc(C(C)(C)N)c3cc(Nc4ccc5c(n4)[C@@H](C)C(C)(C)OC5=O)ncc23)C1] | 554 | $^1$H-NMR (400 MHz, $CD_3OD$): δ ppm 9.37 (s, 1H), 9.35 (s, 1H), 8.16 (s, 1H), 8.13 (d, J = 8.4 Hz, 1H), 7.22 (d, J = 8.8 Hz, 1H), 5.52-5.37 (m, 1H), 3.91-3.75 (m, 1H), 3.10-3.02 (m, 3H), 3.02-2.92 (m, 2H), 2.75-2.61 (m, 2H), 1.82 (d, J = 8.0 Hz, 6H), 1.54 (s, 3H), 1.45 (s, 3H), 1.40 (d, J = 7.2 Hz, 3H), 1.35 (t, J = 7.4 Hz, 3H). | Scheme 1, Intermediate 3 and Intermediate 44 |
| 81 | 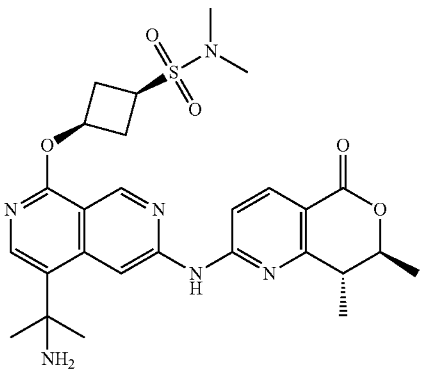 [SMILES: C[C@@H]1OC(=O)c2ccc(Nc3cc4c(C(C)(C)N)cnc(O[C@H]5C[C@@H](S(=O)(=O)N(C)C)C5)c4cn3)nc2[C@H]1C] | 555 | $^1$H-NMR (400 MHz, $CD_3OD$): δ ppm 9.43 (s, 1H), 9.05 (s, 1H), 8.49 (s, 1H), 8.18 (d, J = 8.4 Hz, 1H), 7.37 (d, J = 8.8 Hz, 1H), 5.44-5.40 (m, 1H), 4.67-4.66 (m, 1H), 3.84-3.80 (m, 1H), 3.01-2.90 (m, 3H), 2.90 (s, 6H), 2.75-2.70 (m, 2H), 1.95 (d, J = 6.0 Hz, 6H), 1.52 (d, J = 7.2 Hz, 3H), 1.47 (d, J = 6.8 Hz, 3H). | Scheme 1, Intermediate 1 and Intermediate 64 |

TABLE 1-continued

| Cpd. # | Structure | LCMS (M + 1) | NMR | Synthetic Protocol |
|---|---|---|---|---|
| 82 | 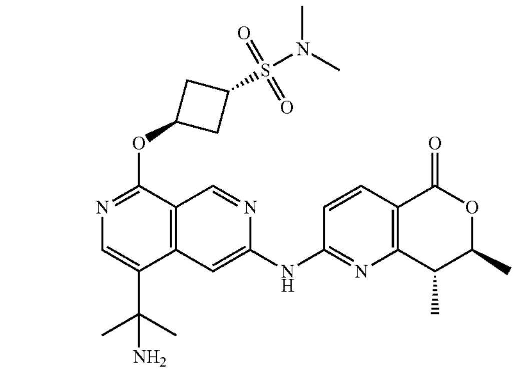 [SMILES: C[C@@H]1OC(=O)c2ccc(Nc3cc4c(C(C)(C)N)cnc(O[C@H]5C[C@H](S(=O)(=O)N(C)C)C5)c4cn3)nc2[C@H]1C] | 555 | $^1$H-NMR (400 MHz, $CD_3OD$): δ ppm 9.41 (d, J = 5.6 Hz, 1H), 9.11 (s, 1H), 8.52 (s, 1H), 8.15 (d, J = 8.8 Hz, 1H), 8.09 (s, 1H), 7.32 (d, J = 8.8 Hz, 1H), 5.66-5.61 (m, 1H), 4.70-4.62 (m, 1H), 4.15-4.05 (m, 1H), 3.07-3.00 (m, 3H), 2.79-2.72 (m, 2H), 1.85 (d, J = 5.6 Hz, 6H), 1.51 (d, J = 7.2 Hz, 3H), 1.45 (d, J = 6.4 Hz, 3H). | Scheme 1, Intermediate 1 and Intermediate 63 |
| 83 | 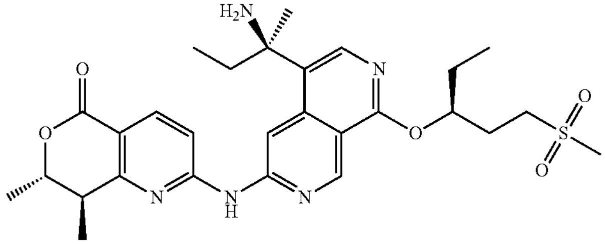 or 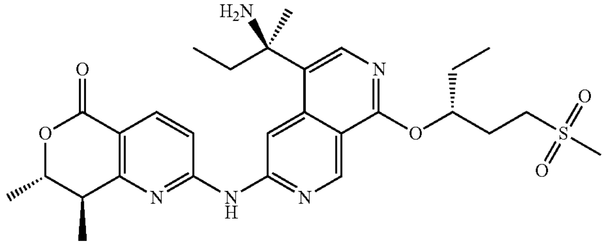 | 556 | $^1$H-NMR (400 MHz, $CD_3OD$): δ ppm 9.41 (s, 1H), 9.14 (s, 1H), 8.18-8.1 (m, 2H), 7.31 (d, J = 8.8 Hz, 1H), 5.59-5.50 (m, 1H), 4.72-4.63 (m, 1H), 3.35-3.32 (m, 1H), 3.29-3.25 (m, 1H), 3.07-3.00 (m, 1H), 2.99 (s, 3H), 2.49-2.38 (m, 1H), 2.38-2.28 (m, 2H), 2.23-2.12 (m, 1H), 1.96-1.84 (m, 2H), 1.78 (s, 3H), 1.50 (d, J = 7.2 Hz, 3H), 1.46 (d, J = 6.8 Hz, 3H), 1.04 (t, J = 7.4 Hz, 3H), 0.75 (t, J = 7.2 Hz, 3H). | Scheme 1, Intermediate 1 and Intermediate 65 2nd eluting isomer from chiral SFC Column: DAICEL CHIRALPAK AS (250 mm*30 mm, 10 um); Mobile phase: [0.1% NH3H2O MEOH]; B %: 50%-50%) |
| 84 | 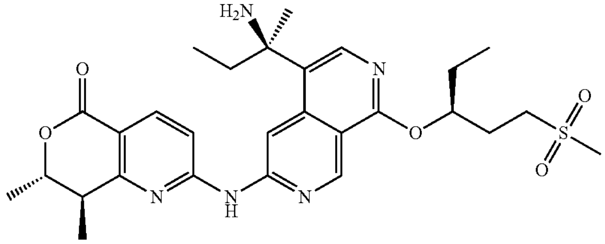 or 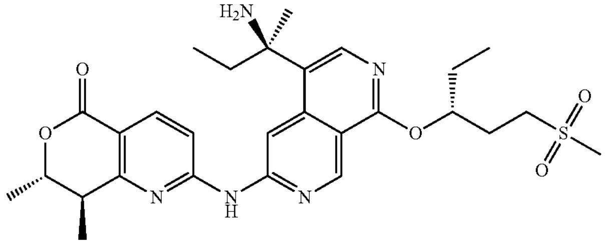 | 556 | $^1$H-NMR (400 MHz, $CD_3OD$): δ ppm 9.41 (s, 1H), 9.14 (s, 1H), 8.18-8.11 (m, 2H), 7.31 (d, J = 8.8 Hz, 1H), 5.59-5.50 (m, 1H), 4.72-4.62 (m, 1H), 3.35 (s, 1H), 3.29 (s, 1H), 3.07-3.01 (m, 1H), 2.99 (s, 3H), 2.48-2.26 (m, 3H), 2.23-2.11 (m, 1H), 1.98-1.83 (m, 2H), 1.77 (s, 3H), 1.50 (d, J = 12 Hz, 3H), 1.46 (d, J = 6.8 Hz, 3H), 1.04 (t, J = 7.4 Hz, 3H), 0.75 (t, J = 7.2 Hz, 3H). | Scheme 1, Intermediate 1 and Intermediate 65 1st eluting isomer from chiral SFC Column: DAICEL CHIRALPAK AS (250 mm*30 mm, 10 um); Mobile phase: [0.1% NH3H2O MEOH]; B %: 50%-50%) |

TABLE 1-continued

| Cpd. # | Structure | LCMS (M + 1) | NMR | Synthetic Protocol |
|---|---|---|---|---|
| 85 | 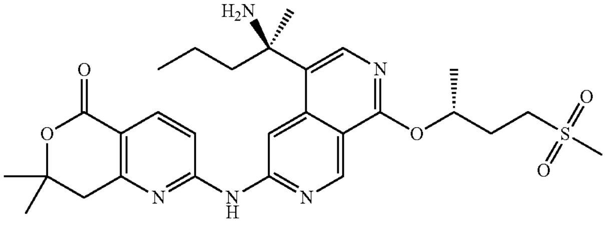<br>or<br>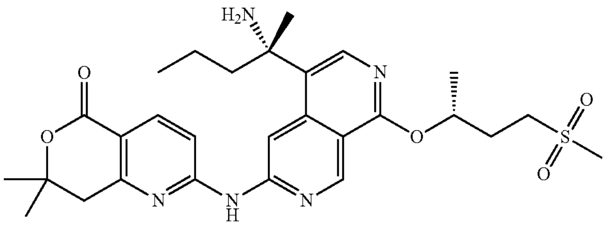 | 556 | $^1$H-NMR (400 MHz, $CD_3OD$): δ ppm 9.45 (s, 1H), 9.17 (s, 1H), 8.19-8.17 (m, 1H), 7.95 (s, 1H), 121-1.25 (m, 1H), 5.67 (s, 1H), 3.36 (s, 1H), 3.22 (s, 2H), 3.01 (s, 3H), 2.68-2.61 (m, 1H), 2.35-2.67 (m, 3H), 2.02 (s, 3H), 1.53 (s, 9H), 1.37-0.98 (m, 3H), 0.90 (s, 3H). | Scheme 1, Intermediate 5 and Intermediate 69 |
| 86 | 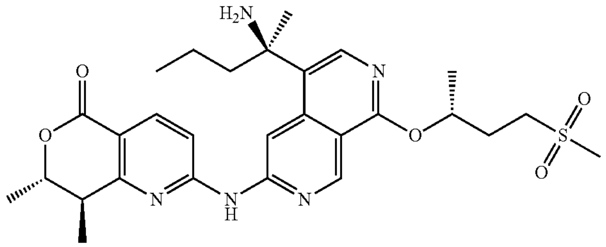<br>or<br>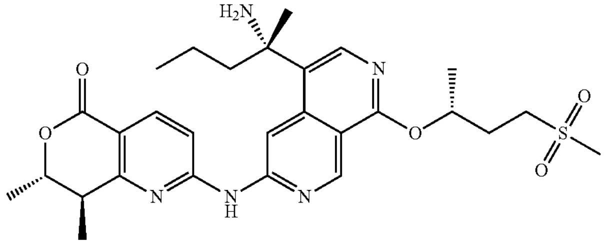 | 556 | $^1$H-NMR (400 MHz, $CD_3OD$): δ ppm 9.47 (s, 1H), 8.95 (s, 1H), 8.20-8.18 (m, 1H), 7.93 (s, 1H), 7.41-7.39 (m, 1H), 5.67 (s, 1H), 4.71 (s, 1H), 3.36 (s, 1H), 3.01 (s, 4H), 2.72-2.66 (m, 1H), 2.36 (s, 2H), 2.25-2.19 (m, 1H), 2.00 (s, 3H), 1.52 (s, 6H), 1.46 (s, 3H), 1.41-1.29 (m, 2H), 1.03-0.98 (m, 1H), 0.89 (s, 3H). | Scheme 1, Intermediate 1 and Intermediate 69 |
| 87 | 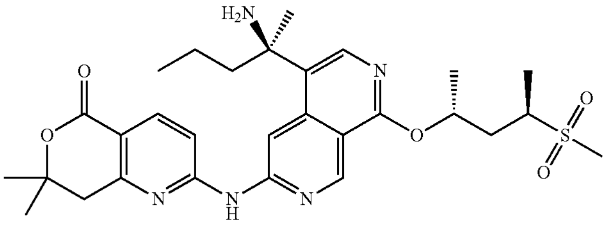 | 556 | $^1$H-NMR (400 MHz, $CD_3OD$): δ ppm 9.35 (d, J = 8.8 Hz, 2H), 8.15-8.12 (m, 2H), 7.19 (d,J = 8.4 Hz, 1H), 5.73-5.65 (m, 1H), 3.41-3.34 (m, 1H), 3.21 (s, 2H), 2.93 (s, 3H), 2.45-2.33 (m, 2H), 2.23-2.08 (m, 2H), 1.76 (s, 3H), 1.53 (s, 6H), 1.51-1.49 (m, 6H), 0.77-0.74 (m, 3H). | Scheme 1, Intermediate 5 and Intermediate 53 |
| 88 | 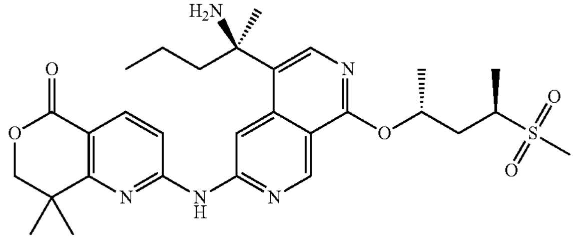 [SMILES: CCC[C@@](C)(N)c1cnc(O[C@H](C)C[C@@H](C)S(C)(=O)=O)c2cnc(Nc3ccc4c(n3)C(C)(C)COC4=O)cc12] | 556 | $^1$H-NMR (400 MHz, $CD_3OD$): δ ppm 9.41 (s, 1H), 8.66 (s, 1H), 8.17-8.15 (m, 2H), 7.53 (d, J = 8.4 Hz, 1H), 5.71-5.66 (m, 1H), 4.31 (s, 2H), 3.39-3.33 (m, 1H), 2.93 (s, 3H), 2.45-2.34 (m, 2H), 2.16-2.08 (m, 2H), 1.74 (s, 3H), 1.51-1.49 (m, 6H), 1.46 (s, 6H), 0.75-0.71 (m, 3H). | Scheme 1, Intermediate 14 and Intermediate 53 |

TABLE 1-continued

| Cpd. # | Structure | LCMS (M + 1) | NMR | Synthetic Protocol |
|---|---|---|---|---|
| 89 | 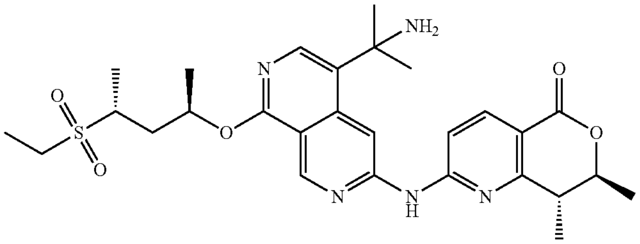 [SMILES: CCS(=O)(=O)[C@H](C)C[C@@H](C)Oc1ncc(C(C)(C)N)c2cc(Nc3ccc4c(n3)[C@@H](C)[C@H](C)OC4=O)ncc12] | 556 | $^1$H-NMR (400 MHz, $CD_3OD$): δ ppm 9.37 (s, 1H), 9.18 (s, 1H), 8.26-8.06 (m, 2H), 7.31 (d, J = 8.4 Hz, 1H), 5.78-5.61 (m, 1H), 4.71-4.60 (m, 1H), 3.43-3.36 (m, 1H), 3.17-2.99 (m, 3H), 2.47-2.35 (m, 1H), 2.18-2.05 (m, 1H), 1.80 (d, J = 4.8 Hz, 6H), 1.54-1.43 (m, 12H), 1.34-1.28 (m, 3H). | Scheme 1, Intermediate 1 and Intermediate 70 |
| 90 | 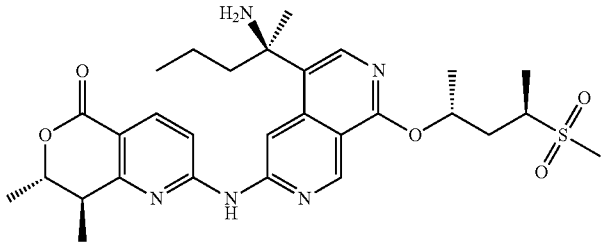 | 556 | $^1$H-NMR (400 MHz, $CD_3OD$): δ ppm 9.38 (s, 1H), 9.17 (s, 1H), 8.19-8.12 (m, 2H), 7.30 (d, J = 8.4 Hz, 1H), 5.74-5.66 (m, 1H), 4.71-4.64 (m, 1H), 3.41-3.33 (m, 1H), 3.08-3.00 (m, 1H), 2.93 (s, 3H), 2.47-2.34 (m, 2H), 2.21-2.07 (m, 2H), 1.74 (s, 3H), 1.54-1.48 (m, 9H), 1.46 (d, J = 6.8 Hz, 3H), 0.74 (t, J = 7.2 Hz, 3H). | Scheme 1, Intermediate 1 and Intermediate 53 |
| 91 | 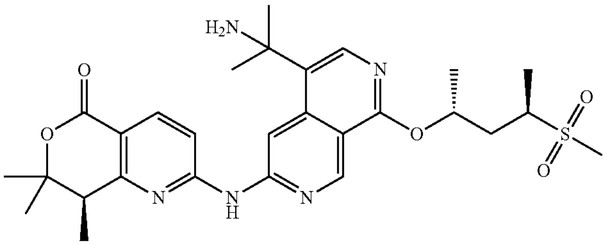 | 556 | $^1$H-NMR (400 MHz, $CD_3OD$): δ ppm 9.39 (s, 1H), 9.28 (s, 1H), 8.17-8.12 (m, 2H), 7.25 (d, J = 8.8 Hz, 1H), 5.75-5.67 (m, 1H), 3.40-3.33 (m, 1H), 3.07-3.00 (m, 1H), 2.93 (s, 3H), 2.44-2.37 (m, 1H), 2.18-2.08 (m, 1H), 1.88 (d, J = 8.8 Hz, 6H), 1.54 (s, 3H), 1.52-1.48 (m, 6H), 1.45 (s, 3H), 1.40 (d, J = 7.2 Hz, 3H). | Scheme 1, Intermediate 3 and Intermediate 52 |
| 92 | 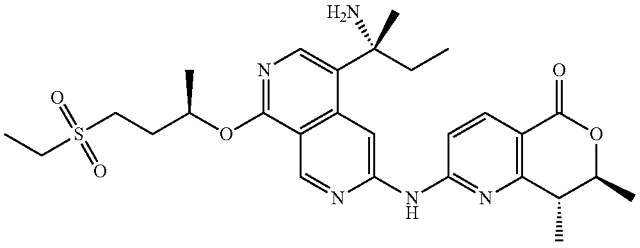 [SMILES: CC[C@@](C)(N)c1cnc(O[C@H](C)CCS(=O)(=O)CC)c2cnc(Nc3ccc4c(n3)[C@@H](C)[C@H](C)OC4=O)cc12]<br>or<br>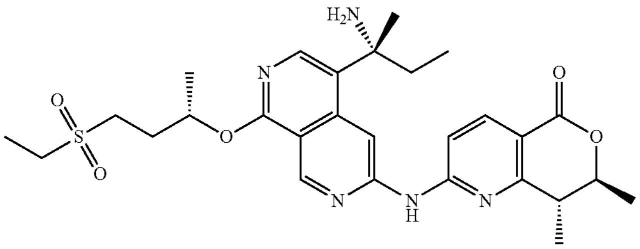 [SMILES: CC[C@@](C)(N)c1cnc(O[C@@H](C)CCS(=O)(=O)CC)c2cnc(Nc3ccc4c(n3)[C@@H](C)[C@H](C)OC4=O)cc12] | 556 | $^1$H-NMR (400 MHz, $CD_3OD$): δ ppm 9.43 (s, 1H), 9.02 (s, 1H), 8.16 (d, J = 8.4 Hz, 1H), 8.04 (s, 1H), 7.34 (d, J = 8.8 Hz, 1H), 5.71-5.57 (m, 1H), 4.75-4.62 (m, 1H), 3.30-3.22 (m, 2H), 3.17-3.08 (m, 2H), 3.05-2.95 (m, 1H), 2.63-2.50 (m, 1H), 2.40-2.29 (m, 2H), 2.28-2.19 (m, 1H), 1.88 (s, 3H), 1.50 (t, J = 6.8 Hz, 6H), 1.46 (d, J = 6.4 Hz, 3H), 1.33 (t, J = 7.4 Hz, 3H), 0.79 (t, J = 7.4 Hz, 3H). | Scheme 1, Intermediate 1 and Intermediate 73 |

TABLE 1-continued

| Cpd. # | Structure | LCMS (M + 1) | NMR | Synthetic Protocol |
|---|---|---|---|---|
| 93 | 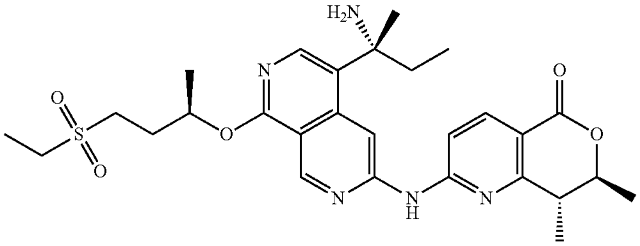 [SMILES: CC[C@@](C)(N)c1cnc(O[C@H](C)CCS(=O)(=O)CC)c2cnc(Nc3ccc4c(n3)[C@@H](C)[C@H](C)OC4=O)cc12] or 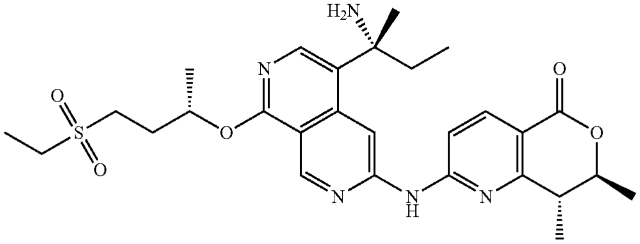 [SMILES: CC[C@@](C)(N)c1cnc(O[C@@H](C)CCS(=O)(=O)CC)c2cnc(Nc3ccc4c(n3)[C@@H](C)[C@H](C)OC4=O)cc12] | 556 | $^1$H-NMR (400 MHz, $CD_3OD$): δ ppm 9.45 (s, 1H), 8.97 (s, 1H), 8.18 (d, J = 8.8 Hz, 1H), 7.99 (s, 1H), 7.37 (d, J = 8.8 Hz, 1H), 5.73-5.58 (m, 1H), 4.74-4.64 (m, 1H), 3.30-3.21 (m, 2H), 3.17-3.08 (m, 2H), 3.06-2.95 (m, 1H), 2.69-2.55 (m, 1H), 2.41-2.20 (m, 3H), 1.94 (s, 3H), 1.55-1.43 (m, 9H), 1.34 (t, J = 7.4 Hz, 3H), 0.83 (t, J = 7.4 Hz, 3H). | Scheme 1, Intermediate 1 and Intermediate 72 |
| 94 | 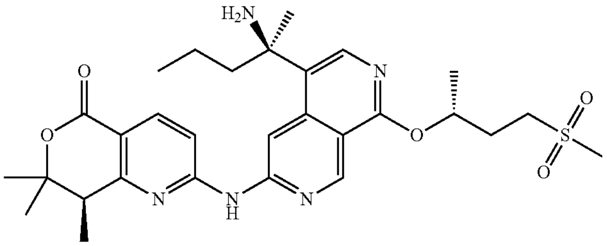 | 556 | $^1$H-NMR (400 MHz, $CD_3OD$): δ ppm 9.40 (s, 1H), 9.29 (s, 1H), 8.54 (s, 1H), 8.14 (d, J = 8.4 Hz, 1H), 8.12 (s, 1H), 7.23 (d, J = 8.8 Hz, 1H), 5.68-5.58 (m. 1H), 3.42-3.33 (m, 2H), 3.06-2.98 (m, 4H), 2.50-2.40 (m. 1H), 2.39-2.28 (m, 2H), 2.28-2.18 (m, 1H), 1.83-1.78 (m, 3H), 1.54 (s, 3H), 1.51 (d, J = 6.0 Hz, 3H), 1.45 (s, 3H), 1.39 (d, J = 7.2 Hz, 3H), 0.78 (t, J = 7.4 Hz, 3H). | Scheme 1, Intermediate 3 and Intermediate 31 |
| 95 | 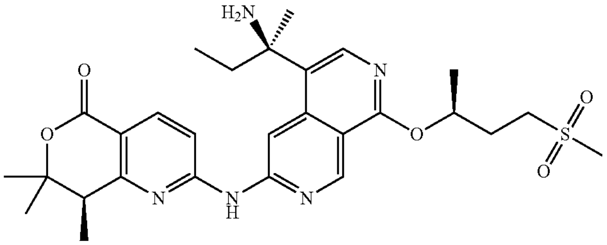 | 556 | $^1$H-NMR (400 MHz, $CD_3OD$): δ ppm 9.42 (s, 1H), 9.23 (s, 1H), 8.14 (d, J = 8.4 Hz, 1H), 8.07 (s, 1H), 7.25 (d, J = 8.8 Hz, 1H), 5.71-5.57 (m, 1H), 3.41-3.3 (m, 2H), 3.06-2.95 (m, 4H), 2.57-2.47 (m, 1H), 2.40-2.21 (m, 3H), 1.86 (s, 3H), 1.57-1.49 (m, 6H), 1.45 (s, 3H), 1.39 (d, J = 7.2 Hz, 3H), 0.80 (t, J = 7.4 Hz, 3H). | Scheme 1, Intermediate 3 and Intermediate 54 |
| 96 | 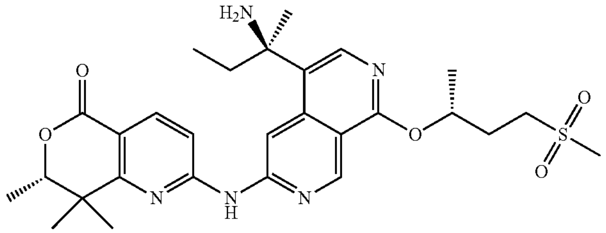 or | 556 | $^1$H-NMR (400 MHz, $CD_3OD$): δ ppm 9.46 (s, 1H), 8.46 (s, 1H), 8.18 (d, J = 8.8 Hz, 1H), 8.06 (s, 1H), 8.18 (d, J = 8.8 Hz, 1H), 5.67-5.60 (m, 1H), 4.65-4.51 (m, 1H), 3.43-3.32 (m, 2H), 3.01 (s, 3H), 2.56-2.45 (m, 1H), 2.42-2.30 (m, 2H), 2.22-2.12 (m, 1H), 1.85 (s, 3H), 1.54-1.42 (m, 9H), 1.31 (s, 3H), 0.80-0.73 (m, 3H). | Scheme 1, Intermediate 97 and Intermediate 31 |

TABLE 1-continued

| Cpd. # | Structure | LCMS (M + 1) | NMR | Synthetic Protocol |
|---|---|---|---|---|
| | 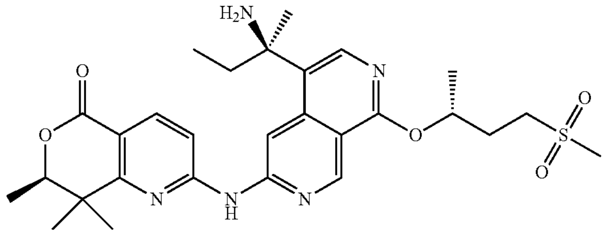 | | | |
| 97 | 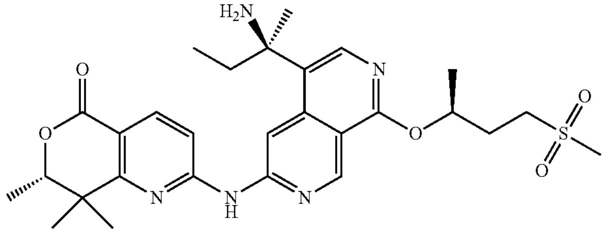<br>or<br>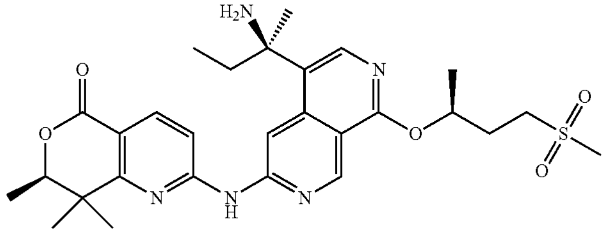 | 556 | $^1$H-NMR (400 MHz, $CD_3OD$): δ ppm 9.43 (s, 1H), 8.55 (s, 1H), 8.16 (d, J= 8.8 Hz, 1H), 8.11 (s, 1H), 7.58 (d, J = 8.8 Hz, 1H), 5.67-5.60 (m, 1H), 4.60-4.51 (m, 1H), 3.40-3.32 (m, 2H), 3.01 (s, 3H), 2.45-2.30 (m, 3H), 2.22-2.12 (m, 1H), 1.77 (s, 3H), 1.54-1.40 (m, 9H), 1.30 (s, 3H), 0.76-0.70 (m, 3H). | Scheme 1, Intermediate 97 and Intermediate 54 |
| 98 | 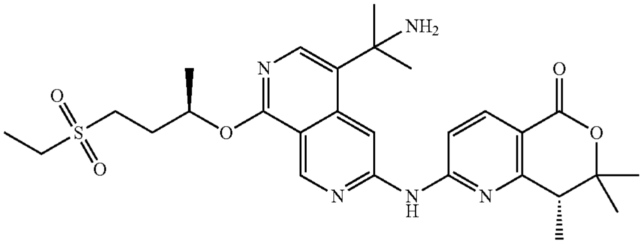 [SMILES: CCS(=O)(=O)CC[C@@H](C)Oc1ncc(C(C)(C)N)c2cc(Nc3ccc4c(n3)[C@@H](C)C(C)(C)OC4=O)ncc12]<br>or<br>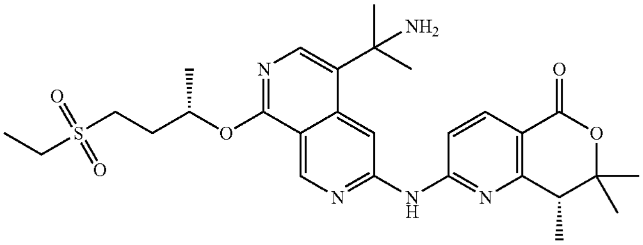 [SMILES: CCS(=O)(=O)CC[C@H](C)Oc1ncc(C(C)(C)N)c2cc(Nc3ccc4c(n3)[C@@H](C)C(C)(C)OC4=O)ncc12] | 556 | $^1$H-NMR (400 MHz, $CD_3OD$): δ ppm 9.38 (d, J = 3.2 Hz, 2H), 8.21 (s, 1H), 8.15 (d, J = 8.8 Hz, 1H), 7.23 (d, J = 8.8 Hz, 1H), 5.65-5.55 (m, 1H), 3.29-3.27 (m, 2H), 3.17-3.06 (m, 2H), 3.05-2.95 (m, 1H), 2.35-2.2.22 (m, 2H), 1.78 (d, J= 8.0 Hz, 6H), 1.48 (d, J = 6.0 Hz, 3H), 1.43 (s, 3H), 1.38 (d, J = 6.8 Hz, 3H), 1.32 (t, J = 7.6 Hz, 3H). | Scheme 1, Intermediate 3 and Intermediate 71 2nd eluting isomer from Chiral SFC Column: Daicel Chiralpak AD (250 mm* 30 mm, 10 um); Mobile phase: [0.1% NH3H2O MEOH]; B %: 50%-50%) |

TABLE 1-continued

| Cpd. # | Structure | LCMS (M + 1) | NMR | Synthetic Protocol |
|---|---|---|---|---|
| 99 | 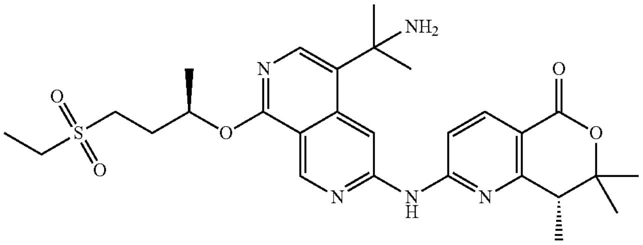 [SMILES: CCS(=O)(=O)CC[C@@H](C)Oc1ncc(C(C)(C)N)c2cc(Nc3ccc4c(n3)[C@@H](C)C(C)(C)OC4=O)ncc12] or 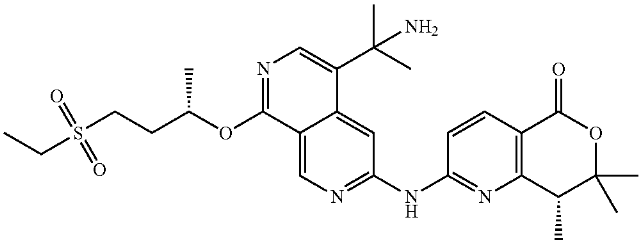 [SMILES: CCS(=O)(=O)CC[C@H](C)Oc1ncc(C(C)(C)N)c2cc(Nc3ccc4c(n3)[C@@H](C)C(C)(C)OC4=O)ncc12] | 556 | $^1$H-NMR (400 MHz, $CD_3OD$): δ ppm 9.38 (d, J = 4.4 Hz, 2H), 8.18 (s, 1H), 8.13 (d, J = 8.8 Hz, 1H), 7.20 (d, J = 8.4 Hz, 1H), 5.65-5.55 (m, 1H), 3.26-3.22 (m, 2H), 3.17-3.06 (m, 2H), 3.05-2.95 (m, 1H), 2.35-2.2.22 (m, 2H), 1.78 (d, J = 8.0 Hz, 6H), 1.48 (d, J = 6.0 Hz, 3H), 1.43 (s, 3H), 1.38 (d, J = 6.8 Hz, 3H), 1.32 (t, J = 7.6 Hz, 3H). | Scheme 1, Intermediate 3 and Intermediate 71 1st eluting isomer from Chiral SFC Column: Daicel Chiralpak AD (250 mm* 30 mm, 10 um); Mobile phase: [0.1% NH3H2O MEOH]; B %: 50%-50%) |
| 100 | 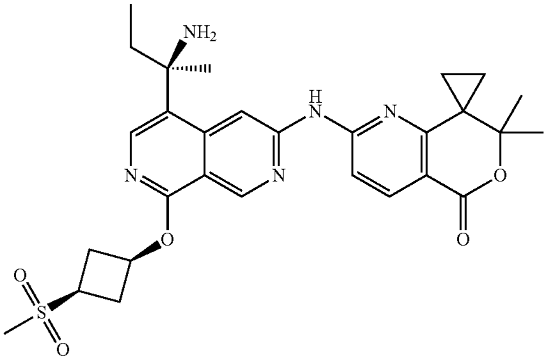 | 566 | $^1$H-NMR (400 MHz, CD3OD): δ ppm 9.41 (s, 1 H), 8.29 (s, 1 H), 8.15 (d, J = 8.8 Hz, 1 H), 8.05 (s, 1 H), 7.63 (d, J = 8.8 Hz, 1 H), 5.5-5.37 (m, 1 H), 3.90-3.76 (m, 1 H), 3.02-2.95 (m, 2 H), 2.93 (s, 3 H), 2.73-2.64 (m, 2 H), 2.42-2.32 (m, 1 H), 2.20-2.09 (m, 1 H), 1.78 (s, 3 H), 1.58-1.51 (m, 2 H), 1.41 (s, 6H), 1.28 (d, J = 2.4 Hz, 2 H), 0.79-0.72 (m, 3 H). | Scheme 1, Intermediate 15 and Intermediate 24 |
| 101 | 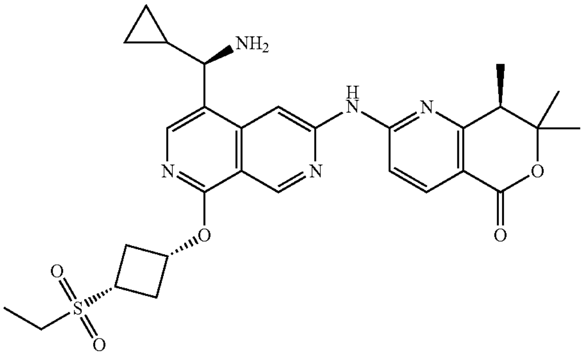 [SMILES: CCS(=O)(=O)[C@H]1C[C@@H](Oc2ncc([C@H](N)C3CC3)c3cc(Nc4ccc5c(n4)[C@@H](C)C(C)(C)OC5=O)ncc23)C1] or | 566 | $^1$H-NMR (400 MHz, $CD_3OD$): δ ppm 9.33 (s, 1H), 8.91 (s, 1H), 8.20 (s, 1H), 8.12 (d, J = 8.8 Hz, 1H), 7.21 (d, J = 8.4 Hz, 1H), 5.56-5.35 (m, 1H), 3.90-3.77 (m, 2H), 3.20-3.12 (m, 1H), 3.10-3.02 (m, 2H), 3.01-2.92 (m, 2H), 2.74-2.64 (m, 2H), 1.53 (s, 3H), 1.49 (d, J = 7.2 Hz, 3H), 1.44 (s, 4 H), 1.37-1.33 (m, 3H), 0.75-0.66 (m, 1H), 0.58-0.49 (m, 1H), 0.46-0.31 (m, 2H). | Scheme 2, Intermediate 3 and Intermediate 74 final compound derived from 1st eluting isomer by prep-HPLC Column: Phenomenex Gemini-NX C18 75 × 30 mm × 3 µm; Mobile phase: [water (0.05% |

TABLE 1-continued

| Cpd. # | Structure | LCMS (M + 1) | NMR | Synthetic Protocol |
|---|---|---|---|---|
| | 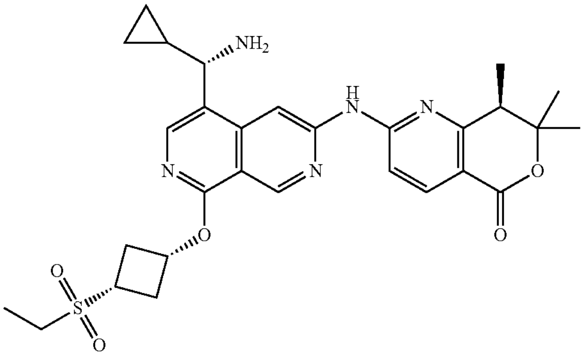 [SMILES: CCS(=O)(=O)[C@H]1C[C@@H](Oc2ncc([C@@H](N)C3CC3)c3cc(Nc4ccc5c(n4)[C@@H](C)C(C)(C)OC5=O)ncc23)C1] | | | ammonia hydroxide v/v)-ACN]; B %: 26%-56%) after Step 1 of Synthetic Method 2 |
| 102 | 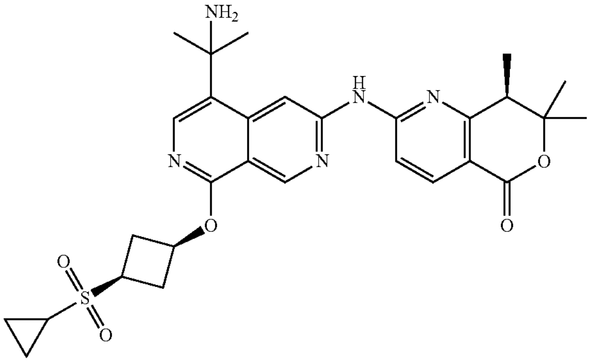 [SMILES: C[C@@H]1c2nc(Nc3cc4c(C(C)(C)N)cnc(O[C@H]5C[C@@H](S(=O)(=O)C6CC6)C5)c4cn3)ccc2C(=O)OC1(C)C] | 566 | $^1$H-NMR (400 MHz, $CD_3OD$): δ ppm 9.37 (s, 1H), 9.28 (s, 1H), 8.16-8.08 (m, 2H), 7.22 (d, J = 8.8 Hz, 1H), 5.53-534 (m, 1H), 3.93-3.77 (m, 1H), 3.06-2.91 (m, 3H), 2.75-2.64 (m, 2H), 2.61-2.51 (m, 1H), 1.86 (d, J = 8.8 Hz, 6H), 1.53 (s, 3H), 1.44 (s, 3H), 1.40 (d, J = 12 Hz, 3H), 1.17-1.04 (m, 4H) | Scheme 1, Intermediate 3 and Intermediate 32 |
| 103 | 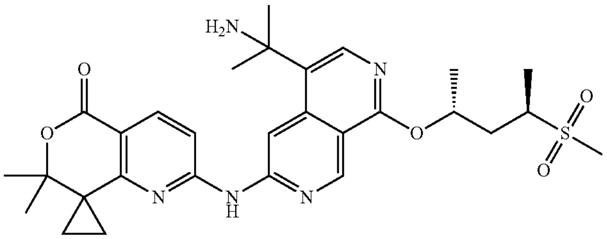 | 568 | $^1$H-NMR (400 MHz, $CD_3OD$): δ ppm 9.40 (s, 1H), 8.44 (s, 1H), 8.18-8.12 (m, 2H), 7.56 (d, J = 8.8 Hz, 1H), 5.74-5.65 (m, 1H), 3.41-3.32 (m, 1H), 2.93 (s, 3H), 2.45-2.37 (m, 1H), 2.16-2.08 (m, 1H), 1.78 (s, 6H), 1.59-1.54 (m, 2H), 1.52-1.46 (m, 6H), 1.44-1.37 (m, 6H), 1.31-1.26 (m, 2H). | Scheme 1, Intermediate 15 and Intermediate 52 |
| 104 | 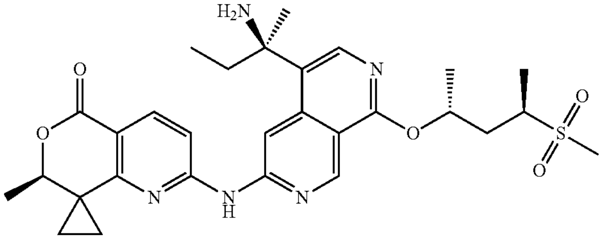 or 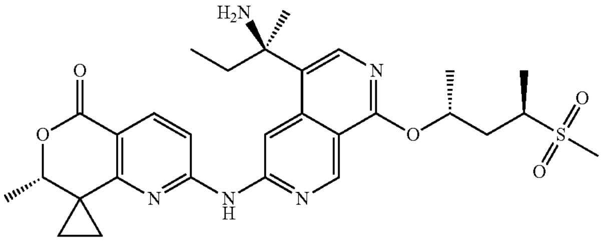 | 568 | $^1$H-NMR (400 MHz, $CD_3OD$): δ ppm 9.41 (s, 1H), 8.37 (s, 1H), 8.16 (d, J = 8.8 Hz, 1H), 8.09 (s, 1H), 7.59 (d, J = 8.8 Hz, 1H), 5.75-5.65 (m, 1H), 4.66-4.60 (m, 1H), 3.40-3.33 (m, 1H), 2.93 (s, 3H), 2.46-2.31 (m, 2H), 2.18-2.08 (m, 1H), 1.77 (s, 3H), 1.67-1.60 (m, 1H), 1.53-1.45 (m, 7H), 1.38 (d, J = 6.8 Hz, 3H), 1.27-1.18 (m, 2H), 0.76 (t, J = 7.2 Hz, 3H). | Scheme 1, Intermediate 12 and Intermediate 53 |

TABLE 1-continued

| Cpd. # | Structure | LCMS (M + 1) | NMR | Synthetic Protocol |
|---|---|---|---|---|
| 105 | 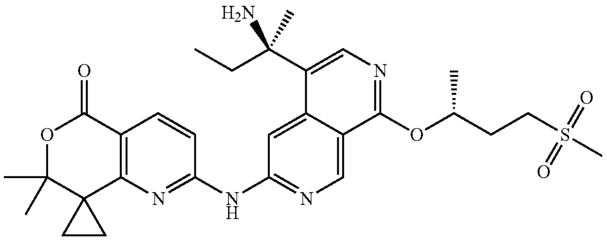 | 568 | $^1$H-NMR (400 MHz, $CD_3OD$): δ ppm 9.41 (s, 1H), 8.40 (s, 1H), 8.15 (d, J = 8.8 Hz, 1H), 8.13 (s, 1H), 7.58 (d, J = 8.8 Hz, 1H), 5.69-5.54 (m, 1H), 3.41-3.33 (m, 2H), 3.00 (s, 3H), 2.43-2.24 (m, 3H), 2.18-2.00 (m, 1H), 1.72 (s, 3H), 1.60-1.53 (m, 2H), 1.51 (d, J = 6.0 Hz, 3H), 1.42 (s, 6H), 1.28 (d, J = 2.8 Hz, 2H), 0.74 (t, J = 1.4 Hz, 3H). | Scheme 1, Intermediate 15 and Intermediate 31 |
| 106 | 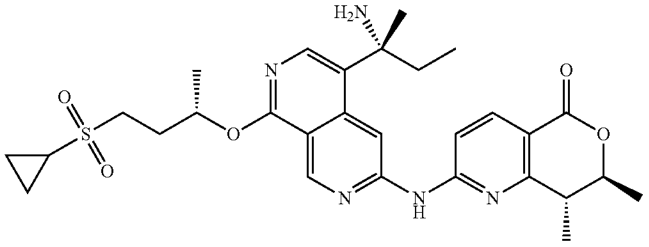 [SMILES: CC[C@@](C)(N)c1cnc(O[C@@H](C)CCS(=O)(=O)C2CC2)c2cnc(Nc3ccc4c(n3)[C@@H](C)[C@H](C)OC4=O)cc12] or 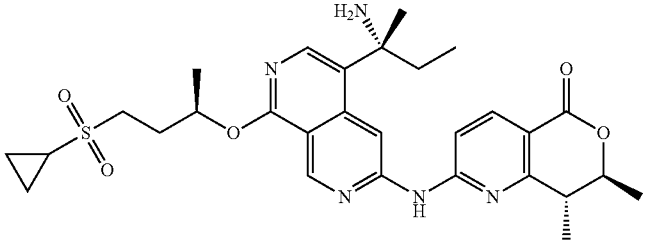 [SMILES: CC[C@@](C)(N)c1cnc(O[C@H](C)CCS(=O)(=O)C2CC2)c2cnc(Nc3ccc4c(n3)[C@@H](C)[C@H](C)OC4=O)cc12] | 568 | $^1$H-NMR (400 MHz, $CD_3OD$): δ ppm 9.39 (s, 1H), 9.15 (s, 1H), 8.18-8.11 (m, 2H), 7.30 (d, J = 8.4 Hz, 1H), 5.68-5.59 (m, 1H), 4.71-4.64 (m, 1H), 3.40-3.33 (m, 2H), 3.07-2.97 (m, 1H), 2.70-2.60 (m, 1H), 2.44-2.33 (m, 3H), 2.22-2.11 (m, 1H), 1.75 (s, 3H), 1.53-1.48 (m, 6H), 1.46 (d, J = 6.4 Hz, 3H), 1.14-1.03 (m, 4H), 0.74 (t, J = 7.2 Hz, 3H). | Scheme 1. Intermediate 1 and Intermediate 75 2nd eluting isomer from chiral SFC Column: Daicel Chiralpak AD(250 mm × 30 mm, 10 μm); Mobile phase: [0.1% $NH_3H_2O$ ETOH]; B %: 50%-50%) |
| 107 | 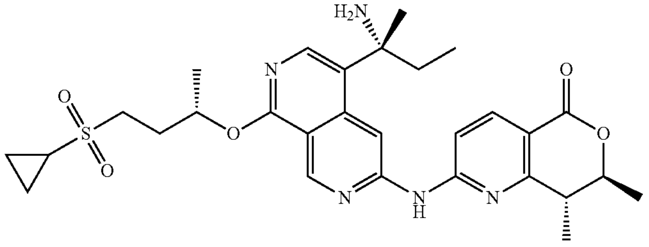 [SMILES: CC[C@@](C)(N)c1cnc(O[C@@H](C)CCS(=O)(=O)C2CC2)c2cnc(Nc3ccc4c(n3)[C@@H](C)[C@H](C)OC4=O)cc12] or 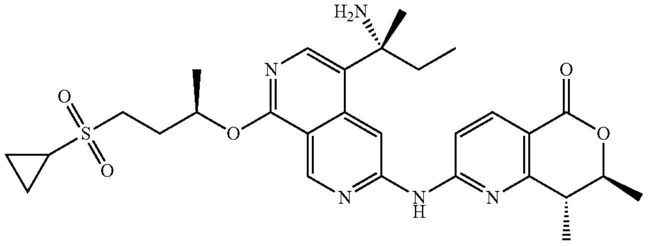 [SMILES: CC[C@@](C)(N)c1cnc(O[C@H](C)CCS(=O)(=O)C2CC2)c2cnc(Nc3ccc4c(n3)[C@@H](C)[C@H](C)OC4=O)cc12] | 568 | $^1$H-NMR (400 MHz, $CD_3OD$): δ ppm 9.39 (s, 1H), 9.17 (s, 1H), 8.18-8.12 (m, 2H), 7.30 (d, J = 8.8 Hz, 1H), 5.67-5.59 (m, 1H), 4.71-4.64 (m, 1H), 3.38-3.32 (m, 2H), 3.08-2.99 (m, 1H), 2.71-2.62 (m, 1H), 2.43-2.32 (m, 3H), 2.21-2.10 (m, 1H), 1.75 (s, 3H), 1.53-1.48 (m, 6H), 1.46 (d, J = 6.8 Hz, 3H), 1.16-1.09 (m, 2H), 1.08-1.02 (m, 2H), 0.74 (t, J = 7.2 Hz, 3H). | Scheme 1. Intermediate 1 and Intermediate 75 1st eluting isomer from chiral SFC Column: Daicel Chiralpak AD(250 mm × 30 mm, 10 μm); Mobile phase: [0.1% $NH_3H_2O$ ETOH]; B %: 50%-50%) |

TABLE 1-continued

| Cpd. # | Structure | LCMS (M + 1) | NMR | Synthetic Protocol |
| --- | --- | --- | --- | --- |
| 108 | 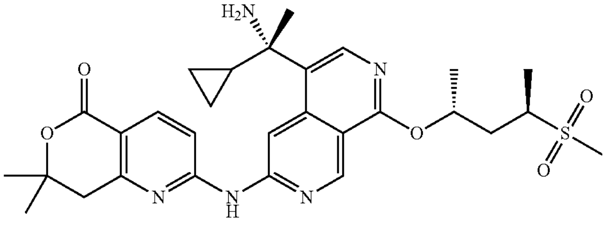<br>or<br>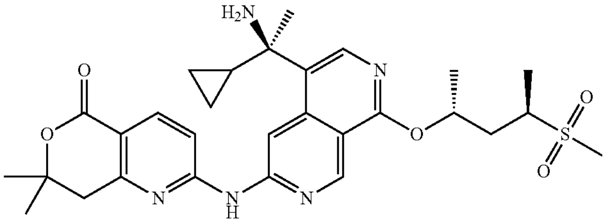 | 568 | $^1$H-NMR (400 MHz, $CD_3OD$): δ ppm 9.46 (s, 1H), 9.36 (s, 1H), 8.30 (s, 1H), 8.14 (d, J = 8.8 Hz, 1H), 7.23 (d, J = 8.8 Hz, 1H), 5.75-5.65 (m, 1H), 3.40-3.34 (m, 1H), 3.21 (s, 2H), 2.94 (s, 3H), 2.46-2.38 (m, 1H), 2.18-2.09 (m, 1H), 1.70 (s, 3H), 1.65-1.59 (m, 1H), 1.55-1.48 (m, 12H), 0.70-0.49 (m, 4H). | Scheme 1, intermediate 5 and Intermediate 76 |
| 109 | 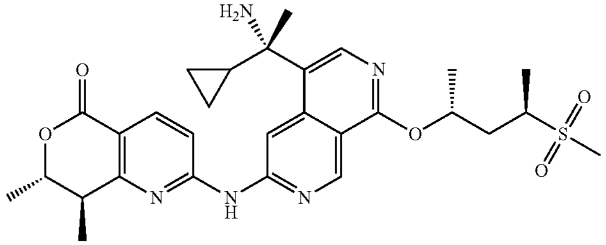<br>or<br>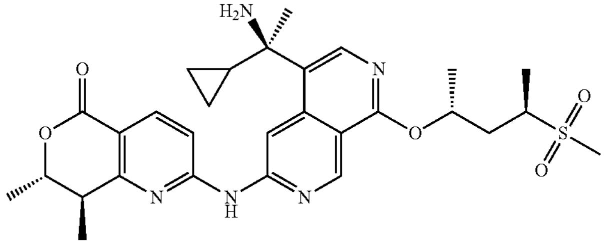 | 568 | $^1$H-NMR (400 MHz, $CD_3OD$): δ ppm 9.37 (s, 1H), 9.28 (s, 1H), 8.29 (s, 1H), 8.14 (d, J = 8.8 Hz, 1H), 7.35 (d, J = 8.8 Hz, 1H), 5.74-5.65 (m, 1H), 4.69-4.60 (m, 1H), 3.40-3.34 (m, 1H), 3.06-2.98 (m, 1H), 2.93 (s, 3H), 2.46-2.38 (m, 1H), 2.17-2.08 (m, 1H), 1.70-1.60 (m, 4H), 1.53-1.44 (m, 12H), 0.66-0.43 (m, 4H). | Scheme 1, intermediate 5 and Intermediate 76 |
| 110 | 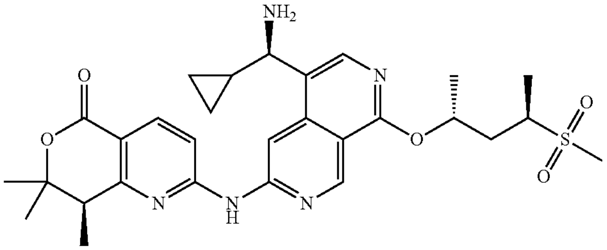<br>or | 568 | $^1$H-NMR (400 MHz, $CD_3OD$): δ ppm 9.41 (s, 1H), 8.69 (s, 1H), 8.53 (s, 1H), 8.35 (s, 1H), 8.15 (br d, J = 8.6 Hz, 1H), 7.34 (d, J = 8.6 Hz, 1H), 5.83-5.71 (m, 1H), 4.27 (br d, J = 8.8 Hz, 1H), 3.44-3.37 (m, 1H), 3.23-3.12 (m, 1H), 2.96 (s, 3H), 2.45 (td, J = 5.0, 14.4 Hz, 1H), 2.17 (td, J = 7.6, 14.8 Hz, 1H), 1.68 (br d, J = 2.4 Hz, 1H), 1.58-1.49 (m, 12H), 1.45 (s, 3H), 0.97-0.88 (m, 1H), 0.76 (br t, J = 8.4 Hz, 1H), 0.57 (br s, 2H) | Scheme 1, intermediate 3 and Intermediate 78 |

TABLE 1-continued

| Cpd. # | Structure | LCMS (M + 1) | NMR | Synthetic Protocol |
|---|---|---|---|---|
| | 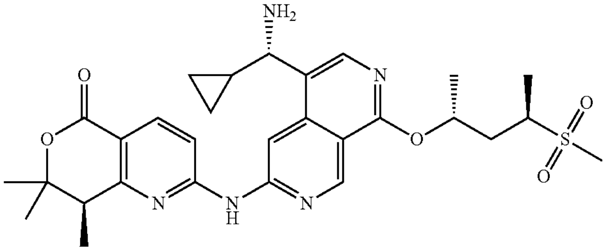 | | | |
| 111 | 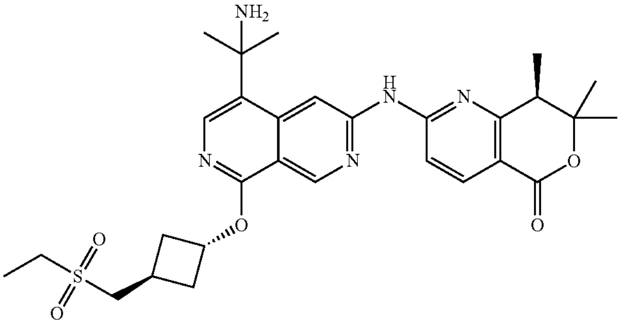 [SMILES: CCS(=O)(=O)C[C@H]1C[C@H](Oc2ncc(C(C)(C)N)c3cc(Nc4ccc5c(n4)[C@@H](C)C(C)(C)OC5=O)ncc23)C1] | 568 | $^1$H-NMR (400 MHz, $CD_3OD$): δ ppm 9.41 (s, 1H), 9.11 (s, 1H), 8.15 (d, J = 8.8 Hz, 1H), 7.98 (s, 1H), 7.29 (d, J = 8.8 Hz, 1H), 5.39 (q, J = 7.4 Hz, 1H), 3.38-3.32 (m, 2H), 3.08 (q, J = 7.6 Hz, 2H), 3.00 (q, J = 7.2 Hz, 1H), 2.91 (dtd, J = 2.8, 7.2, 9.6 Hz, 2H), 2.70-2.55 (m, 1H), 2.24-2.13 (m, 2H), 2.02 (d, J = 13.0 Hz, 6H), 1.53 (s, 3H), 1.45 (s, 3H), 1.42-1.33 (m, 6H) | Scheme 1, Intermediate 3 and Intermediate 80 2nd eluting isomer from chiral SFC Column: DAICEL CHIRALPAK AD(250 mm* 30 mm, 10 um); Mobile phase: [ACN/EtOH (0.1% $NH_3H_2O$)]; B %: 50%-50%) |
| 112 | 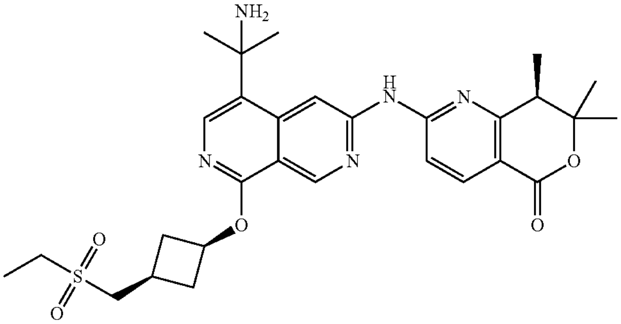 [SMILES: CCS(=O)(=O)C[C@H]1C[C@@H](Oc2ncc(C(C)(C)N)c3cc(Nc4ccc5c(n4)[C@@H](C)C(C)(C)OC5=O)ncc23)C1] | 568 | $^1$H-NMR (400 MHz, $CD_3OD$): δ ppm 9.41 (s, 1H), 9.30 (s, 1H), 8.18-8.07 (m, 2H), 7.23 (d, J = 8.8 Hz, 1H), 5.55 (t, J = 6.0 Hz, 1H), 3.39 (d, J = 7.6 Hz, 2H), 3.15-2.98 (m, 4H), 2.65-2.56 (m, 4H), 1.85 (d, J = 8.8 Hz, 6H), 1.54 (s, 3H), 1.46 (s, 3H), 1.42-1.35 (m, 6H) | Scheme 1, Intermediate 3 and Intermediate 80 1st eluting isomer from chiral SFC Column: DAICEL CHIRALPAK AD(250 mm* 30 mm, 10 um); Mobile phase: [ACN/EtOH (0.1% $NH_3H_2O$)]; B %: 50%-50%) |
| 113 | 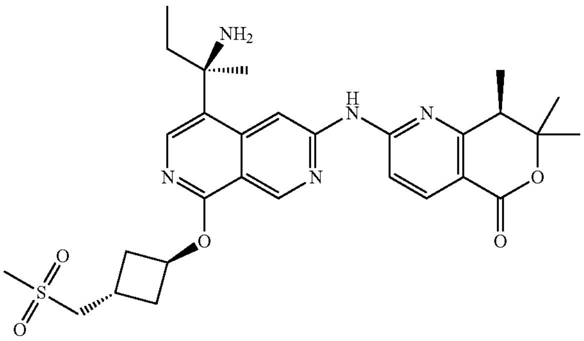 | 568 | $^1$H-NMR (400 MHz, $CD_3OD$): δ ppm 9.39 (s, 1H), 9.35 (s, 1H), 8.15-8.10 (m, 2H), 7.20 (d, J = 8.4 Hz, 1H), 5.58-5.55 (m, 1H), 3.43 (d, J = 7.46 Hz, 2H), 3.12-2.99 (m, 2H), 2.97 (s, 3H), 2.64-2.57 (m, 4 H), 2.40-2.30 (m, 1H), 2.24-2.14 (m, 1H), 1.73 (s, 3H), 1.54 (s, 3H), 1.45 (s, 3H), 1.38 (d, J = 7.2 Hz, 3H), 0.78-0.68 (m, 3H). | Scheme 1, Intermediate 3 and Intermediate 49 |

TABLE 1-continued

| Cpd. # | Structure | LCMS (M + 1) | NMR | Synthetic Protocol |
|---|---|---|---|---|
| 114 | 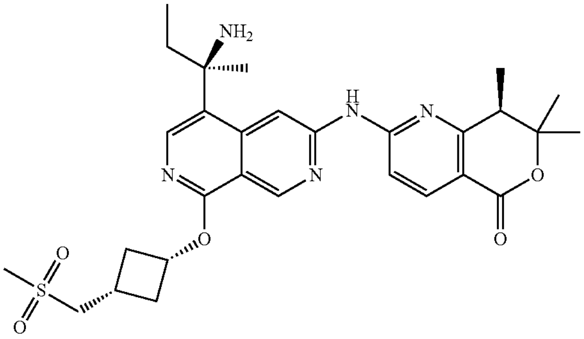 | 568 | $^1$H-NMR (400 MHz, 6d-DMSO): δ ppm 10.73 (s, 1H), 9.50 (s, 1H), 9.30 (s, 1H), 8.17-8.13 (m, 1H), 8.07 (d, J = 8.8 Hz, 1H), 7.31 (d, J = 8.8 Hz, 1H), 5.33-5.23 (m, 1H), 3.36 (d, J = 7.6 Hz, 2H), 3.01-2.96 (m, 1H), 2.94 (s, 3H), 2.82-2.72 (m, 2H), 2.17-2.01 (m, 5 H), 1.63-1.56 (m, 3H), 1.44 (s, 3H), 1.37 (s, 3H), 1.33-1.25 (m, 3H), 0.68-0.61 (m, 3H). | Scheme 1, Intermediate 3 and Intermediate 48 |
| 115 | 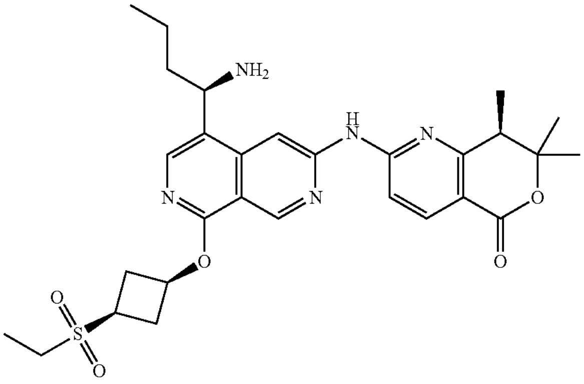 [SMILES: CCC[C@@H](N)c1cnc(O[C@H]2C[C@@H](S(=O)(=O)CC)C2)c2cnc(Nc3ccc4c(n3)[C@@H](C)C(C)(C)OC4=O)cc12] or 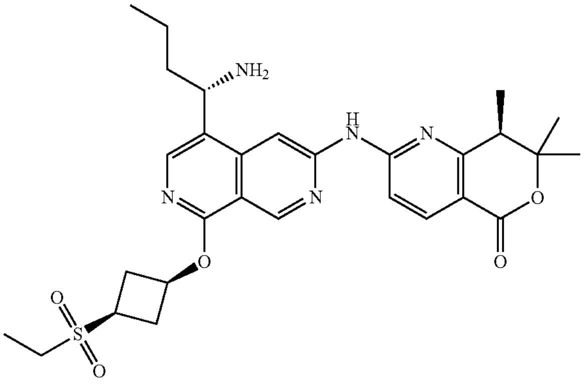 [SMILES: CCC[C@H](N)c1cnc(O[C@H]2C[C@@H](S(=O)(=O)CC)C2)c2cnc(Nc3ccc4c(n3)[C@@H](C)C(C)(C)OC4=O)cc12] | 568 | $^1$H-NMR (400 MHz, $CD_3OD$): δ ppm 9.31 (s, 1H), 8.83 (s, 1H), 8.14-8.06 (m, 2H), 7.22 (d, J = 8.4 Hz, 1H), 5.46-5.38 (m, 1H), 4.48-4.44 (m, 1H), 3.92-3.73 (m, 1H), 3.16-3.10 (m, 1H), 3.09-3.02 (m, 2H), 3.00-2.91 (m, 2H), 2.75-2.63 (m, 2H), 2.03-1.78 (m, 2H), 1.51 (s, 3H), 1.48 (d, J = 7.2 Hz, 3H), 1.44 (s, 3H), 1.42-1.26 (m, 5H), 0.99-0.93 (m, 3H). | Scheme 1, Intermediate 3 and Intermediate 81 |
| 116 | 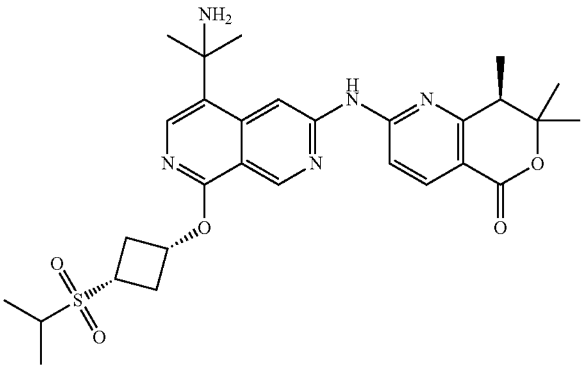 [SMILES: CC(C)S(=O)(=O)[C@H]1C[C@@H](Oc2ncc(C(C)(C)N)c3cc(Nc4ccc5c(n4)[C@@H](C)C(C)(C)OC5=O)ncc23)C1] | 568 | $^1$H-NMR (400 MHz, $CD_3OD$): δ ppm 9.38 (s, 1H), 9.31 (s, 1H), 8.15-8.10 (m, 2H), 7.23 (d, J = 8.8 Hz, 1H), 5.48-5.40 (m, 1H), 3.95-3.80 (m, 1H), 3.24-3.20 (m, 1H), 3.05-2.95 (m, 3H), 2.71-2.60 (m, 2H), 1.85 (d, J = 8.8 Hz, 6H), 1.54 (s, 3H), 1.45 (s, 3H), 1.40 (d, J = 7.2 Hz, 3H), 1.36 (d, J = 6.8 Hz, 6H). | Scheme 1, Intermediate 3 and Intermediate 83 |

TABLE 1-continued

| Cpd. # | Structure | LCMS (M + 1) | NMR | Synthetic Protocol |
|---|---|---|---|---|
| 117 | 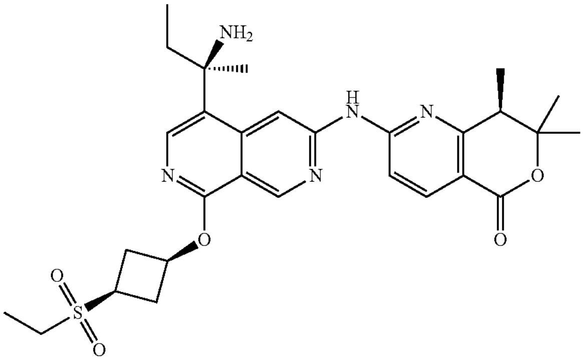 [SMILES: CC[C@@](C)(N)c1cnc(O[C@H]2C[C@@H](S(=O)(=O)CC)C2)c2cnc(Nc3ccc4c(n3)[C@@H](C)C(C)(C)OC4=O)cc12] | 568 | $^1$H-NMR (400 MHz, $CD_3OD$): δ ppm 9.35 (s, 2H), 8.15-8.11 (m, 2H), 7.19 (d, J = 8.8 Hz, 1H), 5.47-5.40 (m, 1H), 3.87-3.78 (m, 1H), 3.09-3.02 (m, 3H), 3.00-2.93 (m, 2H), 2.73-2.65 (m, 2H), 2.42-2.30 (m, 1H), 2.22-2.09 (m, 1H), 1.73 (d, J = 6.0 Hz, 3H), 1.54 (s, 3H), 1.45 (s, 3H), 1.40-1.33 (m, 6H), 0.75-0.71 (m, 3H). | Scheme 1, Intermediate 3 and Intermediate 45 |
| 118 | 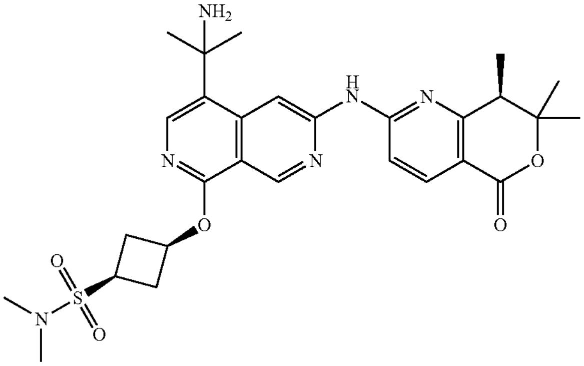 | 569 | $^1$H-NMR (400 MHz, $CD_3OD$): δ ppm 9.43 (s, 1H), 9.21 (s, 1H), 8.52 (s, 1H), 8.16 (d, J = 8.4 Hz, 1H), 8.05 (s, 1H), 7.28 (d, J = 8.4 Hz, 1H), 5.44-5.40 (m, 1H), 3.80-3.75 (m, 1H), 3.08-3.92 (m, 3H), 2.89 (s, 6H), 2.75-2.66 (m, 2H), 1.97 (d, J = 9.8 Hz, 6H), 1.54 (s, 3H), 1.46 (s, 3H), 1.41 (d, J = 7.2 Hz, 3H). | Scheme 1, Intermediate 3 and Intermediate 64 |
| 119 | 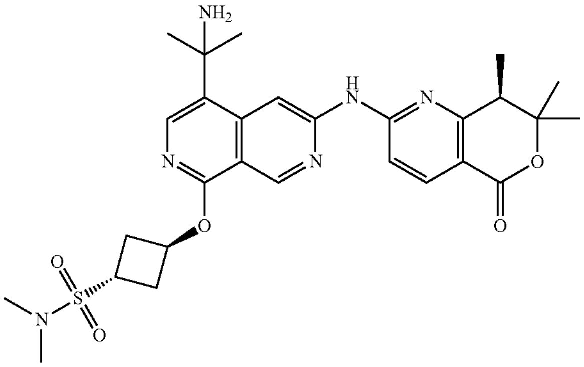 | 569 | $^1$H-NMR (400 MHz, $CD_3OD$): δ ppm 9.42 (s, 1H), 9.29 (s, 1H), 8.55 (s, 1H), 8.14 (d, J = 8.8 Hz, 1H), 8.10 (s, 1H), 7.24 (d, J = 8.8 Hz, 1H), 5.67-5.61 (m, 1H), 4.16-4.07 (m, 1H), 3.10-2.98 (m, 3H), 2.82-2.73 (m, 2H), 1.87 (d, J = 9.2 Hz, 6H), 1.54 (s, 3H), 1.45 (s, 3H), 1.40 (d, J = 7.6 Hz, 3H). | Scheme 1, Intermediate 3 and Intermediate 63 |
| 120 | 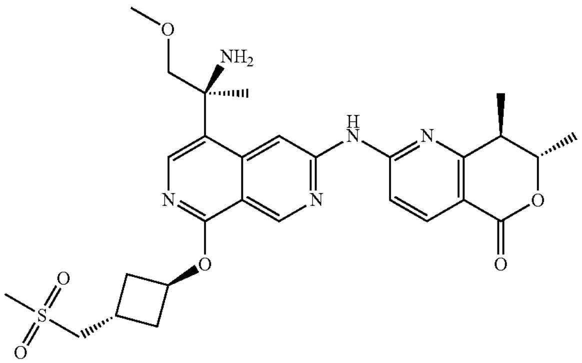 | 570 | $^1$H-NMR (400 MHz, $CD_3OD$): δ ppm 9.41 (s, 1H), 8.98 (s, 1H), 8.51 (s, 1H), 8.13 (d, J = 8.8 Hz, 1H), 7.99 (s, 1H), 7.33 (d, J = 4.8 Hz, 1H), 5.56-5.50 (m, 1H), 4.68-4.63 (m, 1H), 4.00 (s, 2H), 3.41 (d, J = 7.6 Hz, 1H), 3.37 (s, 3H), 3.31-2.97 (m, 2H), 2.96 (s, 3H), 2.59 (t, J = 6.4 Hz, 4H), 1.88 (s, 3H), 1.47 (dd, J = 10, 7.2 Hz, 6H). | Scheme 1, Intermediate 1 and Intermediate 51 |

TABLE 1-continued

| Cpd. # | Structure | LCMS (M + 1) | NMR | Synthetic Protocol |
|---|---|---|---|---|
| 121 | 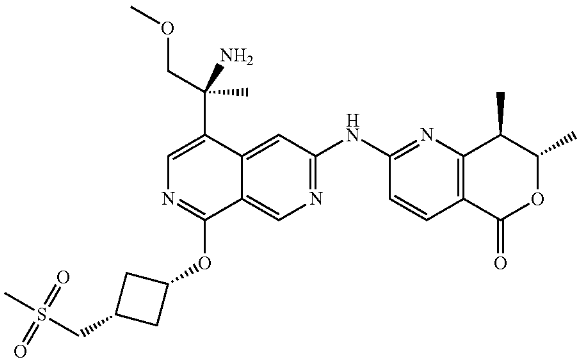 | 570 | $^1$H-NMR (400 MHz, $CD_3OD$): δ ppm 9.39 (s, 1H), 9.09 (s, 1H), 8.51 (s, 1H), 8.17 (d, J = 8.8 Hz, 1H), 8.07 (s, 1H), 7.35 (d, J = 8.8 Hz, 1H), 5.40-5.36 (m, 1H), 4.71-4.65 (m, 1H), 4.00-3.90 (m, 2H), 3.39 (s, 1H), 3.38 (s, 3H), 3.37 (s, 1H), 3.06-3.01 (m, 1H), 2.97 (s, 3H), 2.95-2.87 (m, 2H), 2.66-2.61 (m, 1H), 2.22-2.15 (m, 2H), 1.84 (s, 3H), 1.50 (dd, J = 12.4, 7.2 Hz, 6H). | Scheme 1, Intermediate 1 and Intermediate 50 |
| 122 | 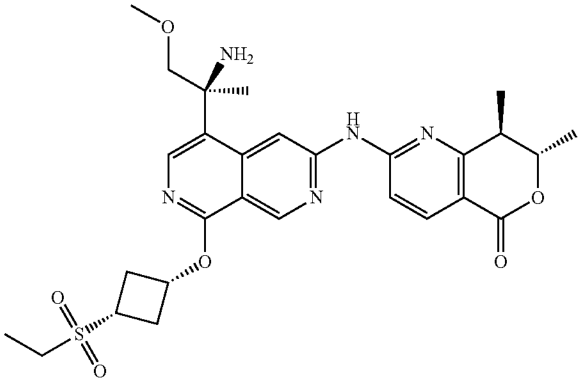 [SMILES: CCS(=O)(=O)[C@H]1C[C@@H](Oc2ncc([C@](C)(N)COC)c3cc(Nc4ccc5c(n4)[C@@H](C)[C@H](C)OC5=O)ncc23)C1] | 570 | $^1$H-NMR (400 MHz, $CD_3OD$): δ ppm 9.37 (s, 1H), 9.12 (s, 1H), 8.15 (d, J = 8.8 Hz, 1H), 8.11-8.08 (m, 1H), 7.32 (d, J = 8.8 Hz, 1H), 5.44 (J = 7.2 Hz, 1H), 4.72-4.63 (m, 1H), 4.58 (s, 1H), 4.03-3.88 (m, 2H), 3.87-3.78 (m, 1H), 3.36 (s, 3H), 3.06 (q, J = 7.6 Hz, 2H), 3.03-2.91 (m, 3H), 2.74-2.64 (m, 2H), 1.80 (s, 3H), 1.49 (dd, J = 6.8, 13.2 Hz, 6H), 1.35 (t, J = 7.6 Hz, 3H) | Scheme 1, Intermediate 1 and Intermediate 84 |
| 123 | 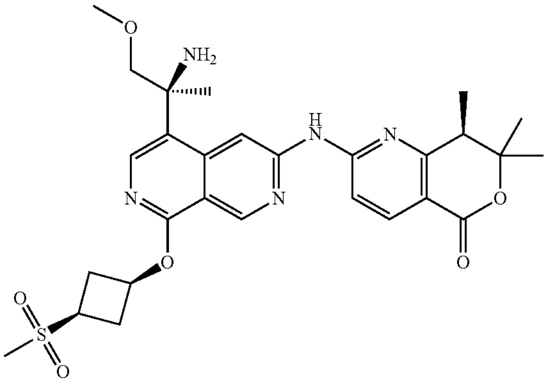 | 570 | $^1$H-NMR (400 MHz, $CD_3OD$): δ ppm 9.37 (s, 1H), 9.33 (s, 1H), 8.15-8.10 (m, 2H), 7.22 (d, J = 8.8 Hz, 1H), 5.48-5.40 (m, 1H), 3.95 (s, 2H), 3.85-3.80 (m, 1H), 3.37 (s, 3H), 3.05-2.95 (m, 6H), 2.70-2.65 (m, 2H), 1.80 (s, 3H), 1.54 (s, 3H), 1.47-1.35 (m, 6H). | Scheme 1, Intermediate 3 and Intermediate 85 |
| 124 | 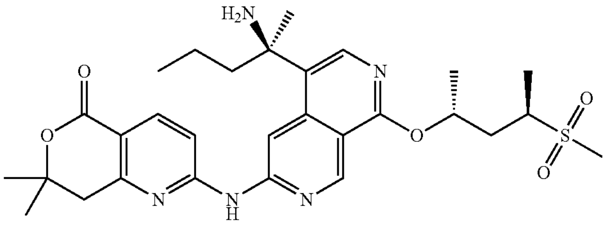 or | 570 | $^1$H-NMR (400 MHz, $CD_3OD$): δ ppm 9.38 (s, 1H), 9.32 (s, 1H), 8.15 (d, J = 8.8 Hz, 1H), 8.09 (s, 1H),7.21 (d, J = 8.8 Hz, 1H), 5.77-5.65 (m, 1H), 3.36 (m, 1H), 3.23 (s, 2H), 2.93 (s, 3H), 2.49-2.36 (m, 2H), 2.24-2.07 (m, 2H), 1.83 (s, 3H), 1.53 (d, J = 2.4 Hz, 6H), 1.50 (m, 6H), 1.27 (m, 1H), 1.10-0.97 (m, 1H), 0.88-0.82 (m, 3H). | Scheme 1, Intermediate 5 and Intermediate 67 |

TABLE 1-continued

| Cpd. # | Structure | LCMS (M + 1) | NMR | Synthetic Protocol |
|---|---|---|---|---|
| | 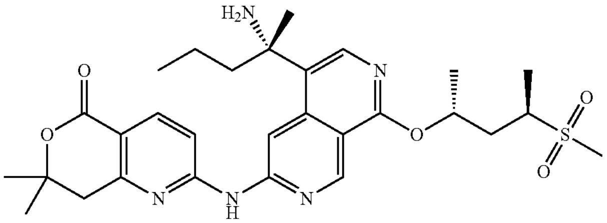 | | | |
| 125 | 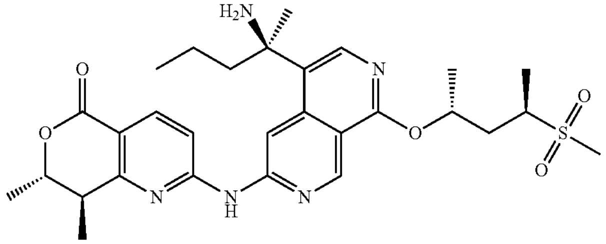 or 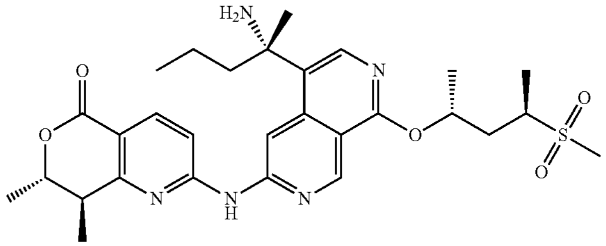 | 570 | $^1$H-NMR (400 MHz, $CD_3OD$): δ ppm 9.43 (s, 1H), 9.06 (s, 1H), 8.54 (s, 1H), 8.17 (d, J = 8.8 Hz, 1H), 8.01 (s, 1H), 7.37 (d, J = 8.4 Hz, 1H), 5.79-5.66 (m, 1H), 4.76-4.64 (m, 1H), 3.42-3.34 (m, 1H), 3.07-2.97 (m, 1H), 2.94 (s, 3H), 2.66-2.52 (m, 1H), 2.42 (m, 1H), 2.23-2.09 (m, 2H), 1.92 (s, 3H), 1.57-1.48 (m, 9H) 1.46 (d, J = 6.4 Hz, 3H), 1.38-1.27 (m, 1H), 1.07-0.93 (m, 1H), 0.91-0.82 (m, 3H). | Scheme 1, Intermediate 1 and Intermediate 67 |
| 126 | 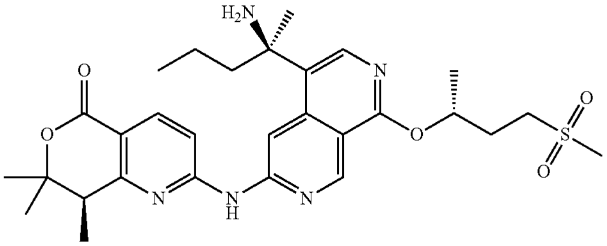 or 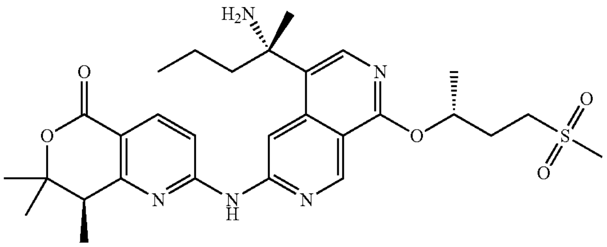 | 570 | $^1$H-NMR (400 MHz, $CD_3OD$): δ ppm 9.40 (d, J = 15.2 Hz, 2H), 8.17-8.12 (m, 2H), 7.19 (d, J = 8.8 Hz, 1H), 5.64-5.59 (m, 1H), 3.37-3.33 (m, 1H), 3.09-3.04 (m, 1H), 3.00 (s, 3H), 2.41-2.30 (m, 3H), 2.15-2.07 (m, 1H), 1.73 (s, 3H), 1.55 (s, 3H), 1.51 (d, J = 6.0 Hz, 3H), 1.44 (s, 3H), 1.40 (d, J = 6.8 Hz, 3H), 1.36-1.17 (m, 2H), 1.05-0.96 (m, 1H), 0.84-0.80 (m, 3H). | Scheme 1, Intermediate 3 and Intermediate 69 |
| 127 | 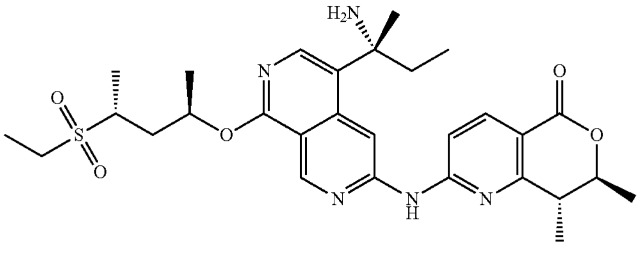 [SMILES: CC[C@@](C)(N)c1cnc(O[C@H](C)C[C@@H](C)S(=O)(=O)CC)c2cnc(Nc3ccc4c(n3)[C@@H](C)[C@H](C)OC4=O)cc12] | 570 | $^1$H-NMR (400 MHz, $CD_3OD$): δ ppm 9.36 (s, 1H), 9.15 (s, 1H), 8.28-8.00 (m, 2H), 7.29 (d, J = 8.8 Hz, 1H), 5.80-5.61 (m, 1H), 4.73-4.56 (m, 1H), 3.45-3.35 (m, 1H), 3.14-3.06 (m, 2H), 3.06-2.98 (m, 1H), 2.49-2.30 (m, 2H), 2.23-2.03 (m, 2H), 1.73 (s, 3H), 1.51-1.43 (m, 12H), 1.34-1.27 (m, 3H), 0.78-0.68 (m, 3H). | Scheme 1, Intermediate 1 and Intermediate 86 |

TABLE 1-continued

| Cpd. # | Structure | LCMS (M + 1) | NMR | Synthetic Protocol |
| --- | --- | --- | --- | --- |
| 128 | 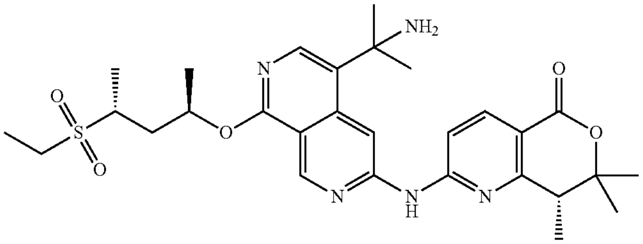 [SMILES: CCS(=O)(=O)[C@H](C)C[C@@H](C)Oc1ncc(C(C)(C)N)c2cc(Nc3ccc4c(n3)[C@@H](C)C(C)(C)OC4=O)ncc12] | 570 | $^1$H-NMR (400 MHz, $CD_3OD$): δ ppm 9.36 (d, J = 3.2 Hz, 2H), 8.20 (s, 1H), 8.12 (d, J = 8.8 Hz, 1H), 7.22 (d, J = 8.8 Hz, 1H), 5.74-5.63 (m, 1H), 3.43-3.34 (m, 1H), 3.14-2.99 (m, 3H), 2.45-2.36 (m, 1H), 2.19-2.06 (m, 1H), 1.80 (d, J = 7.6 Hz, 6H), 1.53 (s, 3H), 1.50-1.46 (m, 6H), 1.45 (s, 3H), 1.39 (d, J = 7.2 Hz, 3H), 1.33-1.28 (m, 3H). | Scheme 1, Intermediate 3 and Intermediate 70 |
| 129 | 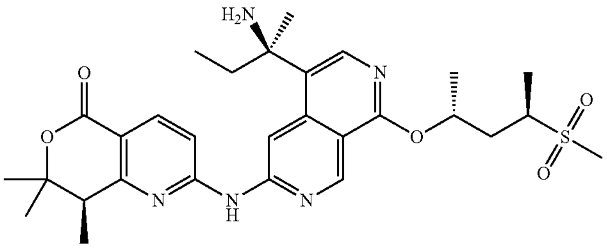 | 570 | $^1$H-NMR (400 MHz, $CD_3OD$): δ ppm 9.40 (s, 1H), 9.28 (s, 1H), 8.14 (d, J = 8.4 Hz, 1H), 8.11 (s, 1H), 7.24 (d, J = 8.8 Hz, 1H), 5.75-5.66 (m, 1H), 3.42-3.35 (m, 1H), 3.05-2.99 (m, 1H), 2.93 (s, 3H), 2.54-2.38 (m, 2H), 2.30-2.20 (m, 1H), 2.18-2.08 (m, 1H), 1.82 (s, 3H), 1.58-1.48 (m, 9H), 1.46 (s, 3H), 1.39 (d, J = 7.2 Hz, 3H), 0.78 (t, J = 7.2 Hz, 3H). | Scheme 1, Intermediate 3 and Intermediate 53 |
| 130 | 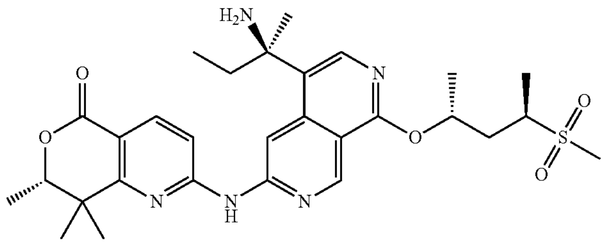<br>or<br>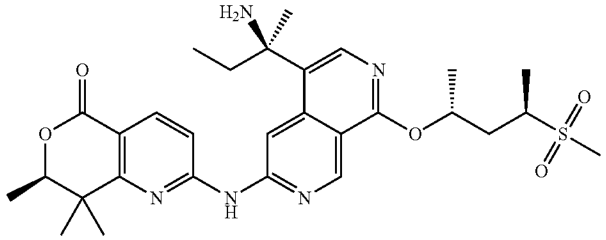 | 570 | $^1$H-NMR (400 MHz, $CD_3OD$): δ ppm 9.41 (s, 1H), 8.59 (s, 1H), 8.16 (d, J = 8.8 Hz, 1H), 8.14 (s, 1H), 7.57 (d, J = 8.8 Hz, 1H), 5.75-5.60 (m, 1H), 4.63-4.53 (m, 1H), 3.41-3.33 (m, 1H), 2.93 (s, 3H), 2.47-2.31 (m, 2H), 2.18-2.02 (m, 2H), 1.75 (s, 3H), 1.53-1.42 (m, 12H), 1.31 (s, 3H), 0.76-0.70 (m, 3H). | Scheme 1, Intermediate 97 and Intermediate 53 |

TABLE 1-continued

| Cpd. # | Structure | LCMS (M + 1) | NMR | Synthetic Protocol |
|---|---|---|---|---|
| 131 | 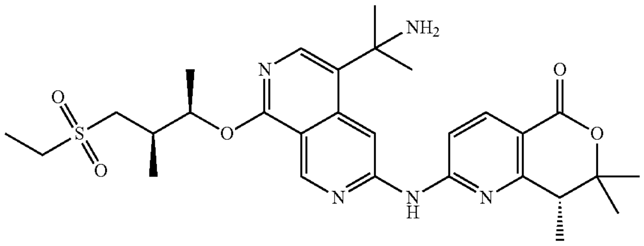 [SMILES: CCS(=O)(=O)C[C@H](C)[C@@H](C)Oc1ncc(C(C)(C)N)c2cc(Nc3ccc4c(n3)[C@@H](C)C(C)(C)OC4=O)ncc12]<br>or<br>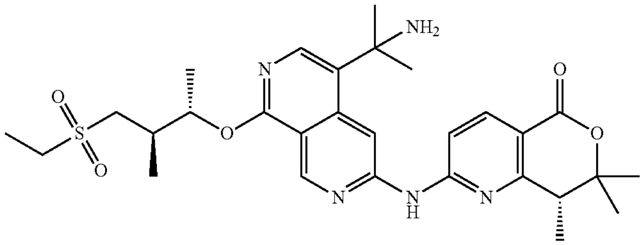 [SMILES: CCS(=O)(=O)C[C@H](C)[C@H](C)Oc1ncc(C(C)(C)N)c2cc(Nc3ccc4c(n3)[C@@H](C)C(C)(C)OC4=O)ncc12]<br>or<br>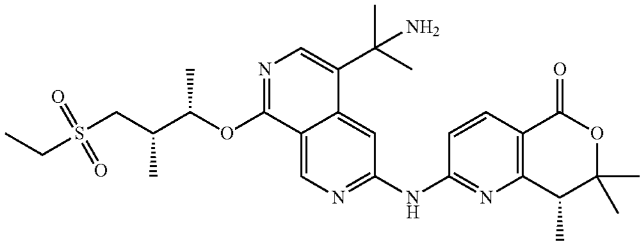 [SMILES: CCS(=O)(=O)C[C@@H](C)[C@H](C)Oc1ncc(C(C)(C)N)c2cc(Nc3ccc4c(n3)[C@@H](C)C(C)(C)OC4=O)ncc12]<br>or<br>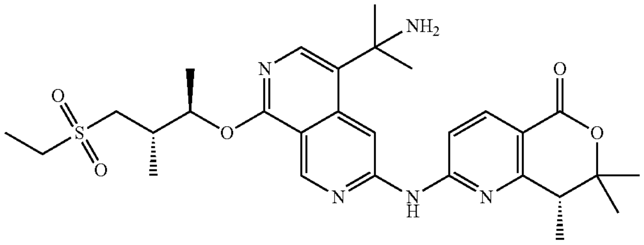 [SMILES: CCS(=O)(=O)C[C@@H](C)[C@@H](C)Oc1ncc(C(C)(C)N)c2cc(Nc3ccc4c(n3)[C@@H](C)C(C)(C)OC4=O)ncc12] | 570 | $^1$H-NMR (400 MHz, $CD_3OD$): δ = 9.29 (s, 1H), 9.22 (s, 1H), 8.06 (d, J = 8.8 Hz, 1H), 8.02 (s, 1H), 7.14 (d, J = 8.8 Hz, 1H), 5.45-5.33 (m, 1H), 3.37-3.30 (m, 1H), 3.08-3.06 (m, 2H), 2.96-2.92 (m, 2H), 2.62-2.55 (m, 1H), 1.75 (d, J = 7.6 Hz, 7H), 1.44 (s, 3H), 1.35 (d, J = 8.4 Hz, 6H), 1.29 (d, J = 7.2 Hz, 3H), 1.27-1.26 (m, 3H), 1.22 (d, J = 7.2 Hz, 3H) | Scheme 1, Intermediate 3 and Intermediate 87 1st peak of 3 from chiral SFC Column: Daicel Chiralpak AS(250 mm* 30 mm, 10 um); Mobile phase: [0.1% NH3H2O ETOH]; B %: 40%-40%), then second eluting isomer after an additional chiral SFC Column: Phcnomencx-Ccllulose-2 (250 mm*30 mm, 10 um); Mobile phase: [0.1% NH3H2O MEOH]; B %: 50%-50%) |
| 132 | or | 570 | $^1$H-NMR (400 MHz, $CD_3OD$): δ ppm 9.43 (s, 1H), 9.20 (s, 1H), 8.15 (d, J = 8.8 Hz, 1H), 8.04 (s, 1H), 7.26 (d, J = 8.4 Hz, 1H), 5.71-5.57 (m, 1H), 3.30-3.23 (m, 2H), 3.17-3.08 (m, 2H), 3.04-2.94 (m, 1H), 2.64-2.51 (m, 1H), 2.42-2.24 (m, 3H), 1.94-1.87 (m, 3H), 1.57-1.49 (m, 6H), 1.48-1.43 (m, 3H), 1.42-1.37 (m, 3H), 1.34 (t, J = 7.4 Hz, 3H), 0.81 (t, J = 7.6 Hz, 3H). | Scheme 1, Intermediate 3 and Intermediate 73 |

TABLE 1-continued

| Cpd. # | Structure | LCMS (M + 1) | NMR | Synthetic Protocol |
|---|---|---|---|---|
| | 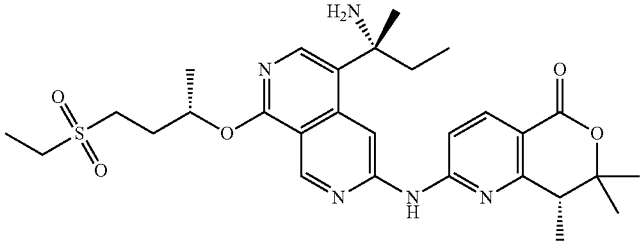 [SMILES: CC[C@@](C)(N)c1cnc(O[C@@H](C)CCS(=O)(=O)CC)c2cnc(Nc3ccc4c(n3)[C@@H](C)C(C)(C)OC4=O)cc12] | | | |
| 133 | 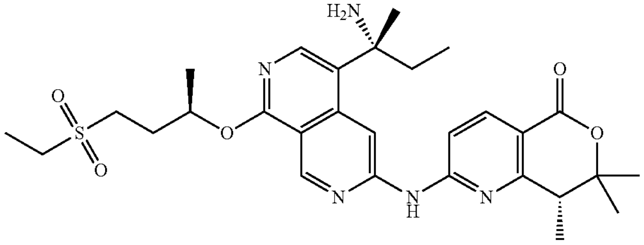 [SMILES: CC[C@@](C)(N)c1cnc(O[C@H](C)CCS(=O)(=O)CC)c2cnc(Nc3ccc4c(n3)[C@@H](C)C(C)(C)OC4=O)cc12]<br>or<br>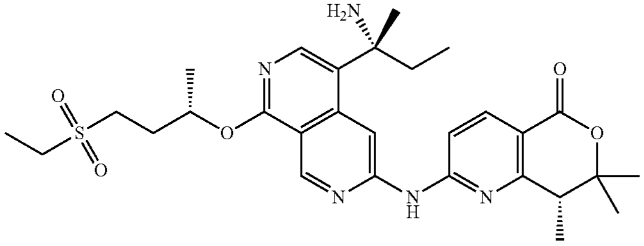 [SMILES: CC[C@@](C)(N)c1cnc(O[C@@H](C)CCS(=O)(=O)CC)c2cnc(Nc3ccc4c(n3)[C@@H](C)C(C)(C)OC4=O)cc12] | 570 | $^1$H-NMR (400 MHz, $CD_3OD$): δ ppm 9.42 (s, 1H), 9.21 (s, 1H), 8.15 (d, J = 8.8 Hz, 1H), 8.05 (s, 1H), 7.26 (d, J = 8.8 Hz, 1H), 5.70-5.57 (m, 1H), 3.30-3.21 (m, 2H), 3.18-3.08 (m, 2H), 3.04-2.95 (m, 1H), 2.63-2.51 (m, 1H), 2.39-2.23 (m, 3H), 1.93-1.85 (m, 3H), 1.58-1.50 (m, 6H), 1.46 (s, 3H), 1.40 (d, J = 8.8 Hz, 3H), 1.34 (t, J = 7.4 Hz, 3H), 0.81 (t, J = 7.4 Hz, 3H). | Scheme 1, Intermediate 3 and Intermediate 72 |
| 134 | 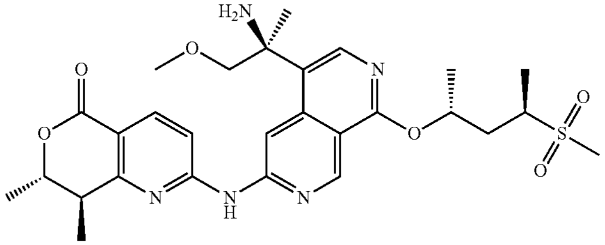 | 572 | $^1$H-NMR (400 MHz, $CD_3OD$): δ ppm 9.37 (s, 1H), 9.21 (s, 1H), 8.18 (s, 1H), 8.15 (d, J = 8.8 Hz, 1H), 7.32 (d, J = 8.8 Hz, 1H), 5.74-5.66 (m, 1H), 4.71-4.63 (m, 1H), 3.98-3.92 (m, 1H), 3.85-3.79 (m, 1H), 3.38-3.35 (m, 1H), 3.34 (s, 3H), 3.08-3.01 (m, 1H), 2.93 (s, 3H), 2.45-2.38 (m, 1H), 2.17-2.08 (m, 1H), 1.73 (s, 3H), 1.53-1.46 (m, 12H). | Scheme 1, Intermediate 1 and Intermediate 88 |
| 135 | 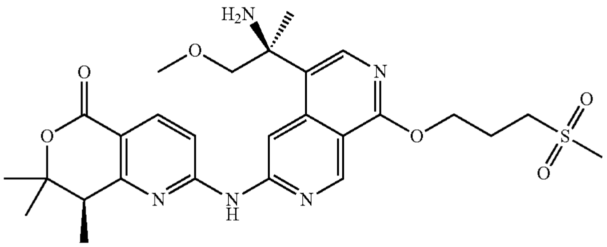 | 558 | $^1$H-NMR (400 MHz, $CD_3OD$): δ ppm 9.44 (s, 1H), 9.24 (s, 1H), 8.14 (d, J = 8.8 Hz, 1H), 8.07 (s, 1H), 7.26 (d, J = 8.8 Hz, 1H), 4.59 (t, J = 6.4 Hz, 2H), 4.05 (d, J = 9.6 Hz, 1H), 3.96 (d, J = 9.6 Hz, 1H), 3.50-3.40 (m, 5H), 3.10-3.00 (m, 4H), 2.50-2.40 (m, 2H), 1.89 (s, 3H), 1.54 (s, 3H), 1.47 (s, 3H), 1.40 (d, J = 7.2 Hz, 3H). | Scheme 1, Intermediate 3 and Intermediate 99 |
| 136 | 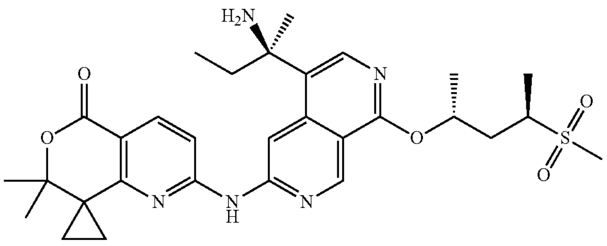 | 582 | $^1$H-NMR (400 MHz, $CD_3OD$): δ ppm 9.41 (s, 1H), 8.33 (s, 1H), 8.16 (d, J = 8.8 Hz, 1H), 8.10 (s, 1H), 7.62 (d, J = 8.8 Hz, 1H), 5.75-5.65 (m, 1H), 3.40-3.33 (m, 1H), 2.93 (s, 3H), 2.45-2.30 (m, 2H), 2.18-2.08 (m, 2H), 1.76 (s, 3H), 1.56-1.53 (m, 2H), 1.52-1.1.47 (m, 6H), 1.42 (s, 6H), 1.31-1.27 (m, 2H), 0.76 (d, J = 7.2 Hz, 3H). | Scheme 1, Intermediate 15 and Intermediate 53 |

TABLE 1-continued

| Cpd. # | Structure | LCMS (M + 1) | NMR | Synthetic Protocol |
|---|---|---|---|---|
| 137 | 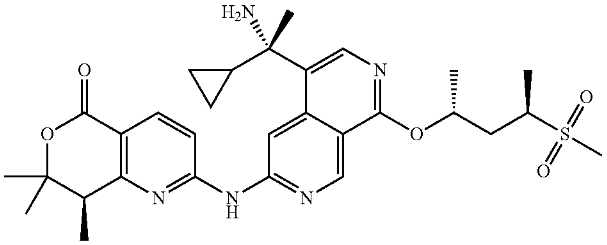 or 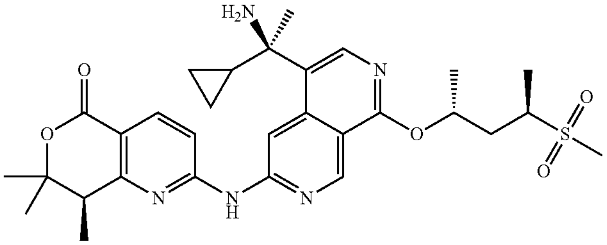 | 582 | $^1$H-NMR (400 MHz, $CD_3OD$): δ ppm 9.44 (s, 1H), 9.37 (s, 1H), 8.28 (s, 1H), 8.13 (d, J = 8.8 Hz, 1H), 7.26 (d, J = 8.8 Hz, 1H), 5.74-5.65 (m, 1H), 3.40-3.33 (m, 1H), 3.06-3.00 (m, 1H), 2.93 (s, 3H), 2.47-2.37 (m, 1H), 2.17-2.08 (m, 1H), 1.71-1.63 (m, 4H), 1.54-1.47 (m, 9H), 1.45 (s, 3H), 1.39 (d, J = 7.2 Hz, 3H), 0.66-0.43 (m, 4H). | Scheme 1, Intermediate 3 and Intermediate 76 |
| 138 | 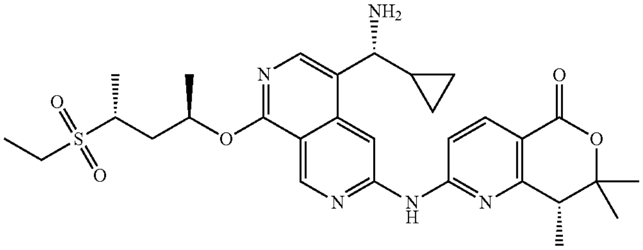 [SMILES: CCS(=O)(=O)[C@H](C)C[C@@H](C)Oc1ncc([C@H](N)C2CC2)c2cc(Nc3ccc4c(n3)[C@@H](C)C(C)(C)OC4=O)ncc12] or 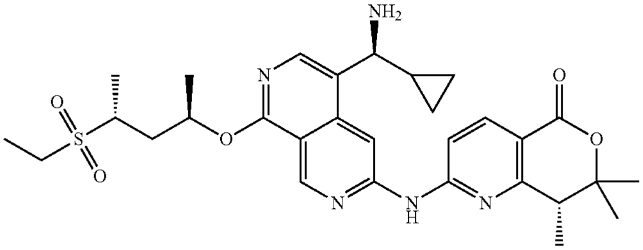 [SMILES: CCS(=O)(=O)[C@H](C)C[C@@H](C)Oc1ncc([C@@H](N)C2CC2)c2cc(Nc3ccc4c(n3)[C@@H](C)C(C)(C)OC4=O)ncc12] | 582 | $^1$H-NMR (400 MHz, $CD_3OD$): δ ppm 9.35 (s, 1H), 8.83 (s, 1H), 8.54 (s, 1H), 8.26 (s, 1H), 8.12 (d, J = 8.6 Hz, 1H), 7.24 (d, J = 8.8 Hz, 1H), 5.79-5.65 (m, 1H), 3.97 (br d, J = 8.8 Hz, 1H), 3.48-3.35 (m, 1H), 3.21-3.05 (m, 3H), 2.42 (td, J = 5.2, 14.4 Hz, 1H), 2.22-2.06 (m, 1H), 1.54-1.43 (m, 16H), 1.36-1.27 (m, 3H), 0.83-0.74 (m, 1H), 0.65-0.55 (m, 1H), 0.50-0.38 (m, 2H). | Scheme 1, Intermediate 3 and Intermediate 89 |
| 139 | 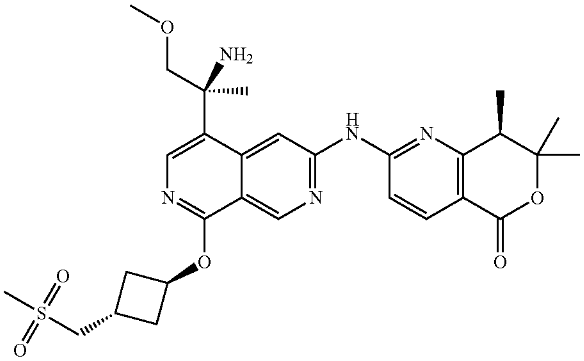 | 584 | $^1$H-NMR (400 MHz, $CD_3OD$): δ ppm 9.42 (s, 1H), 9.28 (s, 1H), 8.53 (s, 1H), 8.14 (d, J = 8.8 Hz, 1H), 8.06 (s, 1H), 7.25 (d, J = 8.8 Hz, 1H), 5.59-5.51 (m, 1H), 4.02-3.93 (m, 2H), 3.43 (d, J = 7.6 Hz, 2H), 3.38 (s, 3H), 3.10-3.01 (m, 2H), 2.97 (s, 3H), 2.61 (t, J = 6.4 Hz, 3H), 1.84 (s, 3H), 1.54 (s, 2H), 1.46 (s, 3H), 1.40 (d , J = 7.2 Hz, 3H). | Scheme 1, Intermediate 3 and Intermediate 51 |

TABLE 1-continued

| Cpd. # | Structure | LCMS (M + 1) | NMR | Synthetic Protocol |
|---|---|---|---|---|
| 140 | 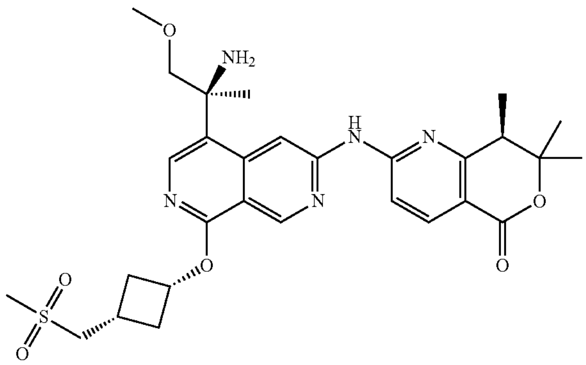 | 584 | $^1$H-NMR (400 MHz, $CD_3OD$): δ ppm 9.39 (s, 1H), 9.22 (s, 1H), 8.51 (s, 1H), 8.15 (d, J = 8.8 Hz, 1H), 8.03 (s, 1H), 7.25 (d, J = 8.4 Hz, 1H), 5.42-5.35 (m, 1H), 4.08 (d, J = 10 Hz, 1H), 3.97 (d, J = 10 Hz, 1H), 3.41 (s, 3H), 3.38 (d, J = 7.2 Hz 1H), 3.02-3.01 (m, 1H), 2.95-2.90 (m, 2H), 2.68-2.58 (m, 1H), 2.25-2.14 (m, 2H), 1.90 (s, 3H), 1.55 (s, 3H), 1.48 (s, 3H), 1.40 (d, J = 7.2 Hz, 3H). | Scheme 1, Intermediate 3 and Intermediate 50 |
| 141 | 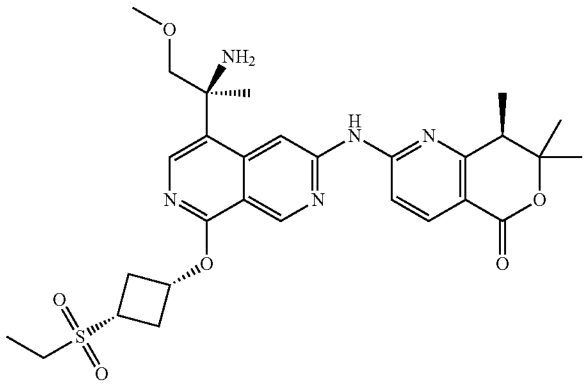 [SMILES: CCS(=O)(=O)[C@H]1C[C@@H](Oc2ncc([C@](C)(N)COC)c3cc(Nc4ccc5c(n4)[C@@H](C)C(C)(C)OC5=O)ncc23)C1] | 584 | $^1$H-NMR (400 MHz, $CD_3OD$): δ ppm 9.39 (s, 1H), 9.36 (s, 1H), 8.17 (s, 1H), 8.13 (d, J = 8.8 Hz, 1H), 7.21 (d, J = 8.8 Hz, 1H), 5.44 (J = 7.2 Hz, 1H), 4.67-4.52 (m, 1H), 3.95-3.85 (m, 2H), 3.85-3.75 (m, 1H), 3.35 (s, 3H), 3.06 (q, J = 7.2 Hz, 3H), 3.02-2.92 (m, 2H), 2.74-2.64 (m, 2H), 1.74 (s, 3H), 1.54 (s, 3H), 1.48-1.45 (m, 3H), 1.40 (d, J = 7.2 Hz, 3H), 1.35 (t, J = 7.6 Hz, 3H) | Scheme 1, Intermediate 3 and Intermediate 84 |
| 142 | 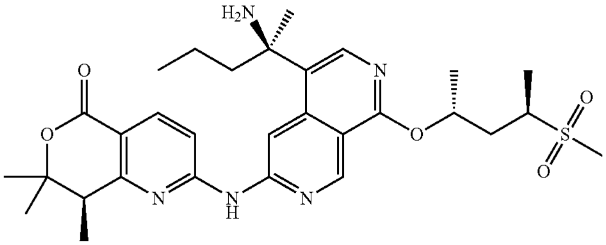 or 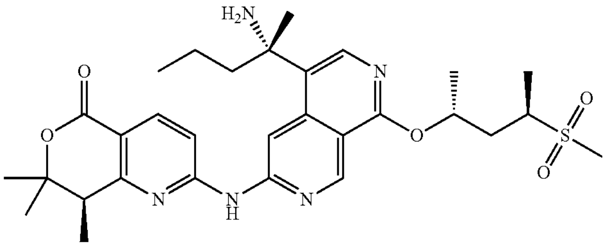 | 584 | $^1$H-NMR (400 MHz, $CD_3OD$): δ ppm 9.39 (s, 1H), 9.34 (s, 1H), 8.14 (d, J = 8.4 Hz, 1H), 8.10 (s, 1H), 7.23 (d, J = 8.8 Hz, 1H), 5.76-5.65 (m, 1H) 3.42-3.33 (m, 1H), 3.09-3.00 (m, 1H), 2.93 (s, 3H), 2.55-2.37 (m, 2H), 2.20-2.06 (m, 2H), 1.82 (s, 3H), 1.55 (s, 3H), 1.52-1.48 (m, 6H), 1.44 (s, 3H), 1.41 (d, J = 6.8 Hz, 3H), 1.34-1.20 (m, 1H), 1.08-0.94 (m, 1H), 0.88-0.81 (m, 3H). | Scheme 1, Intermediate 3 and Intermediate 67 |
| 143 | 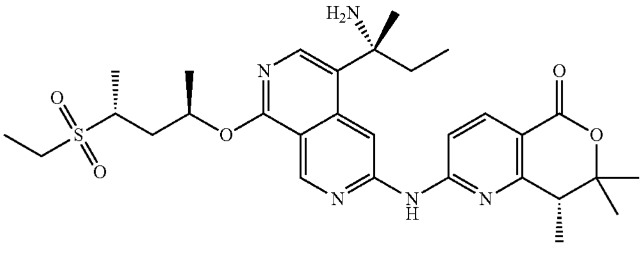 [SMILES: CC[C@@](C)(N)c1cnc(O[C@H](C)C[C@@H](C)S(=O)(=O)CC)c2cnc(Nc3ccc4c(n3)[C@@H](C)C(C)(C)OC4=O)cc12] | 584 | $^1$H-NMR (400 MHz, $CD_3OD$): δ ppm 9.37 (s, 1H), 9.34 (s, 1H), 8.16 (s, 1H), 8.13 (d, J = 8.8 Hz, 1H), 7.21 (d, J = 8.4 Hz, 1H), 5.74-5.63 (m, 1H), 3.45-3.34 (m, 1H), 3.13-3.01 (m, 3H), 2.45-2.32 (m, 2H), 2.24-2.09 (m, 2H), 1.75 (s, 3H), 1.54 (s, 3H), 1.50-1.47 (m, 6H), 1.45 (s, 3H), 1.39 (d, J = 7.2 Hz, 3H), 1.33-1.28 (m, 3H), 0.77-0.71 (m, 3H). | Scheme 1, Intermediate 3 and Intermediate 86 |

TABLE 1-continued

| Cpd. # | Structure | LCMS (M + 1) | NMR | Synthetic Protocol |
|---|---|---|---|---|
| 144 | 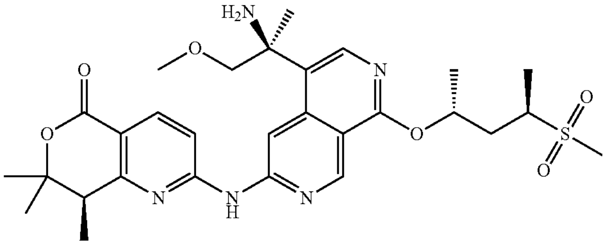 | 586 | $^1$H-NMR (400 MHz, $CD_3OD$): δ ppm 9.38 (s, 1H), 9.36 (s, 1H), 8.19 (s, 1H), 8.13 (d, J = 8.4 Hz, 1H), 7.22 (d, J = 8.8 Hz, 1H), 5.74-5.66 (m, 1H), 3.95-3.85 (m, 2H), 3.37-3.33 (m, 4H), 3.09-3.02 (m, 1H), 2.93 (s, 3H), 2.45-2.37 (m, 1H), 2.18-2.08 (m, 1H), 1.75 (s, 3H), 1.54 (s, 3H), 1.51-1.48 (m, 6H), 1.46 (s, 3H), 1.40 (d, J = 6.8 Hz, 3H). | Scheme 1, Intermediate 3 and Intermediate 88 |
| 145 | 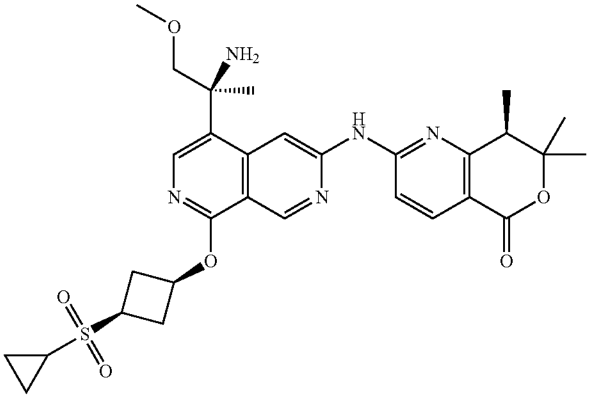 [SMILES: COC[C@@](C)(N)c1cnc(O[C@H]2C[C@@H](S(=O)(=O)C3CC3)C2)c2cnc(Nc3ccc4c(n3)[C@@H](C)C(C)(C)OC4=O)cc12] | 596 | $^1$H-NMR (400 MHz, $CD_3OD$): δ ppm 9.37 (s, 1H), 9.35 (s, 1H), 8.14-8.11 (m, 2H), 7.22 (d, J = 8.8 Hz, 1H), 5.50-5.40 (m, 1H), 3.94 (s, 2H), 3.88-3.84 (m, 1H), 3.37 (s, 3H), 3.04-2.97 (m, 3H), 2.75-2.63 (m, 2H), 2.57-2.52 (m, 1H), 1.80 (s, 3H), 1.54 (s, 3H), 1.47 (s, 3H), 1.40 (d, J = 7.2 Hz, 3H), 1.14-1.05 (m, 4H). | Scheme 1, Intermediate 3 and Intermediate 91 |
| 146 | 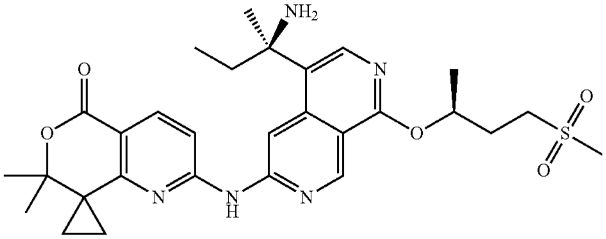 | 568 | $^1$H-NMR (400 MHz, $CD_3OD$): δ ppm 9.42 (s, 1H), 8.31 (s, 1H), 8.15 (d, J = 8.4 Hz, 1H), 8.08 (s, 1H), 7.61 (d, J = 8.4 Hz, 1H), 5.70-5.60 (m, 1H), 3.40-3.30 (m, 2H), 3.00 (s, 3H), 2.40-2.30 (m, 3H), 2.25-2.10 (m, 1H), 1.76 (s, 3H), 1.60-1.55 (m, 5H), 1.50 (s, 6H), 1.35-1.25 (m, 2H), 0.76 (t, J = 7.2 Hz, 3H). | Scheme 1, Intermediate 15 and Intermediate 54 |
| 147 | 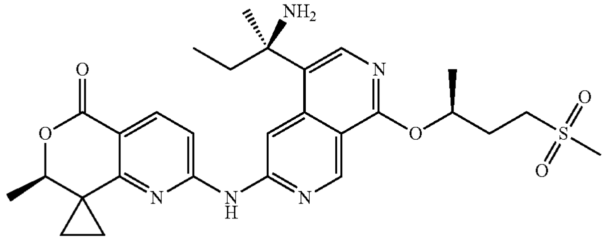 or 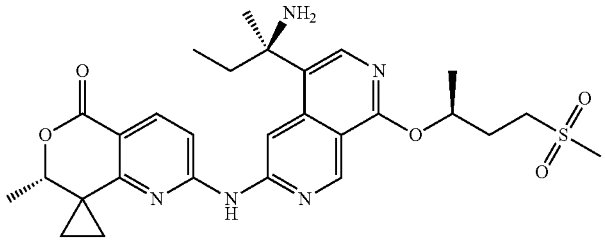 | 554 | $^1$H-NMR (400 MHz, $CD_3OD$): δ ppm 9.44 (s, 1H), 8.58 (s, 1H), 8.24 (s, 1H), 8.15 (d, J = 8.4 Hz, 1H), 8.02 (s, 1H), 7.63 (d, J = 8.4 Hz, 1H), 5.70-5.60 (m, 1H), 4.70-4.60 (m, 1H), 3.45-3.30 (m, 2H), 3.00 (s, 3H), 2.55-2.45 (m, 1H), 2.43-2.40 (m, 2H), 2.39-2.20 (m, 1H), 1.84 (s, 3H), 1.60-1.50 (m, 5H), 1.36 (d, J = 6.8 Hz, 3H), 1.30-1.15 (m, 2H), 0.80 (t, J = 6.8 Hz, 3H). | Scheme 1, Intermediate 12 and Intermediate 54 |

TABLE 1-continued
| Cpd. # | Structure | LCMS (M + 1) | NMR | Synthetic Protocol |
|---|---|---|---|---|
| 148 | 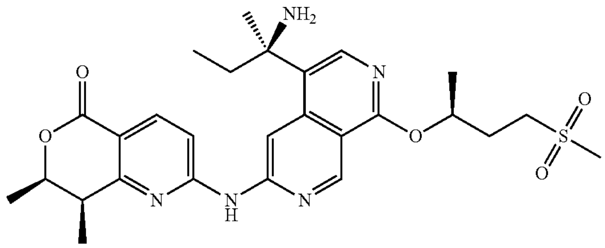 or 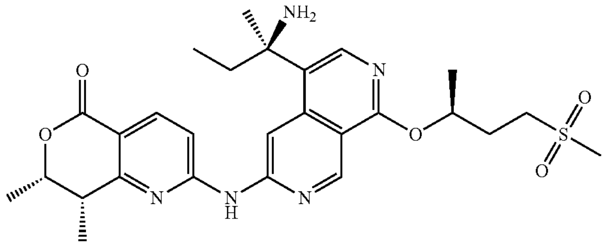 | 542 | $^1$H-NMR (400 MHz, $CD_3OD$): δ ppm 9.42 (s, 1H), 9.34 (s, 1H), 8.56 (s, 1H), 8.15 (d, J = 8.4 Hz, 1H), 8.05 (s, 1H), 7.18 (d, J = 8.4 Hz, 1H), 5.70-5.60 (m, 1H), 4.95-4.90 (m, 1H), 3.40-3.30 (m, 2H), 3.05-2.95 (m, 4H), 2.60-2.55 (m, 1H), 2.40-2.20 (m, 3H), 1.89 (s, 3H), 1.51 (d, J = 6.4 Hz, 6H), 1.32 (d, J = 6.4 Hz, 3H), 0.85 (t, J = 6.4 Hz, 3H). | Scheme 1, Intermediate 93 and Intermediate 54 |
| 149 | 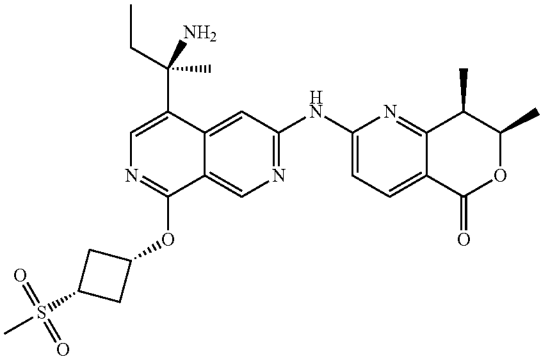 or 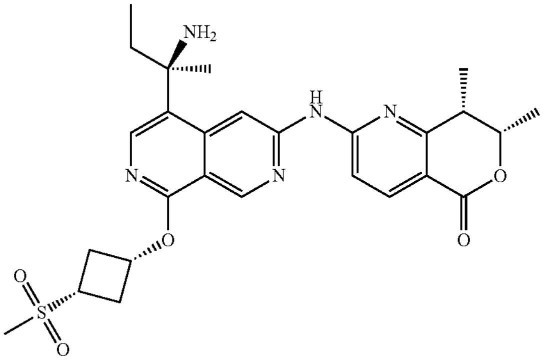 | 540 | $^1$H-NMR (400 MHz, CD3OD): δ ppm 9.40 (s, 1H), 9.33 (s, 1H), 8.56 (s, 1H), 8.14 (d, J = 8.8 Hz, 1H), 8.02 (s, 1H), 7.18 (d, J = 8.8 Hz, 1H), 5.50-5.40 (m, 1H), 4.95-4.90 (m, 1H), 3.85-3.80 (m, 1H), 3.05-2.95 (m, 6H), 2.73-2.55 (m, 3H), 2.35-2.20 (m, 1H), 1.91 (s, 3H), 1.51 (d, J = 6.4 Hz, 3H), 1.31 (d, J = 6.4 Hz, 3H), 0.80 (t, J = 6.4 Hz, 3H). | Scheme 1, Intermediate 93 and Intermediate 24 |

TABLE 1-continued
| Cpd. # | Structure | LCMS (M + 1) | NMR | Synthetic Protocol |
|---|---|---|---|---|
| 150 | 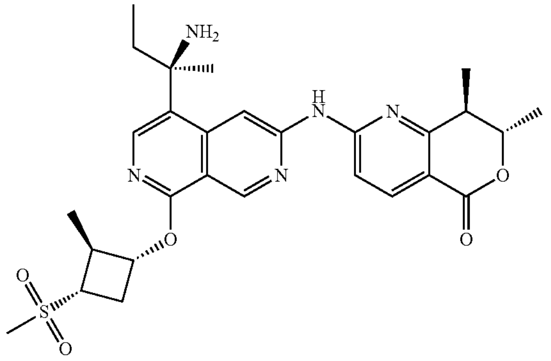 or 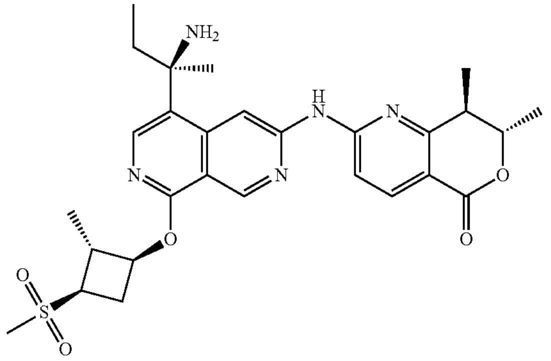 | 554 | $^1$H-NMR (400 MHz, CD3OD): δ ppm 9.41 (s, 1H), 9.06 (s, 1H), 8.52 (s, 1H), 8.18 (d, J = 8.4, 1H), 8.06 (s, 1H), 7.35 (d, J = 8.4, 1H), 5.20-5.10 (m, 1H), 4.73-4.65 (m, 1H), 3.50-3.40 (m, 1H), 3.20-3.03 (m, 2H), 2.95 (s, 3H), 2.60-2.50 (m, 1H), 2.49-2.40 (m, 1H), 2.35-2.20 (m, 1H), 1.92 (s, 3H), 1.53-1.15 (m, 10H), 0.83 (s, 3H). | Scheme 1, Intermediate 1 and Intermediate 96 |
| 151 | 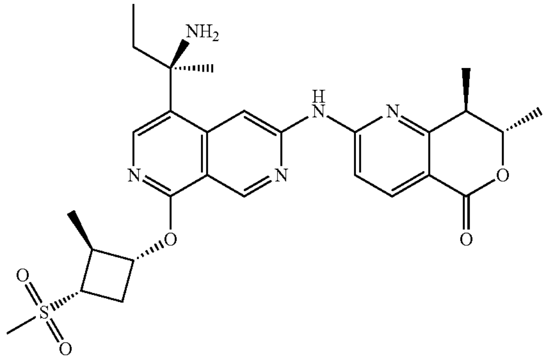 or 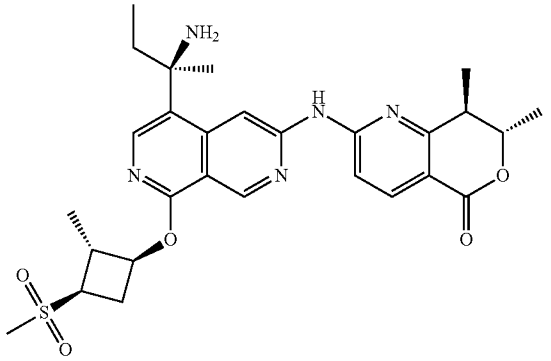 | 554 | $^1$H-NMR (400 MHz, CD3OD): δ ppm 9.41 (s, 1H), 9.06 (s, 1H), 8.55 (s, 1H), 8.18 (d, J = 8.4, 1H), 8.06 (s, 1H), 7.32 (d, J = 8.4, 1H), 5.20-5.10 (m, 1H), 4.73-4.69 (m, 1H), 3.50-3.40 (m, 1H), 3.20-3.03 (m, 2H), 2.94 (s, 3H), 2.60-2.40 (m, 2H), 2.30-2.15 (m, 1H), 1.86 (s, 3H), 1.53-1.13 (m, 10H), 0.82-0.75 (m, 3H). | Scheme 1, Intermediate 1 and Intermediate 95 |

TABLE 1-continued
| Cpd. # | Structure | LCMS (M + 1) | NMR | Synthetic Protocol |
|---|---|---|---|---|
| 152 | 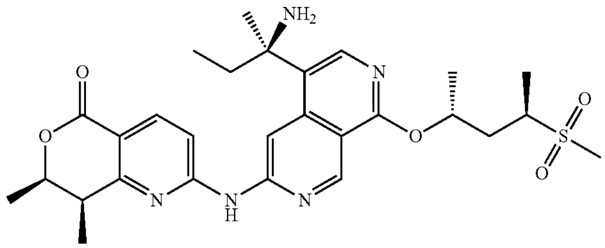<br>or<br>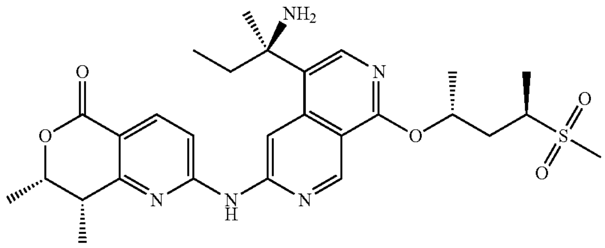 | 556 | $^1$H-NMR (400 MHz, $CD_3OD$): δ ppm 9.39 (s, 2H), 8.16 (d, J = 8.4 Hz, 1H), 8.10 (s, 1H), 7.18 (d, J = 8.4 Hz, 1H), 5.76-5.65 (m, 1H), 4.96-4.90 (m, 1H), 3.43-3.35 (m, 1H), 3.07-2.98 (m, 1H), 2.94 (s, 3H), 2.59-2.47 (m, 1H), 2.47-2.38 (m, 1H), 2.32-2.20 (m, 1H), 2.19-2.09 (m, 1H), 1.85 (s, 3H), 1.56-1.48 (m, 9H), 1.33 (d, J = 7.2 Hz, 3H), 0.79 (t, J = 12 Hz, 3H). | Scheme 1, Intermediate 93 and Intermediate 53 |
| 153 | 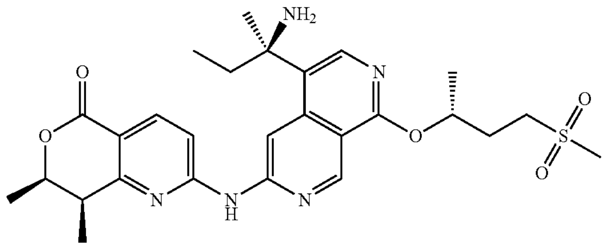<br>or<br>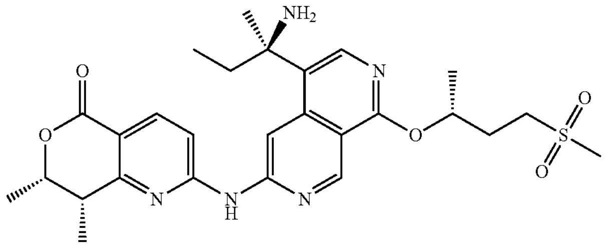 | 542 | $^1$H-NMR (400 MHz, $CD_3OD$): δ ppm 9.43 (s, 1H), 9.39 (s, 1H), 8.15 (s, 1H), 8.13 (d, J = 8.8 Hz, 1H), 7.16 (d, J = 8.8 Hz, 1H), 5.67-5.58 (m, 1H), 4.95-4.91 (m, 1H), 3.42-3.33 (m, 2H), 3.05-3.01 (m, 1H), 3.00 (s, 3H), 2.49-2.40 (m, 1H), 2.39-2.29 (m, 2H), 2.25-2.17 (m, 1H), 1.78 (s, 3H), 1.54-1.49 (m, 6H), 1.32 (d, J = 7.2 Hz, 3H), 0.75 (t, J = 7.4 Hz, 3H). | Scheme 1, Intermediate 93 and Intermediate 31 |

TABLE 1-continued

| Cpd. # | Structure | LCMS (M + 1) | NMR | Synthetic Protocol |
|---|---|---|---|---|
| 154 | 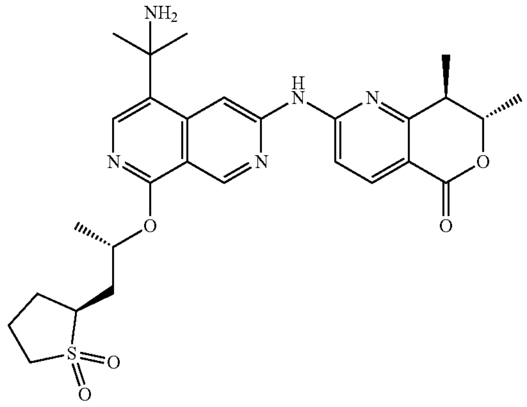 [SMILES: C[C@@H]1OC(=O)c2ccc(Nc3cc4c(C(C)(C)N)cnc(O[C@@H](C)C[C@@H]5CCCS5(=O)=O)c4cn3)nc2[C@H]1C] or 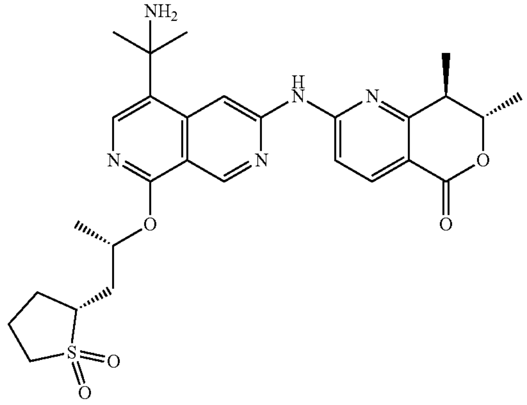 [SMILES: C[C@@H]1OC(=O)c2ccc(Nc3cc4c(C(C)(C)N)cnc(O[C@@H](C)C[C@H]5CCCS5(=O)=O)c4cn3)nc2[C@H]1C] or 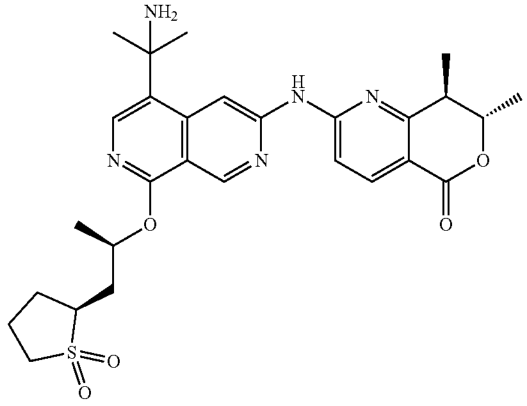 [SMILES: C[C@H](C[C@@H]1CCCS1(=O)=O)Oc1ncc(C(C)(C)N)c2cc(Nc3ccc4c(n3)[C@@H](C)[C@H](C)OC4=O)ncc12] or | 554 | $^1$H-NMR (400 MHz, CD3OD): δ ppm 9.40 (s, 1 H), 9.17 (s, 1 H), 8.18 (s, 1 H), 8.13 (d, J = 8.4 Hz, 1 H), 7.30 (d, J = 8.8 Hz, 1 H), 5.68-5.57 (m, 1 H), 4.69-4.61 (m, 1 H), 3.22-3.09 (m, 2 H), 3.06-2.93 (m, 2 H), 2.50-2.38 (m, 2 H), 2.21-2.10 (m, 1 H), 2.07-1.94 (m, 2 H), 1.91-1.83 (m, 1 H), 1.78 (d, J = 4.4 Hz, 6 H), 1.51-1.47 (m, 6 H), 1.45 (d, J = 6.4 Hz, 3 H). | Scheme 1, intermediate 1 and Intermediate 92 2nd eluting peak by chiral SFC Column: Phenomenex-Cellulose-2 (250 mm × 30 mm, 10 μm); Mobile phase: [0.1% NH3H2O ETOH]; B %: 70%-70%). This peak contained two isomers, which were further separated by a second SFC to give the title isomer as the 2nd peak Column: Daicel Chiralpak IC (250 mm × 50 mm, 10 μm); Mobile phase: [Hexane-IPA (1% TFA)]; B %: 50%-50%) |

TABLE 1-continued

| Cpd. # | Structure | LCMS (M + 1) | NMR | Synthetic Protocol |
|---|---|---|---|---|
| | 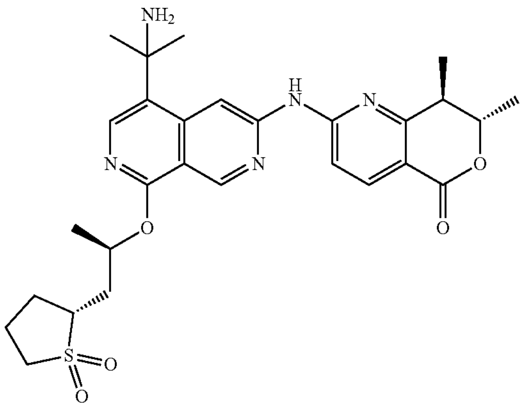 [SMILES: C[C@H](C[C@H]1CCCS1(=O)=O)Oc1ncc(C(C)(C)N)c2cc(Nc3ccc4c(n3)[C@@H](C)[C@H](C)OC4=O)ncc12] | | | |
| 155 | 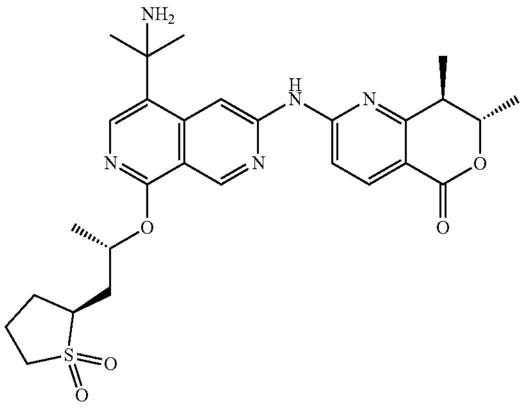 [SMILES: C[C@@H]1OC(=O)c2ccc(Nc3cc4c(C(C)(C)N)cnc(O[C@@H](C)C[C@@H]5CCCS5(=O)=O)c4cn3)nc2[C@H]1C] or 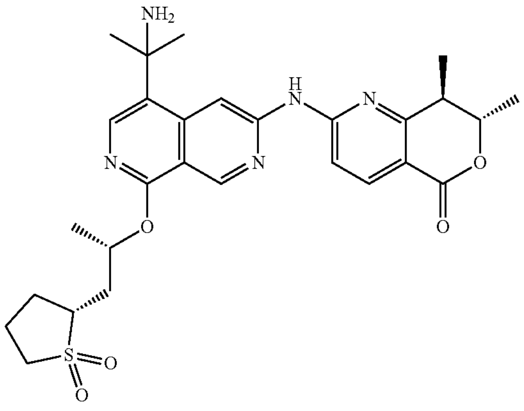 [SMILES: C[C@@H]1OC(=O)c2ccc(Nc3cc4c(C(C)(C)N)cnc(O[C@@H](C)C[C@H]5CCCS5(=O)=O)c4cn3)nc2[C@H]1C] or | 554 | $^1$H-NMR (400 MHz, CD3OD): δ ppm 9.38 (s, 1 H), 9.12 (s, 1 H), 8.16-8.10 (m, 2 H), 7.30 (d, J = 8.8 Hz, 1 H), 5.73-5.61 (m, 1 H), 4.70-4.60 (m, 1 H), 3.17-3.08 (m, 1 H), 3.05-2.92 (m, 2 H), 2.50-2.40 (m, 1 H), 2.35-2.24 (m, 1 H), 2.23-1.99 (m, 4 H), 1.94-1.86 (m, 1 H), 1.80 (d, J = 6.8 Hz, 6H), 1.51-1.47 (m, 6 H), 1.45 (d, J = 6.8 Hz, 3 H). | Scheme 1, intermediate 1 and Intermediate 92 2nd eluting peak by chiral SFC Column: Phenomenex-Cellulose-2 (250 mm × 30 mm, 10 μm); Mobile phase: [0.1% NH3H2O ETOH]; B %: 70%-70%). This peak contained two isomers, which were further separated by a second SFC to give the title isomer as the 1st peak Column: Daicel Chiralpak IC (250 mm × 50 mm, 10 μm); Mobile phase: [Hexane-IPA (1% TFA)]; B %: 50%-50%) |

TABLE 1-continued
| Cpd. # | Structure | LCMS (M + 1) NMR | Synthetic Protocol |
|---|---|---|---|
| | 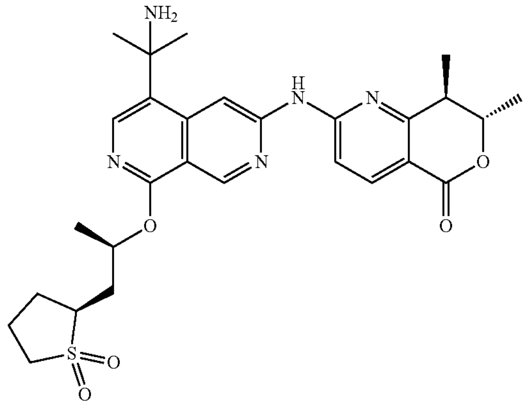 [SMILES: C[C@H](C[C@@H]1CCCS1(=O)=O)Oc1ncc(C(C)(C)N)c2cc(Nc3ccc4c(n3)[C@@H](C)[C@H](C)OC4=O)ncc12] or 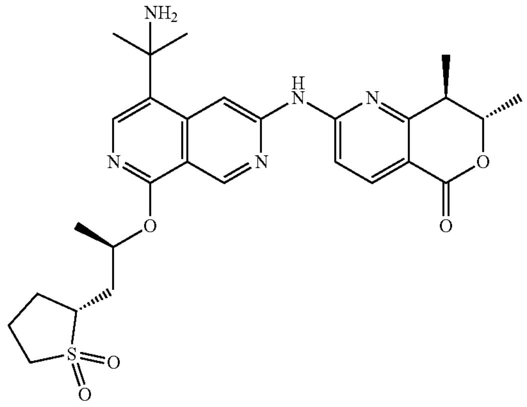 [SMILES: C[C@H](C[C@H]1CCCS1(=O)=O)Oc1ncc(C(C)(C)N)c2cc(Nc3ccc4c(n3)[C@@H](C)[C@H](C)OC4=O)ncc12] | | |

TABLE 1-continued

| Cpd. # | Structure | LCMS (M + 1) | NMR | Synthetic Protocol |
|---|---|---|---|---|
| 156 | 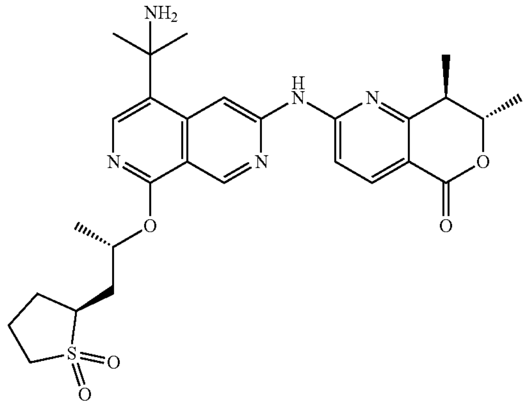 [SMILES: C[C@@H]1OC(=O)c2ccc(Nc3cc4c(C(C)(C)N)cnc(O[C@@H](C)C[C@@H]5CCCS5(=O)=O)c4cn3)nc2[C@H]1C] or 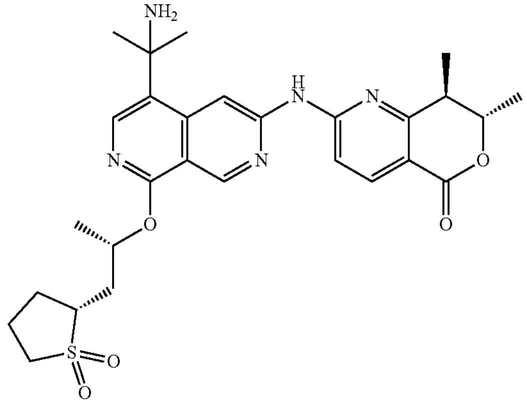 [SMILES: C[C@@H]1OC(=O)c2ccc(Nc3cc4c(C(C)(C)N)cnc(O[C@@H](C)C[C@H]5CCCS5(=O)=O)c4cn3)nc2[C@H]1C] or 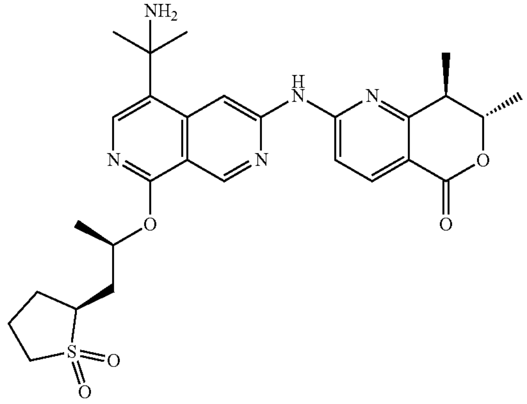 [SMILES: C[C@H](C[C@@H]1CCCS1(=O)=O)Oc1ncc(C(C)(C)N)c2cc(Nc3ccc4c(n3)[C@@H](C)[C@H](C)OC4=O)ncc12] or | 554 | $^1$H-NMR (400 MHz, CD3OD): δ 9.40 (s, 1 H), 9.13 (s, 1 H), 8.17 (s, 1 H), 8.11 (d, J = 8.8 Hz, 1 H), 7.29 (d, J = 8.8 Hz, 1 H), 5.69-5.53 (m, 1 H), 4.67-4.58 (m, 1 H), 3.26-3.10 (m, 2 H), 3.06-2.95 (m, 2 H), 2.49-2.39 (m, 2 H), 2.22-2.11 (m, 1 H), 2.08-1.94 (m, 2 H), 1.92-1.82 (m, 1 H), 1.79 (d, J = 5.6 Hz, 6H), 1.47-1.51 (m, 6 H), 1.44 (d, J = 6.8 Hz, 3 H). | Scheme 1, intermediate 1 and intermediate 92 1st eluting peak by chiral SFC Column: Phenomenex-Cellulose-2 (250 mm × 30 mm, 10 μm); Mobile phase: [0.1% NH3H2O ETOH]; B %: 70%-70%), This peak contained two isomers, which were further separated by a second SFC to give the title isomer as the 2nd peak Column: DAICEL CHIRALPAK IC (250 mm × 30 mm, 10 μm); Mobile phase: [0.1% NH3H2O MEOH]; B %: 70%-70%) |

TABLE 1-continued

| Cpd. # | Structure | LCMS (M + 1) | NMR | Synthetic Protocol |
|---|---|---|---|---|
| | 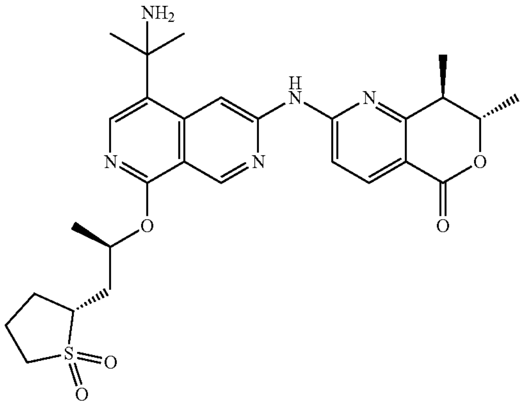 [SMILES: C[C@H](C[C@H]1CCCS1(=O)=O)Oc1ncc(C(C)(C)N)c2cc(Nc3ccc4c(n3)[C@@H](C)[C@H](C)OC4=O)ncc12] | | | |
| 157 | 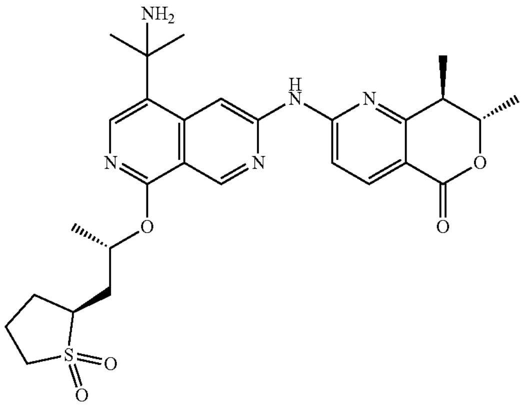 [SMILES: C[C@@H]1OC(=O)c2ccc(Nc3cc4c(C(C)(C)N)cnc(O[C@@H](C)C[C@@H]5CCCS5(=O)=O)c4cn3)nc2[C@H]1C]<br>or<br>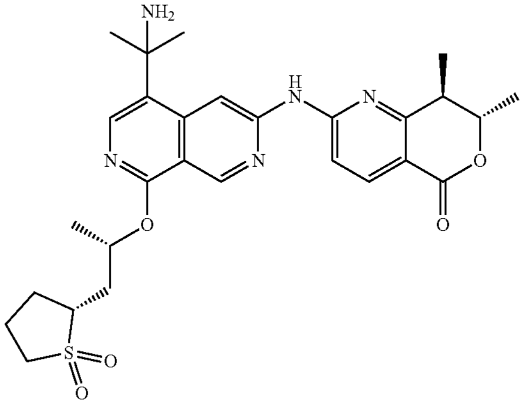 [SMILES: C[C@@H]1OC(=O)c2ccc(Nc3cc4c(C(C)(C)N)cnc(O[C@@H](C)C[C@H]5CCCS5(=O)=O)c4cn3)nc2[C@H]1C]<br>or | 554 | $^1$H-NMR (400 MHz, CD3OD): δ ppm 9.37 (s, 1 H), 9.13 (s, 1 H), 8.17 (s, 1 H), 8.12 (d, J = 8.8 Hz, 1 H), 7.29 (d, J = 8.8 Hz, 1 H), 5.73-5.60 (m, 1 H), 4.68-4.59 (m, 1 H), 3.18-3.09 (m, 1 H), 3.06-2.95 (m, 2 H), 2.50-2.40 (m, 1 H), 2.34-2.24 (m, 1 H), 2.22-1.99 (m, 4 H), 1.98-1.83 (m, 1 H),1.77 (d, J = 5.6 Hz, 6 H), 1.51-1.47 (m, 6 H), 1.45 (d, J = 6.4 Hz, 3 H). | Scheme 1, intermediate 1 and intermediate 92 1st eluting peak by chiral SFC Column: Phenomenex-Cellulose-2 (250 mm × 30 mm, 10 μm); Mobile phase: [0.1% NH3H2O ETOH]; B %: 70%-70%), This peak contained two isomers, which were further separated by a second SFC to give the title isomer as the 1st peak Column: DAICEL CHIRALPAK IC (250 mm × 30 mm, 10 μm); Mobile phase: [0.1% NH3H2O MEOH]; B %: 70%-70%) |

TABLE 1-continued
| Cpd. # | Structure | LCMS (M + 1) NMR | Synthetic Protocol |
|---|---|---|---|
| | 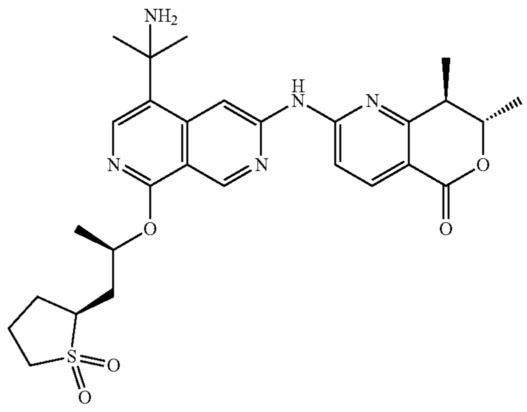 [SMILES: C[C@H](C[C@@H]1CCCS1(=O)=O)Oc1ncc(C(C)(C)N)c2cc(Nc3ccc4c(n3)[C@@H](C)[C@H](C)OC4=O)ncc12] or 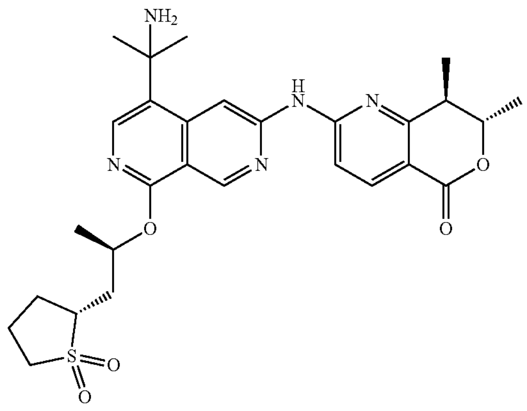 [SMILES: C[C@H](C[C@H]1CCCS1(=O)=O)Oc1ncc(C(C)(C)N)c2cc(Nc3ccc4c(n3)[C@@H](C)[C@H](C)OC4=O)ncc12] | | |

TABLE 1-continued

| Cpd. # | Structure | LCMS (M + 1) | NMR | Synthetic Protocol |
|---|---|---|---|---|
| 158 | 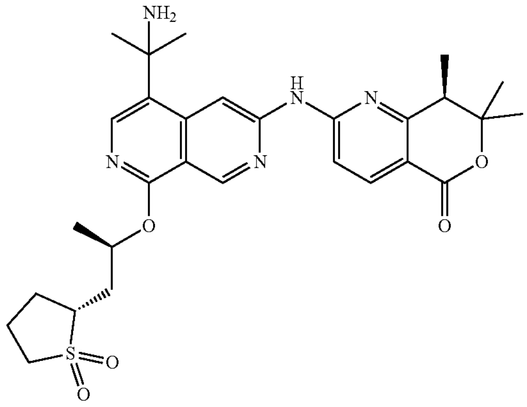 [SMILES: C[C@H](C[C@H]1CCCS1(=O)=O)Oc1ncc(C(C)(C)N)c2cc(Nc3ccc4c(n3)[C@@H](C)C(C)(C)OC4=O)ncc12] or 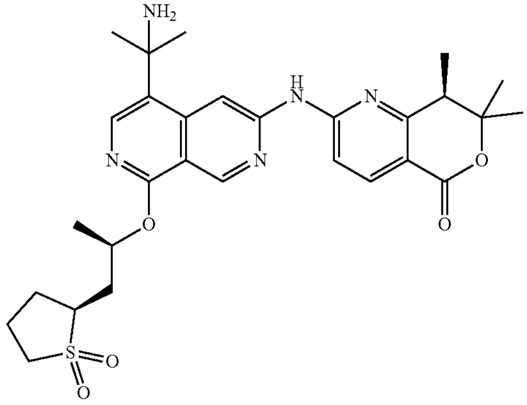 [SMILES: C[C@H](C[C@@H]1CCCS1(=O)=O)Oc1ncc(C(C)(C)N)c2cc(Nc3ccc4c(n3)[C@@H](C)C(C)(C)OC4=O)ncc12] or 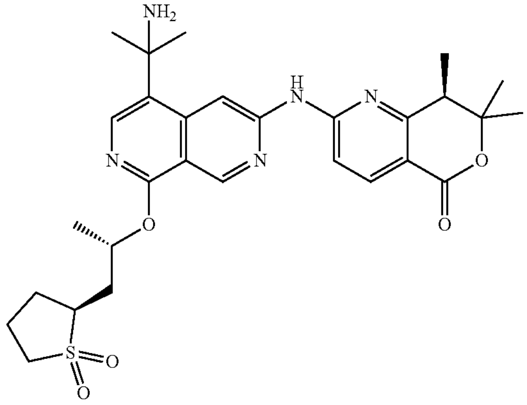 [SMILES: C[C@@H]1c2nc(Nc3cc4c(C(C)(C)N)cnc(O[C@@H](C)C[C@@H]5CCCS5(=O)=O)c4cn3)ccc2C(=O)OC1(C)C] or | 568 | $^1$H-NMR (400 MHz, CD3OD): δ ppm 9.40 (s, 1 H), 9.36 (s, 1 H), 8.20 (s, 1 H), 8.13 (d, J = 8.8 Hz, 1 H), 7.21 (d, J = 8.8 Hz, 1 H), 5.69-5.58 (m, 1 H), 3.21-3.11 (m, 2 H), 3.05-2.96 (m, 2 H), 2.50-2.39 (m, 2 H), 2.22-2.12 (m, 1 H), 2.08-1.95 (m, 2 H), 1.88-1.83 (m, 1 H), 1.79 (d, J = 6.8 Hz, 6 H), 1.54 (s, 3 H), 1.50 (d, J = 6.0 Hz, 3 H), 1.45 (s, 3 H), 1.40 (d, J = 7.2 Hz, 3 H). | Scheme 1, intermediate 3 and Intermediate 92 2nd eluting peak by chiral SFC Column: Daicel Chiralpak OD (250 mm × 30 mm, 10 μm); Mobile phase: [0.1% NH3H2O MEOH]; B %: 55%-55%), This peak contained two isomers, which were further separated by a second SFC to give the title isomer as the 2nd peak Column: Daicel Chiralpak IC (250 mm × 50 mm, 10 μm); Mobile phase: [Hexane-IPA (1% TFA)]; B %: 40%-40%) |

TABLE 1-continued

| Cpd. # | Structure | LCMS (M + 1) | NMR | Synthetic Protocol |
|---|---|---|---|---|
| | 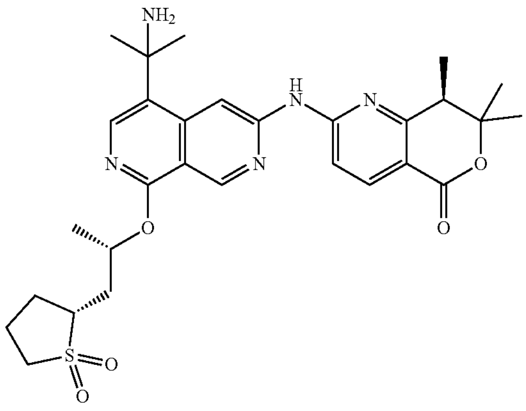 [SMILES: C[C@@H]1c2nc(Nc3cc4c(C(C)(C)N)cnc(O[C@@H](C)C[C@H]5CCCS5(=O)=O)c4cn3)ccc2C(=O)OC1(C)C] | | | |
| 159 | 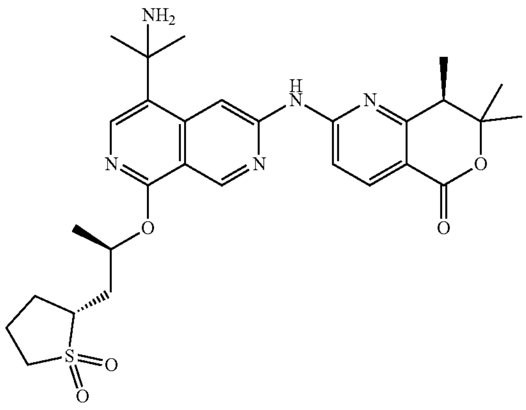 [SMILES: C[C@H](C[C@H]1CCCS1(=O)=O)Oc1ncc(C(C)(C)N)c2cc(Nc3ccc4c(n3)[C@@H](C)C(C)(C)OC4=O)ncc12]<br>or<br>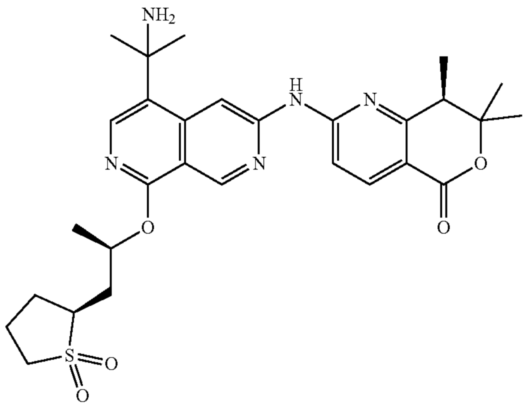 [SMILES: C[C@H](C[C@@H]1CCCS1(=O)=O)Oc1ncc(C(C)(C)N)c2cc(Nc3ccc4c(n3)[C@@H](C)C(C)(C)OC4=O)ncc12]<br>or | 568 | $^1$H-NMR (400 MHz, CD3OD): δ ppm 9.37 (s, 1 H), 9.32 (s, 1 H), 8.17 (s, 1 H), 8.12 (d, J = 8.4 Hz, 1 H), 7.21 (d, J = 8.4 Hz, 1 H), 5.72-5.62 (m, 1 H), 3.18-3.09 (m, 1 H), 3.08-2.95 (m, 2 H), 2.51-2.40 (m, 1 H), 2.34-2.24 (m, 1 H), 2.23-1.98 (m, 4 H), 1.96-1.85 (m, 1 H), 1.78 (d, J = 9.6 Hz, 6 H), 1.53 (s, 3 H), 1.49 (d, J = 6.0 Hz, 3 H), 1.45 (s, 3 H), 1.39 (d, J = 6.4 Hz, 3 H). | Scheme 1, intermediate 3 and Intermediate 92 2nd eluting peak by chiral SFC Column: Daicel Chiralpak OD (250 mm × 30 mm, 10 μm); Mobile phase: [0.1% NH3H2O MEOH]; B %: 55%-55%), This peak contained two isomers, which were further separated by a second SFC to give the title isomer as the 1st peak Column: Daicel Chiralpak IC (250 mm × 50 mm, 10 μm); Mobile phase: [Hexane-IPA (1% TFA)]; B %: 40%-40%) |

TABLE 1-continued
| Cpd. # | Structure | LCMS (M + 1) NMR | Synthetic Protocol |
|---|---|---|---|
| | 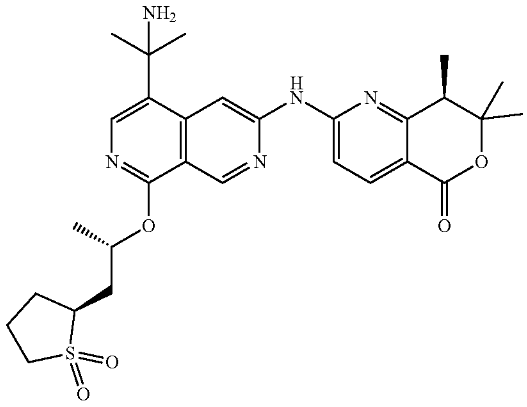 [SMILES: C[C@@H]1c2nc(Nc3cc4c(C(C)(C)N)cnc(O[C@@H](C)C[C@@H]5CCCS5(=O)=O)c4cn3)ccc2C(=O)OC1(C)C] or 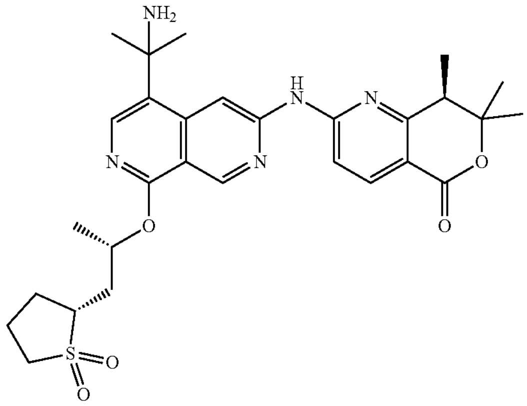 [SMILES: C[C@@H]1c2nc(Nc3cc4c(C(C)(C)N)cnc(O[C@@H](C)C[C@H]5CCCS5(=O)=O)c4cn3)ccc2C(=O)OC1(C)C] | | |

TABLE 1-continued

| Cpd. # | Structure | LCMS (M + 1) | NMR | Synthetic Protocol |
|---|---|---|---|---|
| 160 | 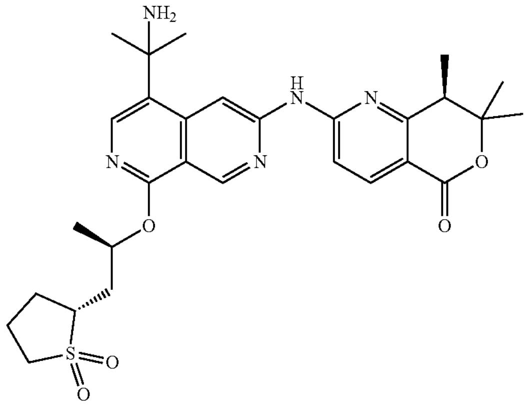 [SMILES: C[C@H](C[C@H]1CCCS1(=O)=O)Oc1ncc(C(C)(C)N)c2cc(Nc3ccc4c(n3)[C@@H](C)C(C)(C)OC4=O)ncc12] or 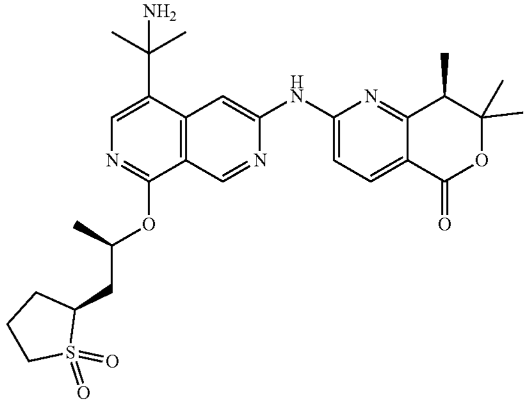 [SMILES: C[C@H](C[C@@H]1CCCS1(=O)=O)Oc1ncc(C(C)(C)N)c2cc(Nc3ccc4c(n3)[C@@H](C)C(C)(C)OC4=O)ncc12] or 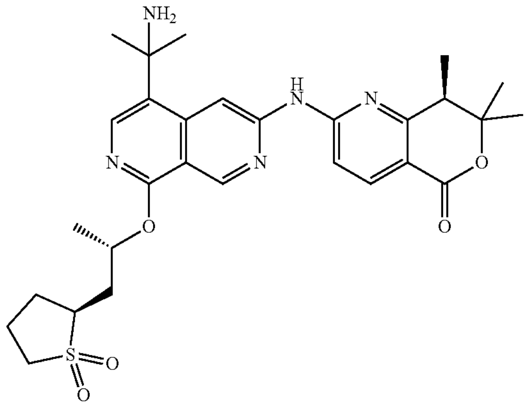 [SMILES: C[C@@H]1c2nc(Nc3cc4c(C(C)(C)N)cnc(O[C@@H](C)C[C@@H]5CCCS5(=O)=O)c4cn3)ccc2C(=O)OC1(C)C] or | 568 | $^1$H-NMR (400 MHz, CD3OD): δ ppm 9.40 (s, 1 H), 9.33 (s, 1 H), 8.18 (s, 1 H), 8.12 (d, J = 8.8 Hz, 1 H), 7.21 (d, J = 8.8 Hz, 1 H), 5.68-5.58 (m, 1 H), 3.22-3.11 (m, 2 H), 3.07-2.95 (m, 2 H), 2.50-2.37 (m, 2 H), 2.22-2.11 (m, 1 H), 2.06-1.93 (m, 2 H), 1.91-1.82 (m, 1 H), 1.79 (d, J = 8.4 Hz, 6 H), 1.53 (s, 3 H), 1.49 (d, J = 6.4 Hz, 3 H), 1.44 (s, 3 H), 1.39 (d, J = 7.2 Hz, 3 H). | Scheme 1, Intermediate 3 and Intermediate 92 1st eluting peak by chiral SFC Column: Daicel Chiralpak OD (250 mm × 30 mm, 10 μm); Mobile phase: [0.1% NH3H2O MEOH]; B %: 55%-55%), This peak contained two isomers, which were further separated by a second SFC to give the title isomer as the 2nd peak Column: Daicel Chiralpak IC (250 mm × 30 mm, 10 μm); Mobile phase: [0.1% NH3H2O MEOH]; B %: 70%-70%) |

TABLE 1-continued

| Cpd. # | Structure | LCMS (M + 1) | NMR | Synthetic Protocol |
|---|---|---|---|---|
| | 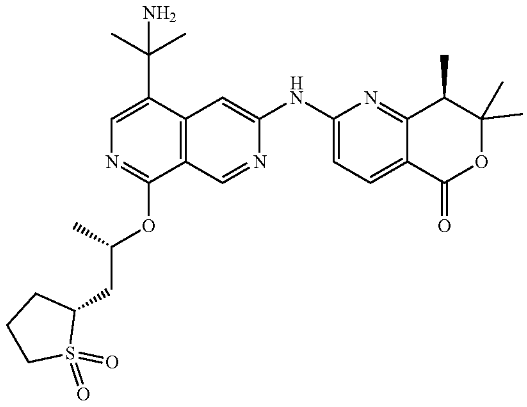 [SMILES: C[C@@H]1c2nc(Nc3cc4c(C(C)(C)N)cnc(O[C@@H](C)C[C@H]5CCCS5(=O)=O)c4cn3)ccc2C(=O)OC1(C)C] | | | |
| 161 | 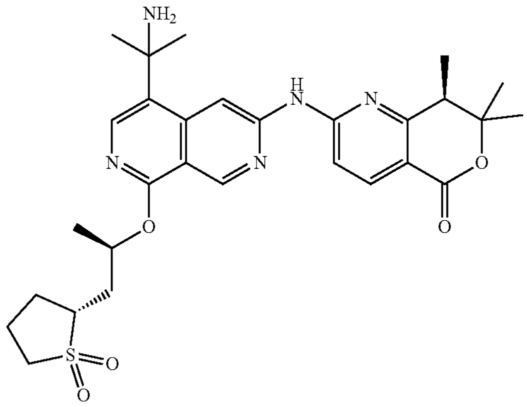 [SMILES: C[C@H](C[C@H]1CCCS1(=O)=O)Oc1ncc(C(C)(C)N)c2cc(Nc3ccc4c(n3)[C@@H](C)C(C)(C)OC4=O)ncc12] or 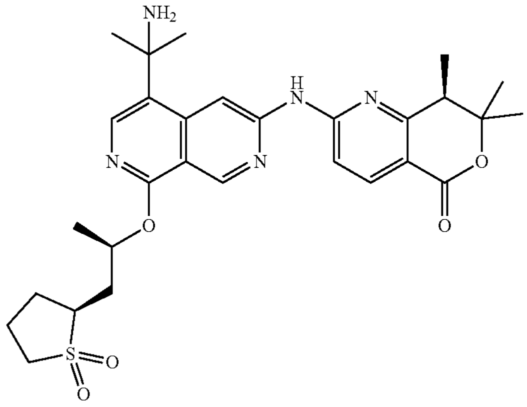 [SMILES: C[C@H](C[C@@H]1CCCS1(=O)=O)Oc1ncc(C(C)(C)N)c2cc(Nc3ccc4c(n3)[C@@H](C)C(C)(C)OC4=O)ncc12] or | 568 | $^1$H-NMR (400 MHz, CD3OD): δ ppm 9.40 (s, 1 H), 9.35 (s, 1 H), 8.21 (s, 1 H), 8.14 (d, J = 8.8 Hz, 1 H), 7.23 (d, J = 8.8 Hz, 1 H), 5.74-5.63 (m, 1 H), 3.20-3.11 (m, 1 H), 3.08-2.98 (m, 2 H), 2.52-2.41 (m, 1 H), 2.36-2.27 (m, 1 H), 2.23-2.16 (m, 2 H), 2.15-2.01 (m, 2 H), 1.99-1.88 (m, 1 H), 1.81 (d, J = 8.0 Hz, 5 H), 1.56 (s, 3 H), 1.51 (d, J = 6.4 Hz, 3 H), 1.46 (s, 3 H), 1.41 (d, J = 7.2 Hz, 3 H). | Scheme 1, Intermediate 3 and Intermediate 92 1st eluting peak by chiral SFC Column: Daicel Chiralpak OD (250 mm × 30 mm, 10 μm); Mobile phase: [0.1% NH3H2O MEOH]; B %: 55%-55%), This peak contained two isomers, which were further separated by a second SFC to give the title isomer as the 1st peak Column: Daicel Chiralpak IC (250 mm × 30 mm, 10 μm); Mobile phase: [0.1% NH3H2O MEOH]; B %: 70%-70%) |

TABLE 1-continued
| Cpd. # | Structure | LCMS (M + 1) | NMR | Synthetic Protocol |
|---|---|---|---|---|
| | 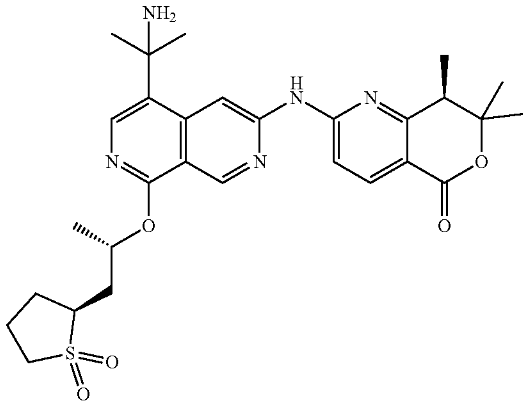 [SMILES: C[C@@H]1c2nc(Nc3cc4c(C(C)(C)N)cnc(O[C@@H](C)C[C@@H]5CCCS5(=O)=O)c4cn3)ccc2C(=O)OC1(C)C] or 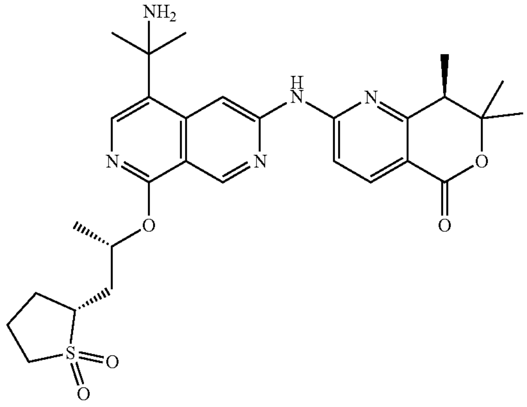 [SMILES: C[C@@H]1c2nc(Nc3cc4c(C(C)(C)N)cnc(O[C@@H](C)C[C@H]5CCCS5(=O)=O)c4cn3)ccc2C(=O)OC1(C)C] | | | |
| 162 | 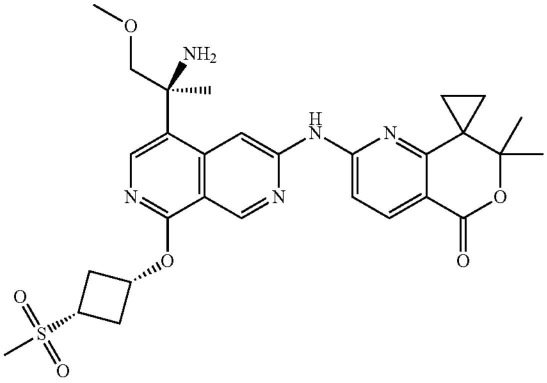 | 582 | $^1$H-NMR (400 MHz, $CD_3OD$): δ ppm 9.39 (s, 1H), 8.58 (s, 1H), 8.16 (d, J = 8.8 Hz, 1H), 8.10 (s, 1H), 7.53 (d, J = 8.8 Hz, 1H), 5.43 (t, J = 7.4 Hz, 1H), 3.93 (d, J = 9.6 Hz, 1H), 3.86-3.78 (m, 1H), 3.74 (d, J = 9.2 Hz, 1H), 3.36 (s, 3H), 3.02-2.94 (m, 2H), 2.93 (s, 3H), 2.74-2.63 (m, 2H), 2.03 (s, 1H), 1.70 (s, 3H), 1.63-1.56 (m, 2H), 1.42 (s, 6H), 1.29 (d, J = 2.8 Hz, 2 H). | Scheme 1, Intermediate 15 and Intermediate 85 |

TABLE 1-continued

| Cpd. # | Structure | LCMS (M + 1) | NMR | Synthetic Protocol |
| --- | --- | --- | --- | --- |
| 163 | 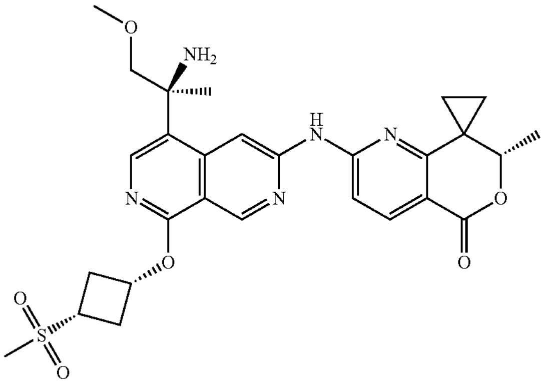<br>or<br>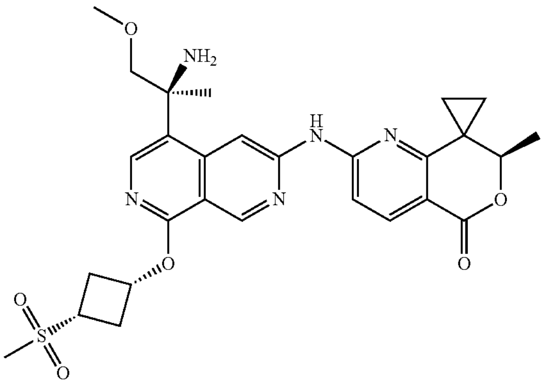 | 568 | $^1$H-NMR (400 MHz, $CD_3OD$): δ ppm 9.38 (s, 1H), 8.59 (s, 1H), 8.15 (d, J = 8.8 Hz, 1H), 8.09 (s, 1H), 7.50 (d, J = 8.8 Hz, 1H), 5.48-5.36 (m, 1H), 4.69-4.60 (m, 1H), 3.92 (d, J = 9.2 Hz, 1H), 3.87-3.72 (m, 2H), 3.37 (s, 3H), 3.03-2.94 (m, 2H), 2.93 (s, 3H), 2.74-2.62 (m, 2H), 1.72 (s, 3H), 1.68-1.62 (m, 1H), 1.58-1.49 (m, 1H), 1.38 (d, J = 6.4 Hz, 3H), 1.26-1.16 (m, 2H). | Scheme 1, Intermediate 12 and Intermediate 85 |
| 164 | 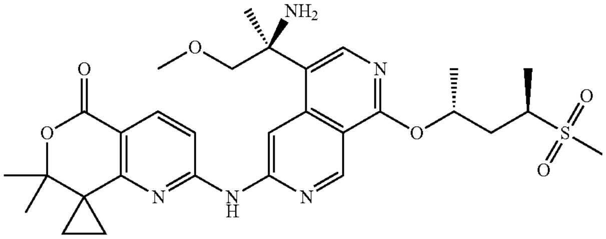 | 598 | $^1$H-NMR (400 MHz, $CD_3OD$): δ ppm 9.38 (s, 1H), 8.58 (s, 1H), 8.15 (d, J = 8.8 Hz, 2H), 8.14 (s, 1H), 7.53 (d, J = 8.8 Hz, 1H), 5.73-5.64 (m, 1H), 3.98-3.90 (m, 1H), 3.75-3.70 (m, 1H), 3.36 (s, 3H), 3.35-3.33 (m, 1H), 2.93 (s, 3H), 2.45-2.37 (m, 1H), 2.17-2.07 (m, 1H), 1.69 (s, 3H), 1.62-1.56 (m, 2H), 1.52-1.47 (m, 6H), 1.42 (s, 6H), 1.32-1.27 (m, 2H). | Scheme 1, Intermediate 15 and Intermediate 88 |
| 165 | 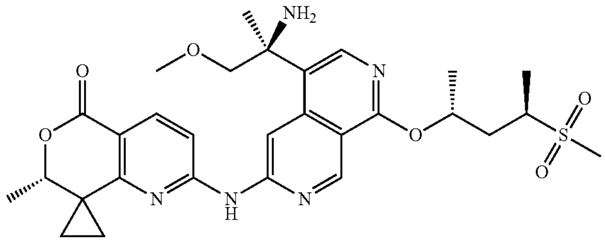<br>or | 584 | $^1$H-NMR (400 MHz, $CD_3OD$): δ ppm 9.37 (s, 1H), 8.63 (s, 1H), 8.15 (d, J = 8.4 Hz, 1H), 8.13 (s, 1H), 7.49 (d, J = 8.4 Hz, 1H), 5.73-5.64 (m, 1H), 4.67-4.61 (m, 1H), 3.95-3.88 (m, 1H), 3.77-3.70 (m, 1H), 3.36 (s, 3H), 3.35-3.33 (m, 1H), 2.93 (s, 3H), 2.45-2.36 (m, 1H), 2.17-2.07 (m, 1H), 1.69 (s, 3H), 1.67-1.63 (m, 1H), 1.58-1.53 (m, 1H), 1.52-1.47 (m, 6H), 1.38 (d, J = 6.4 Hz, 3H), 1.26-1.17 (m, 2H). | Scheme 1, Intermediate 12 and Intermediate 88 |

TABLE 1-continued

| Cpd. # | Structure | LCMS (M + 1) | NMR | Synthetic Protocol |
|---|---|---|---|---|
| | 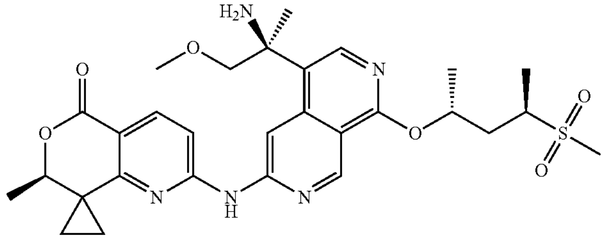 | | | |
| 166 | 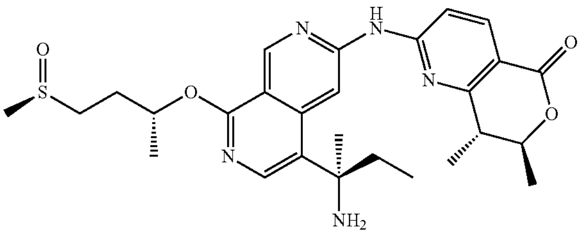 [SMILES: CC[C@@](C)(N)c1cnc(O[C@H](C)CC[S@@](C)=O)c2cnc(Nc3ccc4c(n3)[C@@H](C)[C@H](C)OC4=O)cc12]<br>or<br>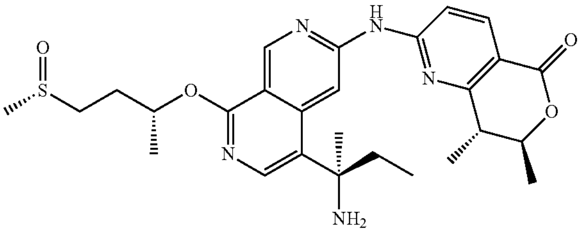 [SMILES: CC[C@@](C)(N)c1cnc(O[C@H](C)CC[S@](C)=O)c2cnc(Nc3ccc4c(n3)[C@@H](C)[C@H](C)OC4=O)cc12] | 526 | $^1$H-NMR (400 MHz, $CD_3OD$): δ ppm 9.45 (s, 1H), 8.94 (s, 1H), 8.65-8.38 (m, 1H), 8.17 (d, J = 8.8 Hz, 1H), 7.99 (s, 1H), 7.38 (d, J = 8.8 Hz, 1H), 5.76-5.60 (m, 1H), 4.68-4.57 (m, 1H), 3.11-2.92 (m, 3H), 2.75-2.59 (m, 4H), 2.39-2.24 (m, 3H), 1.97 (s, 3H), 1.56-1.43 (m, 9H), 0.85-0.80 (m, 3H). | Scheme 1, Intermediate 101 and Intermediate 1 |
| 167 | 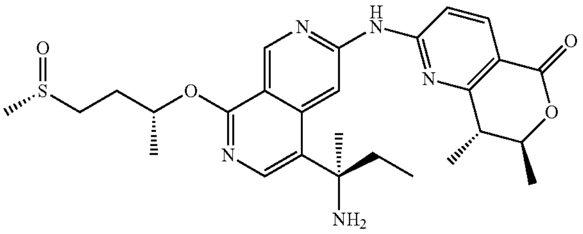 [SMILES: CC[C@@](C)(N)c1cnc(O[C@H](C)CC[S@](C)=O)c2cnc(Nc3ccc4c(n3)[C@@H](C)[C@H](C)OC4=O)cc12]<br>or<br>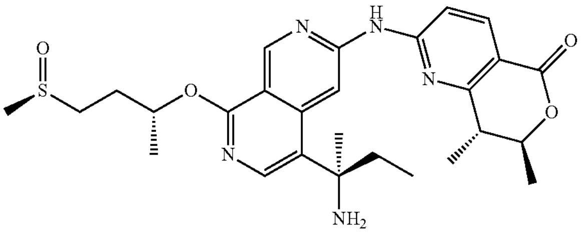 [SMILES: CC[C@@](C)(N)c1cnc(O[C@H](C)CC[S@@](C)=O)c2cnc(Nc3ccc4c(n3)[C@@H](C)[C@H](C)OC4=O)cc12] | 526 | $^1$H-NMR (400 MHz, CD3OD): δ ppm 9.46 (s, 1H), 8.94 (s, 1H), 8.65-8.38 (m, 1H), 8.17 (d, J = 8.8 Hz, 1H), 7.99 (s, 1H), 7.38 (d, J = 8.8 Hz, 1H), 5.68-5.60 (m, 1H), 4.68-4.57 (m, 1H), 3.11-2.92 (m, 3H), 2.75-2.59 (m, 4H), 2.39-2.24 (m, 3H), 1.97 (s, 3H), 1.56-1.43 (m, 9H), 0.85-0.80 (m, 3H). | Scheme 1, Intermediate 102 and Intermediate 1 |
| 168 | 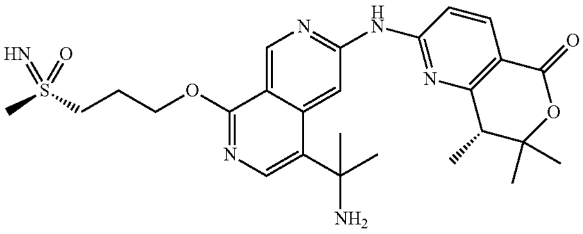 [SMILES: C[C@@H]1c2nc(Nc3cc4c(C(C)(C)N)cnc(OCCC[S@](C)(=N)=O)c4cn3)ccc2C(=O)OC1(C)C]<br>or | 527 | $^1$H-NMR (400 MHz, $CD_3OD$): δ ppm 9.48 (s, 1H), 9.16 (s, 1H), 8.16 (d, J = 8.8 Hz, 1H), 8.02 (s, 1H), 7.29 (d, J = 8.8 Hz, 1H), 4.73-4.70 (m, 2H), 3.53-3.45 (m, 2H), 3.10 (s, 3H), 3.01-3.00 (m, 1H), 2.48-2.44 (m, 2H), 2.04-1.99 (m, 6H), 1.54 (s, 3H), 1.48-1.40 (m, 6H). | Scheme 1, Intermediate 103 and Intermediate 3 |

TABLE 1-continued
| Cpd. # | Structure | LCMS (M + 1) | NMR | Synthetic Protocol |
| --- | --- | --- | --- | --- |
| | 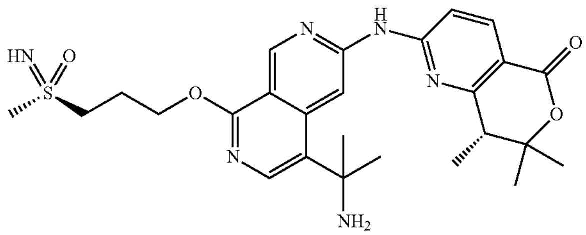 [SMILES: C[C@@H]1c2nc(Nc3cc4c(C(C)(C)N)cnc(OCCC[S@@](C)(=N)=O)c4cn3)ccc2C(=O)OC1(C)C] | | | |
| 169 | 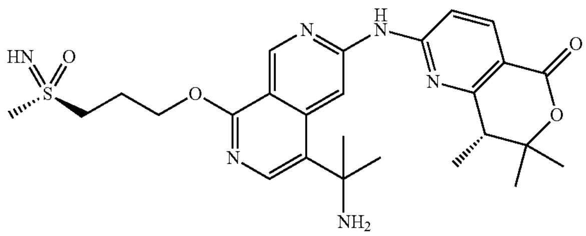 [SMILES: C[C@@H]1c2nc(Nc3cc4c(C(C)(C)N)cnc(OCCC[S@@](C)(=N)=O)c4cn3)ccc2C(=O)OC1(C)C]<br>or<br>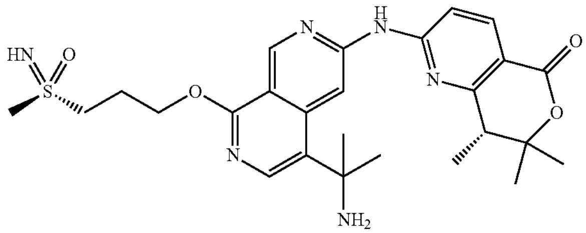 [SMILES: C[C@@H]1c2nc(Nc3cc4c(C(C)(C)N)cnc(OCCC[S@](C)(=N)=O)c4cn3)ccc2C(=O)OC1(C)C] | 527 | $^1$H-NMR (400 MHz, $CD_3OD$): δ ppm 9.46 (s, 1H), 9.10 (s, 1H), 8.14 (d, J = 8.8 Hz, 1H), 8.01 (s, 1H), 7.27 (d, J = 8.8 Hz, 1H), 4.73-4.70 (m, 2H), 3.53-3.45 (m, 2H), 3.10 (s, 3H), 3.01-3.00 (m, 1H), 2.48-2.44 (m, 2H), 2.04-1.99 (m, 6H), 1.52 (s, 3H), 1.48-1.40 (m, 6H). | Scheme 1, Intermediate 104 and Intermediate 3 |
| 170 | 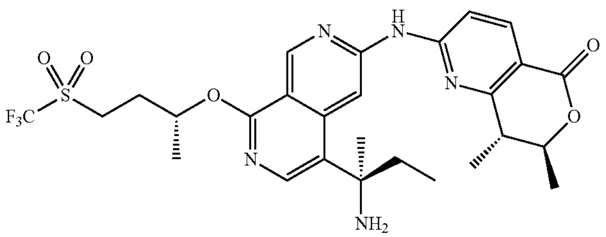 [SMILES: CC[C@@](C)(N)c1cnc(O[C@H](C)CCS(=O)(=O)C(F)(F)F)c2cnc(Nc3ccc4c(n3)[C@@H](C)[C@H](C)OC4=O)cc12]<br>or<br>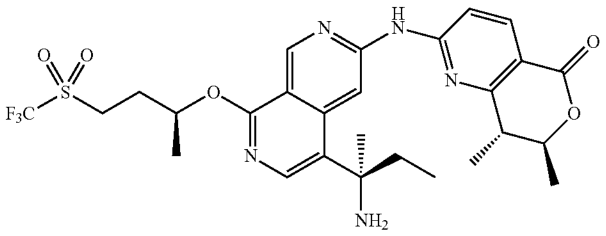 [SMILES: CC[C@@](C)(N)c1cnc(O[C@@H](C)CCS(=O)(=O)C(F)(F)F)c2cnc(Nc3ccc4c(n3)[C@@H](C)[C@H](C)OC4=O)cc12] | | | |

TABLE 1-continued
| Cpd. # | Structure | LCMS (M + 1) | NMR | Synthetic Protocol |
| --- | --- | --- | --- | --- |
| 171 | 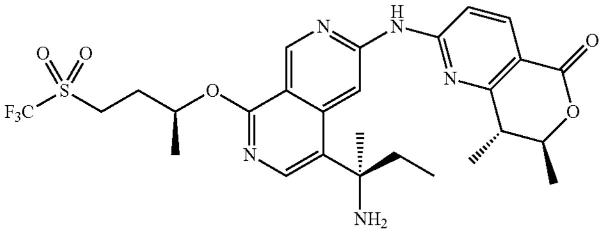 [SMILES: CC[C@@](C)(N)c1cnc(O[C@@H](C)CCS(=O)(=O)C(F)(F)F)c2cnc(Nc3ccc4c(n3)[C@@H](C)[C@H](C)OC4=O)cc12]<br>or<br>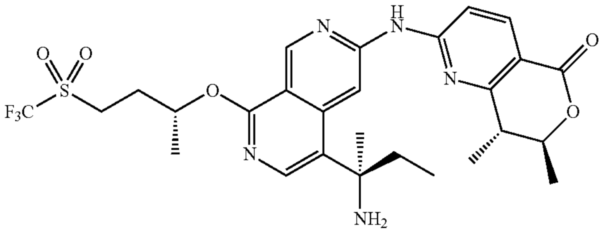 [SMILES: CC[C@@](C)(N)c1cnc(O[C@H](C)CCS(=O)(=O)C(F)(F)F)c2cnc(Nc3ccc4c(n3)[C@@H](C)[C@H](C)OC4=O)cc12] | | | |
| 172 | 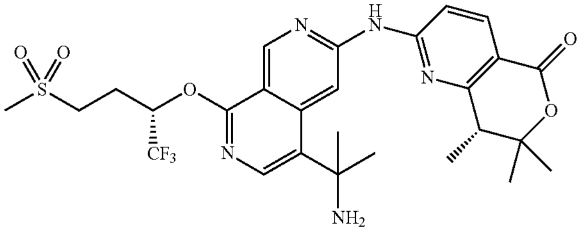 [SMILES: C[C@@H]1c2nc(Nc3cc4c(C(C)(C)N)cnc(O[C@@H](CCS(C)(=O)=O)C(F)(F)F)c4cn3)ccc2C(=O)OC1(C)C]<br>or<br>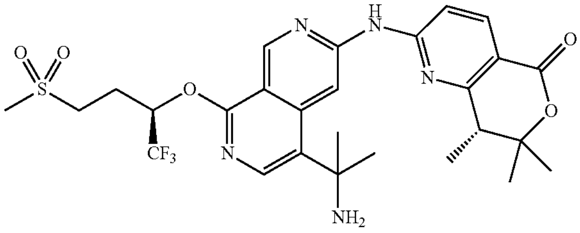 [SMILES: C[C@@H]1c2nc(Nc3cc4c(C(C)(C)N)cnc(O[C@H](CCS(C)(=O)=O)C(F)(F)F)c4cn3)ccc2C(=O)OC1(C)C] | 596 | $^1$H-NMR (400 MHz, $CD_3OD$): δ ppm 9.41 (s, 1H), 9.37 (s, 1H), 8.20-8.10 (m, 2H), 7.24 (d, J = 8.8 Hz, 1H), 6.45-6.37 (m, 1H), 3.48-3.32 (m, 2H), 3.07-2.96 (m, 4H), 2.62-2.46 (m, 2H), 1.90-1.86 (m, 6H), 1.54 (s, 3H), 1.47-1.38 (m, 6H). | Scheme 1, Intermediate 105 and Intermediate 3 |
| 173 | 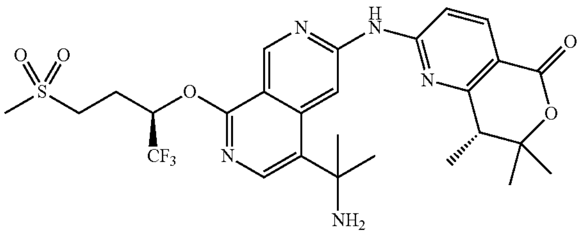 [SMILES: C[C@@H]1c2nc(Nc3cc4c(C(C)(C)N)cnc(O[C@H](CCS(C)(=O)=O)C(F)(F)F)c4cn3)ccc2C(=O)OC1(C)C]<br>or<br>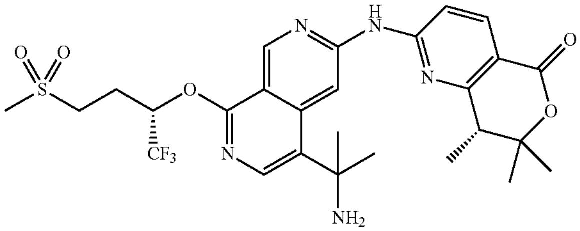 [SMILES: C[C@@H]1c2nc(Nc3cc4c(C(C)(C)N)cnc(O[C@@H](CCS(C)(=O)=O)C(F)(F)F)c4cn3)ccc2C(=O)OC1(C)C] | 596 | $^1$H-NMR (400 MHz, $CD_3OD$): δ ppm 9.41 (s, 1H), 9.34 (s, 1H), 8.20-8.10 (m, 2H), 7.26 (d, J = 8.8 Hz, 1H), 6.45-6.37 (m, 1H), 3.48-3.32 (m, 2H), 3.07-2.96 (m, 4H), 2.62-2.46 (m, 2H), 1.90-1.86 (m, 6H), 1.54 (s, 3H), 1.45-1.38 (m, 6H). | Scheme 1, Intermediate 106 and Intermediate 3 |

TABLE 1-continued

| Cpd. # | Structure | LCMS (M + 1) | NMR | Synthetic Protocol |
| --- | --- | --- | --- | --- |
| 174 | 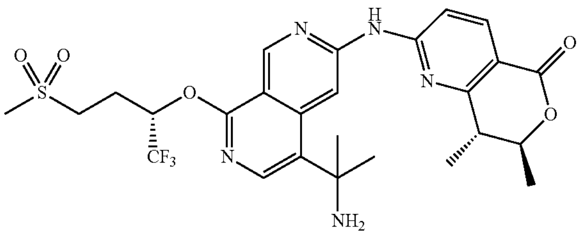 [SMILES: C[C@@H]1OC(=O)c2ccc(Nc3cc4c(C(C)(C)N)cnc(O[C@@H](CCS(C)(=O)=O)C(F)(F)F)c4cn3)nc2[C@H]1C] or 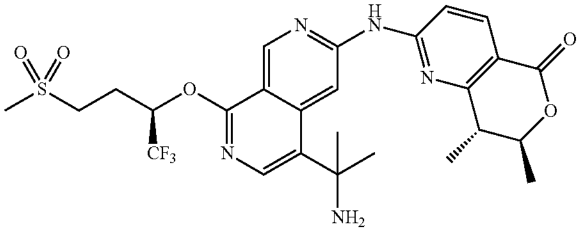 [SMILES: C[C@@H]1OC(=O)c2ccc(Nc3cc4c(C(C)(C)N)cnc(O[C@H](CCS(C)(=O)=O)C(F)(F)F)c4cn3)nc2[C@H]1C] | 582 | $^1$H-NMR (400 MHz, $CD_3OD$): δ ppm 9.41 (s, 1H), 9.24 (s, 1H), 8.20 (s, 1H), 8.16 (d, J = 8.8 Hz, 1H), 7.32 (d, J = 8.8 Hz, 1H), 6.45-6.37 (m, 1H), 4.71-4.65 (m, 1H), 3.46-3.33 (m, 2H), 3.08-3.00 (m, 4H), 2.56-2.50 (m, 2H), 1.85-1.80 (m, 6H), 1.53-1.44 (m, 6H). | Scheme 1, Intermediate 105 and Intermediate 1 |
| 175 | 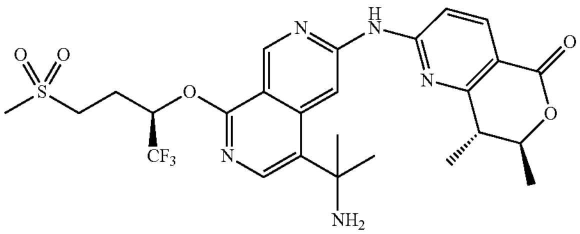 [SMILES: C[C@@H]1OC(=O)c2ccc(Nc3cc4c(C(C)(C)N)cnc(O[C@H](CCS(C)(=O)=O)C(F)(F)F)c4cn3)nc2[C@H]1C] or 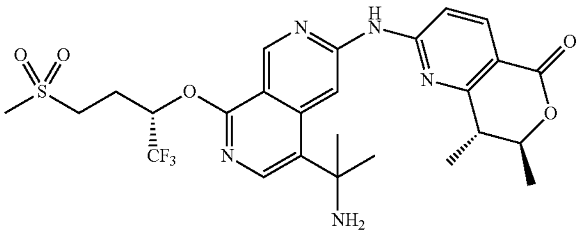 [SMILES: C[C@@H]1OC(=O)c2ccc(Nc3cc4c(C(C)(C)N)cnc(O[C@@H](CCS(C)(=O)=O)C(F)(F)F)c4cn3)nc2[C@H]1C] | 582 | $^1$H-NMR (400 MHz, $CD_3OD$): δ ppm 9.47 (s, 1H), 9.04 (s, 1H), 8.18 (d, J = 8.8 Hz, 1H), 8.03 (s, 1H), 7.38 (d, J = 8.8 Hz, 1H), 6.45-6.37 (m, 1H), 4.71-4.65 (m, 1H), 3.46-3.33 (m, 2H), 3.08-3.00 (m, 4H), 2.58-2.50 (m, 2H), 2.05-2.00 (m, 6H), 1.53-1.44 (m, 6H). | Scheme 1, Intermediate 106 and Intermediate 1 |
| 176 | 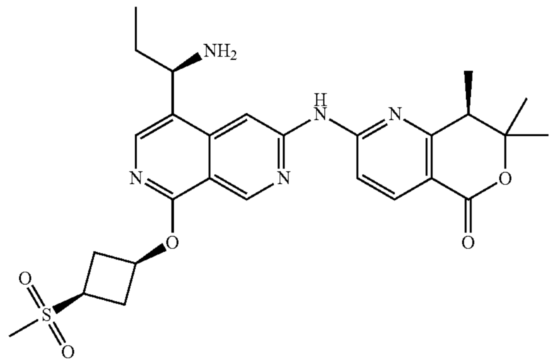 or | 540 | $^1$H-NMR (400 MHz, $CDCl_3$): δ ppm 9.36 (s, 1H), 8.86 (s, 1H), 8.19-8.08 (m, 2H), 7.26 (d, J = 8.8 Hz, 1H), 5.54-5.33 (m, 1H), 4.47-4.41 (m, 1H), 3.94-3.73 (m, 1H), 3.22-3.12 (m, 1H), 3.04-2.96 (m, 2H), 2.94 (s, 3H), 2.75-2.64 (m, 2H), 2.09-1.85 (m, 2H), 1.56-1.47 (m, 6H), 1.45 (s, 3H), 1.03-0.97 (m, 3H). | Scheme 2, Intermediate 115 and Intermediate 3 |

TABLE 1-continued

| Cpd. # | Structure | LCMS (M + 1) | NMR | Synthetic Protocol |
|---|---|---|---|---|
| | 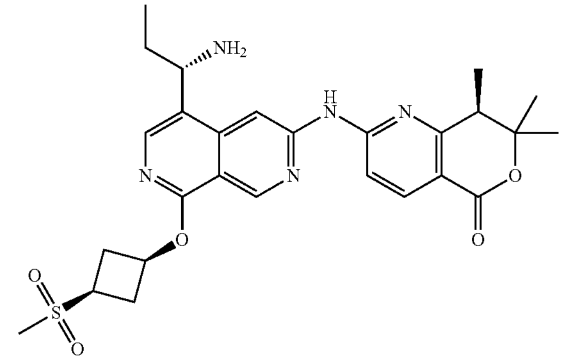 | | | |
| 177 | 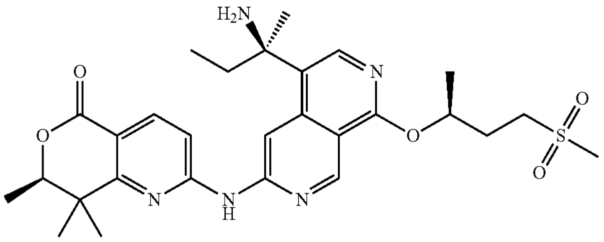 | 556 | $^1$H-NMR (400 MHz, $CD_3OD$): δ ppm 9.42 (s, 1H), 8.55 (s, 1H), 8.15 (d, J = 8.8 Hz, 1H), 8.11 (s, 1H), 7.58 (d, J = 8.8 Hz, 1H), 5.65-5.60 (m, 1H), 4.62-4.50 (m, 1H), 3.42-3.35 (m, 1H), 3.00 (s, 3H), 2.44-2.28 (m, 3H), 2.18-2.05 (m, 1H), 1.77 (s, 3H), 1.54-1.40 (m, 9H), 1.30 (s, 3H), 0.79-0.67 (m, 3H). | Scheme 1, Intermediate 54 and Intermediate 97 |
| 178 | 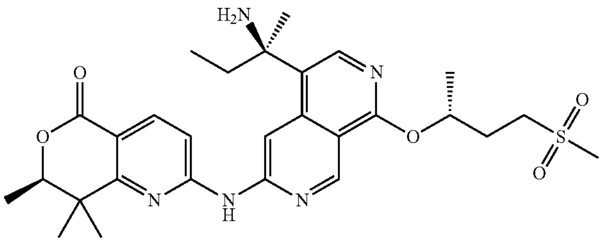 | 556 | $^1$H-NMR (400 MHz, $CD_3OD$): δ ppm 9.46 (s, 1H), 8.46 (s, 1H), 8.18 (d, J = 8.8 Hz, 1H), 8.05 (s, 1H), 7.64 (d, J = 8.8 Hz, 1H), 5.67-5.55 (m, 1H), 4.65-4.51 (m, 1H), 3.43-3.33 (m, 2H), 3.01 (s, 3H), 2.57-2.45 (m, 1H), 2.42-2.30 (m, 2H), 2.22-2.13 (m, 1H), 1.85 (s, 3H), 1.54-1.49 (m, 6H), 1.48-1.42 (m, 3H), 1.31 (s, 3H), 0.81-0.73 (m, 3H). | Scheme 1, Intermediate 31 and Intermediate 97 |
| 179 | 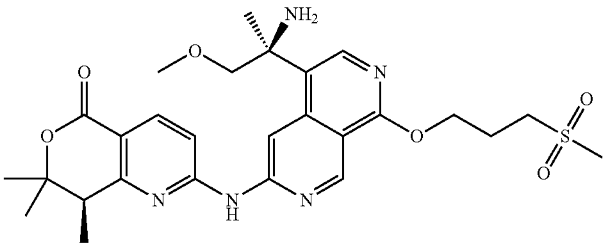 or 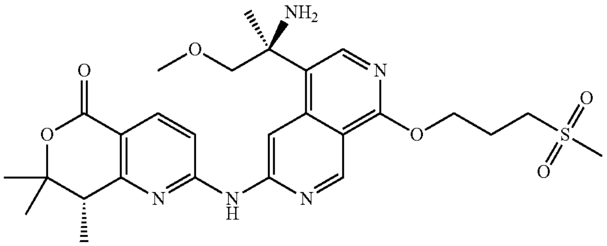 | 558 | $^1$H-NMR (400 MHz, $CD_3OD$): δ ppm 9.43 (s, 1H), 9.24 (s, 1H), 8.15 (d, J = 8.8 Hz, 1H), 8.07 (s, 1H), 7.26 (d, J = 8.8 Hz, 1H), 4.70-4.67 (m, 2H), 4.07-4.04 (m, 1H), 4.00-3.92 (m, 1H), 3.43-3.36 (m, 5H), 3.05-3.01 (m, 4H), 2.49-2.40 (m, 2H), 1.89 (s, 3H), 1.54 (s, 3H), 1.47 (s, 3H), 1.40 (d, J = 7.2 Hz, 3H). | Scheme 1, Intermediate 3 and Intermediate 99 |

TABLE 1-continued
| Cpd. # | Structure | LCMS (M + 1) | NMR | Synthetic Protocol |
|---|---|---|---|---|
| 180 | 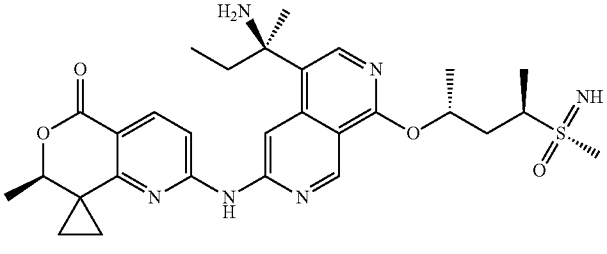<br>Or<br>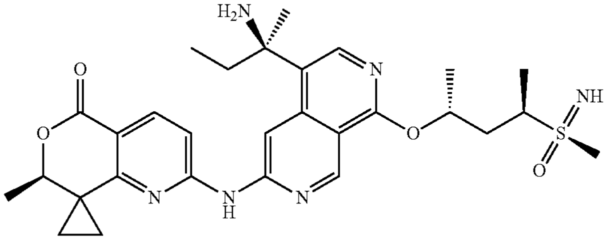<br>or<br>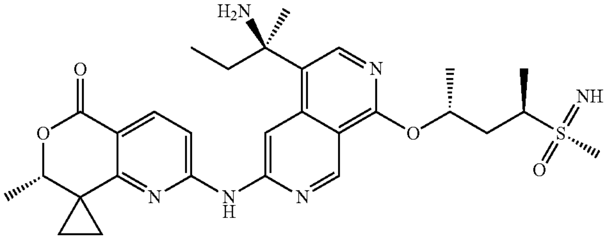<br>Or<br>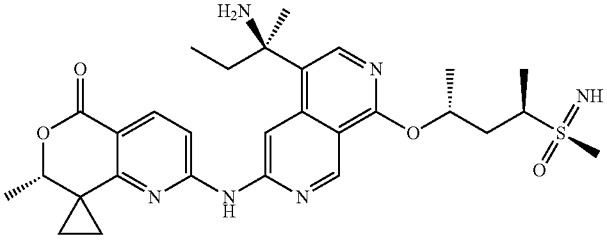 | 567 | $^1$H-NMR (400 MHz, $CD_3OD$): δ ppm 9.49 (s, 1 H), 8.19 (d, J = 8.8 Hz, 1 H), 8.06 (s, 1 H), 7.94 (s, 1 H), 7.76 (d, J = 8.8 Hz, 1 H), 5.76-5.71 (m, 1 H), 4.68-4.62 (m, 1 H), 4.20-4.17 (m, 1 H), 3.31 (s, 3 H), 2.64-2.57 (m, 2 H), 2.32-2.12 (m, 2 H), 1.92 (s, 3 H), 1.72 (d, J = 8.0 Hz, 3 H), 1.55 (d, J = 8.0 Hz, 3 H), 1.49-1.42 (m, 1 H), 1.37 (d, J = 6.4 Hz, 3 H), 1.24-1.20 (m, 4 H), 0.85-0.79 (m, 3 H). | Scheme 1, Intermediate 107 and Intermediate 12 |
| 181 | 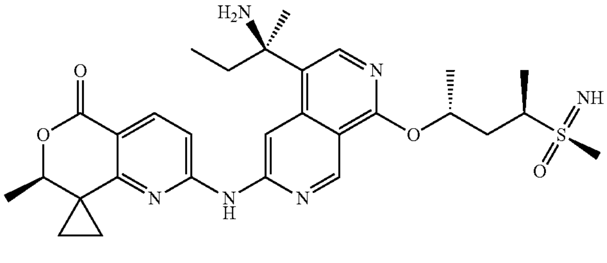<br>Or | 567 | $^1$H-NMR (400 MHz, $CD_3OD$): δ ppm 9.45 (s, 1 H), 8.48 (s, 1 H), 8.18 (d, J = 8.8 Hz, 1 H), 8.12 (s, 1 H), 7.95 (s, 1 H), 7.70 (d, J = 8.8 Hz, 1 H), 5.78-5.65 (m, 1 H), 4.68-4.58 (m, 1 H), 3.38-3.32 (m, 1 H), 2.96 (s, 3 H), 2.64-2.40 (m, 2 H), 2.32-2.12 (m, 2 H), 1.92 (s, 3 H), 1.58-1.50 (m, 7 H), 1.49-1.42 (m, 1 H), 1.37 (d, J = 6.4 Hz, 3 H), 1.26-1.17 (m, 2 H), 0.85-0.79 (m, 3 H). | Scheme 1, Intermediate 108 and Intermediate 12 |

TABLE 1-continued
| Cpd. # | Structure | LCMS (M + 1) | NMR | Synthetic Protocol |
|---|---|---|---|---|
| | 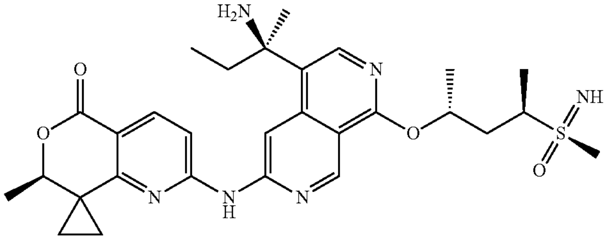 or 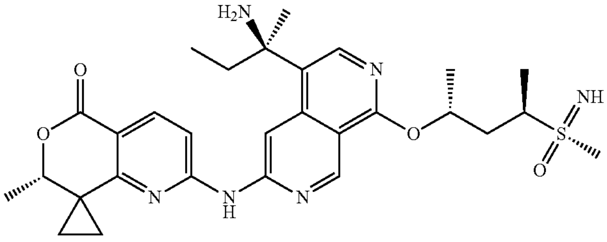 Or 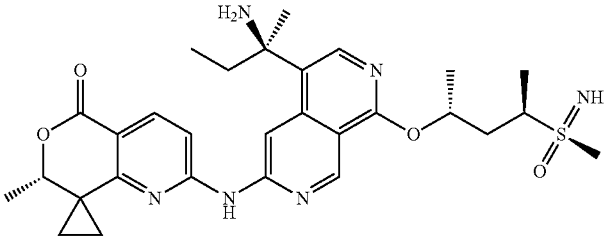 | | | |
| 182 | 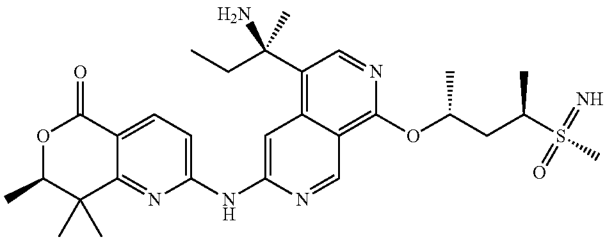 Or 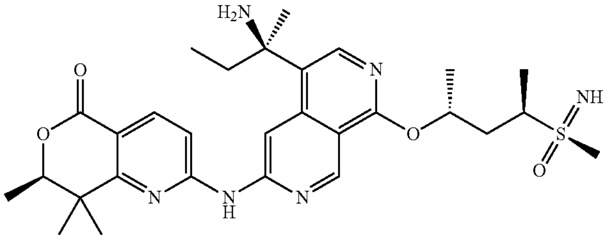 or | 569 | $^1$H-NMR (400 MHz, $CD_3OD$): δ ppm 9.41 (s, 1H), 8.64 (s, 1H), 8.17-8.14 (m, 2H), 7.57 (d, J = 8.8 Hz, 1H), 5.72-5.68 (m, 1H), 4.59-4.54 (m, 1H), 3.43-3.40 (m,lH), 2.96 (s, 3H), 2.47-2.37 (m, 2H), 2.15-2.09 (m, 2H), 1.75 (s, 3H), 1.60-1.40 (m, 12H), 1.31 (s, 3H), 0.75-0.71 (m, 3H). | Scheme 1, Intermediate 108 and Intermediate 97 |

TABLE 1-continued
| Cpd. # | Structure | LCMS (M + 1) | NMR | Synthetic Protocol |
|---|---|---|---|---|
| | 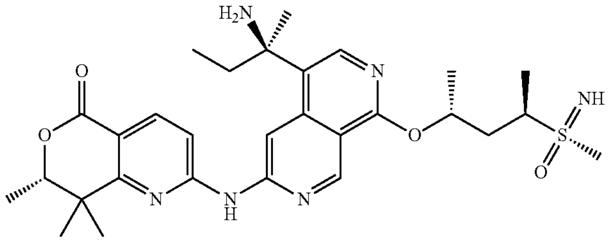 | | | |
| | Or | | | |
| | 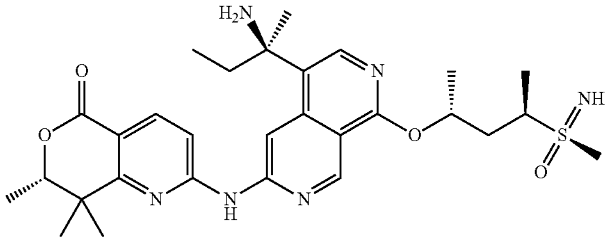 | | | |
| 183 | 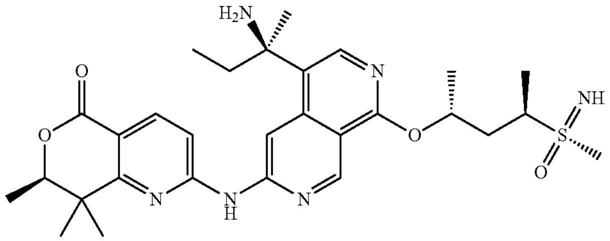 | 569 | $^1$H-NMR (400 MHz, CD3OD): δ ppm 9.42 (s, 1H), 8.65 (s, 1H), 8.17-8.14 (m, 2H), 7.57 (d, J = 8.8 Hz, 1H), 5.72-5.68 (m, 1H), 4.61-4.54 (m, 1H), 3.43-3.40 (m, 1H), 2.98 (s, 3H), 2.47-2.37 (m, 1H), 2.17-2.05 (m, 3H), 1.74 (s, 3H), 1.60-1.40 (m, 12H), 1.33 (s, 3H), 0.75-0.71 (m, 3H). | Scheme 1, Intermediate 107 and Intermediate 97 |
| | Or | | | |
| | 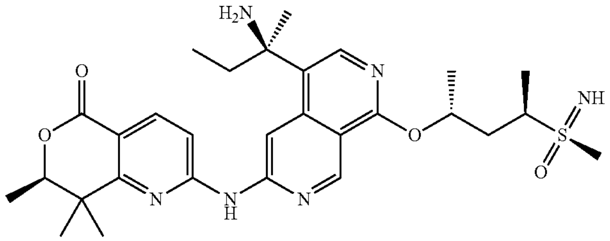 | | | |
| | or | | | |
| | 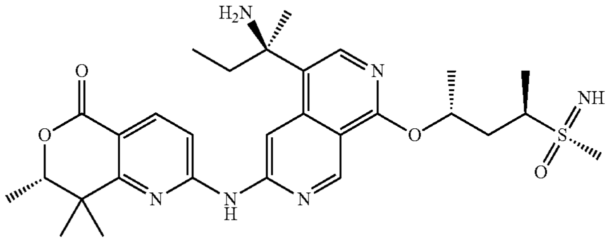 | | | |
| | Or | | | |

TABLE 1-continued
| Cpd. # | Structure | LCMS (M + 1) | NMR | Synthetic Protocol |
| --- | --- | --- | --- | --- |
| | 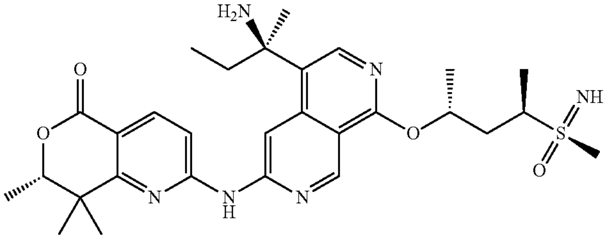 | | | |
| 184 | 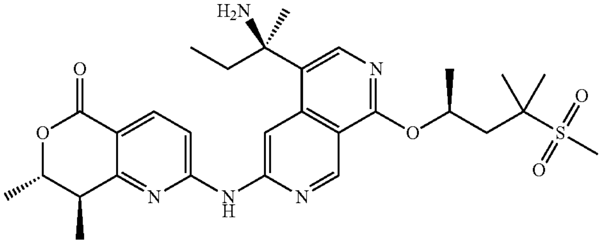<br>Or<br>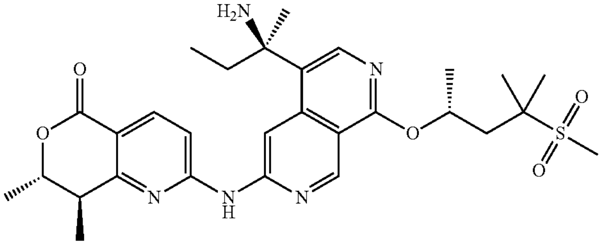 | 570 | $^1$H-NMR (400 MHz, $CD_3OD$): δ ppm 9.38 (s, 1H), 9.16 (s, 1H), 8.10-8.05 (m, 2H), 7.23 (d, J = 8.4 Hz, 1H), 5.88-5.81 (m, 1H), 4.68-4.65 (m, 1H), 3.08-2.99 (m, 1H), 2.95 (s, 3H), 2.50-2.43 (m, 2H), 2.25-2.21 (m, 2H), 1.81 (s, 3H), 1.52-1.44 (m, 15H), 0.79-0.72 (m, 3H). | Scheme 1, Intermediate 110 and Intermediate 1 |
| 185 | 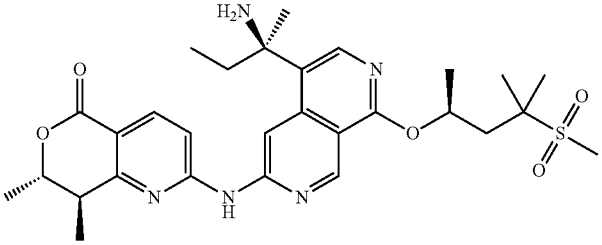<br>Or<br>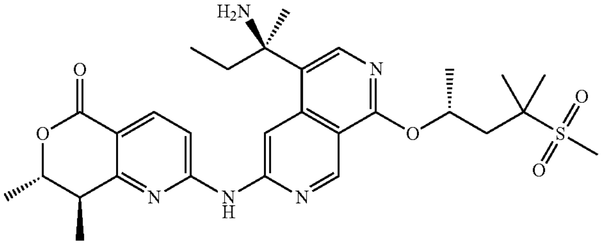 | 570 | $^1$H-NMR (400 MHz, $CD_3OD$): δ ppm 9.38 (s, 1H), 9.11 (s, 1H), 8.10-8.05 (m, 2H), 7.33 (d, J = 8.4 Hz, 1H), 5.88-5.81 (m, 1H), 4.68-4.65 (m, 1H), 3.00-2.99 (m, 3H), 2.93 (s, 3H), 2.50-2.43 (m, 2H), 2.25-2.21 (m, 2H), 1.81 (s, 3H), 1.52-1.44 (m, 15H), 0.79-0.72 (m, 3H). | Scheme 1, Intermediate 109 and Intermediate 1 |

TABLE 1-continued
| Cpd. # | Structure | LCMS (M + 1) | NMR | Synthetic Protocol |
|---|---|---|---|---|
| 186 | 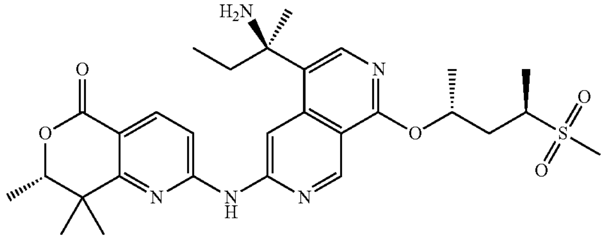 Or 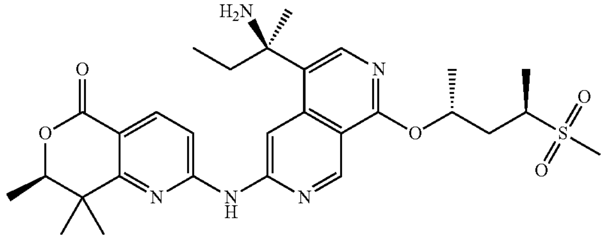 | 570 | $^1$H-NMR (400 MHz, $CD_3OD$): δ ppm 9.41 (s, 1H), 8.59 (s, 1H), 8.16 (d, J = 8.8 Hz, 1H), 8.14 (s, 1H), 7.57 (d, J = 8.8 Hz, 1H), 5.80-5.60 (m, 1H),4.63-4.53 (m, 2H), 3.41-3.33 (m, 1H), 2.93 (s, 3H), 2.47-2.31 (m, 2H), 2.18-2.02 (m, 2H), 1.75 (s, 3H), 1.53-1.42 (m, 12H), 1.31 (s, 3H), 0.75-0.71 (m, 3H). | Scheme 1, Intermediate 53 and Intermediate 97 |
| 187 | 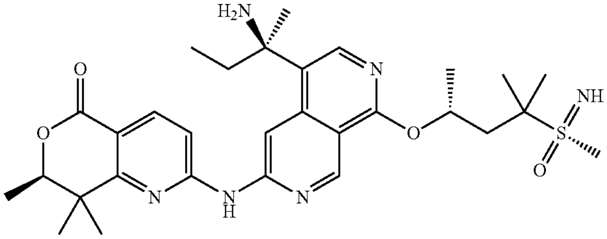 Or 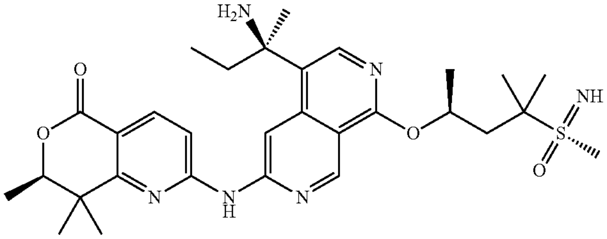 Or 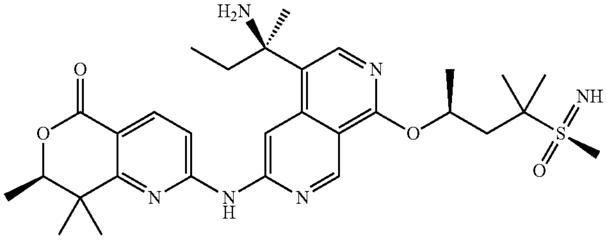 Or | 583 | $^1$H-NMR (400 MHz, $CD_3OD$): δ ppm 9.40 (s, 1H), 8.63 (s, 1H), 8.20-8.15 (m, 2H), 7.56 (d, J = 8.8 Hz, 1H), 5.85-5.78 (m, 1H), 4.61-4.54 (m, 1H), 2.96 (s, 3H), 2.50-2.45 (m, 1H), 2.40-2.20 (m, 2H), 2.15-2.05 (m, 1H), 1.74 (s, 3H), 1.55-1.44 (m, 15H), 1.31 (s, 3H), 0.76-0.72 (m, 3H). | Scheme 1, Intermediate 114 and Intermediate 97 |

TABLE 1-continued
| Cpd. # | Structure | LCMS (M + 1) NMR | Synthetic Protocol |
|---|---|---|---|
| | 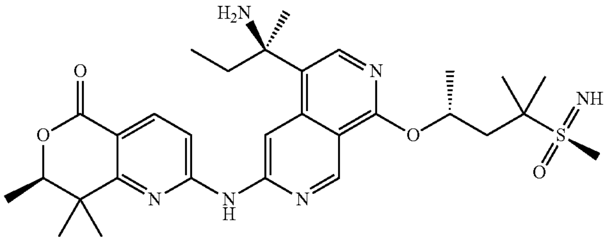<br>Or<br>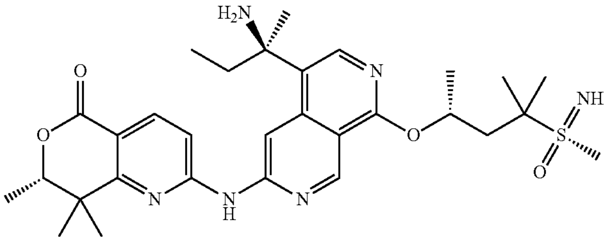<br>Or<br>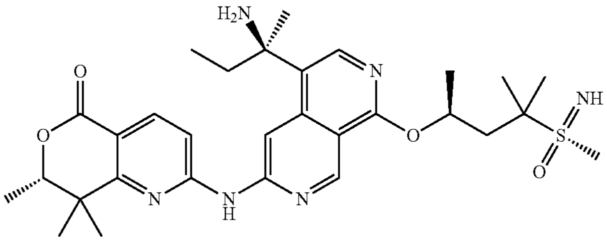<br>Or<br>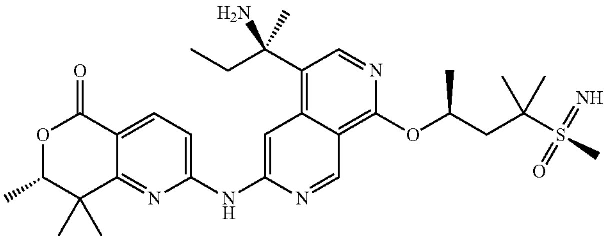<br>Or<br>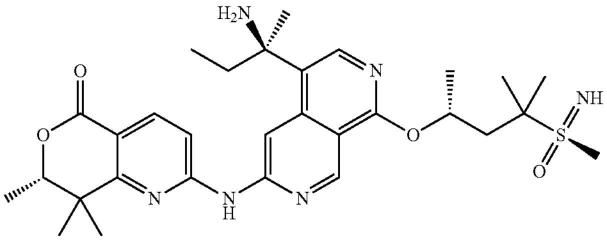 | | |

TABLE 1-continued
| Cpd. # | Structure | LCMS (M + 1) | NMR | Synthetic Protocol |
|---|---|---|---|---|
| 188 | 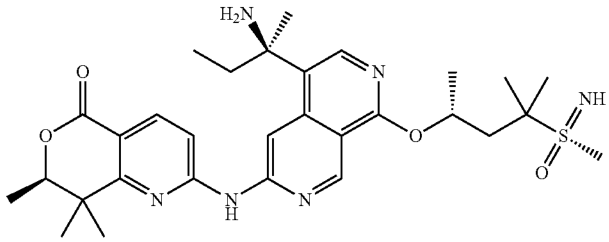 Or 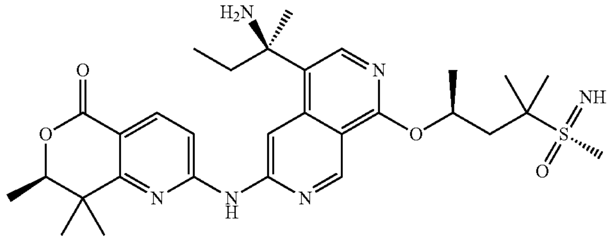 Or 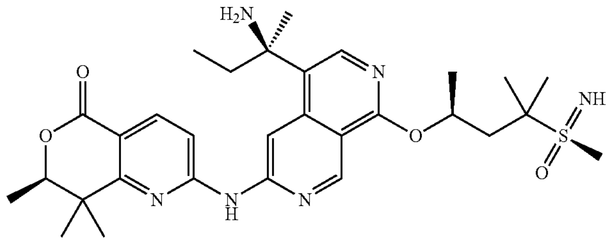 Or 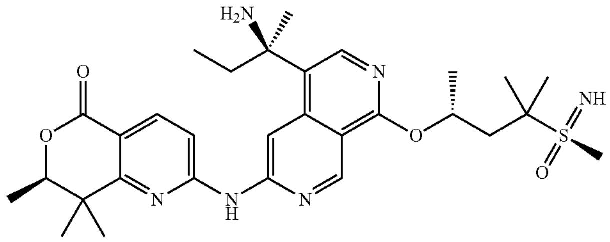 Or 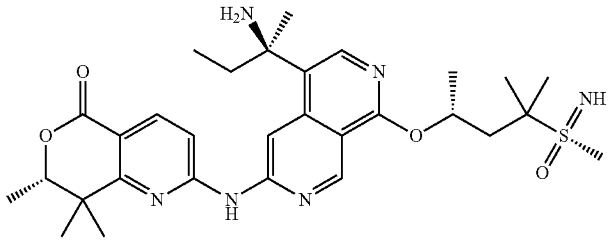 Or | 583 | $^1$H-NMR (400 MHz, $CD_3OD$): δ ppm 9.40 (s, 1H), 8.63 (s, 1H), 8.20-8.15 (m, 2H), 7.57 (d, J = 8.8 Hz, 1H), 5.85-5.78 (m, 1H), 4.61-4.54 (m, 1H), 2.96 (s, 3H), 2.50-2.45 (m, 1H), 2.40-2.20 (m, 2H), 2.15-2.05 (m, 1H), 1.73 (s, 3H), 1.55-1.44 (m, 15H), 1.31 (s, 3H), 0.76-0.72 (m, 3H). | Scheme 1, Intermediate 112 and Intermediate 97 |

TABLE 1-continued
| Cpd. # | Structure | LCMS (M + 1) | NMR | Synthetic Protocol |
| --- | --- | --- | --- | --- |
| | 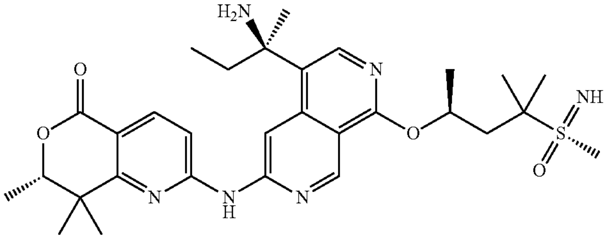<br>Or<br>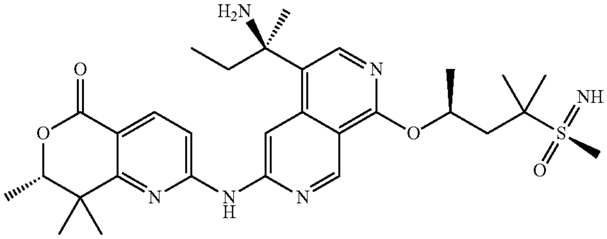<br>Or<br>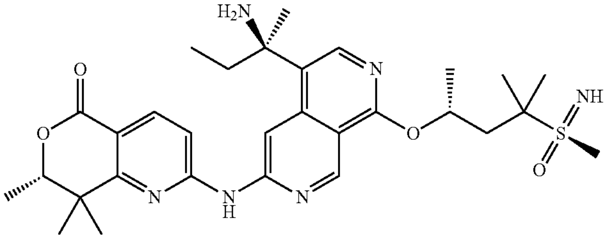 | | | |
| 189 | 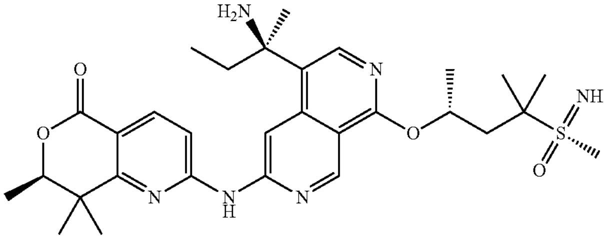<br>Or<br>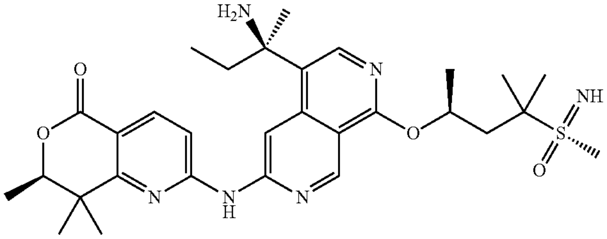<br>Or | 583 | $^{1}$H-NMR (400 MHz, $CD_3OD$): δ ppm 9.40 (s, 1H), 8.63 (s, 1H), 8.20-8.15 (m, 2H), 7.57 (d, J = 8.8 Hz, 1H), 5.85-5.78 (m, 1H), 4.61-4.54 (m, 1H), 2.96 (s, 3H), 2.50-2.45 (m, 1H), 2.40-2.20 (m, 2H), 2.15-2.05 (m, 1H), 1.73 (s, 3H), 1.55-1.44 (m, 15H), 1.32 (s, 3H),0.76-0.72 (m, 3H). | Scheme 1, Intermediate 111 and Intermediate 97 |

TABLE 1-continued
| Cpd. # | Structure | LCMS (M + 1) NMR | Synthetic Protocol |
|---|---|---|---|
| | 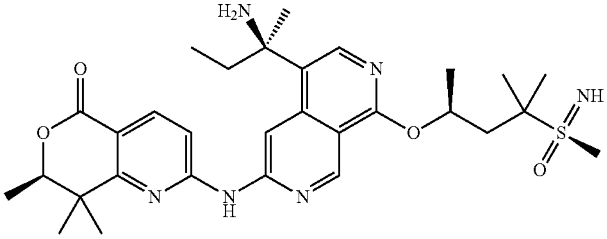 Or 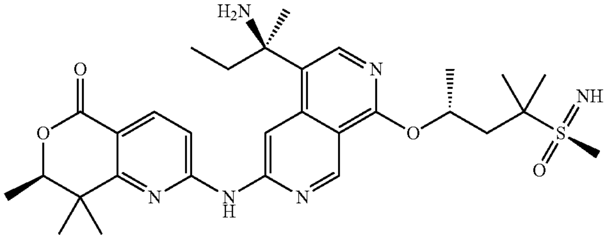 Or 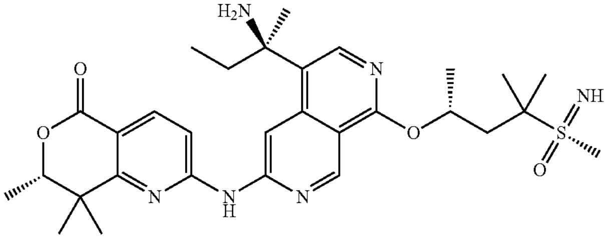 Or 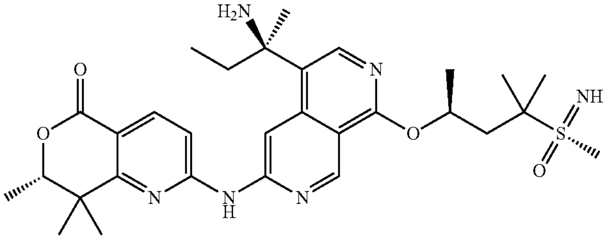 Or 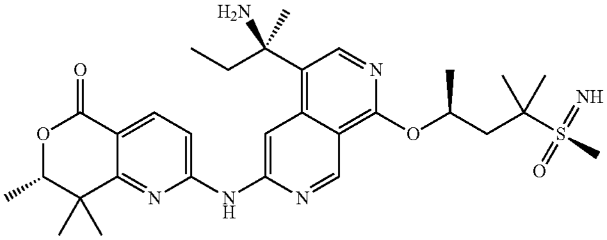 Or | | |

TABLE 1-continued
| Cpd. # | Structure | LCMS (M + 1) | NMR | Synthetic Protocol |
|---|---|---|---|---|
| | 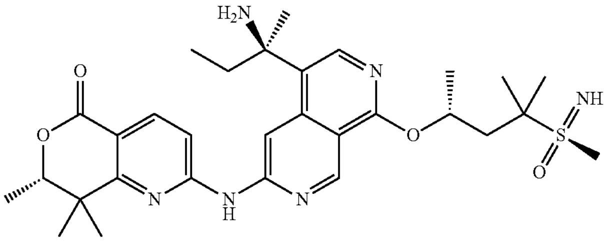 | | | |
| 190 | 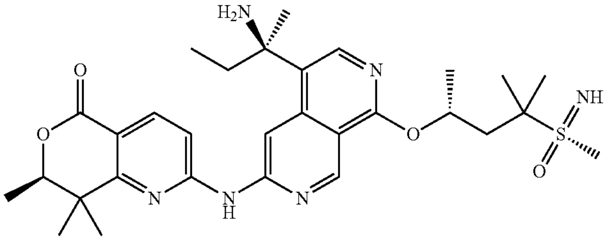<br>Or<br>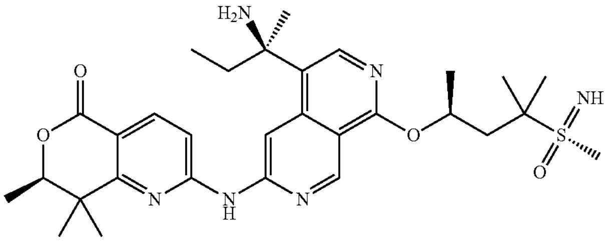<br>Or<br>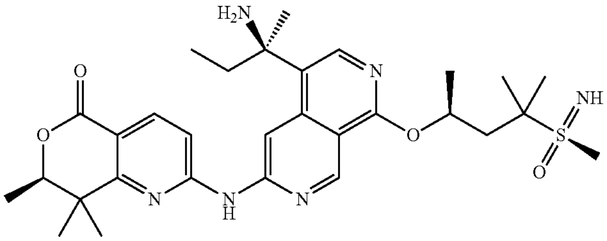<br>Or<br>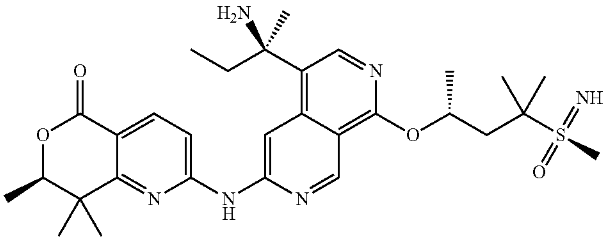<br>Or | 583 | $^1$H-NMR (400 MHz, $CD_3OD$): δ ppm 9.40 (s, 1H), 8.63 (s, 1H), 8.20-8.15 (m, 2H), 7.57 (d, J = 8.8 Hz, 1H), 5.85-5.80 (m, 1H), 4.61-4.54 (m, 1H), 2.96 (s, 3H), 2.50-2.45 (m, 1H), 2.40-2.20 (m, 2H), 2.15-2.05 (m, 1H), 1.74 (s, 3H), 1.55-1.44 (m, 15H), 1.31 (s, 3H), 0.76-0.72 (m, 3H). | Scheme 1, Intermediate 113 and Intermediate 97 |

TABLE 1-continued
| Cpd. # | Structure | LCMS (M + 1) | NMR | Synthetic Protocol |
|---|---|---|---|---|
| | 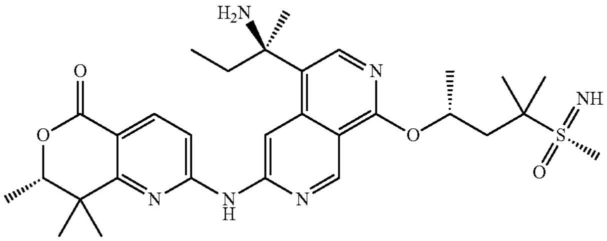 Or 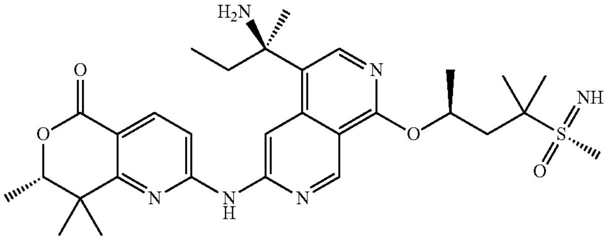 Or 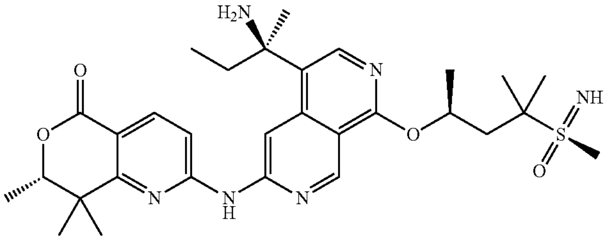 Or 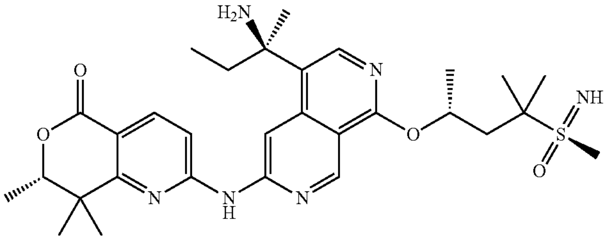 | | | |
| 191 | 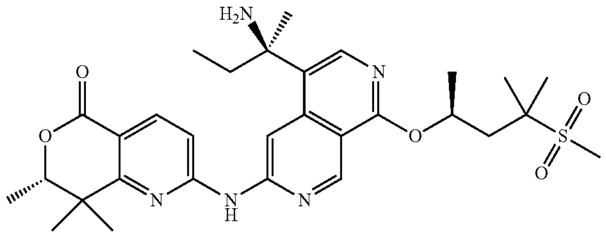 Or | 584 | $^1$H-NMR (400 MHz, $CD_3OD$): δ ppm 9.42 (s, 1H), 8.58 (s, 1H), 8.20-8.15 (m, 2H), 7.62 (d, J = 8.8 Hz, 1H), 5.88-5.81 (m, 1H), 4.61-4.54 (m, 1H), 2.94 (s, 3H), 2.50-2.25 (m, 2H), 2.20-2.09 (m, 2H), 1.79 (s, 3H), 1.52-1.44 (m, 15H), 1.32 (s, 3H), 0.79-0.72 (m, 3H). | Scheme 1, Intermediate 110 and Intermediate 97 |

TABLE 1-continued
| Cpd. # | Structure | LCMS (M + 1) | NMR | Synthetic Protocol |
|---|---|---|---|---|
| | 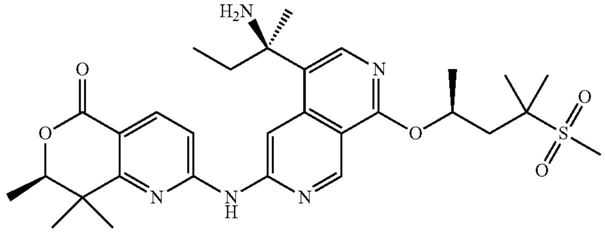<br>Or<br>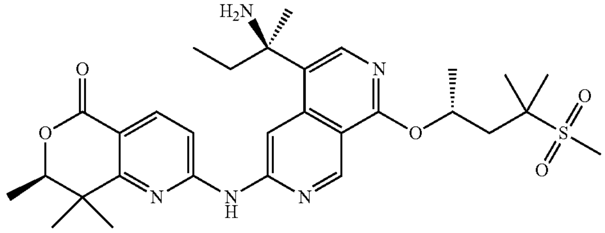<br>Or<br>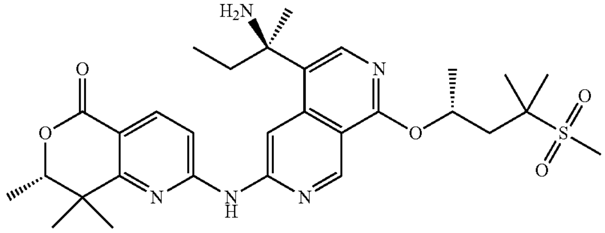 | | | |
| 192 | 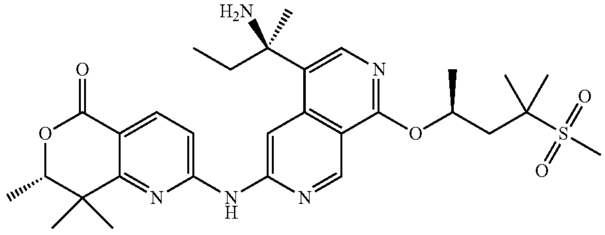<br>Or<br>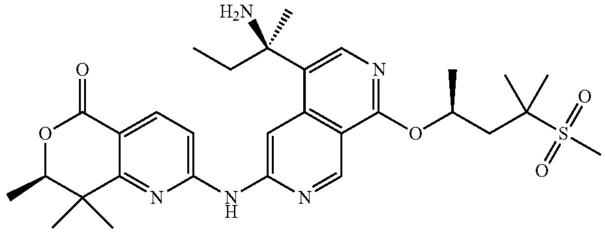<br>Or | 584 | $^1$H-NMR (400 MHz, $CD_3OD$): δ ppm 9.40 (s, 1H), 8.60 (s, 1H), 8.17-8.15 (m, 2H), 7.58 (d, J = 8.8 Hz, 1H), 5.85-5.81 (m, 1H), 4.59-4.54 (m, 1H), 2.94 (s, 3H), 2.50-2.31 (m, 2H), 2.27-2.09 (m, 2H), 1.75 (s, 3H), 1.52-1.44 (m, 15H), 1.31 (s, 3H), 0.76-0.72 (m, 3H). | Scheme 1, Intermediate 109 and Intermediate 97 |

TABLE 1-continued

| Cpd. # | Structure | LCMS (M + 1) | NMR | Synthetic Protocol |
| --- | --- | --- | --- | --- |
| | 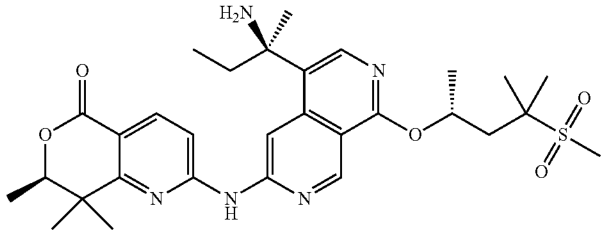 Or 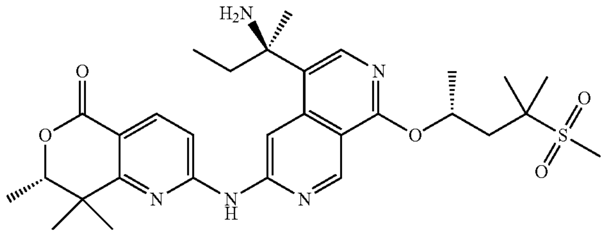 | | | |

Included in the present teachings are pharmaceutically acceptable salts of the compounds disclosed herein (including compounds 1-192 disclosed in Table 1 and the Exemplification) as well as the corresponding charge neutral form e.g., free base.

Another embodiment of the disclosure is a compound disclosed herein, including a compound of Formulae I, II, III, IV, V, VI or VII, or a compound in Table 1 or in the Exemplification, or a pharmaceutically acceptable salt of any of the foregoing, in which one or more hydrogen atoms is replaced with deuterium. The deuterium enrichment at any one of the sites where hydrogen has been replaced by deuterium is at least 50%, 75%, 85%, 90%, 95%, 98% or 99%. Deuterium enrichment is a mole percent and is obtained by dividing the number of compounds with deuterium enrichment at the site of enrichment with the number of compounds having hydrogen or deuterium at the site of enrichment.

Definitions

As used herein, the term "pharmaceutically acceptable salt" refers to pharmaceutical salts that are, within the scope of sound medical judgment, suitable for use in contact with the tissues of humans and lower animals without undue toxicity, irritation, and allergic response, and are commensurate with a reasonable benefit/risk ratio. Pharmaceutically acceptable salts are well known in the art. For example, S. M. Berge et al. describes pharmacologically acceptable salts in *J. Pharm. Sci*. (1977) 66:1-19. Compounds of the present teachings with basic groups can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, nitric, and sulfuric acids) and of organic acids (such as acetic acid, benzenesulfonic, benzoic, methanesulfonic, and p-toluenesulfonic acids). Compounds of the present teachings with acidic groups can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

The term "alkyl" used alone or as part of a larger moiety, such as "alkoxy", "hydroxyalkyl" and the like, means a saturated aliphatic straight-chain or branched monovalent hydrocarbon radical. Unless otherwise specified, an alkyl group typically has 1 to 6 carbon atoms ($C_{1-6}$ alkyl), (i.e., 1, 2, 3, 4, 5 or 6) alternatively, 1 to 3 carbon atoms ($C_{1-3}$ alkyl) (i.e., 1, 2 or 3). "$C_{1-6}$ alkyl" is means a radical having 1 to 6 carbon atoms in a linear or branched arrangement, such as methyl, ethyl, propyl, isopropyl, butyl, isobutyl, tert-butyl, and the like.

The term "alkylene" means a bivalent alkyl group, for example $C_1$-$C_6$ alkyl is a group —$(CH_2)n$—where n is 1 to 6, $C_1$-$C_3$ alkyl is a group —$(CH_2)n$—where n is 1 to 3, unless otherwise specified.

"Cycloalkyl" means a saturated aliphatic cyclic hydrocarbon ring radical. Unless otherwise specified, a cycloalkyl has 3 to 8 ring carbon atoms ($C_{3-8}$ cycloalkyl) (i.e., 3, 4, 5, 6, 7, or 8), alternatively, 3 to 6 ring carbon atoms ($C_{3-6}$ cycloalkyl) (i.e., 3, 4, 5, or 6), alternatively, 3 to 5 carbon atoms ($C_{3-5}$ cycloalkyl) (i.e., 3, 4, or 5). "$C_{3-6}$ Cycloalkyl" means a radical having from 3 to 6 carbon atoms arranged in a monocyclic ring. A $C_{3-6}$ cycloalkyl includes cyclopropyl, cyclobutyl, cyclopentyl, and cyclohexyl. A $C_{3-5}$ cycloalkyl includes cyclopropyl, cyclobutyl, and cyclopentyl.

The term "halogen" or "halo" means fluorine or fluoro (F), chlorine or chloro (Cl), bromine or bromo (Br), or iodine or iodo (I).

The term "heterocycle" refers to a monocyclic non-aromatic ring radical containing unless otherwise specified, 3 to 8 ring atoms (i.e., "3, 4, 5, 6, 7, or 8 membered") selected from carbon atom and 1 or 2 heteroatoms. Each heteroatom is independently selected from nitrogen, quaternary nitrogen, oxidized nitrogen (e.g., NO); oxygen; and sulfur, including sulfoxide and sulfone. For example, 4-6 membered heterocycle containing nitrogen refers to a monocyclic non-aromatic ring radical containing 2-5 carbon atoms and 1 or 2 nitrogen atoms; 4-6 membered heterocycle containing oxygen atoms refers to a monocyclic non-aromatic ring radical containing 2-5 carbon atoms and 1 or 2 oxygen. Representative heterocycles include azetidinyl, morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like.

The term "hydroxyl" or "hydroxy" refers to the group OH.

The term "substituted", whether preceded by the term "optionally" or not, refers to the replacement of a hydrogen substituent in a given structure with a non-hydrogen substituent. Thus, for example, a substituted alkyl is an alkyl wherein at least one non-hydrogen substituent is in the place of a hydrogen substituent on the alkyl group. To illustrate, monofluoroalkyl is an alkyl substituted with a fluoro substituent, and difluoroalkyl is an alkyl substituted with two fluoro substituents. It should be recognized that if there is more than one substitution on a substituent, each non-hydrogen substituent can be identical or different (unless otherwise stated).

If a group is described as "optionally substituted", the group can be either (1) not substituted or (2) substituted. If a group is described as optionally substituted with up to a particular number of non-hydrogen substituents, that group can be either (1) not substituted; or (2) substituted by up to that particular number of non-hydrogen substituents or by up to the maximum number of substitutable positions on the substituent, whichever is less. Thus, for example, if a group is described as a cycloalkyl optionally substituted with up to 3 non-hydrogen substituents, then any cycloalkyl with less than 3 substitutable positions would be optionally substituted by up to only as many non-hydrogen substituents as the cycloalkyl has substitutable positions.

The term "sulfone" refers to the group $—S(O)_2—$.

Compounds having one or more chiral centers can exist in various stereoisomeric forms, i.e., each chiral center can have an R or S configuration or can be a mixture of both. Stereoisomers are compounds that differ only in their spatial arrangement. Stereoisomers include all diastereomeric and enantiomeric forms of a compound. Enantiomers are stereoisomers that are non-superimposable mirror images of each other. Diastereomers are stereoisomers having two or more chiral centers that are not identical and are not mirror images of each other.

When the stereochemical configuration at a chiral center in a compound having one or more chiral centers is depicted by its chemical name (e.g., where the configuration is indicated in the chemical name by "R" or "S") or structure (e.g., the configuration is indicated by "wedge" bonds), the enrichment of the indicated configuration relative to the opposite configuration is greater than 50%, 60%, 70%, 80%, 90%, 99% or 99.9% (except when the designation "rac" or "racemate accompanies the structure or name, as explained in the following two paragraphs). "Enrichment of the indicated configuration relative to the opposite configuration" is a mole percent and is determined by dividing the number of compounds with the indicated stereochemical configuration at the chiral center(s) by the total number of all of the compounds with the same or opposite stereochemical configuration in a mixture.

When the stereochemical configuration at a chiral center in a compound is depicted by chemical name (e.g., where the configuration is indicated in the name by "R" or "S") or structure (e.g., the configuration is indicated by "wedge" bonds) and the designation "rac" or "racemate" accompanies the structure or is designated in the chemical name, a racemic mixture is intended.

When two or more stereoisomers are depicted by their chemical names or structures, and the names or structures are connected by an "or", one or the other of the two or more stereoisomers is intended, but not both. The enrichment of one stereoisomer relative to the other is as indicated above.

When a disclosed compound having a chiral center is depicted by a structure without showing a configuration at that chiral center, the structure is meant to encompass the compound with the S configuration at that chiral center, the compound with the R configuration at that chiral center, or the compound with a mixture of the R and S configuration at that chiral center. When a disclosed compound having a chiral center is depicted by its chemical name without indicating a configuration at that chiral center with "S" or "R", the name is meant to encompass the compound with the S configuration at that chiral center, the compound with the R configuration at that chiral center or the compound with a mixture of the R and S configuration at that chiral center.

A racemic mixture means a mixture of 50% of one enantiomer and 50% of its corresponding enantiomer. The present teachings encompass all enantiomerically-pure, enantiomerically-enriched, diastereomerically pure, diastereomerically enriched, and racemic mixtures, and diastereomeric mixtures of the compounds described herein.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

"Peak 1" or "first eluting isomer" in the Experimental section refers to an intended reaction product compound obtained from a chromatography separation/purification that elutes earlier than a second intended reaction product compound from the same preceding reaction. The second intended product compound is referred to as "peak 2" or "second eluting isomer".

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that, unless otherwise indicated, one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

Use Embodiments

Compounds of the disclosure are MAP4K1 inhibitors. The use of the word "inhibitor" means that a compound or a pharmaceutically acceptable salt thereof inhibits activity of MAP4K1. By "inhibit" herein is meant to decrease the activity of the target enzyme as compared to the activity of that enzyme in the absence of the inhibitor. In some alternatives, the term "inhibit" means a decrease in MAP4K1 activity of at least 5%, at least 10%, at least 20%, at least 50%, at least 60%, at least 79%, at least 80%, at least 90% or at least 95%. In other alternatives, inhibit means a decrease in MAP4K1 activity of 5% to 25%, 25% to 50%, 50 to 70%, 75 to 100%. In some embodiments, inhibit means a decrease in MAP4K1 activity about 95% to 100%, e.g., a decrease in activity of 95%, 96%, 97%, 98%, 99%, or 100%. Such decreases can be measured using a variety of techniques that would be recognizable by one of skill in the art, including in vitro kinase assays.

Compounds of the disclosure are selective MAP4K1 inhibitors. As used herein, a "selective MAP4K1 inhibitor" refers to a compound or a pharmaceutically acceptable salt thereof, which has the ability to selectively inhibit MAP4K1 kinase over other targets. More specifically, a selective MAP4K1 inhibitor has the ability to selectively inhibit MAP4K1 over another kinases. A selective MAP4K1 inhibitor has the ability to selectively reduce target signaling activity relative to off-target signaling activity, via direct or indirect interaction with the target. The ability to selectively target MAP4K1 with a compound or pharmaceutically acceptable salt thereof provides advantages in terms of improved potency on the desired target, less off-target activity and an increased probability of clinical success in comparison with a non-selective compound or salt.

A MAP4K1 inhibitor that selectively inhibits MAP4K1 may have an activity that is at least 2-fold relative to another kinase (e.g., at least 10-fold; at least 15-fold; at least 20-fold; at least 30-fold; at least 40-fold selectivity; at least 50-fold; at least 60-fold; at least 70-fold; at least 80-fold; at least 90-fold; at least 100-fold; at least 125-fold; at least 150-fold; at least 175-fold; or at least 200-fold. In some alternatives, a selective MAP4K1 inhibitor exhibits at least 15-fold selectivity over another kinase, e.g., LCK and MAP4K family members (MAP4K4 (HGK) and MAP4K3 (GLK)). In some alternatives, the selective MAP4K1 inhibitors are selective over EGFR and L858R/T790M EGFR. In some alternatives, the selective MAP4K1 inhibitors of the disclosure are selective over BTK. In some alternatives, the selective MAP4K1 inhibitors of the disclosure are selective over INK.

The disclosure provides methods of modulating (e.g., inhibiting) MAP4K1 activity in a subject in need thereof, said method comprising administering to the subject a compound provided herein, or a pharmaceutically acceptable salt thereof. In certain embodiments, the compounds of the disclosure, or pharmaceutically acceptable salts thereof, are useful for therapeutic administration to enhance, stimulate and/or increase immunity in subjects in need thereof, e.g., in cancer patients or patients with viral infection. In some instances, the compounds of the disclosure, or pharmaceutically acceptable salts thereof reduce, inhibit, or otherwise diminish phosphorylation of SLP76.

In some instances, the compounds of the disclosure, or pharmaceutically acceptable salts thereof, are useful for therapeutic administration to enhance at least one of activation, priming, migration, proliferation, survival and cytolytic activity of T cells relative to prior to administration. In certain aspects, T cell activation is characterized by enhanced levels of IL-2, IFN-gamma, or granzyme B production by T cells relative to prior to administration of the compound or pharmaceutically acceptable salt thereof. In some instances, the compounds of the disclosure, or pharmaceutically acceptable salts thereof, are useful for therapeutic administration to induce a change in cell cycle or cell viability. In some instances, the compounds of the disclosure, or pharmaceutically acceptable salts thereof, are useful for improving function of T effector cells. In some instances, the compounds of the disclosure, or pharmaceutically acceptable salts thereof, are useful for inhibiting the suppressive effects of T regulatory cells or improving the T cell response to immune suppressive factors including adenosine and PGE2.

In some instances, the compounds of the disclosure, or pharmaceutically acceptable salts thereof, are useful for increasing the frequency of CD8+ tumor infiltrating lymphocytes (TILS). In some instances, the compounds of the disclosure, or pharmaceutically acceptable salts thereof, are useful for enhancing CD3+/Treg ratios. In some instances, the compounds of the disclosure, or pharmaceutically acceptable salts thereof, are useful for enhancing cytokines. In some instances, the compounds of the disclosure, or pharmaceutically acceptable salts thereof, are useful for enhancing cytokines with no impact on IL-6. In some instances, the compounds of the disclosure, or pharmaceutically acceptable salts thereof, indirectly inhibit the growth of cancer cells. In some instances, the compounds of the disclosure, or pharmaceutically acceptable salts thereof, are useful for priming of the immune response (i.e., vaccines) to tumors or viruses for booting or generating anti-viral/anti-tumor immunity. In one instance, the compounds of the disclosure, or pharmaceutically acceptable salts thereof, are used for enhancing or boosting response to a vaccine (such as a cancer vaccine or a personalized cancer vaccine (PCV)) or a CAR-T cell therapy.

Methods of treating a MAP4K1-dependent disease or disorder can include administering to a subject in need thereof a therapeutically effective amount of a compound provided herein, or a pharmaceutically acceptable salt thereof. For example, the MAP4K1-dependent disease or disorder is a cancer. The term "cancer" encompasses all forms of cancer including, but not limited to, all forms of carcinomas, melanomas, blastomas, sarcomas, lymphomas, and leukemias. In some embodiments, cancer includes metastatic forms. Additionally, the disclosure includes refractory or recurrent malignancies whose growth may be inhibited using the compounds of the disclosure or pharmaceutically acceptable salts thereof. For the uses described herein, any of the compounds of the disclosure, or pharmaceutically acceptable salts thereof, may be used alone or in combination with other therapeutic agents.

In some embodiments, the treatment results in a sustained response in the subject after cessation of the treatment. "Sustained response" refers to the sustained effect on reducing tumor growth after cessation of a treatment. For example, the tumor size may remain the same or smaller as compared to the size at the beginning of the administration phase. In some embodiments, the sustained response has a duration at least the same as the treatment duration, at least 1.5×, 2.0×, 2.5×, or 3.0× length of the treatment duration.

The treatment methods disclosed herein may result in a partial or complete response. As used herein, "complete response" or "CR" refers to disappearance of all target lesions; "partial response" or "PR" refers to at least a 30% decrease in the sum of the longest diameters (SLD) of target lesions, taking as reference the baseline SLD; and"stable disease" or "SD" refers to neither sufficient shrinkage of target lesions to qualify for PR, nor sufficient increase to qualify for PD, taking as reference the smallest SLD since the treatment started. As used herein, "overall response rate" (ORR) refers to the sum of complete response (CR) rate and partial response (PR) rate.

The treatment methods disclosed herein can lead to an increase in progression free survival and overall survival of the subject administered the selective MAP4K1 inhibitor. As used herein, "progression free survival" (PFS) refers to the length of time during and after treatment during which the disease being treated (e.g., cancer) does not get worse. Progression-free survival may include the amount of time subjects have experienced a complete response or a partial response, as well as the amount of time subjects have experienced stable disease.

As used herein, "overall survival" (OS) refers to the percentage of subjects in a group who are likely to be alive after a particular duration of time.

In some embodiments, cancers treatable with compounds of the disclosure or pharmaceutically acceptable salts thereof, include colon cancer, pancreatic cancer, breast cancer, prostate cancer, lung cancer, ovarian cancer, cervical cancer, renal cancer, bladder cancer, stomach cancer, liver cancer, gastric cancer, cancer of the head and neck, lymphoma, leukemia, urothelial carcinoma, merkel cell carcinoma, gastroesophageal junction carcinoma, esophageal squamous cell carcinoma, skin squamous cell carcinoma and melanoma. In some embodiments, the cancer is gastroesophageal cancer (GEC).

In some embodiments, cancers treatable with compounds of the disclosure or pharmaceutically acceptable salts thereof include colon cancer, pancreatic cancer, breast cancer, prostate cancer, lung cancer, ovarian cancer, cervical cancer, renal cancer, bladder cancer, stomach cancer, liver cancer, cancer of the head and neck, lymphoma, leukemia, and melanoma.

In some embodiments, cancers that are treatable using the compounds of the disclosure or pharmaceutically acceptable salts thereof include, but are not limited to, solid tumors, including prostate cancer, colon cancer, esophageal cancer, endometrial cancer, ovarian cancer, uterine cancer, renal cancer, hepatic cancer, pancreatic cancer, gastric cancer, breast cancer, lung cancer, head and neck cancer, thyroid cancer, brain cancer, and bladder cancer and hematological cancer, including lymphoma, leukemia (chronic and acute forms) such as acute lymphatic leukemia (ALL), acute myeloid leukemia (AML), chronic lymphatic leukemia (CLL), chronic myeloid leukemia (CML), diffuse large B-cell lymphoma (DLBCL), mantle cell lymphoma, Non-Hodgkin's lymphoma (NHL), including relapsed or refractory NHL and recurrent follicular, Hodgkin's lymphoma and multiple myeloma, and myeloproliferative diseases.

In some embodiments, diseases and disorders that are treatable using the compounds of the disclosure or pharmaceutically acceptable salts thereof include, but are not limited to hematological cancer, sarcomas, respiratory cancer, gastrointestinal cancer, genitourinary tract cancer, liver cancer, bone cancer, nervous system cancer, gynecological cancer, and skin cancer.

Exemplary hematological cancer includes, for example, lymphomas and leukemias such as ALL, AML, acute promyelocyte leukemia (APL), CLL, CML, DLBCL, mantle cell lymphoma, Non-Hodgkin lymphoma (NHL), including Primary mediastinal B-cell lymphoma (PMBCL), relapsed or refractory NHL, recurrent follicular, and primary CNS lymphoma, Hodgkin's lymphoma, myeloproliferative diseases, including, primary myelofibrosis (PMF), polycythemia vera (PV), essential thrombocytosis (ET), myelodysplasia syndrome (MDS), T-cell acute lymphoblastic lymphoma (T-ALL), multiple myeloma, cutaneous T-cell lymphoma, Waldenstrom's Macroglobulinemia, hairy cell lymphoma, chronic melogenic lymphoma, and Burkitt's lymphoma.

Exemplary sarcoma includes, for example, chondrosarcoma, Ewing's sarcoma, Kaposi's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, sarcoma of the soft tissue, and teratoma.

Exemplary respiratory tract cancer includes, for example, lung cancer such as non-small cell lung cancer (NSCLC), small cell lung cancer, epidermoid cancer, bronchogenic carcinoma, including squamous cell, undifferentiated small cell, undifferentiated large cell, adenocarcinoma, alveolar (bronchiolar) carcinoma, bronchial adenoma, chondromatous hamartoma, mesothelioma, and pleuropulmonary blastoma.

Exemplary gastrointestinal cancer includes, for example, cancers of the esophagus, including squamous cell carcinoma, adenocarcinoma, leiomyosarcoma, and lymphoma; stomach, including carcinoma, lymphoma, and leiomyosarcoma; pancreas, including ductal adenocarcinoma, insulinoma, glucagonoma, gastrinoma, carcinoid tumors, and vipoma; small intestine, including adenocarcinoma, lymphoma, carcinoid tumors, Kaposi's sarcoma, leiomyoma, hemangioma, lipoma, neurofibroma, and fibroma; large intestine, including adenocarcinoma, tubular adenoma, villous adenoma, hamartoma, and leiomyoma; colon; and gall bladder, including adenocarcinoma; and intestinal type and diffuse type gastric adenocarcinoma, rectum carcinoma, familiar adenomatous polyposis carcinoma and hereditary non-polyposis colorectal cancer (CRC).

Exemplary genitourinary tract cancer includes, for example, cancers of the kidney, including adenocarcinoma, Wilm's tumor [nephroblastoma], renal cell carcinoma, urothelial carcinoma, juxtaglomerular cell tumor (reninoma), angiomyolipoma, renal oncocytoma, Bellinio duct carcinoma, clear-cell sarcoma of the kidney, and mesoblastic nephroma; adrenal gland; renal pelvis; bladder, including transitional cell carcinoma, squamous cell carcinoma, adenocarcinoma, sarcoma, and small cell carcinoma; urethra, including squamous cell carcinoma, transitional cell carcinoma, and adenocarcinoma; prostate, including adenocarcinoma, sarcoma, and carcinoma; testis, including seminoma, teratoma, embryonal carcinoma, teratocarcinoma, choriocarcinoma, sarcoma, interstitial cell carcinoma, fibroma, fibroadenoma, adenomatoid tumors, and lipoma; penis; and pancreas.

Exemplary liver cancer includes, for example, hepatoma, including hepatocellular carcinoma, cholangiocarcinoma, hepatoblastoma, angiosarcoma, hepatocellular adenoma, biliary tract cancer, and hemangioma.

Exemplary bone cancer includes, for example, osteogenic sarcoma, fibrosarcoma, malignant fibrous histiocytoma, chondrosarcoma, Ewing's sarcoma, malignant lymphoma, including reticulum cell sarcoma, multiple myeloma, malignant giant cell tumor chordoma, osteochronfroma, including osteocartilaginous exostoses, benign chondroma, chondroblastoma, chondromyxofibroma, osteoid osteoma, and giant cell tumors Exemplary nervous system cancer includes, for example, cancer of the skull, including osteoma, hemangioma, granuloma, xanthoma, and osteitis deformans; meninges including, meningioma, meningiosarcoma, and gliomatosis; brain, including astrocytoma, meduoblastoma, glioma, ependymoma, germinoma (pinealoma), neuroectodermal tumor, glioblastoma, glioblastoma multiform, oligodendroglioma, schwannoma, retinoblastoma, congenital tumors, brain stem and hypothalmic glioma; and spinal cord, including neurofibroma, meningioma, glioma, and sarcoma; as well as neuroblastoma and Lhermitte-Duclos disease.

Exemplary gynecological cancer includes, for example, cancer of the uterus, including endometrial carcinoma; cervix, including cervical carcinoma, pre-tumor cervical dysplasia, squamous cell carcinoma, adenocarcinoma, adenosquamous carcinoma, small cell carcinoma, neuroendocrine tumor, glassy cell carcinoma and villoglandular adenocarcinoma; ovaries, including ovarian carcinoma (serous cystadenocarcinoma, mucinous cystadenocarcinoma, unclassified carcinoma, endometroid tumor, high-grade serous carcinoma (HGSC) or high-grade serous ovarian cancer (HGSOC)), granulosa-thecal cell tumors, Sertoli-Leydig cell tumors, dysgerminoma, malignant teratoma, and arrhenoblastoma; vulva (squamous cell carcinoma, intraepithelial carcinoma, adenocarcinoma, fibrosarcoma, and melanoma; vagina, including clear cell carcinoma, squamous cell carcinoma, and botryoid sarcoma (embryonal rhabdomyosarcoma); labia; and fallopian tubes.

Exemplary skin cancer includes, for example, melanoma, sebaceous gland carcinoma, basal cell carcinoma, squamous cell carcinoma, Kaposi's sarcoma, Merkel cell skin cancer, moles dysplastic nevi, lipoma, angioma, dermatofibroma, and keloids.

Examples of breast cancer include, for example, ER+/HER2− breast cancer, triple-negative breast cancer (TNBC), invasive ductal carcinoma, invasive lobular carcinoma, ductal carcinoma in situ, and lobular carcinoma in situ.

Exemplary head and neck cancer includes, for example, glioblastoma, melanoma, rhabdosarcoma, lymphosarcoma, osteosarcoma, squamous cell carcinomas, adenocarcinomas, oral cancer, throat cancer, including oropharyngeal cancer, laryngeal cancer, nasopharyngeal cancer, nasal and paranasal cancer, salivary gland cancer, mouth cancer, eye cancer, acoustic neuroma, pituitary adenoma, hypopharynx, and thyroid (medullary and papillary) and parathyroid cancer.

Other cancers include, for example, sweat gland cancer, spinal axis tumor, chest cancer, sickle cell anemia, and environmentally induced cancers including those induced by asbestos.

In some embodiments, compounds of the disclosure or pharmaceutically acceptable salts thereof are for the treatment of advanced melanoma, advanced NSCLC, or head and neck squamous cell cancer, including advanced head and neck squamous cell cancer, including where the subject was refractory to, or had a partial response to, immune checkpoint inhibitor therapy.

In some instances, the MAP4K1-dependent disease or disorder is a viral infection, such as infection caused by hepatitis B virus (HBV), hepatitis C virus (HCV), human papilloma virus (HPV), cytomegalovirus (CMV), herpes simplex virus (HSV), Epstein-Barr virus (EBV), varicella zoster virus, coxsackie virus, and human immunodeficiency virus (HIV).

Combination Therapies

Compounds of the disclosure or pharmaceutically acceptable salts thereof can be administered as the sole pharmaceutical agent or in combination with one or more other anti-cancer agents for the treatment of cancer, where the combination causes no unacceptable adverse effects. In some embodiments, the other anti-cancer agents are immune-oncology agent, anticancer agents that are enzyme/protein/receptor inhibitors, radiation or chemotherapy.

Compounds of the disclosure or pharmaceutically acceptable salts thereof can be co-formulated with an immuno-oncology agent. Immuno-oncology agents include, for example, a small molecule drug, antibody, antibody drug conjugate, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human. In another aspect, the antibody is a bispecific antibody.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators, in some instances immune checkpoint inhibitors).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fnl4, TWEAK, BAFFR, EDAR, XEDAR, TACI, APRIL, BCMA, LTfiR, LIGHT, DcR3, HVEM, VEGI/TL1A, TRAMP/DR3, EDAR, EDA1, XEDAR, EDA2, TNFR1, Lymphotoxin α/TNPβ, TNFR2, TNF a, LT R, Lymphotoxin a 1β2, FAS, FASL, RELT, DR6, TROY, NGFR.

In one aspect, T cell responses can be stimulated by a combination of a compound of the disclosure or a pharmaceutically acceptable salt thereof and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In one aspect, compounds of the disclosure or pharmaceutically acceptable salts thereof can be administered in combination with at least one other immune checkpoint inhibitor. In other aspects, compounds of the disclosure or pharmaceutically acceptable salts thereof can be administered for the treatment of immune checkpoint inhibitor-resistant NSCLC, including where the subject is refractory to, or had a partial response to, platinum and/or paclitaxel and/or docetaxel therapy. Optionally, compounds of the disclosure or pharmaceutically acceptable salts thereof can be administered in combination with at least one other anti-cancer agent, such as paclitaxel, docetaxel or platinum anticancer therapy. In some aspects, compounds of the disclosure or pharmaceutically acceptable salts thereof can be administered post-platinum therapy as second or third line treatment. Compounds of the disclosure or pharmaceutically acceptable salts thereof can be administered for the treatment of first line NSCLC expressing high PD-L1 (≥50% Tumor Proportion Score (TPS)), wild-type EGFR, or wild-type ALK.

Other agents that can be combined with compounds of the disclosure or pharmaceutically acceptable salts thereof for the treatment of cancer include antagonists of inhibitory receptors on NK cells or agonists of activating receptors on NK cells. For example, compounds of the disclosure or pharmaceutically acceptable salts thereof can be combined with antagonists of KIR, such as lirilumab.

Yet other agents for combination therapies with the MAP4K1 inhibitors disclosed herein include agents that inhibit or deplete macrophages or monocytes, including but not limited to CSF-1R antagonists such as CSF-1R antagonist antibodies including RG7155 or FPA-008.

In another aspect, compounds of the disclosure or pharmaceutically acceptable salts thereof can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In some embodiments, the immuno-oncology agent is a CTLA-4 antagonist, such as an antagonistic CTLA-4 antibody. Suitable CTLA-4 antibodies include, for example, YERVOY (ipilimumab) or tremelimumab. In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgGl, called AMP-224.

In another aspect, the immuno-oncology agent is a PD-L1 antagonist, such as an antagonistic PD-L1 antibody. Suitable PD-L1 antibodies include, for example, atezolizumab, (RG7446; WO2010/077634), durvalumab (MED14736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469. In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The compounds of the disclosure or pharmaceutically acceptable salts thereof can be used in combination with anticancer agents that are enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

The compounds of the disclosure or pharmaceutically acceptable salts thereof can be used in combination with one or more other enzyme/protein/receptor inhibitors for the treatment of cancer. For example, the compounds of the disclosure or pharmaceutically acceptable salts thereof can be combined with one or more inhibitors of the following kinases for the treatment of cancer: Aktl, Akt2, Akt3, TGF-βPv, PKA, PKG, PKC, CaM-kinase, phosphorylase kinase, MEKK, ERK, MAPK, mTOR, EGFR, HER2, HER3, HER4, INS—R, IGF-1R, IR—R, PDGFotR, PDGFpR, CSFIR, KIT, FLK-II, KDR/FLK-1, KRAS, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK, and B-Raf.

In some embodiments, the compounds of the disclosure or pharmaceutically acceptable salts thereof can be combined with one or more of the following inhibitors for the treatment of cancer. Non-limiting examples of inhibitors that can be combined with the compounds of the disclosure or pharmaceutically acceptable salts thereof for treatment of cancers include an FGFR inhibitor (FGFR1, FGFR2, FGFR3 or FGFR4, e.g., fisogatinib, AZD4547, BAY 1187982, ARQ087, BGJ398, BIBF1120, TKI258, lucitanib, dovitinib, TAS-120, J J-42756493, Debiol347, INCB54828, INCB62079, and INCB63904), a JAK inhibitor (JAK1 and/or JAK2, e.g., ruxolitinib, baricitinib, or itacitinib (INCB39110)), an IDO inhibitor (e.g., epacadostat and NLG919), an LSD1 inhibitor (e.g., GSK2979552, INCB59872 and INCB60003), a TDO inhibitor, a PI3K-delta inhibitor (e.g., INCB50797 and INCB50465), a PI3K-gamma inhibitor such as a PI3K-gamma selective inhibitor (e.g., eganelisib) or a dual PI3K-delta/gamma selective inhibitor (e.g, duvelisib), a CSF1R inhibitor (e.g., PLX3397 and LY3022855), a TAM receptor tyrosine kinases (Tyro-3, Axl, and Mer), an angiogenesis inhibitor (e.g, bevacizumab), an interleukin receptor inhibitor, bromo and extra terminal family members inhibitors (for example, bromodomain inhibitors or BET inhibitors e.g., OTX015, CPI-0610, INCB54329, and INCB57643), and an adenosine receptor antagonist or combinations thereof. Inhibitors of HDAC e.g., panobinostat and vorinostat can be combined with the compounds of the disclosure or pharmaceutically acceptable salts thereof. Inhibitors of c-Met e.g., onartuzumab, tivantinib, and capmatinib (INC-280) be combined with the compounds of the disclosure or pharmaceutically acceptable salts thereof. Inhibitors of BTK such as ibrutinib can be combined with the compounds of the disclosure or pharmaceutically acceptable salts thereof. Inhibitors of mTOR e.g., rapamycin, sirolimus, temsirolimus, and everolimus can be combined with the compounds of the disclosure or pharmaceutically acceptable salts thereof. Inhibitors of Raf, e.g., vemurafenib and dabrafenib can be combined with the compounds of the disclosure or pharmaceutically acceptable salts thereof. Inhibitors of MEK e.g., trametinib, selumetinib and GDC-0973 can be combined with the compounds of the disclosure or pharmaceutically acceptable salts thereof. Inhibitors of KIT e.g., avapritinib, BLU-263, imatinib, sunitinib, regorafenib, ripretinib (DCC2618), PLX9486, PLX3397, crenolanib, CDX-0158, and CDX-0159. Inhibitors of RET e.g., pralsetinib, selperctinib, alectinib, lenvatinib, cabozantinib, BOS172738 (DS-5010), SL-1001, TPX-0046, sitravatinib (MGCD516), and RXDX-105. Inhibitors of Hsp90 (e.g., tanespimycin), cyclin dependent kinases (e.g., palbociclib), PARP (e.g., olaparib), Pim kinases (e.g., LGH447, INCB053914, and SGI-1776), and KRAS (e.g. sotorasib) can also be combined with compounds of the disclosure or pharmaceutically acceptable salts thereof.

Compounds of the disclosure or pharmaceutically acceptable salts thereof can be used in combination with one or more agents for the treatment of cancer. In some embodiments, the agent is an alkylating agent, a proteasome inhibitor, a corticosteroid, or an immunomodulatory agent. Examples of an alkylating agent include bendamustine, nitrogen mustards, ethylenimine derivatives, alkyl sulfonates, nitrosoureas and triazenes, uracil mustard, chlormethine, cyclophosphamide, ifosfamide, melphalan, chlorambucil, pipobroman, triethylene-melamine, triethylenethiophosphoramine, busulfan, carmustine, lomustine, streptozocin, dacarbazine, and temozolomide. In some embodiments, the proteasome inhibitor is carfilzomib. In some embodiments, the corticosteroid is dexamethasone.

The compounds of the disclosure or pharmaceutically acceptable salts thereof can be administered in combination with one or more anti-cancer drugs, such as a chemotherapeutics. Example chemotherapeutics include any of: abarelix, abiraterone, afatinib, aflibercept, aldesleukin, alemtuzumab, alitretinoin, allopurinol, altretamine, anastrozole, arsenic trioxide, asparaginase, axitinib, azacitidine, bevacizumab, bexarotene, baricitinib, bicalutamide, bleomycin, bortezomib, bortezomib, brivanib, buparlisib, busulfan intravenous, busulfan oral, calusterone, capecitabine, carmustine, cediranib, cetuximab, chlorambucil, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, docetaxel, doxorubicin, droloxafine, dromostanolone propionate, eculizumab, enzalutamide, epidophyllotoxin, epirubicin, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mithramycin, mitomycin C, mitotane, mitoxantrone, nandrolone phenpropionate, navelbine, necitumumab, nelarabine, neratinib, nilotinib, nilutamide, nofetumomab, oserelin, paclitaxel, pamidronate, panitumumab, pazopanib, pegaspargase, pegfilgrastim, pemetrexed disodium, pentostatin, pilaralisib, pipobroman, plicamycin, cisplatin, carboplatin, oxaliplatin, ponatinib, prednisone, procarbazine, quinacrine, rasburicase, regorafenib, raloxifene, rituximab, ruxolitinib, sorafenib, streptozocin, sunitinib, sunitinib maleate, tamoxifen, tegafur, temozolomide, teniposide, testolactone, thalidomide, thioguanine, thiotepa, topotecan, toremifene, tositumomab, trastuzumab, tretinoin, triptorelin, uracil mustard, valrubicin, vandetanib, vinblastine, vincristine, vinorelbine, vorinostat, and zoledronate.

Other anti-cancer agent(s) include antibody therapeutics e.g., trastuzumab.

Compounds of the disclosure or pharmaceutically acceptable salts thereof can be administered as the sole pharmaceutical agent or in combination with one or more anti-viral agents for the treatment of chronic viral infections, where the combination causes no unacceptable adverse effects. Chronic viral infections include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, coxsackie virus, human immunodeficiency virus (HIV). Parasitic infections (e.g., malaria) may also be treated by the above methods wherein compounds known to treat the parasitic conditions are optionally added in place of the antiviral agents.

Suitable antiviral agents contemplated for use in combination with the compound of the disclosure or a pharmaceutically acceptable salt thereof can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include e.g., zidovudine (AZT); didanosine (ddl); zalcitabine (ddC); stavudine (d4T); lamivudine (3TC); abacavir (1592 U89); adefovir dipivoxil [bis(POM)-PMEA]; lobucavir (BMS-180194); BCH—I0652; emtricitabine [(−)-FTC]; beta-L-FD4 (also called beta-L-D4C and named beta-L-2',3'-dicleoxy-5-fluoro-cytidine); DAPD, ((−)-beta-D-2,6-diamino-purine dioxolane); and lodenosine (FddA). Typical suitable NNRTIs include nevirapine (BI-RG-587); delaviridine (BHAP, U-90152); efavirenz (DMP-266); PNU-142721; AG-1549; MKC-442 (1-(ethoxy-methyl)-5-(1-methylethyl)-6-(phenylmethyl)-(2, 4(1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfinavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

When more than one pharmaceutical agent is administered to a subject, they can be administered simultaneously, separately, sequentially, or in combination (e.g., for more than two agents). For examples, when administered together with an additional anti-cancer or antiviral agent, the disclosed compounds or pharmaceutically acceptable salts thereof can be administered simultaneously in the same pharmaceutical formulation or simultaneously in separate pharmaceutical formulations. Alternatively, when administered together with an additional anti-cancer or antiviral agent, the disclosed compounds or pharmaceutically acceptable salts thereof can be administered at separate times, depending the dosing requirements of the additional anti-cancer or antiviral agent.

Pharmaceutical compositions are disclosed that include one or more compounds provided herein (such as the compound of Formulas I, II, III, IV, V, VI or VII), and typically at least one additional substance, such as an excipient, a known therapeutic other than those of the disclosure, and combinations thereof. In some embodiments, the disclosed compounds or pharmaceutically acceptable salts thereof can be used in combination with other agents known to have beneficial activity targeting diseases or disorders listed above. For example, disclosed compounds or pharmaceutically acceptable salts thereof can be administered alone or in combination with one or more anti-cancer or antiviral agent.

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa.

A "subject" is a mammal in need of medical treatment, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

The precise amount of compound or pharmaceutically acceptable salt thereof administered to provide an "effective amount" to the subject will depend on the mode of administration, the type, and severity of the disease or condition, and on the characteristics of the subject, such as general health, age, sex, body weight, and tolerance to drugs. The skilled artisan will be able to determine appropriate dosages depending on these and other factors. When administered in combination with other therapeutic agents, e.g., when administered in combination with an anti-cancer or antiviral agent, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound of the disclosure or a pharmaceutically acceptable salt thereof being used by following, for example, dosages reported in the literature and recommended in the *Physician's Desk Reference* (57th ed., 2003).

The term "effective amount" means an amount when administered to the subject which results in beneficial or desired results, including clinical results, e.g., inhibits, suppresses or reduces the symptoms of the condition being treated in the subject as compared to a control. For example, a therapeutically effective amount can be given in unit dosage form (e.g., 0.1 mg to about 50 g per day, alternatively from 1 mg to about 5 grams per day; and in another alternatively from 10 mg to 1 gram per day).

The particular mode of administration and the dosage regimen will be selected by the attending clinician, taking into account the particulars of the case (e.g. the subject, the disease, the disease state involved, the particular treatment, and whether the treatment is prophylactic). Treatment can involve daily or multi-daily or less than daily (such as weekly or monthly etc.) doses over a period of a few days to months, or even years.

The pharmaceutical composition of the disclosure is formulated to be compatible with its intended route of administration. In an embodiment, the composition is formulated in accordance with routine procedures as a pharmaceutical composition adapted for intravenous, subcutaneous, intramuscular, oral, intranasal, or topical administration to human beings. In preferred embodiments, the pharmaceutical composition is formulated for intravenous administration.

"Pharmaceutically acceptable excipient" and "pharmaceutically acceptable carrier" refer to a substance that aids the formulation and/or administration of an active agent to and/or absorption by a subject and can be included in the compositions of the disclosure without causing a significant adverse toxicological effect on the subject. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds.

General Synthetic Methods and Intermediates

The synthetic protocol used to prepare the compounds in Table 1 is listed in the last column of Table 1 and full details for each synthetic protocol are described in Schemes 1 and 2 (below) in the General Synthetic Methods and Intermediates section.

Scheme 1

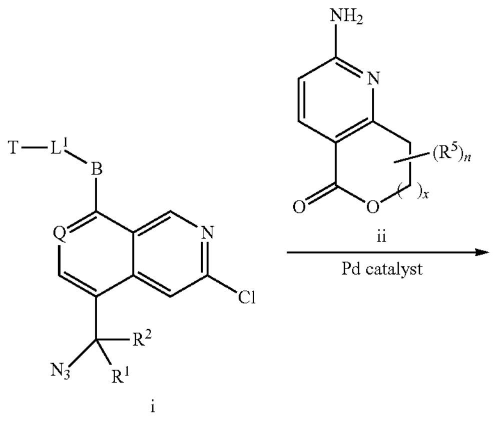

-continued

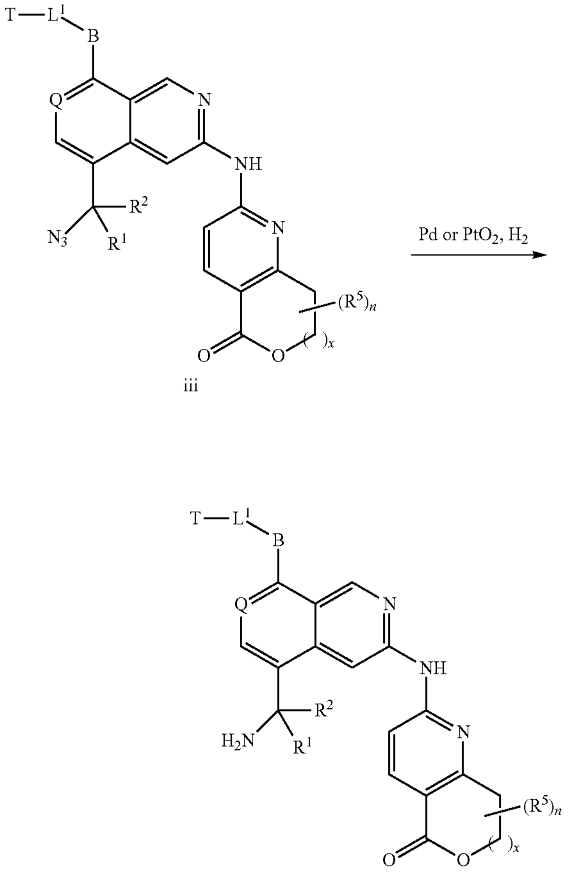

iii iv

Scheme 1 shows a synthetic protocol for the preparation of compounds of formula iv The azide-substituted chloro heterocyclic intermediates i can be coupled to the substituted anilines ii under Pd-catalyzed coupling conditions to give iii. The azide intermediate iii can be reduced under catalytic hydrogenation conditions with a catalyst such as Pd/C or $PtO_2$ to give the amine compounds iv which are examples of MAP4K1 inhibitors described herein.

Scheme 2

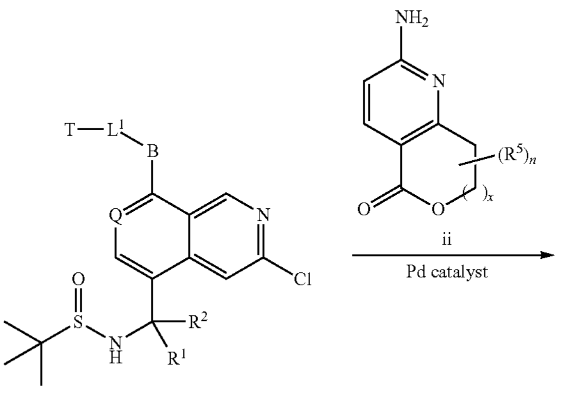

i

-continued

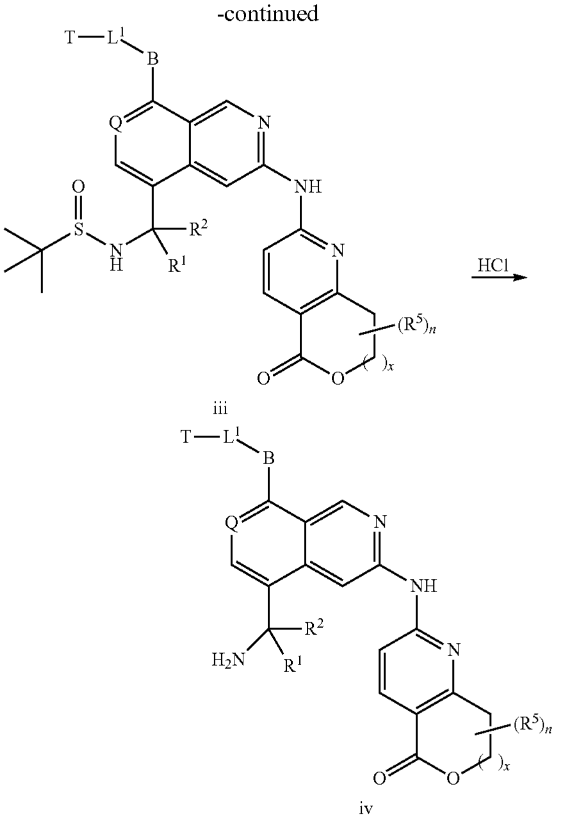

iii iv

Scheme 2 shows a synthetic protocol for the preparation of compounds of formula iv The sulfinamide-substituted chloro heterocyclic intermediates i can be coupled to the substituted anilines ii under Pd-catalyzed coupling conditions to give iii. The sulfinamide group of intermediate iii can converted to an amine under acidic conditions such as HCl to give amine compounds iv which are examples of MAP4K1 inhibitors described herein.

The following examples are intended to be illustrative and are not meant in any way to be limiting.

EXEMPLIFICATION

Abbreviations

ACN acetonitrile ("MeCN")
AcOH acetic acid
ATP adenosine triphosphate
BrettPhos Dicyclohexyl(2',4',6'-triisopropyl-3,6-dimethoxy-[1,1'-biphenyl]-2-yl)phosphine
t-BuOK potassium tert-butoxide
C Celsius
DBU diazabicyclo[5.4.0]undec-7-ene
DCE dichloroethane
DCM dichloromethane
DIAD disopropyl azodicarboxylate
DIBAL diisobutylaluminium hydride
DIPEA diisopropylethylamine
$DMBNH_2$ 2,4-dimethoxybenzylamine
DMF dimethyl formamide
DMSO dimethyl sulfoxide
DTT dithiothreitol
eq equivalents EA ethyl acetate
EDTA ethylenediaminetetraacetic acid
$Et_2O$ diethyl ether
EtSH ethanethiol
FA formic acid
h hours
HEPES 4-(2-hydroxyethyl)-1-piperazineethanesulfonic acid
HPLC high performance liquid chromatography
IBX 2-iodoxybenzoic acid
IC50 inhibitory concentration 50%
IPA isopropanol
KF potassium fluoride
KOAc potassium acetate
LiHMDS lithium bis(trimethylsilyl)amide
MeMgBr methyl magnesium bromide
min minutes
MTBE methyl tert-butyl ether
MeOH methanol
MsCl methanesulfonyl chloride
NBS N-bromosuccinimide
NMO N-methylmorpholine N-oxide
NMP N-methyl-2-pyrrolidone
Oxone potassium peroxymonosulfate
PE petroleum ether
PrMgBr isopropyl magnesium bromide
SFC supercritical fluid chromatography
TEA trimethylamine
THF tetrahydrofuran
TFA trifluoroacetic acid
TfOH trifluoromethanesulfonic acid
TMEDA tetramethylethylenediamine
$TMSN_3$ azidotrimethylsilane Methods for preparing compounds of the disclosure can be carried out in suitable solvents which can be readily selected by one of skill in the art of organic synthesis. Suitable solvents can be substantially non-reactive with the starting materials (reactants), intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the disclosure can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 5th ed., John Wiley & Sons: New Jersey, (2014), which is incorporated herein by reference in its entirety.

Reactions can be monitored according to any suitable method known in the art. For example, product formation can be monitored by spectroscopic means, such as nuclear magnetic resonance (NMR) spectroscopy (e.g., $^1H$ or $^{13}C$), infrared (IR) spectroscopy, spectrophotometry (e.g., UV-visible), mass spectrometry (MS), or by chromatographic methods such as high performance liquid chromatography (HPLC) or thin layer chromatography (TLC). Analytical instruments and methods for compound characterization:

LC-MS: Unless otherwise indicated, all liquid chromatography-mass spectrometry (LC-MS) data (sample analyzed for purity and identity) were obtained with an Agilent model-1260 LC system using an Agilent model 6120 mass spectrometer utilizing ES-API ionization fitted with an Agilent Poroshel 120 (EC-C18, 2.7 um particle size, 3.0×50 mm dimensions) reverse-phase column at 22.4 degrees Celsius. The mobile phase consisted of a mixture of solvent 0.1% FA in water and 0.1% FA in acetonitrile. A constant gradient from 95% aqueous/5% organic to 5% aqueous/95% organic mobile phase over the course of 4 minutes was utilized. The flow rate was constant at 1 mL/min.

Prep LC-MS: Preparative HPLC was performed on a Shimadzu Discovery VP® Preparative system fitted with a Luna 5u C18(2) 100A, AXIA packed, 250×21.2 mm reverse-phase column at 22.4 degrees Celsius. The mobile phase consisted of a mixture of solvent 0.1% FA in water and 0.1% FA in ACN. A constant gradient from 95% aqueous/5% organic to 5% aqueous/95% organic mobile phase over the course of 25 minutes was utilized. The flow rate was constant at 20 mL/min. Reactions carried out in a microwave were done so in a Biotage Initiator microwave unit.

Silica gel chromatography: Silica gel chromatography was performed on either a Teledyne Isco CombiFlash® Rf unit or a Biotage® Isolera Four unit.

Proton NMR: Unless otherwise indicated, all $^1H$ NMR spectra were obtained with a Varian 400 MHz Unity Inova 400 MHz NMR instrument (acquisition time=3.5 seconds with a 1 second delay; 16 to 64 scans). Where characterized, all protons were reported in DMSO-d6 solvent as parts-per million (ppm) with respect to residual DMSO (2.50 ppm).

One of ordinary skill in the art will recognize that modifications of the gradient, column length, and flow rate are possible and that some conditions may be more suitable for compound characterization than others, depending on the chemical species being analyzed.

Synthesis of Intermediates

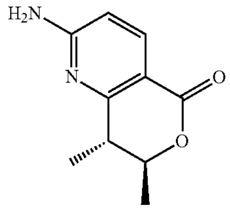
and
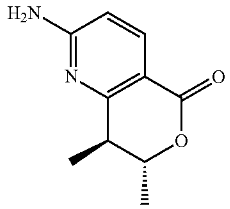

Intermediates 1 and 2: (7S,8R)-2-Amino-7,8-dimethyl-7,8-dihydro-5H-pyrano[4,3-b]pyridin-5-one (Intermediate 1) and (7R,8S)-2-amino-7,8-dimethyl-7,8-dihydro-5H-pyrano[4,3-b]pyridin-5-one (Intermediate 2) ($2^{nd}$ Eluting Isomer)

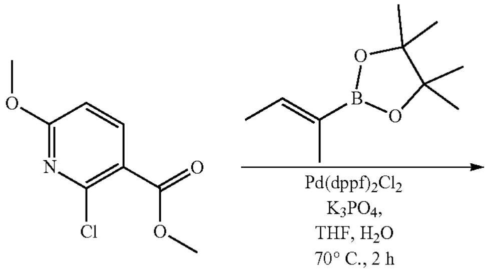

-continued

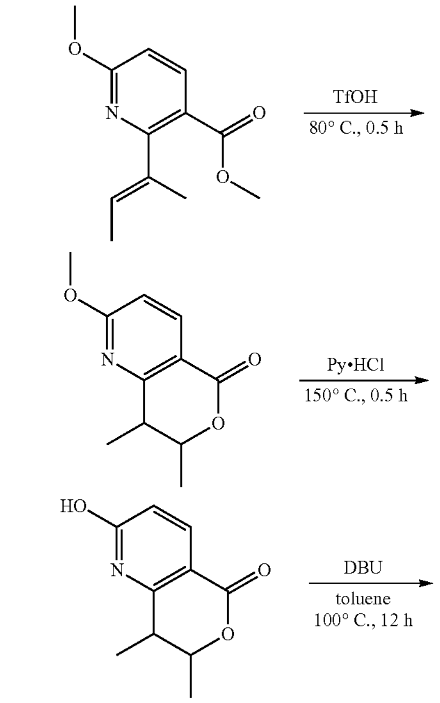

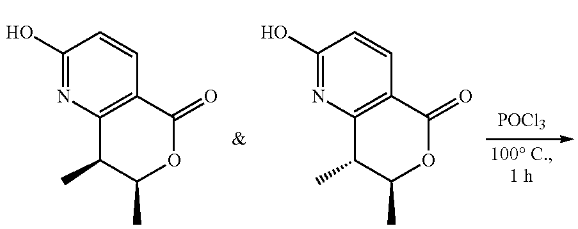

(cis rac) (trans rac)

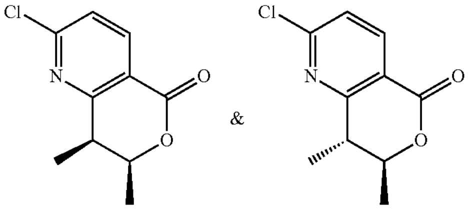

(cis rac) (trans rac)

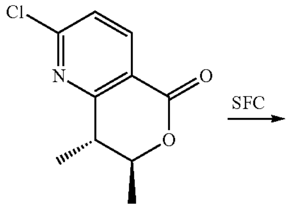

Precursor I of Intermediate 1 (1st eluting isomer) and Precursor I of Intermediate 2 (2nd eluting isomer)

(trans rac)

each of which is represented by the structures shown below:

(Precursor I of Intermediate 1)

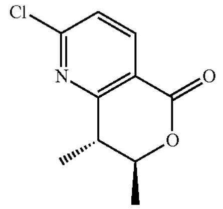

and (Precursor I of Intermediate 2)

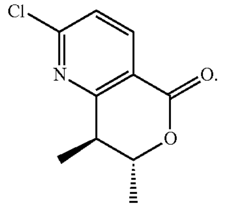

Precursor I of Intermediate 1 (1st eluting isomer) or Precursor I of Intermediate 2 (2nd eluting isomer)

$DMBNH_2$

DIEA, NMP

100° C., 1 h

Precursor II of Intermediate 1 or Precursor II of Intermediate 2 each of which is represented by the structures shown below:

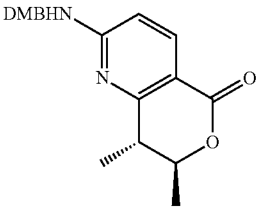

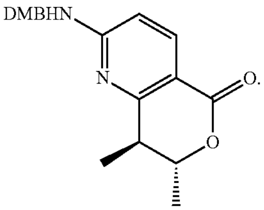

(Precursor II of Intermediate 1) and (Precursor II of Intermediate 2)

Precursor II of Intermediate 1 or Precursor II of Intermediate 2

HCl/dioxane

70° C., 1 h

Intermediate 1 or Intermediate 2 each of which is represented by the structures shown below:

(Intermediate 1)

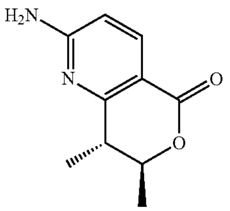

and (Intermediate 2)

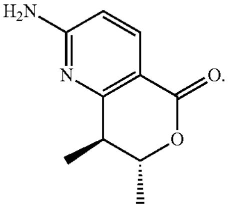

Step 1: Methyl (E)-2-(but-2-en-2-yl)-6-methoxynicotinate $K_3PO_4$ (120 g, 565 mmol, 3.00 eq) and Pd(dppf)$Cl_2$—$CH_2Cl_2$ (7.70 g, 9.42 mmol, 0.05 eq) were added to a solution of methyl 2-chloro-6-methoxynicotinate (38.0 g, 188 mmol, 1.00 eq) and (Z)-2-(but-2-en-2-yl)-4,4,5,5-tetramethyl-1,3,2-dioxaborolane (44.6 g, 245 mmol, 1.30 eq) in THF (320 mL) and $H_2O$ (80.0 mL). The reaction mixture was stirred under $N_2$ at 70° C. for 2 h. The reaction mixture was diluted with water (300 mL) and extracted with EA (250 mL×3). The organic layers were combined and dried over sodium sulfate, then filtered and concentrated in vacuo to give the residue. The residue was purified by prep-HPLC (ACN-$H_2O$ gradient with 0.1% TFA additive). The product-containing fractions were adjusted to pH=8-9 with solid sodium carbonate and the mixture was extracted with EA (300 mL×3). The combined organic layers were washed with brine (500 mL), dried over $Na_2SO_4$, filtered and concentrated to give the title compound (37.0 g, 167 mmol, 88.7% yield) as a yellow oil.

Step 2: 2-Methoxy-7,8-dimethyl-7,8-dihydro-5H-pyrano[4,3-b]pyridin-5-one

A solution of methyl (E)-2-(but-2-en-2-yl)-6-methoxynicotinate (37.0 g, 167 mmol, 1.00 eq) in TfOH (171 g, 1.15 mol, 101 mL, 6.85 eq) was stirred at 80° C. for 0.5 h. The mixture was then cooled to ambient temperature, poured into saturated aqueous $NaHCO_3$ solution (1000 mL) and extracted with EA (300 mL×5). The organic layers were dried over sodium sulfate, filtered, and concentrated to give a residue. The residue was purified by flash-column chromatography on silica gel (gradient elution, 1% to 25% EA-PE) to give the title compound (30.0 g, 144 mmol, 86.6% yield) as a yellow oil.

Steps 3: 2-Hydroxy-7,8-dimethyl-7,8-dihydro-5H-pyrano[4,3-b]pyridin-5-one

A mixture of 2-methoxy-7,8-dimethyl-7,8-dihydro-5H-pyrano[4,3-b]pyridin-5-one (30.0 g, 144 mmol, 1.00 eq) and pyridine-hydrochloride (41.8 g, 361 mmol, 2.50 eq) was stirred at 150° C. for 0.5 h. The reaction mixture was purified directly by flash-column chromatography on silica gel (gradient elution, 2% to 10% MeOH-DCM) to give the title compound (26.0 g, 134 mmol, 92.9% yield) as a yellow solid.

Step 4: rac-(7S,8S)-2-Hydroxy-7,8-dimethyl-7,8-dihydro-5H-pyrano[4,3-b]pyridin-5-one and rac-(7S,8R)-2-hydroxy-7,8-dimethyl-7,8-dihydro-5H-pyrano[4,3-b]pyridin-5-one DBU (60.8 mL, 403 mmol, 3.00 eq) was added to a solution of 2-hydroxy-7,8-dimethyl-7,8-dihydro-5H-pyrano[4,3-b]pyridin-5-one (26.0 g, 134 mmol, 1.00 eq) in toluene (290 mL). The reaction mixture was stirred at 100° C. for 12 h, then was cooled to ambient temperature and concentrated under vacuum. The residue was purified by flash-column chromatography on silica gel (gradient elution, 1% to 10% MeOH-DCM) to afford the title compounds as a mixture of isomers that were used in the next step without further purification.

Step 5: rac-(7S,8S)-2-Chloro-7,8-dimethyl-7,8-dihydro-5H-pyrano[4,3-b]pyridin-5-one and rac-(7S,8R)-2-chloro-7,8-dimethyl-7,8-dihydro-5H-pyrano[4,3-b]pyridin-5-one A mixture of rac-(7S,8S)-2-hydroxy-7,8-dimethyl-7,8-dihydro-5H-pyrano[4,3-b]pyridin-5-one and rac-(7S,8R)-2-hydroxy-7,8-dimethyl-7,8-dihydro-5H-pyrano[4,3-b]pyridin-5-one (26.0 g, 134 mmol, 1 equiv) in $POCl_3$ (150 mL, 1.61 mol, 11.9 equiv) was stirred at 100° C. for 1 h. The reaction mixture was then cooled to ambient temperature and poured into saturated aqueous $NaHCO_3$ solution (2 L) at 0-10° C. The quenched mixture was extracted with EA (300 mL×3) and the combined organic layers were washed with brine, dried over sodium sulfate, filtered, and concentrated. The cis- and trans racemic isomers were separated by prep-HPLC (column: Phenomenex Luna C18 250*50 mm*10 um; mobile phase: [water(0.1% TFA)-ACN]; B %: 35% ACN-55% CAN over 20 min). rac-(7S,8S)-2-Chloro-7,8-dimethyl-7,8-dihydro-5H-pyrano[4,3-b]pyridin-5-one was the first compound to elute and was obtained as a white solid. MS (ES+) $C_{10}H_{10}ClNO_2$ requires: 211, found: 212 $[M+H]^+$. $^1H$ NMR: 400 MHz, $CDCl_3$ δ 8.29 (d, J=8.2 Hz, 1H), 7.39 (d, J=8.2 Hz, 1H), 4.83 (dq, J=3.2, 6.6 Hz, 1H), 3.09 (dq, J=3.2, 7.2 Hz, 1H), 1.49 (d, J=6.5 Hz, 3H), 1.30 (d, J=7.2 Hz, 3H). rac-(7S,8R)-2-Chloro-7,8-dimethyl-7,8-dihydro-5H-pyrano[4,3-b]pyridin-5-one was the second compound to elute and was obtained as a white solid. MS (ES+) $C_{10}H_{10}ClNO_2$ requires: 211, found: 212$[M+H]^+$. $^1H$ NMR: 400 MHz, $CDCl_3$ δ 8.28 (d, J=8.2 Hz, 1H), 7.38 (d, J=8.2 Hz, 1H), 4.58-4.43 (m, 1H), 3.05 (quin, J=7.2 Hz, 1H), 1.56-1.40 (m, 6H).

Step 6: (7S,8R)-2-Chloro-7,8-dimethyl-7,8-dihydro-5H-pyrano[4,3-b]pyridin-5-one and (7R,8S)-2-chloro-7,8-dimethyl-7,8-dihydro-5H-pyrano[4,3-b]pyridin-5-one rac-(7S,8R)-2-Chloro-7,8-dimethyl-7,8-dihydro-5H-pyrano[4,3-b]pyridin-5-one was separated by SFC (column: DAICEL CHIRALPAK AD (250 mm×50 mm, 10 um); mobile phase: MeOH in $CO_2$) to give the first eluting isomer (peak 1) as a white solid and second eluting isomer (peak 2) as a white solid.

Step 7: (7S,8R)-2-((2,4-Dimethoxybenzyl)amino)-7,8-dimethyl-7,8-dihydro-5H-pyrano[4,3-b]pyridin-5-one DIPEA (7.48 g, 57.8 mmol, 10.1 mL, 2.50 eq) and $DMBNH_2$ (5.03 g, 30.1 mmol, 4.53 mL, 1.30 eq) were added to a solution of (7S,8R)-2-chloro-7,8-dimethyl-7,8-dihydro-5H-pyrano[4,3-b]pyridin-5-one ($1^{st}$ eluting isomer (peak 1) from Step 6 above) (4.90 g, 23.1 mmol, 1.00 eq) in NMP (50.0 mL). The reaction mixture was stirred at 100° C. for 1 h, then was poured into water (500 mL) and extracted with EA (100 mL×3). The combined organic layers were washed with brine (200 mL), dried over sodium sulfate, filtered and concentrated to give the title compound (7.93 g, crude) as a yellow oil that was used directly in the next step. MS (ES+) $C_{19}H_{11}N_2O_4$ requires: 342, found: 343$[M+H]^+$.

Step 8: (7S,8R)-2-Amino-7,8-dimethyl-7,8-dihydro-5H-pyrano[4,3-b]pyridin-5-one

A solution of (7S,8R)-2-((2,4-Dimethoxybenzyl)amino)-7,8-dimethyl-7,8-dihydro-5H-pyrano[4,3-b]pyridin-5-one (7.93 g, 23.1 mmol, 1.00 eq) in HCl/dioxane (4.00 M, 50.0 mL, 8.64 eq) was stirred at 70° C. for 1 h. The reaction mixture was then concentrated and partitioned between saturated aqueous sodium bicarbonate solution (100 mL) and was extracted with DCM (100 mL×3). The combined organic layer was washed with brine (200 mL), dried over sodium sulfate, filtered and concentrated. The residue was triturated in MTBE (50 mL) for 10 mins and filtered to get a yellow solid. The yellow solid was dried under vacuum to give the title compound, Intermediate 1(3.23 g, 16.4 mmol, 71.2% yield, 98.1% purity). MS (ES+) $C_{10}H_{12}N_2O_2$ requires: 192, found: 193[M+H]$^+$. $^1$H NMR: 400 MHz, DMSO-$d_6$ δ 7.77 (d, J=8.6 Hz, 1H), 6.97 (s, 2H), 6.40 (d, J=8.6 Hz, 1H), 4.43-4.21 (m, 1H), 2.88-2.65 (m, 1H), 1.35 (d, J=6.4 Hz, 3H), 1.25 (d, J=7.0 Hz, 3H). The absolute stereochemistry of the title compound was determined by X-ray crystal structure of a final compound prepared from this intermediate.

Steps 9 and 10: (7R,8S)-2-Amino-7,8-dimethyl-7,8-dihydro-5H-pyrano[4,3-b]pyridin-5-one The title compound (Intermediate 2) was prepared separately from (7R,8S)-2-chloro-7,8-dimethyl-7,8-dihydro-5H-pyrano[4,3-b]pyridin-5-one (the second eluting isomer (peak 2) of Step 6) using the same two-step procedure as described in Steps 7 and 8 for Intermediate 2. MS (ES+) $C_{10}H_{12}N_2O_2$ requires: 192, found: 193[M+H]$^+$. $^1$H NMR: 400 MHz, DMSO-$d_6$ δ 7.77 (d, J=8.6 Hz, 1H), 6.97 (s, 2H), 6.40 (d, J=8.6 Hz, 1H), 4.43-4.21 (m, 1H), 2.88-2.65 (m, 1H), 1.35 (d, J=6.4 Hz, 3H), 1.25 (d, J=7.0 Hz, 3H).

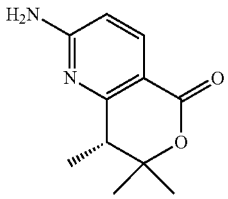

and

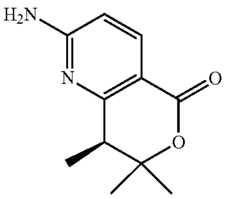

Intermediates 3 and 4: (R)-2-amino-7,7,8-trimethyl-7,8-dihydro-5H-pyrano[4,3-b]pyridin-5-one and (S)-2-amino-7,7,8-trimethyl-7,8-dihydro-5H-pyrano[4,3-b]pyridin-5-one

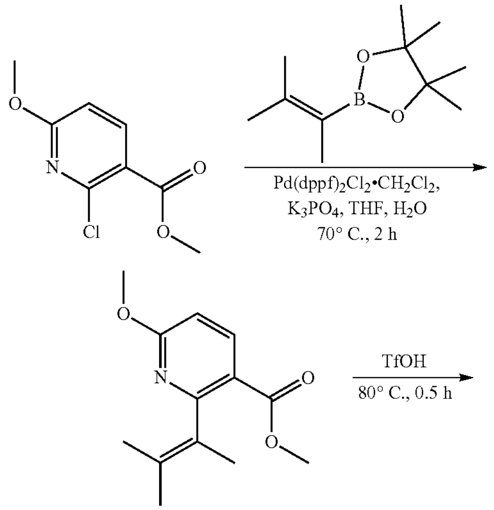

-continued

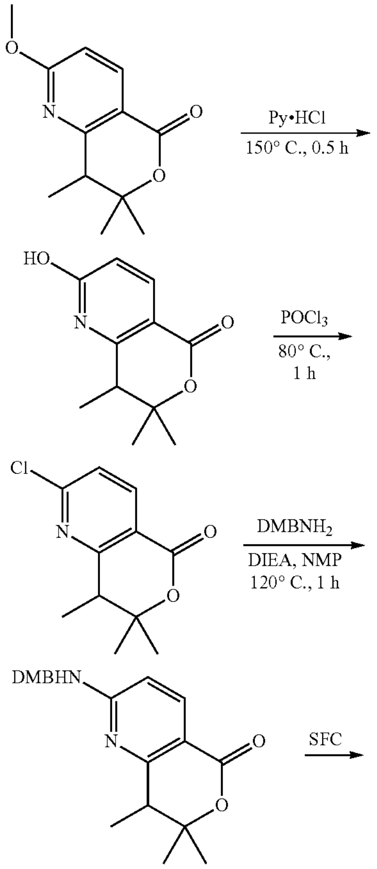

Precursor of Intermediate 3 (1$^{st}$ eluting isomer) and Precursor of Intermediate 4 (2$^{nd}$ eluting isomer)

each of which is represented by the structure shown below:

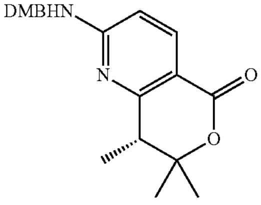

(Precursor of Intermediate 3) and

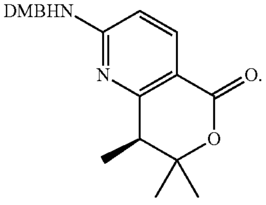

(Precursor of Intermediate 4)

Precursor of Intermediate 3 (1$^{st}$ eluting isomer) or Precursor of Intermediate 4 (2$^{nd}$ eluting isomer)

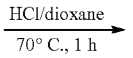

Intermediate 3 or Intermediate 4 each of which is represented by the structure shown below:

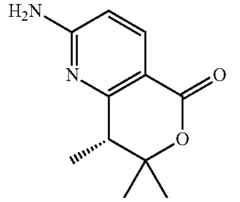

(Intermediate 3)

and

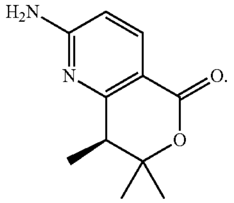

(Intermediate 4)

Steps 1-5: rac 2-((2,4-Dimethoxybenzyl)amino)-7,7,8-trimethyl-7,8-dihydro-5H-pyrano[4,3-b]pyridin-5-one The title compound was prepared from methyl 2-chloro-6-methoxynicotinate and 4,4,5,5-tetramethyl-2-(3-methyl-but-2-en-2-yl)-1,3,2-dioxaborolane using similar procedures as described above in Steps 1-3, 5, and 7 for Intermediate 1.

Step 6: (R)-2-((2,4-Dimethoxybenzyl)amino)-7,7,8-trimethyl-7,8-dihydro-5H-pyrano[4,3-b]pyridin-5-one and (S)-2-((2,4-Dimethoxybenzyl)amino)-7,7,8-trimethyl-7,8-dihydro-5H-pyrano[4,3-b]pyridin-5-one Rac 2-((2,4-Dimethoxybenzyl)amino)-7,7,8-trimethyl-7,8-dihydro-5H-pyrano[4,3-b]pyridin-5-one was separated by SFC (column: DAICEL CHIRALPAK AS-H (250 mm*30 mm, 5 um); mobile phase: [0.1% $NH_4OH$ MeOH in $CO_2$]) to give (R)-2-((2,4-dimethoxybenzyl)amino)-7,7,8-trimethyl-7,8-dihydro-5H-pyrano[4,3-b]pyridin-5-one ($1^{st}$ eluting isomer (Precursor to Intermediate 3), 0.55 g, 79% yield) and (S)-2-((2,4-dimethoxybenzyl)amino)-7,7,8-trimethyl-7,8-dihydro-5H-pyrano[4,3-b]pyridin-5-one ($2^{nd}$ eluting isomer (Precursor to Intermediate 4), 0.55 g, 79% yield). Each intermediate was isolated as a yellow oil.

Step 7 and 8: (R)-2-amino-7,7,8-trimethyl-7,8-dihydro-5H-pyrano[4,3-b]pyridin-5-one and (S)-2-amino-7,7,8-trimethyl-7,8-dihydro-5H-pyrano[4,3-b]pyridin-5-one The title compounds (Intermediates 3 and 4) were prepared separately from the $1^{st}$ and $2^{nd}$ eluting isomers, i.e., (R)-2-((2,4-dimethoxybenzyl)amino)-7,7,8-trimethyl-7,8-dihydro-5H-pyrano[4,3-b]pyridin-5-one and (S)-2-((2,4-Dimethoxybenzyl)amino)-7,7,8-trimethyl-7,8-dihydro-5H-pyrano[4,3-b]pyridin-5-one, using the same procedure as described in Step 8 of Intermediate 1. Intermediate 3, (R)-2-amino-7,7,8-trimethyl-7,8-dihydro-5H-pyrano[4,3-b]pyridin-5-one, was obtained as a yellow solid. MS (ES+) $C_{11}H_{14}N_2O_2$ requires: 206, found: 207[M+H]$^+$. $^1$H-NMR (400 MHz, $CD_3OD$): δ ppm 7.89 (d, J=8.8 Hz, 1H), 6.50 (d, J=8.8 Hz, 1H), 2.85-2.80 (m, 1H), 1.41 (s, 6H), 1.27 (d, J=7.2 Hz, 3H). Intermediate 4, (S)-2-Amino-7,7,8-trimethyl-7,8-dihydro-5H-pyrano[4,3-b]pyridin-5-one, was obtained as a yellow solid. MS (ES+) $C_{11}H_{14}N_2O_2$ requires: 206, found: 207[M+H]$^+$. $^1$H-NMR (400 MHz, $CD_3OD$): δ ppm 7.89 (d, J=8.8 Hz, 1H), 6.50 (d, J=8.8 Hz, 1H), 2.85-2.80 (m, 1H), 1.41 (s, 6H), 1.27 (d, J=7.2 Hz, 3H). The absolute stereochemistry of the title compound was determined by X-ray crystal structure of a final compound prepared from this intermediate.

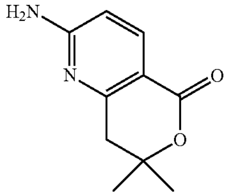

Intermediate 5: 2-Amino-7,7-dimethyl-7,8-dihydro-5H-pyrano[4,3-b]pyridin-5-one

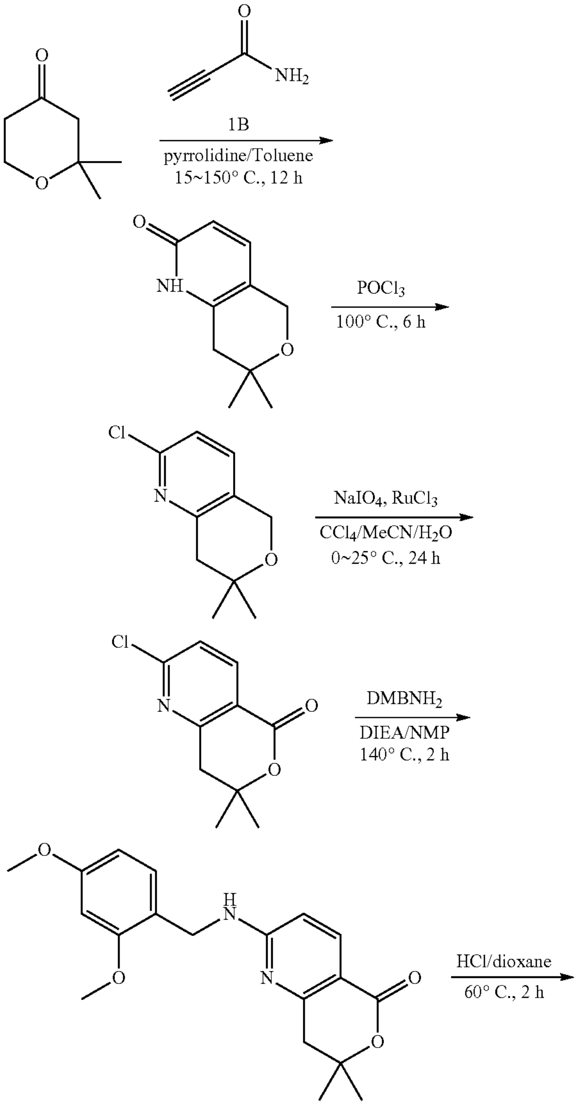

-continued

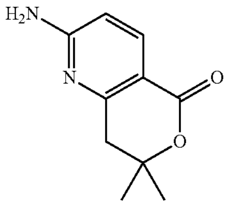

Step 1: 7,7-Dimethyl-1,5,7,8-tetrahydro-2H-pyrano[4,3-b]pyridin-2-one

A mixture of 2,2-dimethyltetrahydro-4H-pyran-4-one (500 g, 3.90 mol, 1.00 eq) and pyrrolidine (391 mL, 4.68 mol, 1.20 eq) in toluene (4.00 L) was heated at 145° C. with a Dean-Stark trap for 2 h. The water layer (~16 mL) was removed from the Dean-Stark trap and the reaction mixture was cooled to 15° C. After cooling, prop-2-ynamide (539 g, 7.80 mol, 2.00 eq) was added and the reaction mixture was heated to 150° C. The reaction mixture was heated at 150° C. for 10 h, then was cooled to ambient temperature. The cooled reaction mixture was filtered, and the filtrate was concentrated under reduced pressure to give a residue. The residue was purified by flash-column chromatography on silica gel (10% methanol-dichloromethane) to give the title compound (560 g, 62% yield) as a yellow solid.

Step 2: 2-Chloro-7,7-dimethyl-7,8-dihydro-5H-pyrano[4,3-b]pyridine

A solution of 7,7-dimethyl-1,5,7,8-tetrahydro-2H-pyrano[4,3-b]pyridin-2-one (500 g, 2.23 mol, 1 eq) in $POCl_3$ (350 mL, 3.77 mol, 9.64 eq) was heated to 100° C. for 6 h. The reaction mixture then cooled to ambient temperature and concentrated under vacuum. The residue was poured over ice-water (1.00 L). The mixture was extracted with EA (750 mL×2). The combined organic layers were dried over $Na_2SO_4$, filtered and concentrated under vacuum to give the title compound (363 g, 82.2% yield) as a brown oil.

Step 3: 2-Chloro-7,7-dimethyl-7,8-dihydro-5H-pyrano[4,3-b]pyridin-5-one

A solution of $NaIO_4$ (487 g, 2.28 mol, 3.00 eq) in water (1.20 L) as added to a mixture of 2-chloro-7,7-dimethyl-7,8-dihydro-5H-pyrano[4,3-b]pyridine (150 g, 759 mmol, 1.00 eq) in MeCN (50.0 mL) and CCl4 (2.70 L). The mixture was cooled to 0° C., and then $RuCl_3$ (11.0 g, 53.1 mmol, 0.07 eq) was added. The reaction mixture was stirred at 0° C. for 0.5 h, then was warmed to 20° C. for 11.5 h. Saturated aqueous sodium sulfite solution (1.00 L) was added, and the mixture was filtered. The filtrate was extracted with EA (500 mL×3), and the organic layers were combined. The combined organic layer was washed with brine (1.00 L), dried over $Na_2SO_4$, filtered and concentrated to give the title compound (132 g, 624 mmol, 82.1% yield) as a yellow solid.

Step 4: 2-((2,4-Dimethoxybenzyl)amino)-7,7-dimethyl-7,8-dihydro-5H-pyrano[4,3-b]pyridin-5-one (2,4-Dimethoxyphenyl) methanamine (160 g, 957 mmol, 1.50 eq) was added to a solution of 2-chloro-7,7-dimethyl-7,8-dihydro-5H-pyrano[4,3-b]pyridin-5-one (135 g, 638 mmol, 1.00 eq) and DIPEA (222 mL, 1.28 mol, 2.00 eq) in NMP (1.08 L) at ambient temperature. The reaction mixture was heated to 140° C. for 2 h, and then was cooled to ambient temperature. The reaction mixture was then partitioned between water (700 mL) and EA. The layers were separated, and the aqueous layer was further extracted with EA (500 mL×3). The organic layers were combined and washed with brine (400 mL×3), dried over anhydrous sodium sulfate, filtered and concentrated to afford the title compound as a yellow solid (160 g). The crude product was used for next step directly.

Step 5: 2-Amino-7,7-dimethyl-7,8-dihydro-5H-pyrano[4,3-b]pyridin-5-one

HCl (4.0 M in dioxane, 1.20 L, 11.0 equiv) was added to: 2-((2,4-dimethoxybenzyl)amino)-7,7-dimethyl-7,8-dihydro-5H-pyrano[4,3-b]pyridin-5-one (150 g, 438 mmol, 1.00 eq) at 20° C. The reaction mixture was heated to 60° C. for 2 h, then was cooled to ambient temperature and concentrated under vacuum. The residue was poured into saturated $NaHCO_3$ aqueous solution (1.00 L) and extracted with EA (500 mL×4). The combined organic layer was washed with brine (500×2), dried over $Na_2SO_4$, filtered and concentrated. The residue was dissolved in EA (300 mL) and petroleum ether (150 mL) was added drop wise to get yellow slurry. The solids were filtered and collected to give the title compound (52.0 g, 60.9% yield) as a yellow solid. MS (ES+) $C_{10}H_{12}N_2O_2$ requires: 192, found: 193[M+H]$^+$. $^1H$ NMR (400 MHz, DMSO-d6) δ 7.76 (d, J=8.4 Hz, 1H), 6.98 (s, 2H), 6.39 (d, J=8.8 Hz, 1H), 2.89 (s, 2H), 1.37 (s, 6H).

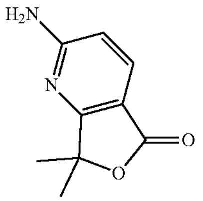

Intermediate 6:_2-Amino-7,7-dimethylfuro[3,4-b]pyridin-5(7H)-one

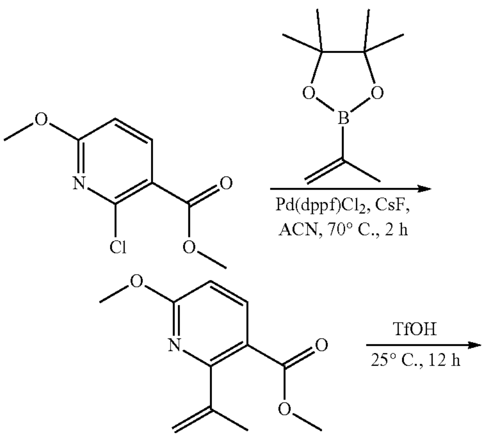

-continued

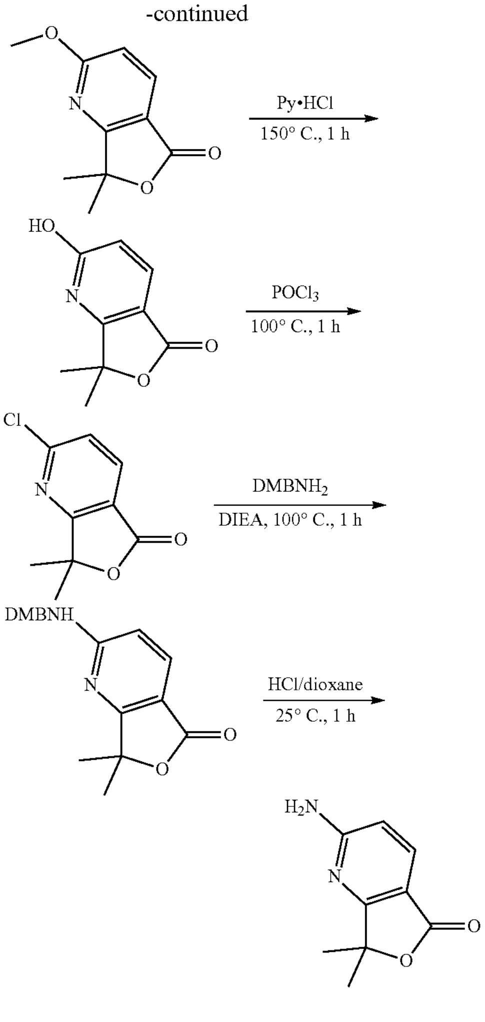

Step 1: Methyl 6-methoxy-2-(prop-1-en-2-yl)nicotinate

Pd(dppf)$Cl_2$ (544 mg, 744 umol, 0.500 equiv) and cesium fluoride (4.52 g, 29.8 mmol, 2.00 equiv) were added to a mixture of methyl 2-chloro-6-methoxynicotinate (3.00 g, 14.9 mmol) and 4,4,5,5-tetramethyl-2-(prop-1-en-2-yl)-1,3,2-dioxaborolane (3.75 g, 22.3 mmol) in MeCN (50 mL). The mixture was stirred at 70° C. for 2 h under nitrogen atmosphere, then was cooled to ambient temperature. The reaction mixture was then poured onto water (200 mL) and extracted with EA (50 mL×3). The combined organic layers were dried over anhydrous sodium sulfate, filtered and concentrated in vacuo to give a residue. The residue was purified by flash-column chromatography on silica gel (gradient elution, 1% to 2% EA-petroleum ether) to give the title compound (3.0 g, crude) as a colorless oil.

Step 2: 2-Methoxy-7,7-dimethylfuro[3,4-b]pyridin-5(7H)-one

A solution of Methyl 6-methoxy-2-(prop-1-en-2-yl)nicotinate (3.00 g, 14.5 mmol) in TfOH (17.0 g, 113 mmol, 10 mL) was stirred at 25° C. for 12 h. The reaction mixture was then poured over water (50 mL) and saturated aqueous sodium bicarbonate solution was added to adjust the pH to 7. The mixture was extracted with EA (30 mL×3). The combined organic layers were dried over anhydrous sodium sulfate, filtered and concentrated in vacuo to give a residue. The residue was purified by flash-column chromatography on silica gel (gradient elution, 10% to 33% EA-petroleum ether) to give the title compound (2.3 g, 82% yield) as a yellow solid.

Steps 3-6: 2-Amino-7,7-dimethylfuro[3,4-b]pyridin-5(7H)-one

The title compound was prepared from 2-Methoxy-7,7-dimethylfuro[3,4-b]pyridin-5(7H)-one using the four-step procedure described in Steps 3, 5, 7 and 8 for Intermediate 1. MS (ES+) $C_9H_{10}N_2O_2$ requires: 178, found: 179$[M+H]^+$.

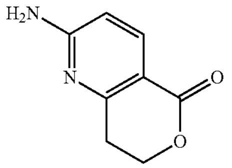 [SMILES: Nc1ccc2c(n1)CCOC2=O]

Intermediate 7: 2-Amino-7,8-dihydro-5H-pyrano[4,3-b]pyridin-5-one

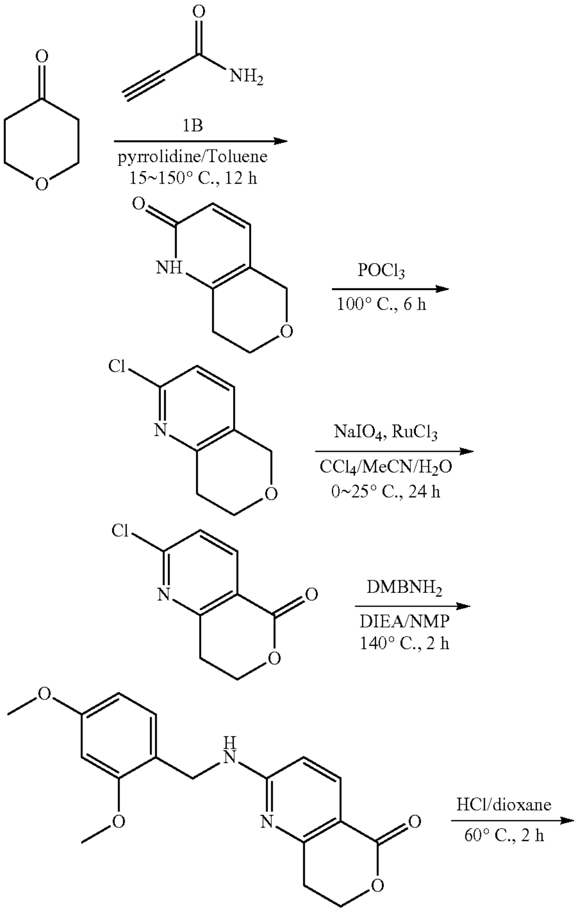

-continued

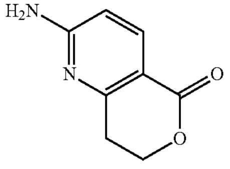

Step 1: 2-Amino-7,8-dihydro-5H-pyrano[4,3-b]pyridin-5-one

The title compound was prepared from tetrahydro-4H-pyran-4-one using the same five-step procedure described in Steps 1-5 for Intermediate 5. MS (ES+) $C_8H_8N_2O_2$ requires: 164, found: 165[M+H]$^+$. $^1$H NMR, 400 MHz, DMSO-d6, 6=7.77 (d, J=8.8 Hz, 1H), 7.01 (s, 2H), 6.41 (d, J=8.8 Hz, 1H), 4.44-4.41 (m, 2H), 2.88-2.85 (m, 2H).

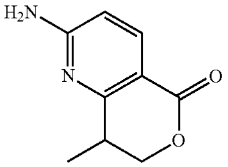

Intermediate 8: 2-Amino-8-methyl-7,8-dihydro-5H-pyrano[4,3-b]pyridin-5-one

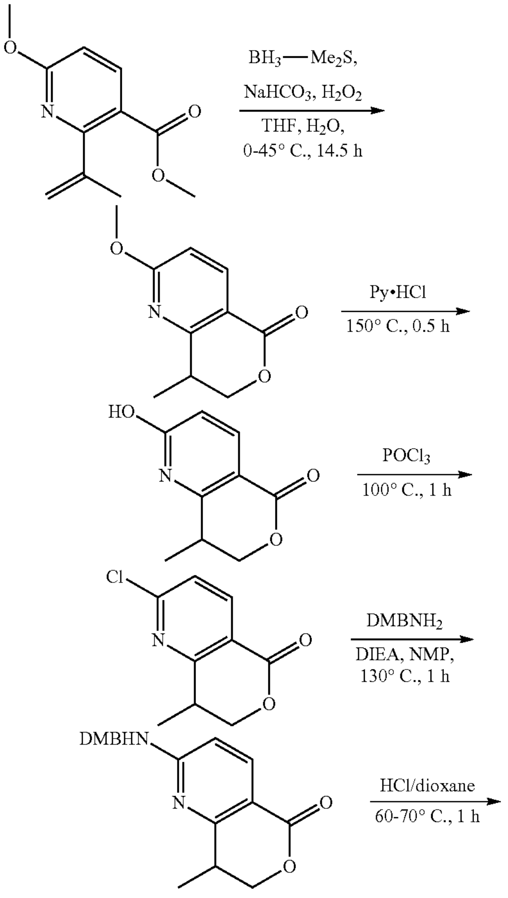

-continued

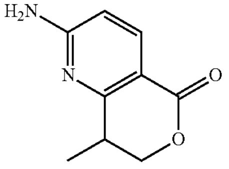

Step 1: 2-Methoxy-8-methyl-7,8-dihydro-5H-pyrano[4,3-b]pyridin-5-one $BH_3$-$Me_2S$ (10 M, 5.31 mL, 53.1 mmol, 1.10 equiv) was added dropwise to a solution of methyl 6-methoxy-2-(prop-1-en-2-yl)nicotinate (10.0 g, 48.3 mmol, 1.00 eq) in THF (100 mL) at 0° C. The mixture was warmed to 20° C. and stirred at that temperature for 2 h. The reaction mixture was then cooled to 0° C. and $NaHCO_3$ (20.3 g, 241 mmol, 5.00 eq) in water (35.0 mL) and $H_2O_2$(30% in water, 69.6 mL, 724 mmol, 15.0 eq) were added dropwise. The reaction mixture was stirred at 20° C. for 30 min and at 30-45° C. for 12 h. The reaction mixture was then poured into saturated aqueous $Na_2SO_3$ solution (200 mL) and extracted with EA (50.0 mL×3). The organic layers were combined and washed with brine (200 mL), dried over $Na_2SO_4$, filtered and concentrated. The residue was purified by flash-column chromatography on silica gel (gradient elution, 5% to 15% EA-petroleum ether) to give the title compound (15.0 g, 77.6 mmol, 80.4% yield) as yellow solid.

Steps 2-5: -Amino-8-methyl-7,8-dihydro-5H-pyrano[4,3-b]pyridin-5-one

The title compound was prepared from 2-methoxy-8-methyl-7,8-dihydro-5H-pyrano[4,3-b]pyridin-5-one using the four-step procedure described in Steps 3, 5, 7 and 8 for Intermediate 1. MS (ES+) $C_9H_{10}N_2O_2$ requires: 178, found: 179[M+H]$^+$. $^1$H NMR: 400 MHz, DMSO-$d_6$ δ 7.76 (d, J=8.6 Hz, 1H), 7.01 (s, 2H), 6.40 (d, J=8.6 Hz, 1H), 4.44 (dd, J=11.2 Hz, 4.4 Hz, 1H), 4.12 (dd, J=11.0 Hz, 6.8 Hz, 1H), 2.93 (td, J=7.0 Hz, 4.4 Hz, 1H), 1.20 (d, J=7.0 Hz, 3H).

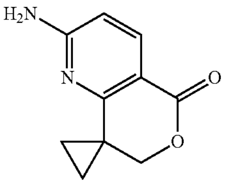 [SMILES: Nc1ccc2c(n1)C1(CC1)COC2=O]

Intermediate 9: 2'-Amino-5'H,7'H-spiro[cyclopropane-1,8'-pyrano[4,3-b]pyridin]-5'-one

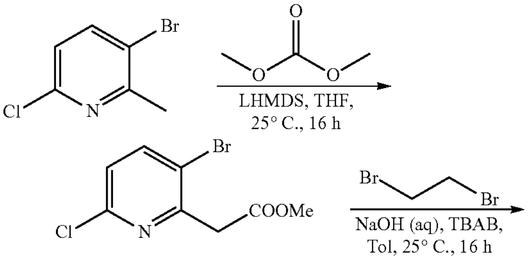

-continued

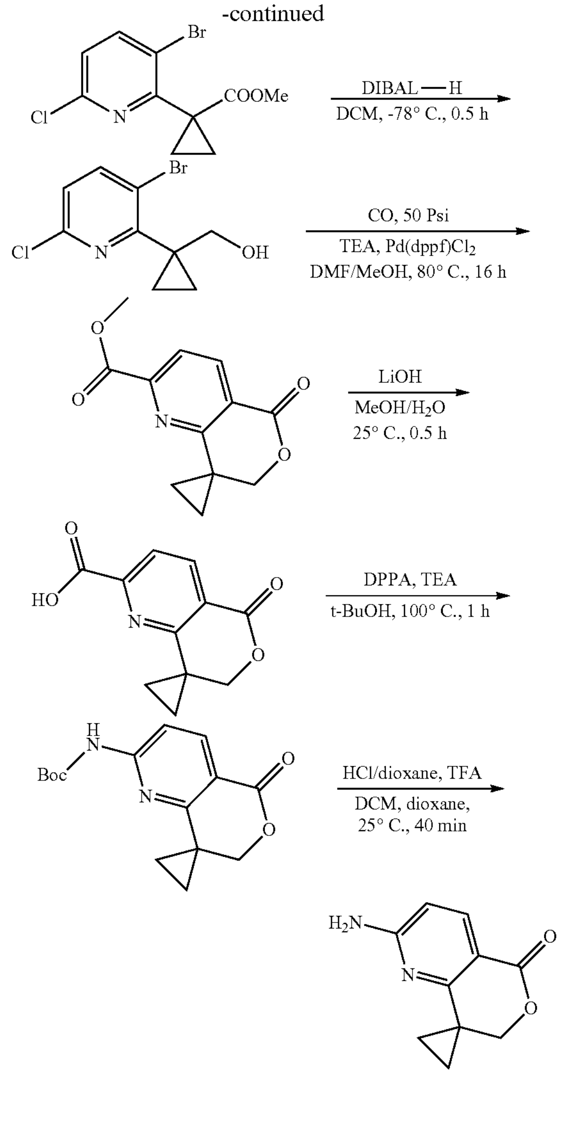

Step 1: Methyl 2-(3-bromo-6-chloropyridin-2-yl)acetate

LiHMDS (1 M, 388 mL) was added to a solution of 3-bromo-6-chloro-2-methylpyridine (20.0 g, 96.9 mmol) in THF (300 mL) at 25° C. under nitrogen. After 2.5 h, dimethyl carbonate (14.0 g, 155 mmol) was added to the mixture and stirred at 25° C. for 13.5 h. The reaction mixture was then was added to saturated aqueous $NH_4Cl$ (1000 mL) and extracted with EA (60 mL×3). The combined organic layers were dried over anhydrous sodium sulfate, filtered and concentrated to give a residue. The residue was purified by flash-column chromatography on silica gel (gradient elution, 0% to 10% EA-petroleum ether) to give the title compound (18.0 g, 70% yield) as a yellow oil. $^1H$ NMR (400 MHz, CDC13): δ ppm 7.81 (d, J=8.4 Hz, 1H), 7.16 (d, J=8.0 Hz, 1H), 4.03 9s, 2H), 3.74 (s, 3H).

Step 2: Methyl 1-(3-bromo-6-chloropyridin-2-yl) cyclopropane-1-carboxylate

Tetrabutylammonium bromide (2.44 g, 7.56 mmol) and NaOH (50 mL, 50 wt % in water) were added to a solution of 1,2-dibromoethane (10.7 g, 56.7 mmol) and methyl 2-(3-bromo-6-chloropyridin-2-yl)acetate (10.0 g, 37.8 mmol) in toluene (50 mL) at 25° C. The reaction mixture was stirred at 25° C. for 16 h, then was diluted with water (300 mL) and extracted with EA (200 mL×3). The combined organic layers were dried over anhydrous sodium sulfate, filtered and concentrated to give a residue. The residue was purified by flash-column chromatography on silica gel (gradient elution, 0% to 10% EA-petroleum ether) to give the title compound (6.10 g, 56% yield) as a yellow solid. $^1H$ NMR (400 MHz, $CDCl_3$): δ ppm 7.81 (d, J=8.4 Hz, 1H), 7.15 (d, J=8.0 Hz, 1H), 3.66 (s, 3H), 1.81-1.75 (m, 2H), 1.46-1.41 (m, 2H).

Step 3: (1-(3-Bromo-6-chloropyridin-2-yl)cyclopropyl)methanol

Diisobutylaluminium hydride (1 M, 56 mL) was added to a solution of methyl 1-(3-bromo-6-chloropyridin-2-yl)cyclopropane-1-carboxylate (5.40 g, 18.6 mmol) in DCM (80 mL) at −78° C. under nitrogen. The reaction mixture was stirred at −78° C. for 0.5 h, then was quenched by addition of aqueous saturated $NH_4Cl$ solution (50 mL), diluted with water (200 mL) and extracted with EA (200 mL×3). The combined organic layers were dried over anhydrous sodium sulfate, filtered and concentrated to give the crude title compound (5.00 g, crude) as a yellow solid which was used in the next step without further purification.

Step 4: Methyl 5'-oxo-5'H,7'H-spiro[cyclopropane-1,8'-pyrano[4,3-b]pyridine]-2'-carboxylate Triethylamine (2.31 g, 22.9 mmol) and $Pd(dppf)Cl_2$ (557 mg, 762 μmol) were added to a solution of (1-(3-Bromo-6-chloropyridin-2-yl)cyclopropyl)methanol in MeOH (25 mL) and DMF (25 mL) under nitrogen atmosphere. The suspension was degassed under vacuum and purged with carbon monoxide several times. The mixture was stirred under carbon monoxide (50 psi) at 80° C. for 16 h. The reaction mixture was then concentrated to remove methanol, diluted with water (100 mL) and extracted with EA (60 mL×3). The combined organic layers were washed with brine (100 mL×3), dried over anhydrous sodium sulfate, filtered and concentrated to give a residue. The title compound (1.8 g, crude) was obtained as a yellow solid and used in the next step without further purification. MS (ES+) $C_{10}H_{10}N_2O_2$ requires: 233, found: 234[M+H]$^+$.

Step 5: 5'-Oxo-5'H,7'H-spiro[cyclopropane-1,8'-pyrano[4,3-b]pyridine]-2'-carboxylic Acid Lithium hydroxide (555 mg, 23.2 mmol) was added to a solution of methyl 5'-oxo-5'H,7'H-spiro[cyclopropane-1,8'-pyrano[4,3-b]pyridine]-2'-carboxylate (1.80 g, 7.72 mmol) in methanol (30 mL) and water (10 mL). The reaction mixture was stirred at 25° C. for 0.5 h, then was concentrated to remove the methanol. The mixture was diluted with water (60 mL) and extracted with EA (50 mL×3). The aqueous layer was acidified by addition aqueous hydrochloric acid solution (6 M, 5 mL), then the mixture was extracted with EA (50 mL×3). The combined organic layers were dried over anhydrous sodium sulfate, filtered and concentrated to give the title compound (1.20 g, 71% yield) as a brown solid that was used without further purification.

Step 6: tert-Butyl (5'-oxo-5'H,7'H-spiro[cyclopropane-1,8'-pyrano[4,3-b]pyridin]-2'-yl)carbamate Triethylamine (831 mg, 8.21 mmol) and diphenyl phosphoryl azide (2.26 g, 8.21 mmol) were added to a solution of 5'-oxo-5'H,7'H-spiro[cyclopropane-1,8'-pyrano[4,3-b] pyridine]-2'-carboxylic acid (1.20 g, 5.47 mmol) in tert-butanol (20 mL). The reaction mixture was stirred at 100° C. for 1 h, then was cooled to ambient temperature, diluted with water (60 mL), and extracted with EA (50 mL×3). The combined organic layers were dried over anhydrous sodium sulfate, filtered and concentrated to give a residue. The residue was purified by flash-column chromatography on silica gel (gradient elution, 0% to 50% EA-petroleum ether) to give the title compound (330 mg, 19% yield) as a yellow solid and 2'-amino-5'H,7'H-spiro[cyclopropane-1,8'-pyrano [4,3-b]pyridin]-5'-one (420 mg, 28% yield) as a yellow oil.

Step 7: 2'-Amino-5'H,7'H-spiro[cyclopropane-1,8'-pyrano[4,3-b]pyridin]-5'-one

HCl in dioxane (4.0 M, 0.5 mL) was added to a solution of tert-butyl (5'-oxo-5'H,7'H-spiro[cyclopropane-1,8'-pyrano[4,3-b]pyridin]-2'-yl)carbamate (100 mg, 344 μmol) in dioxane (1.5 mL) at 25° C. The reaction mixture was stirred for 10 min, then was concentrated. DCM (2 mL) and TFA (1 mL, 13.5 mmol) were added to the residue, and the reaction mixture was stirred at 25° C. for 30 min. The reaction mixture was then concentrated and EA (5 mL) was added to the residue. The mixture was neutralized by addition of saturated aqueous $NaHCO_3$ (20 mL) and extracted with EA (15 mL×3). The combined organic layers were dried over anhydrous sodium sulfate, filtered and concentrated under to give the title compound (60.0 mg, 92% yield) as a yellow oil that was used in the next step without further purification. MS (ES+) $C_{12}H_{11}NO_4$ requires: 190, found: 191[M+H]$^+$.

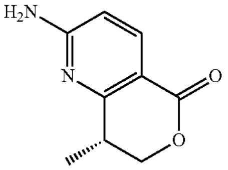

And

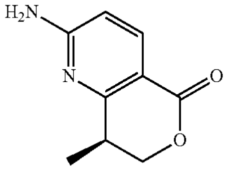

Intermediates 10 and 11: (R)-2-Amino-8-methyl-7,8-dihydro-5H-pyrano[4,3-b]pyridin-5-one and (S)-2-amino-8-methyl-7,8-dihydro-5H-pyrano[4,3-b] pyridin-5-one

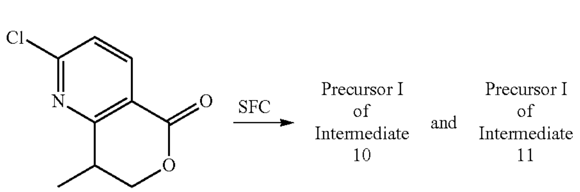

each of which is represented by one of the structures shown below:

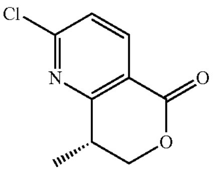

and

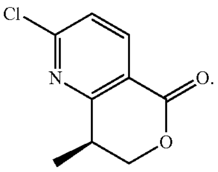

-continued

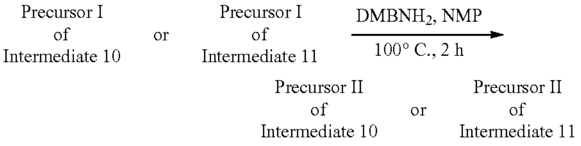

which is represented by one of the structures shown below:

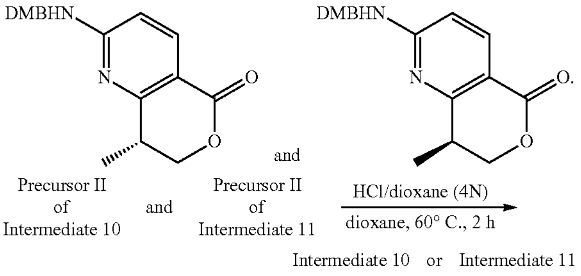

which is represented by one of the structures shown below:

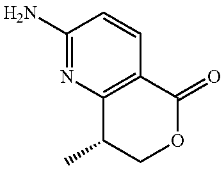

and

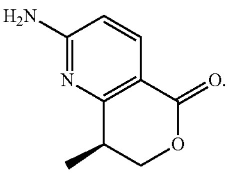

Step 1: (R)-2-chloro-8-methyl-7,8-dihydro-5H-pyrano[4,3-b]pyridin-5-one and (S)-2-chloro-8-methyl-7,8-dihydro-5H-pyrano[4,3-b]pyridin-5-one rac-2-Chloro-8-methyl-7,8-dihydro-5H-pyrano[4,3-b] pyridin-5-one (title compound from Step 3 of Intermediate 8, 700 mg, 3.54 mmol) was separated by SFC (Daicel Chiralpak IG, MeOH gradient in $CO_2$ with 0.1% $NH_4OH$) to give two peaks separately. The first eluting isomer (330 mg, 47% yield) and second eluting isomer (330 mg, 47% yield) were obtained as yellow solids.

Steps 2 and 3: One of (R or S)-2-amino-8-methyl-7,8-dihydro-5H-pyrano[4,3-b]pyridin-5-one The title compound (Intermediate 10) was prepared from one of (R or S)-2-chloro-8-methyl-7,8-dihydro-5H-pyrano [4,3-b]pyridin-5-one (first eluting isomer from step 1) using the same two-step procedure as described in Steps 4 and 5 for Intermediate 5. MS (ES+) $C_9H_{10}N_2O_2$ requires: 178, found: 179[M+H]$^+$.

Steps 3 and 4: The remaining one of (R or S)-2-amino-8-methyl-7,8-dihydro-5H-pyrano[4,3-b]pyridin-5-one The title compound (Intermediate 11) was prepared from the remaining one of (R or S)-2-chloro-8-methyl-7,8-dihydro-5H-pyrano[4,3-b]pyridin-5-one (second eluting isomer from step 1) using the same two-step procedure as described in Steps 4 and 5 for Intermediate 2. MS (ES+) $C_9H_{10}N_2O_2$ requires: 178, found: 179[M+H]$^+$.

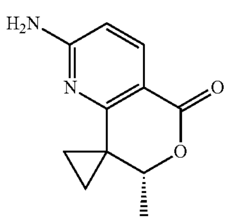

and

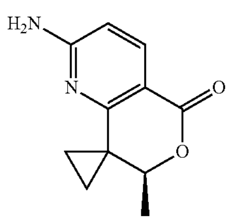

Intermediates 12 and 13: (R)-2'-Amino-7'-methyl-5'H,7'H-spiro[cyclopropane-1,8'-pyrano[4,3-b]pyridin]-5'-one and (S)-2'-Amino-7'-methyl-5'H,7'H-spiro[cyclopropane-1,8'-pyrano[4,3-b]pyridin]-5'-one

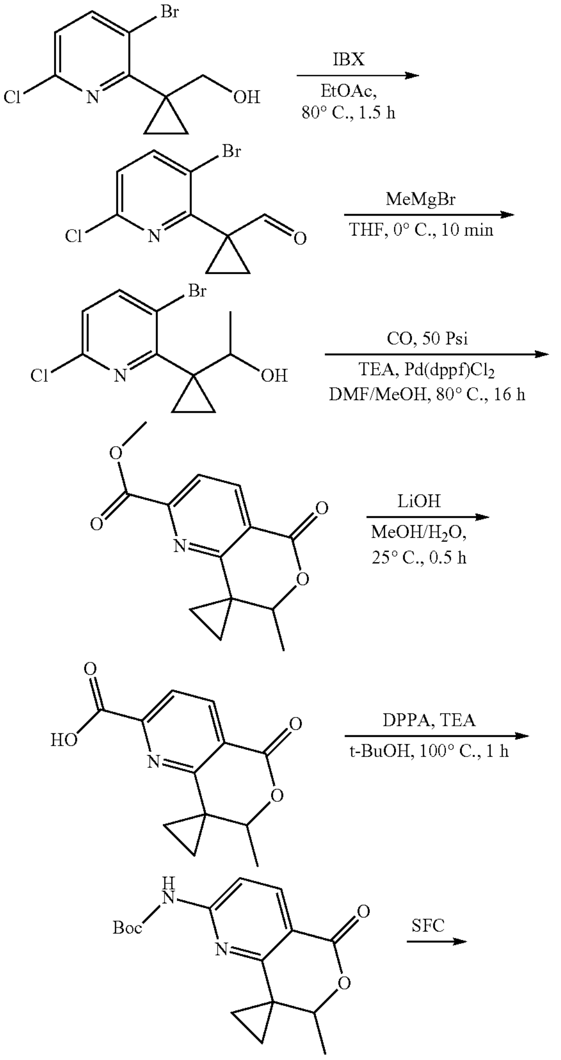

Precursor I of Intermediate 12 and Precursor I of Intermediate 13 each of which is represented by one of the structures shown below:

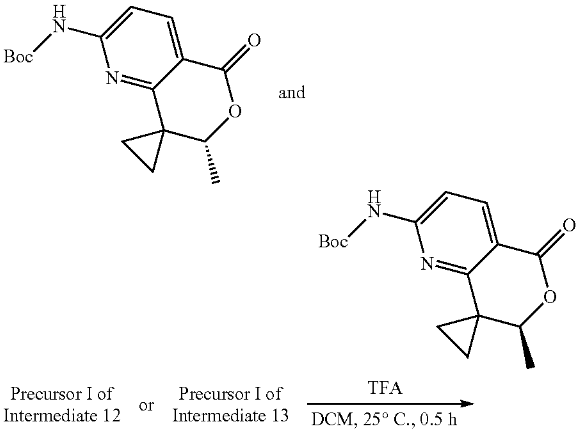

Intermediate 12 or Intermediate 13 which is represented by one of the structures shown below:

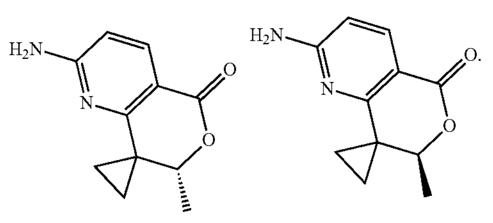

Step 1: 1-(3-Bromo-6-chloropyridin-2-yl)cyclopropane-1-carbaldehyde

IBX (6.50 g, 10.7 mmol, 46% purity) was added to a solution of (1-(3-bromo-6-chloropyridin-2-yl)cyclopropyl)methanol (2.65 g, 10.1 mmol) in EA (80 mL). The reaction mixture was stirred at 80° C. for 1 h, then additional IBX (2.00 g, 3.29 mmol, 46% purity) was added. The reaction mixture was stirred at 80° C. for 0.5 h, then was filtered and concentrated to give the title compound (2.60 g, crude) as a yellow solid that was used without further purification. MS (ES+) $C_9H_7BrClNO$ requires: 261, found: 262 $[M+H]^+$.

Step 2: 1-(1-(3-Bromo-6-chloropyridin-2-yl)cyclopropyl)ethan-1-ol

Methylmagnesium bromide (3 M, 17 mL) was added to a solution of 1-(3-bromo-6-chloropyridin-2-yl)cyclopropane-1-carbaldehyde (2.60 g, 9.98 mmol) in THF (80 mL) at 0° C. The reaction mixture was stirred for 10 min, then was quenched by addition of aqueous saturated $NH_4Cl$ solution (80 mL), diluted with water (40 mL) and extracted with EA (80 mL×3). The combined organic layers were dried over anhydrous sodium sulfate, filtered and concentrated to give the title compound (2.70 g, crude) as a yellow oil that was used without further purification. MS (ES+) $C_{10}H_{11}N_2O_2$ requires: 277, found: 278 $[M+H]^+$.

Steps 3-5: tert-Butyl (7'-methyl-5'-oxo-5'H,7'H-spiro[cyclopropane-1,8'-pyrano[4,3-b]pyridin]-2'-yl) carbamate The title compound was prepared from 1-(1-(3-bromo-6-chloropyridin-2-yl)cyclopropyl)ethan-1-ol using a similar procedure as described in Steps 4-6 for Intermediate 9 above. $^1$H NMR (400 MHz, $CDCl_3$): δ ppm 8.29 (d, J=8.8 Hz, 1H), 7.90 (d, J=8.8 Hz, 1H), 7.31 (s, 1H), 4.63-4.53 (m, 1H), 1.61 (s, 3H), 1.53 (s, 9H), 1.38-1.35 (m, 1H), 1.09-1.00 (m, 2H).

Step 6: tert-Butyl (R)-(7'-methyl-5'-oxo-5'H,7'H-spiro[cyclopropane-1,8'-pyrano[4,3-b]pyridin]-2'-yl) carbamate and tert-butyl (S)-(7'-methyl-5'-oxo-5'H, 7'H-spiro[cyclopropane-1,8'-pyrano[4,3-b]pyridin]-2'-yl)carbamate tert-Butyl (7'-methyl-5'-oxo-5'H,7'H-spiro[cyclopropane-1,8'-pyrano[4,3-b]pyridin]-2'-yl)carbamate (400 mg) was separated by SFC (column: REGIS (s,s) WHELK-01 (250 mm×50 mm, 10 um), EtOH gradient in $CO_2$ with 0.1% $NH_4OH$) to give two separate peaks. The first eluting isomer (100 mg, 24% yield) and second eluting isomer (140 mg, 34% yield) were obtained as yellow solids.

Step 7: One of (R or S)-2'-amino-7'-methyl-5'H, 7'H-spiro[cyclopropane-1,8'-pyrano[4,3-b]pyridin]-5'-one TFA (2.31 g, 20.3 mmol) was added to a solution of one of tert-butyl (R or S)-(7'-methyl-5'-oxo-5'H,7'H-spiro[cyclopropane-1,8'-pyrano[4,3-b]pyridin]-2'-yl)carbamate (first eluting isomer from Step 6, 100 mg) in DCM (6 mL). The reaction mixture was stirred at 25° C. for 30 min, then was quenched with saturated aqueous $NaHCO_3$ solution (30 mL) and extracted with DCM (20 mL×3). The combined organic layers were dried over anhydrous sodium sulfate, filtered and concentrated to give the title compound (Intermediate 12, 70 mg, crude) as a yellow oil that was used without further purification. MS (ES+) $C_{11}H_{12}N_2O_2$ requires: 204, found: 205[M+H]$^+$.

Step 8: The remaining one of (R or S)-2'-amino-7'-methyl-5'H,7'H-spiro[cyclopropane-1,8'-pyrano[4,3-b]pyridin]-5'-one The title compound (Intermediate 13) was prepared from one of tert-butyl (R or S)-(7'-methyl-5'-oxo-5'H,7'H-spiro[cyclopropane-1,8'-pyrano[4,3-b]pyridin]-2'-yl)carbamate (second eluting isomer from Step 6) using the same procedure as described in Step 7 for Intermediate 12. MS (ES+) $C_{11}H_{12}N_2O_2$ requires: 204, found: 205[M+H]$^+$.

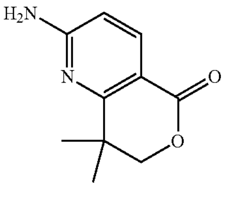

Intermediate 14: 2-Amino-8,8-dimethyl-7,8-dihydro-5H-pyrano[4,3-b]pyridin-5-one

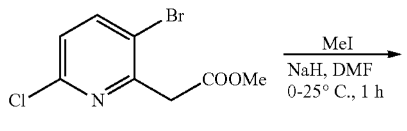

-continued

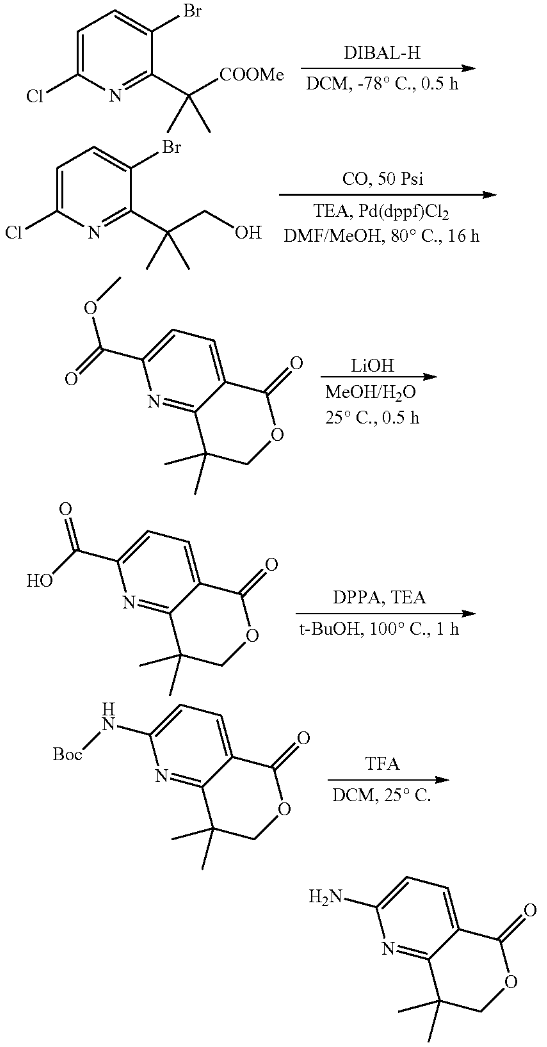

Step 1: Methyl 2-(3-bromo-6-chloropyridin-2-yl)-2-methylpropanoate

Sodium hydride (2.91 g, 72.8 mmol, 60% purity) was added to a solution of methyl 2-(3-bromo-6-chloropyridin-2-yl)acetate (5.50 g, 20.8 mmol) in THF (20 mL) at 0° C. The reaction mixture was stirred for 15 minutes at 0° C., then iodomethane (7.38 g, 51.9 mmol) was added. The reaction mixture was warmed to 25° C. and stirred for 45 min, then was quenched with water (30 mL) and extracted with EA (30 mL×2). The combined organic layers were concentrated to give a residue. The residue was purified by flash-column chromatography on silica gel (gradient elution, 0% to 10% EA-petroleum ether) to give the title compound (5.5 g, 90% yield) as a yellow oil. $^1$H NMR (400 MHz, $CD_3OD$): δ ppm 7.97 (d, J=8.4 Hz, 1H), 7.20 (d, J=8.4 Hz, 1H), 3.95 (s, 2H), 1.50 (s, 6H)

Steps 2-6: 2-Amino-8,8-dimethyl-7,8-dihydro-5H-pyrano[4,3-b]pyridin-5-one

The title compound was prepared using similar procedures as described in Steps 3-6 of Intermediate 9 and Step 7 of Intermediate 12. MS (ES+) $C_{10}H_{12}N_2O_2$ requires: 192, found: 193 [M+H]$^+$. $^1$H NMR (400 MHz, 6d-DMSO): δ ppm 7.77 (d, J=8.8 Hz, 1H), 7.01 (s, 2H), 6.40 (d, J=8.8 Hz, 1H), 4.15 (s, 2H), 1.21 (s, 6H).

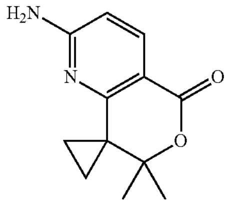

Intermediate 15: 2'-Amino-7',7'-dimethyl-5'H,7'H-spiro[cyclopropane-1,8'-pyrano[4,3-b]pyridin]-5'-one

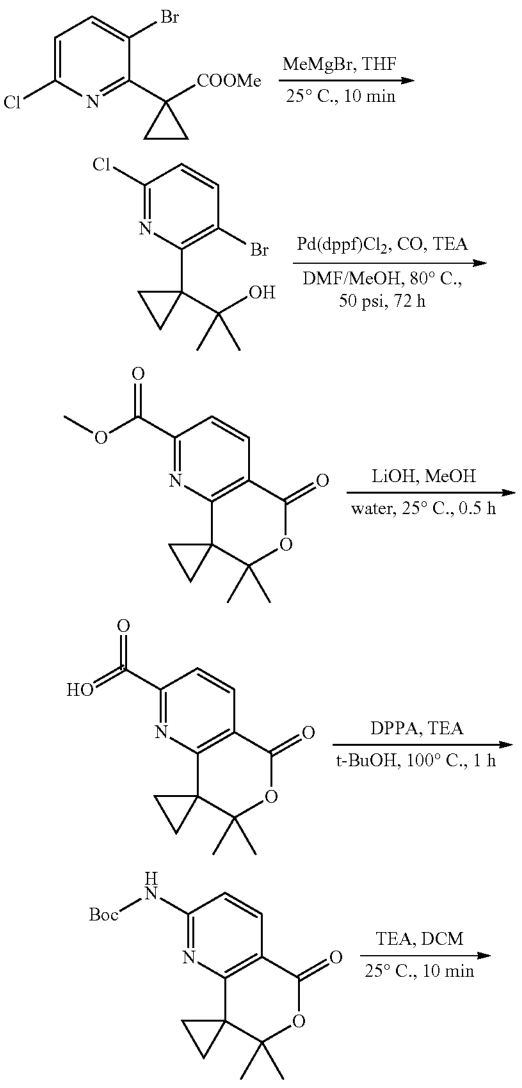

-continued

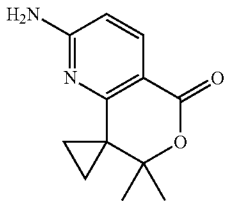 [SMILES: CC1(C)OC(=O)c2ccc(N)nc2C12CC2]

Step 1: 2-(1-(3-Bromo-6-chloropyridin-2-yl)cyclopropyl)propan-2-ol

To a solution of methyl 1-(3-bromo-6-chloropyridin-2-yl) cyclopropane-1-carboxylate (1.3 g, 4.47 mmol) in THF (10 mL) was added MeMgBr (3 M, 14.9 mL) at 25° C. The reaction mixture was stirred at 25° C. for 10 min, then was poured into water (20 mL) and extracted with EA (50 mL×3). The organic layers were combined and dried over sodium sulfate, filtered, and concentrated to give a residue. The residue was purified by column chromatography ($SiO_2$, PE/EA=1/0 to 50/1) to give the title compound (500 mg, 38% yield) as colorless oil.

Steps 2-5: 2'-Amino-7',7'-dimethyl-5'H,7'H-spiro[cyclopropane-1,8'-pyrano[4,3-b]pyridin]-5'-one The title compound was prepared from 2-(1-(3-Bromo-6-chloropyridin-2-yl)cyclopropyl)propan-2-ol using a similar procedure as described in Steps 4-6 for Intermediate 9 and Step 7 of Intermediate 12 above. $^1$H NMR (400 MHz, $CDCl_3$): δ ppm 8.05 (d, J=8.4 Hz, 1H), 6.36 (d, J=8.8 Hz, 1H), 4.85 (s, 2H), 1.42-1.32 (m, 8H), 1.06-1.03 (m, 2H).

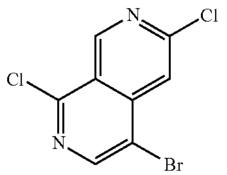

Intermediate 16: 4-Bromo-1,6-dichloro-2,7-naphthyridine

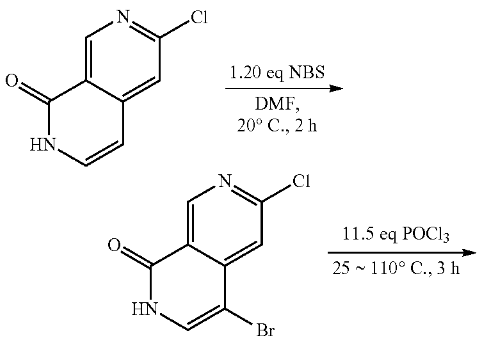

-continued

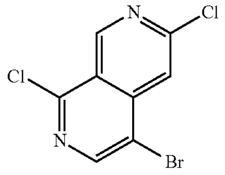 [SMILES: Clc1cc2c(Br)cnc(Cl)c2cn1]

Step 1: 4-Bromo-6-chloro-2,7-naphthyridin-1(2H)-one

NBS (70.9 g, 398 mmol, 1.20 eq) was added to a solution of 6-chloro-2,7-naphthyridin-1(2H)-one (60.0 g, 332 mmol, 1.00 eq) in DMF (600 mL). The reaction mixture was stirred at 20° C. for 2 h, then was poured into water (1 L) and filtered. The filter cake was dried under vacuum to give 4-bromo-6-chloro-2,7-naphthyridin-1(2H)-one (90.8 g, crude) as a brown solid. MS (ES+) $C_8H_4BrClN_2O$ requires: 260, found: 261[M+H]$^+$.

Step 2: 4-Bromo-1,6-dichloro-2,7-naphthyridine

4-Bromo-6-chloro-2,7-naphthyridin-1(2H)-one (70.8 g, 272 mmol, 1.00 eq) was added in portions to $POCl_3$ (484 g, 3.16 mol, 293 mL, 11.5 eq) at 25° C. The reaction mixture was then stirred at 110° C. for 3 h. The reaction mixture was then concentrated under vacuum, and the residue was adjusted to pH=8 with saturated aqueous $Na_2CO_3$ at 25° C. The mixture was extracted with DCM (500 mL×3), washed with brine (500 mL), dried over $Na_2SO_4$, filtered and concentrated under vacuum to give the title compound (75.0 g, 269 mmol, 98.9% yield) as a yellow solid. MS (ES+) $C_8H_3BrCl_2N_2$ requires: 278, found: 279[M+H]$^+$.

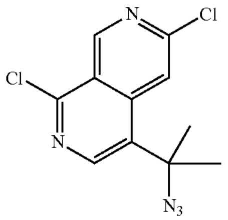 [SMILES: CC(C)(N=[N+]=[N-])c1cnc(Cl)c2cnc(Cl)cc12]

Intermediate 17: 4-(2-Azidopropan-2-yl)-1,6-dichloro-2,7-naphthyridine

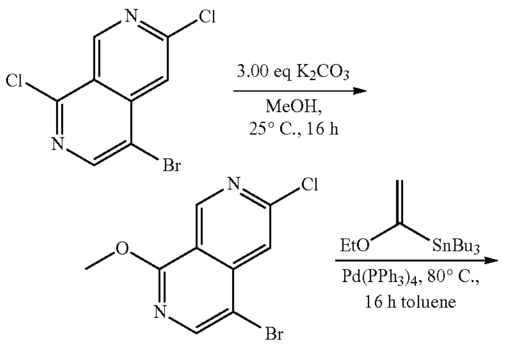

-continued

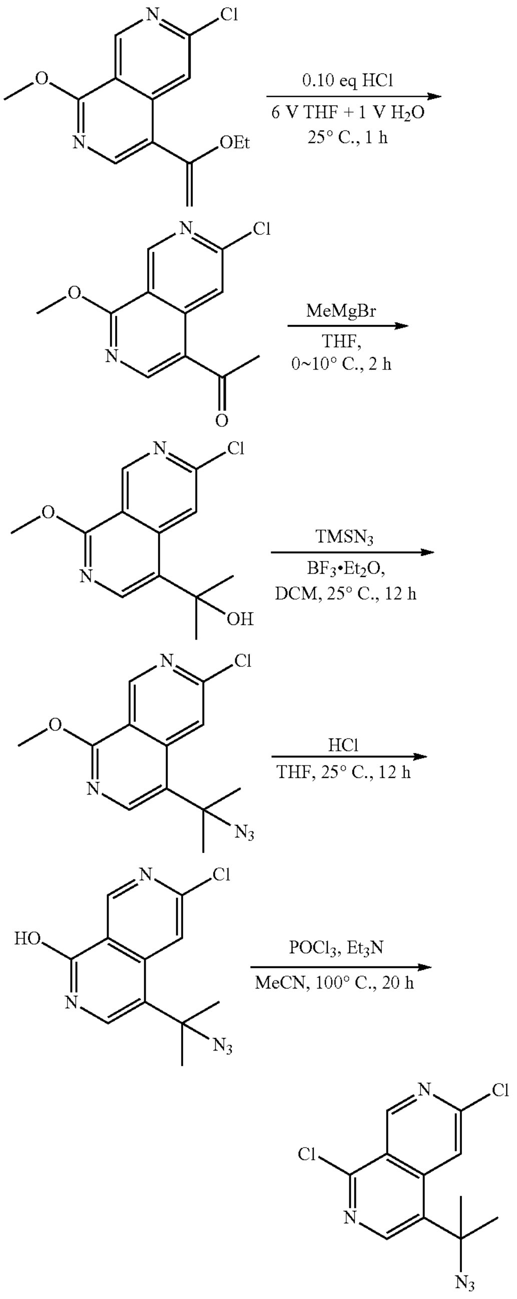

Step 1: 4-Bromo-6-chloro-1-methoxy-2,7-naphthyridine

A suspension of 4-bromo-1,6-dichloro-2,7-naphthyridine (75.0 g, 269 mmol, 1.00 eq), $K_2CO_3$ (111 g, 809 mmol, 3.00 eq) in MeOH (3 L) was stirred at 25° C. for 16 h. The reaction mixture was then concentrated under vacuum, and the residue was dissolved in $H_2O$ (300 mL) and extracted with DCM (100 mL×2). The combined organic layers were concentrated under vacuum to give a residue. The residue was triturated in PE/EA (40 mL 20:1) and filtered. The filter cake was dried under vacuum to give the title compound (47.0 g, 171 mmol, 63.6% yield) as a yellow solid.

Step 2: 6-Chloro-4-(1-ethoxyvinyl)-1-methoxy-2,7-naphthyridine

A solution of 4-bromo-6-chloro-1-methoxy-2,7-naphthyridine (47.0 g, 171 mmol, 1.00 eq), tributyl(1-ethoxyvinyl) stannane (74.4 g, 206 mmol, 69.6 mL, 1.20 eq) and $Pd(PPh_3)_4$(19.8 g, 17.1 mmol, 0.10 eq) in toluene (500 mL) was stirred at 80° C. for 16 h under $N_2$. The reaction mixture was then cooled to 20° C. and poured into saturated aqueous KF solution (500 mL) and stirred for 1 h. The aqueous mixture was extracted with EA (300 mL×3), and the organic layers were combined. The combined organic layer was concentrated under vacuum to give the title compound (64.0 g, crude) as a yellow oil. MS (ES+) $C_{13}H_{13}ClN_2O_2$ requires: 264, found: 265[M+H]$^+$.

Step 3: 1-(6-Chloro-1-methoxy-2,7-naphthyridin-4-yl) ethan-1-one Aqueous HCl (1.50 M, 20.1 mL, 0.10 eq) was added to a solution of 6-chloro-4-(1-ethoxyvinyl)-1-methoxy-2,7-naphthyridine (80.0 g, 302 mmol, 1.00 eq) in THF (480 mL) and $H_2O$ (80 mL). The reaction mixture was stirred at 25° C. for 1 h. The reaction mixture was then poured into saturated aqueous $NaHCO_3$ solution (500 mL) and extracted with EA (300 mL×2). The organic layers were combined and concentrated under vacuum. The residue was purified by flash-column chromatography on silica gel (gradient elution, 5% to 50% EA-PE) to give the title compound (28.0 g, 118 mmol, 39.1% yield) as a white solid. MS (ES+) $C_{11}H_9ClN_2O_2$ requires: 236, found: 237[M+H]$^+$.

Step 4: 2-(6-Chloro-1-methoxy-2,7-naphthyridin-4-yl)propan-2-ol

MeMgBr (3.0 M in diethyl ether, 118 mL, 3.00 eq) was added to a solution of 1-(6-chloro-1-methoxy-2,7-naphthyridin-4-yl)ethan-1-one (28.0 g, 118 mmol, 1.00 eq) in THF (300 mL) at 0-10° C. The mixture was stirred at 0-10° C. for 2 h, and then was poured into saturated aqueous $NH_4Cl$ solution (300 mL) and extracted with EA (200 mL×2). The organic layers were combined and concentrated under vacuum to give the title compound (33 g, crude) as a yellow oil. MS (ES+) $C_{12}H_{13}ClN_2O_2$ requires: 252, found: 253[M+H]$^+$.

Step 5: 4-(2-Azidopropan-2-yl)-6-chloro-1-methoxy-2,7-naphthyridine $TMSN_3$ (14.4 g, 125 mmol, 16.5 mL, 2.50 eq) was added to a solution of 2-(6-chloro-1-methoxy-2,7-naphthyridin-4-yl)propan-2-ol (28.0 g, 50.3 mmol, 45.4% purity, 1.00 eq) and $BF_3 \cdot Et_2O$ (15.5 g, 50.3 mmol, 13.5 mL, 46.0% purity, 1.00 eq) in DCM (280 mL) at 25° C. The reaction mixture was stirred at 25° C. for 12 h, then was partitioned between saturated aqueous $NaHCO_3$ solution (350 mL) and DCM (200 mL). The layers were separated, and the aqueous layer was further extracted with DCM (200 mL). The organic layers were combined and washed with brine (200 mL), dried over sodium sulfate, filtered, and then concentrated. The residue was purified by flash-column chromatography on silica gel (gradient elution, 2% to 50% EA-PE) to give the title compound (20.0 g, 65.% yield, 91% purity) as an off-white solid. MS (ES+) $C_{12}H_{12}ClN_5O$ requires: 277, found: 278[M+H]$^+$.

Step 6: 4-(2-Azidopropan-2-yl)-6-chloro-2,7-naphthyridin-1-ol

Aqueous HCl (2 M, 163 mL, 5.00 eq) was added to a solution of 4-(2-azidopropan-2-yl)-6-chloro-1-methoxy-2,7-naphthyridine (20.0 g, 65.5 mmol, 91% purity, 1.00 eq) in THF (200 mL) at 25° C. The reaction mixture was stirred at 25° C. for 12 h, then was poured into saturated aqueous $NaHCO_3$ (1.00 L) and extracted with EA (500 mL*2). The organic layers were combined and washed with brine (500 mL), dried over sodium sulfate, filtered, and concentrated to give the title compound (19.0 g, 96% yield, 88% purity) as a yellow solid. MS (ES+) $C_{11}H_{10}ClN_5O$ requires: 263, found: 264[M+H]$^+$.

Step 7: 4-(2-Azidopropan-2-yl)-1,6-dichloro-2,7-naphthyridine $POCl_3$ (2.54 g, 16.5 mmol, 1.54 mL, 4.37 eq) and $Et_3N$ (1.01 g, 9.99 mmol, 1.39 mL, 2.63 eq) were added to a mixture of 4-(2-azidopropan-2-yl)-6-chloro-2,7-naphthyridin-1-ol 7 (1.00 g, 3.79 mmol, 1.00 eq) in ACN (20.0 mL). The reaction mixture was then heated to 100° C. for 20 h. The reaction mixture was then concentrated, and the residue was diluted with EA. The diluted residue was quenched with water, and the mixture was adjusted to pH=8 with aqueous sodium carbonate. The mixture was then extracted with EA, and the organic layer was washed with brine. The washed organic layer was dried over sodium sulfate, filtered, and concentrated. The residue was purified by flash-column chromatography on silica gel (gradient elution, 0% to 5% EA-PE) to give the title compound (14.2 g, 84% yield) as a light yellow solid. MS (ES+) $C_{11}H_9Cl_2N_2$ requires: 281, found: 282[M+H]$^+$. $^1$H-NMR (400 MHz, DMSO-$d_6$): δ ppm 9.57 (s, 1H), 8.61 (s, 1H), 8.45 (s, 1H), 1.83 (s, 6H).

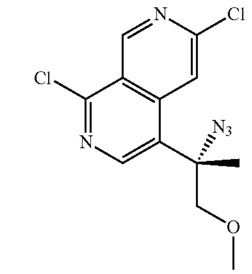

Intermediate 18: (S)-4-(2-Azido-1-methoxypropan-2-yl)-1,6-dichloro-2,7-naphthyridine

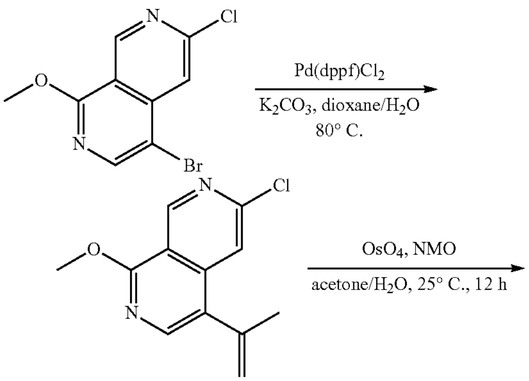

-continued

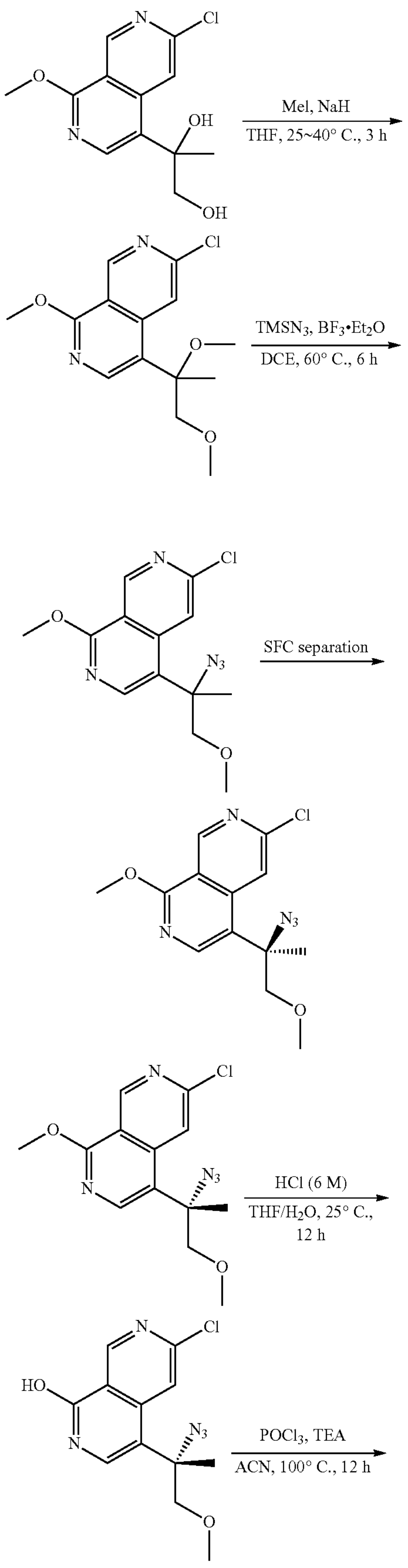

-continued

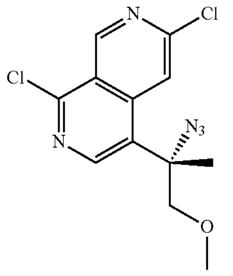 [SMILES: COC[C@@](C)(N=[N+]=[N-])c1cnc(Cl)c2cnc(Cl)cc12]

Step 1: 6-Chloro-1-methoxy-4-(prop-1-en-2-yl)-2,7-naphthyridine

To a solution of 4-bromo-6-chloro-1-methoxy-2,7-naphthyridine (Title compound from Step 1 of Intermediate 17, 12.4 g, 45.3 mmol) and 4,4,5,5-tetramethyl-2-(prop-1-en-2-yl)-1,3,2-dioxaborolane (7.62 g, 45.3 mmol) in dioxane (500 mL) and water (50 mL) was added Pd(dppf)$Cl_2$ (3.32 g, 4.53 mmol), $K_2CO_3$ (12.5 g, 90.6 mmol). The mixture was stirred at 80° C. for 2 hours under nitrogen atmosphere, then the reaction mixture was diluted with water (200 mL) and extracted with EA (100 mL×3). The combined organic layers were dried over anhydrous sodium sulfate, filtered and concentrated under reduced pressure to give a residue. The residue was purified by flash-column chromatography on silica gel (PE/EA=100/1 to 10/1) to give the title compound (7.00 g, 65% yield) as a white solid.

Step 2: 2-(6-Chloro-1-methoxy-2,7-naphthyridin-4-yl)propane-1,2-diol

OsO4 (1.02 g, 4.01 mmol) was added to a mixture of 6-chloro-1-methoxy-4-(prop-1-en-2-yl)-2,7-naphthyridine (9.4 g, 40.0 mmol) and NMO (9.38 g, 80.1 mmol) in acetone (160 mL) and $H_2O$ (40 mL). The reaction mixture was stirred at 25° C. for 12 h, then was quenched saturated aqueous KF solution (150 mL) and filtered. The solution was extracted with EA (2×300 mL). The organic phase was dried over $Na_2SO_4$, filtered and concentrated to give the title compound (9.3 g, 86% yield) as yellow oil which was used in the next step without further purification.

Step 3: 6-Chloro-4-(1,2-dimethoxypropan-2-yl)-1-methoxy-2,7-naphthyridine

NaH (4.85 g, 121 mmol, 60% purity) was added to a solution of 2-(6-chloro-1-methoxy-2,7-naphthyridin-4-yl)propane-1,2-diol (9.3 g, 34.6 mmol) in THF (150 mL). The reaction mixture was stirred at 25° C. for 0.5 h, then MeI (12.3 g, 86.5 mmol) was added. The reaction mixture was stirred at 25° C. for 0.5 h, and then stirred at 40° C. for 2 h. The reaction mixture was then added into a stirring solution of the saturated aqueous $NH_4Cl$ (50 mL) and extracted with EA (300 mL). The organic layer was washed with saturated aqueous $NH_4Cl$ (100 mL×3), dried over $Na_2SO_4$, filtered and concentrated to give the title compound (10 g, 85% yield) as a yellow oil which was used in the next step without further purification.

Step 4: 4-(2-Azido-1-methoxypropan-2-yl)-6-chloro-1-methoxy-2,7-naphthyridine $BF_3{\cdot}Et_2O$ (8.80 g, 62.0 mmol) was added to a mixture of 6-chloro-4-(1,2-dimethoxypropan-2-yl)-1-methoxy-2,7- naphthyridine (9.2 g, 31.0 mmol), $TMSN_3$ (17.9 g, 155 mmol) in DCE (150 mL) at 25° C. The reaction mixture heated to 60° C. for 6 h under $N_2$. The reaction mixture was then added into a stirring solution of aqueous saturated $NaHCO_3$ (300 mL) and extracted with EA (300 mL). The organic layer was dried over $Na_2SO_4$, filtered and concentrated to give a residue. The residue was purified by flash-column chromatography on silica gel (20% EA-PE) to give the title compound (8 g, 73% yield) as a colorless oil.

Step 4: (R)-4-(2-Azido-1-methoxypropan-2-yl)-6-chloro-1-methoxy-2,7-naphthyridine and (S)-4-(2-azido-1-methoxypropan-2-yl)-6-chloro-1-methoxy-2,7-naphthyridine The title compounds were prepared by chiral SFC separation of 4-(2-azido-1-methoxypropan-2-yl)-6-chloro-1-methoxy-2,7-naphthyridine (column: Daicel ChiralPak IG (250*30 mm, 10 um); mobile phase: [15% (IPA with 0.1% $NH_4OH$)] to give the title two isomers. The first eluting isomer was (R)-4-(2-Azido-1-methoxypropan-2-yl)-6-chloro-1-methoxy-2,7-naphthyridine and the second eluting isomer was (S)-4-(2-azido-1-methoxypropan-2-yl)-6-chloro-1-methoxy-2,7-naphthyridine. The absolute stereochemistry of the title compounds was determined by X-ray crystal structure of a final compound prepared from the second eluting isomer.

Step 5: (S)-4-(2-Azido-1-methoxypropan-2-yl)-6-chloro-2,7-naphthyridin-1-ol

Aqueous HCl (6 M, 5.41 mL) was added to a solution of (S)-4-(2-azido-1-methoxypropan-2-yl)-6-chloro-1-methoxy-2,7-naphthyridine (3 g, 9.75 mmol) in THF (240 mL). The mixture was stirred at 25° C. for 12 h, then was adjusted to pH ~8 with addition of solid $NaHCO_3$. The mixture was extracted with EA (2×150 mL) and the organic layer was dried over $Na_2SO_4$, filtered and concentrated to give the title compound (2.7 g, 83% yield, 88% purity) as a white solid which was used in the next step without further purification.

Step 6: (S)-4-(2-Azido-1-methoxypropan-2-yl)-1,6-dichloro-2,7-naphthyridine $POCl_3$ (3.34 g, 21.8 mmol) was added to a mixture of (S)-4-(2-azido-1-methoxypropan-2-yl)-6-chloro-2,7-naphthyridin-1-ol (1.28 g, 4.36 mmol) and TEA (1.16 g, 11.5 mmol) in ACN (20 mL). The mixture was heated to 100° C. for 12 h. The reaction mixture was then added to saturated aqueous $NH_4Cl$ (50 mL) and extracted with EA (100 mL×3). The organic layers were combined and dried over $Na_2SO_4$, filtered, and concentrated to give a residue. The residue was purified by flash-column chromatography on silica gel (25% EA-PE) to give the title compound (1.2 g, 88% yield) as a yellow oil. $^1H$ NMR (400 MHz, $CDCl_3$): δ ppm 9.61 (s, 1H), 8.57 (s, 1H), 8.48 (s, 1H), 3.98 (d, J=9.6 Hz, 1H), 3.78 (d, J=9.6 Hz, 1H), 3.41 (s, 3H), 1.80 (s, 3H).

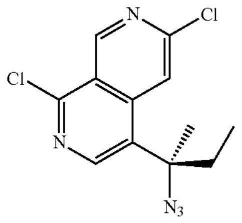 [SMILES: CC[C@@](C)(N=[N+]=[N-])c1cnc(Cl)c2cnc(Cl)cc12]

Intermediate 19:_(R)-4-(2-Azidobutan-2-yl)-1,6-dichloro-2,7-naphthyridine

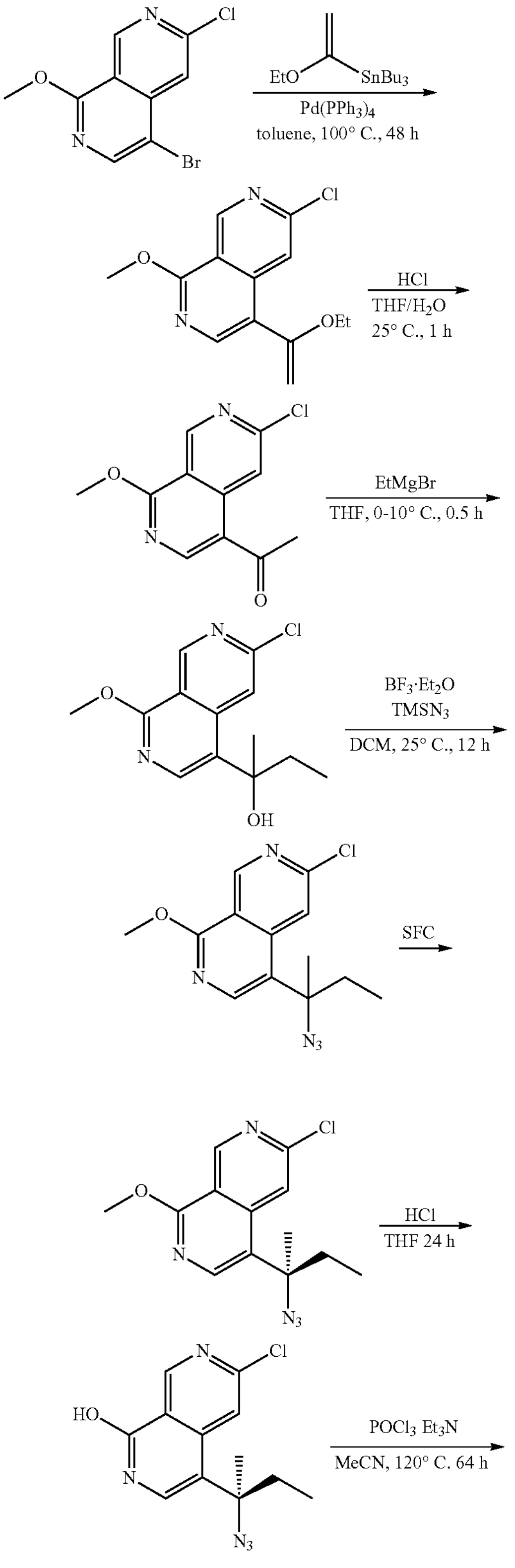

-continued

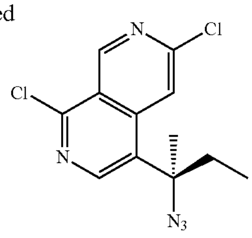

Step 1: 6-Chloro-4-(1-ethoxyvinyl)-1-methoxy-2,7-naphthyridine

A suspension of 4-bromo-6-chloro-1-methoxy-2,7-naphthyridine (220 g, 804 mmol, 1.00 eq), tributyl(1-ethoxyvinyl)stannane (264 g, 731 mmol, 246 mL, 0.90 eq), $Pd(PPh_3)_4$(46.4 g, 40.2 mmol, 0.05 eq) in toluene (2.20 L) was stirred at 100° C. under $N_2$ for 36 h. The mixture was cooled to 25° C. and more tributyl(1-ethoxyvinyl)stannane (0.35 eq) was added to above solution under $N_2$. The mixture was stirred at 100° C. for 12 h. The mixture was cooled to 25° C. and poured into saturated aqueous KF solution (2.00 L). The mixture was filtered through a pad of celite and the filtrate was extracted with EA (1.00 L×2). The combined organic layer was concentrated, and the residue was purified by column chromatography ($SiO_2$, PE/EA=20/1~10/1) to give the title compound (157 g, 668 mmol, 83.1% yield) as a white solid.

Step 2: 1-(6-Chloro-1-methoxy-2,7-naphthyridin-4-yl)ethan-1-one

To a solution of 6-chloro-4-(1-ethoxyvinyl)-1-methoxy-2,7-naphthyridine (157 g, 593 mmol, 1.00 eq) in THF (942 mL) and $H_2O$ (157 mL) was added HCl (1.50 M, 39.5 mL, 0.10 eq), then the suspension was stirred 25° C. for 1 h. The mixture was poured into saturated aqueous $NaHCO_3$ solution (1.50 L) and extracted with EA (1.50 L×2). The combined organic layer was concentrated to give a residue. The residue was slurried in PE/EA=10:1 (550 mL) at 20-25° C. for 10 mins, then the suspension was filtered, and the filter cake dried to give the title compound (114 g) as a white solid. MS (ES+) $C_{11}H_9ClN_2O_2$ requires: 236, found: 237 $[M+H]^+$.

Step 3: 2-(6-Chloro-1-methoxy-2,7-naphthyridin-4-yl)butan-2-ol

A solution of 1-(6-chloro-1-methoxy-2,7-naphthyridin-4-yl)ethan-1-one (114 g, 481 mmol, 1.00 eq) in THF (2.28 L) was added to a mixture of EtMgBr (3.00 M, 481 mL, 3.00 eq) at 0-10° C. The reaction mixture was stirred at 0-10° C. for 0.5 h, then was poured into saturated aqueous $NH_4Cl$ solution (1.50 L) and extracted with EA (1.00 L*2). The combined organic layer was washed with brine (1.00 L), dried over with $Na_2SO_4$, filtered, and concentrated. The residue was purified by silica gel chromatography (PE/EA=5/1 to 2/1) to give the title compound (100 g) as a yellow oil. MS (ES+) $C_{13}H_{15}ClN_2O_2$ requires: 266, found: 267$[M+H]^+$.

Step 4: 4-(2-Azidobutan-2-yl)-6-chloro-1-methoxy-2,7-naphthyridine

To a solution of 2-(6-chloro-1-methoxy-2,7-naphthyridin-4-yl)butan-2-ol (100 g, 374 mmol, 1.00 eq) and $BF_3·Et_2O$ (49.2 mL, 187 mmol, 47.0% purity, 0.50 eq) in DCM (1.00 L) was added $TMSN_3$ (123 mL, 937 mmol, 2.50 eq) at 25° C. The reaction mixture was stirred at 25° C. for 12 hrs. The reaction mixture was then added slowly to saturated aqueous $NaHCO_3$ solution (1.00 L) and extracted with DCM (200 mL×2). The organic layer was washed with brine (1.00 L), dried over with $Na_2SO_4$, filtered, and concentrated. The residue was purified by silica gel chromatography (PE/EA=100/1~5/1) to give a solid. The solid was slurried in PE/EA=8/1 (90.0 mL) at 25° C. for 10 min, then was filtered and the filter cake was dried to give the title compound (46.0 g, 155 mmol, 41.5% yield) as a white solid. MS (ES+) $C_{13}H_{14}ClN_5O$ requires: 291, found: 292$[M+H]^+$.

Step 5: (R)-4-(2-Azidobutan-2-yl)-6-chloro-1-methoxy-2,7-naphthyridine 4-(2-Azidobutan-2-yl)-6-chloro-1-methoxy-2,7-naphthyridine (46.0 g, 157 mmol, 98.7% purity, 1.00 eq) was separated by SFC (column: Daicel ChiralPak IG (250*30 mm, 10 um); mobile phase: [0.1% $NH_3H_2O$ MEOH]; B %: 20%-20%). The second eluting peak was concentrated to give the title compound (21.5 g, 46.7% yield) as a white solid. The absolute stereochemistry of the title compound was determined by X-ray crystal structure of a final compound prepared from this Intermediate 19. MS (ES+) $C_{13}H_{14}ClN_5O$ requires: 291, found: 292$[M+H]^+$.

Step 6: (R)-4-(2-Azidobutan-2-yl)-6-chloro-2,7-naphthyridin-1-ol

To a solution of (R)-4-(2-azidobutan-2-yl)-6-chloro-1-methoxy-2,7-naphthyridine (21.5 g, 72.7 mmol, 1.00 eq) in THF (215 mL) was added HCl (3.00 M, 122 mL, 5.07 eq) at 25° C., then the suspension was stirred at 25° C. for 12 h, followed by stirring at 30° C. for 12 h. The reaction mixture poured into saturated aqueous $NaHCO_3$ (500 mL) and extracted with EA (150 mL×2), washed with brine (200 mL), dried over $Na_2SO_4$, filtered, and concentrated. The residue was slurried in PE (100 mL) at 25° C. for 10 mins, then was filtered and the filter cake was dried to give the title compound (18.5 g) as a white solid. MS (ES+) $C_{12}H_{12}ClN_5O$ requires: 277, found: 278$[M+H]^+$.

Step 7: (R)-4-(2-Azidobutan-2-yl)-1,6-dichloro-2,7-naphthyridine

Three reactions below were carried out in parallel and combined for purification. To a solution of (R)-4-(2-azidobutan-2-yl)-6-chloro-2,7-naphthyridin-1-ol (6.16 g, 22.1 mmol, 1.00 eq) in MeCN (190 mL) was added $POCl_3$ (10.3 mL, 110 mmol, 5.00 eq) and $Et_3N$ (8.03 mL, 57.6 mmol, 2.60 eq). The reaction mixture was stirred at 120° C. for 64 h, then was concentrated to give a residue. The residue was diluted with EA (500 mL), then was quenched with water (500 mL) at 20~30° C. and stirred at 30° C. for 30 min. The mixture was adjusted pH=8 with addition of saturated aqueous $Na_2CO_3$ solution at 25° C., then was extracted with EA (500 mL×2). The combined organic layer was washed with brine (500 mL), dried over with $Na_2SO_4$, filtered, and concentrated. The residue was purified by silica gel chromatography (PE/EA=1/0~8/1) to give the title compound (18.0 g, 88.4% yield) as a light yellow solid. MS (ES+) $C_{12}H_{11}Cl_2N_5$ requires: 295, found: 296$[M+H]^+$. $^1H$ NMR (400 MHz, $CDCl_3$): δ 9.62 (s, 1H), 8.52 (s, 1H), 8.43 (s, 1H), 2.03-2.16 (m, 2H), 1.61-1.89 (m, 3H), 0.85-0.89 (m, 3H).

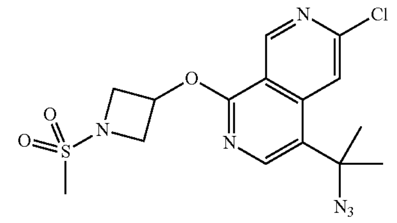 [SMILES: CC(C)(N=[N+]=[N-])c1cnc(OC2CN(S(C)(=O)=O)C2)c2cnc(Cl)cc12]

Intermediate 20: 4-(2-Azidopropan-2-yl)-6-chloro-1-((1-(methylsulfonyl)azetidin-3-yl)oxy)-2,7-naphthyridine

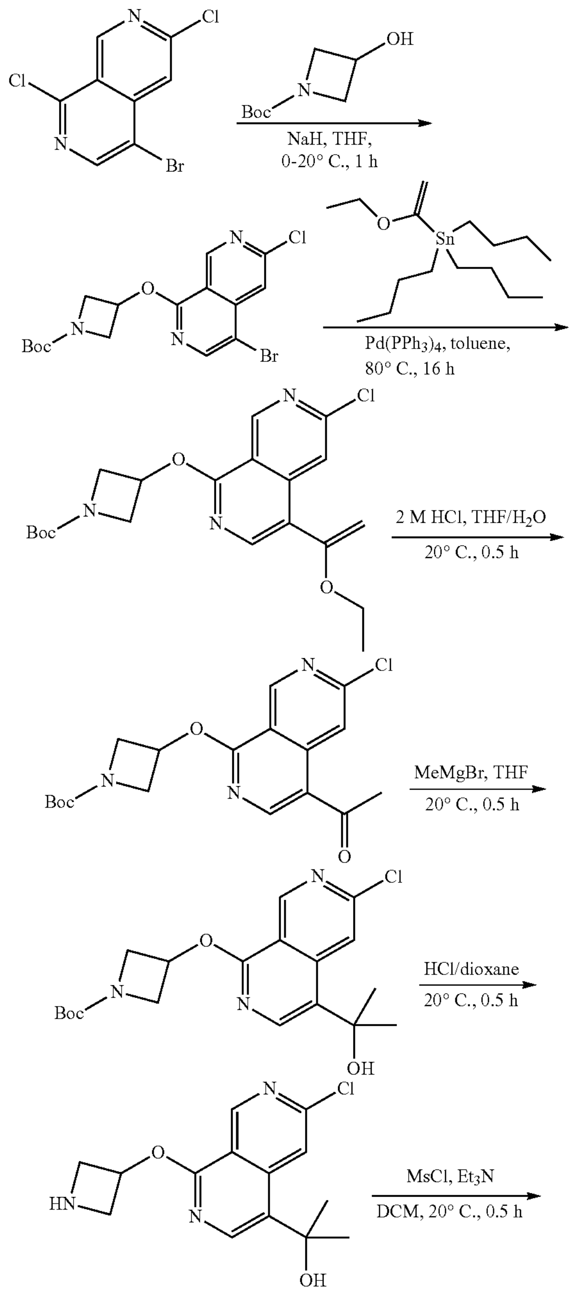

-continued

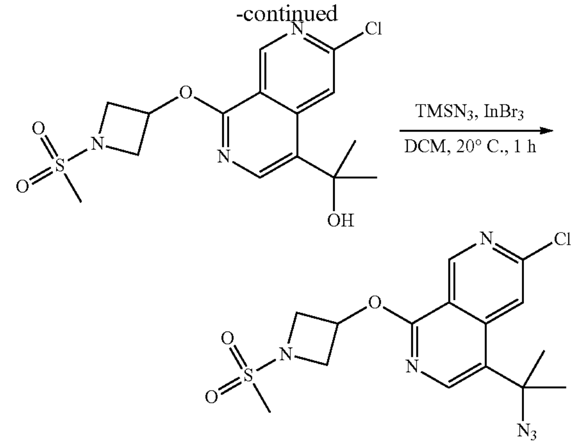

Step 1: tert-Butyl 3-((4-bromo-6-chloro-2,7-naphthyridin-1-yl)oxy)azetidine-1-carboxylate To a solution of tert-butyl 3-hydroxyazetidine-1-carboxylate (2.06 g, 11.9 mmol) in THF (84 mL) was added NaH (518 mg, 13.0 mmol, 60% purity) at 0° C. The reaction mixture was stirred at 20° C. for 0.5 h, then 4-bromo-1,6-dichloro-2,7-naphthyridine (3 g, 10.8 mmol) was added and the obtained mixture was stirred at 20° C. for 0.5 h. The reaction mixture was then quenched by addition water 80 mL slowly at 0° C., then extracted with EA (100 mL×3). The combined organic layers were dried over by anhydrous sodium sulfate, filtered and concentrated to give a residue. The residue was purified by column chromatography ($SiO_2$, PE/EA=1/0 to 10/1) to give the title compound (4.00 g, 88% yield) as a white solid. MS (ES+) $C_{16}H_{17}BrClN_3O_3$ requires: 415, found: 416[M+H]$^+$.

Step 2: tert-Butyl 3-((6-chloro-4-(1-ethoxyvinyl)-2,7-naphthyridin-1-yl)oxy)azetidine-1-carboxylate To a solution of tert-butyl 3-((4-bromo-6-chloro-2,7-naphthyridin-1-yl)oxy)azetidine-1-carboxylate (4.00 g, 9.65 mmol) in toluene (100 mL) was added $Pd(PPh_3)_4$(1.11 g, 965 umol) and tributyl(1-ethoxyvinyl)stannane (3.48 g, 9.65 mmol, 3.26 mL). The reaction mixture was stirred at 80° C. for 16 h under nitrogen, then saturated aqueous potassium fluoride solution was added. The mixture was stirred for 4 h, then was extracted with EA (100 mL×3). The combined organic layers were dried over sodium sulfate, filtered, and concentrated to give a residue. The residue was purified by column chromatography ($SiO_2$, PE/EA=1/0 to 10/1) to give the title compound (3.40 g, 43% yield) as a white solid.

Step 3: tert-Butyl 3-((4-acetyl-6-chloro-2,7-naphthyridin-1-yl)oxy)azetidine-1-carboxylate To a solution of tert-butyl 3-((6-chloro-4-(1-ethoxyvinyl)-2,7-naphthyridin-1-yl)oxy)azetidine-1-carboxylate (3.40 g, 4.19 mmol) in THF (68 mL) and $H_2O$ (8 mL) was added HCl (2 M, 2.09 mL). The mixture was stirred at 20° C. for 0.5 h, then was diluted with water (20 mL) and the pH of the mixture was adjusted to 8-9 by addition of saturated aqueous sodium bicarbonate solution. The mixture was extracted with DCM (20 mL×3), the combined organic layers were washed with water (30 mL×3), dried over by anhydrous sodium sulfate, filtered, and concentrated under reduced pressure to give a residue. The residue was purified by column chromatography ($SiO_2$, PE/EA=10/0 to 1/1) to give the title compound (1.4 g, 83% yield) as a white solid.

Step 4: tert-Butyl 3-((6-chloro-4-(2-hydroxypropan-2-yl)-2,7-naphthyridin-1-yl)oxy)azetidine-1-carboxylate To a solution of tert-butyl 3-((4-acetyl-6-chloro-2,7-naphthyridin-1-yl)oxy)azetidine-1-carboxylate (1.4 g, 3.71 mmol, 1 eq) in THF (30 mL) was added methyl magnesium bromide (3 M, 6.18 mL, 5 eq). The reaction mixture was stirred at 20° C. for 1 h, then was poured into saturated aqueous ammonium chloride solution (30 mL), diluted with water (20 mL) and extracted with EA (3×50 mL). The combined organic layers were dried over sodium sulfate, filtered, and concentrated to give a residue. The residue was purified by column chromatography ($SiO_2$, PE/EA=10/0 to 1/1) to give the title compound (1.2 g, 76% yield) as a white solid.

Step 5: 2-(1-(Azetidin-3-yloxy)-6-chloro-2,7-naphthyridin-4-yl)propan-2-ol tert-Butyl 3-((6-chloro-4-(2-hydroxypropan-2-yl)-2,7-naphthyridin-1-yl)oxy)azetidine-1-carboxylate (1.10 g, 2.79 mmol) was added to a solution of HCl in dioxane (4 M, 11 mL). The reaction mixture was stirred at 20° C. for 0.5 h, then was concentrated to give a residue. Saturated aqueous sodium bicarbonate solution was added, and the mixture was extracted with DCM (20 mL×3). The combined organic layers were washed with water (30 mL×3), dried over by anhydrous sodium sulfate, filtered, and concentrated to give a residue. The residue was purified by pre-HPLC (column: Waters Xbridge BEH C18 250*50 mm*10 um; mobile phase: [water (0.05% ammonia hydroxide v/v)-ACN]; B %: 12%-42%, 20 min). to give the title compound (300 mg, 32% yield) as a white solid.

Step 6: 2-(6-Chloro-1-((1-(methylsulfonyl)azetidin-3-yl)oxy)-2,7-naphthyridin-4-yl)propan-2-ol To a solution of 2-(1-(azetidin-3-yloxy)-6-chloro-2,7-naphthyridin-4-yl)propan-2-ol (50 mg, 170 umol) and triethylamine (51.7 mg, 511 umol, 71.1 uL) in DCM (5 mL) was added MsCl (21.5 mg, 187 umol, 14.5 uL). The reaction mixture was stirred at 25° C. for 2 h, then was quenched by addition of water (20 mL). The mixture was extracted with EA (20 mL×3), and the combined organic layers were dried over anhydrous sodium sulfate, filtered and concentrated to give a residue. The residue was purified by prep-TLC (PE/EA=0:1) to give the title compound (40 mg, 61% yield) as a white solid.

Step 7: 4-(2-Azidopropan-2-yl)-6-chloro-1-((1-(methylsulfonyl)azetidin-3-yl)oxy)-2,7-naphthyridine To a solution of 2-(6-chloro-1-((1-(methylsulfonyl)azetidin-3-yl)oxy)-2,7-naphthyridin-4-yl)propan-2-ol (150 mg, 403 umol) in DCM (5 mL) was added $TMSN_3$ (265 uL, 2.02 mmol) and $InBr_3$ (172 mg). The mixture was stirred at 20° C. for 1 h, then water (20 mL) was added and the pH was adjusted to 8-9 by addition of saturated sodium bicarbonate solution. The mixture was extracted with DCM (20 mL×3) and the combined organic layers were washed with water (30 mL×3), dried over anhydrous sodium sulfate, filtered, and concentrated to give a residue. The residue was purified by column chromatography ($SiO_2$, PE/EA=1/1 to 0/1) to give the title compound (120 mg, 75% yield) as a white solid. MS (ES+) $C_{15}H_{17}ClN_6O_3S$ requires: 396, found: 397[M+H]$^+$.

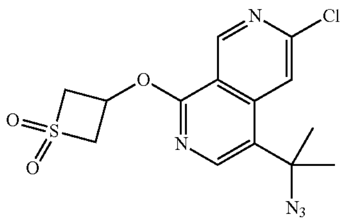 [SMILES: CC(C)(N=[N+]=[N-])c1cnc(OC2CS(=O)(=O)C2)c2cnc(Cl)cc12]

Intermediate 21: 3-((4-(2-Azidopropan-2-yl)-6-chloro-2,7-naphthyridin-1-yl)oxy)thietane 1,1-dioxide

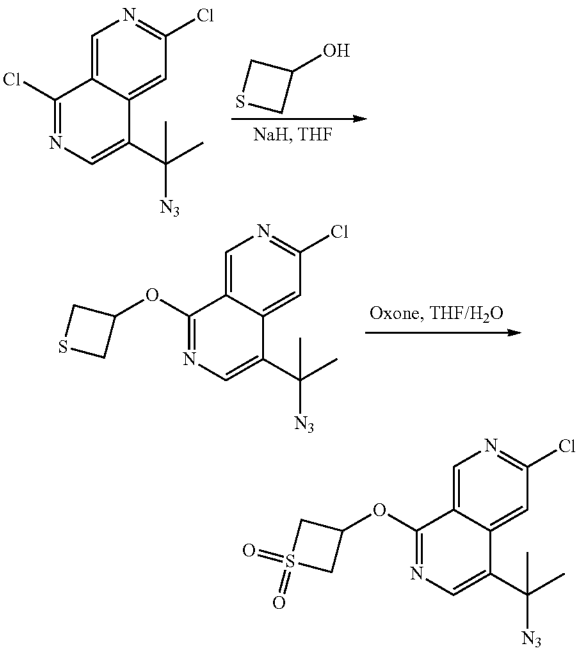

Step 1: 4-(2-Azidopropan-2-yl)-6-chloro-1-(thietan-3-yloxy)-2,7-naphthyridine

To a solution of thietan-3-ol (17.6 mg, 195 umol) in THF (1 mL) was added NaH (10.6 mg, 266 umol, 60% purity). The mixture was stirred for 10 min, then 4-(2-azidopropan-2-yl)-1,6-dichloro-2,7-naphthyridine (Intermediate 17, 50 mg, 177 umol) was added and the mixture was stirred at 20° C. for 50 min. The reaction mixture was quenched by addition of saturated aqueous ammonium chloride (2 mL) and extracted with EA (10 mL). The organic layer was dried over anhydrous sodium sulfate, filtered, and concentrated to give the title compound (59 mg, 99% yield) as a white solid.

Step 2: 3-((4-(2-Azidopropan-2-yl)-6-chloro-2,7-naphthyridin-1-yl)oxy)thietane 1,1-dioxide To a solution 4-(2-azidopropan-2-yl)-6-chloro-1-(thietan-3-yloxy)-2,7-naphthyridine (59.0 mg, 176 umol) in THF (0.9 mL) and water (0.3 mL) was added Oxone (216 mg, 351 umol). The mixture was stirred at 20° C. for 1 h, then was quenched by addition of saturated aqueous sodium sulfite (10 mL) and extracted with EA (30 mL). The organic layer was dried over anhydrous sodium sulfate, filtered, and concentrated to give the title compound (60 mg, 93% yield) as a white solid. $^{1}$H-NMR (400 MHz, $CDCl_3$): δ ppm 9.47 (s, 1H), 8.41 (s, 1H), 8.17 (s, 1H), 5.72 (tt, J=4.0, 7.8 Hz, 1H), 4.81-4.70 (m, 2H), 4.45 (dd, J=3.8, 15.6 Hz, 2H), 1.82 (s, 6H).

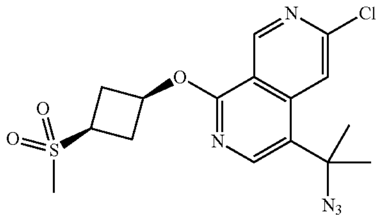 [SMILES: CC(C)(N=[N+]=[N-])c1cnc(O[C@H]2C[C@@H](S(C)(=O)=O)C2)c2cnc(Cl)cc12]

Intermediate 22: 4-(2-Azidopropan-2-yl)-6-chloro-1-(cis-3-(methylsulfonyl)cyclobutoxy)-2,7-naphthyridine

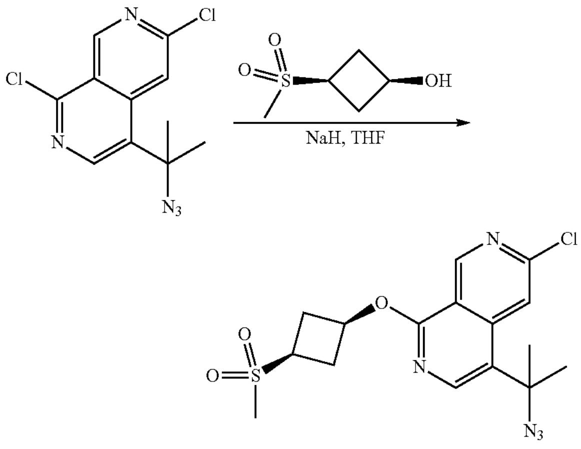

Step 1: 4-(2-Azidopropan-2-yl)-6-chloro-1-(cis-3-(methylsulfonyl)cyclobutoxy)-2,7-naphthyridine To a solution of cis-3-(methylsulfonyl)cyclobutan-1-ol (5.70 g, 37.9 mmol) in THF (260 mL) was added NaH (1.97 g, 49.3 mmol, 60% purity) at 0° C. The mixture was stirred for 0.5 h, then 4-(2-azidopropan-2-yl)-1,6-dichloro-2,7-naphthyridine (10.7 g, 37.9 mmol) was added and the reaction mixture was stirred at 25° C. for 0.5 h. The reaction mixture was quenched by addition of water (200 mL) and extracted with EA (200 mL×3). The combined organic layers were dried over anhydrous sodium sulfate, filtered, and concentrated to give the title compound (16 g, crude) as a white solid that was used in the next step without further purification. MS (ES+) $C_{16}H_{18}ClN_5O_3S$ requires: 395, found: 396[M+H]$^+$.

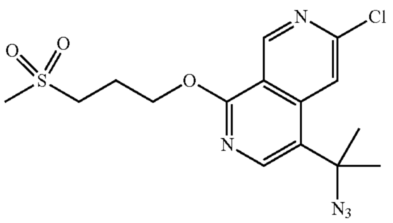 [SMILES: CC(C)(N=[N+]=[N-])c1cnc(OCCCS(C)(=O)=O)c2cnc(Cl)cc12]

Intermediate 23: 4-(2-Azidopropan-2-yl)-6-chloro-1-(3-(methylsulfonyl)propoxy)-2,7-naphthyridine

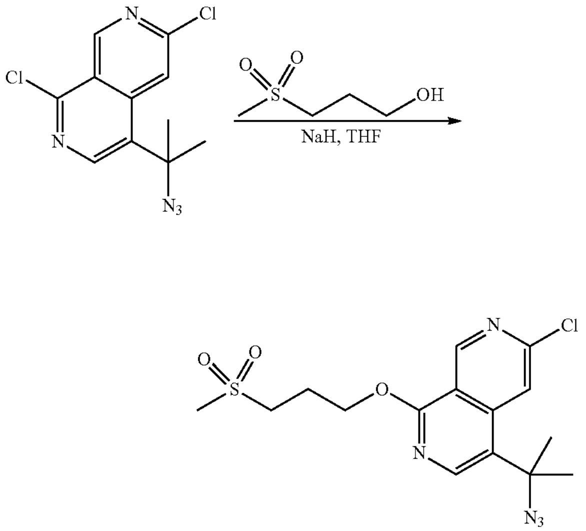

Step 1: 4-(2-Azidopropan-2-yl)-6-chloro-1-(3-(methylsulfonyl)propoxy)-2,7-naphthyridine The title compound was prepared from 4-(2-azidopropan-2-yl)-1,6-dichloro-2,7-naphthyridine and 3-(methylsulfonyl)propan-1-ol using a similar procedure as described above for Intermediate 22. MS (ES+) $C_{15}H_{18}ClN_5O_3S$ requires: 383, found: 384[M+H]$^+$.

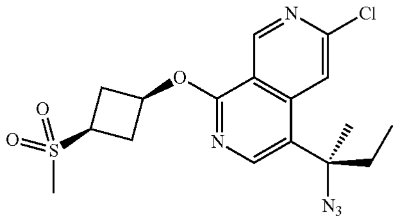 [SMILES: CC[C@@](C)(N=[N+]=[N-])c1cnc(O[C@H]2C[C@@H](S(C)(=O)=O)C2)c2cnc(Cl)cc12]

Intermediate 24: 4—((R)-2-azidobutan-2-yl)-6-chloro-1-((1s,3S)-3-(methylsulfonyl)cyclobutoxy)-2,7-naphthyridine

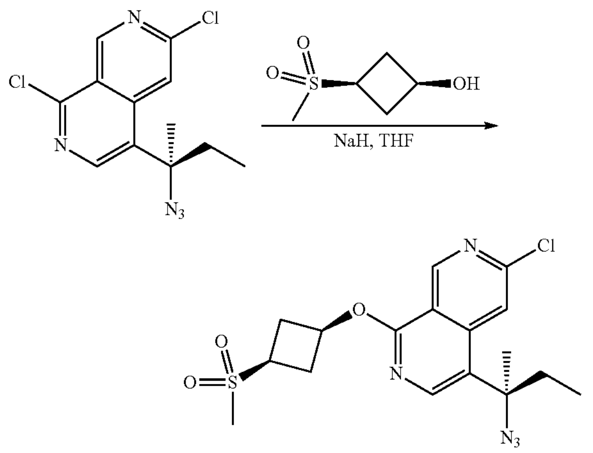

The title compound was prepared from (R)-4-(2-azidobutan-2-yl)-1,6-dichloro-2,7-naphthyridine (Intermediate 19) and cis-3-(methylsulfonyl)cyclobutan-1-ol using a similar procedure as described above for Intermediate 22. MS (ES+) $C_{17}H_{20}ClN_5O_3S$ requires: 409, found: 410[M+H]$^+$.

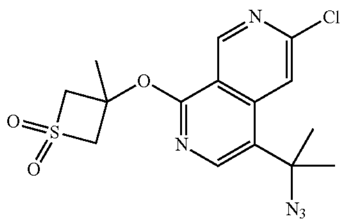 [SMILES: CC1(Oc2ncc(C(C)(C)N=[N+]=[N-])c3cc(Cl)ncc23)CS(=O)(=O)C1]

Intermediate 25: 3-((4-(2-Azidopropan-2-yl)-6-chloro-2,7-naphthyridin-1-yl)oxy)-3-methylthietane 1,1-dioxide

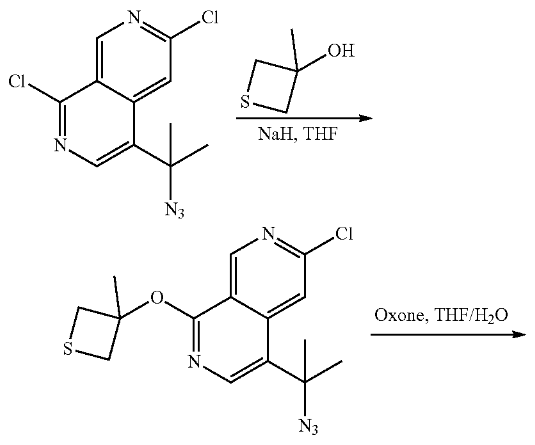

-continued

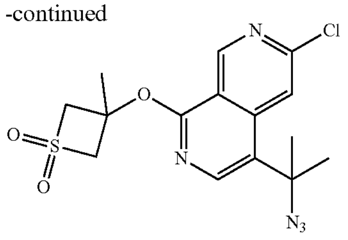

Steps 1-2: 3-((4-(2-Azidopropan-2-yl)-6-chloro-2,7-naphthyridin-1-yl)oxy)-3-methylthietane 1,1-dioxide The title compound was prepared from 4-(2-azidopropan-2-yl)-1,6-dichloro-2,7-naphthyridine and 3-methylthietane-3-ol using a similar procedure as described in Steps 1-2 of Intermediate 21. MS (ES+) $C_{15}H_{16}ClN_5O_3S$ requires: 381, found: 382[M+H]$^+$.

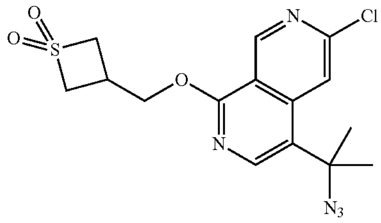 [SMILES: CC(C)(N=[N+]=[N-])c1cnc(OCC2CS(=O)(=O)C2)c2cnc(Cl)cc12]

Intermediate 26: 3-(((4-(2-Azidopropan-2-yl)-6-chloro-2,7-naphthyridin-1-yl)oxy)methyl)thietane 1,1-dioxide

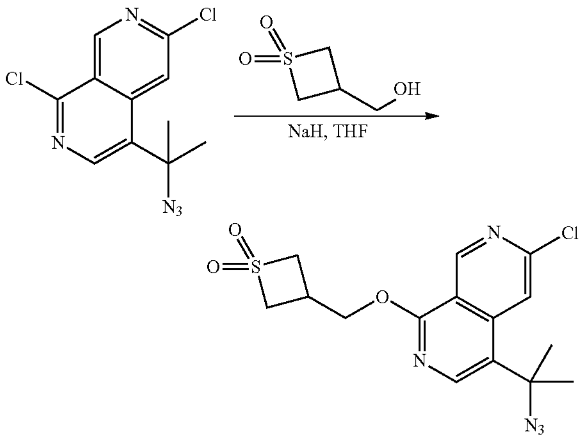

Step 1: 3-(((4-(2-Azidopropan-2-yl)-6-chloro-2,7-naphthyridin-1-yl)oxy)methyl)thietane 1,1-dioxide The title compound was prepared from 4-(2-azidopropan-2-yl)-1,6-dichloro-2,7-naphthyridine and 3-(hydroxymethyl)thietane 1,1-dioxide using a similar procedure as described above for Intermediate 22. MS (ES+) $C_{15}H_{16}ClN_5O_3S$ requires: 381, found: 382[M+H]$^+$.

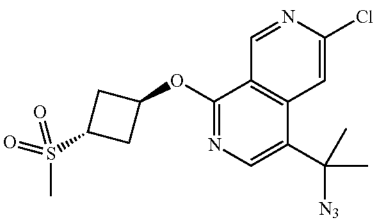 [SMILES: CC(C)(N=[N+]=[N-])c1cnc(O[C@H]2C[C@H](S(C)(=O)=O)C2)c2cnc(Cl)cc12]

Intermediate 27: 4-(2-Azidopropan-2-yl)-6-chloro-1-(trans-3-(methylsulfonyl)cyclobutoxy)-2,7-naphthyridine

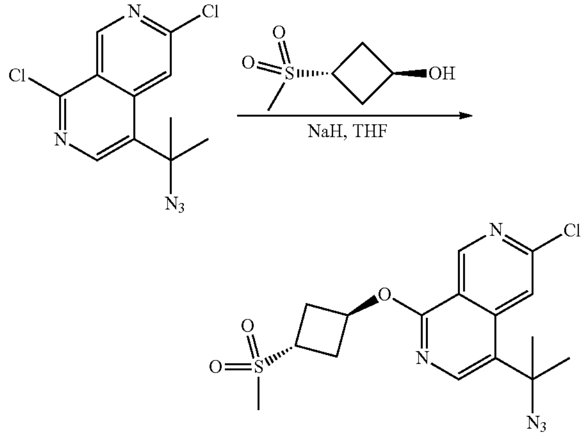

Step 1: 4-(2-Azidopropan-2-yl)-6-chloro-1-(trans-3-(methylsulfonyl)cyclobutoxy)-2,7-naphthyridine The title compound was prepared from 4-(2-azidopropan-2-yl)-1,6-dichloro-2,7-naphthyridine and trans-3-(methylsulfonyl)cyclobutan-1-ol using a similar procedure as described above for Intermediate 22. MS (ES+) $C_{16}H_{18}ClN_5O_3S$ requires: 395, found: 396[M+H]$^+$.

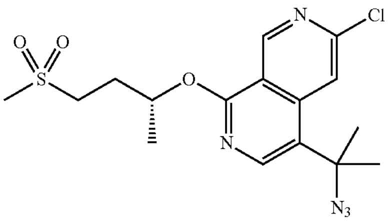

and

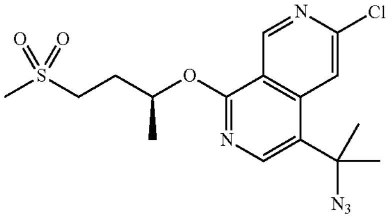

Intermediates 28 and 29: (R)-4-(2-Azidopropan-2-yl)-6-chloro-1-((4-(methylsulfonyl)butan-2-yl)oxy)-2,7-naphthyridine and (S)-4-(2-azidopropan-2-yl)-6-chloro-1-((4-(methylsulfonyl)butan-2-yl)oxy)-2,7-naphthyridine

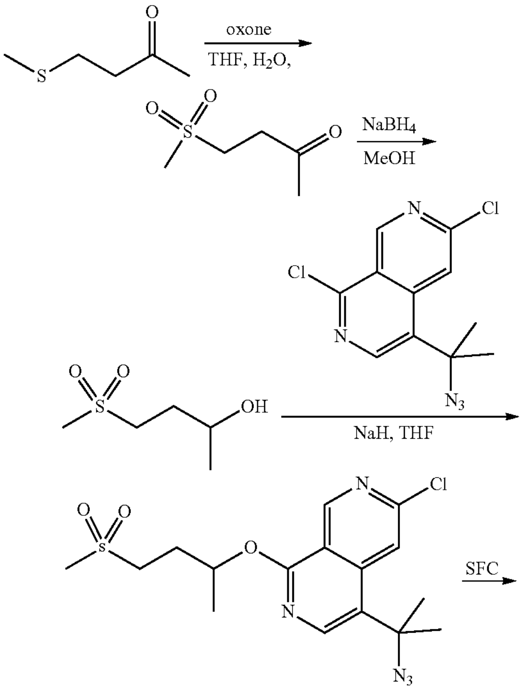

Intermediate 28 and Intermediate 29 each of which is represented by one of the structures shown below:

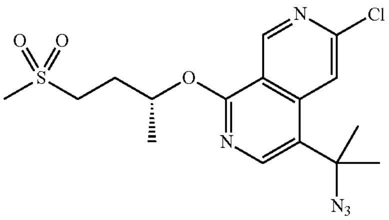

and

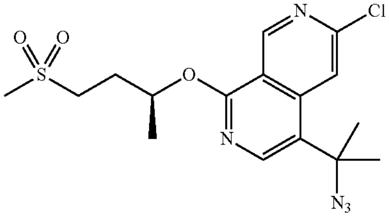

Step 1: 4-(Methylsulfonyl)butan-2-one

To the solution of 4-(methylthio)butan-2-one (2.00 g, 16.9 mmol) in THF (100 mL) and water (20 mL) was added Oxone® (10.4 g, 16.9 mmol). The reaction mixture was stirred for 2 h at 25° C., then was quenched with water (30 mL) and adjusted to pH=8 by addition of saturated aqueous sodium carbonate solution (20 mL) and extracted with EA (30 mL×3). The combined organic layers were washed with a saturated solution of sodium thiosulfate (30 mL) and brine. The organic layer was dried over sodium sulfate, filtered, and concentrated to give a residue. The residue was purified by column chromatography ($SiO_2$, PE/EA=3:1 to 0:1) to give the title compound (0.80 g, 31% yield) as white solid.

Step 2: 4-(Methylsulfonyl)butan-2-ol

To a solution of 4-(methylsulfonyl)butan-2-one (400 mg, 2.66 mmol) in methanol (10 mL) was added $NaBH_4$ (202 mg, 5.33 mmol) in portions. The mixture was stirred for 0.5 h at 25° C., then was poured into water (40 mL) and extracted with EA (50 mL). The organic layer was dried over sodium sulfate, filtered, and concentrated to give a residue. The residue was purified by column chromatography ($SiO_2$, PE/EA=0:1) to give the title compound (300 mg, 74% yield) as yellow gum.

Step 3: 4-(2-Azidopropan-2-yl)-6-chloro-1-((4-(methylsulfonyl)butan-2-yl)oxy)-2,7-naphthyridine The title compound was prepared from 4-(2-azidopropan-2-yl)-1,6-dichloro-2,7-naphthyridine and 4-(methylsulfonyl)butan-2-ol using a similar procedure as described above for Intermediate 22. MS (ES+) $C_{16}H_{20}ClN_5O_3S$ requires: 397, found: 398[M+H]$^+$.

Step 4: (R)-4-(2-Azidopropan-2-yl)-6-chloro-1-((4-(methylsulfonyl)butan-2-yl)oxy)-2,7-naphthyridine and (S)-4-(2-azidopropan-2-yl)-6-chloro-1-((4-(methylsulfonyl)butan-2-yl)oxy)-2,7-naphthyridine 4-(2-Azidopropan-2-yl)-6-chloro-1-((4-(methylsulfonyl)butan-2-yl)oxy)-2,7-naphthyridine (330 mg, 829 umol) was separated by chiral SFC (column: Daicel Chiralpak AD (250 mm*30 mm, 10 um); mobile phase:[0.1% $NH_3H_2O$ IPA]; B %: 30%-30%) to give one of (R or S)-4-(2-azidopropan-2-yl)-6-chloro-1-((4-(methylsulfonyl)butan-2-yl)oxy)-2,7-naphthyridine (130 mg, 45% yield, yellow oil, Intermediate 28) as the first eluting isomer and the other one of (R or S)-4-(2-azidopropan-2-yl)-6-chloro-1-((4-(methylsulfonyl)butan-2-yl)oxy)-2,7-naphthyridine (130 mg, 39% yield, yellow oil, Intermediate 29) as the second eluting isomer. Intermediate 28: MS (ES+) $C_{16}H_{20}ClN_5O_3S$ requires: 397, found: 398[M+H]$^+$. Intermediate 29: MS (ES+) $C_{16}H_{20}ClN_5O_3S$ requires: 397, found: 398[M+H]$^+$.

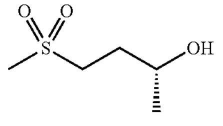

Intermediate 30: (R)-4-(methylsulfonyl)butan-2-ol

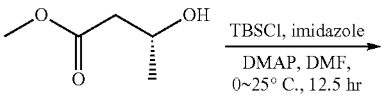

-continued

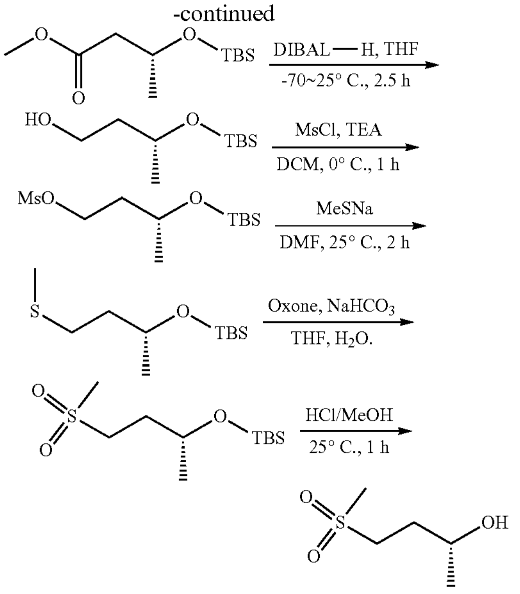

Step 1: Methyl (R)-3-((tert-butyldimethylsilyl)oxy)butanoate

To a mixture of methyl (R)-3-hydroxybutanoate (50 g, 423 mmol, 48.5 mL), imidazole (43.2 g, 635 mmol) and DMAP (25.9 g, 212 mmol) in DMF (1000 mL) was added TBSCl (67.0 g, 444 mmol) in portions at 0° C. The reaction mixture was stirred at 0° C. for 30 min, and then warmed to 25° C. and stirred for another 12 h. The reaction mixture was then diluted with $H_2O$ (300 mL) and EA (500 mL). The organic layer was washed with saturated aqueous $NH_4Cl$ (3×300 mL), dried over $Na_2SO_4$, filtered and concentrated to give a residue. The residue was purified by column chromatography (PE/EA=50/1) to give the title compound (91 g, 93% yield) as a colorless oil.

Step 2: (R)-3-((tert-Butyldimethylsilyl)oxy)butan-1-ol

A mixture of methyl (R)-3-((tert-butyldimethylsilyl)oxy)butanoate (45.5 g, 196 mmol) in THF (500 mL) was cooled to −70° C., then DIBAL (1 M in toluene, 450 mL) was added dropwise. The resulting mixture was stirred for 30 min at −70° C., then allowed to warm to 25° C. and stirred for another 2 h. The reaction mixture was added into a stirring solution of NaOH (58.7 g, 1.47 mol) in $H_2O$ (300 mL), and filtered to remove the solids. The filtrate was washed with brine (3×300 mL), saturated aqueous $Na_2SO_3$ (200 mL), dried over $Na_2SO_4$, filtered and concentrated to give the title compound (40 g, crude) as a colorless oil, which was used directly for next step without further purification.

Step 3: (R)-3-((tert-Butyldimethylsilyl)oxy)butyl methanesulfonate

To a mixture of (R)-3-((tert-butyldimethylsilyl)oxy)butan-1-ol (80 g, 391 mmol) and TEA (70.5 g, 697 mmol) in DCM (500 mL) was added MsCl (61.0 g, 532 mmol) at 0° C. The reaction mixture was stirred at 0° C. for 1 h, then was diluted with $H_2O$ (100 mL). The organic layer was washed with the saturated aqueous $NH_4Cl$ (3×300 mL). The organic layer was dried over $Na_2SO_4$, filtered and concentrated to give the title compound (110 g, crude) as colorless oil.

Step 4: (R)-tert-Butyldimethyl((4-(methylthio)butan-2-yl)oxy)silane

A mixture of sodium thiomethoxide (54.6 g, 779 mmol), (R)-3-((tert-butyldimethylsilyl)oxy)butyl methanesulfonate (110 g, 389 mmol) in DMF (500 mL) was stirred at 25° C. for 2 h. The reaction mixture then was diluted with EA (500 mL), the organic layer was washed with brine (3×300 mL), and concentrated to give the title compound (82.6 g, 90% yield) as a colorless oil, which was used directly for next step without further purification.

Step 5: (R)-tert-Butyldimethyl((4-(methylsulfonyl)butan-2-yl)oxy)silane

To a mixture of (R)-tert-butyldimethyl((4-(methylthio)butan-2-yl)oxy)silane (77.6 g, 331 mmol) and $NaHCO_3$ (222 g, 2.65 mol) in THF (1000 mL) and $H_2O$ (200 mL) was added Oxone® (509 g, 827 mmol) by portions. The mixture was stirred at 25° C. for 3 h. The reaction mixture was filtered, the organic layer of the filtrate was washed with the saturated aqueous $Na_2SO_3$ (3×300 mL), dried over $Na_2SO_4$, filtered, and concentrated to give 81 g of the crude product, which contained 60% of the corresponding sulfoxide. Half of the crude product (42 g) and $NaHCO_3$ (113 g, 1.34 mol) were re-dissolved in THF (1000 mL) and $H_2O$ (500 mL), and then Oxone (206 g, 335 mmol) was added by portions. The mixture was stirred at 25° C. for 2 h, then was filtered. The organic layer of the filtrate was washed with the saturated aqueous $Na_2SO_3$ (500 mL), dried over $Na_2SO_4$, filtered and concentrated in vacuo to give title compound (44.6 g, 99.8% yield) as a colorless oil, which was used directly in the next step without further purification.

Step 6: (R)-4-(Methylsulfonyl)butan-2-ol (R)-tert-Butyldimethyl((4-(methylsulfonyl)butan-2-yl)oxy)silane (44.6 g, 167 mmol) was added to HCl/MeOH (4 M, 178 mL) at 25° C. The mixture was stirred at 25° C. for 1 h, then was filtered and concentrated to give a residue. The residue was purified by column chromatography (PE/EA=5/1, and then MeOH) to give the title compound (18.7 g, 73% yield) as a yellow semisolid. $^1$H NMR (400 MHz, $CD_3Cl$): δ ppm 4.08-3.95 (m, 1H), 3.25-3.10 (m, 2H), 2.94 (s, 3H), 2.30 (br s, 1H), 2.06-1.87 (m, 2H), 1.27 (d, J=6.0 Hz, 3H).

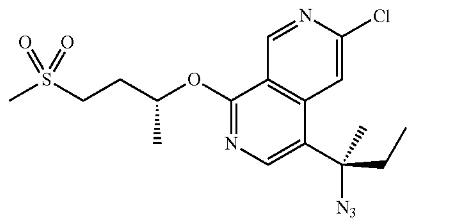 [SMILES: CC[C@@](C)(N=[N+]=[N-])c1cnc(O[C@H](C)CCS(C)(=O)=O)c2cnc(Cl)cc12]

Intermediate 31: 4—((R)-2-Azidobutan-2-yl)-6-chloro-1-(((R)-4-(methylsulfonyl)butan-2-yl)oxy)-2,7-naphthyridine

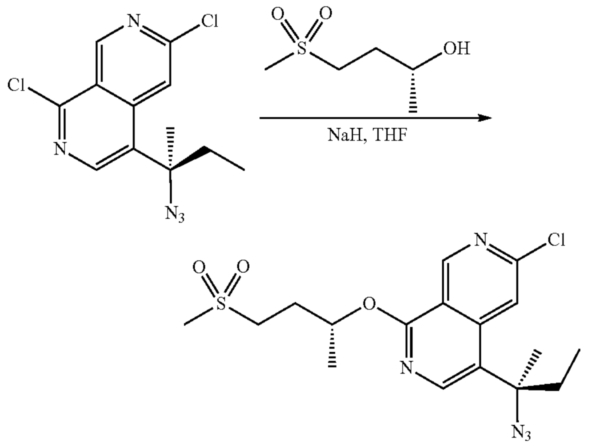

Step 1: To a mixture of (R)-4-(methylsulfonyl)butan-2-ol (15.37 g, 101 mmol) in THF (300 mL) was added NaH (7.14 g, 179 mmol, 60% purity) at 25° C. The mixture was stirred for 1 h, then (R)-4-(2-Azidobutan-2-yl)-1,6-dichloro-2,7-naphthyridine (23 g, 77.7 mmol) in THF (150 mL) was added. The reaction mixture was stirred at 25° C. for 1.5 h, then was poured into saturated aqueous $NH_4Cl$ solution (500 mL). The mixture was extracted with EA (500 mL), and the organic layer was dried over $Na_2SO_4$, filtered, and concentrated to give the title compound (31 g, 93% yield) as yellow oil. $^1$H NMR (400 MHz, $CDCl_3$): δ ppm 9.41 (s, 1H), 8.37 (s, 1H), 8.13 (s, 1H), 5.71-5.64 (m, 1H), 3.26-3.16 (m, 2H), 2.95 (s, 3H), 2.40-2.36 (m, 2H), 2.10-2.05 (m, 1H), 1.97-1.80 (m, 4H), 1.52 (d, J=6.0 Hz, 3H), 0.90-0.85 (m, 3H).

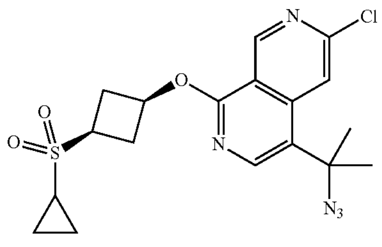 [SMILES: CC(C)(N=[N+]=[N-])c1cnc(O[C@H]2C[C@@H](S(=O)(=O)C3CC3)C2)c2cnc(Cl)cc12]

Intermediate 32: 4-(2-Azidopropan-2-yl)-6-chloro-1-(cis-3-(cyclopropylsulfonyl)cyclobutoxy)-2,7-naphthyridine

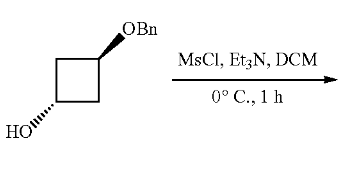

-continued

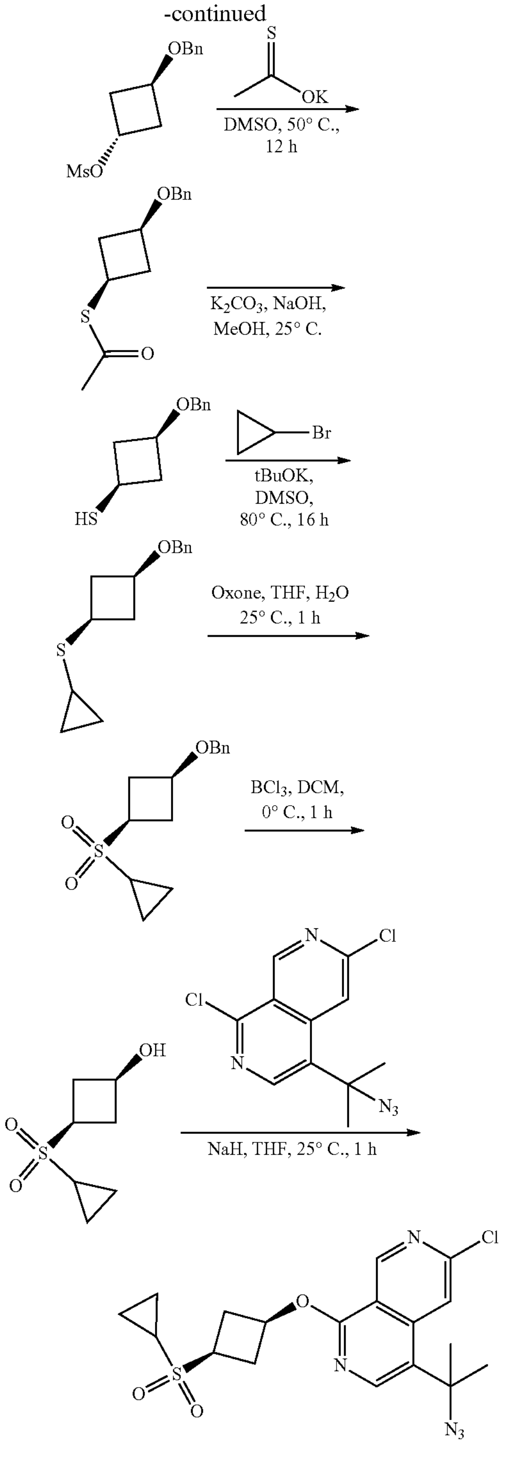

Step 1: trans-3-(Benzyloxy)cyclobutyl Methanesulfonate

To a solution of trans-3-(benzyloxy)cyclobutan-1-ol (1.9 g, 10.7 mmol) and $NEt_3$ (3.24 g, 32.0 mmol) in DCM (38 mL) was added MsCl (2.44 g, 21.3 mmol) at 0° C. The reaction mixture was stirred at 0° C. for 1 h, then was diluted with water (40 mL) and extracted with DCM (40 mL×3). The combined organic layers were dried over anhydrous sodium sulfate, filtered, and concentrated to give the title compound (2.9 g, crude) as yellow oil that was used in the next step without further purification.

Step 2: S-trans-3-(Benzyloxy)cyclobutyl) ethanethioate

A solution of trans-3-(benzyloxy)cyclobutyl methanesulfonate (1.5 g, 5.85 mmol) and potassium ethanethioate (802 mg, 7.02 mmol) in DMSO (12 mL) was stirred at 50° C. for 12 h. The reaction mixture was diluted with water (40 mL) and extracted with PE (40 mL×3). The combined organic layers were dried over anhydrous sodium sulfate, filtered, and concentrated to give the title compound (890 mg, 64% yield) as a white oil that was used in the next step without further purification. MS (ES+) $C_{13}H_{16}O_2S$ requires: 236, found: 237[M+H]$^+$.

Step 3: cis-3-(Benzyloxy)cyclobutane-1-thiol

To a solution of S-trans-3-(benzyloxy)cyclobutyl) ethanethioate (840 mg, 3.55 mmol) in methanol (20 mL) was added $K_2CO_3$ (1.47 g, 10.7 mmol). The reaction mixture was stirred at 70° C. for 1 h, then NaOH (284 mg, 7.11 mmol) was added and the mixture was stirred at 70° C. for an additional 2 h. The reaction mixture was diluted with water (40 mL) and was extracted with EA (40 mL×3). The combined organic layers were dried over anhydrous sodium sulfate, filtered, and concentrated to give a residue. The residue was purified by column chromatography ($SiO_2$, PE/EA=1/0 to 10/1) to give the title compound (500 mg, 72% yield) as a white oil.

Step 4: cis-3-(Benzyloxy)cyclobutyl)(cyclopropyl)sulfane

To a solution of cis-3-(benzyloxy)cyclobutane-1-thiol (250 mg, 1.29 mmol) in DMSO (6 mL) was added potassium tert-butoxide (173 mg, 1.54 mmol) and bromocyclopropane (202 mg, 1.67 mmol, 134 uL). The reaction mixture was at 80° C. for 2 h, then was diluted with water (15 mL) and extracted with EA (15 mL×4). The combined organic layers were washed with brine (15 mL×3), dried over anhydrous sodium sulfate, filtered, and concentrated to give a residue. The residue was purified by column chromatography ($SiO_2$, PE/EA=1/0 to 10/1) to give the title compound (120 mg, 40% yield) as a yellow oil. MS (ES+) $C_{14}H_{18}OS$ requires: 234, found: 235[M+H]$^+$.

Step 5: ((cis-3-(Cyclopropylsulfonyl)cyclobutoxy) methyl)benzene

To a solution of cis-3-(benzyloxy)cyclobutyl)(cyclopropyl)sulfane (120 mg, 512 umol) in THF (9 mL) and water (3 mL) was added Oxone® (629 mg, 1.02 mmol). The reaction mixture was stirred at 25° C. for 1 h, then was quenched by addition of saturated aqueous sodium sulfite (40 mL). The reaction mixture was diluted with water (20 mL) and extracted with EA (60 mL×3). The combined organic layers were dried over anhydrous sodium sulfate, filtered, and concentrated to the title compound (120 mg, 88% yield) as a white oil that was used in the next step without further purification.

Step 6: cis-3-(Cyclopropylsulfonyl)cyclobutan-1-ol

To a solution of ((cis-3-(cyclopropylsulfonyl)cyclobutoxy)methyl)benzene (100 mg, 375 umol) in DCM (4 mL)

was added a solution of $BCl_3$ (1 M, 2 mL) at 0° C. The reaction mixture was stirred at 0° C. for 1 h, then was quenched by addition of methanol (40 mL), dried over anhydrous sodium sulfate, filtered, and concentrated to give a residue. The residue was purified by column chromatography ($SiO_2$, PE/EA=1/0 to 0/1) to give the title compound (65 mg, 98% yield) as a white oil. MS (ES+) $C_7H_{12}O_3S$ requires: 176, found: 177[M+H]$^+$.

Step 7: 4-(2-Azidopropan-2-yl)-6-chloro-1-(cis-3-(cyclopropylsulfonyl)cyclobutoxy)-2,7-naphthyridine The title compound was prepared from 4-(2-azidopropan-2-yl)-1,6-dichloro-2,7-naphthyridine and cis-3-(cyclopropylsulfonyl)cyclobutan-1-ol using a similar procedure as described above for Intermediate 22. MS (ES+) $C18H_{20}ClN_5O_3S$ requires: 421, found: 422[M+H]$^+$.

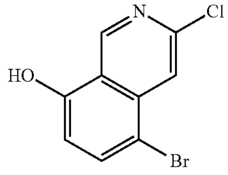 [SMILES: Oc1ccc(Br)c2cc(Cl)ncc12]

Intermediate 33: 5-Bromo-3-chloroisoquinolin-8-ol

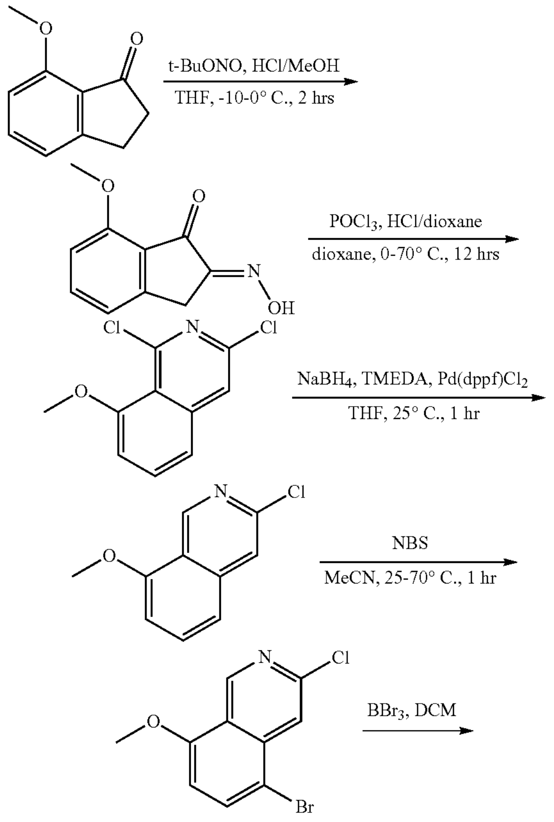

-continued

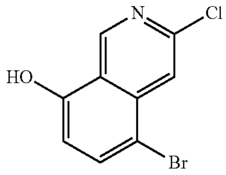

Step 1: (E)-2-(Hydroxyimino)-7-methoxy-2,3-dihydro-1H-inden-1-one t-BuONO (67.9 g, 659 mmol, 78.4 mL, 1.10 eq) was added to a solution of 7-methoxy-2,3-dihydro-1H-inden-1-one (99.0 g, 599 mmol, 1.00 eq) in THF (500 mL) at −10-0° C., followed by dropwise addition of HCl (4 M in MeOH, 15.0 mL, 0.10 eq) to the mixture at −10-0° C. The reaction mixture was stirred at 0° C. for 2 h, then was concentrated to give a residue. The residue was slurried in PE/EA=20:1 (200 mL) and filtered to give the title compound (107 g, 87% yield) as yellow solid. MS (ES+) $C_{10}H_9NO_3$ requires: 191, found: 192[M+H]$^+$.

Step 2: 1,3-Dichloro-8-methoxyisoquinoline

To a solution of (E)-2-(hydroxyimino)-7-methoxy-2,3-dihydro-1H-inden-1-one (107 g, 522 mmol, 1.00 eq) in dioxane (500 mL) was added $POCl_3$ (126 g, 827 mmol, 76.9 mL, 1.59 eq) and HCl (4 M in dioxane, 1.31 mL, 0.01 eq) at 0-10° C. The reaction mixture was stirred at 70° C. for 12 h, then was cooled to 25° C. and quenched with water (2.00 L). The quenched mixture was extracted with DCM (500 mL×4) and the organic layers were washed with brine (500 mL×2), dried over $Na_2SO_4$, filtered and concentrated to give a residue. The residue was purified by column chromatography ($SiO_2$, PE/EA=20/1 to 10/1) to give the title compound (48.8 g, 40.9% yield) as light yellow solid. MS (ES+) $C_{10}H_7Cl_2NO$ requires: 227, found: 228[M+H]$^+$.

Step 3: 3-Chloro-8-methoxyisoquinoline

To a solution of 1,3-dichloro-8-methoxyisoquinoline (48.8 g, 213 mmol, 1.00 eq) in THF (250 mL) was added TMEDA (37.3 g, 320 mmol, 48.4 mL, 1.50 eq) and Pd(dppf)$Cl_2$ (1.57 g, 2.14 mmol, 0.01 eq) at 25° C. Then $NaBH_4$ (17.2 g, 456 mmol, 2.13 eq) was slowly added to the reaction mixture and the reaction mixture was stirred at 25° C. for 1 h. The reaction mixture was poured into 1N HCl (1.00 L), extracted with EA (200 mL×3). The combined organic layers were filtered through Celite® and the filtrate was washed with brine (500 mL), dried over $Na_2SO_4$, filtered and concentrated to give a residue. The residue was purified by column chromatography ($SiO_2$, PE/EA=20/1 to 5/1) to give the title compound (26.7 g, 64.3% yield) as a light yellow solid. MS (ES+) $C_{10}H_8ClNO$ requires: 193, found: 194[M+H]$^+$.

Step 4: 5-Bromo-3-chloro-8-methoxyisoquinoline

To a solution of 3-chloro-8-methoxyisoquinoline (26.7 g, 137 mmol, 1.00 eq) in MeCN (300 mL) was added NBS (29.3 g, 165 mmol, 1.20 eq) at 25° C. The reaction mixture was stirred at 70° C. for 1 h, then was cooled to 25° C. The mixture was filtered, and the filter cake was washed with MeCN (100 mL). The filter cake was collected and dried under vacuum. The filtrate was purified by column chromatography ($SiO_2$, PE/EA=1:0 to 1:1, Rf=0.45) to give the title compound (26.17 g, 69.6% yield) as an off-white solid. MS (ES+) $C_{10}H_7BrClNO$ requires: 273, found: 274$[M+H]^+$.

Step 5: 5-Bromo-3-chloroisoquinolin-8-ol

To a solution of 5-bromo-3-chloro-8-methoxyisoquinoline (3.00 g, 11.01 mmol) in DCM (50 mL) was added $BBr_3$ (13.8 g, 55.0 mmol) in one portion. The reaction mixture was stirred at 50° C. for 12 h, then was quenched with MeOH (15 mL) and concentrated to give a residue. The residue was purified by column chromatography (PE/EA=10:1 to 1:1) to give the title compound (2.5 g, 88% yield) as a yellow solid. $^1H$ NMR (400 MHz, 6d-DMSO): δ ppm 11.3 (s, 1H), 9.21 (s, 1H), 7.84 (d, J=8.4 Hz, 1H), 7.72 (s, 1H), 8.85 (d, J=8.4 Hz, 1H).

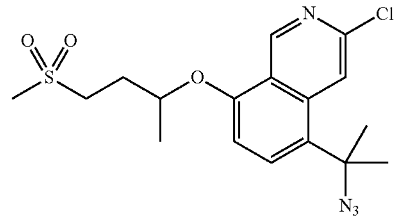 [SMILES: CC(CCS(C)(=O)=O)Oc1ccc(C(C)(C)N=[N+]=[N-])c2cc(Cl)ncc12]

Intermediate 34: 5-(2-Azidopropan-2-yl)-3-chloro-8-((4-(methylsulfonyl)butan-2-yl)oxy)isoquinoline

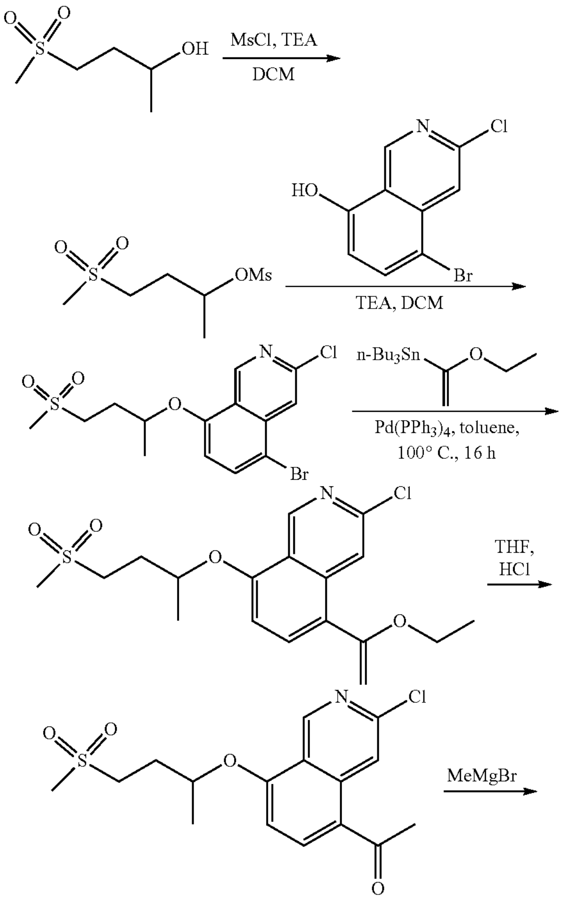

-continued

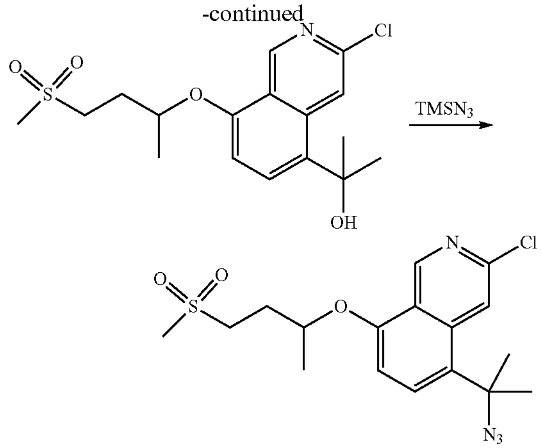

Step 1: 4-(Methylsulfonyl)butan-2-yl methanesulfonate

To a solution of 4-(methylsulfonyl)butan-2-ol (50 mg, 328 umol) in DCM (5 mL) was added TEA (99.7 mg, 985 umol) and MsCl (753 mg, 657 umol). The reaction mixture was stirred at 25° C. for 2 h, then was poured into water (20 mL) and extracted with DCM (20 mL×3). The organic layer was washed with water (20 mL×3) and concentrated to give the title compound (60.0 mg, 79% yield) as a yellow solid that was used in the next step without further purification.

Step 2: 5-Bromo-3-chloro-8-((4-(methylsulfonyl)butan-2-yl)oxy)isoquinoline

To a solution of compound 4-(methylsulfonyl)butan-2-yl methanesulfonate (400 mg, 1.55 mmol) in DMF (3 mL) was added $K_2CO_3$ (642 mg, 4.64 mmol) in one portion at 25° C., then 5-bromo-3-chloroisoquinolin-8-ol (Intermediate 33) (756 mg, 3.28 mmol) was added to the reaction mixture. The reaction mixture was stirred at 45° C. for 12 h, then was poured into water (20 mL) and extracted with DCM (20 mL×3). The combined organic layers were washed with water (20 mL×3) and concentrated to give a residue. The residue was purified by prep-TLC (PE/EA=1:1) to give the title compound (600 mg, 1.53 mmol, 99% yield) as a yellow solid.

Steps 3-6: 5-(2-Azidopropan-2-yl)-3-chloro-8-((4-(methylsulfonyl)butan-2-yl)oxy)isoquinoline The title compound was prepared using a similar four-step procedure as described in Steps 2-5 of Intermediate 17.

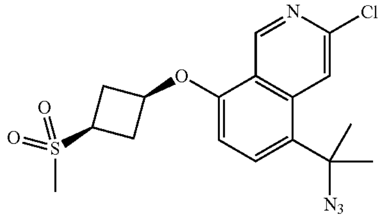

Intermediate 35: 5-(2-Azidopropan-2-yl)-3-chloro-8-(cis-3-(methylsulfonyl)cyclobutoxy)isoquinoline

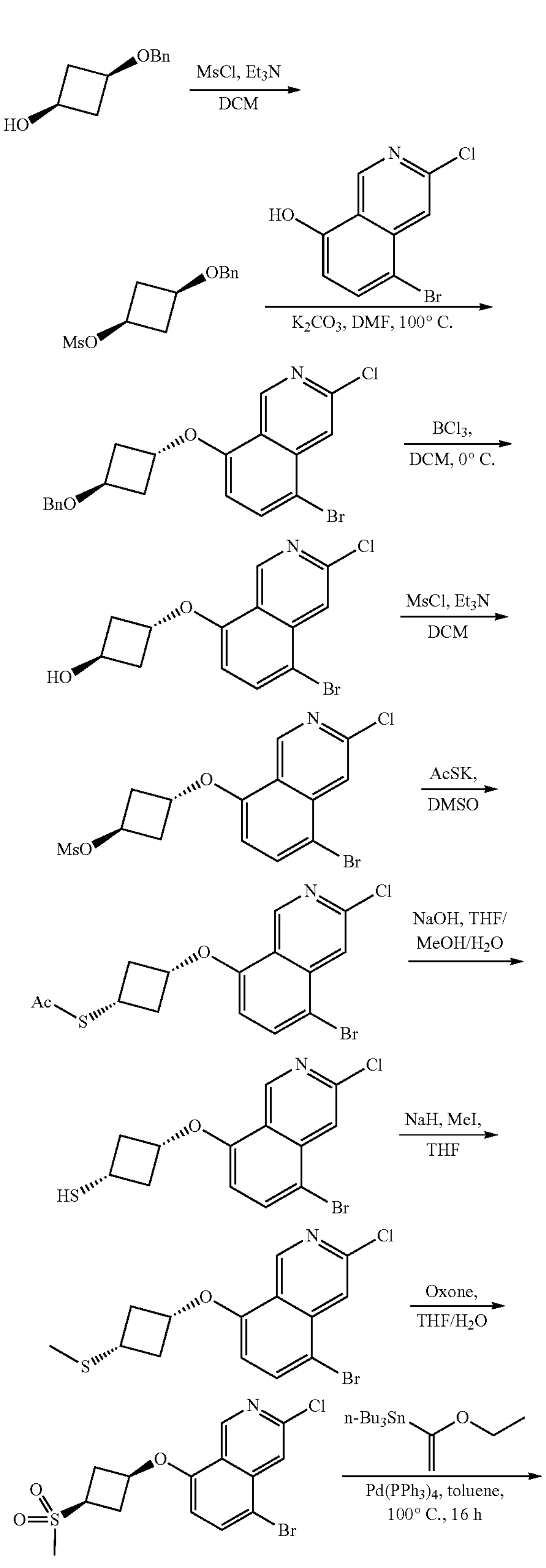

-continued

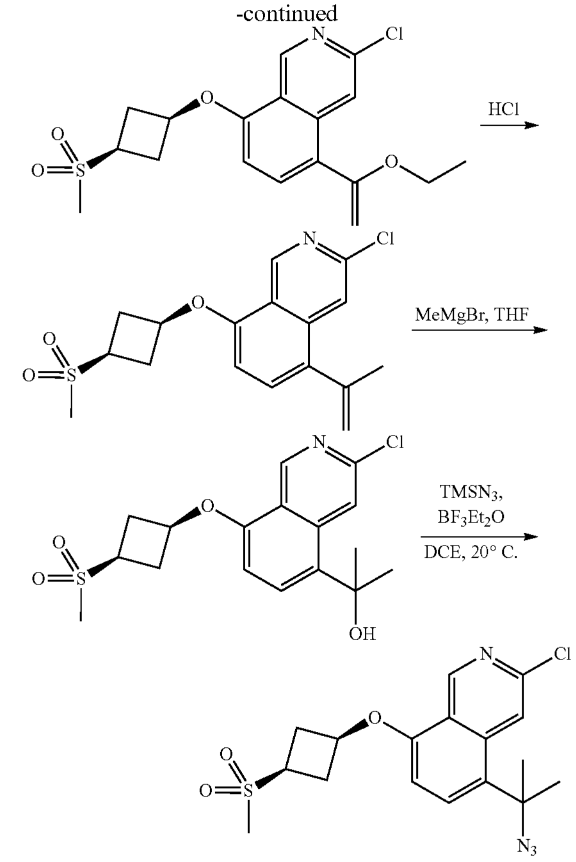

Step 1: cis-3-(Benzyloxy)cyclobutyl methanesulfonate

To a solution of 3-benzyloxycyclobutanol (2.5 g, 14.0 mmol) and TEA (4.26 g, 42.1 mmol) in DCM (25 mL) was added MsCl (2.41 g, 21.0 mmol) at 0° C. The reaction mixture was stirred at 25° C. for 1 h, then was poured into water (20 mL) and extracted with DCM (20 mL×2). The combined organic layers were washed with brine (40 mL×2), dried over anhydrous sodium sulfate, filtered, and concentrated to give the title compound (3.5 g, 97% yield) as a yellow solid.

Step 2: 8-(trans-3-(Benzyloxy)cyclobutoxy)-5-bromo-3-chloroisoquinoline

To a solution of 5-bromo-3-chloro-isoquinolin-8-ol (Intermediate 33)(2.3 g, 8.90 mmol) and cis-3-(benzyloxy)cyclobutyl methanesulfonate (3.5 g, 13.7 mmol) in DMF (20 mL) was added $K_2CO_3$ (2.46 g, 17.8 mmol) at 25° C. The reaction mixture was stirred at 100° C. for 6 h, then was diluted with water (50 mL) and extracted with EA (50 mL×3). The combined organic layers were washed with brine (80 mL×3), dried over anhydrous sodium sulfate, filtered, and concentrated. The residue was purified by column chromatography ($SiO_2$, PE/EA=40/1 to 6/1) to give the title compound (2.7 g, 72% yield) as a white solid. $^1$H-NMR (400 MHz, $CDCl_3$): δ ppm 9.40 (s, 1H), 7.97 (s, 1H), 7.83-7.79 (m, 1H), 7.41-7.28 (m, 5H), 6.55 (d, J=8.4 Hz, 1H), 5.10-5.01 (m, 1H), 4.53-4.47 (m, 2H), 4.46-4.38 (m, 1H), 3.00-2.32 (m, 4H).

Step 3: trans-3-((5-Bromo-3-chloroisoquinolin-8-yl)oxy)cyclobutan-1-ol

To a solution of 8-(trans-3-(benzyloxy)cyclobutoxy)-5-bromo-3-chloroisoquinoline (2.0 g, 4.78 mmol) in the DCM (30 mL) was added $BCl_3$ (1 M, 14.3 mL) at 0° C. The reaction mixture was stirred at 0° C. for 1 h, then was poured into saturated aqueous sodium bicarbonate (100 mL) and extracted with EA (2×200 mL). The combined organic layers were dried over anhydrous sodium sulfate, filtered, and concentrated to give the title compound (1.55 g, 99% yield) as a white solid.

Step 4: trans-3-((5-Bromo-3-chloroisoquinolin-8-yl)oxy)cyclobutyl methanesulfonate To a solution of trans-3-((5-bromo-3-chloroisoquinolin-8-yl)oxy)cyclobutan-1-ol (1.55 g, 4.72 mmol) in the DCM (30 mL) was added TEA (1.43 g, 14.2 mmol) and MsCl (810 mg, 7.08 mmol) at 0° C. The reaction mixture was stirred at 0° C. for 1 h, then was poured into water (50 mL) and extracted with DCM (2×100 mL). The combined organic layers were dried over anhydrous sodium sulfate, filtered and concentrated to give the title compound (1.9 g, 99% yield) as a white solid.

Step 5: S-(cis-3-((5-Bromo-3-chloroisoquinolin-8-yl)oxy)cyclobutyl) ethanethioate To a solution of trans-3-((5-bromo-3-chloroisoquinolin-8-yl)oxy)cyclobutyl methanesulfonate (1.9 g, 4.67 mmol) in the DMSO (30 mL) was added potassium ethanethioate (1.60 g, 14.0 mmol). The mixture was stirred at 100° C. for 2 h, then was poured into water (150 mL) and extracted with EA (3×150 mL). The combined organic layers were washed with brine, dried over anhydrous sodium sulfate, filtered, and concentrated. The residue was purified by column chromatography $SiO_2$ (PE/EA=50:1 to 20:1) to give the title compound (1.8 g, 99% yield) as a yellow solid.

Step 6: cis-3-((5-Bromo-3-chloroisoquinolin-8-yl)oxy)cyclobutane-1-thiol

To a solution of S-(cis-3-((5-bromo-3-chloroisoquinolin-8-yl)oxy)cyclobutyl) ethanethioate (1.80 g, 4.65 mmol) in the THF (20 mL), MeOH (10 mL) and water (10 mL) was added NaOH (931 mg, 23.3 mmol). The reaction mixture was stirred at 20° C. for 2 h, then was adjusted to pH=5-6 by addition of aqueous HCl (1 M). Then mixture was diluted with EA (100 mL) and washed with brine (50 mL). The organic layer was dried over anhydrous sodium sulfate, filtered, and concentrated to give the title compound (1.5 g, 93% yield) as a yellow solid.

Step 7: 5-Bromo-3-chloro-8-(cis-3-(methylthio)cyclobutoxy)isoquinoline

To a solution of cis-3-((5-bromo-3-chloroisoquinolin-8-yl)oxy)cyclobutane-1-thiol (400 mg, 1.16 mmol) in THF (8 mL) was added NaH (69.6 mg, 1.74 mmol, 60% purity) and methyl iodide (494 mg, 3.48 mmol). The reaction mixture was stirred at 20° C. for 1 h, then was quenched with water (20 mL) and extracted with DCM (2×50 mL). The combined organic layers were dried over anhydrous sodium sulfate, filtered and concentrated. The residue was purified by column chromatography $SiO_2$ (PE/EA=50:1 to 20:1) to give the title compound (400 mg, 96% yield) as a white solid.

Step 8: 5-Bromo-3-chloro-8-(cis-3-(methylsulfonyl)cyclobutoxy)isoquinoline

To a solution of 5-bromo-3-chloro-8-(cis-3-(methylthio)cyclobutoxy)isoquinoline (200 mg, 558 umol) in THF (3 mL) and water (1 mL) was added Oxone® (686 mg, 1.12 mmol). The reaction mixture was stirred at 20° C. for 1 h, then was quenched by addition of saturated aqueous sodium sulfite (5 mL) and extracted with DCM (2×20 mL). The combined organic layers were dried over anhydrous sodium sulfate, filtered and concentrated to give the title compound (210 mg, 96% yield) as a white solid.

Steps 9-12: 5-(2-Azidopropan-2-yl)-3-chloro-8-(cis-3-(methylsulfonyl)cyclobutoxy)isoquinoline The title compound was prepared using a similar four-step procedure as described in Steps 2-5 of Intermediate 17.

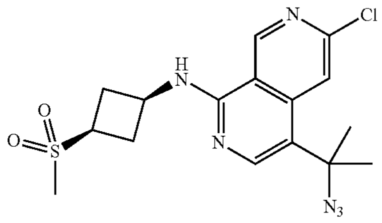 [SMILES: CC(C)(N=[N+]=[N-])c1cnc(N[C@H]2C[C@@H](S(C)(=O)=O)C2)c2cnc(Cl)cc12]

Intermediate 36: 4-(2-Azidopropan-2-yl)-6-chloro-N-(cis-3-(methylsulfonyl)cyclobutyl)-2,7-naphthyridin-1-amine

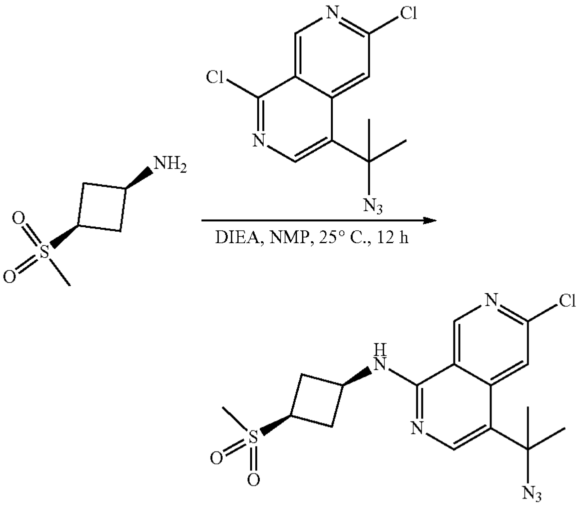

Step 1: 4-(2-Azidopropan-2-yl)-6-chloro-N-(cis-3-(methylsulfonyl)cyclobutyl)-2,7-naphthyridin-1-amine To a solution of 4-(2-azidopropan-2-yl)-1,6-dichloro-2,7-naphthyridine (100 mg, 354 umol) in NMP (2 mL) was added DIEA (68.7 mg, 532 umol, 92.6 uL) and cis-3-(methylsulfonyl)cyclobutan-1-amine (79.3 mg, 532 umol) at 25° C. The reaction mixture was stirred at 25° C. for 2 h, then was diluted with water (20 mL) and extracted with EA (30 mL×4). The combined organic layers were washed with brine (30 mL×3), dried over anhydrous sodium sulfate, filtered and concentrated to give a residue. The residue was purified by prep-TLC (PE/EA=1:1) to give the title compound (100 mg, 58% yield) as a yellow oil. MS (ES+) $C_{16}H_{19}ClN_6O_2S$ requires: 394, found: 395[M+H]+.

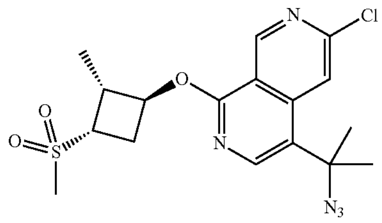

rac

Intermediate 37: 4-(2-Azidopropan-2-yl)-6-chloro-1-((1S,2R,3S and 1R,2S,3R)-2-methyl-3-(methylsulfonyl)cyclobutoxy)-2,7-naphthyridine

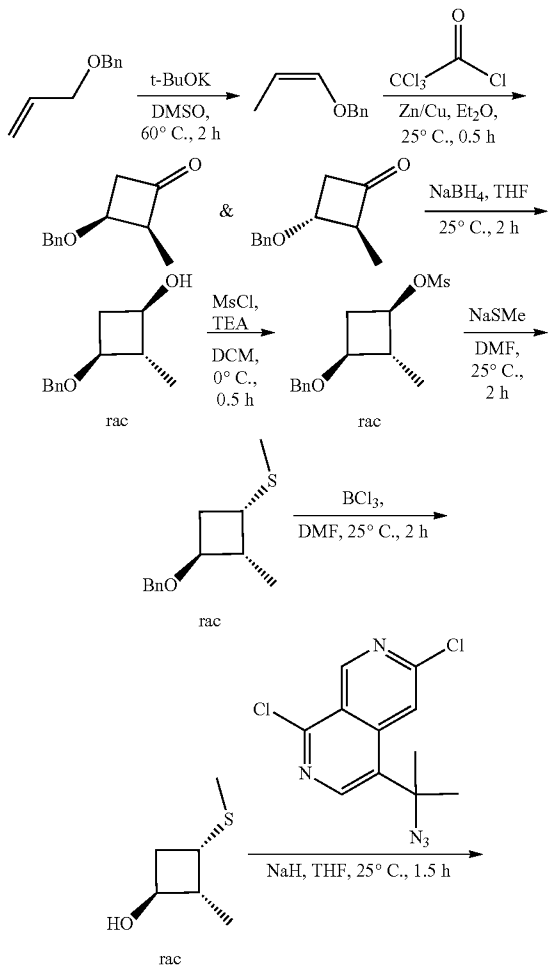

-continued

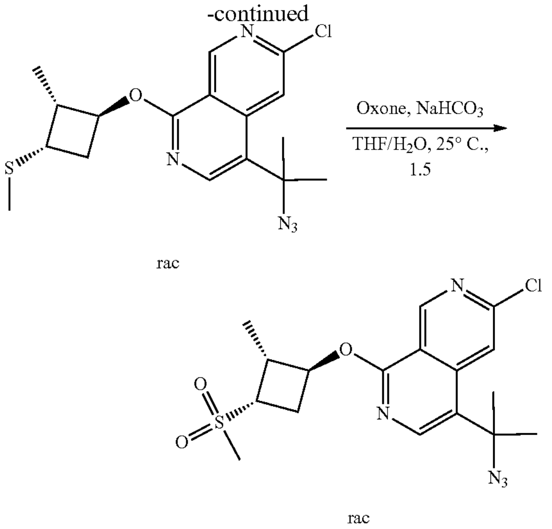

Step 1: ((Prop-1-en-1-yloxy)methyl)benzene

To a solution of ((allyloxy)methyl)benzene (1 g, 6.75 mmol) in DMSO (10 mL) was added t-BuOK (1.14 g, 10.1 mmol), then the mixture was stirred at 60° C. for 2 h. The reaction mixture was diluted with saturated aqueous $NH_4Cl$ solution (300 mL) and extracted with EA (500 mL). The organic layer was washed with brine (3×300 mL), dried over sodium sulfate, filtered, and concentrated to give the title compound (823 mg, 82% yield) as a yellow oil, which was used to next step without further purification.

Steps 2 and 3: (1R,2S,3S and 1S,2R,3R)-3-(Benzyloxy)-2-methylcyclobutan-1-ol

To a mixture of ((prop-1-en-1-yloxy)methyl)benzene (2 g, 13.5 mmol) and copper/zinc (16.0 g, 124 mmol) in $Et_2O$ (40 mL) was added 2,2,2-trichloroacetyl chloride (4.91 g, 27.0 mmol) drop-wise at 25° C. The reaction mixture was stirred at 25° C. for 0.5 h, then was added into a mixture solution of saturated aqueous $NH_4Cl$ (40 mL) and MeOH (50 mL). The resulting mixture was stirred at 50° C. for 10 min, then filtered and concentrated to remove residual MeOH. The mixture was extracted with EA (100 mL) and the organic layer was dried over $Na_2SO_4$, filtered and concentrated. The residue was purified by column chromatography on silica gel (PE/EA=50/1 to 30/1) to give a mixture of (2S,3S and 2R,3R)-3-(benzyloxy)-2-methylcyclobutan-1-one and (2S,3R and 2R,3S)-3-(benzyloxy)-2-methylcyclobutan-1-one (660 mg, 26% yield) as a colorless oil. The mixture of diastereomers (460 mg, 2.42 mmol) was dissolved in THF (10 mL) and $NaBH_4$ (183 mg, 4.84 mmol) was added. The reaction mixture was stirred at 25° C. for 2 h, then was diluted with $H_2O$ (20 mL) and extracted with EA (50 mL). The organic layer was dried in vacuo to give the title compound (450 mg, 97% yield, not a pure diastereomer) as a colorless oil, which was used to next step without further purification.

Step 4: (1R,2R,3S and 1S,2S,3R)-3-(Benzyloxy)-2-methylcyclobutyl Methanesulfonate To a mixture of (1R,2S,3S and 1S,2R,3R)-3-(benzyloxy)-2-methylcyclobutan-1-ol (450 mg, 2.34 mmol) and TEA (474 mg, 4.68 mmol) in DCM (10 mL) was added MsCl (402 mg, 3.51 mmol) at 0° C. The reaction mixture was stirred at 0° C. for 0.5 h, then was diluted with EA (50 mL) and washed with the saturated aqueous $NH_4Cl$ solution (3×50 mL). The organic layer was concentrated to give the title compound (600 mg, crude) as a colorless oil, which was used to next step without further purification.

Step 5: ((1S,2R,3S and 1R,2S,3R)-3-(Benzyloxy)-2-methylcyclobutyl)(methyl)sulfane A mixture of sodium methanethiolate (259 mg, 3.70 mmol) and (1R,2R,3S and 1S,2S,3R)-3-(benzyloxy)-2-methylcyclobutyl methanesulfonate (500 mg, 1.85 mmol) in DMF (10 mL) was stirred at 25° C. for 2 h. The reaction mixture was then diluted with EA (100 mL), washed with brine (3×100 mL), and the organic layer was concentrated to give title compound (420 mg, crude) as a yellow oil, which was used to next step without further purification.

Step 6: (1S,2R,3S and 1R,2S,3R)-2-Methyl-3-(methylthio)cyclobutan-1-ol

To a solution of ((1S,2R,3S and 1R,2S,3R)-3-(benzyloxy)-2-methylcyclobutyl)(methyl)sulfane (420 mg, 1.89 mmol) in DCM (5 mL) was added $BCl_3$ (2.37 g, 20.2 mmol). The reaction mixture was stirred at 25° C. for 2 h, then methanol was added, and the mixture was filtered and concentrated. The residue was purified by column chromatography on silica gel (PE/EA=5/1 and then MeOH) to give the title compound (180 mg, 72% yield) as a yellow oil.

Step 7: 4-(2-Azidopropan-2-yl)-6-chloro-1-((1S,2R,3S and 1R,2S,3R)-2-methyl-3-(methylthio)cyclobutoxy)-2,7-naphthyridine To a solution of (1S,2R,3S and 1R,2S,3R)-2-methyl-3-(methylthio)cyclobutan-1-ol (180 mg, 1.36 mmol) in THF (10 mL) was added NaH (136 mg, 3.40 mmol, 60% purity) and the mixture was stirred at 25° C. for 0.5 h, then 4-(2-azidopropan-2-yl)-1,6-dichloro-2,7-naphthyridine (384 mg, 1.36 mmol) in THF (10 mL) was added. The mixture was stirred at 25° C. for 1 h, then was quenched with water (20 mL) and extracted with EA (15 mL×3). The combined organic layers were dried over $Na_2SO_4$, filtered, and concentrated to give a residue. The residue was purified by column chromatography on silica gel (PE/EA=20/1 to 5/1) and then further purified by Prep-HPLC (column: Phenomenex Luna C18 150*25 mm*10 um; mobile phase: [water (0.225% FA)-ACN]; B %: 70%-100%, 10 min) to give the title compound (130 mg, 48% yield) as a colorless oil. $^1H$ NMR (400 MHz, $CDCl_3$): δ ppm 9.44 (s, 1H), 8.33 (s, 1H), 8.17 (s, 1H), 5.34-5.25 (m, 1H), 3.59-3.53 (m, 1H), 3.05-3.00 (m, 1H), 2.55-2.50 (m, 2H), 2.11 (s, 3H), 1.79 (s, 6H), 1.34 (d, J=7.2 Hz, 3H).

Step 8: 4-(2-Azidopropan-2-yl)-6-chloro-1-((1S,2R,3S and 1R,2S,3R)-2-methyl-3-(methylsulfonyl)cyclobutoxy)-2,7-naphthyridine To a mixture of 4-(2-azidopropan-2-yl)-6-chloro-1-((1S,2R,3S and 1R,2S,3R)-2-methyl-3-(methylthio)cyclobutoxy)-2,7-naphthyridine (130 mg, 344.01 umol), $NaHCO_3$ (231 mg, 2.75 mmol, 107 uL) in THF (10 mL) and $H_2O$ (4 mL) was added Oxone (529 mg, 860 umol). The reaction mixture was stirred at 25° C. for 1.5 h, then was diluted with EA (50 mL) and $H_2O$ (30 mL). The organic layer was dried over $Na_2SO_4$, filtered and concentrated to give the title compound (120 mg, 85% yield) as a colorless oil. MS (ES+) $C_{17}H_{20}ClN_5O_3S$ requires: 409, found: 410[M+H]$^+$.

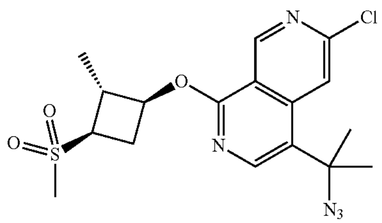

rac

Intermediate 38: 4-(2-Azidopropan-2-yl)-6-chloro-1-((1S,2R,3R and 1R,2S,3S)-2-methyl-3-(methylsulfonyl)cyclobutoxy)-2,7-naphthyridine

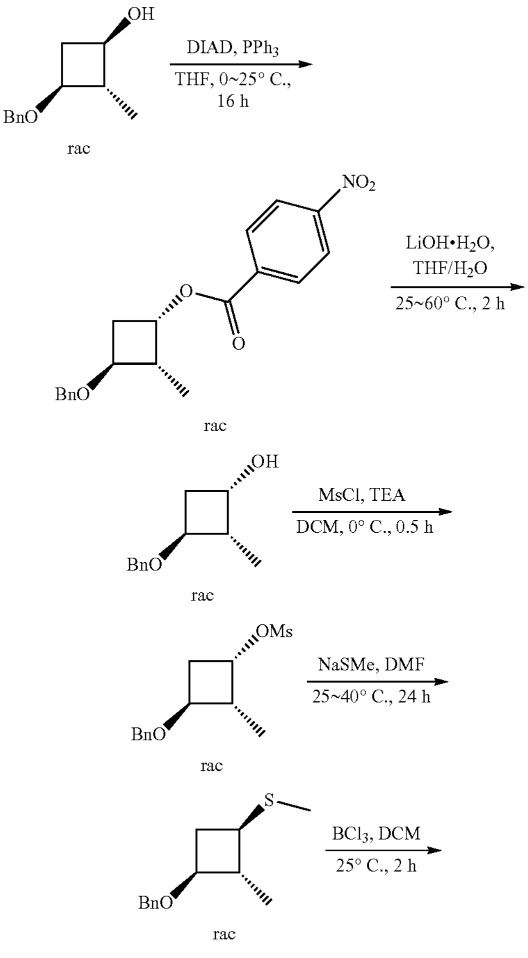

-continued

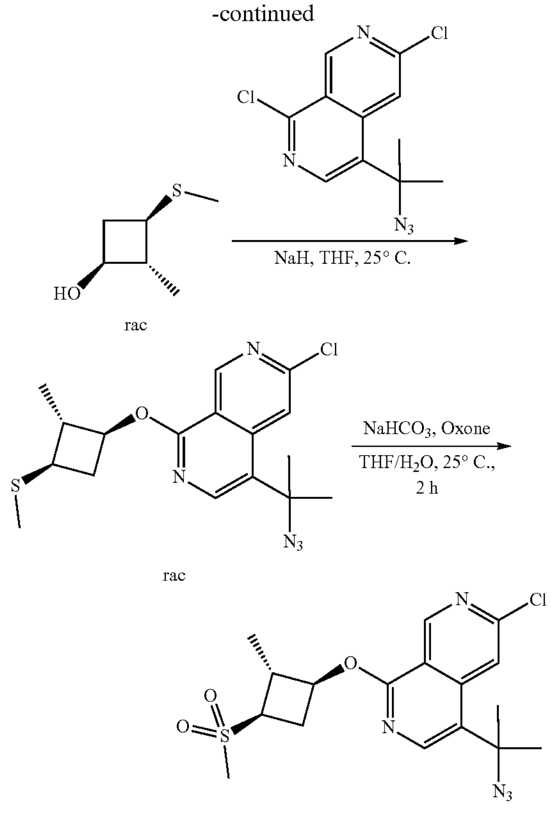

Step 1: (1S,2R,3S and 1R,2S,3R)-3-(Benzyloxy)-2-methylcyclobutyl 4-nitrobenzoate To a solution of (1R,2S,3S and 1S,2R,3R)-3-(benzyloxy)-2-methylcyclobutan-1-ol (1.4 g, 7.28 mmol), 4-nitrobenzoic acid (2.43 g, 14.6 mmol) and $PPh_3$ (5.73 g, 21.9 mmol) in THF (30 mL) was added DIAD (4.42 g, 21.9 mmol) dropwise at 0° C. The reaction mixture was stirred at 25° C. for 16 h, then was diluted with saturated aqueous $NH_4Cl$ solution (50 mL) and extracted with EA (150 mL). The organic layer was dried over $Na_2SO_4$, filtered and concentrated to give a residue. The residue was purified by column chromatography ($SiO_2$, PE/EA=20/1) to give the title compound (2 g, 80% yield) as a colorless oil.

Step 2: (1S,2S,3S)-3-(Benzyloxy)-2-methylcyclobutan-1-ol and (1R,2R,3R)-3-(benzyloxy)-2-methylcyclobutan-1-ol To a solution of (1S,2R,3S and 1R,2S,3R)-3-(benzyloxy)-2-methylcyclobutyl 4-nitrobenzoate (2.0 g, 5.86 mmol) in THF (15 mL) and $H_2O$ (5 mL) was added $LiOH \cdot H_2O$ (2.46 g, 58.6 mmol) at 25° C. The reaction mixture was stirred at 25° C. for 1 h, and then stirred at 60° C. for 1 h. The reaction mixture was then diluted with aqueous $NaHCO_3$ solution (50 mL) and EA (100 mL). The organic layer was washed with saturated aqueous $NaHCO_3$ solution (3×50 mL, dried over $Na_2SO_4$, filtered and concentrated to give the title compound (1.02 g, 90% yield) as a colorless oil.

Steps 3-7: 4-(2-Azidopropan-2-yl)-6-chloro-1-((1S,2R,3R and 1R,2S,3S)-2-methyl-3-(methylsulfonyl)cyclobutoxy)-2,7-naphthyridine The title compound was prepared from (1S,2S,3S)-3-(benzyloxy)-2-methylcyclobutan-1-ol and (1R,2R,3R)-3-(benzyloxy)-2-methylcyclobutan-1-ol using similar procedures as described in Steps 4-8 for Intermediate 37. During Step 6, the penultimate intermediate was purified by prep-HPLC (column: Phenomenex Luna C18 150*40 mm*15 um; mobile phase: [water (0.225% FA)-ACN]; B %: 78%-88%, 10 min) to remove a minor stereoisomer. MS (ES+) $C_{17}H_{20}ClN_5O_3S$ requires: 409, found: 410[M+H]$^+$.

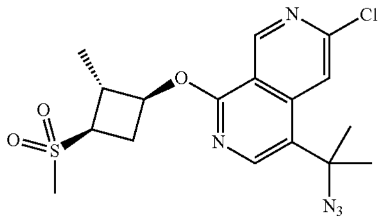

and

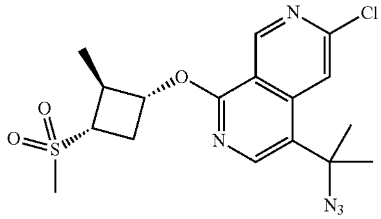

Intermediates 39 and 40: 4-(2-Azidopropan-2-yl)-6-chloro-1-((1S,2R,3R)-2-methyl-3-(methylsulfonyl)cyclobutoxy)-2,7-naphthyridine and 4-(2-azidopropan-2-yl)-6-chloro-1-((1R,2S,3S)-2-methyl-3-(methylsulfonyl)cyclobutoxy)-2,7-naphthyridine

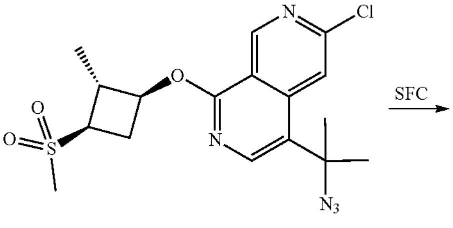

rac

Intermediate 39 and Intermediate 40 each of which is represented by one of the structures shown below:

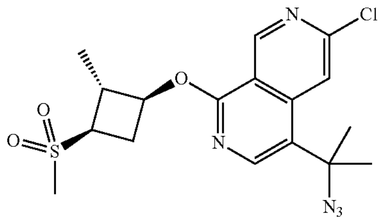

and

-continued

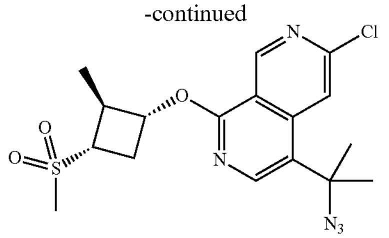

Step 1: 4-(2-Azidopropan-2-yl)-6-chloro-1-((1S,2R,3R)-2-methyl-3-(methylsulfonyl)cyclobutoxy)-2,7-naphthyridine and 4-(2-azidopropan-2-yl)-6-chloro-1-((1R,2S,3S)-2-methyl-3-(methylsulfonyl)cyclobutoxy)-2,7-naphthyridine rac-4-(2-Azidopropan-2-yl)-6-chloro-1-((1S,2R,3R and 1R,2S,3S)-2-methyl-3-(methylsulfonyl)cyclobutoxy)-2,7-naphthyridine (190 mg, 464 umol) was separated by Chiral-SFC (column: Daicel ChiralPak IG (250*30 mm, 10 um); mobile phase: [0.1%NH3H2O MEOH]; B %: 40%-40%) to give to peaks. The first peak (Intermediate 39 (50 mg, 26% yield) was isolated as a white solid and the second peak (Intermediate 40, 57 mg, 30% yield) was isolated as a white solid.

Intermediate 39: MS (ES+) $C_{17}H_{20}ClN_5O_3S$ requires: 409, found: 410[M+H]$^+$.

Intermediate 40: MS (ES+) $C_{17}H_{20}ClN_5O_3S$ requires: 409, found: 410[M+H]$^+$.

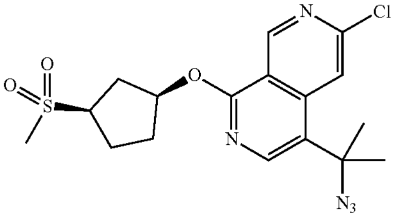

and rac

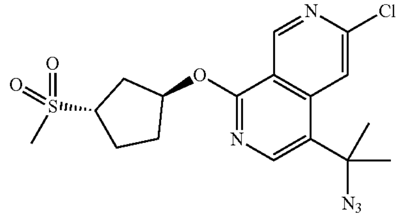

rac

Intermediates 41 and 42: cis-4-(2-Azidopropan-2-yl)-6-chloro-1-((-3-(methylsulfonyl)cyclopentyl)oxy)-2,7-naphthyridine and trans-4-(2-azidopropan-2-yl)-6-chloro-1-((-3-(methylsulfonyl)cyclopentyl)oxy)-2,7-naphthyridine

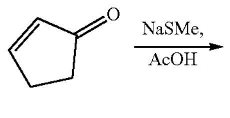

-continued

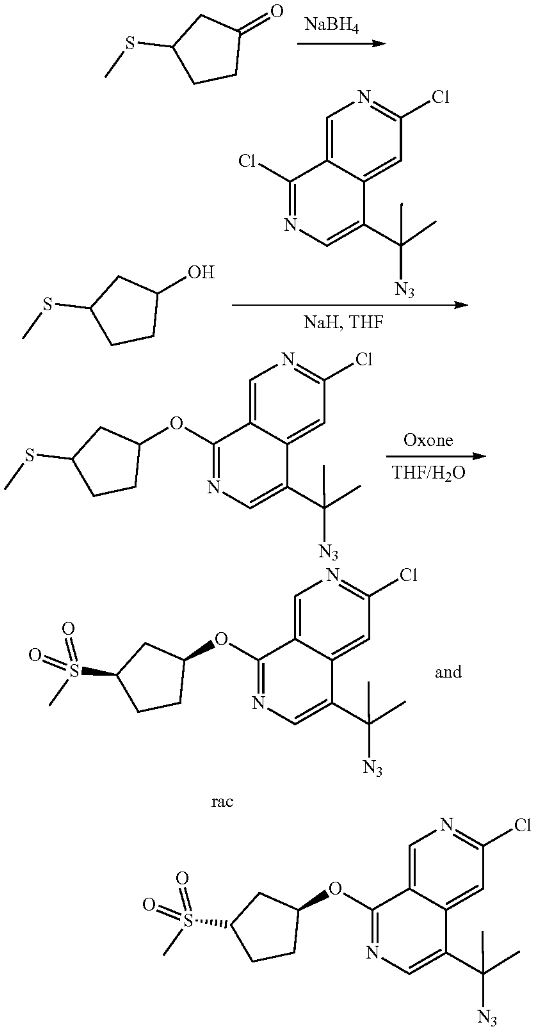

and rac rac

Step 1: 3-(Methylthio)cyclopentan-1-one

To a solution of cyclopent-2-en-1-one (10.0 g, 122 mmol) in ACN (100 mL) was added AcOH (8.05 g, 134 mmol) in one portion at 0° C., then sodium methanethiolate (17.7 g, 253 mmol) in water (50 mL) was added to the solution dropwise at 0° C. The reaction mixture was stirred at 60° C. for 1.5 h, then was poured into water (20 mL) and extracted with EA (20 mL×3). The combined organic layers were washed with water (20 mL×3), dried over anhydrous sodium sulfate, filtered, and concentrated to give a residue. The residue was purified by column chromatography on silica gel (PE/EA=10:1-1:1) to give the title compound (15.0 g, 95% yield) as a yellow oil.

Step 2: 3-(Methylthio)cyclopentan-1-ol

To a solution of 3-(methylthio)cyclopentan-1-one (2.00 g, 15.4 mmol) in MeOH (20 mL) was added $NaBH_4$ (1.16 g, 30.7 mmol) in portions. The reaction mixture was stirred at 25° C. for 2 h, then was poured into water (20 mL) and extracted with EA (20 mL×3). The combined organic layers were washed with water (20 mL×3), dried over anhydrous sodium sulfate, filtered, and concentrated to give a residue. The residue was purified by column chromatography on silica gel (PE:EA=10:1-1:1) and concentrated in vacuo to give the title compound (1.50 g, 74% yield) as a yellow oil.

Steps 3 and 4: cis-4-(2-Azidopropan-2-yl)-6-chloro-1-((−3-(methylsulfonyl)cyclopentyl)oxy)-2,7-naphthyridine and trans-4-(2-azidopropan-2-yl)-6-chloro-1-((−3-(methylsulfonyl)cyclopentyl)oxy)-2,7-naphthyridine The title compounds were prepared from 3-(methylthio) cyclopentan-1-ol and 4-(2-azidopropan-2-yl)-1,6-dichloro-2,7-naphthyridine using a similar procedure as described in Steps 1 and 2 of Intermediate 21. The cis and trans isomers were separated by prep-TLC (PE/EA=1:1) to give Intermediate 42 (racemic trans isomer, 100 mg, 16% yield) and Intermediate 41 (racemic cis isomer, 100 mg, 16% yield)

Intermediate 41: MS (ES+) $C_{17}H_{20}ClN_5O_3S$ requires: 409, found: 410[M+H]$^+$.

Intermediate 42: $^1$H NMR (400 MHz, $CDCl_3$): δ ppm 9.36 (s, 1H), 8.35 (s, 1H), 8.19 (s, 1H), 5.80-5.75 (m, 1H), 3.75-3.70 (m, 1H), 3.48 (s, 2H), 2.93 (s, 3H), 2.57-2.48 (m, 2H), 2.30-2.25 (m, 3H), 2.23-2.20 (m, 1H), 1.80 (s, 6H). MS (ES+) $C_{17}H_{20}ClN_5O_3S$ requires: 409, found: 410[M+H]$^+$.

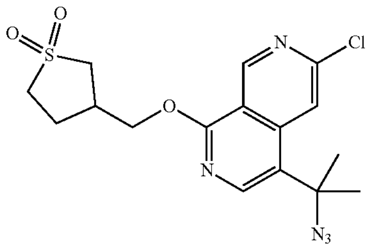 [SMILES: CC(C)(N=[N+]=[N-])c1cnc(OCC2CCS(=O)(=O)C2)c2cnc(Cl)cc12]

Intermediate 43: 3-(((4-(2-Azidopropan-2-yl)-6-chloro-2,7-naphthyridin-1-yl)oxy)methyl)tetrahydrothiophene 1,1-dioxide

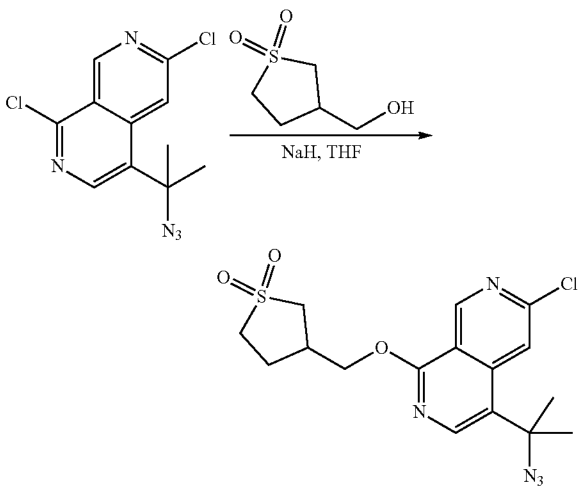

Step 1: 3-(((4-(2-Azidopropan-2-yl)-6-chloro-2,7-naphthyridin-1-yl)oxy)methyl)tetrahydrothiophene 1,1-dioxide The title compound was prepared from 4-(2-azidopropan-2-yl)-1,6-dichloro-2,7-naphthyridine and 3-(hydroxymethyl)tetrahydrothiophene 1,1-dioxide using a similar procedure as described above for Intermediate 22. MS (ES+) $C_{16}H_{18}ClN_5O_3S$ requires: 395, found: 396[M+H]$^+$.

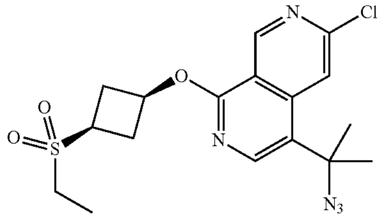 [SMILES: CCS(=O)(=O)[C@H]1C[C@@H](Oc2ncc(C(C)(C)N=[N+]=[N-])c3cc(Cl)ncc23)C1]

Intermediate 44: 4-(2-Azidopropan-2-yl)-6-chloro-1-(cis-3-(ethylsulfonyl)cyclobutoxy)-2,7-naphthyridine

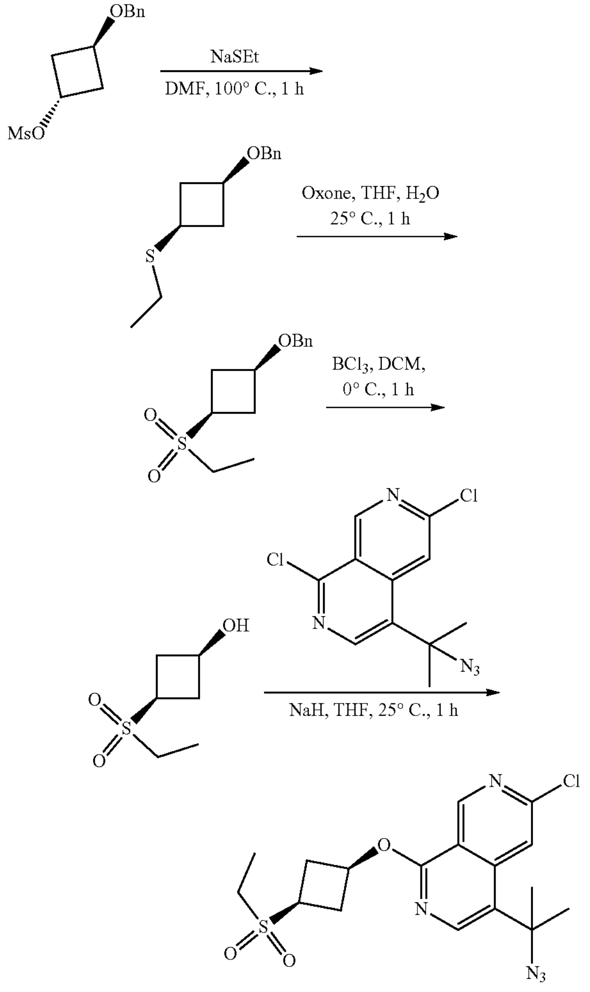

Step 1: (cis-3-(Benzyloxy)cyclobutyl)(ethyl)sulfane

To a solution of trans-3-(benzyloxy)cyclobutyl methanesulfonate (0.5 g, 1.95 mmol) in DMF (2 mL) was added sodium ethanethiolate (328 mg, 3.90 mmol). The reaction mixture was stirred at 100° C. for 0.5 h, then was diluted with water (100 mL) and extracted with EA (100 mL×3). The combined organic layers were washed with brine, dried over anhydrous sodium sulfate, filtered, and concentrated to give a residue. The residue was purified by silica gel chromatography (PE/EA=1: 0 to 20: 1) to give the title compound (160 mg, 37% yield) as colorless oil.

Steps 2-4: 4-(2-Azidopropan-2-yl)-6-chloro-1-(cis-3-(ethylsulfonyl)cyclobutoxy)-2,7-naphthyridine The title compound was prepared using a similar procedure as described in Steps 5-7 of Intermediate 32.

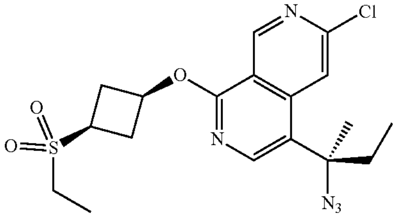 [SMILES: CC[C@@](C)(N=[N+]=[N-])c1cnc(O[C@H]2C[C@@H](S(=O)(=O)CC)C2)c2cnc(Cl)cc12]

Intermediate 45: 4—((R)-2-Azidobutan-2-yl)-6-chloro-1-(cis-3-(ethylsulfonyl)cyclobutoxy)-2,7-naphthyridine

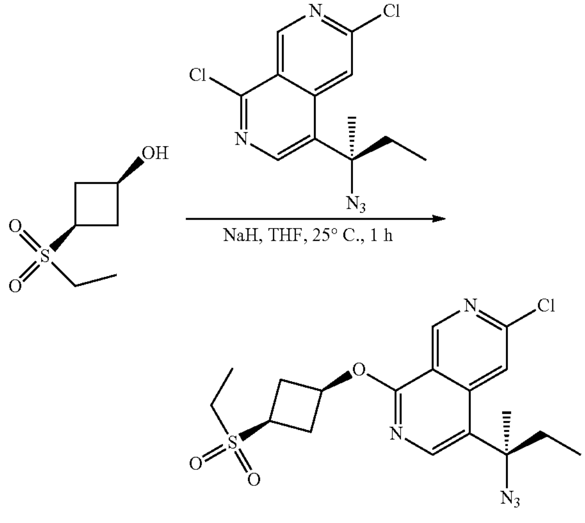

Step 1: 4—((R)-2-Azidobutan-2-yl)-6-chloro-1-(cis-3-(ethylsulfonyl)cyclobutoxy)-2,7-naphthyridine The title compound was prepared from (R)-4-(2-azidobutan-2-yl)-1,6-dichloro-2,7-naphthyridine and cis-3-(ethylsulfonyl)cyclobutan-1-ol (described in the preparation of Intermediate 44) using a similar procedure as described in Step 1 of Intermediate 22. MS (ES+) $C18H_{22}ClN_5O_3S$ requires: 423, found: 424[M+H]$^+$.

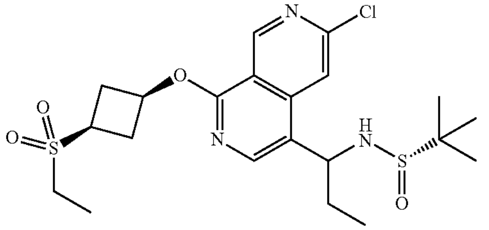 [SMILES: CCC(N[S@@](=O)C(C)(C)C)c1cnc(O[C@H]2C[C@@H](S(=O)(=O)CC)C2)c2cnc(Cl)cc12]

Intermediate 46: (S)—N-(1-(6-Chloro-1-(cis-3-(ethylsulfonyl)cyclobutoxy)-2,7-naphthyridin-4-yl)propyl)-2-methylpropane-2-sulfinamide

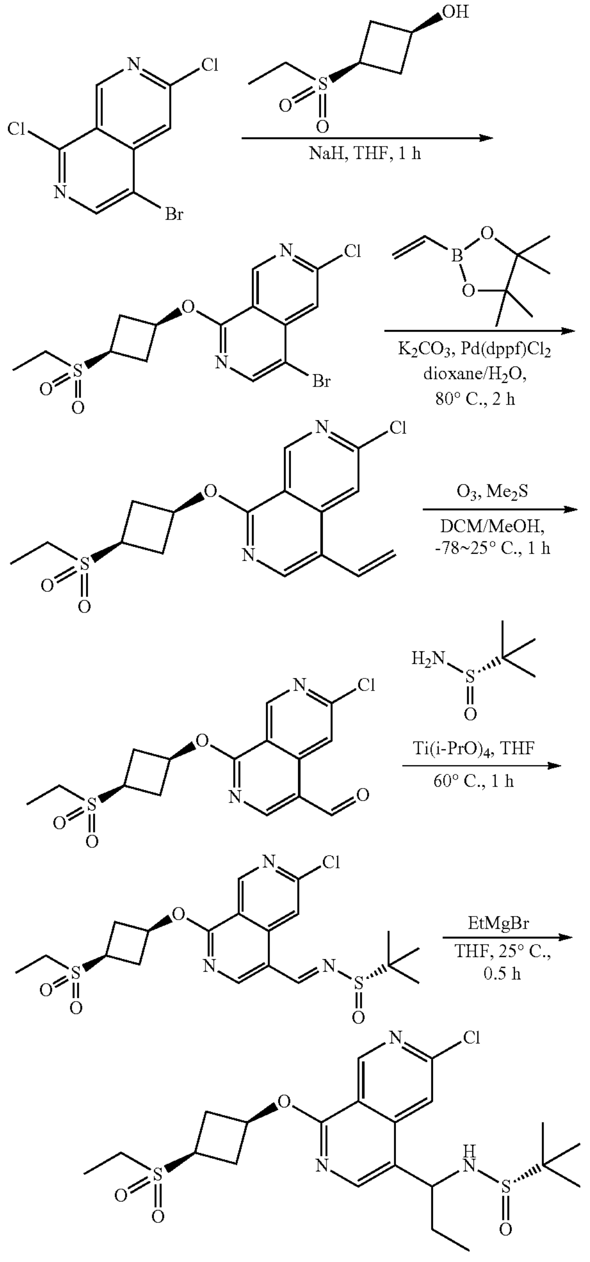

Step 1: 4-Bromo-6-chloro-1-(cis-3-(ethylsulfonyl) cyclobutoxy)-2,7-naphthyridine The title compound was prepared from 4-bromo-1,6-dichloro-2,7-naphthyridine and cis-3-(ethylsulfonyl)cyclobutan-1-ol (described in the preparation of Intermediate 44) using a similar procedure as described in Step 1 of Intermediate 22.

Step 2: 6-Chloro-1-(cis-3-(ethylsulfonyl)cyclobutoxy)-4-vinyl-2,7-naphthyridine

A mixture of compound 4-bromo-6-chloro-1-(cis-3-(ethylsulfonyl)cyclobutoxy)-2,7-naphthyridine (1.35 g, 3.33 mmol, 1 eq), 4,4,5,5-tetramethyl-2-vinyl-1,3,2-dioxaborolane (563.75 mg, 3.66 mmol, 620.87 uL, 1.1 eq), Pd(dppf)$Cl_2$ (243.49 mg, 332.76 umol, 0.1 eq), and $K_2CO_3$ (919.82 mg, 6.66 mmol, 2 eq) in $H_2O$ (2 mL) and dioxane (10 mL) was degassed and purged with $N_2$ 3 times, and then the mixture was stirred at 80° C. for 2 h. The reaction mixture was then diluted with $H_2O$ (100 mL) and extracted with EA (100 mL×3). The combined organic layers were dried over anhydrous sodium sulfate, filtered, and concentrated to give a residue. The residue was purified by column chromatography ($SiO_2$, PE/EA=10/1 to 1/1) to give the title compound (700 mg, 60% yield) as a yellow oil.

Step 3: 6-Chloro-1-(cis-3-(ethylsulfonyl)cyclobutoxy)-2,7-naphthyridine-4-carbaldehyde Ozone was bubbled into a solution of 6-chloro-1-(cis-3-(ethylsulfonyl)cyclobutoxy)-4-vinyl-2,7-naphthyridine (700 mg, 1.98 mmol) in DCM (30 mL) for 10 min at −78° C. The reaction mixture was then flushed with nitrogen and quenched with $Me_2S$ (1.02 mL, 13.89 mmol, 7 eq). The reaction mixture was allowed to warm to 25° C. and stirred for 50 min, then was concentrated. The residue was purified by silica gel column chromatography (PE/EA=1:0 to 1:1) to give the title compound (500 mg, 71% yield) as a yellow solid. MS (ES+) $C_{15}H_{15}ClN_2O_4S$ requires: 354, found: 355[M+H]$^+$.

Step 4: (S)—N—((E)-(6-Chloro-1-(cis-3-(ethylsulfonyl)cyclobutoxy)-2,7-naphthyridin-4-yl)methylene)-2-methylpropane-2-sulfinamide To a solution of 6-chloro-1-(cis-3-(ethylsulfonyl)cyclobutoxy)-2,7-naphthyridine-4-carbaldehyde (0.85 g, 2.40 mmol, 1 eq) and (S)-2-methylpropane-2-sulfinamide (435.53 mg, 3.59 mmol, 1.5 eq) in THF (10 mL) was added Ti(Oi-Pr)$_4$ (2.04 g, 7.19 mmol, 2.12 mL, 3 eq). The mixture was stirred at 60° C. for 2 h, then was quenched by addition of $H_2O$ (50 mL) at 25° C., diluted with EA (50 mL), and filtered. The filtrate was extracted with EA (80 mL×3), and the combined organic layers were dried over anhydrous sodium sulfate, filtered and concentrated to give a residue. The residue was purified by column chromatography ($SiO_2$, PE/EA=0/1 to 1/1) to give the title compound (1 g, 91% yield) as a yellow solid.

Step 4: (S)—N-(1-(6-Chloro-1-(cis-3-(ethylsulfonyl) cyclobutoxy)-2,7-naphthyridin-4-yl)propyl)-2-methylpropane-2-sulfinamide To a solution of compound (S)—N—((E)-(6-chloro-1-(cis-3-(ethylsulfonyl)cyclobutoxy)-2,7-naphthyridin-4-yl) methylene)-2-methylpropane-2-sulfinamide (300 mg, 655 umol, 1 eq) in THF (10 mL) was added EtMgBr (3 M, 655 μL, 3 eq) at 0° C. The reaction mixture was stirred at 25° C. for 15 min, then was quenched by addition of aqueous ammonium chloride solution (45 mL) and extracted with EA (45 mL×3). The combined organic layers were dried over anhydrous sodium sulfate, filtered and concentrated to give the title compound (400 mg, crude) as a yellow oil that was used in the next step without further purification. MS (ES+) $C_{21}H_{30}ClN_3O_4S_2$ requires: 487, found: 488[M+H]$^+$.

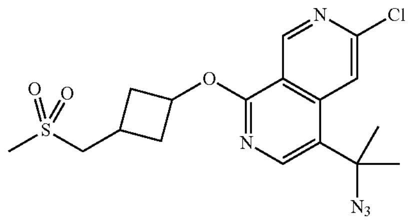 [SMILES: CC(C)(N=[N+]=[N-])c1cnc(OC2CC(CS(C)(=O)=O)C2)c2cnc(Cl)cc12]

Intermediate 47: 4-(2-Azidopropan-2-yl)-6-chloro-1-(3-((methylsulfonyl)methyl)cyclobutoxy)-2,7-naphthyridine

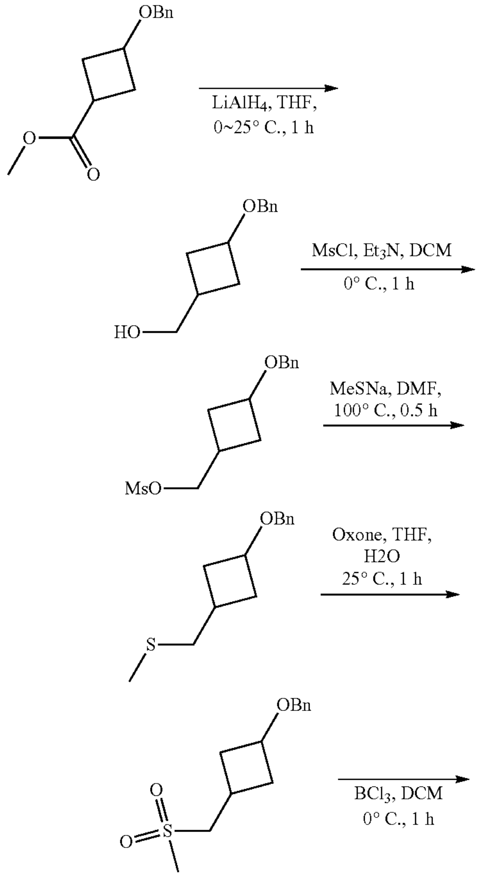

-continued

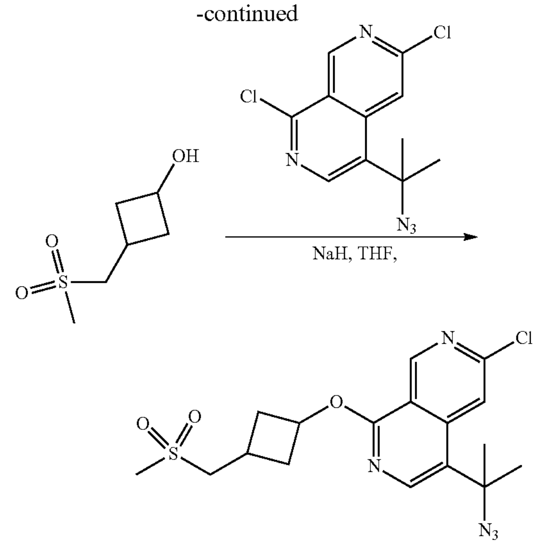

Step 1: (3-(Benzyloxy)cyclobutyl)methanol

To a solution of methyl 3-(benzyloxy)cyclobutane-1-carboxylate (2 g, 9.08 mmol) in THF (60 mL) was added $LiAlH_4$ (689 mg, 18.16 mmol) at 0° C. The reaction mixture was stirred at 0~25° C. for 1 h, then was quenched by addition of water (6 mL) and aqueous NaOH solution (20 mL, 15% MW) at 0° C. The reaction mixture was then extracted with EA (40 mL), dried over sodium sulfate, filtered, and concentrated to give the title compound (1.8 g, crude) as a colorless oil that was used directly in the next step. MS (ES+) $C_{12}H_{16}O_2$ requires: 192, found: 193[M+H]$^+$.

Step 2: (3-(Benzyloxy)cyclobutyl)methyl Methanesulfonate

The title compound was prepared from (3-(benzyloxy)cyclobutyl)methanol using a procedure similar to that described in Step 3 of Intermediate 30.

Step 3: ((3-(Benzyloxy)cyclobutyl)methyl)(methyl)sulfane

To a solution of (3-(benzyloxy)cyclobutyl)methyl methanesulfonate (1.5 g, 5.55 mmol) in DMF (10 mL) was added MeSNa (1.82 g, 11.1 mmol). The reaction mixture was stirred at 100° C. for 1 h, then was diluted with water (40 mL) and extracted with EA (40 mL×3). The combined organic layers were dried over anhydrous sodium sulfate, filtered and concentrated to give a residue. The residue was purified by column chromatography ($SiO_2$, PE/EA=1/0 to 10/1) to give the title compound (2 g) as a colorless oil. MS (ES+) $C_{13}H_{18}OS$ requires: 222, found: 223[M+H]$^+$.

Steps 4-6: 4-(2-Azidopropan-2-yl)-6-chloro-1-(3-((methylsulfonyl)methyl)cyclobutoxy)-2,7-naphthyridine The title compound was prepared using a similar procedure as described in Steps 5-7 of Intermediate 32. MS (ES+) $C_{17}H_{20}ClN_5O_3S$ requires: 409, found: 410[M+H]$^+$.

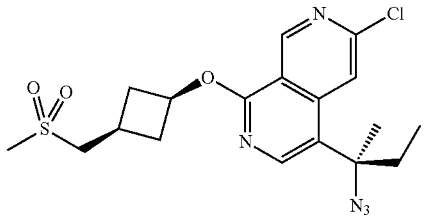
and
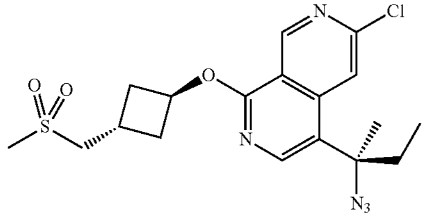

Intermediates 48 and 49: 4-((R)-2-Azidobutan-2-yl)-6-chloro-1-(cis-3-((methylsulfonyl)methyl)cyclobutoxy)-2,7-naphthyridine and 4-((R)-2-azidobutan-2-yl)-6-chloro-1-(trans-3-((methylsulfonyl)methyl)cyclobutoxy)-2,7-naphthyridine

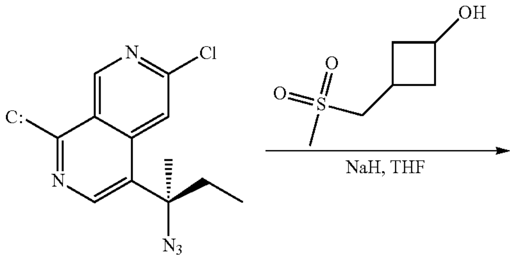

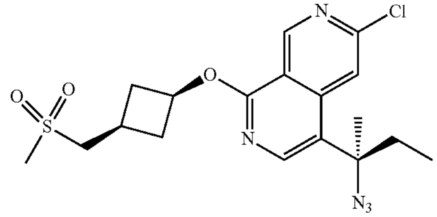
and
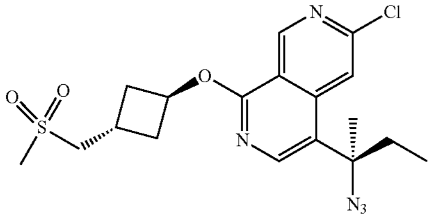

Step 1: 4-((R)-2-Azidobutan-2-yl)-6-chloro-1-(cis-3-((methylsulfonyl)methyl)cyclobutoxy)-2,7-naphthyridine and 4-((R)-2-azidobutan-2-yl)-6-chloro-1-(trans-3-((methylsulfonyl)methyl)cyclobutoxy)-2,7-naphthyridine The title compounds were prepared from 3-((methylsulfonyl)methyl)cyclobutan-1-ol and (R)-4-(2-azidobutan-2-yl)-1,6-dichloro-2,7-naphthyridine using a similar procedure as described in Step 1 of Intermediate 31. The mixture of diastereomers was separated by SFC (column: Daicel ChiralPak IG (250×30 mm, 10 m); mobile phase: [0.1%NH3$H_2O$ ETOH]; B %: 60%-60%) to give Intermediate 48 (cis isomer, 220 mg, 63% yield) as a colorless oil and Intermediate 49 (trans isomer 90 mg, 26% yield) obtained as a colorless oil.

Intermediate 48: MS (ES+) C18$H_{22}ClN_5O_3S$ requires: 423, found: 424$[M+H]^+$.

Intermediate 49: MS (ES+) C18$H_{22}ClN_5O_3S$ requires: 423, found: 424$[M+H]^+$.

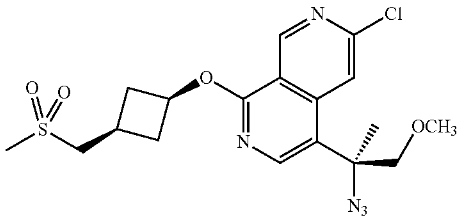

and

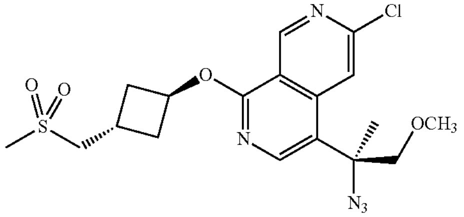

Intermediates 50 and 51: 4—((S)-2-Azido-1-methoxypropan-2-yl)-6-chloro-1-(cis-3-((methylsulfonyl)methyl)cyclobutoxy)-2,7-naphthyridine and 4-((S)-2-azido-1-methoxypropan-2-yl)-6-chloro-1-(trans-3-((methylsulfonyl)methyl)cyclobutoxy)-2,7-naphthyridine

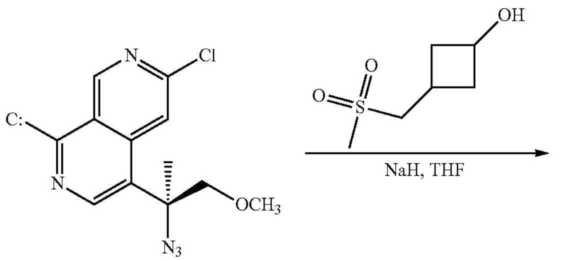

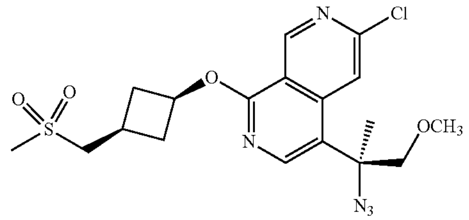

and

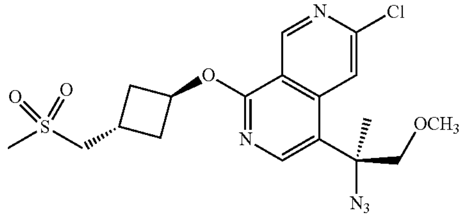

Step 1: 4—((S)-2-Azido-1-methoxypropan-2-yl)-6-chloro-1-(cis-3-((methylsulfonyl)methyl)cyclobutoxy)-2,7-naphthyridine and 4-((S)-2-azido-1-methoxypropan-2-yl)-6-chloro-1-(trans-3-((methylsulfonyl)methyl)cyclobutoxy)-2,7-naphthyridine The title compounds were prepared from 3-((methylsulfonyl)methyl)cyclobutan-1-ol and (S)-4-(2-azido-1-methoxypropan-2-yl)-1,6-dichloro-2,7-naphthyridine (Intermediate 18) using a similar procedure as described in Step 1 of Intermediate 31. The mixture of diastereomers was separated by SFC (column: Daicel ChiralPak IG (250*30 mm, 10 um); mobile phase: [0.1% $NH_3H_2O$ MeOH]; B %: 70%-70%) to give Intermediate 50 (cis isomer, 360 mg, 20% yield) as a yellow oil and Intermediate 51 (trans isomer, 120 mg, 6.50% yield) as a yellow oil.

Intermediate 50: MS (ES+) C18$H_{22}ClN_5O_4S$ requires: 439, found: 440$[M+H]^+$.

Intermediate 51: MS (ES+) C18$H_{22}ClN_5O_4S$ requires: 439, found: 440$[M+H]^+$.

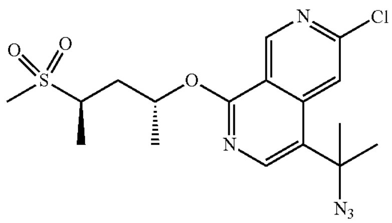 [SMILES: C[C@H](C[C@@H](C)S(C)(=O)=O)Oc1ncc(C(C)(C)N=[N+]=[N-])c2cc(Cl)ncc12]

Intermediate 52: 4-(2-Azidopropan-2-yl)-6-chloro-1-(((2R,4R)-4-(methylsulfonyl)pentan-2-yl)oxy)-2,7-naphthyridine

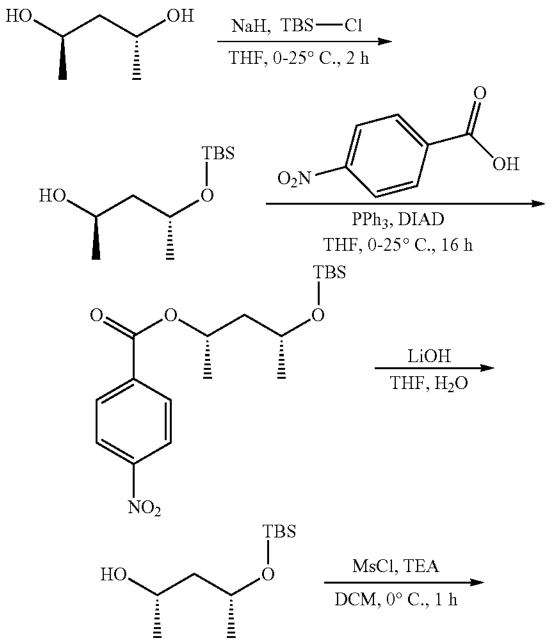

-continued

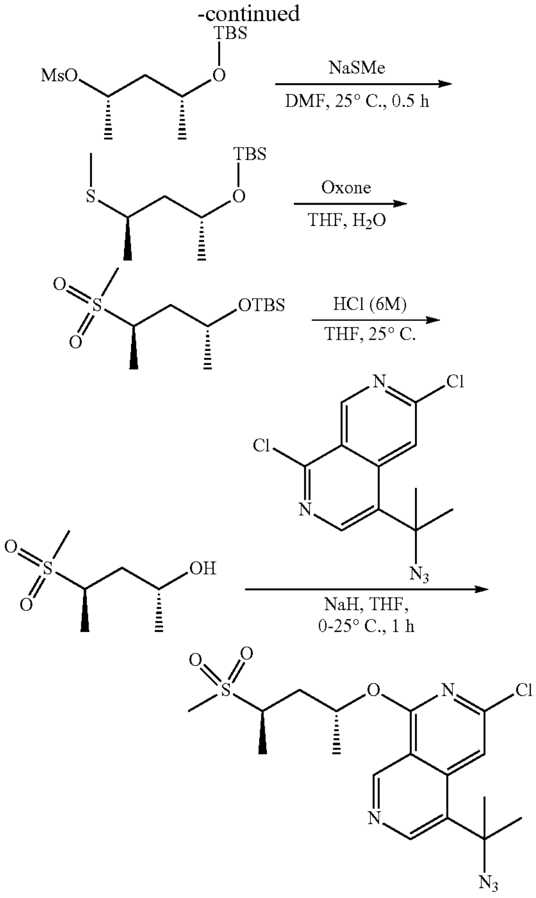

Step 1: (2R,4R)-4-((tert-Butyldimethylsilyl)oxy)pentan-2-ol

To a solution of (2R,4R)-pentane-2,4-diol (3.80 g, 36.5 mmol) in THF (120 mL) was added NaH (1.75 g, 43.8 mmol, 60% purity) at 0° C. The reaction mixture was stirred for 30 min, then tert-butyldimethylsilyl chloride (6.05 g, 40.1 mmol) was added and the reaction mixture was stirred at 25° C. for 1.5 h. The reaction mixture was then added to water (200 mL) and extracted with EA (150 mL×3). The combined organic layers were dried over anhydrous sodium sulfate, filtered and concentrated to give a residue. The residue was purified by silica gel column chromatography (PE/EA=1:0 to 5:1) to give the title compound (7.80 g, 98% yield) as a colorless oil.

Step 2: (2S,4R)-4-((tert-Butyldimethylsilyl)oxy)pentan-2-yl 4-nitrobenzoate

To a solution of (2R,4R)-4-((tert-butyldimethylsilyl)oxy)pentan-2-ol (1.00 g, 4.58 mmol), compound 4-nitrobenzoic acid (1.53 g, 9.16 mmol), and triphenylphosphine (3.60 g, 13.7 mmol) in THF (34 mL) was added DIAD (2.78 g, 13.74 mmol) at 0° C. The reaction mixture was stirred at 0° C. for 30 min, then was stirred at 25° C. for 15.5 h, diluted with water (50 mL) and extracted with EA (40 mL×3). The combined organic layers were dried over anhydrous sodium sulfate, filtered and concentrated to give a residue. The residue was purified by silica gel column chromatography (PE/EA=1:0 to 10:1) to give the title compound (1.50 g, 78% yield) as a yellow oil.

Step 3: (2S,4R)-4-((tert-Butyldimethylsilyl)oxy)pentan-2-ol

To a solution of (2S,4R)-4-((tert-butyldimethylsilyl)oxy)pentan-2-yl 4-nitrobenzoate (1.50 g, 4.08 mmol) in THF (12 mL) and water (4 mL) was added $LiOH \cdot H_2O$ (977 mg, 40.8 mmol). The reaction mixture was stirred at 60° C. for 1 h, then was diluted with water (50 mL) and extracted with EA (40 mL×3). The combined organic layers were dried over anhydrous sodium sulfate, filtered and concentrated to give the title compound (890 mg, 100% yield) as a yellow oil that was used in the next step without further purification.

Step 4: (2S,4R)-4-((tert-Butyldimethylsilyl)oxy)pentan-2-yl methanesulfonate

To a solution of (2S,4R)-4-((tert-butyldimethylsilyl)oxy)pentan-2-ol (890 mg, 4.07 mmol) in DCM (15 mL) was added TEA (1.24 g, 12.2 mmol) and MsCl (934 mg, 8.15 mmol) at 0° C. The reaction mixture was stirred for 1 h, then was diluted with water (100 mL) and extracted with DCM (80 mL×3). The combined organic layers were dried over anhydrous sodium sulfate, filtered and concentrated to give the title compound (1.20 g, 99% yield) as a yellow oil that was used in the next step without further purification.

Step 5: tert-Butyldimethyl(((2R,4R)-4-(methylthio)pentan-2-yl)oxy)silane

To a solution of compound (2S,4R)-4-((tert-butyldimethylsilyl)oxy)pentan-2-yl methanesulfonate (1.20 g, 4.05 mmol) in DMF (30 mL) was added sodium methanethiolate (709 mg, 10.1 mmol). The reaction mixture was stirred at 25° C. for 0.5 h, then was diluted with water (80 mL) and extracted with EA (60 mL×3). The combined organic layers were dried over anhydrous sodium sulfate, filtered and concentrated to give the title compound (1.00 g, 99% yield) as a yellow oil that was used in the next step without further purification.

Step 6: tert-Butyldimethyl(((2R,4R)-4-(methylsulfonyl)pentan-2-yl)oxy)silane

To a solution of tert-butyldimethyl(((2R,4R)-4-(methylthio)pentan-2-yl)oxy)silane (1.00 g, 4.02 mmol) in THF (14 mL) and water (7 mL) was added Oxone® (4.95 g, 8.05 mmol). The reaction mixture was stirred at 25° C. for 0.5 h, then was quenched by addition of saturated aqueous sodium sulfite solution (30 mL) and extracted with EA (20 mL×3). The combined organic layers were dried over anhydrous sodium sulfate, filtered and concentrated to give the title compound (1.10 g, 97% yield) as a yellow oil that was used without further purification.

Step 7: (2R,4R)-4-(Methylsulfonyl)pentan-2-ol

To a solution of tert-butyldimethyl(((2R,4R)-4-(methylsulfonyl)pentan-2-yl)oxy)silane (1.10 g, 3.92 mmol) in THF (8 mL) was added aqueous HCl (6 M, 2 mL). The reaction mixture was stirred at 25° C. for 0.5 h, then was diluted with water (50 mL) and extracted with EA (40 mL×3). The combined organic layers were dried over anhydrous sodium sulfate, filtered and concentrated to give a residue. The residue was purified by silica gel column chromatography (PE/EA=1:0 to 0:1) to give the title compound (230 mg, 35% yield) as a yellow oil.

Step 8: 4-(2-Azidopropan-2-yl)-6-chloro-1-(((2R,4R)-4-(methylsulfonyl)pentan-2-yl)oxy)-2,7-naphthyridine The title compound was prepared from (2R,4R)-4-(methylsulfonyl)pentan-2-ol and 4-(2-azidopropan-2-yl)-1,6-dichloro-2,7-naphthyridine using a similar procedure as described in Step 1 of Intermediate 22. MS (ES+) $C_{17}H_{22}ClN_5O_3S$ requires: 411, found: 412[M+H]$^+$.

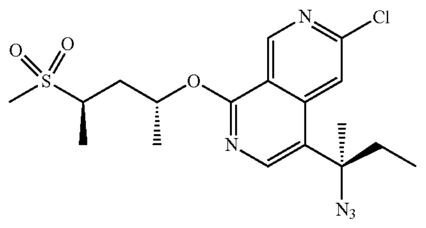 [SMILES: CC[C@@](C)(N=[N+]=[N-])c1cnc(O[C@H](C)C[C@@H](C)S(C)(=O)=O)c2cnc(Cl)cc12]

Intermediate 53: 4—((R)-2-Azidobutan-2-yl)-6-chloro-1-(((2R,4R)-4-(methylsulfonyl)pentan-2-yl)oxy)-2,7-naphthyridine

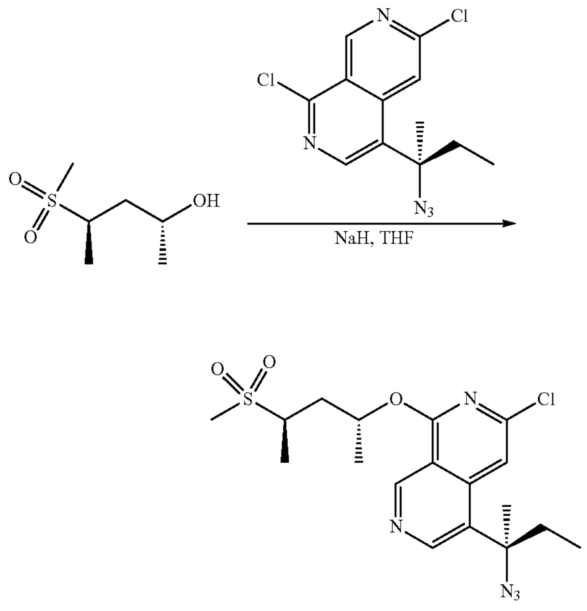

Step 1: 4—((R)-2-Azidobutan-2-yl)-6-chloro-1-(((2R,4R)-4-(methylsulfonyl)pentan-2-yl)oxy)-2,7-naphthyridine The title compound was prepared from (2R,4R)-4-(methylsulfonyl)pentan-2-ol and (R)-4-(2-azidobutan-2-yl)-1,6-dichloro-2,7-naphthyridine using a similar procedure as described in Step 1 of Intermediate 22. MS (ES+) $C18H_{24}ClN_5O_3S$ requires: 425, found: 426[M+H]$^+$.

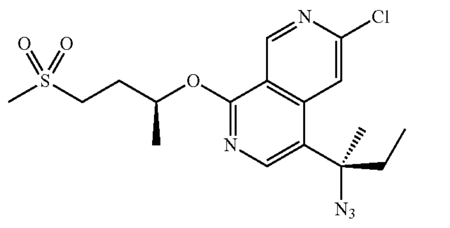 [SMILES: CC[C@@](C)(N=[N+]=[N-])c1cnc(O[C@@H](C)CCS(C)(=O)=O)c2cnc(Cl)cc12]

Intermediate 54: 4—((R)-2-Azidobutan-2-yl)-6-chloro-1-(((S)-4-(methylsulfonyl)butan-2-yl)oxy)-2,7-naphthyridine

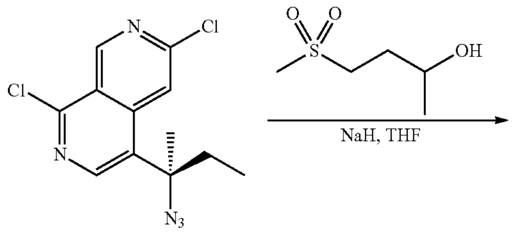

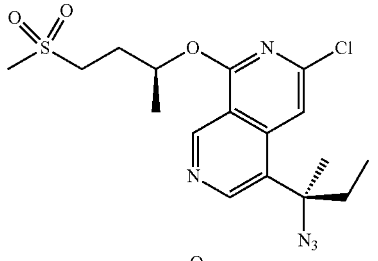

and

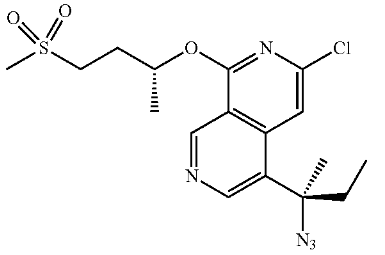

Step 1: 4—((R)-2-Azidobutan-2-yl)-6-chloro-1-(((S)-4-(methylsulfonyl)butan-2-yl)oxy)-2,7-naphthyridine The title compound was prepared from 4-(methylsulfonyl)butan-2-ol and (R)-4-(2-azidobutan-2-yl)-1,6-dichloro-2,7-naphthyridine using a similar procedure as described in Step 1 of Intermediate 22. The resulting mixture of diastereomers was separated by SFC (column: Daicel Chiralpak AD-H (250 mm*30 mm, 5 um); mobile phase: [0.1% $NH_3H_2O$ IPA]; B %: 35%-35%). to give the title compound as the first eluting isomer. The stereochemistry of was determined by chiral SFC analysis of this mixture and Intermediate 31, which was prepared from an enantiomerically pure starting material.

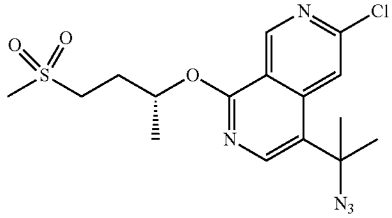 [SMILES: C[C@H](CCS(C)(=O)=O)Oc1ncc(C(C)(C)N=[N+]=[N-])c2cc(Cl)ncc12]

Intermediate 55: (R)-4-(2-Azidopropan-2-yl)-6-chloro-1-((4-(methylsulfonyl)butan-2-yl)oxy)-2,7-naphthyridine

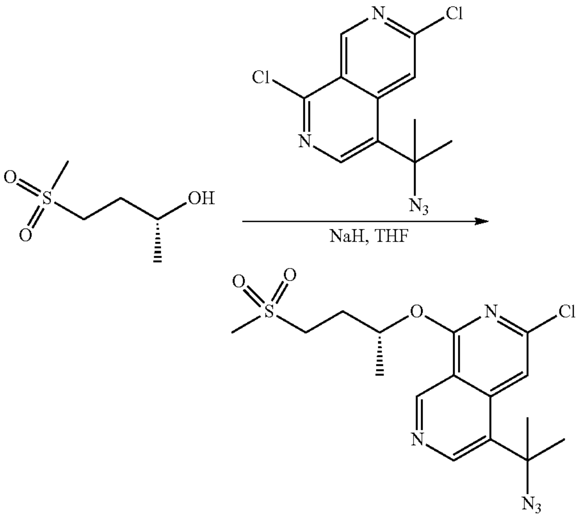

Step 1: (R)-4-(2-Azidopropan-2-yl)-6-chloro-1-((4-(methylsulfonyl)butan-2-yl)oxy)-2,7-naphthyridine The title compound was prepared from 4-(2-azidopropan-2-yl)-1,6-dichloro-2,7-naphthyridine and (R)-4-(methylsulfonyl)butan-2-ol using a similar procedure as described in Step 1 of Intermediate 22. MS (ES+) $C_{16}H_{20}ClN_5O_3S$ requires: 397, found: 398[M+H]$^+$.

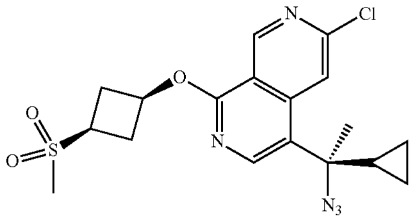

and

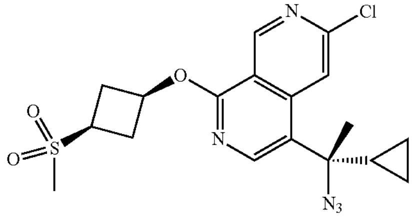

Intermediates 56 and 57: 4—((R)-1-Azido-1-cyclopropylethyl)-6-chloro-1-(cis-3-(methylsulfonyl)cyclobutoxy)-2,7-naphthyridine and 4-((S)-1-azido-1-cyclopropylethyl)-6-chloro-1-(cis-3-(methylsulfonyl)cyclobutoxy)-2,7-naphthyridine

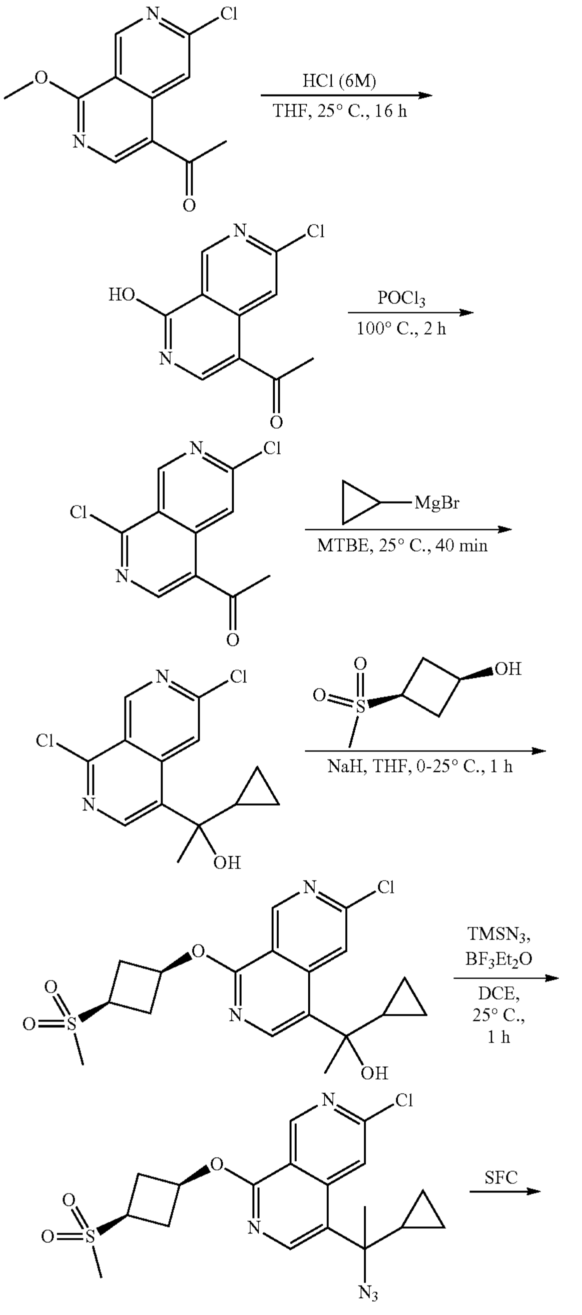

Intermediate 56 and Intermediate 57 each of which is represented by one of the structures shown below:

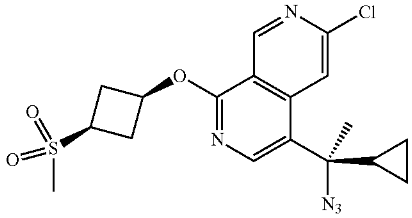

and

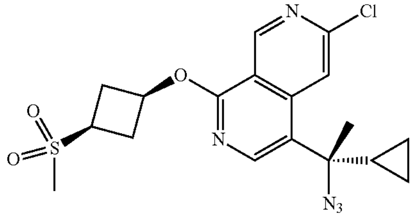

Step 1: 1-(6-Chloro-1-hydroxy-2,7-naphthyridin-4-yl)ethan-1-one

To a solution of 1-(6-chloro-1-methoxy-2,7-naphthyridin-4-yl)ethan-1-one (Title compound from Step 3 of Intermediate 17, 3.00 g, 12.7 mmol) in THF (30 mL) was added aqueous HCl (6 M, 20 mL). The reaction mixture was stirred at 25° C. for 16 h, then was diluted with water (80 mL) and extracted with EA (60 mL×3). The combined organic layers were dried over anhydrous sodium sulfate, filtered and concentrated to give the title compound (2.80 g, crude) which was used in the next step without any further purification.

Step 2: 1-(1,6-Dichloro-2,7-naphthyridin-4-yl)ethan-1-one 1-(6-Chloro-1-hydroxy-2,7-naphthyridin-4-yl)ethan-1-one (1.00 g, 4.49 mmol) was added to $POCl_3$ (10 mL) and the reaction mixture was stirred at 100° C. for 2 h, then was cooled to room temperature and poured slowly into saturated aqueous sodium bicarbonate solution (500 mL). The mixture was extracted with EA (200 mL×3), and the combined organic layers were dried over anhydrous sodium sulfate, filtered, and concentrated. The residue was purified by silica gel column chromatography (PE/EA=1:0 to 3:1) to give the title compound (660 mg, 58% yield) as a white solid.

Step 3: 1-Cyclopropyl-1-(1,6-dichloro-2,7-naphthyridin-4-yl)ethan-1-ol

To a solution of 1-(1,6-dichloro-2,7-naphthyridin-4-yl) ethan-1-one (600 mg, 2.49 mmol) in MTBE (200 mL) was added cyclopropylmagnesium bromide (0.5 M, 15 mL) at 25° C. The reaction mixture was stirred at 25° C. for 40 min, then was diluted with water (80 mL) and extracted with EA (60 mL×3). The combined organic layers were dried over anhydrous sodium sulfate, filtered and concentrated to give a residue. The residue was purified by silica gel column chromatography (PE/EA=1:0 to 3:1) to give the title compound (550 mg, 78% yield) as a yellow solid.

Step 4: 1-(6-Chloro-1-(cis-3-(methylsulfonyl)cyclobutoxy)-2,7-naphthyridin-4-yl)-1-cyclopropylethan-1-ol To a solution of cis-3-(methylsulfonyl)cyclobutan-1-ol (167 mg, 1.11 mmol) in THF (20 mL) was added NaH (85.0 mg, 2.12 mmol, 60% purity) at 0° C. The reaction mixture was stirred at 0° C. for 15 min, then 1-cyclopropyl-1-(1,6-dichloro-2,7-naphthyridin-4-yl)ethan-1-ol (300 mg, 1.06 mmol) was added and the mixture was stirred at 25° C. for 45 min. The reaction mixture was then diluted with water (50 mL) and extracted with EA (30 mL×3). The combined organic layers were dried over anhydrous sodium sulfate, filtered and concentrated to give the title compound (390 mg, crude) as a yellow oil that was used in the next step without further purification.

Step 5: 4-(1-Azido-1-cyclopropylethyl)-6-chloro-1-(cis-3-(methylsulfonyl)cyclobutoxy)-2,7-naphthyridine To a solution of 1-(6-chloro-1-(cis-3-(methylsulfonyl)cyclobutoxy)-2,7-naphthyridin-4-yl)-1-cyclopropylethan-1-ol (390 mg, 983 μmol) in 1,2-DCE (10 mL) was added $TMSN_3$ (340 mg, 2.95 mmol) and $BF_3{\cdot}Et_2O$ (279 mg, 1.97 mmol). The reaction mixture was stirred at 25° C. for 1 h, then was diluted with water (80 mL) and extracted with DCE (60 mL×3). The combined organic layers were dried over anhydrous sodium sulfate, filtered and concentrated to give a residue. The residue was purified by silica gel column chromatography (PE/EA=1:0 to 0:1) to give the title compound (240 mg, 58% yield) as a yellow oil.

Step 6: 4—((R)-1-Azido-1-cyclopropylethyl)-6-chloro-1-(cis-3-(methylsulfonyl)cyclobutoxy)-2,7-naphthyridine and 4-((S)-1-azido-1-cyclopropylethyl)-6-chloro-1-(cis-3-(methylsulfonyl) cyclobutoxy)-2,7-naphthyridine 4-(1-Azido-1-cyclopropylethyl)-6-chloro-1-(cis-3-(methylsulfonyl)cyclobutoxy)-2,7-naphthyridine (240 mg, 569 μmol) was separated by SFC (column: Daicel Chiralpak AY-H (250 mm×30 mm, 10 um); mobile phase: [0.1% $NH_3H_2O$ IPA]; B %: 40%-40%) to give one of 4-((R)-1-azido-1-cyclopropylethyl)-6-chloro-1-(cis-3-(methylsulfonyl)cyclobutoxy)-2,7-naphthyridine or 4-((S)-1-azido-1-cyclopropylethyl)-6-chloro-1-(cis-3-(methylsulfonyl) cyclobutoxy)-2,7-naphthyridine as the first eluting isomer (Intermediate 56, 110 mg, 45% yield) as a yellow oil and the other one of 4-((R)-1-azido-1-cyclopropylethyl)-6-chloro-1-(cis-3-(methylsulfonyl)cyclobutoxy)-2,7-naphthyridine or 4-((S)-1-azido-1-cyclopropylethyl)-6-chloro-1-(cis-3-(methylsulfonyl)cyclobutoxy)-2,7-naphthyridine as the second eluting isomer (Intermediate 57, 110 mg, 45% yield) as a yellow oil.

Intermediate 56: MS (ES+) $C18H_{20}ClN_5O_3S$ requires: 421, found: 422[M+H]$^+$.

Intermediate 57: MS (ES+) $C18H_{20}ClN_5O_3S$ requires: 421, found: 422[M+H]$^+$.

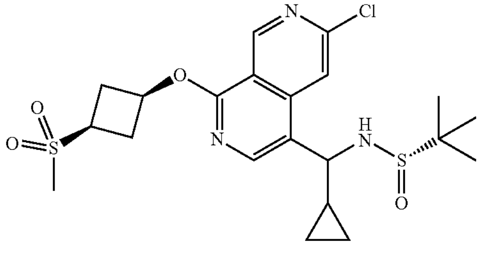 [SMILES: CC(C)(C)[S@](=O)NC(c1cnc(O[C@H]2C[C@@H](S(C)(=O)=O)C2)c2cnc(Cl)cc12)C1CC1]

Intermediate 58: (S)—N-((6-Chloro-1-(cis-3-(methylsulfonyl)cyclobutoxy)-2,7-naphthyridin-4-yl)(cyclopropyl)methyl)-2-methylpropane-2-sulfinamide

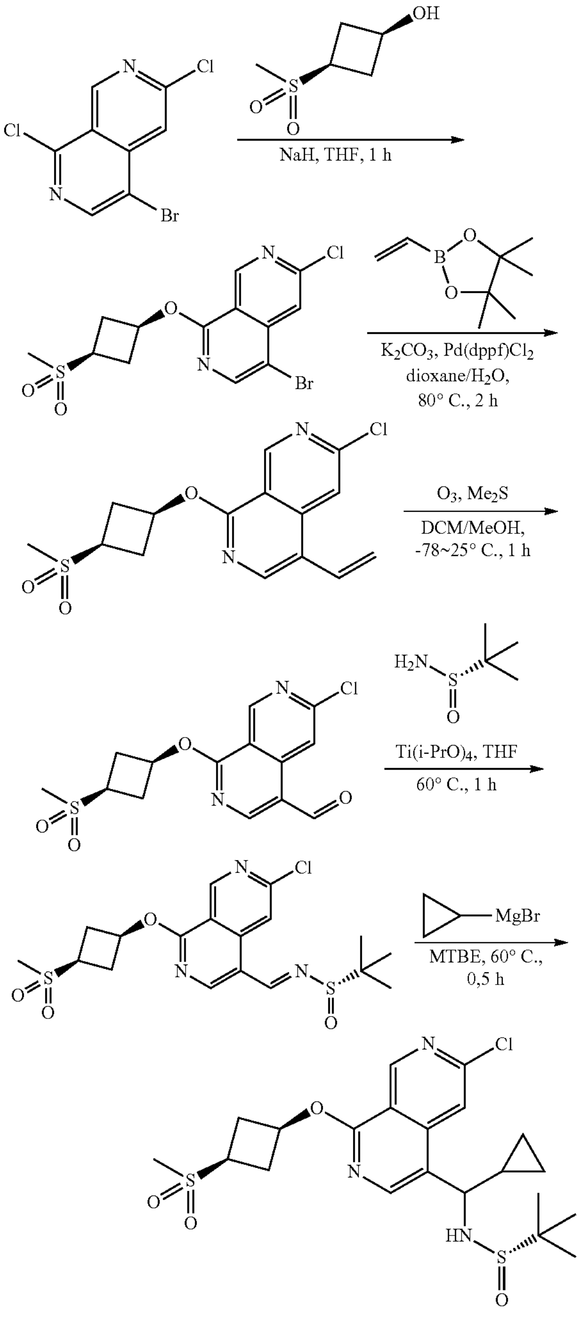

Steps 1-4: (S)—N—((E)-(6-Chloro-1-(cis-3-(methylsulfonyl)cyclobutoxy)-2,7-naphthyridin-4-yl)methylene)-2-methylpropane-2-sulfinamide The title compound was prepared from 4-bromo-1,6-dichloro-2,7-naphthyridine and cis-3-(methylsulfonyl)cyclobutan-1-ol using a similar procedure as described in Steps 1-4 of Intermediate 46.

Step 5: (S)—N-((6-Chloro-1-(cis-3-(methylsulfonyl)cyclobutoxy)-2,7-naphthyridin-4-yl)(cyclopropyl)methyl)-2-methylpropane-2-sulfinamide To a solution of (S)—N—((E)-(6-chloro-1-(cis-3-(methylsulfonyl)cyclobutoxy)-2,7-naphthyridin-4-yl)methylene)-2-methylpropane-2-sulfinamide (500 mg, 1.13 mmol) in MTBE (60 mL) was added cyclopropylmagnesium bromide (0.5 M, 10.0 mL). The reaction mixture was stirred at 60° C. 0.5 h, then was quenched by addition of saturated aqueous $NH_4Cl$ solution (20 mL). The mixture was diluted with water (20 mL) and extracted with EA (40 mL×3). The combined organic layers were dried over anhydrous sodium sulfate, filtered and concentrated to give a residue. The residue was purified by flash silica gel chromatography (PE/EA 1:0 to 0:1) to give the title compound (100 mg, 16% yield) as a yellow oil. MS (ES+) $C_{21}H_{28}ClN_3O_4S_2$ requires: 485, found: 486[M+H]$^+$.

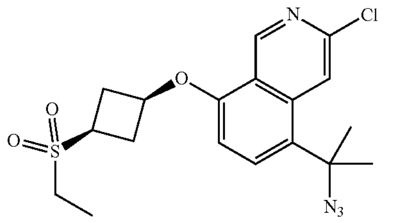 [SMILES: CCS(=O)(=O)[C@H]1C[C@@H](Oc2ccc(C(C)(C)N=[N+]=[N-])c3cc(Cl)ncc23)C1]

Intermediate 59: 5-(2-Azidopropan-2-yl)-3-chloro-8-(cis-3-(ethylsulfonyl)cyclobutoxy)isoquinoline

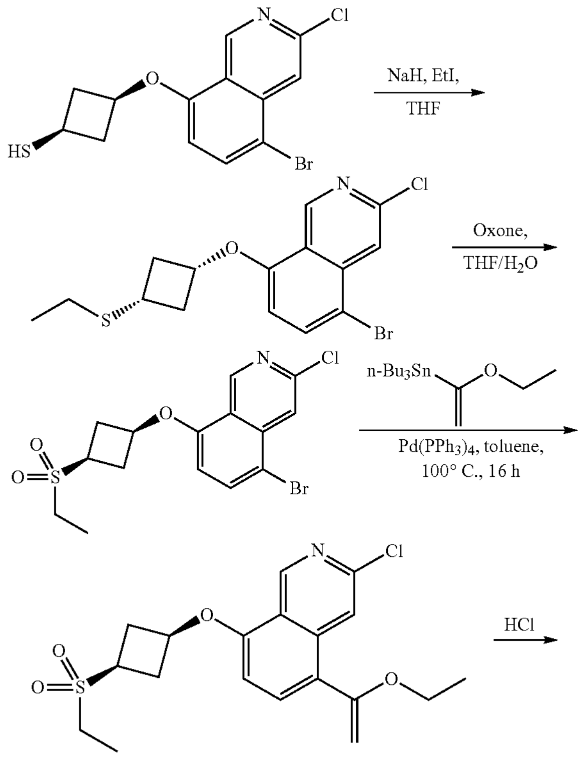

-continued

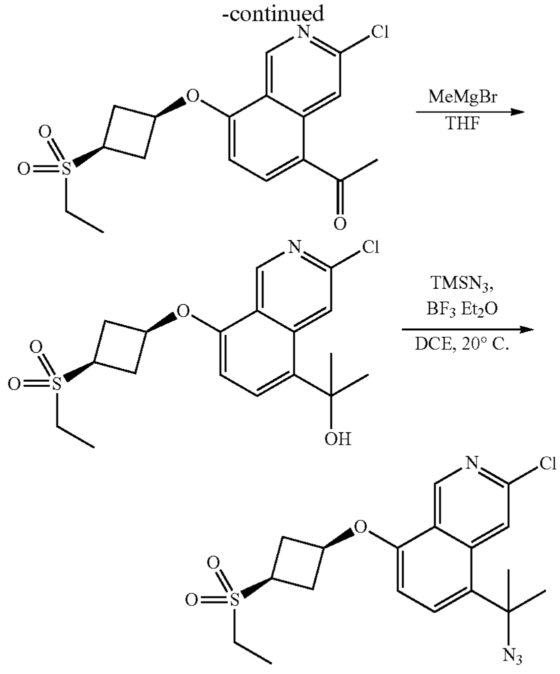

Steps 1-6: 5-(2-Azidopropan-2-yl)-3-chloro-8-(cis-3-(ethylsulfonyl)cyclobutoxy)isoquinoline The title compound was prepared from cis-3-((5-bromo-3-chloroisoquinolin-8-yl)oxy)cyclobutane-1-thiol (Intermediate 35, step 6) and ethyl iodide using a procedure similar to that described in Steps 7-12 for Intermediate 35. MS (ES+) $C18H_{21}ClN_4O_3S$ requires: 408, found: 409[M+H]$^+$.

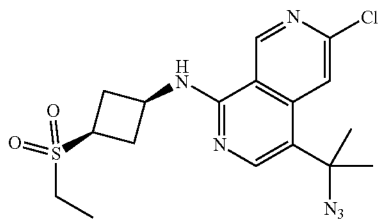 [SMILES: CCS(=O)(=O)[C@H]1C[C@@H](Nc2ncc(C(C)(C)N=[N+]=[N-])c3cc(Cl)ncc23)C1]

Intermediate 60: 4-(2-Azidopropan-2-yl)-6-chloro-N-(cis-3-(ethylsulfonyl)cyclobutyl)-2,7-naphthyridin-1-amine

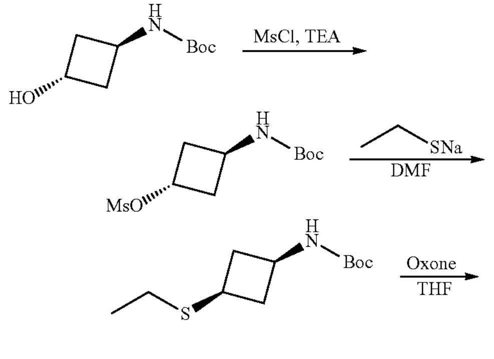

-continued

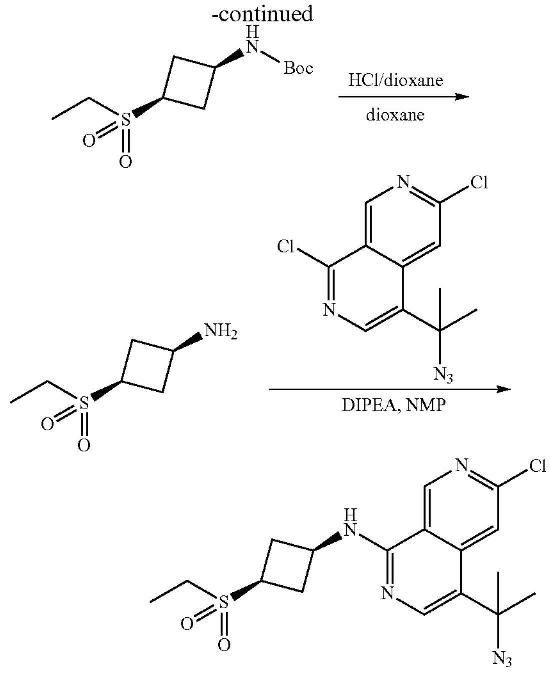

Step 1: trans-3-((tert-Butoxycarbonyl)amino)cyclobutyl Methanesulfonate

To a solution of tert-butyl (trans-3-hydroxycyclobutyl) carbamate (2.00 g, 10.7 mmol) in DCM (20 mL) was added TEA (4.46 mL, 32.1 mmol) and MsCl (2.45 g, 21.4 mmol) in one portion at 0° C. The reaction mixture was stirred at 0° C. for 1 h, then was poured into water (20 mL) and extracted with DCM (20 mL×3). The combined organic layers were washed with water (20 mL×3), dried over anhydrous sodium sulfate, filtered, and concentrated to give the title compound (2.83 g, crude) as a yellow oil that was used directly in the next step.

Step 2: tert-Butyl (cis-3-(ethylthio)cyclobutyl)carbamate

To a solution of trans-3-((tert-butoxycarbonyl)amino)cyclobutyl methanesulfonate (2.83 g, 10.7 mmol) in DMF (20 mL) was added sodium ethanethiolate (1.80 g, 21.3 mmol). The reaction mixture was stirred at 100° C. for 1 h, then was poured into water (20 mL) and extracted with DCM (20 mL×3). The combined organic layers were washed with water (20 mL×3), dried over anhydrous sodium sulfate, filtered, and concentrated to give the title compound (1.40 g, 57% yield) as a yellow solid.

Step 3: tert-Butyl (cis-3-(ethylsulfonyl)cyclobutyl)carbamate

To a solution of tert-butyl (cis-3-(ethylthio)cyclobutyl) carbamate (700 mg, 3.03 mmol) in THF (10 mL) and water (5 mL) was added Oxone® (1.86 g, 3.03 mmol). The reaction mixture was stirred at 25° C. for 1 h, then was poured into water (20 mL) and extracted with EA (20 mL×3). The combined organic layers were washed with water (20 mL×3), dried over anhydrous sodium sulfate, filtered, and concentrated. The residue was purified by column chromatography on silica gel (PE/EA=10:1-1:1) to give the title compound (200 mg, 25% yield) as a yellow solid.

Step 4: cis-3-(Ethylsulfonyl)cyclobutan-1-amine

To a solution of tert-butyl (cis-3-(ethylsulfonyl)cyclobutyl)carbamate (150 mg, 570 umol) in dioxane (2 mL) was added HCl (4 M solution in dioxane, 427 uL) at 0° C. The reaction mixture was stirred at 0° C. for 1 h, then was concentrated to give the title compound (90 mg, crude) as a yellow oil that was used in the next step without further purification.

Step 5: 4-(2-Azidopropan-2-yl)-6-chloro-N-(cis-3-(ethylsulfonyl)cyclobutyl)-2,7-naphthyridin-1-amine To a solution of cis-3-(ethylsulfonyl)cyclobutan-1-amine (90.0 mg, 551 umol) and 4-(2-azidopropan-2-yl)-1,6-dichloro-2,7-naphthyridine (156 mg, 551 umol) in NMP (1 mL) was added DIPEA (214 mg, 1.65 mmol). The reaction mixture was stirred at 25° C. for 2 h, then was poured into water (20 mL) and extracted with EA (20 mL×3). The combined organic layers were washed with water (20 mL×3), dried over anhydrous sodium sulfate, filtered, and concentrated. The residue was purified by column chromatography on silica gel (PE/EA=10:1-1:1) to give the title compound (150 mg, 67% yield) as a yellow oil. MS (ES+) $C_{17}H_{21}ClN_6O_2S$ requires: 409, found: 410[M+H]$^+$.

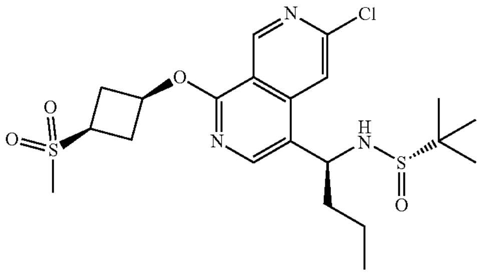

and

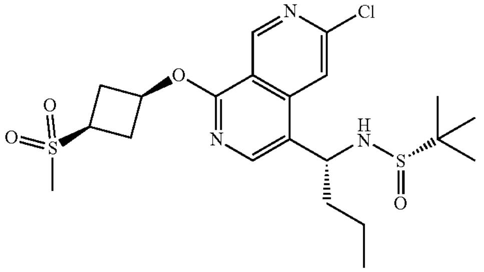

Intermediates 61 and 62: (S)—N—((S)-1-(6-Chloro-1-(cis-3-(methylsulfonyl)cyclobutoxy)-2,7-naphthyridin-4-yl)butyl)-2-methylpropane-2-sulfinamide and (S)—N—((R)-1-(6-chloro-1-(cis-3-(methylsulfonyl)cyclobutoxy)-2,7-naphthyridin-4-yl)butyl)-2-methylpropane-2-sulfinamide

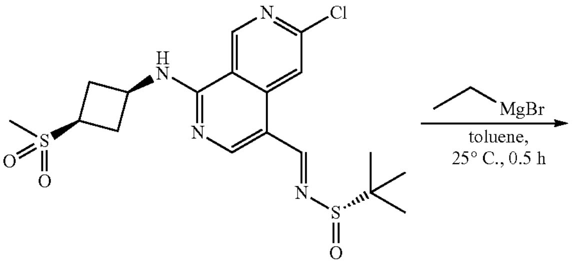

Intermediate 61 and Intermediate 62 each of which is represented by one of the structures shown below:

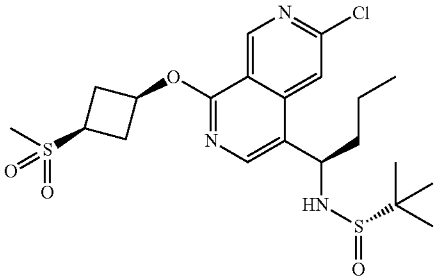

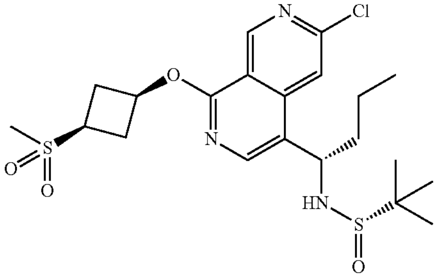

Step 1: (S)—N—((S)-1-(6-Chloro-1-(cis-3-(methylsulfonyl)cyclobutoxy)-2,7-naphthyridin-4-yl)butyl)-2-methylpropane-2-sulfinamide and (S)—N—((R)-1-(6-chloro-1-(cis-3-(methylsulfonyl)cyclobutoxy)-2,7-naphthyridin-4-yl)butyl)-2-methylpropane-2-sulfinamide To a solution of (S)—N—((E)-(6-chloro-1-(cis-3-(methylsulfonyl)cyclobutoxy)-2,7-naphthyridin-4-yl)methylene)-2-methylpropane-2-sulfinamide (Title compound from Step 4 of Intermediate 58, 200 mg, 450 umol) in toluene (10 mL) was added n-PrMgBr (2 M, 1.13 mL) at 25° C. The reaction mixture was stirred at 25° C. for 30 min, then was quenched by addition of saturated aqueous ammonium chloride (20 mL). The mixture was diluted with water (20 mL) and extracted with EA (30 mL×3). The combined organic layers were dried over anhydrous sodium sulfate, filtered, and concentrated to give a residue. The residue was purified by prep-HPLC (column: Phenomenex Luna C18 150×25 mm×10 m; mobile phase: [water (0.225% FA)-ACN]; B %: 40%-70%) to give one of (S)—N—((S)-1-(6-chloro-1-(cis-3-(methylsulfonyl)cyclobutoxy)-2,7-naphthyridin-4-yl)butyl)-2-methylpropane-2-sulfinamide or (S)—N—((R)-1-(6-chloro-1-(cis-3-(methylsulfonyl)cyclobutoxy)-2,7-naphthyridin-4-yl)butyl)-2-methylpropane-2-sulfinamide as the first eluting isomer (Intermediate 61, 25 mg, 5.5% yield) as a white solid and the other one of (S)—N—((S)-1-(6-chloro-1-(cis-3-(methylsulfonyl)cyclobutoxy)-2,7-naphthyridin-4-yl)butyl)-2-methylpropane-2-sulfinamide or (S)—N—((R)-1-(6-chloro-1-(cis-3-(methylsulfonyl)cyclobutoxy)-2,7-naphthyridin-4-yl)butyl)-2-methylpropane-2-sulfinamide as the second eluting isomer (Intermediate 62, 30 mg, 6.7% yield) as a white solid.

Intermediate 61: MS (ES+) $C_{21}H_{30}ClN_3O_4S_2$ requires: 487, found: 488[M+H]$^+$.

Intermediate 62: MS (ES+) $C_{21}H_{30}ClN_3O_4S_2$ requires: 487, found: 488[M+H]$^+$.

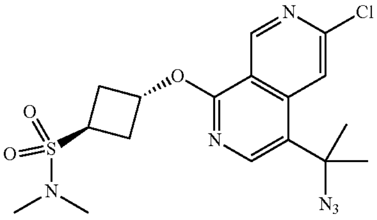

and

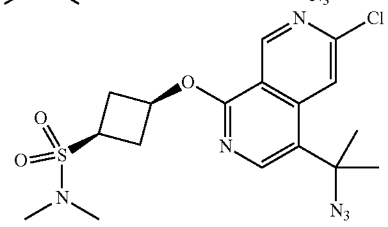

Intermediates 63 and 64: trans-3-((4-(2-Azidopropan-2-yl)-6-chloro-2,7-naphthyridin-1-yl)oxy)-N,N-dimethylcyclobutane-1-sulfonamide and cis-3-((4-(2-Azidopropan-2-yl)-6-chloro-2,7-naphthyridin-1-yl)oxy)-N,N-dimethylcyclobutane-1-sulfonamide

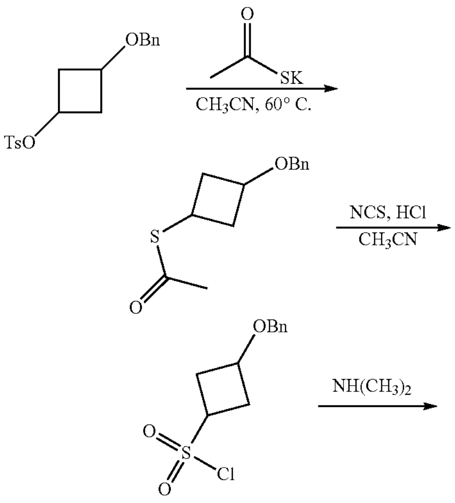

-continued

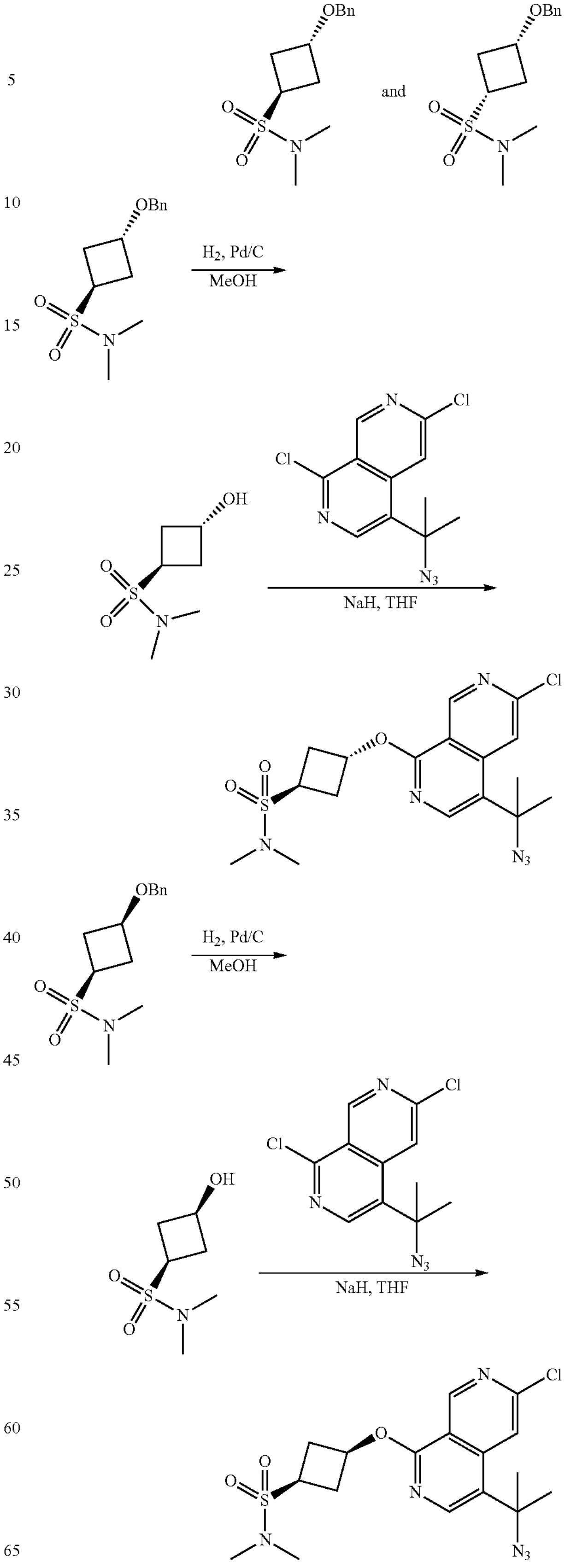

Step 1: S-(3-(benzyloxy)cyclobutyl) ethanethioate

The solution of compound 3-(benzyloxy)cyclobutyl 4-methylbenzenesulfonate (1.00 g, 3.01 mmol) in ACN (1 mL) and DMF (4 mL) was added potassium ethanethioate (2.63 g, 23.0 mmol). The reaction mixture was stirred at 60° C. for 1 h, then was poured into water (20 mL) and extracted with DCM (20 mL×3). The combined organic layers were washed with water (20 mL×3), dried over sodium sulfate, filtered and concentrated to give the title compound (400 mg, 56% yield) as a yellow solid.

Steps 2 and 3: trans-3-(Benzyloxy)-N,N-dimethylcyclobutane-1-sulfonamide and cis-3-(benzyloxy)-N,N-dimethylcyclobutane-1-sulfonamide To a solution of S-(3-(benzyloxy)cyclobutyl) ethanethioate (400 mg, 1.69 mmol) in ACN (20 mL) and concentrated HCl (845 mg, 8.46 mmol) was added NCS (1.02 g, 7.62 mmol) at 0° C. The reaction mixture was stirred at 25° C. for 3 h, then was poured into water (10 mL) and extracted with EA (20 mL×3). The combined organic layers were washed with water (20 mL×3), dried over sodium sulfate, filtered and concentrated. The organic phase was concentrated in vacuo to give a residue. Then dimethylamine (2 M, 3.39 mL) was added to the residue, and the reaction mixture was stirred at 25° C. for 12 h. The reaction mixture was then was poured into water (10 mL) and extracted with EA (20 mL×3). The combined organic layers were washed with water (20 mL×3), dried over anhydrous sodium sulfate, filtered, and concentrated. The residue was purified by prep-HPLC (column: Phenomenex Synergi C18 150*25 mm*10 um; mobile phase: [water(0.225% FA)-ACN]; B %: 11%-41%) to give trans-3-(benzyloxy)-N,N-dimethylcyclobutane-1-sulfonamide (200 mg, 44% yield) as a yellow solid, and cis-3-(benzyloxy)-N,N-dimethylcyclobutane-1-sulfonamide (200 mg, 44% yield) as a yellow solid. trans-3-(Benzyloxy)-N,N-dimethylcyclobutane-1-sulfonamide: $^1$H NMR (400 MHz, $CDCl_3$): δ ppm7.37-7.28 (m, 5H), 4.37 (s, 2H), 4.00-3.94 (m, 1H), 3.32-3.25 (m, 1H), 2.88 (s, 6H), 2.58-2.51 (m, 4H).

cis-3-(Benzyloxy)-N,N-dimethylcyclobutane-1-sulfonamide: $^1$H NMR (400 MHz, $CDCl_3$): δ ppm7.30-7.22 (m, 5H), 4.35 (s, 2H), 4.50-4.40 (m, 1H), 3.75-3.65 (m, 1H), 2.40-2.30 (m, 4H), 1.49 (s, 6H).

Step 4: trans-3-Hydroxy-N,N-dimethylcyclobutane-1-sulfonamide

To a solution of trans-3-(benzyloxy)-N,N-dimethylcyclobutane-1-sulfonamide (200 mg, 743 umol in methanol (10 mL) was added Pd/C (5 mg, 74.25 umol). The reaction mixture was stirred under hydrogen (15 Psi) at 25° C. for 12 h, then was filtered and concentrated to give the title compound (120 mg, 90% yield) as a yellow solid.

Step 5: trans-3-((4-(2-Azidopropan-2-yl)-6-chloro-2,7-naphthyridin-1-yl)oxy)-N,N-dimethylcyclobutane-1-sulfonamide (Intermediate 63)

The title compound was prepared from trans-3-hydroxy-N,N-dimethylcyclobutane-1-sulfonamide and 4-(2-azidopropan-2-yl)-1,6-dichloro-2,7-naphthyridine using a similar procedure as described in Step 1 of Intermediate 22.

Step 6: cis-3-Hydroxy-N,N-dimethylcyclobutane-1-sulfonamide

The title compound was prepared from cis-3-(benzyloxy)-N,N-dimethylcyclobutane-1-sulfonamide using a similar procedure as described in Step 4 above for the trans isomer.

Step 7: cis-3-((4-(2-Azidopropan-2-yl)-6-chloro-2,7-naphthyridin-1-yl)oxy)-N,N-dimethylcyclobutane-1-sulfonamide (Intermediate 64)

The title compound was prepared from cis-3-hydroxy-N,N-dimethylcyclobutane-1-sulfonamide and 4-(2-azidopropan-2-yl)-1,6-dichloro-2,7-naphthyridine using a similar procedure as described in Step 1 of Intermediate 22.

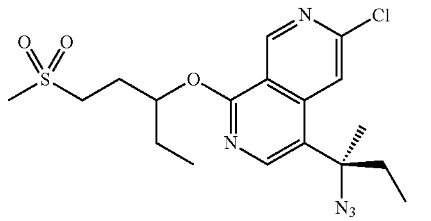 [SMILES: CCC(CCS(C)(=O)=O)Oc1ncc([C@@](C)(CC)N=[N+]=[N-])c2cc(Cl)ncc12]

Intermediate 65: 4—((R)-2-Azidobutan-2-yl)-6-chloro-1-((1-(methylsulfonyl)pentan-3-yl)oxy)-2,7-naphthyridine

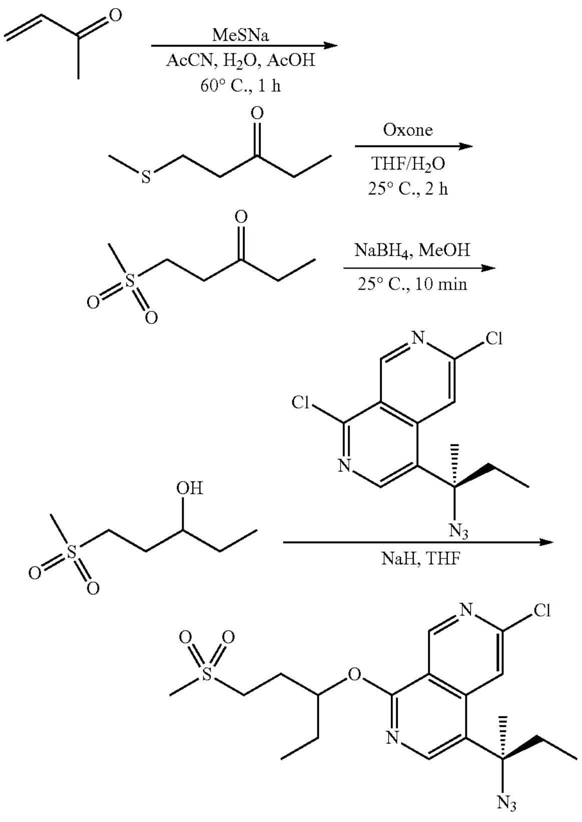

Step 1: 1-(Methylthio)pentan-3-one

To a solution of pent-1-en-3-one (1 g, 11.9 mmol) in ACN (10 mL) and water (10 mL) was added AcOH (785 mg, 13.1 mmol) and sodium methanethiolate (1.25 g, 17.8 mmol). The reaction mixture was stirred at 60° C. for 1 h, then was diluted with water (20 mL) and extracted with EA (20 mL×3). The combined organic layers were dried over anhydrous sodium sulfate, filtered and concentrated to give a residue. The residue was purified by silica gel chromatography (PE/EA=1: 0 to 50: 1) to give the title compound (1.10 g, 70% yield) as yellow oil.

Step 2: 1-(Methylsulfonyl)pentan-3-one

To a solution of 1-(methylthio)pentan-3-one (1.1 g, 8.32 mmol) in THF (40 mL) and water (20 mL) was added Oxone® (6.14 g, 9.98 mmol). The reaction mixture was stirred at 25° C. for 2 h, then was diluted with water (50 mL) and extracted with EA (50 mL×3). The combined organic layers were washed with saturated aqueous sodium sulfite solution (100 mL), dried over anhydrous sodium sulfate, filtered and concentrated to give the title compound (1.30 g, 95% yield) as a white solid that was used in the next step without further purification.

Step 3: 1-(Methylsulfonyl)pentan-3-ol

To a solution of 1-(methylsulfonyl)pentan-3-one (2.60 g, 1.30 mmol) in MeOH (50 mL) was slowly added $NaBH_4$ (449 mg, 11.9 mmol). The reaction mixture was stirred at 25° C. for 10 min, then was diluted with water (100 mL) and concentrated to remove the MeOH. The mixture was then extracted with EA (100 mL×3). The combined organic layers were dried over anhydrous sodium sulfate, filtered and concentrated to give the title compound (650 mg, 50% yield) as a yellow solid that was used in the next step without further purification.

Step 4: 4—((R)-2-Azidobutan-2-yl)-6-chloro-1-((1-(methylsulfonyl)pentan-3-yl)oxy)-2,7-naphthyridine The title compound was prepared from 1-(methylsulfonyl)pentan-3-ol and (R)-4-(2-azidobutan-2-yl)-1,6-dichloro-2,7-naphthyridine using a similar procedure as described in Step 1 of Intermediate 22. MS (ES+) $C18H_{24}ClN_5O_3S$ requires: 425, found: 426$[M+H]^+$.

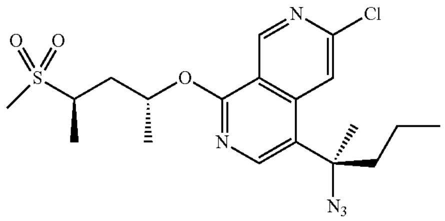

and

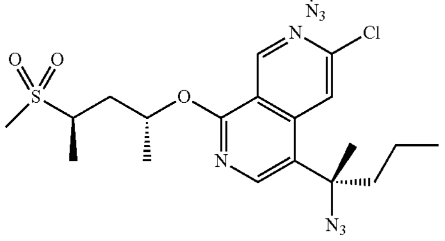

Intermediates 66 and 67: 4—((R)-2-Azidopentan-2-yl)-6-chloro-1-(((2R,4R)-4-(methylsulfonyl)pentan-2-yl)oxy)-2,7-naphthyridine and 4-((S)-2-azidopentan-2-yl)-6-chloro-1-(((2R,4R)-4-(methylsulfonyl)pentan-2-yl)oxy)-2,7-naphthyridine

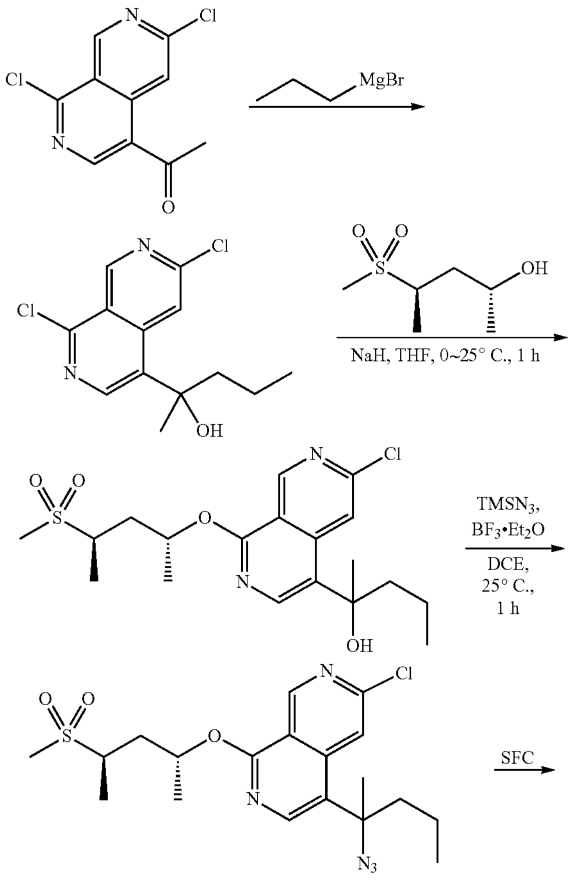

Intermediate 66 and Intermediate 67 each of which is represented by one of the structures shown below:

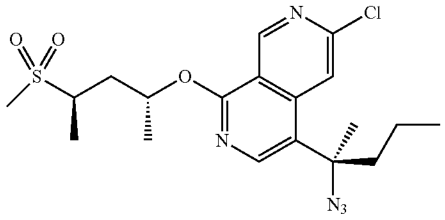

and

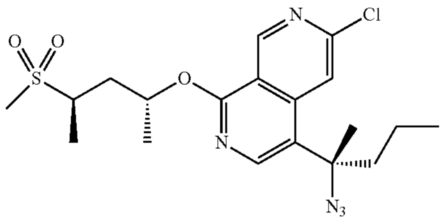

Steps 1-3: 4-(2-Azidopentan-2-yl)-6-chloro-1-(((2R,4R)-4-(methylsulfonyl)pentan-2-yl)oxy)-2,7-naphthyridine The title compound was prepared from 1-(1,6-dichloro-2,7-naphthyridin-4-yl)ethan-1-one (Title compound from Steps 2 of Intermediate 56) and n-PrMgBr using a similar procedure as described in Steps 3-5 of Intermediates 56 and 57.

Step 4: 4—((R)-2-Azidopentan-2-yl)-6-chloro-1-(((2R,4R)-4-(methylsulfonyl)pentan-2-yl)oxy)-2,7-naphthyridine and 4-((S)-2-azidopentan-2-yl)-6-chloro-1-(((2R,4R)-4-(methylsulfonyl)pentan-2-yl)oxy)-2,7-naphthyridine 4-(2-Azidopentan-2-yl)-6-chloro-1-(((2R,4R)-4-(methylsulfonyl)pentan-2-yl)oxy)-2,7-naphthyridine (300 mg, 682 μmol) was separated by SFC (column: Daicel Chiralpak IC (250 mm*30 mm, 10 um); mobile phase: [0.1% $NH_3H_2O$ IPA]; B %: 60%-60%) to give one of 4-((R)-2-azidopentan-2-yl)-6-chloro-1-(((2R,4R)-4-(methylsulfonyl)pentan-2-yl)oxy)-2,7-naphthyridine or 4-((S)-2-azidopentan-2-yl)-6-chloro-1-(((2R,4R)-4-(methylsulfonyl)pentan-2-yl)oxy)-2,7-naphthyridine as the first eluting isomer (Intermediate 66, 135 mg, 44% yield) as a yellow solid and the other one of 4-((R)-2-azidopentan-2-yl)-6-chloro-1-(((2R,4R)-4-(methylsulfonyl)pentan-2-yl)oxy)-2,7-naphthyridine or 4-((S)-2-azidopentan-2-yl)-6-chloro-1-(((2R,4R)-4-(methylsulfonyl)pentan-2-yl)oxy)-2,7-naphthyridine as the second eluting isomer (Intermediate 67, 120 mg, 40% yield) as a yellow solid.

Intermediate 66: MS (ES+) $C_{19}H_{26}ClN_5O_3S$ requires: 439, found: 440[M+H]$^+$.

Intermediate 67: MS (ES+) $C_{19}H_{26}ClN_5O_3S$ requires: 439, found: 440[M+H]$^+$.

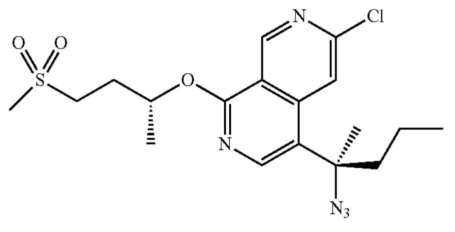

and

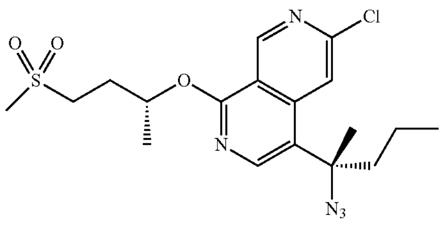

Intermediates 68 and 69: 4—((R)-2-Azidopentan-2-yl)-6-chloro-1-(((R)-4-(methylsulfonyl)butan-2-yl)oxy)-2,7-naphthyridine and 4-((S)-2-azidopentan-2-yl)-6-chloro-1-(((R)-4-(methylsulfonyl)butan-2-yl)oxy)-2,7-naphthyridine

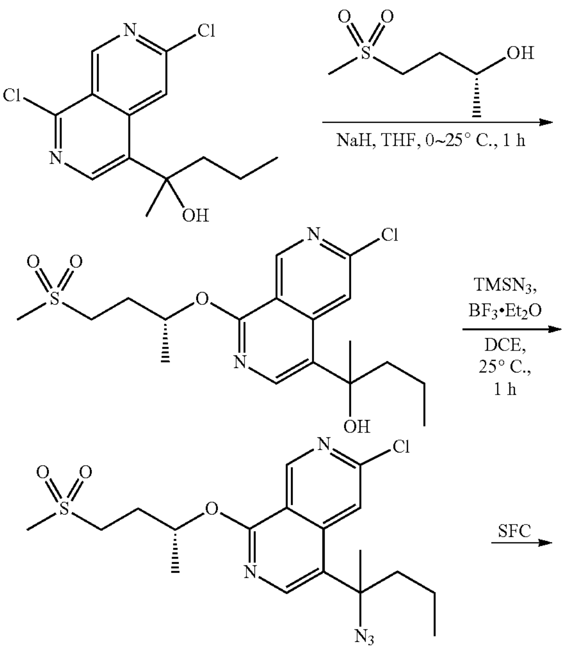

Intermediate 68 and Intermediate 69 each of which is represented by one of the structures shown below:

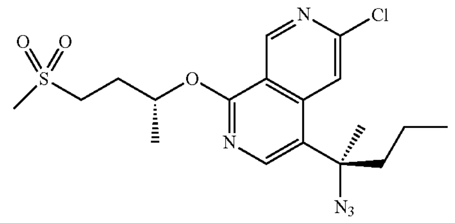

and

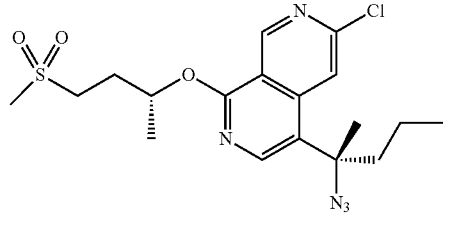

Steps 1-2: 4-(2-Azidopentan-2-yl)-6-chloro-1-(((R)-4-(methylsulfonyl)butan-2-yl)oxy)-2,7-naphthyridine The title compound was prepared from 2-(1,6-dichloro-2,7-naphthyridin-4-yl)pentan-2-ol (Title compound from Step 1 of Intermediate 66) and (R)-4-(methylsulfonyl)butan-2-ol using a similar procedure as described in Steps 4-5 of Intermediates 56 and 57.

Step 3: 4—((R)-2-Azidopentan-2-yl)-6-chloro-1-(((R)-4-(methylsulfonyl)butan-2-yl)oxy)-2,7-naphthyridine and 4-((S)-2-azidopentan-2-yl)-6-chloro-1-(((R)-4-(methylsulfonyl)butan-2-yl)oxy)-2,7-naphthyridine 4-(2-Azidopentan-2-yl)-6-chloro-1-(((R)-4-(methylsulfonyl)butan-2-yl)oxy)-2,7-naphthyridine (350 mg, 822 mol) was separated by SFC (column: DAICEL CHIRALPAK AD (250 mm*30 mm, 10 um); mobile phase: [0.1% $NH_3H_2O$ IPA]; B %: 70%-70%) to give one of 4-((R)-2-azidopentan-2-yl)-6-chloro-1-(((R)-4-(methylsulfonyl)butan-2-yl)oxy)-2,7-naphthyridine or 4-((S)-2-azidopentan-2-yl)-6-chloro-1-(((R)-4-(methylsulfonyl)butan-2-yl)oxy)-2,7-naphthyridine as the first eluting isomer (Intermediate 68, 185 mg, 52% yield) as a colorless oil and the other one of 4-((R)-2-azidopentan-2-yl)-6-chloro-1-(((R)-4-(methylsulfonyl)butan-2-yl)oxy)-2,7-naphthyridine or 4-((S)-2-azidopentan-2-yl)-6-chloro-1-(((R)-4-(methylsulfonyl)butan-2-yl)oxy)-2,7-naphthyridine as the second eluting isomer (Intermediate 69, 190 mg, 54% yield) as a colorless oil.

Intermediate 68: MS (ES+) $C18H_{24}ClN_5O_3S$ requires: 425, found: 426[M+H]$^+$.

Intermediate 69: MS (ES+) $C18H_{24}ClN_5O_3S$ requires: 425, found: 426[M+H]$^+$.

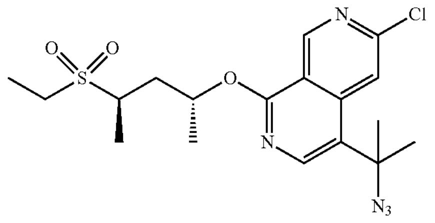 [SMILES: CCS(=O)(=O)[C@H](C)C[C@@H](C)Oc1ncc(C(C)(C)N=[N+]=[N-])c2cc(Cl)ncc12]

Intermediate 70: 4-(2-Azidopropan-2-yl)-6-chloro-1-(((2R,4R)-4-(ethylsulfonyl)pentan-2-yl)oxy)-2,7-naphthyridine

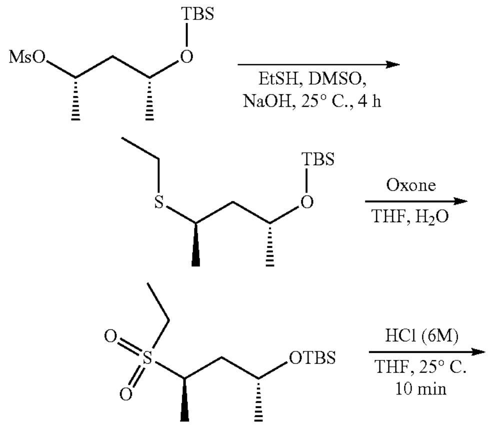

-continued

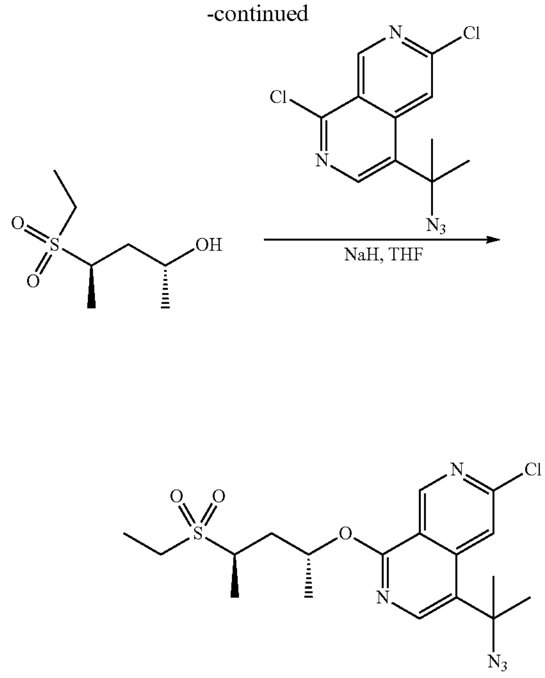

Step 1: tert-Butyl(((2R,4R)-4-(ethylthio)pentan-2-yl)oxy)dimethylsilane

To a solution of EtSH (1.94 g, 31.2 mmol) in DMSO (40 mL) was added NaOH (1.08 g, 27.0 mmol) at 25° C. The suspension was stirred for 0.5 h at 25° C., then (2S,4R)-4-((tert-butyldimethylsilyl)oxy)pentan-2-yl methanesulfonate (4 g, 13.5 mmol) in DMSO (10 mL) was added to the reaction mixture. The reaction mixture was stirred at 25° C. for 3.5 h, then was diluted with water (40 mL) and extracted with EA (60 mL×4). The combined organic layers were washed with brine (40 mL×3), dried over anhydrous sodium sulfate, filtered and concentrated to give the title compound (3.6 g, crude) as a white oil that was used in the next step directly.

Steps 2-4: 4-(2-Azidopropan-2-yl)-6-chloro-1-(((2R,4R)-4-(ethylsulfonyl)pentan-2-yl)oxy)-2,7-naphthyridine The title compound was prepared from tert-butyl(((2R,4R)-4-(ethylthio)pentan-2-yl)oxy)dimethylsilane using a similar procedure as described in Steps 6 and 7 of Intermediate 52 and Step 1 of Intermediate 22. MS (ES+) $C18H_{24}ClN_5O_3S$ requires: 425, found: 426[M+H]$^+$.

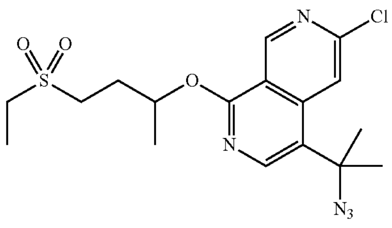 [SMILES: CCS(=O)(=O)CCC(C)Oc1ncc(C(C)(C)N=[N+]=[N-])c2cc(Cl)ncc12]

Intermediate 71: 4-(2-Azidopropan-2-yl)-6-chloro-1-((4-(ethylsulfonyl)butan-2-yl)oxy)-2,7-naphthyridine

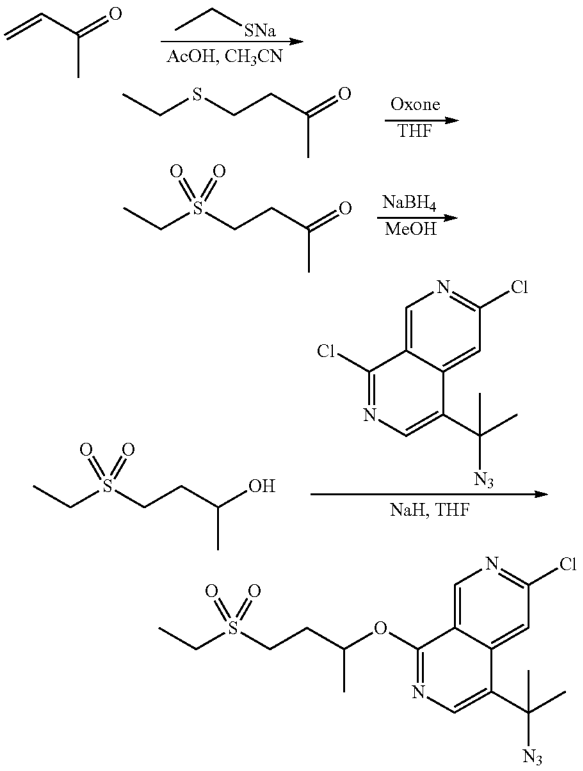

Steps 1-4: 4-(2-Azidopropan-2-yl)-6-chloro-1-((4-(ethylsulfonyl)butan-2-yl)oxy)-2,7-naphthyridine The title compound was prepared from sodium ethanethiolate and but-3-en-2-one using a similar procedure as described in Steps 1-3 of Intermediate 65 and Step 1 of Intermediate 22. MS (ES+) $C_{17}H_{22}ClN_5O_3S$ requires: 411, found: 412[M+H]$^+$.

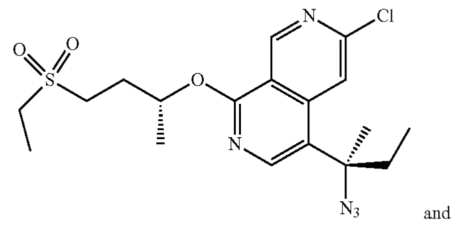

and

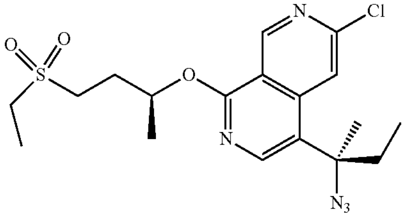

Intermediates 72 and 73: 4—((R)-2-Azidobutan-2-yl)-6-chloro-1-(((R)-4-(ethylsulfonyl)butan-2-yl)oxy)-2,7-naphthyridine and 4-((R)-2-azidobutan-2-yl)-6-chloro-1-(((S)-4-(ethylsulfonyl)butan-2-yl)oxy)-2,7-naphthyridine

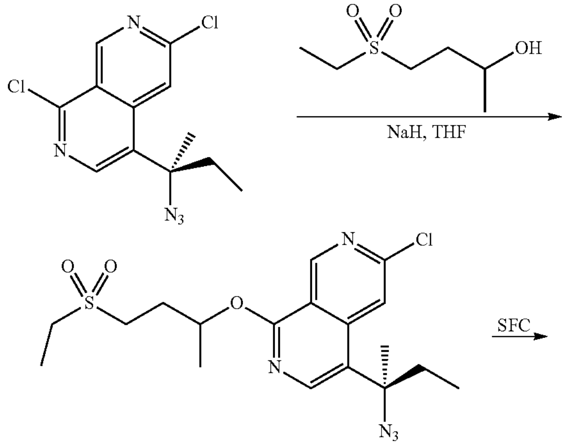

Intermediate 72 and Intermediate 73 each of which is represented by one of the structures shown below:

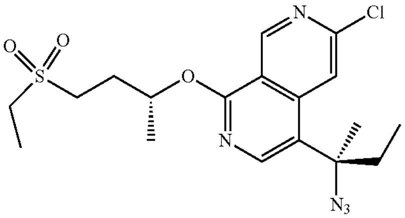

and

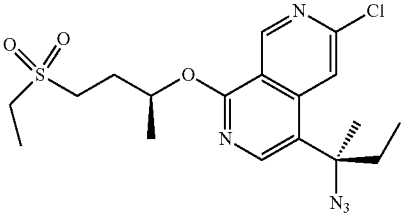

Step 1: 4—((R)-2-Azidobutan-2-yl)-6-chloro-1-((4-(ethylsulfonyl)butan-2-yl)oxy)-2,7-naphthyridine The title compound was prepared from (R)-4-(2-Azidobutan-2-yl)-1,6-dichloro-2,7-naphthyridine and 4-(ethylsulfonyl)butan-2-ol using a similar procedure as described in Step 1 of Intermediate 22.

Step 2: 4—((R)-2-Azidobutan-2-yl)-6-chloro-1-(((R)-4-(ethylsulfonyl)butan-2-yl)oxy)-2,7-naphthyridine and 4-((R)-2-azidobutan-2-yl)-6-chloro-1-(((S)-4-(ethylsulfonyl)butan-2-yl)oxy)-2,7-naphthyridine 4-((R)-2-Azidobutan-2-yl)-6-chloro-1-((4-(ethylsulfonyl)butan-2-yl)oxy)-2,7-naphthyridine (370 mg, 869 μmol) was separated by SFC (column: Daicel Chiralpak IG (250 mm*30 mm, 10 um); mobile phase: [0.1% $NH_3H_2O$ IPA]; B %: 70%-70%) to give one of 4-((R)-2-azidobutan-2-yl)-6-chloro-1-(((R)-4-(ethylsulfonyl)butan-2-yl)oxy)-2,7-naphthyridine or 4-((R)-2-azidobutan-2-yl)-6-chloro-1-(((S)-4-(ethylsulfonyl)butan-2-yl)oxy)-2,7-naphthyridine as the first eluting isomer (Intermediate 72, 140 mg, 38% yield) as colorless oil and the other one of 4-((R)-2-azidobutan-2-yl)-6-chloro-1-(((R)-4-(ethylsulfonyl)butan-2-yl)oxy)-2,7-naphthyridine or 4-((R)-2-azidobutan-2-yl)-6-chloro-1-(((S)-4-(ethylsulfonyl)butan-2-yl)oxy)-2,7-naphthyridine as the second eluting isomer (Intermediate 73, 135 mg, 36% yield) as colorless oil.

Intermediate 72: MS (ES+) $C18H_{24}ClN_5O_3S$ requires: 425, found: 426[M+H]$^+$.

Intermediate 73: MS (ES+) $C18H_{24}ClN_5O_3S$ requires: 425, found: 426[M+H]$^+$.

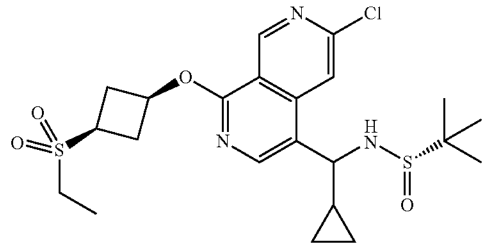 [SMILES: CCS(=O)(=O)[C@H]1C[C@@H](Oc2ncc(C(N[S@@](=O)C(C)(C)C)C3CC3)c3cc(Cl)ncc23)C1]

Intermediate 74: (S)—N-((6-Chloro-1-(cis-3-(ethylsulfonyl)cyclobutoxy)-2,7-naphthyridin-4-yl)(cyclopropyl)methyl)-2-methylpropane-2-sulfinamide

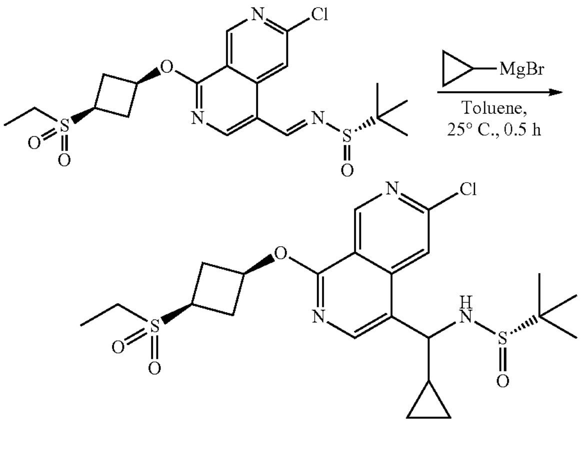

Step 1: (S)—N-((6-Chloro-1-(cis-3-(ethylsulfonyl)cyclobutoxy)-2,7-naphthyridin-4-yl)(cyclopropyl)methyl)-2-methylpropane-2-sulfinamide To a solution of (S)—N—((E)-(6-chloro-1-(cis-3-(ethylsulfonyl)cyclobutoxy)-2,7-naphthyridin-4-yl)methylene)-2-methylpropane-2-sulfinamide (300 mg, 655 umol) in toluene (30 mL) was added cyclopropylmagnesium bromide (0.5 M, 6.55 mL) at 25° C. The reaction mixture was stirred at 25° C. for 0.5 h, then was quenched by addition of saturated aqueous ammonium chloride (20 mL). The mixture was diluted with water (10 mL) and extracted with EA (40 mL×3). The combined organic layers were dried over anhydrous sodium sulfate, filtered and concentrated to give a residue. The residue was purified by flash silica gel chromatography (PE/EA 1:0 to 0:1) to give the title compound (70 mg, 20% yield) as a yellow oil. MS (ES+) $C_{22}H_{30}ClN_3O_4S_2$ requires: 499, found: 500[M+H]$^+$.

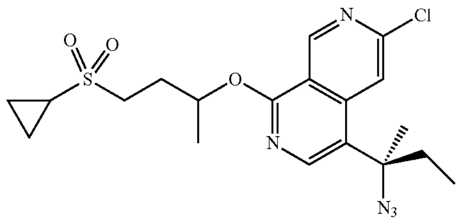 [SMILES: CC[C@@](C)(N=[N+]=[N-])c1cnc(OC(C)CCS(=O)(=O)C2CC2)c2cnc(Cl)cc12]

Intermediate 75: 4—((R)-2-Azidobutan-2-yl)-6-chloro-1-((4-(cyclopropylsulfonyl)butan-2-yl)oxy)-2,7-naphthyridine

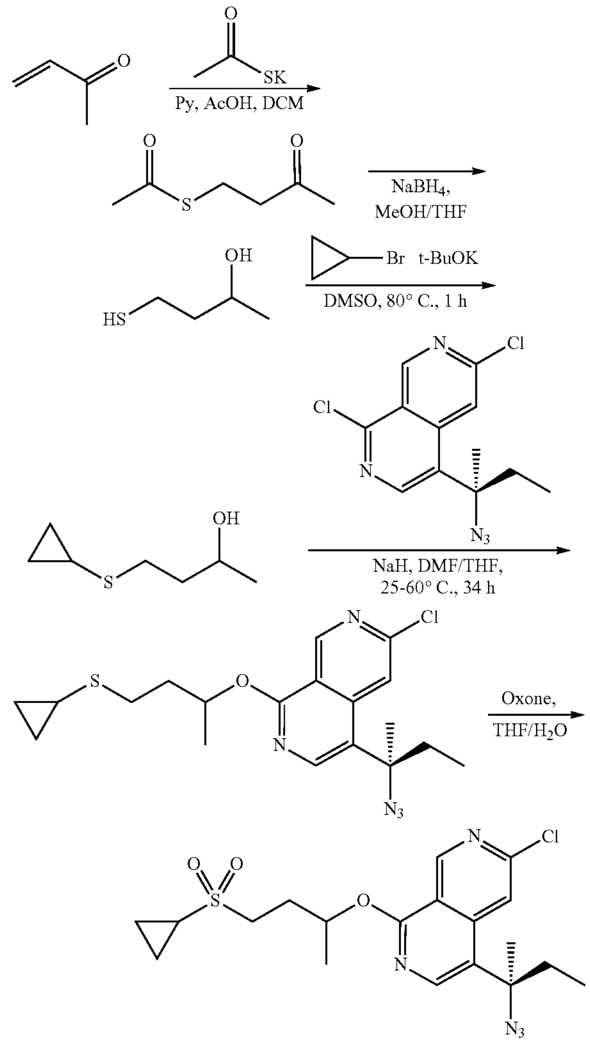

Step 1: S-(3-Oxobutyl) ethanethioate

To a solution of pyridine (11.3 g, 143 mmol) and AcOH (6.51 g, 108 mmol) in DCM (120 mL) was added but-3-en-2-one (5.00 g, 71.3 mmol) and potassium ethanethioate (12.3 g, 108 mmol) at 0° C. The reaction mixture was stirred at 25° C. for 16 h, then the reaction mixture was diluted with DCM (80 mL). The organic layer was washed with aqueous hydrochloric acid (1 M, 200 mL), saturated aqueous sodium bicarbonate solution (250 mL×3), and brine (300 mL). The organic layer was dried over anhydrous sodium sulfate, filtered and concentrated. The residue was purified by silica gel column chromatography (PE/EA=1:0 to 3:1) to give the title compound (5.40 g, 52% yield) as a yellow oil.

Step 2: 4-Mercaptobutan-2-ol

To a solution of S-(3-oxobutyl) ethanethioate (3.00 g, 20.52 mmol) in THF (60 mL) and MeOH (6 mL) was added $NaBH_4$ (1.16 g, 30.8 mmol) at 0° C. The reaction mixture was stirred at 25° C. for 1 h, then was diluted with $H_2O$ (100 mL) and extracted with EA (80 mL×3). The combined organic layers were dried over anhydrous sodium sulfate, filtered and concentrated to give a residue. The residue was purified by silica gel column chromatography (PE/EA=1:0 to 3:1) to give the title compound (2.00 g, 92% yield) as a yellow oil.

Step 3: 4-(Cyclopropylthio)butan-2-ol

To a solution of 4-mercaptobutan-2-ol (200 mg, 1.88 mmol) and bromocyclopropane (453 mg, 3.74 mmol) in DMSO (2 mL) was added potassium tert-butoxide (254 mg, 2.26 mmol). The reaction mixture was stirred at 80° C. for 1 h, then was diluted with water (50 mL) and extracted with EA (30 mL×3). The combined organic layers were washed with brine (30 mL×3), dried over anhydrous sodium sulfate, filtered and concentrated to give a residue. The residue was purified by silica gel column chromatography (PE/EA=1:0 to 3:1) to give the title compound (150 mg, 54% yield) as a colorless oil.

Step 4: 4—((R)-2-Azidobutan-2-yl)-6-chloro-1-((4-(cyclopropylthio)butan-2-yl)oxy)-2,7-naphthyridine To a solution of 4-(cyclopropylthio)butan-2-ol (30.0 mg, 205 μmol) in THF (10 mL) was added NaH (10.0 mg, 250 μmol, 60% purity) at 25° C. After 0.5 h, (R)-4-(2-azidobutan-2-yl)-1,6-dichloro-2,7-naphthyridine (40.0 mg, 135 μmol) was added and the reaction mixture was stirred at 25° C. for 15.5. DMF (0.05 mL) was then added, and the reaction mixture was stirred at 60° C. for 16 h. The reaction mixture was diluted with water (30 mL) and extracted with EA (20 mL×3). The combined organic layers were dried over anhydrous sodium sulfate, filtered and concentrated to give a residue. The residue was purified by silica gel column chromatography (PE/EA=1:0 to 3:1) to give the title compound (40.0 mg, 62% yield) as a yellow oil.

Step 5: 4—((R)-2-Azidobutan-2-yl)-6-chloro-1-((4-(cyclopropylsulfonyl)butan-2-yl)oxy)-2,7-naphthyridine To a solution of 4-((R)-2-azidobutan-2-yl)-6-chloro-1-((4-(cyclopropylthio)butan-2-yl)oxy)-2,7-naphthyridine (70.0 mg, 172 μmol) in THF (10 mL) and $H_2O$ (5 mL) was added Oxone® (212 mg, 345 μmol). The reaction mixture was stirred at 15° C. for 1 h, then was quenched by addition of saturated aqueous sodium sulfite solution (100 mL) and stirred at 25° C. for 10 min. The quenched reaction mixture was extracted with EA (50 mL×3). The combined organic layers were dried over anhydrous sodium sulfate, filtered and concentrated to give a residue. The residue was purified by silica gel column chromatography (PE/EA=1:0 to 1:1) to give the title compound (70.0 mg, 91% yield) as a yellow oil. MS (ES+) $C_{19}H_{24}ClN_5O_3S$ requires: 437, found: 438[M+H]$^+$.

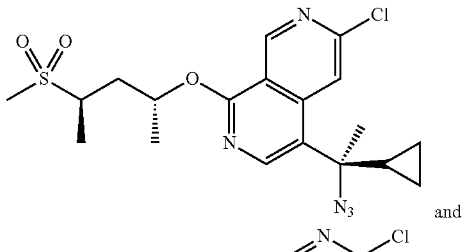

and

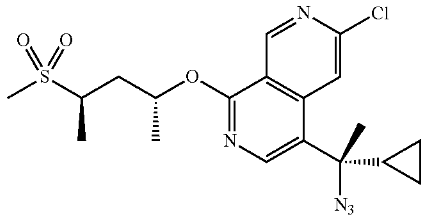

Intermediates 76 and 77: 4—((R)-1-Azido-1-cyclopropylethyl)-6-chloro-1-(((2R,4R)-4-(methylsulfonyl)pentan-2-yl)oxy)-2,7-naphthyridine and 4-((S)-1-azido-1-cyclopropylethyl)-6-chloro-1-(((2R,4R)-4-(methylsulfonyl)pentan-2-yl)oxy)-2,7-naphthyridine and

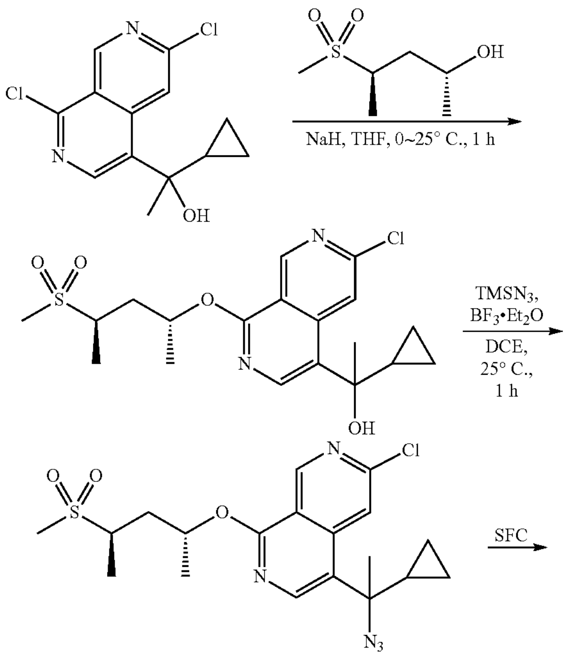

Intermediate 76 and Intermediate 77 each of which is represented by one of the structures shown below:

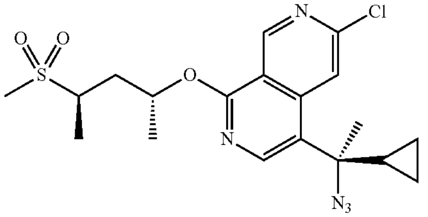

and

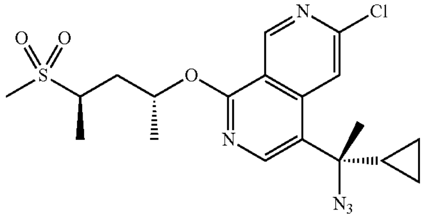

Steps 1-2: 4-(1-Azido-1-cyclopropylethyl)-6-chloro-1-(((2R,4R)-4-(methylsulfonyl)pentan-2-yl)oxy)-2,7-naphthyridine The title compound was prepared from 1-cyclopropyl-1-(1,6-dichloro-2,7-naphthyridin-4-yl)ethan-1-ol (Title compound from Step 3 of Intermediate 56) and (2R,4R)-4-(methylsulfonyl) pentan-2-ol (Step 7, Intermediate 52) using a similar procedure as described in Steps 4 and 5 of Intermediates 56 and 57. MS (ES+) $C_{19}H_{24}ClN_5O_3S$ requires: 437, found: 438$[M+H]^+$.

Step 3: 4—((R)-1-Azido-1-cyclopropylethyl)-6-chloro-1-(((2R,4R)-4-(methylsulfonyl)pentan-2-yl) oxy)-2,7-naphthyridine and 4-((S)-1-azido-1-cyclopropylethyl)-6-chloro-1-(((2R,4R)-4-(methylsulfonyl)pentan-2-yl)oxy)-2,7-naphthyridine 4-(1-Azido-1-cyclopropylethyl)-6-chloro-1-(((2R,4R)-4-(methylsulfonyl)pentan-2-yl)oxy)-2,7-naphthyridine (360 mg, 822 μmol) was separated by SFC (column: Daicel Chiralpak IG (250 mm×30 mm, 10 um); mobile phase: [0.1% $NH_3H_2O$ MeOH]; B %: 60%-60%) to give one of 4-((R)-1-azido-1-cyclopropylethyl)-6-chloro-1-(((2R,4R)-4-(methylsulfonyl)pentan-2-yl)oxy)-2,7-naphthyridine or 4-((S)-1-azido-1-cyclopropylethyl)-6-chloro-1-(((2R,4R)-4-(methylsulfonyl)pentan-2-yl)oxy)-2,7-naphthyridine as the first eluting isomer (Intermediate 76, (120 mg, 32% yield) as a yellow oil and the other one of 4-((R)-1-azido-1-cyclopropylethyl)-6-chloro-1-(((2R,4R)-4-(methylsulfonyl)pentan-2-yl)oxy)-2,7-naphthyridine or 4-((S)-1-azido-1-cyclopropylethyl)-6-chloro-1-(((2R,4R)-4-(methylsulfonyl) pentan-2-yl)oxy)-2,7-naphthyridine as the second eluting isomer (Intermediate 77, 170 mg, 44% yield) as a yellow oil.

Intermediate 76: MS (ES+) $C_{19}H_{24}ClN_5O_3S$ requires: 437, found: 438$[M+H]^+$.

Intermediate 77: MS (ES+) $C_{19}H_{24}ClN_5O_3S$ requires: 437, found: 438$[M+H]^+$.

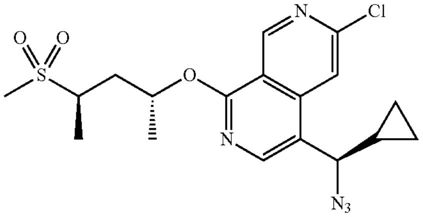

and

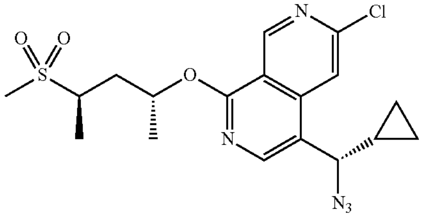

Intermediates 78 and 79: 4—((R)-Azido(cyclopropyl)methyl)-6-chloro-1-(((2R,4R)-4-(methylsulfonyl)pentan-2-yl)oxy)-2,7-naphthyridine and 4-((S)-azido(cyclopropyl)methyl)-6-chloro-1-(((2R,4R)-4-(methylsulfonyl)pentan-2-yl)oxy)-2,7-naphthyridine

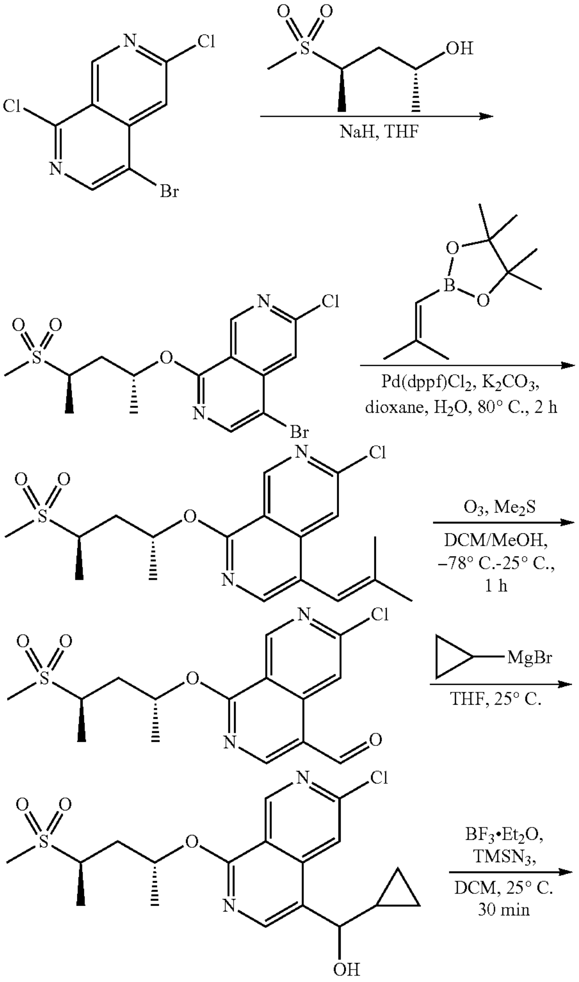

-continued

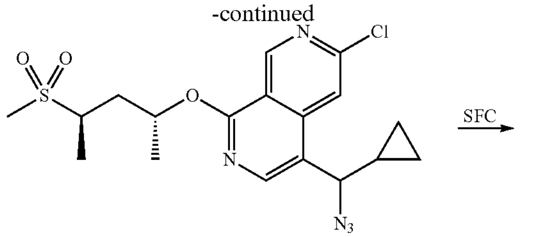

Intermediate 78 and Intermediate 79 each of which is represented by one of the structures shown below:

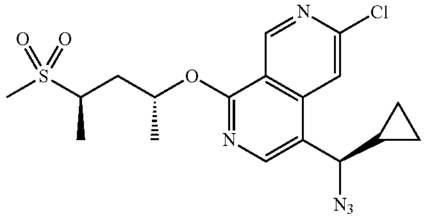

and

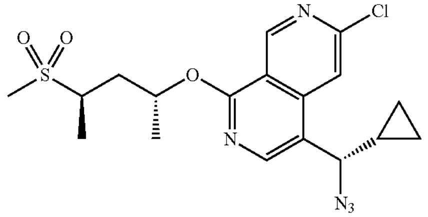

Step 1: 4-Bromo-6-chloro-1-(((2R,4R)-4-(methylsulfonyl)pentan-2-yl)oxy)-2,7-naphthyridine The title compound was prepared from 4-bromo-1,6-dichloro-2,7-naphthyridine and (2R,4R)-4-(methylsulfonyl)pentan-2-olusing a similar procedure as described in Step 1 of Intermediate 22.

Step 2: 6-Chloro-4-(2-methylprop-1-en-1-yl)-1-(((2R,4R)-4-(methylsulfonyl)pentan-2-yl)oxy)-2,7-naphthyridine A mixture of 4-bromo-6-chloro-1-(((2R,4R)-4-(methylsulfonyl)pentan-2-yl)oxy)-2,7-naphthyridine (890 mg, 2.18 mmol, 1 eq), 4,4,5,5-tetramethyl-2-(2-methylprop-1-en-1-yl)-1,3,2-dioxaborolane (397.44 mg, 2.18 mmol, 1 eq), Pd(dppf)$Cl_2$ (159.73 mg, 218.29 umol, 0.1 eq) and $K_2CO_3$ (603.40 mg, 4.37 mmol, 2 eq) in $H_2O$ (2 mL) and dioxane (10 mL) was degassed and purged with $N_2$ 3 times, and then the mixture was stirred at 80° C. for 2 h. The reaction mixture was diluted with $H_2O$ (80 mL) and extracted with EA (100 mL*3). The combined organic layers were dried over anhydrous sodium sulfate, filtered and concentrated to give a residue. The residue was purified by column chromatography ($SiO_2$, PE/EA=10/1 to 3/1) to give the title compound (620 mg, 74.18% yield) as a yellow oil.

Step 3: 6-Chloro-1-(((2R,4R)-4-(methylsulfonyl)pentan-2-yl)oxy)-2,7-naphthyridine-4-carbaldehyde Ozone was bubbled into a solution of 6-chloro-4-(2-methylprop-1-en-1-yl)-1-(((2R,4R)-4-(methylsulfonyl)pentan-2-yl)oxy)-2,7-naphthyridine (520 mg, 1.36 mmol, 1 eq) in DCM (60 mL) and MeOH (6 mL) at −78° C. for 10 minutes. The reaction mixture was then flushed with nitrogen and $Me_2S$ (590.63 mg, 9.51 mmol, 698.14 uL, 7 eq) was added to the mixture. The reaction mixture was allowed to warm to 25° C. and stirred for 50 min, then was concentrated to give the title compound (580 mg, crude) as a yellow oil that was used in the next step without further purification.

Step 4: (6-Chloro-1-(((2R,4R)-4-(methylsulfonyl)pentan-2-yl)oxy)-2,7-naphthyridin-4-yl)(cyclopropyl)methanol To a solution of 6-chloro-1-(((2R,4R)-4-(methylsulfonyl)pentan-2-yl)oxy)-2,7-naphthyridine-4-carbaldehyde (530 mg, 1.49 mmol, 1 eq) in THF (10 mL) was added cyclopropylmagnesium bromide (0.5 M, 5.94 mL, 2 eq) at 0° C. The reaction mixture was stirred at 25° C. for 30 min, then was quenched by addition of aqueous ammonium chloride solution (20 mL) at 25° C. and extracted with ethyl acetate (50 mL×3). The combined organic layers were dried over anhydrous sodium sulfate, filtered and concentrated to give the title compound (580 mg, crude) as a yellow solid that was used in the next step without further purification. MS (ES+) $C18H_{23}ClN_2O_4S$ requires: 398, found: 399[M+H]$^+$.

Step 5: 4-(Azido(cyclopropyl)methyl)-6-chloro-1-(((2R,4R)-4-(methylsulfonyl)pentan-2-yl)oxy)-2,7-naphthyridine To a solution of (6-chloro-1-(((2R,4R)-4-(methylsulfonyl)pentan-2-yl)oxy)-2,7-naphthyridin-4-yl)(cyclopropyl)methanol (530 mg, 1.33 mmol, 1 eq) in DCE (10 mL) was added $TMSN_3$ (765.36 mg, 6.64 mmol, 873.70 uL, 5 eq) and $BF_3{\cdot}Et_2O$ (377.15 mg, 2.66 mmol, 327.96 uL, 2 eq). The mixture was stirred at 25° C. for 10 min, then was diluted with $H_2O$ (30 mL) and extracted with DCM (30 mL×3). The combined organic layers were dried over anhydrous sodium sulfate, filtered and concentrated to give a residue. The residue was purified by column chromatography ($SiO_2$, PE/EA=10/1 to 1/1) and prep-HPLC (column: Phenomenex Luna C18 150*40 mm*15 um; mobile phase: [water(0.1% TFA)-ACN]; B %: 44%-74%, 11 min) to give the title compound (120 mg, 21% yield) as a light yellow solid. MS (ES+) $C18H_{22}ClN_5O_3S$ requires: 423, found: 424M+H]$^+$.

Step 6: 4—((R)-Azido(cyclopropyl)methyl)-6-chloro-1-(((2R,4R)-4-(methylsulfonyl)pentan-2-yl)oxy)-2,7-naphthyridine and 4-((S)-azido(cyclopropyl)methyl)-6-chloro-1-(((2R,4R)-4-(methylsulfonyl)pentan-2-yl)oxy)-2,7-naphthyridine 4-(Azido(cyclopropyl)methyl)-6-chloro-1-(((2R,4R)-4-(methylsulfonyl)pentan-2-yl)oxy)-2,7-naphthyridine (120 mg, 283 umol, 1 eq) was separated by SFC (column: Daicel ChiralPak IG (250*30 mm, 10 um); mobile phase: [0.1% $NH_3H_2O$ MeOH]; B %: 70%-70%) to give one of 4-((R)-azido(cyclopropyl)methyl)-6-chloro-1-(((2R,4R)-4-(methylsulfonyl)pentan-2-yl)oxy)-2,7-naphthyridine or 4-((S)-azido(cyclopropyl)methyl)-6-chloro-1-(((2R,4R)-4-(methylsulfonyl)pentan-2-yl)oxy)-2,7-naphthyridine as the first eluting isomer (Intermediate 78, 40 mg, 33% yield) as a white solid and the other one of 4-((R)-azido(cyclopropyl)methyl)-6-chloro-1-(((2R,4R)-4-(methylsulfonyl)pentan-2-yl)oxy)-2,7-naphthyridine or 4-((S)-azido(cyclopropyl)methyl)-6-chloro-1-(((2R,4R)-4-(methylsulfonyl)pentan-2- yl)oxy)-2,7-naphthyridine as the second eluting isomer (Intermediate 79, 35 mg, 29% yield) as a white solid Intermediate 78: MS (ES+) $C18H_{22}ClN_5O_3S$ requires: 423, found: 424[M+H]$^+$.

Intermediate 79: MS (ES+) $C18H_{22}ClN_5O_3S$ requires: 423, found: 424[M+H]$^+$.

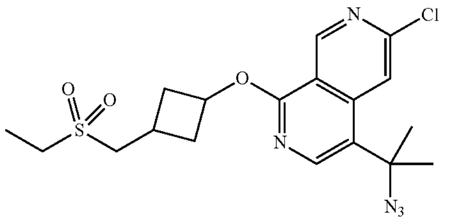 [SMILES: CCS(=O)(=O)CC1CC(Oc2ncc(C(C)(C)N=[N+]=[N-])c3cc(Cl)ncc23)C1]

Intermediate 80: 4-(2-Azidopropan-2-yl)-6-chloro-1-(3-((ethylsulfonyl)methyl)cyclobutoxy)-2,7-naphthyridine

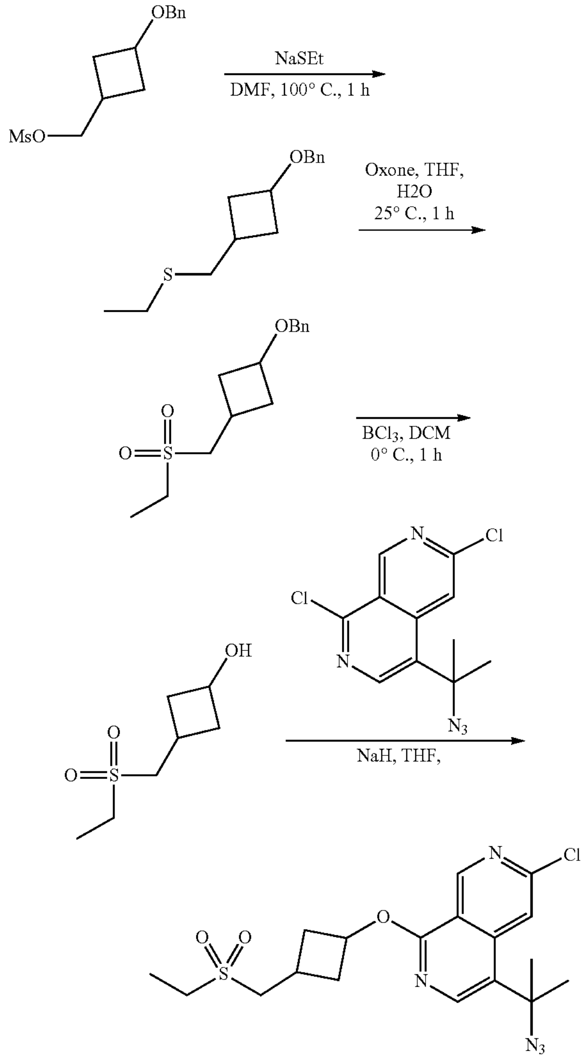

Step 1: ((3-(Benzyloxy)cyclobutyl)methyl)(ethyl)sulfane

To a solution of (3-(benzyloxy)cyclobutyl)methyl methanesulfonate (2.4 g, 8.88 mmol, 1 eq) in DMF (30 mL) was added NaSEt (1.49 g, 17.76 mmol, 2 eq). The reaction mixture was stirred at 100° C. for 1 h, then was quenched by addition of saturated aqueous sodium hypochlorite solution (30 mL) at 25° C. The mixture was extracted with EA (50 mL×3) and the combined organic layers were washed with brine (50 mL*3), dried over anhydrous sodium sulfate, filtered and concentrated to give the title compound (1.6 g, crude) as a colorless oil that was used in the next step without further purification.

Steps 2-4: 4-(2-Azidopropan-2-yl)-6-chloro-1-(3-((ethylsulfonyl)methyl)cyclobutoxy)-2,7-naphthyridine The title compound was prepared using a similar procedure as described in Steps 5-7 of Intermediate 32. MS (ES+) $C18H_{22}ClN_5O_3S$ requires: 423, found: 424[M+H]$^+$.

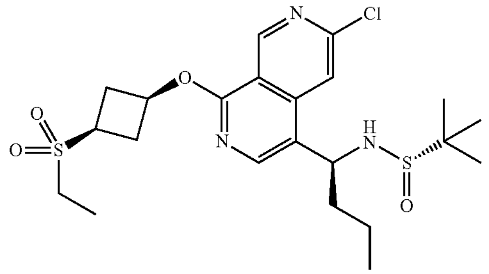

and

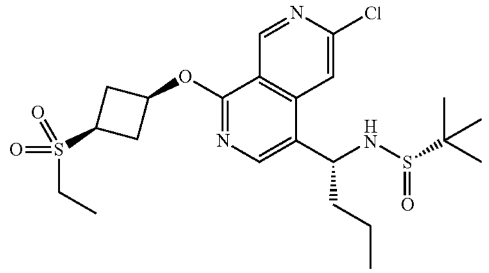

Intermediates 81 and 82: (S)—N—((S)-1-(6-Chloro-1-(cis-3-(ethylsulfonyl)cyclobutoxy)-2,7-naphthyridin-4-yl)butyl)-2-methylpropane-2-sulfinamide and (S)—N—((R)-1-(6-chloro-1-(cis-3-(ethylsulfonyl)cyclobutoxy)-2,7-naphthyridin-4-yl)butyl)-2-methylpropane-2-sulfinamide

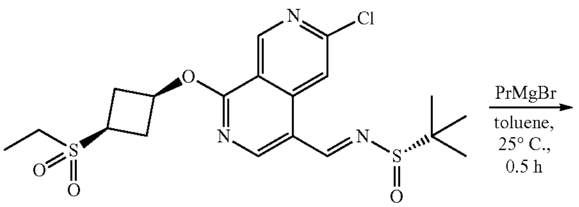

Intermediate 81 and Intermediate 82 each of which is represented by the structures shown below:

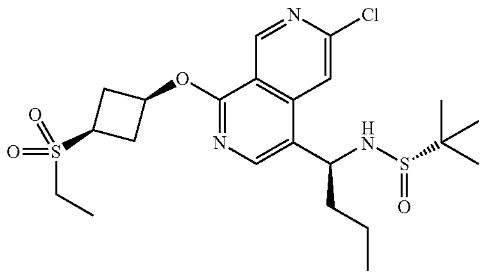

and

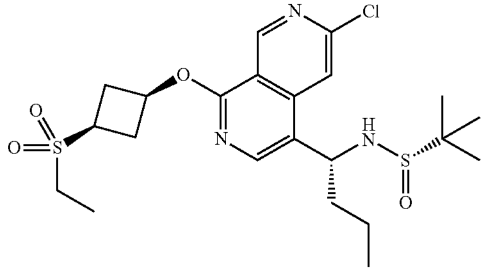

Step 1: (S)—N—((S)-1-(6-Chloro-1-(cis-3-(ethylsulfonyl)cyclobutoxy)-2,7-naphthyridin-4-yl)butyl)-2-methylpropane-2-sulfinamide and (S)—N—((R)-1-(6-chloro-1-(cis-3-(ethylsulfonyl)cyclobutoxy)-2,7-naphthyridin-4-yl)butyl)-2-methylpropane-2-sulfinamide To a solution of (S)—N—((E)-(6-chloro-1-(cis-3-(ethylsulfonyl)cyclobutoxy)-2,7-naphthyridin-4-yl)methylene)-2-methylpropane-2-sulfinamide (300 mg, 655 umol) in toluene (20 mL) was added PrMgBr (2 M, 1.64 mL) at 25° C. The reaction mixture was stirred at 25° C. for 1 h, then saturated aqueous ammonium chloride (20 mL) was added. The mixture was diluted with water (10 mL) and extracted with EA (40 mL×3). The combined organic layers were dried over anhydrous sodium sulfate, filtered and concentrated to give a residue. The residue was purified by prep-HPLC (column: Phenomenex Gemini-NX C18 75×30 mm×3 m; mobile phase: [water (0.225% FA)-ACN]; B %: 48%-58%) to give one of (S)—N—((S)-1-(6-chloro-1-(cis-3-(ethylsulfonyl)cyclobutoxy)-2,7-naphthyridin-4-yl)butyl)-2-methylpropane-2-sulfinamide or (S)—N—((R)-1-(6-chloro-1-(cis-3-(ethylsulfonyl)cyclobutoxy)-2,7-naphthyridin-4-yl)butyl)-2-methylpropane-2-sulfinamide as the first eluting isomer (Intermediate 81, 50 mg, 15% yield) and the other one of (S)—N—((S)-1-(6-chloro-1-(cis-3-(ethylsulfonyl)cyclobutoxy)-2,7-naphthyridin-4-yl)butyl)-2-methylpropane-2-sulfinamide or (S)—N—((R)-1-(6-chloro-1-(cis-3-(ethylsulfonyl)cyclobutoxy)-2,7-naphthyridin-4-yl)butyl)-2-methylpropane-2-sulfinamide as the second eluting isomer (Intermediate 82, 40 mg, 12% yield) as a white solid.

Intermediate 81: MS (ES+) $C_{22}H_{32}ClN_3O_4S_2$ requires: 501, found: 502[M+H]$^+$.

Intermediate 82: MS (ES+) $C_{22}H_{32}ClN_3O_4S_2$ requires: 501, found: 502[M+H]$^+$.

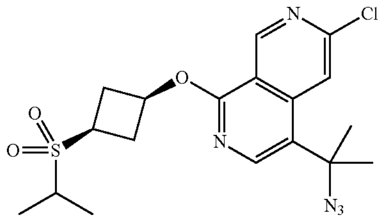 [SMILES: CC(C)S(=O)(=O)[C@H]1C[C@@H](Oc2ncc(C(C)(C)N=[N+]=[N-])c3cc(Cl)ncc23)C1]

Intermediate 83: 4-(2-Azidopropan-2-yl)-6-chloro-1-(cis-3-(isopropylsulfonyl)cyclobutoxy)-2,7-naphthyridine

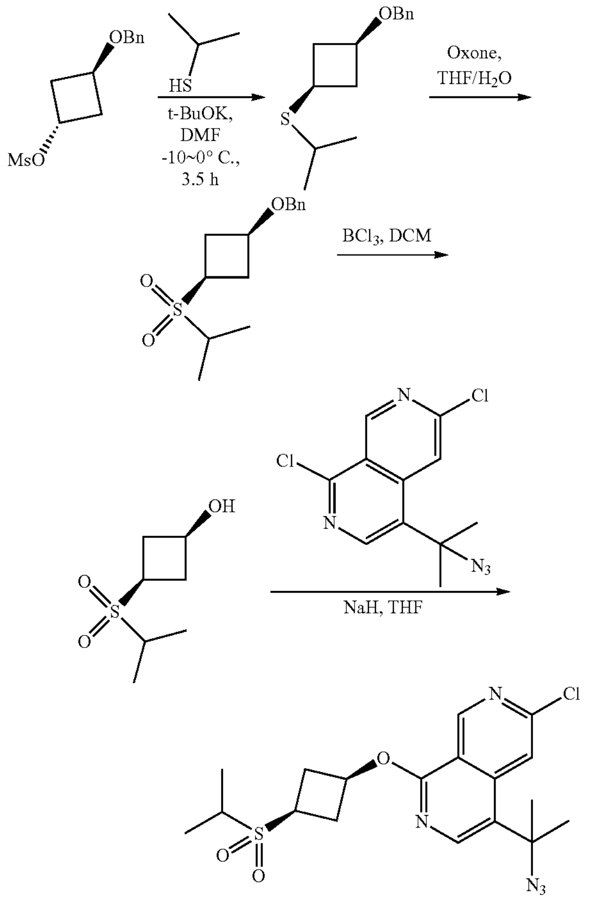

Step 1: (cis-3-(Benzyloxy)cyclobutyl)(isopropyl)sulfane

To a solution of propane-2-thiol (579 mg, 7.61 mmol) in DMF (30 mL) was added t-BuOK (1.14 g, 10.1 mmol) at −10° C. The reaction mixture was stirred at −10° C. for 0.5 h, then trans-3-(benzyloxy)cyclobutyl methanesulfonate (1.3 g, 5.07 mmol) in DMF (3 mL) was added. The reaction mixture was stirred at −10~0° C. for 3 h, then was diluted with saturated aqueous $NH_4Cl$ (300 mL) and extracted with EA (200 mL). The organic layer was washed with brine (3×50 mL), dried over $Na_2SO_4$, filtered and concentrated. The residue was purified by prep-HPLC (column: Phenomenex Luna C18 150*40 mm*15 um; mobile phase: [water (0.225% FA)-ACN]; B %: 65%-72%, 10 min) to give the title compound (311 mg, 26% yield) as colorless oil.

Steps 2-4: 4-(2-Azidopropan-2-yl)-6-chloro-1-(cis-3-(isopropylsulfonyl)cyclobutoxy)-2,7-naphthyridine The title compound was prepared using a similar procedure as described in Steps 5-7 of Intermediate 32.

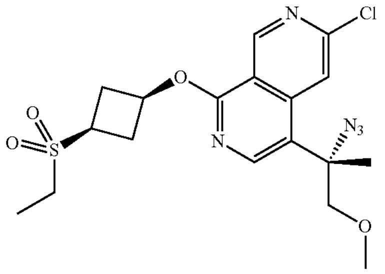 [SMILES: CCS(=O)(=O)[C@H]1C[C@@H](Oc2ncc([C@@](C)(COC)N=[N+]=[N-])c3cc(Cl)ncc23)C1]

Intermediate 84: 4-((S)-2-Azido-1-methoxypropan-2-yl)-6-chloro-1-(cis-3-(ethylsulfonyl)cyclobutoxy)-2,7-naphthyridine

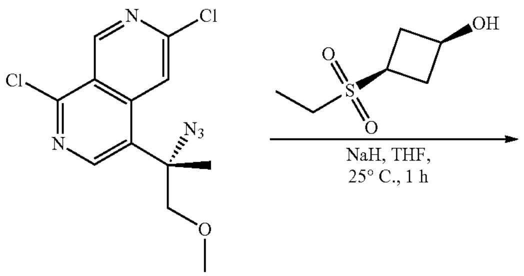

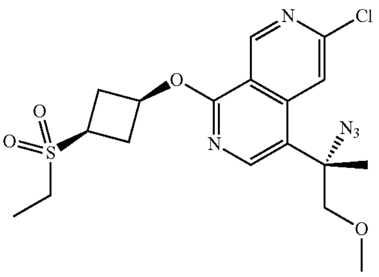

Step 1: 4-((S)-2-Azido-1-methoxypropan-2-yl)-6-chloro-1-(cis-3-(ethylsulfonyl)cyclobutoxy)-2,7-naphthyridine The title compound was prepared from (S)-4-(2-azido-1-methoxypropan-2-yl)-1,6-dichloro-2,7-naphthyridine and cis-3-(ethylsulfonyl)cyclobutan-1-ol using a similar procedure as described above for Intermediate 22. MS (ES+) C18$H_{22}ClN_5O_4S$ requires: 439, found: 440$[M+H]^+$.

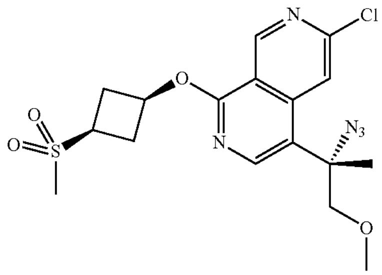

Intermediate 85: 4-((S)-2-Azido-1-methoxypropan-2-yl)-6-chloro-1-(cis-3-(methylsulfonyl)cyclobutoxy)-2,7-naphthyridine

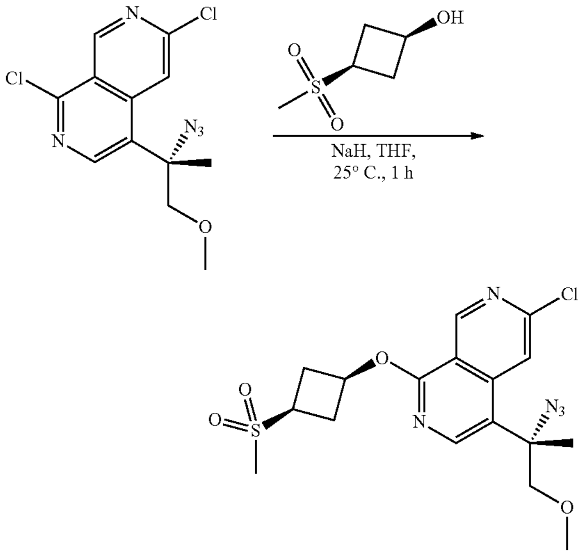

Step 1: 4-((S)-2-Azido-1-methoxypropan-2-yl)-6-chloro-1-(cis-3-(ethylsulfonyl)cyclobutoxy)-2,7-naphthyridine The title compound was prepared from (S)-4-(2-azido-1-methoxypropan-2-yl)-1,6-dichloro-2,7-naphthyridine and cis-3-(methylsulfonyl)cyclobutan-1-ol using a similar procedure as described above for Intermediate 22. MS (ES+) $C_{17}H_{20}ClN_5O_4S$ requires: 425, found: 426$[M+H]^+$.

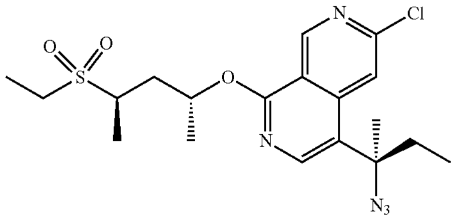 [SMILES: CC[C@@](C)(N=[N+]=[N-])c1cnc(O[C@H](C)C[C@@H](C)S(=O)(=O)CC)c2cnc(Cl)cc12]

Intermediate 86: 4—((R)-2-Azidobutan-2-yl)-6-chloro-1-(((2R,4R)-4-(ethylsulfonyl)pentan-2-yl)oxy)-2,7-naphthyridine

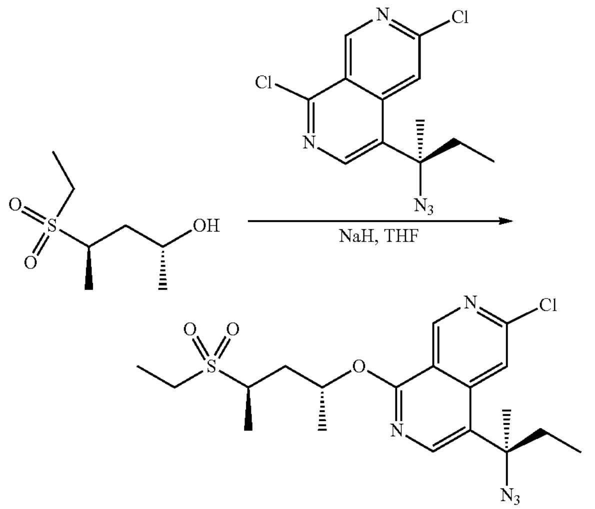

Step 2: 4—((R)-2-Azidobutan-2-yl)-6-chloro-1-(((2R,4R)-4-(ethylsulfonyl)pentan-2-yl)oxy)-2,7-naphthyridine The title compound was prepared from (R)-4-(2-azidobutan-2-yl)-1,6-dichloro-2,7-naphthyridine and (2R,4R)-4-(ethylsulfonyl)pentan-2-ol (Step 7, Intermediate 52) using a similar procedure as described in Step 1 of Intermediate 22. MS (ES+) $C_{19}H_{26}ClN_5O_3S$ requires: 439, found: 440[M+H]$^+$.

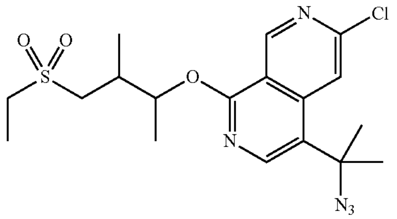 [SMILES: CCS(=O)(=O)CC(C)C(C)Oc1ncc(C(C)(C)N=[N+]=[N-])c2cc(Cl)ncc12]

Intermediate 87: 4-(2-Azidopropan-2-yl)-6-chloro-1-((4-(ethylsulfonyl)-3-methylbutan-2-yl)oxy)-2,7-naphthyridine

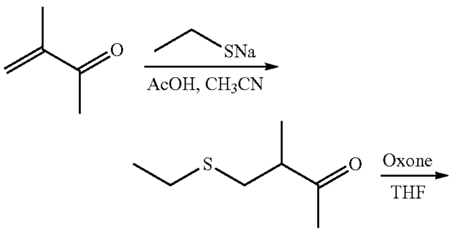

-continued

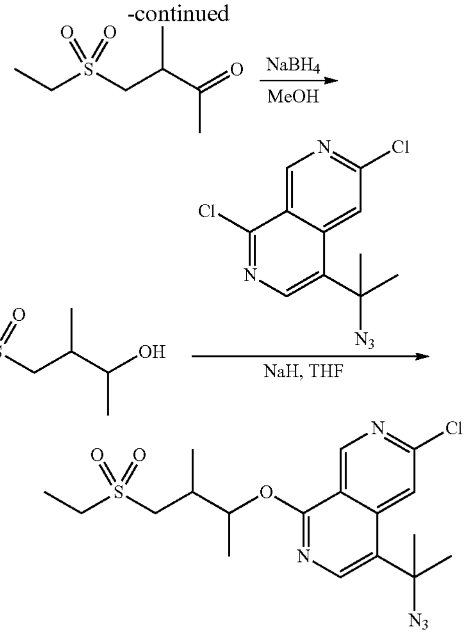

Steps 1-4: 4-(2-Azidopropan-2-yl)-6-chloro-1-((4-(ethylsulfonyl)-3-methylbutan-2-yl)oxy)-2,7-naphthyridine The title compound was prepared from sodium ethanethiolate and but-3-en-2-one using a similar procedure as described in Steps 1-3 of Intermediate 65 and Step 1 of Intermediate 22. MS (ES+) $C18H_{24}ClN_5O_3S$ requires: 425, found: 426[M+H]$^+$.

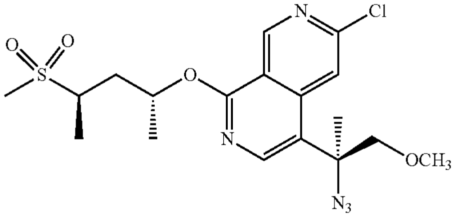 [SMILES: COC[C@@](C)(N=[N+]=[N-])c1cnc(O[C@H](C)C[C@@H](C)S(C)(=O)=O)c2cnc(Cl)cc12]

Intermediate 88: 4—((S)-2-Azido-1-methoxypropan-2-yl)-6-chloro-1-(((2R,4R)-4-(methylsulfonyl)pentan-2-yl)oxy)-2,7-naphthyridine

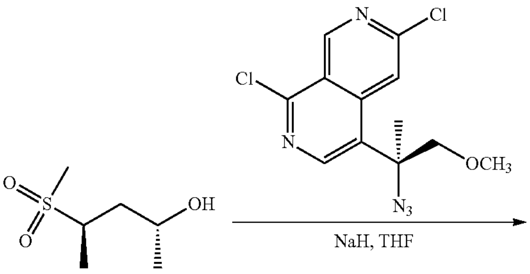

-continued

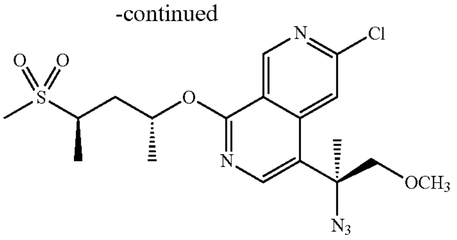

Intermediate 88: 4-((S)-2-Azido-1-methoxypropan-2-yl)-6-chloro-1-((2R,4R)-4-(methylsulfonyl)pentan-2-yl)oxy)-2,7-naphthyridine

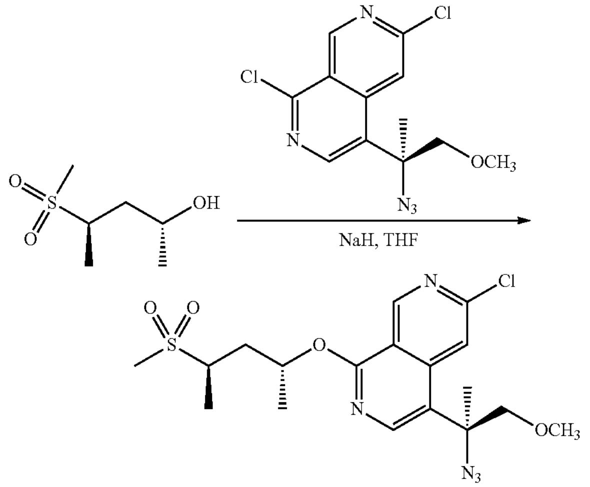

Step 1: 4—((S)-2-Azido-1-methoxypropan-2-yl)-6-chloro-1-(((2R,4R)-4-(methylsulfonyl)pentan-2-yl)oxy)-2,7-naphthyridine The title compound was prepared from (S)-4-(2-azido-1-methoxypropan-2-yl)-1,6-dichloro-2,7-naphthyridine and (2R,4R)-4-(methylsulfonyl)pentan-2-ol using a similar procedure as described in Step 1 of Intermediate 22. MS (ES+) $C_{18}H_{24}ClN_5O_4S$ requires: 441, found: 442[M+H]$^+$.

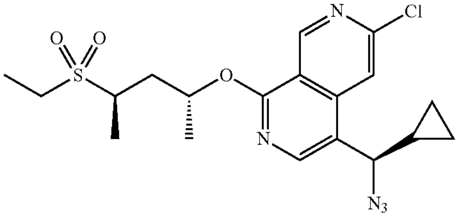

and

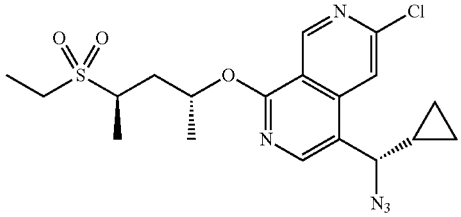

Step 1: 4—((S)-2-Azido-1-methoxypropan-2-yl)-6-chloro-1-(((2R,4R)-4-(methylsulfonyl)pentan-2-yl)oxy)-2,7-naphthyridine The title compound was prepared from (S)-4-(2-azido-1-methoxypropan-2-yl)-1,6-dichloro-2,7-naphthyridine and (2R,4R)-4-(methylsulfonyl)pentan-2-ol using a similar procedure as described in Step 1 of Intermediate 22. MS (ES+) C18$H_{24}ClN_5O_4S$ requires: 441, found: 442[M+H]$^+$.

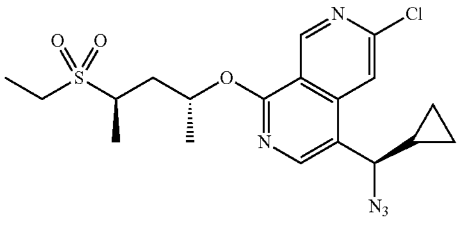

and

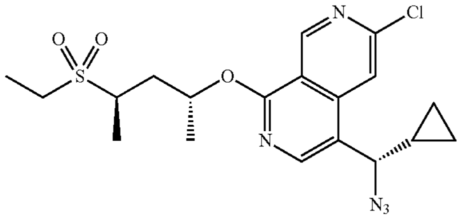

Intermediates 89 and 90: 4—((R)-Azido(cyclopropyl)methyl)-6-chloro-1-(((2R,4R)-4-(ethylsulfonyl)pentan-2-yl)oxy)-2,7-naphthyridine and 4-((S)-azido(cyclopropyl)methyl)-6-chloro-1-(((2R,4R)-4-(ethylsulfonyl)pentan-2-yl)oxy)-2,7-naphthyridine

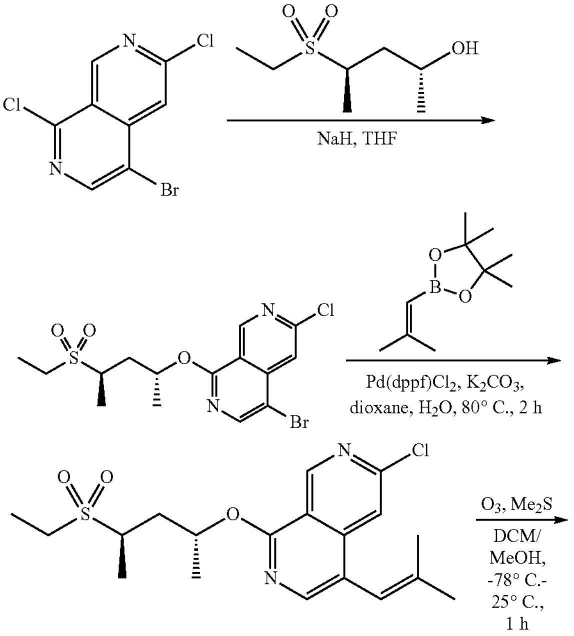

-continued

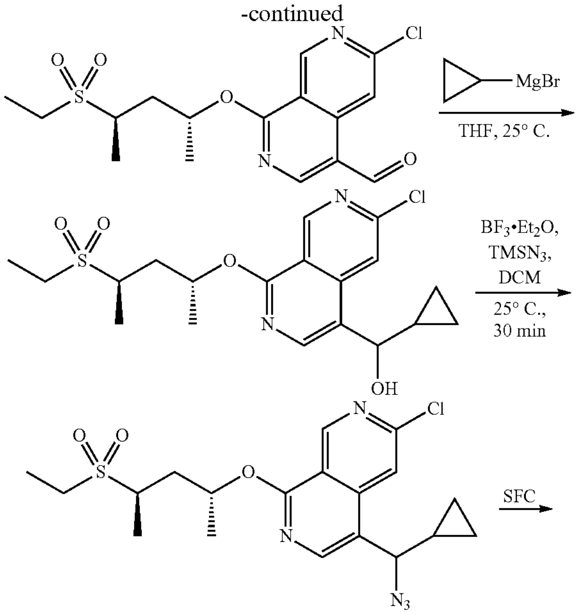

Intermediaite 89 and Intermediate 90 each of which is represented by the structures shown below:

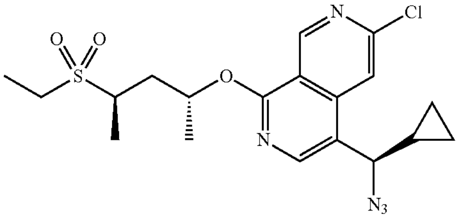

and

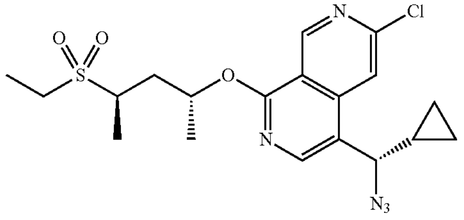

Steps 1-5: 4-(Azido(cyclopropyl)methyl)-6-chloro-1-(((2R,4R)-4-(ethylsulfonyl)pentan-2-yl)oxy)-2,7-naphthyridine The title compound was prepared using a similar procedure as described in Steps 1-5 of Intermediates 78 and 79.

Step 6: 4—((R)-Azido(cyclopropyl)methyl)-6-chloro-1-(((2R,4R)-4-(ethylsulfonyl)pentan-2-yl)oxy)-2,7-naphthyridine and 4-((S)-azido(cyclopropyl)methyl)-6-chloro-1-(((2R,4R)-4-(ethylsulfonyl)pentan-2-yl)oxy)-2,7-naphthyridine 4-(Azido(cyclopropyl)methyl)-6-chloro-1-(((2R,4R)-4-(ethylsulfonyl)pentan-2-yl)oxy)-2,7-naphthyridine (150 mg) was separated by SFC (Daicel Chiralpak AD-H (250 mm*30 mm, 5 um); mobile phase: [0.1% $NH_3H_2O$ IPA]; B %: 30%-30%) to give one of 4-((R)-azido(cyclopropyl)methyl)-6-chloro-1-(((2R,4R)-4-(ethylsulfonyl)pentan-2-yl)oxy)-2,7-naphthyridine or 4-((S)-azido(cyclopropyl)methyl)-6-chloro-1-(((2R,4R)-4-(ethylsulfonyl)pentan-2-yl)oxy)-2,7-naphthyridine as the first eluting isomer (Intermediate 89, 70 mg) as a white solid and the other one of 4-((R)-azido(cyclopropyl)methyl)-6-chloro-1-(((2R,4R)-4-(ethylsulfonyl)pentan-2-yl)oxy)-2,7-naphthyridine or 4-((S)-azido(cyclopropyl)methyl)-6-chloro-1-(((2R,4R)-4-(ethylsulfonyl)pentan-2-yl)oxy)-2,7-naphthyridine as the second eluting isomer (Intermediate 90, 70 mg) as a white solid.

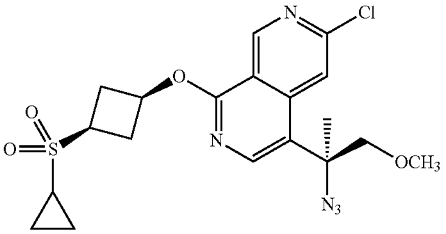 [SMILES: COC[C@@](C)(N=[N+]=[N-])c1cnc(O[C@H]2C[C@@H](S(=O)(=O)C3CC3)C2)c2cnc(Cl)cc12]

Intermediate 91: 4—((S)-2-Azido-1-methoxypropan-2-yl)-6-chloro-1-(cis-3-(cyclopropylsulfonyl)cyclobutoxy)-2,7-naphthyridine

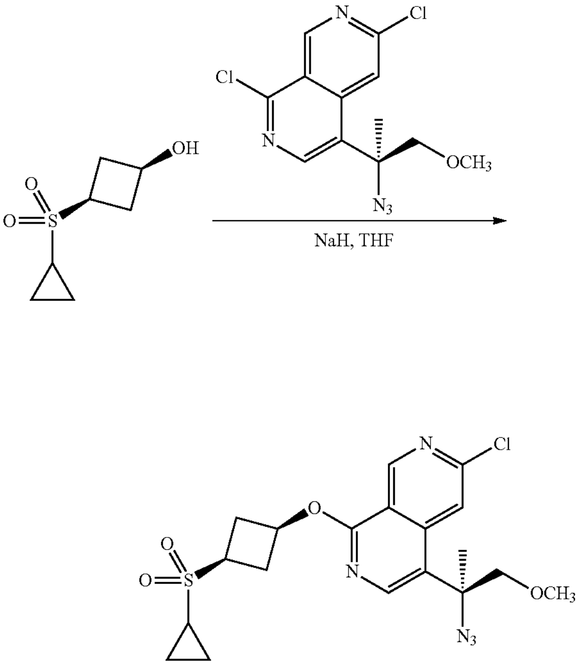

Step 1: 4—((S)-2-Azido-1-methoxypropan-2-yl)-6-chloro-1-(cis-3-(cyclopropylsulfonyl)cyclobutoxy)-2,7-naphthyridine The title compound was prepared from (S)-4-(2-azido-1-methoxypropan-2-yl)-1,6-dichloro-2,7-naphthyridine and cis-3-(cyclopropylsulfonyl)cyclobutan-1-ol using a similar procedure as described in Step 1 of Intermediate 22. MS (ES+) $C_{19}H_{22}ClN_5O_4S$ requires: 451, found: 452[M+H]$^+$.

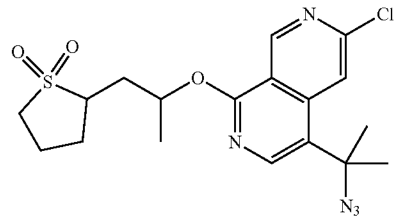 [SMILES: CC(CC1CCCS1(=O)=O)Oc1ncc(C(C)(C)N=[N+]=[N-])c2cc(Cl)ncc12]

Intermediate 92: 2-(2-((4-(2-Azidopropan-2-yl)-6-chloro-2,7-naphthyridin-1-yl)oxy)propyl)tetrahydrothiophene 1,1-dioxide

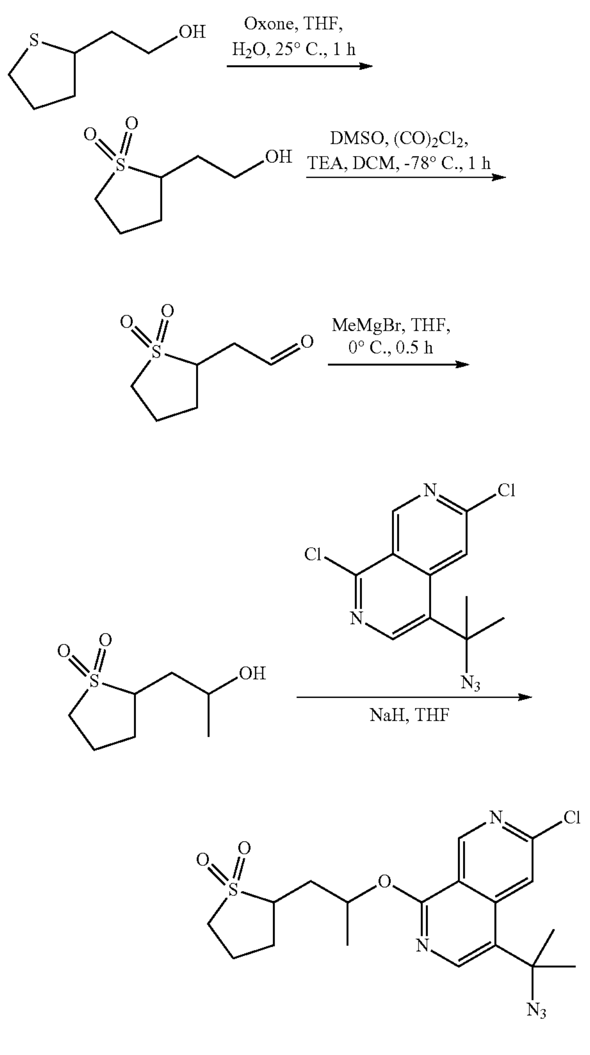

Step 1: 2-(2-Hydroxyethyl)tetrahydrothiophene 1,1-dioxide

To a solution of 2-(tetrahydrothiophen-2-yl)ethan-1-ol (1 g, 7.56 mmol) in THF (18 mL) and water (6 mL) was added Oxone® (9.30 g, 15.1 mmol). The reaction mixture was stirred at 25° C. for 1 h, then was quenched by addition of saturated aqueous sodium sulfite (20 mL). The mixture was diluted with water (20 mL) and extracted with EA (40 mL×3). The combined organic layers were dried over anhydrous sodium sulfate, filtered and concentrated to give the title compound (750 mg, crude) as a colorless solid. MS (ES+) $C_6H_{12}O_3S$ requires: 164, found: 165[M+H]$^+$.

Step 2: 2-(1,1-Dioxidotetrahydrothiophen-2-yl)acetaldehyde

To a solution of DMSO (1.43 g, 18.3 mmol, 1.43 mL) in DCM (30 mL) was added oxalyl chloride (1.74 g, 13.7 mmol, 1.20 mL) at −78° C. The reaction mixture was stirred at −78° C. for 20 min, then 2-(2-hydroxyethyl)tetrahydrothiophene 1,1-dioxide (750 mg, 4.57 mmol) in DCM (10 mL). The reaction mixture was stirred at −78° C. for another 20 min, then TEA (2.77 g, 27.4 mmol) in DCM (10 mL) was added dropwise to the reaction mixture as the temperature was kept below −60° C. After the addition, the mixture was stirred at −78° C. for 20 min, then was diluted with water (40 mL) and extracted with EA (40 mL×3). The combined organic layers were dried over anhydrous sodium sulfate, filtered and concentrated to give the title compound (1.1 g, crude) was obtained as a colorless oil that was used in the next step without purification.

Step 3: 2-(2-Hydroxypropyl)tetrahydrothiophene 1,1-dioxide

To a solution of 2-(1,1-dioxidotetrahydrothiophen-2-yl) acetaldehyde (1 g, 6.16 mmol) in THF (30 mL) was added MeMgBr (3 M, 6.16 mL) at 0° C., then the mixture was stirred at 0° C. for 0.5 h. The reaction mixture was diluted with water (40 mL) and extracted with EA (40 mL×3), the combined organic layers were dried over anhydrous sodium sulfate, filtered and concentrated to give a residue. The residue was purified by column chromatography ($SiO_2$, PE/EA=1/0 to 0/1) to give the title compound (270 mg, 25% yield) as a yellow oil. MS (ES+) $C_7H_{14}O_3S$ requires: 178, found: 179[M+H]$^+$.

Step 4: 2-(2-((4-(2-Azidopropan-2-yl)-6-chloro-2,7-naphthyridin-1-yl)oxy)propyl)tetrahydrothiophene 1,1-dioxide The title compound was prepared from 4-(2-azidopropan-2-yl)-1,6-dichloro-2,7-naphthyridine and 2-(2-hydroxypropyl)tetrahydrothiophene 1,1-dioxide using a similar procedure as described above for Intermediate 22. MS (ES+) $C18H_{22}ClN_5O_3S$ requires: 423, found: 424[M+H]$^+$.

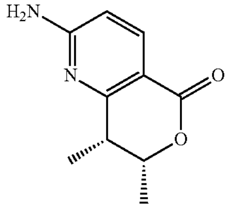

And

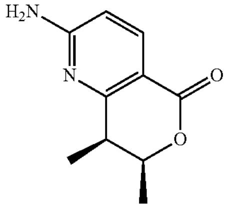

Intermediates 93 and 94: (7R,8R)-2-Amino-7,8-dimethyl-7,8-dihydro-5H-pyrano[4,3-b]pyridin-5-one and (7S,8S)-2-amino-7,8-dimethyl-7,8-dihydro-5H-pyrano[4,3-b]pyridin-5-one

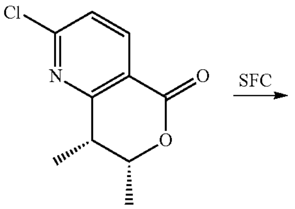

Precursor I of Intermediate 93 (Cis first eluting isomer) and Precursor I of Intermediate 94 (Cis second eluting isomer)

each of which is represented by one of the structures shown below:

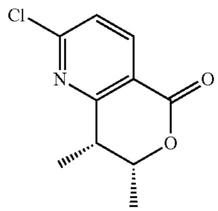

and

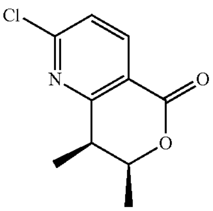

Precursor I of Intermediate 93 (Cis first eluting isomer) or Precursor I of Intermediate 94 (Cis second eluting isomer)

DMBNH2, NMP

100° C., 2 h

Precursor II of Intermediate 93 or Precursor II of Intermediate 94 which is represented by one of the structures shown below:

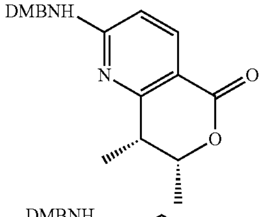

and

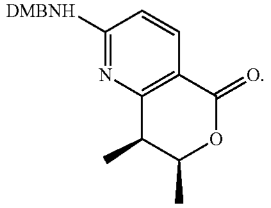

Precursor II of Intermediate 93 or Precursor II of Intermediate 94

HCl/dioxane (4 N)

dioxane, 60° C., 2 h

Intermediate 93 or Intermediate 94 which is represented by one of the structures shown below:

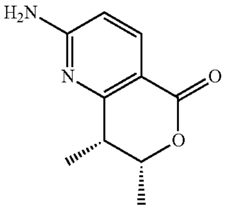

and

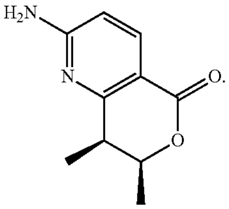

Step 1: (7R,8R)-2-Chloro-7,8-dimethyl-7,8-dihydro-5H-pyrano[4,3-b]pyridin-5-one and (7S,8S)-2-chloro-7,8-dimethyl-7,8-dihydro-5H-pyrano[4,3-b]pyridin-5-one rac-(7R,8R)-2-Chloro-7,8-dimethyl-7,8-dihydro-5H-pyrano[4,3-b]pyridin-5-one (reported in Step 5 of Intermediates 1 and 2) (6.0 g, 28.3 mmol) was separated by SFC (Daicel Chiralpak AD, MeOH gradient in $CO_2$ with 0.1% $NH_4OH$) to give two peaks separately. The first eluting isomer (3 g, 50% yield) and second eluting isomer (2.8 g, 46% yield) were obtained as yellow solids.

Steps 2 and 3: One of (7R,8R)- or (7S,8S)-2-Amino-7,8-dimethyl-7,8-dihydro-5H-pyrano[4,3-b]pyridin-5-one The title compound (Intermediate 93) was prepared from one of (7R,8R)- or (7S,8S)-2-chloro-7,8-dimethyl-7,8-dihydro-5H-pyrano[4,3-b]pyridin-5-one (first eluting isomer from step 1) using the same two-step procedure as described in Steps 7 and 8 for Intermediate 1. $^1$H-NMR (400 MHz, 6d-DMSO): δ ppm 7.76 (d, J=8.8 Hz, 1H), 7.02 (s, 2H), 6.41 (d, J=8.8 Hz, 1H), 4.70 (d, J=3.2, 6.4 Hz, 1H), 2.77-2.66 (m, 1H), 1.31 (d, J=6.8 Hz, 3H), 1.08 (d, J=7.2 Hz, 3H). MS (ES+) $C_{10}H_{12}N_2O_2$ requires: 192, found: 193[M+H]$^+$.

Steps 4 and 5: The remaining one of (7R,8R)- or (7S,8S)-2-Amino-7,8-dimethyl-7,8-dihydro-5H-pyrano[4,3-b]pyridin-5-one The title compound (Intermediate 94) was prepared from the remaining one of (7R,8R)- or (7S,8S)-2-chloro-7,8-dimethyl-7,8-dihydro-5H-pyrano[4,3-b]pyridin-5-one (second eluting isomer from step 1) using the same two-step procedure as described in Steps 7 and 8 for Intermediate 1. MS (ES+) $C_{10}H_{12}N_2O_2$ requires: 192, found: 193[M+H]$^+$.

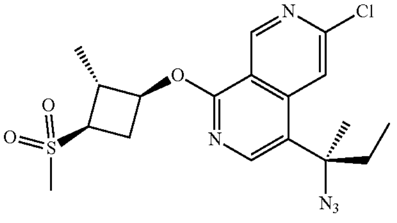

and

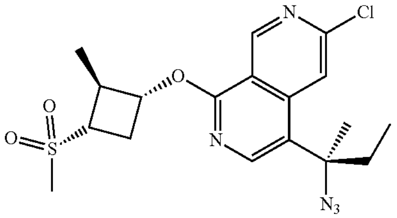

Intermediates 95 and 96: 4—((R)-2-Azidobutan-2-yl)-6-chloro-1-((1S,2R,3R)-2-methyl-3-(methylsulfonyl)cyclobutoxy)-2,7-naphthyridine and 4-((R)-2-azidobutan-2-yl)-6-chloro-1-((1R,2S,3R)-2-methyl-3-(methylsulfonyl)cyclobutoxy)-2,7-naphthyridine

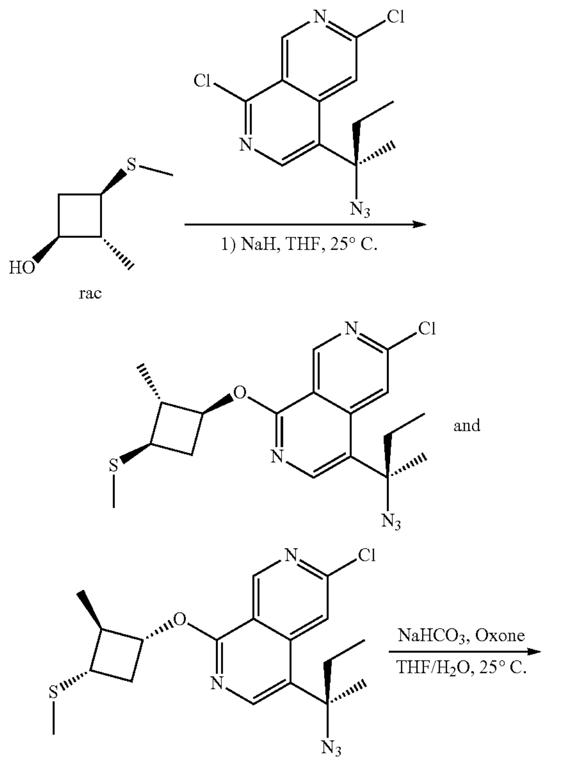

Intermediate 95 and Intermediate 96 each of which is represented by one of the structures below:

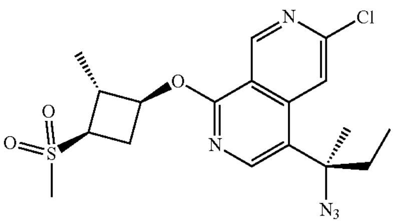

and

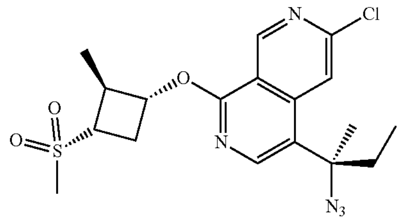

Step 1: 4—((R)-2-Azidobutan-2-yl)-6-chloro-1-((1S,2R,3R)-2-methyl-3-(methylthio)cyclobutoxy)-2,7-naphthyridine and 4-((R)-2-azidobutan-2-yl)-6-chloro-1-((1R,2S,3S)-2-methyl-3-(methylthio)cyclobutoxy)-2,7-naphthyridine The title compounds were prepared from rac-(1S,2R,3R)-2-methyl-3-(methylthio)cyclobutan-1-ol and (R)-4-(2-azidobutan-2-yl)-1,6-dichloro-2,7-naphthyridine using a similar procedure as described above for Intermediate 22. The title compounds were not separated and carried into the next step. MS (ES+) $C18H_{22}ClN_5OS$ requires: 391, found: 392 $[M+H]^+$.

Step 2: 4—((R)-2-Azidobutan-2-yl)-6-chloro-1-((1S,2R,3R)-2-methyl-3-(methylsulfonyl)cyclobutoxy)-2,7-naphthyridine and 4-((R)-2-azidobutan-2-yl)-6-chloro-1-((1R,2S,3R)-2-methyl-3-(methylsulfonyl)cyclobutoxy)-2,7-naphthyridine To a mixture of 4-((R)-2-azidobutan-2-yl)-6-chloro-1-((1S,2R,3R)-2-methyl-3-(methylthio)cyclobutoxy)-2,7-naphthyridine and 4-((R)-2-azidobutan-2-yl)-6-chloro-1-((1R,2S,3S)-2-methyl-3-(methylthio)cyclobutoxy)-2,7-naphthyridine (730 mg, 1.86 mmol), $NaHCO_3$ (1.25 g, 14.9 mmol) in THF (20 mL) and $H_2O$ (4 mL) was added Oxone® (2.86 g, 4.66 mmol). The reaction mixture was stirred at 25° C. for 2 h, then was filtered, diluted with water (20 mL) and extracted with EA (50 mL). The organic layer was dried over $Na_2SO_4$, filtered and concentrated. The residue was re-dissolved into a mixture solution of THF (20 mL) and $H_2O$ (4 mL), and $NaHCO_3$ (1.25 g, 14.9 mmol) and Oxone (2.86 g, 4.66 mmol) were added. The mixture was stirred at 25° C. for 1 h, then was filtered, diluted with $H_2O$ (20 mL) and extracted with EA (50 mL). The organic layer was dried to give a mixture of the title compounds (780 mg, 96% yield) as a colorless semisolid. The mixture was separated by chiral SFC (column: Daicel Chiralpak AD-H (250 mm*30 mm, 5 um); mobile phase: [0.10% $NH_3H_2O$ IPA]; B %: 30%-30%) to give one of 4-((R)-2-azidobutan-2-yl)-6-chloro-1-((1S,2R,3R)-2-methyl-3-(methylsulfonyl)cyclobutoxy)-2,7-naphthyridine or 4-((R)-2-azidobutan-2-yl)-6-chloro-1-((1R,2S,3R)-2-methyl-3-(methylsulfonyl)cyclobutoxy)-2,7-naphthyridine (first eluting isomer, Intermediate 95, 240 mg, 31% yield) as a colorless semisolid and the other one of 4-((R)-2-azidobutan-2-yl)-6-chloro-1-((1S,2R,3R)-2-methyl-3-(methylsulfonyl)cyclobutoxy)-2,7-naphthyridine or 4-((R)-2-azidobutan-2-yl)-6-chloro-1-((1R,2S,3R)-2-methyl-3-(methylsulfonyl)cyclobutoxy)-2,7-naphthyridine (second eluting isomer, Intermediate 96, 260 mg, 33% yield) as a colorless semisolid.

Intermediate 95: MS (ES+) $C18H_{22}ClN_5O_3S$ requires: 423, found: 424$[M+H]^+$. Intermediate 96: MS (ES+) $C18H_{22}ClN_5O_3S$ requires: 423, found: 424$[M+H]^+$.

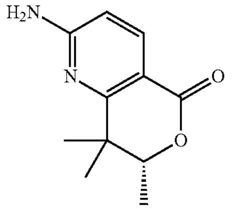

and

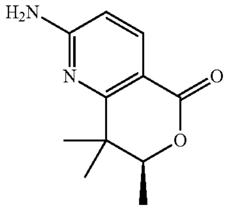

Intermediates 97 and 98: (R)-2-Amino-7,8,8-trimethyl-7,8-dihydro-5H-pyrano[4,3-b]pyridin-5-one and (S)-2-amino-7,8,8-trimethyl-7,8-dihydro-5H-pyrano[4,3-b]pyridin-5-one

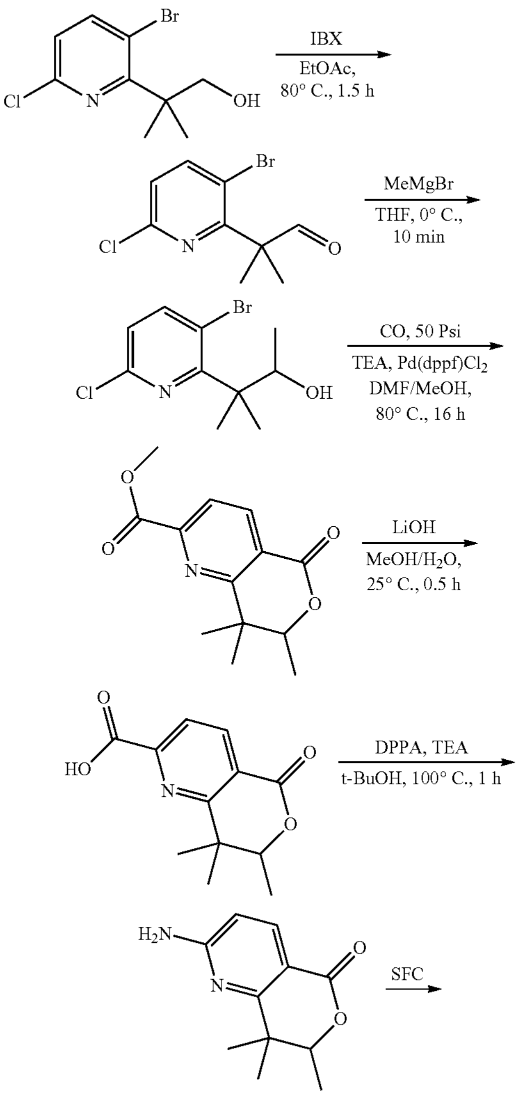

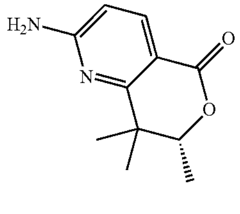

and

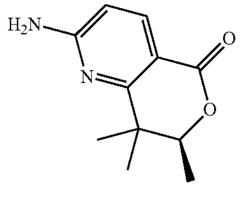

Steps 1-5: (rac)-2-Amino-7,8,8-trimethyl-7,8-dihydro-5H-pyrano[4,3-b]pyridin-5-one The title compound was prepared from 2-(3-bromo-6-chloropyridin-2-yl)-2-methylpropan-1-ol using a similar procedure as described in Steps 1-5 of Intermediate 12. $C_{11}H_{14}N_2O_2$ requires: 206, found: 207 $[M+H]^+$.

Step 6: (R)-2-Amino-7,8,8-trimethyl-7,8-dihydro-5H-pyrano[4,3-b]pyridin-5-one and (S)-2-amino-7,8,8-trimethyl-7,8-dihydro-5H-pyrano[4,3-b]pyridin-5-one (rac)-2-Amino-7,8,8-trimethyl-7,8-dihydro-5H-pyrano[4,3-b]pyridin-5-one (120 mg) was separated by SFC (column: REGIS (s,s) WHELK-01 (250 mm×50 mm, 10 um), MeOH gradient in $CO_2$ with 0.1% $NH_4OH$) to give two peaks separately. The first eluting isomer, one of (R or S)-2-Amino-7,8,8-trimethyl-7,8-dihydro-5H-pyrano[4,3-b]pyridin-5-one (Intermediate 97, 60 mg, 50% yield) and second eluting isomer, one of (R or S)-2-Amino-7,8,8-trimethyl-7,8-dihydro-5H-pyrano[4,3-b]pyridin-5-one (Intermediate 98, 60 mg, 50% yield) were obtained as yellow solids.

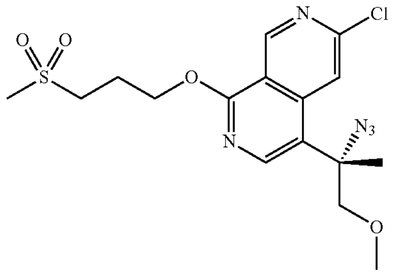 [SMILES: COC[C@@](C)(N=[N+]=[N-])c1cnc(OCCCS(C)(=O)=O)c2cnc(Cl)cc12]

Intermediate 99: (S)-4-(2-Azido-1-methoxypropan-2-yl)-6-chloro-1-(3-(methylsulfonyl)propoxy)-2,7-naphthyridine

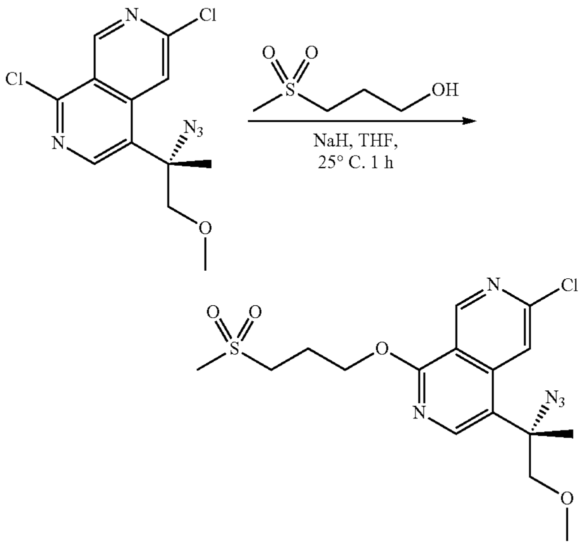

Step 1: (S)-4-(2-Azido-1-methoxypropan-2-yl)-6-chloro-1-(3-(methylsulfonyl)propoxy)-2,7-naphthyridine The title compound was prepared from (S)-4-(2-azido-1-methoxypropan-2-yl)-1,6-dichloro-2,7-naphthyridine and 3-(methylsulfonyl)propan-1-ol using a similar procedure as described above for Intermediate 22. MS (ES+) $C_{16}H_{20}ClN_5O_4S$ requires: 413, found: 414$[M+H]^+$.

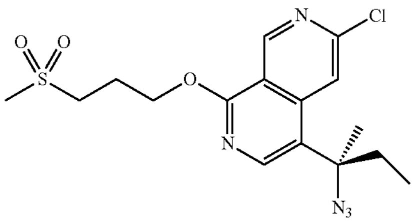 [SMILES: CC[C@@](C)(N=[N+]=[N-])c1cnc(OCCCS(C)(=O)=O)c2cnc(Cl)cc12]

Intermediate 100: (R)-4-(2-Azidobutan-2-yl)-6-chloro-1-(3-(methylsulfonyl)propoxy)-2,7-naphthyridine

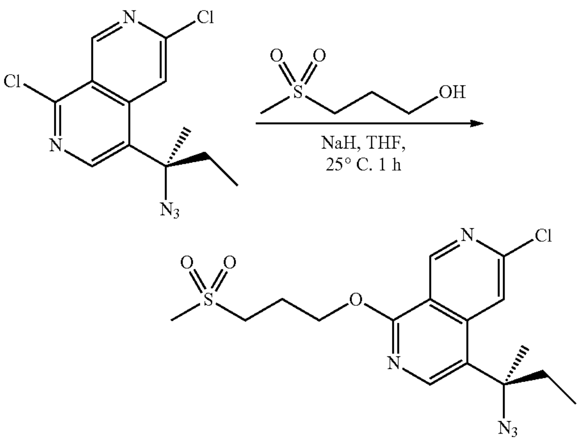

Step 1: (R)-4-(2-Azidobutan-2-yl)-6-chloro-1-(3-(methylsulfonyl)propoxy)-2,7-naphthyridine The title compound was prepared from (R)-4-(2-azidobutan-2-yl)-1,6-dichloro-2,7-naphthyridine and 3-(methylsulfonyl)propan-1-ol using a similar procedure as described above for Intermediate 22. MS (ES+) $C_{16}H_{20}ClN_5O_3S$ requires: 397, found: 398[M+H]$^+$.

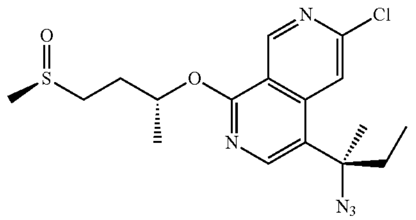

and

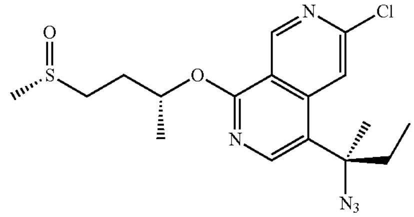

Intermediates 101 and 102: 4—((R)-2-Azidobutan-2-yl)-6-chloro-1-(((R)-4-((R)-methylsulfinyl)butan-2-yl)oxy)-2,7-naphthyridine and 4-((R)-2-azidobutan-2-yl)-6-chloro-1-(((R)-4-((S)-methylsulfinyl)butan-2-yl)oxy)-2,7-naphthyridine

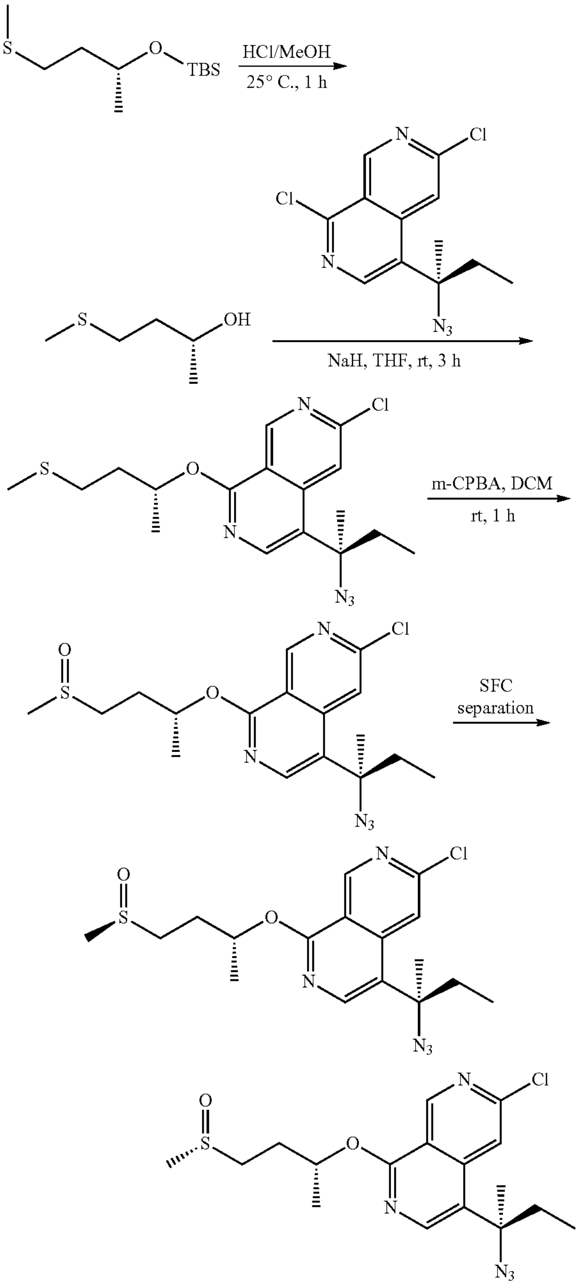

Step 1: (R)-4-(Methylthio)butan-2-ol

The title compound was prepared from (R)-tert-butyldimethyl((4-(methylthio)butan-2-yl)oxy)silane using a similar procedure as described above in Step 5 of Intermediate 30.

Step 2: 4—((R)-2-Azidobutan-2-yl)-6-chloro-1-(((R)-4-(methylthio)butan-2-yl)oxy)-2,7-naphthyridine The title compound was prepared from (R)-4-(methylthio)butan-2-ol and (R)-4-(2-azidobutan-2-yl)-1,6-dichloro-2,7-naphthyridine using a similar procedure as described above for Intermediate 22. MS (ES+) $C_{17}H_{22}ClN_5OS$ requires: 379, found: 380[M+H]$^+$.

Step 3: 4—((R)-2-Azidobutan-2-yl)-6-chloro-1-(((2R)-4-(methylsulfinyl)butan-2-yl)oxy)-2,7-naphthyridine To a solution of 4-((R)-2-azidobutan-2-yl)-6-chloro-1-(((R)-4-(methylthio)butan-2-yl)oxy)-2,7-naphthyridine (280 mg, 643 umol, 87.2% purity) in DCM (8 mL) was added m-CPBA (196 mg, 964 umol, 85% purity) at 25° C. The mixture was stirred at 25° C. for 1 h, then was diluted with DCM (15 mL), washed with water (20 mL×2), filtered, and concentrated to give a residue. The residue was purified by prep-TLC (PE/EA=1/2) to give the title compound (220 mg, 86% yield) as a white solid. MS (ES+) $C_{17}H_{22}ClN_5O_2S$ requires: 395, found: 396[M+H]$^+$.

Step 4: 4—((R)-2-Azidobutan-2-yl)-6-chloro-1-(((R)-4-((R)-methylsulfinyl)butan-2-yl)oxy)-2,7-naphthyridine and 4-((R)-2-azidobutan-2-yl)-6-chloro-1-(((R)-4-((S)-methylsulfinyl)butan-2-yl)oxy)-2,7-naphthyridine 4-((R)-2-Azidobutan-2-yl)-6-chloro-1-(((2R)-4-(methylsulfinyl)butan-2-yl)oxy)-2,7-naphthyridine (220 mg) was separated by SFC (column: Daicel Chiralpak AD (250 mm*30 mm, 10 um); mobile phase: [0.1% $NH_3H_2O$-MeOH]; B %: 60%-60%) to give two peaks separately. The first eluting isomer, one of 4-((R)-2-azidobutan-2-yl)-6-chloro-1-(((R)-4-((R)-methylsulfinyl)butan-2-yl)oxy)-2,7-naphthyridine or 4-((R)-2-azidobutan-2-yl)-6-chloro-1-(((R)-4-((S)-methylsulfinyl)butan-2-yl)oxy)-2,7-naphthyridine (Intermediate 101, 95 mg, 42% yield) and second eluting isomer, one of 4-((R)-2-azidobutan-2-yl)-6-chloro-1-(((R)-4-((R)-methylsulfinyl)butan-2-yl)oxy)-2,7-naphthyridine or 4-((R)-2-azidobutan-2-yl)-6-chloro-1-(((R)-4-((S)-methylsulfinyl)butan-2-yl)oxy)-2,7-naphthyridine (Intermediate 102, 101 mg, 45% yield) were obtained as colorless oils. MS (ES+) $C_{17}H_{22}ClN_5O_2S$ requires: 395, found: 396[M+H]$^+$.

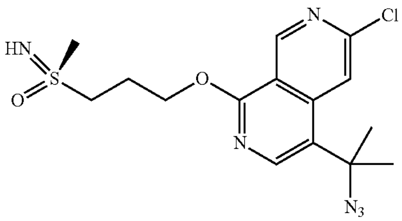

and

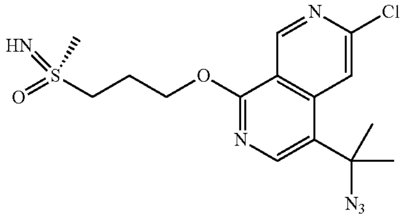

Intermediates 103 and 104: (S)-(3-((4-(2-Azidopropan-2-yl)-6-chloro-2,7-naphthyridin-1-yl)oxy)propyl)(imino)(methyl)-λ$^6$-sulfanone and (R)-(3-((4-(2-azidopropan-2-yl)-6-chloro-2,7-naphthyridin-1-yl)oxy)propyl)(imino)(methyl)-λ$^6$-sulfanone

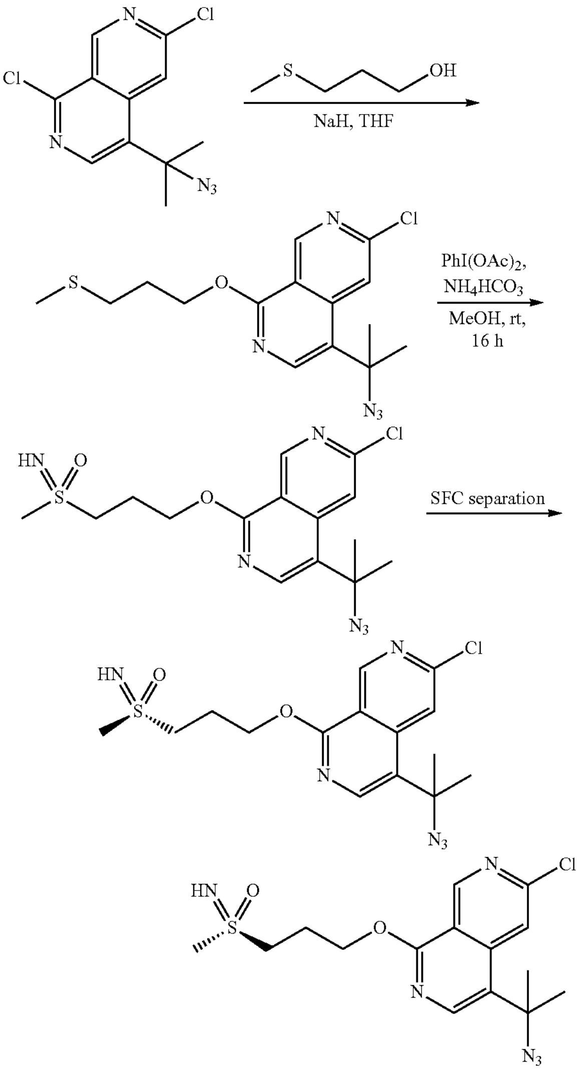

Step 1: 4-(2-Azidopropan-2-yl)-6-chloro-1-(3-(methylthio)propoxy)-2,7-naphthyridine The title compound was prepared from 4-(2-azidopropan-2-yl)-1,6-dichloro-2,7-naphthyridine and 3-(methylthio)propan-1-ol using a similar procedure as described above for Intermediate 22. MS (ES+) $C_{15}H_{18}ClN_5OS$ requires: 351, found: 352[M+H]$^+$.

Step 2: (3-((4-(2-Azidopropan-2-yl)-6-chloro-2,7-naphthyridin-1-yl)oxy)propyl)(imino)(methyl)-λ$^6$-sulfanone 4-(2-Azidopropan-2-yl)-6-chloro-1-(3-(methylthio)propoxy)-2,7-naphthyridine (320 mg, 909 umol) was dissolved in MeOH (10 mL), and then $NH_4HCO_3$ (108 mg, 1.36 mmol) and $PhI(OAc)_2$ (586 mg, 1.82 mmol) were added. The reaction mixture was stirred at 25° C. for 16 h, then was diluted with saturated aqueous $NH_4Cl$ solution (50 mL) and extracted with EA (50 mL). The organic layer was dried over sodium sulfate, filtered and concentrated. The residue was purified by prep-TLC (PE:EA=0:1) to give the title compound (283 mg, 73% yield) as a yellow solid. MS (ES+) $C_{15}H_{19}ClN_6O_2S$ requires: 382, found: 383[M+H]$^+$. LCMS data: M+1 (382.9); MW (382.1).

Step 3: (S)-(3-((4-(2-Azidopropan-2-yl)-6-chloro-2,7-naphthyridin-1-yl)oxy)propyl)(imino)(methyl)-λ$^6$-sulfanone and (R)-(3-((4-(2-azidopropan-2-yl)-6-chloro-2,7-naphthyridin-1-yl)oxy)propyl)(imino)(methyl)-λ$^6$-sulfanone (3-((4-(2-Azidopropan-2-yl)-6-chloro-2,7-naphthyridin-1-yl)oxy)propyl)(imino)(methyl)-λ$^6$-sulfanone (283 mg) was separated by SFC ((column: Daicel Chiralpak AY-H (250 mm×30 mm, 10 um); mobile phase: [0.1% $NH_3H_2O$ EtOH]; B %: 50%-50%) to give two peaks separately. The first eluting isomer, one of (S)-(3-((4-(2-azidopropan-2-yl)-6-chloro-2,7-naphthyridin-1-yl)oxy)propyl)(imino)(methyl)-λ$^6$-sulfanone or (R)-(3-((4-(2-azidopropan-2-yl)-6-chloro-2,7-naphthyridin-1-yl)oxy)propyl)(imino)(methyl)-λ$^6$-sulfanone (Intermediate 103, 129 mg, 41% yield) and second eluting isomer, one of (S)-(3-((4-(2-azidopropan-2-yl)-6-chloro-2,7-naphthyridin-1-yl)oxy)propyl)(imino)(methyl)-λ$^6$-sulfanone or (R)-(3-((4-(2-azidopropan-2-yl)-6-chloro-2,7-naphthyridin-1-yl)oxy)propyl)(imino)(methyl)-λ$^6$-sulfanone (Intermediate 104, 114 mg, 39% yield) were obtained as yellow solids. MS (ES+) $C_{15}H_{19}ClN_6O_2S$ requires: 382, found: 383[M+H]$^+$.

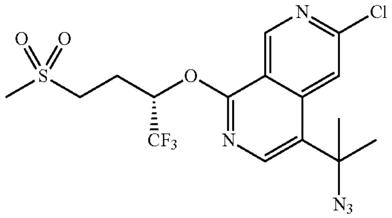

and

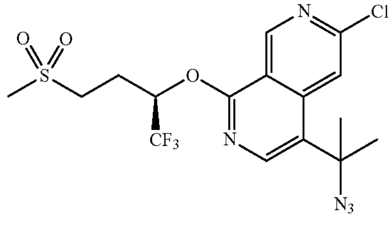

Intermediates 105 and 106: (S)-4-(2-Azidopropan-2-yl)-6-chloro-1-((1,1,1-trifluoro-4-(methylsulfonyl)butan-2-yl)oxy)-2,7-naphthyridine and (R)-4-(2-azidopropan-2-yl)-6-chloro-1-((1,1,1-trifluoro-4-(methylsulfonyl)butan-2-yl)oxy)-2,7-naphthyridine

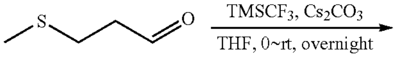

-continued

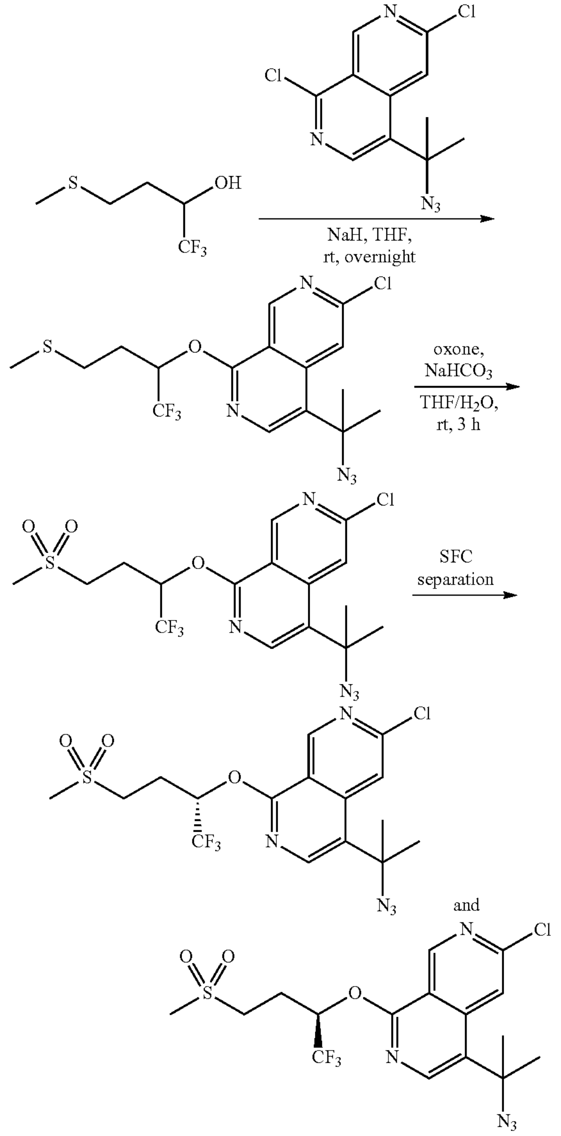

Step 1: 1,1,1-Trifluoro-4-(methylthio)butan-2-ol

To a solution of 3-(methylthio)propanal (2 g, 19.2 mmol) and $TMSCF_3$ (13.7 g, 96.0 mmol) in THF (40 mL) was added $Cs_2CO_3$ (6.26 g, 19.2 mmol) at 0° C., then the mixture was stirred at 25° C. for 16 h. The organic layer was dried over sodium sulfate, filtered, and concentrated. The residue was purified by flash-column chromatography (PE/EA=5/1) to give WH105714-2 (1.4 g) as a colorless oil.

Step 2: 4-(2-Azidopropan-2-yl)-6-chloro-1-((1,1,1-trifluoro-4-(methylthio)butan-2-yl)oxy)-2,7-naphthyridine The title compound was prepared from 4-(2-azidopropan-2-yl)-1,6-dichloro-2,7-naphthyridine and 1,1,1-Trifluoro-4-(methylthio)butan-2-ol using a similar procedure as described above for Intermediate 22, except that the reaction mixture was stirred for 16 h. MS (ES+) $C_{16}H_{17}C_1F_3N_{50}S$ requires: 419, found: 420[M+H]$^+$.

Step 3: 4-(2-Azidopropan-2-yl)-6-chloro-1-((1,1,1-trifluoro-4-(methylsulfonyl)butan-2-yl)oxy)-2,7-naphthyridine The title compound was prepared from 4-(2-azidopropan-2-yl)-6-chloro-1-((1,1,1-trifluoro-4-(methylthio)butan-2-yl)oxy)-2,7-naphthyridine using a similar procedure as described in Step 5 of Intermediate 30. MS (ES+) $C_{16}H_{17}C_1F_3N_5O_3S$ requires: 451, found: 452[M+H]$^+$.

Step 4: (S)-4-(2-Azidopropan-2-yl)-6-chloro-1-((1,1,1-trifluoro-4-(methylsulfonyl)butan-2-yl)oxy)-2,7-naphthyridine and (R)-4-(2-azidopropan-2-yl)-6-chloro-1-((1,1,1-trifluoro-4-(methylsulfonyl)butan-2-yl)oxy)-2,7-naphthyridine 4-(2-Azidopropan-2-yl)-6-chloro-1-((1,1,1-trifluoro-4-(methylsulfonyl)butan-2-yl)oxy)-2,7-naphthyridine (100 mg) was separated by SFC (column: Daicel Chiralpak IG (250 mm×30 mm, 10 um); mobile phase: [0.1% $NH_3H_2O$ ETOH]; B %: 35%-35%) to give two peaks separately. The first eluting isomer, one of (S)-4-(2-azidopropan-2-yl)-6-chloro-1-((1,1,1-trifluoro-4-(methylsulfonyl)butan-2-yl)oxy)-2,7-naphthyridine or (R)-4-(2-azidopropan-2-yl)-6-chloro-1-((1,1,1-trifluoro-4-(methylsulfonyl)butan-2-yl)oxy)-2,7-naphthyridine (Intermediate 105, 35 mg, 35% yield) and second eluting isomer, one of (S)-4-(2-azidopropan-2-yl)-6-chloro-1-((1,1,1-trifluoro-4-(methylsulfonyl)butan-2-yl)oxy)-2,7-naphthyridine and (R)-4-(2-azidopropan-2-yl)-6-chloro-1-((1,1,1-trifluoro-4-(methylsulfonyl)butan-2-yl)oxy)-2,7-naphthyridine (Intermediate 106, 36 mg, 35% yield) were obtained as colorless oils. MS (ES+) $C_{16}H_{17}C_1F_3N_5O_3S$ requires: 451, found: 452[M+H]$^+$.

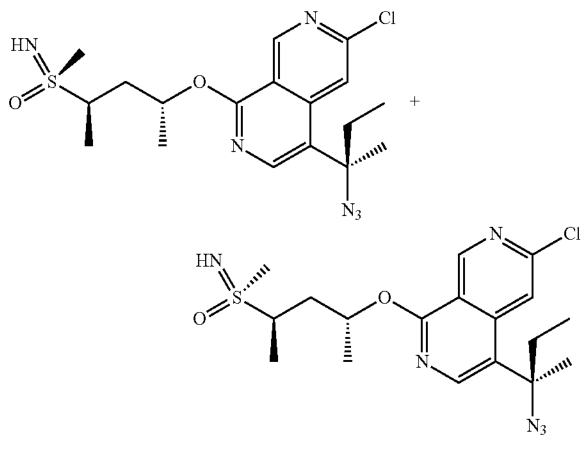

Intermediates 107 and 108: (S)-((2R,4R)-4-((4-((R)-2-Azidobutan-2-yl)-6-chloro-2,7-naphthyridin-1-yl)oxy)pentan-2-yl)(imino)(methyl)-λ6-sulfanone and (R)-((2R,4R)-4-((4-((R)-2-Azidobutan-2-yl)-6-chloro-2,7-naphthyridin-1-yl)oxy)pentan-2-yl)(imino)(methyl)-λ6-sulfanone

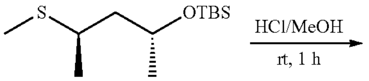

-continued

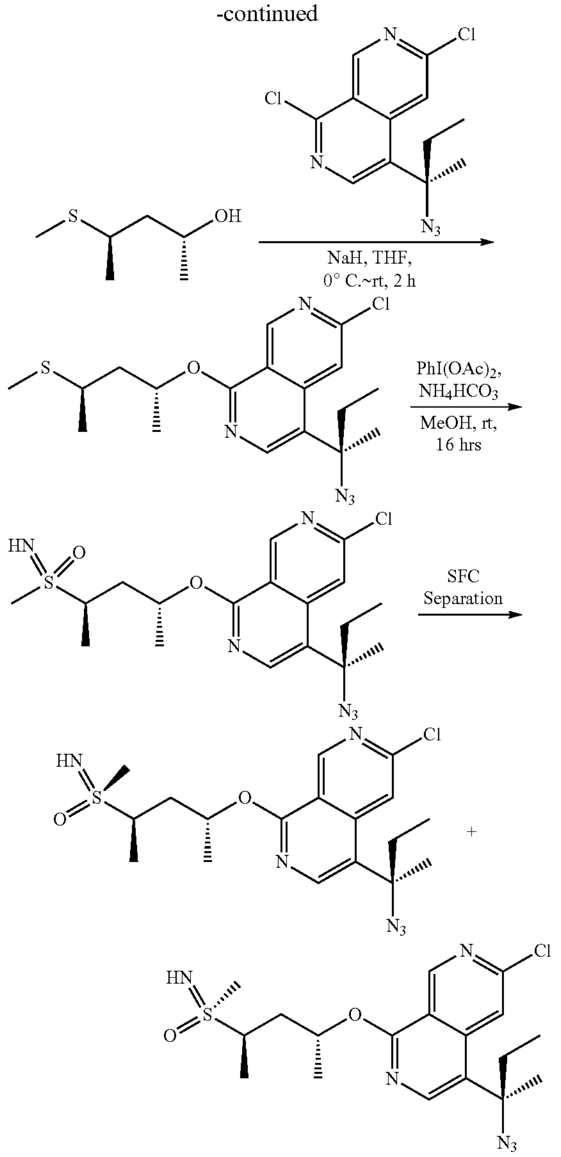

Step 1: (2R,4R)-4-(Methylthio)pentan-2-ol

A solution of t-butyldimethyl(((2R,4R)-4-(methylthio)pentan-2-yl)oxy)silane (8.8 g, 35.4 mmol) in HCl/MeOH (4 M, 100 mL) was stirred at 25° C. for 1 h. The reaction mixture was then concentrated to give a residue. The residue was purified by flash-column chromatography (gradient elution, 5-100% EA/PE) to give the title compound (3.04 g, 64% yield) as a slightly yellow oil.

Step 2: 4—((R)-2-Azidobutan-2-yl)-6-chloro-1-(((2R,4R)-4-(methylthio)pentan-2-yl)oxy)-2,7-naphthyridine The title compound was prepared from (2R,4R)-4-(methylthio)pentan-2-ol and (R)-4-(2-azidobutan-2-yl)-1,6-dichloro-2,7-naphthyridine using a similar procedure as described above for Intermediate 22. MS (ES+) $C18H_{24}ClN_5OS$ requires: 393, found: 394[M+H]$^+$.

Step 3: ((2R,4R)-4-((4-((R)-2-Azidobutan-2-yl)-6-chloro-2,7-naphthyridin-1-yl)oxy)pentan-2-yl)(imino)(methyl)-λ6-sulfanone To a mixture of 4-((R)-2-azidobutan-2-yl)-6-chloro-1-(((2R,4R)-4-(methylthio)pentan-2-yl)oxy)-2,7-naphthyridine (600 mg, 1.52 mmol) and $NH_4HCO_3$ (421 mg, 5.33 mmol) in MeOH (20 mL) was added $PhI(OAc)_2$ (1.96 g, 6.09 mmol) at 25° C. The reaction mixture was stirred at 25° C. for 16 h, then was diluted with saturated aqueous $NH_4Cl$ solution (30 mL) and extracted with EA (50 mL). The organic layer was dried over $Na_2SO_4$, filtered, and concentrated. The residue was purified by prep-HPLC (column: Phenomenex luna C18 150×40 mm×15 um; mobile phase: [water (FA)-ACN]; B %: 42%-72%, 10 min) to give the title compound (360 mg, 47% yield, 84.3% purity) as a slight yellow semisolid. MS (ES+) $C18H_{25}ClN_6O_2S$ requires: 424, found: 425[M+H]$^+$.

Step 4: (S)-((2R,4R)-4-((4-((R)-2-Azidobutan-2-yl)-6-chloro-2,7-naphthyridin-1-yl)oxy)pentan-2-yl)(imino)(methyl)-λ6-sulfanone and (R)-((2R,4R)-4-((4-((R)-2-Azidobutan-2-yl)-6-chloro-2,7-naphthyridin-1-yl)oxy)pentan-2-yl)(imino)(methyl)-λ6-sulfanone ((2R,4R)-4-((4-((R)-2-Azidobutan-2-yl)-6-chloro-2,7-naphthyridin-1-yl)oxy)pentan-2-yl)(imino)(methyl)-λ6-sulfanone (700 mg) was separated by SFC (column: Daicel Chiralcel OJ-H (250 mm×30 mm, 5 um); mobile phase: [0.1% $NH_3H_2O$-IPA]; B %: 20%-20%) to give two peaks separately. The first eluting isomer, one of (S)-((2R,4R)-4-((4-((R)-2-azidobutan-2-yl)-6-chloro-2,7-naphthyridin-1-yl)oxy)pentan-2-yl)(imino)(methyl)-λ6-sulfanone or (R)-((2R,4R)-4-((4-((R)-2-Azidobutan-2-yl)-6-chloro-2,7-naphthyridin-1-yl)oxy)pentan-2-yl)(imino)(methyl)-λ6-sulfanone (Intermediate 107, 276 mg, 38% yield) and second eluting isomer, one of (S)-((2R,4R)-4-((4-((R)-2-azidobutan-2-yl)-6-chloro-2,7-naphthyridin-1-yl)oxy)pentan-2-yl)(imino)(methyl)-λ6-sulfanone or (R)-((2R,4R)-4-((4-((R)-2-Azidobutan-2-yl)-6-chloro-2,7-naphthyridin-1-yl)oxy)pentan-2-yl)(imino)(methyl)-λ6-sulfanone (Intermediate 108, 453 mg, 64% yield) were obtained as white semisolids. MS (ES+) $C18H_{25}ClN_6O_2S$ requires: 424, found: 425[M+H]$^+$.

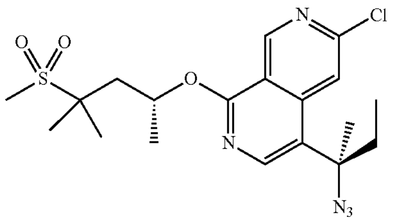

and

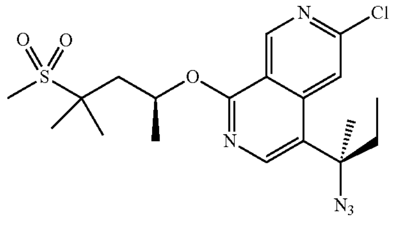

Intermediates 109 and 110: 4—((R)-2-Azidobutan-2-yl)-6-chloro-1-(((R)-4-methyl-4-(methylsulfonyl)pentan-2-yl)oxy)-2,7-naphthyridine and 4-((R)-2-azidobutan-2-yl)-6-chloro-1-(((S)-4-methyl-4-(methylsulfonyl)pentan-2-yl)oxy)-2,7-naphthyridine

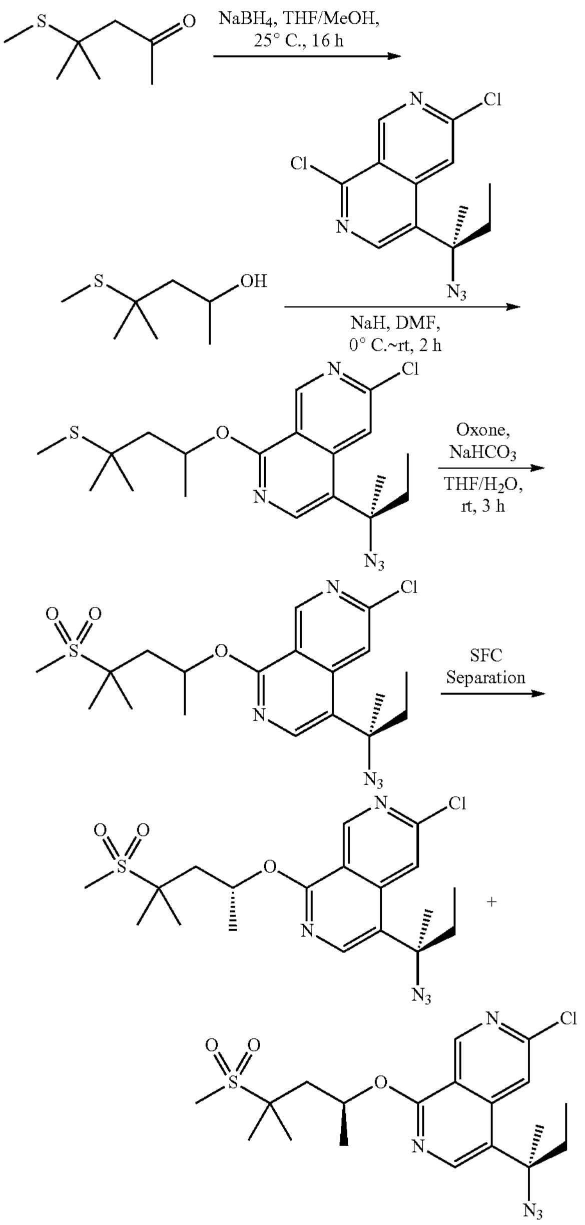

Step 1: 4-Methyl-4-(methylthio)pentan-2-ol

To a mixture of 4-methyl-4-(methylthio)pentan-2-one (1 g, 6.84 mmol) in THF (10 mL) and MeOH (1 mL) was added $NaBH_4$ (517 mg, 13.7 mmol) at 25° C. The reaction mixture was stirred at 25° C. for 16 h, then was quenched with $H_2O$ (30 mL) and extracted with EA (100 mL). The organic layer was dried over $Na_2SO_4$, filtered, and concentrated to give the title compound (970 mg, 96% yield, crude) as a colorless oil Step 2: 4—((R)-2-Azidobutan-2-yl)-6-chloro-1-((4-methyl-4-(methylthio)pentan-2-yl)oxy)-2,7-naphthyridine The title compound was prepared from 4-methyl-4-(methylthio)pentan-2-ol and (R)-4-(2-azidobutan-2-yl)-1,6-dichloro-2,7-naphthyridine using a similar procedure as described above for Intermediate 22. MS (ES+) $C_{19}H_{26}ClN_5OS$ requires: 407, found: 408$[M+H]^+$.

Step 3: 4—((R)-2-Azidobutan-2-yl)-6-chloro-1-((4-methyl-4-(methylsulfonyl)pentan-2-yl)oxy)-2,7-naphthyridine The title compound was prepared from 4-((R)-2-azidobutan-2-yl)-6-chloro-1-((4-methyl-4-(methylthio)pentan-2-yl)oxy)-2,7-naphthyridine using a similar procedure as described in Step 5 of Intermediate 30. MS (ES+) $C_{19}H_{26}ClN_5O_3S$ requires: 439, found: 440$[M+H]^+$.

Step 4: 4—((R)-2-Azidobutan-2-yl)-6-chloro-1-(((R)-4-methyl-4-(methylsulfonyl)pentan-2-yl)oxy)-2,7-naphthyridine and 4-((R)-2-azidobutan-2-yl)-6-chloro-1-(((S)-4-methyl-4-(methylsulfonyl)pentan-2-yl)oxy)-2,7-naphthyridine 4-((R)-2-Azidobutan-2-yl)-6-chloro-1-((4-methyl-4-(methylsulfonyl)pentan-2-yl)oxy)-2,7-naphthyridine (215 mg) was separated by SFC (column: Daicel Chiralpak IG (250 mm×50 mm, 10 um); mobile phase: [0.1% $NH_3H_2O$ MEOH]; B %: 40%-40%) to give two peaks separately. The first eluting isomer, one of 4-((R)-2-azidobutan-2-yl)-6-chloro-1-(((R)-4-methyl-4-(methylsulfonyl)pentan-2-yl)oxy)-2,7-naphthyridine or 4-((R)-2-azidobutan-2-yl)-6-chloro-1-(((S)-4-methyl-4-(methylsulfonyl)pentan-2-yl)oxy)-2,7-naphthyridine (Intermediate 109, 100 mg, 47% yield) and second eluting isomer, one of 4-((R)-2-azidobutan-2-yl)-6-chloro-1-(((R)-4-methyl-4-(methylsulfonyl)pentan-2-yl)oxy)-2,7-naphthyridine or 4-((R)-2-azidobutan-2-yl)-6-chloro-1-(((S)-4-methyl-4-(methylsulfonyl)pentan-2-yl)oxy)-2,7-naphthyridine (Intermediate 110, 100 mg, 46% yield) were obtained as white solids. MS (ES+) $C_{19}H_{26}ClN_5O_3S$ requires: 439, found: 440$[M+H]^+$.

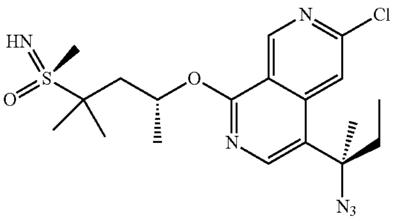

and

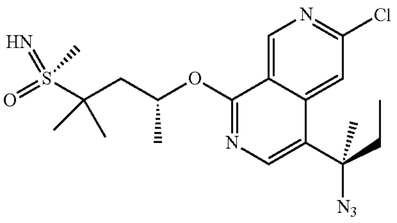

and

-continued

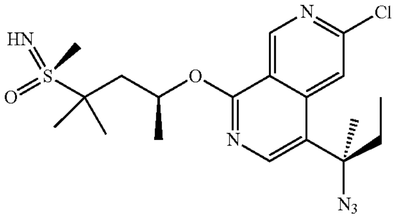

and

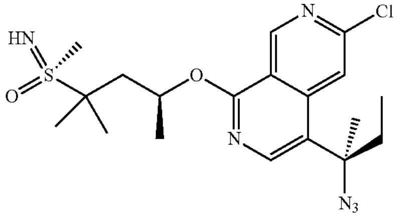

Intermediates 111, 112, 113, and 114: (S)-((R)-4-((4-((R)-2-Azidobutan-2-yl)-6-chloro-2,7-naphthyridin-1-yl)oxy)-2-methylpentan-2-yl)(imino)(methyl)-λ6-sulfanone and (R)-((R)-4-((4-((R)-2-azidobutan-2-yl)-6-chloro-2,7-naphthyridin-1-yl)oxy)-2-methylpentan-2-yl)(imino)(methyl)-λ6-sulfanone and (S)-((S)-4-((4-((R)-2-azidobutan-2-yl)-6-chloro-2,7-naphthyridin-1-yl)oxy)-2-methylpentan-2-yl)(imino)(methyl)-λ6-sulfanone and (R)-((S)-4-((4-((R)-2-azidobutan-2-yl)-6-chloro-2,7-naphthyridin-1-yl)oxy)-2-methylpentan-2-yl)(imino)(methyl)-λ6-sulfanone

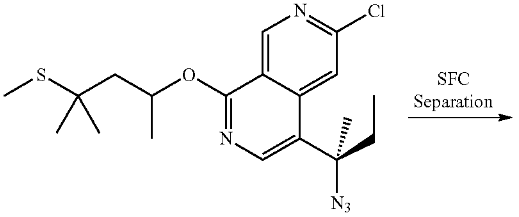

Precursor I of Intermediates 111 and 112 (1st eluting isomer)

Precursor I of Intermediates 113 and 114 (2nd eluting isomer)

each of which is represented by one of the structures below:

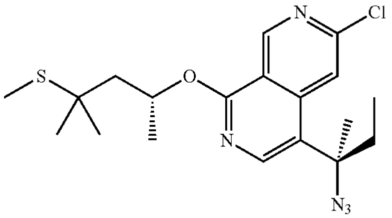

or

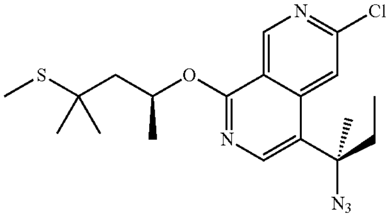

-continued

Precursor I of Intermediates 111 and 112 $\xrightarrow[\text{MeOH, rt, 16 hrs}]{PhI(OAc)_2,\ NH_4HCO_3}$ Precursor II of Intermediates 111 and 112 which is represented by one of the structures below:

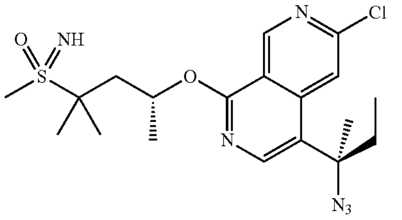

or

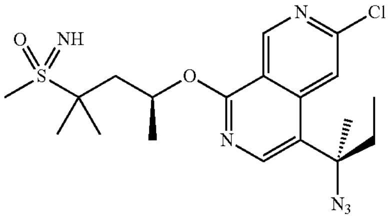

Precursor II of Intermediates 111 and 112 $\xrightarrow{\text{SFC separation}}$ Intermediate 111 (1st eluting isomer) and Intermediate 112 (2nd eluting isomer)

Each of which is represented by one of the four structures below:

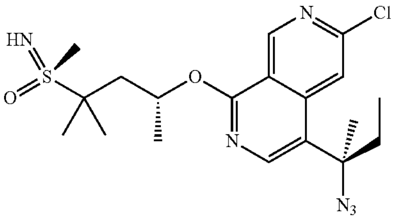

or

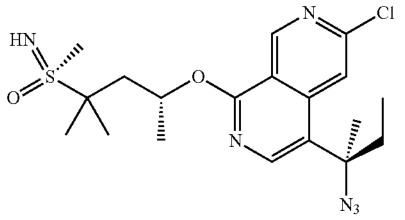

or

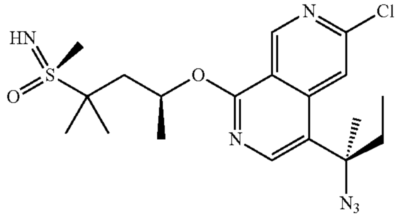

or

-continued

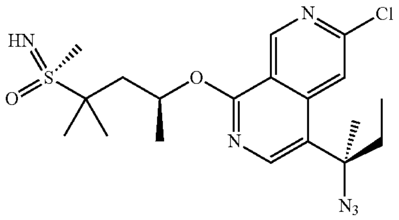

Precursor I of Intermediates 113 and 114 $\xrightarrow[\text{MeOH, rt, 16 hrs}]{PhI(OAc)_2,\ NH_4HCO_3}$ Precursor II of Intermediates 113 and 114 which is represented by one of the structures below:

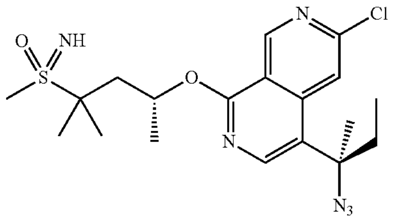

or

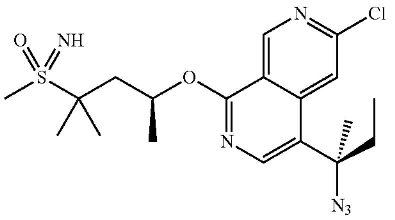

Precursor II of Intermediates 113 and 114 $\xrightarrow{\text{SFC separation}}$ Intermediate 113 (1st eluting isomer) and Intermediate 114 (2nd eluting isomer)

Each of which is represented by one of the four structures below:

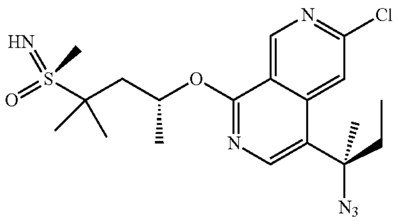

or

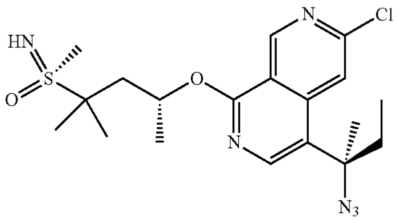

or

-continued

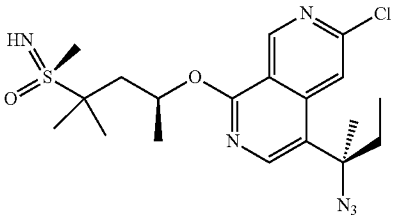

or

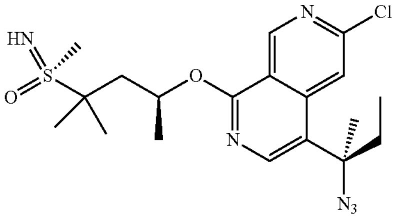

Step 1: 4—((R)-2-Azidobutan-2-yl)-6-chloro-1-(((R)-4-methyl-4-(methylthio)pentan-2-yl)oxy)-2,7-naphthyridine and 4-((R)-2-azidobutan-2-yl)-6-chloro-1-(((S)-4-methyl-4-(methylthio)pentan-2-yl)oxy)-2,7-naphthyridine 4-((R)-2-Azidobutan-2-yl)-6-chloro-1-((4-methyl-4-(methylthio)pentan-2-yl)oxy)-2,7-naphthyridine (500 mg) was separated by SFC (column: Daicel Chiralpak IG (250 mm×30 mm, 10 um); mobile phase: [0.1% $NH_3H_2O$ MeOH]; B %: 15%-15%) to give two peaks separately. The first eluting isomer, one of 4-((R)-2-azidobutan-2-yl)-6-chloro-1-(((R)-4-methyl-4-(methylthio)pentan-2-yl)oxy)-2,7-naphthyridine and 4-((R)-2-azidobutan-2-yl)-6-chloro-1-(((S)-4-methyl-4-(methylthio)pentan-2-yl)oxy)-2,7-naphthyridine (Precursor I to Intermediates 111 and 112, 200 mg, 40% yield) and second eluting isomer, one of 4-((R)-2-azidobutan-2-yl)-6-chloro-1-(((R)-4-methyl-4-(methylthio)pentan-2-yl)oxy)-2,7-naphthyridine and 4-((R)-2-azidobutan-2-yl)-6-chloro-1-(((S)-4-methyl-4-(methylthio)pentan-2-yl)oxy)-2,7-naphthyridine (Precursor I to Intermediates 113 and 114, 200 mg, 40% yield) were obtained as colorless oils. MS (ES+) $C_{19}H_{26}ClN_5OS$ requires: 407, found: 408[M+H]$^+$.

Step 2: ((R)-4-((4-((R)-2-Azidobutan-2-yl)-6-chloro-2,7-naphthyridin-1-yl)oxy)-2-methylpentan-2-yl)(imino)(methyl)-λ6-sulfanone or ((S)-4-((4-((R)-2-azidobutan-2-yl)-6-chloro-2,7-naphthyridin-1-yl)oxy)-2-methylpentan-2-yl)(imino)(methyl)-λ6-sulfanone The title compound (Precursor II to Intermediates 111 and 112) was prepared from 4-((R)-2-azidobutan-2-yl)-6-chloro-1-(((R)-4-methyl-4-(methylthio)pentan-2-yl)oxy)-2,7-naphthyridine or 4-((R)-2-azidobutan-2-yl)-6-chloro-1-(((S)-4-methyl-4-(methylthio)pentan-2-yl)oxy)-2,7-naphthyridine (Precursor 1 to Intermediates 111 and 112, 1$^{st}$ eluting isomer from above) using a procedure similar to that described in Step 3 of Intermediate 107. MS (ES+) $C_{19}H_{27}ClN_6O_2S$ requires: 438, found: 439[M+H]$^+$.

Step 3: (S)-((R)-4-((4-((R)-2-Azidobutan-2-yl)-6-chloro-2,7-naphthyridin-1-yl)oxy)-2-methylpentan-2-yl)(imino)(methyl)-λ6-sulfanone and (R)-((R)-4-((4-((R)-2-azidobutan-2-yl)-6-chloro-2,7-naphthyridin-1-yl)oxy)-2-methylpentan-2-yl)(imino)(methyl)-λ6-sulfanone and (S)-((S)-4-((4-((R)-2-azidobutan-2-yl)-6-chloro-2,7-naphthyridin-1-yl)oxy)-2-methylpentan-2-yl)(imino)(methyl)-λ6-sulfanone and (R)-((S)-4-((4-((R)-2-azidobutan-2-yl)-6-chloro-2,7-naphthyridin-1-yl)oxy)-2-methylpentan-2-yl)(imino)(methyl)-λ6-sulfanone ((R)-4-((4-((R)-2-Azidobutan-2-yl)-6-chloro-2,7-naphthyridin-1-yl)oxy)-2-methylpentan-2-yl)(imino)(methyl)-λ6-sulfanone or ((S)-4-((4-((R)-2-azidobutan-2-yl)-6-chloro-2,7-naphthyridin-1-yl)oxy)-2-methylpentan-2-yl)(imino)(methyl)-λ6-sulfanone (Precursor II to Intermediates 111 and 112, 120 mg) was separated by SFC (column: Daicel Chiralpak IG (250 mm×30 mm, 10 um); mobile phase: [0.1% $NH_3H_2O$ IPA]; B %: 55%-55%) to give two peaks separately. The first eluting isomer, one of (S)-((R)-4-((4-((R)-2-azidobutan-2-yl)-6-chloro-2,7-naphthyridin-1-yl)oxy)-2-methylpentan-2-yl)(imino)(methyl)-λ6-sulfanone or (R)-((R)-4-((4-((R)-2-azidobutan-2-yl)-6-chloro-2,7-naphthyridin-1-yl)oxy)-2-methylpentan-2-yl)(imino)(methyl)-λ6-sulfanone or (S)-((S)-4-((4-((R)-2-azidobutan-2-yl)-6-chloro-2,7-naphthyridin-1-yl)oxy)-2-methylpentan-2-yl)(imino)(methyl)-λ6-sulfanone or (R)-((S)-4-((4-((R)-2-azidobutan-2-yl)-6-chloro-2,7-naphthyridin-1-yl)oxy)-2-methylpentan-2-yl)(imino)(methyl)-λ6-sulfanone (Intermediate 111, 31 mg, 24% yield) and second eluting isomer, one of (S)-((R)-4-((4-((R)-2-azidobutan-2-yl)-6-chloro-2,7-naphthyridin-1-yl)oxy)-2-methylpentan-2-yl)(imino)(methyl)-λ6-sulfanone or (R)-((R)-4-((4-((R)-2-azidobutan-2-yl)-6-chloro-2,7-naphthyridin-1-yl)oxy)-2-methylpentan-2-yl)(imino)(methyl)-λ6-sulfanone or (S)-((S)-4-((4-((R)-2-azidobutan-2-yl)-6-chloro-2,7-naphthyridin-1-yl)oxy)-2-methylpentan-2-yl)(imino)(methyl)-λ6-sulfanone or (R)-((S)-4-((4-((R)-2-azidobutan-2-yl)-6-chloro-2,7-naphthyridin-1-yl)oxy)-2-methylpentan-2-yl)(imino)(methyl)-λ6-sulfanone (Intermediate 112, 75 mg, 59% yield) were obtained as white solids. MS (ES+) $C_{19}H_{27}ClN_6O_2S$ requires: 438, found: 439[M+H]$^+$.

Step 4: ((R)-4-((4-((R)-2-Azidobutan-2-yl)-6-chloro-2,7-naphthyridin-1-yl)oxy)-2-methylpentan-2-yl)(imino)(methyl)-λ6-sulfanone or ((S)-4-((4-((R)-2-azidobutan-2-yl)-6-chloro-2,7-naphthyridin-1-yl)oxy)-2-methylpentan-2-yl)(imino)(methyl)-λ6-sulfanone The title compound (Precursor II to Intermediates 113 and 114) was prepared from 4-((R)-2-azidobutan-2-yl)-6-chloro-1-(((R)-4-methyl-4-(methylthio)pentan-2-yl)oxy)-2,7-naphthyridine or 4-((R)-2-azidobutan-2-yl)-6-chloro-1-(((S)-4-methyl-4-(methylthio)pentan-2-yl)oxy)-2,7-naphthyridine (Precursor 1 to Intermediates 113 and 114, 2$^{nd}$ eluting isomer from above) using a procedure similar to that described in Step 3 of Intermediate 107. MS (ES+) $C_{19}H_{27}ClN_6O_2S$ requires: 438, found: 439[M+H]$^+$.

Step 5: (S)-((R)-4-((4-((R)-2-Azidobutan-2-yl)-6-chloro-2,7-naphthyridin-1-yl)oxy)-2-methylpentan-2-yl)(imino)(methyl)-λ6-sulfanone and (R)-((R)-4-((4-((R)-2-azidobutan-2-yl)-6-chloro-2,7-naphthyridin-1-yl)oxy)-2-methylpentan-2-yl)(imino)(methyl)-λ6-sulfanone and (S)-((S)-4-((4-((R)-2-azidobutan-2-yl)-6-chloro-2,7-naphthyridin-1-yl)oxy)-2-methylpentan-2-yl)(imino)(methyl)-λ6-sulfanone and (R)-((S)-4-((4-((R)-2-azidobutan-2-yl)-6-chloro-2,7-naphthyridin-1-yl)oxy)-2-methylpentan-2-yl)(imino)(methyl)-λ6-sulfanone ((R)-4-((4-((R)-2-Azidobutan-2-yl)-6-chloro-2,7-naphthyridin-1-yl)oxy)-2-methylpentan-2-yl)(imino)(methyl)-λ6-sulfanone or ((S)-4-((4-((R)-2-azidobutan-2-yl)-6-chloro-2,7-naphthyridin-1-yl)oxy)-2-methylpentan-2-yl)(imino)(methyl)-λ6-sulfanone (Precursor II to Intermediates 113 and 114, 120 mg) was separated by SFC (column: Daicel Chiralpak AD-H (250 mm×30 mm, 5 um); mobile phase: [0.10% $NH_3H_2O$ EtOH]; B %: 20%-20%) to give two peaks separately. The first eluting isomer, one of (S)-((R)-4-((4-((R)-2-azidobutan-2-yl)-6-chloro-2,7-naphthyridin-1-yl)oxy)-2-methylpentan-2-yl)(imino)(methyl)-λ6-sulfanone or (R)-((R)-4-((4-((R)-2-azidobutan-2-yl)-6-chloro-2,7-naphthyridin-1-yl)oxy)-2-methylpentan-2-yl)(imino)(methyl)-λ6-sulfanone or (S)-((S)-4-((4-((R)-2-azidobutan-2-yl)-6-chloro-2,7-naphthyridin-1-yl)oxy)-2-methylpentan-2-yl)(imino)(methyl)-λ6-sulfanone or (R)-((S)-4-((4-((R)-2-azidobutan-2-yl)-6-chloro-2,7-naphthyridin-1-yl)oxy)-2-methylpentan-2-yl)(imino)(methyl)-λ6-sulfanone (Intermediate 113, 31 mg, 25% yield) and second eluting isomer, one of (S)-((R)-4-((4-((R)-2-azidobutan-2-yl)-6-chloro-2,7-naphthyridin-1-yl)oxy)-2-methylpentan-2-yl)(imino)(methyl)-λ6-sulfanone or (R)-((R)-4-((4-((R)-2-azidobutan-2-yl)-6-chloro-2,7-naphthyridin-1-yl)oxy)-2-methylpentan-2-yl)(imino)(methyl)-λ6-sulfanone or (S)-((S)-4-((4-((R)-2-azidobutan-2-yl)-6-chloro-2,7-naphthyridin-1-yl)oxy)-2-methylpentan-2-yl)(imino)(methyl)-λ6-sulfanone or (R)-((S)-4-((4-((R)-2-azidobutan-2-yl)-6-chloro-2,7-naphthyridin-1-yl)oxy)-2-methylpentan-2-yl)(imino)(methyl)-λ6-sulfanone (Intermediate 114, 60 mg, 5947% yield) were obtained as white solids. MS (ES+) $C_{19}H_{27}ClN_6O_2S$ requires: 438, found: 439$[M+H]^+$.

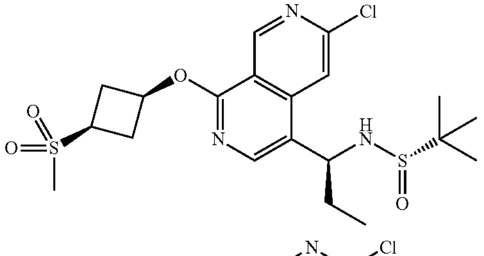

and

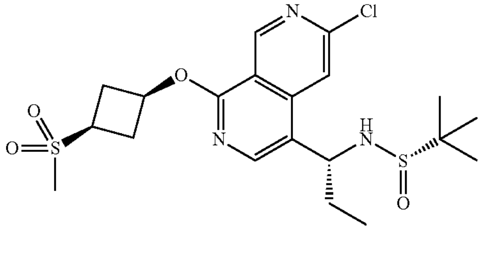

Intermediates 115 and 116: (S)—N—((S)-1-(6-Chloro-1-((cis)-3-(methylsulfonyl)cyclobutoxy)-2,7-naphthyridin-4-yl)propyl)-2-methylpropane-2-sulfinamide and (S)—N—((R)-1-(6-chloro-1-((cis)-3-(methylsulfonyl)cyclobutoxy)-2,7-naphthyridin-4-yl)propyl)-2-methylpropane-2-sulfinamide

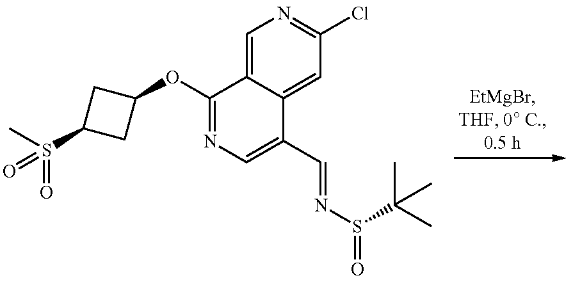

Intermediate 115 and Intermediate 116 each of which is represented by one of the structures shown below:

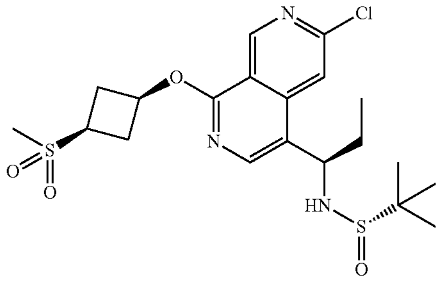

and

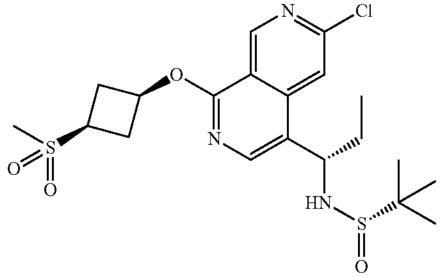

Step 1: (S)—N—((S)-1-(6-Chloro-1-(cis-3-(methylsulfonyl)cyclobutoxy)-2,7-naphthyridin-4-yl)butyl)-2-methylpropane-2-sulfinamide and (S)—N—((R)-1-(6-chloro-1-(cis-3-(methylsulfonyl)cyclobutoxy)-2,7-naphthyridin-4-yl)butyl)-2-methylpropane-2-sulfinamide To a solution of (S)—N—((E)-(6-chloro-1-(cis-3-(methylsulfonyl)cyclobutoxy)-2,7-naphthyridin-4-yl)methylene)-2-methylpropane-2-sulfinamide (500 mg, 1.13 mmol) in THF (20 mL) was added EtMgBr (3 M, 1.13 mL) at 0° C. The cooling bath was removed, and the reaction mixture was stirred at 25° C. for 30 min. The reaction mixture was then quenched by addition of saturated aqueous $NH_4Cl$ solution (40 mL) and extracted with EA (40 mL×3). The combined organic layers were dried over anhydrous sodium sulfate, filtered, and concentrated to give a residue. The residue was purified by prep-HPLC (column: Phenomenex luna C18 150×40 mm×15 um; mobile phase: [water (0.10% TFA)-ACN]; B %: 36%-46%, 10 min) to give one of (S)—N—((S)-1-(6-chloro-1-((cis)-3-(methylsulfonyl)cyclobutoxy)-2,7-naphthyridin-4-yl)propyl)-2-methylpropane-2-sulfinamide or (S)—N—((R)-1-(6-chloro-1-((cis)-3-(methylsulfonyl)cyclobutoxy)-2,7-naphthyridin-4-yl)propyl)-2-methylpropane-2-sulfinamide as the first eluting isomer (Intermediate 115, 100 mg, 16% yield) as a white solid and the other one of (S)—N—((S)-1-(6-chloro-1-((cis)-3-(methylsulfonyl)cyclobutoxy)-2,7-naphthyridin-4-yl)propyl)-2-methylpropane-2-sulfinamide or (S)—N—((R)-1-(6-chloro-1-((cis)-3-(methylsulfonyl)cyclobutoxy)-2,7-naphthyridin-4-yl)propyl)-2-methylpropane-2-sulfinamide as the second eluting isomer (Intermediate 116, 100 mg, 17% yield, the second fraction) as a white solid.

Intermediate 115: MS (ES+) $C_{20}H_{28}ClN_3O_4S_2$ requires: 44, found: 474[M+H]$^+$.

Intermediate 116: MS (ES+) $C_{20}H_{28}ClN_3O_4S_2$ requires: 44, found: 474[M+H]$^+$.

Representative Methods to Synthesize Compounds in Table 1

Example 1a: Synthetic Method 1

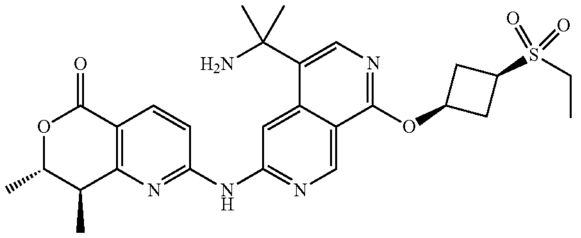 [SMILES: CCS(=O)(=O)[C@H]1C[C@@H](Oc2ncc(C(C)(C)N)c3cc(Nc4ccc5c(n4)[C@@H](C)[C@H](C)OC5=O)ncc23)C1]

(7S,8R)-2-((5-(2-Aminopropan-2-yl)-8-((cis)-3-(ethylsulfonyl)cyclobutoxy)-2,7-naphthyridin-3-yl)amino)-7,8-dimethyl-7,8-dihydro-5H-pyrano[4,3-b]pyridin-5-one (Compound 39)

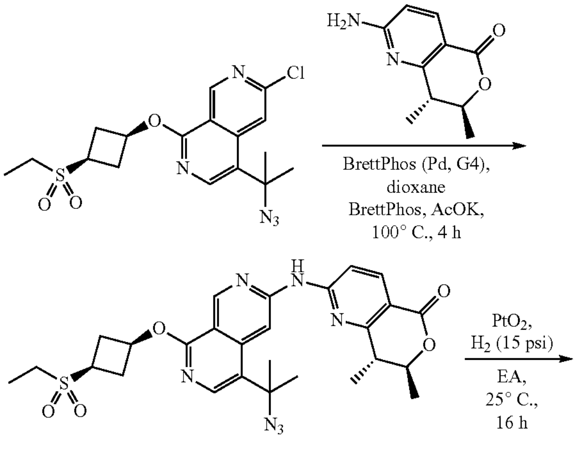

-continued

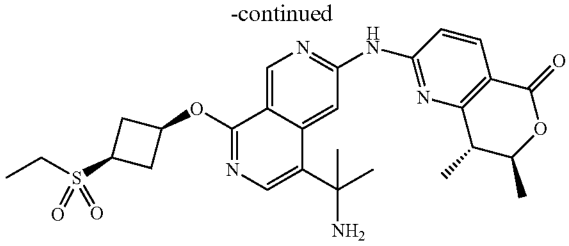

Step 1: (7S,8R)-2-((5-((R)-2-Azidobutan-2-yl)-8-(cis-3-(ethylsulfonyl)cyclobutoxy)-2,7-naphthyridin-3-yl)amino)-7,8-dimethyl-7,8-dihydro-5H-pyrano[4,3-b]pyridin-5-one A mixture of 4-(2-azidopropan-2-yl)-6-chloro-1-(cis-3-(ethylsulfonyl)cyclobutoxy)-2,7-naphthyridine (Intermediate 44, 60 mg, 146 μmol), (7S,8R)-2-amino-7,8-dimethyl-7,8-dihydro-5H-pyrano[4,3-b]pyridin-5-one (Intermediate 1, 31.0 mg, 161 μmol), BrettPhos G4 precatalyst (6.74 mg, 7.32 μmol), BrettPhos (3.93 mg, 7.32 μmol) and KOAc (35.9 mg, 366 μmol) in dioxane (2 mL) was degassed and purged with nitrogen 3 times, then the mixture was stirred at 100° C. for 4 h. The reaction mixture was then filtered and concentrated to give a residue. The residue was purified by prep-TLC (PE/EA=0:1) to give the title compound (40.0 mg, 49% yield) as a white solid.

Step 2: (7S,8R)-2-((5-(2-Aminopropan-2-yl)-8-((cis)-3-(ethylsulfonyl)cyclobutoxy)-2,7-naphthyridin-3-yl)amino)-7,8-dimethyl-7,8-dihydro-5H-pyrano[4,3-b]pyridin-5-one To a solution of (7S,8R)-2-((5-((R)-2-azidobutan-2-yl)-8-(cis-3-(ethylsulfonyl)cyclobutoxy)-2,7-naphthyridin-3-yl)amino)-7,8-dimethyl-7,8-dihydro-5H-pyrano[4,3-b]pyridin-5-one (40.0 mg, 70.7 μmol) in EA (30 mL) was added platinum dioxide (12.1 mg, 53.1 μmol). The suspension was degassed under vacuum and purged with hydrogen several times. The reaction mixture was then stirred under hydrogen (15 psi) at 25° C. for 16 h. The reaction mixture was then filtered and concentrated to give a residue. The residue was purified by prep-HPLC (column: Phenomenex Gemini-NX C18 75*30 mm*3 um; mobile phase: [water (10 mM $NH_4HCO_3$)-ACN]; B %: 22%-52%) to give the title compound (11.7 mg, 31% yield) as a yellow solid. MS (ES+) $C_{27}H_{33}N_5O_5S$ requires: 539, found: 540[M+H]$^+$. $^1$H NMR (400 MHz, $CD_3OD$): δ ppm 10.70 (s, 1H), 9.42 (s, 1H), 9.32 (s, 1H), 8.14 (s, 1H), 8.08 (d, J=8.63 Hz, 1H) 7.37 (d, J=8.8 Hz, 1H), 5.42-5.30 (m, 1H), 4.67-4.49 (m, 1H), 3.99-3.77 (m, 1H), 3.10-3.04 (m, 2H), 3.02-2.95 (m, 1H), 2.89-2.82 (m, 2H), 2.57-2.53 (m, 1H), 1.65 (d, J=2.4 Hz, 6H), 1.44 (d, J=7.2 Hz, 3H), 1.37 (d, J=6.4 Hz, 3H), 1.21 (t, J=7.4 Hz, 3H).

Example 1b: Synthetic Method 1

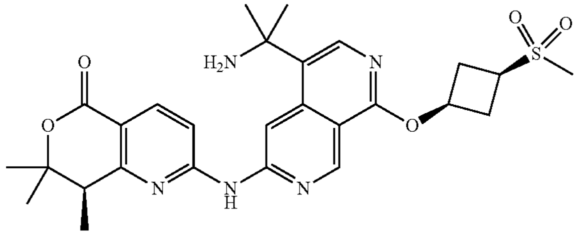

(R)-2-((5-(2-Aminopropan-2-yl)-8-(cis-3-(methylsulfonyl)cyclobutoxy)-2,7-naphthyridin-3-yl)amino)-7,7,8-trimethyl-7,8-dihydro-5H-pyrano[4,3-b]pyridin-5-one (Compound 42)

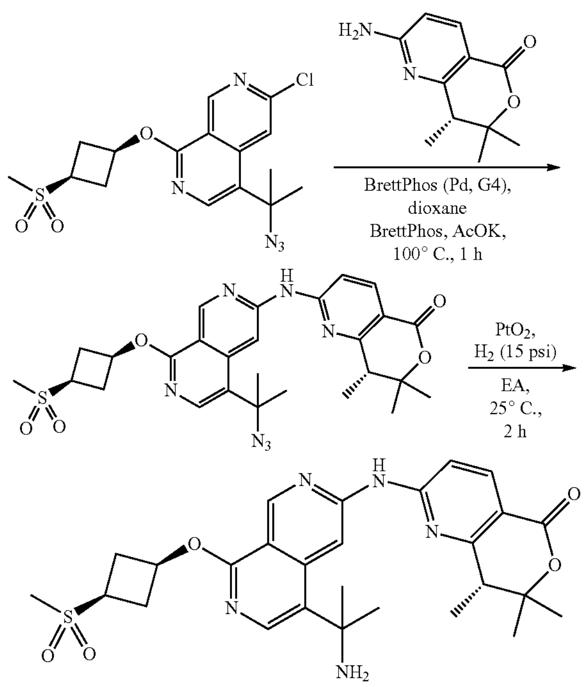

Step 1: (R)-2-((5-(2-Azidopropan-2-yl)-8-(cis-3-(methylsulfonyl)cyclobutoxy)-2,7-naphthyridin-3-yl)amino)-7,7,8-trimethyl-7,8-dihydro-5H-pyrano[4,3-b]pyridin-5-one A mixture of 4-(2-azidopropan-2-yl)-6-chloro-1-(cis-3-(methylsulfonyl)cyclobutoxy)-2,7-naphthyridine (Intermediate 22, 400 mg, 1.01 mmol), (R)-2-amino-7,7,8-trimethyl-7,8-dihydro-5H-pyrano[4,3-b]pyridin-5-one (Intermediate 3, 229 mg, 1.11 mmol), BrettPhos G4 precatalyst (93.0 mg, 101 umol), BrettPhos (108 mg, 202 umol) and KOAc (298 mg, 3.03 mmol) in dioxane (8 mL) was degassed and purged with nitrogen 3 times, then the mixture was stirred at 100° C. for 1 h. The reaction mixture was then filtered and concentrated to give a residue. The residue was purified by flash-column chromatography on silica gel (0 to 60% EA/PE) to give the title compound (370 mg, 61% yield) as a yellow solid.

Step 2: (R)-2-((5-(2-Aminopropan-2-yl)-8-(cis-3-(methylsulfonyl)cyclobutoxy)-2,7-naphthyridin-3-yl)amino)-7,7,8-trimethyl-7,8-dihydro-5H-pyrano[4,3-b]pyridin-5-one To a solution of (R)-2-((5-(2-Azidopropan-2-yl)-8-(cis-3-(methylsulfonyl)cyclobutoxy)-2,7-naphthyridin-3-yl)amino)-7,7,8-trimethyl-7,8-dihydro-5H-pyrano[4,3-b]pyridin-5-one (370 mg, 654 umol) in EA (12 mL) was added platinum dioxide (44.6 mg, 196 umol). The suspension was degassed under vacuum and purged with hydrogen several times. The reaction mixture was then stirred under hydrogen (15 psi) at 25° C. for 2 h. The reaction mixture was then filtered and concentrated to give a residue. The residue was purified by prep-HPLC (column: Phenomenex luna C18 150×40 mm×15 μm; mobile phase: [water (0.225% FA)-ACN]; B %: 10%-40%) to give the title compound (279 mg, 79% yield) as an off-white solid. MS (ES+) $C_{27}H_{33}N_5O_5S$ requires: 539, found: 540[M+H]$^+$. $^1$H NMR (400 MHz, $CD_3OD$): δ ppm 9.39 (s, 1H), 9.21 (s, 1H), 8.54 (s, 1H), 8.14 (d, J=8.8 Hz, 1H), 8.07-8.03 (m, 1H), 7.25 (d, J=8.8 Hz, 1H), 5.51-5.36 (m, 1H), 3.92-3.75 (m, 1H), 3.05-2.95 (m, 3H), 2.93 (s, 3H), 2.76-2.63 (m, 2H), 1.94 (d, J=11.2 Hz, 6H), 1.53 (s, 3H), 1.45 (s, 3H), 1.40 (d, J=7.2 Hz, 3H).

Example 1c: Synthetic Method 1

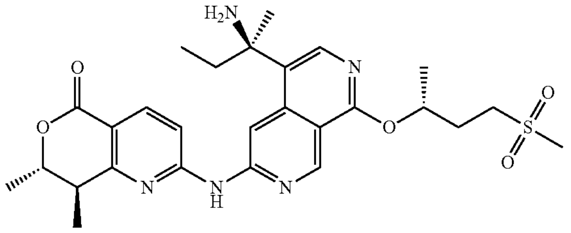

(7S,8R)-2-((5-((R)-2-Aminobutan-2-yl)-8-(((R)-4-(methylsulfonyl)butan-2-yl)oxy)-2,7-naphthyridin-3-yl)amino)-7,8-dimethyl-7,8-dihydro-5H-pyrano[4,3-b]pyridin-5-one (Compound 52)

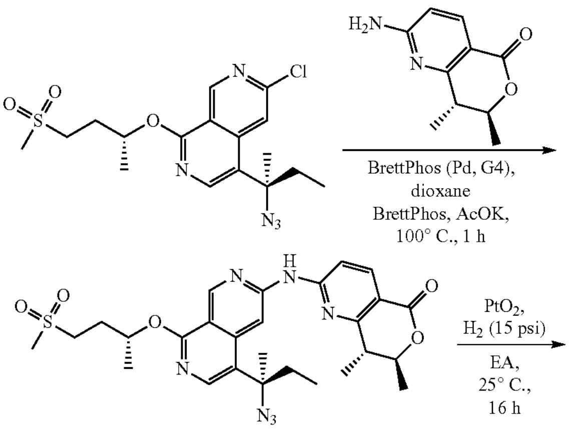

-continued

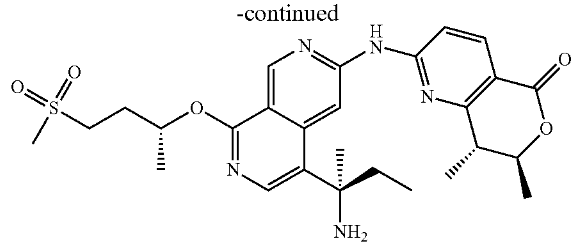

Step 1: (7S,8R)-2-((5-((R)-2-Azidobutan-2-yl)-8-(((R)-4-(methylsulfonyl)butan-2-yl)oxy)-2,7-naphthyridin-3-yl)amino)-7,8-dimethyl-7,8-dihydro-5H-pyrano[4,3-b]pyridin-5-one A mixture of 4-((R)-2-azidobutan-2-yl)-6-chloro-1-(((R)-4-(methylsulfonyl)butan-2-yl)oxy)-2,7-naphthyridine (Intermediate 31, 130 mg, 316 μmol), (7S,8R)-2-amino-7,8-dimethyl-7,8-dihydro-5H-pyrano[4,3-b]pyridin-5-one (Intermediate 1, 60.7 mg, 316 μmol), BrettPhos G4 precatalyst (29.1 mg, 31.6 umol), BrettPhos (16.9 mg, 31.6 μmol) and KOAc (77.4 mg, 789 mol) in dioxane (3 mL) was degassed and purged with nitrogen 3 times, then the mixture was stirred at 100° C. for 1 h. The reaction mixture was then filtered and concentrated to give a residue. The residue was purified by prep-TLC (PE/EA=1: 2) to give the title compound (130 mg, 73% yield) as a yellow solid.

Step 2: (7S,8R)-2-((5-((R)-2-Aminobutan-2-yl)-8-(((R)-4-(methylsulfonyl)butan-2-yl)oxy)-2,7-naphthyridin-3-yl)amino)-7,8-dimethyl-7,8-dihydro-5H-pyrano[4,3-b]pyridin-5-one To a solution of (7S,8R)-2-((5-((R)-2-azidobutan-2-yl)-8-(((R)-4-(methylsulfonyl)butan-2-yl)oxy)-2,7-naphthyridin-3-yl)amino)-7,8-dimethyl-7,8-dihydro-5H-pyrano[4,3-b]pyridin-5-one (130 mg, 229 μmol) in EA (10 mL) was added platinum dioxide (39.2 mg, 172 μmol). The suspension was degassed under vacuum and purged with hydrogen several times. The reaction mixture was then stirred under hydrogen (15 psi) at 25° C. for 16 h. The reaction mixture was then filtered and concentrated to give a residue. The residue was purified by silica gel chromatography (PE/EA=1:0 to 0:1, followed by EA/MeOH=1:0 to 10:1) to give the title compound (59.0 mg, 46% yield) as a yellow solid. MS (ES+) $C_{27}H_{35}N_5O_5S$ requires: 541, found: 542[M+H]$^+$. $^1$H NMR (400 MHz, $CD_3OD$): δ ppm 9.40 (s, 1H), 9.14 (s, 1H), 8.20-8.11 (m, 2H), 7.31 (d, J=8.8 Hz, 1H), 5.71-5.53 (m, 1H), 4.73-4.63 (m, 1H), 3.42-3.32 (m, 2H), 3.07-2.97 (m, 4H), 2.50-2.39 (m, 1H), 2.37-2.29 (m, 2H), 2.24-2.11 (m, 1H), 1.78 (s, 3H), 1.54-1.48 (m, 6H), 1.46 (d, J=6.8 Hz, 3H), 0.75 (t, J=7.4 Hz, 3H).

Example 1d: Synthetic Method 1

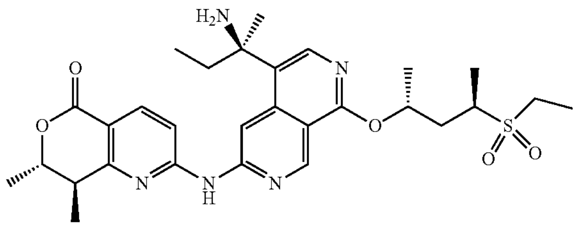 [SMILES: CC[C@@](C)(N)c1cnc(O[C@H](C)C[C@@H](C)S(=O)(=O)CC)c2cnc(Nc3ccc4c(n3)[C@@H](C)[C@H](C)OC4=O)cc12]

(7S,8R)-2-((5-((R)-2-Aminobutan-2-yl)-8-(((2R,4R)-4-(ethylsulfonyl)pentan-2-yl)oxy)-2,7-naphthyridin-3-yl)amino)-7,8-dimethyl-7,8-dihydro-5H-pyrano[4,3-b]pyridin-5-one (Compound 127)

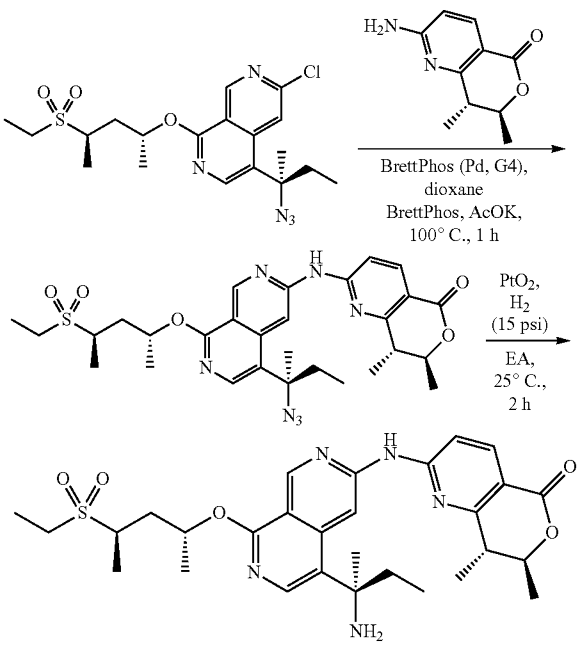 [SMILES: CC[C@@](C)(N=[N+]=[N-])c1cnc(O[C@H](C)C[C@@H](C)S(=O)(=O)CC)c2cnc(Cl)cc12 ; C[C@@H]1OC(=O)c2ccc(N)nc2[C@H]1C ; CC[C@@](C)(N=[N+]=[N-])c1cnc(O[C@H](C)C[C@@H](C)S(=O)(=O)CC)c2cnc(Nc3ccc4c(n3)[C@@H](C)[C@H](C)OC4=O)cc12 ; CC[C@@](C)(N)c1cnc(O[C@H](C)C[C@@H](C)S(=O)(=O)CC)c2cnc(Nc3ccc4c(n3)[C@@H](C)[C@H](C)OC4=O)cc12]

Step 1: (7S,8R)-2-((5-((R)-2-Azidobutan-2-yl)-8-(((2R,4R)-4-(ethylsulfonyl)pentan-2-yl)oxy)-2,7-naphthyridin-3-yl)amino)-7,8-dimethyl-7,8-dihydro-5H-pyrano[4,3-b]pyridin-5-one A mixture of 4-((R)-2-azidobutan-2-yl)-6-chloro-1-(((2R,4R)-4-(ethylsulfonyl)pentan-2-yl)oxy)-2,7-naphthyridine (Intermediate 86, 85 mg, 193 umol), (7S,8R)-2-amino-7,8-dimethyl-7,8-dihydro-5H-pyrano[4,3-b]pyridin-5-one (Intermediate 1, 37.1 mg, 193 umol), BrettPhos G4 precatalyst (17.8 mg, 19.3 umol), BrettPhos (20.7 mg, 38.6 umol) and KOAc (56.9 mg, 579 umol) in dioxane (3 mL) was degassed and purged with nitrogen 3 times, then the mixture was stirred at 100° C. for 1 h. The reaction mixture was then filtered and concentrated to give a residue. The residue was purified by flash-column chromatography on silica gel (0 to 60% EA/PE) to give the title compound (120 mg, 54% yield) as a white solid.

Step 2: (7S,8R)-2-((5-((R)-2-Aminobutan-2-yl)-8-(((2R,4R)-4-(ethylsulfonyl)pentan-2-yl)oxy)-2,7-naphthyridin-3-yl)amino)-7,8-dimethyl-7,8-dihydro-5H-pyrano[4,3-b]pyridin-5-one To a solution of (7S,8R)-2-((5-((R)-2-Azidobutan-2-yl)-8-(((2R,4R)-4-(ethylsulfonyl)pentan-2-yl)oxy)-2,7-naphthyridin-3-yl)amino)-7,8-dimethyl-7,8-dihydro-5H-pyrano[4,3-b]pyridin-5-one (120 mg, 201 umol) in EA (16 mL) was added platinum dioxide ((13.7 mg, 60.4 umol). The suspension was degassed under vacuum and purged with hydrogen several times. The reaction mixture was then stirred under hydrogen (15 psi) at 25° C. for 2 h. The reaction mixture was then filtered and concentrated to give a residue. The residue was purified by prep-TLC (EA/MeOH=1:1) to give the title compound (31.2 mg, 27% yield) as a white solid. MS (ES+) $C_{29}H_{39}N_5O_5S$ requires: 569, found: 570[M+H]$^+$. $^1$H NMR (400 MHz, CD3OD): δ ppm 9.36 (s, 1H), 9.15 (s, 1H), 8.28-8.00 (m, 2H), 7.29 (d, J=8.8 Hz, 1H), 5.80-5.61 (m, 1H), 4.73-4.56 (m, 1H), 3.45-3.35 (m, 1H), 3.14-3.06 (m, 2H), 3.06-2.98 (m, 1H), 2.49-2.30 (m, 2H), 2.23-2.03 (m, 2H), 1.73 (s, 3H), 1.51-1.43 (m, 12H), 1.34-1.27 (m, 3H), 0.78-0.68 (m, 3H).

Example 1e: Synthetic Method 1

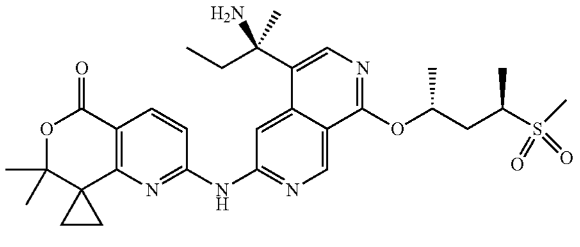

2'-((5-((R)-2-Aminobutan-2-yl)-8-(((2R,4R)-4-(methylsulfonyl)pentan-2-yl)oxy)-2,7-naphthyridin-3-yl)amino)-7',7'-dimethyl-5'H,7'H-spiro[cyclopropane-1,8'-pyrano[4,3-b]pyridin]-5'-one (Compound 136)

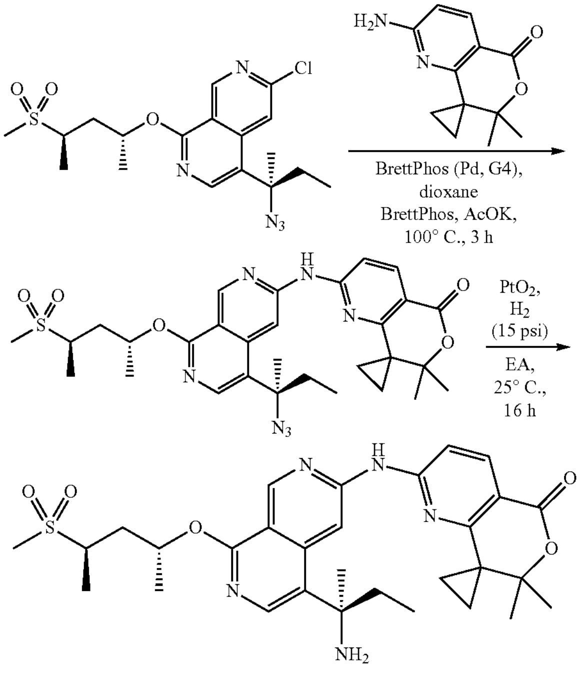

Step 1: 2'-((5-((R)-2-Azidobutan-2-yl)-8-(((2R,4R)-4-(methylsulfonyl)pentan-2-yl)oxy)-2,7-naphthyridin-3-yl)amino)-7',7'-dimethyl-5'H,7'H-spiro[cyclopropane-1,8'-pyrano[4,3-b]pyridin]-5'-one A mixture of 4-((R)-2-azidobutan-2-yl)-6-chloro-1-(((2R,4R)-4-(methylsulfonyl)pentan-2-yl)oxy)-2,7-naphthyridine (Intermediate 53, 70.0 mg, 164 μmol), 2'-amino-7',7'-dimethyl-5'H,7'H-spiro[cyclopropane-1,8'-pyrano[4,3-b]pyridin]-5'-one (Intermediate 15, 36.0 mg, 164 mol), BrettPhos G4 precatalyst (8.00 mg, 8.22 μmol), BrettPhos (9.00 mg, 16.4 μmol) and KOAc (48.0 mg, 493 μmol) in dioxane (2 mL) was degassed and purged with nitrogen 3 times, then the mixture was stirred at 100° C. for 3 h. The reaction mixture was then filtered and concentrated to give a residue. The residue (90.0 mg, 90% yield, yellow oil) was used in the next step without further purification.

Step 2: 2'-((5-((R)-2-Aminobutan-2-yl)-8-(((2R,4R)-4-(methylsulfonyl)pentan-2-yl)oxy)-2,7-naphthyridin-3-yl)amino)-7',7'-dimethyl-5'H,7'H-spiro[cyclopropane-1,8'-pyrano[4,3-b]pyridin]-5'-one To a solution of 2'-((5-((R)-2-Azidobutan-2-yl)-8-(((2R,4R)-4-(methylsulfonyl)pentan-2-yl)oxy)-2,7-naphthyridin-3-yl)amino)-7',7'-dimethyl-5'H,7'H-spiro[cyclopropane-1,8'-pyrano[4,3-b]pyridin]-5'-one (90.0 mg, 148 μmol) in EA (10 mL) was added platinum dioxide (13.0 mg, 55.3 μmol). The suspension was degassed under vacuum and purged with hydrogen several times. The reaction mixture was then stirred under hydrogen (15 psi) at 25° C. for 16 h. The reaction mixture was then filtered and concentrated to give a residue. The residue was purified by prep-TLC (EA/MeOH=10:1) to give the title compound (30.2 mg, 33% yield) as a yellow solid. MS (ES+) $C_{30}H_{39}N_5O_5S$ requires: 581, found: 582[M+H]$^+$. $^1$H NMR (400 MHz, $CD_3OD$): δ ppm 9.41 (s, 1H), 8.33 (s, 1H), 8.16 (d, J=8.8 Hz, 1H), 8.10 (s, 1H), 7.62 (d, J=8.8 Hz, 1H), 5.75-5.65 (m, 1H), 3.40-3.33 (m, 1H), 2.93 (s, 3H), 2.45-2.30 (m, 2H), 2.18-2.08 (m, 2H), 1.76 (s, 3H), 1.559-1.53 (m, 2H), 1.52-1.47 (m, 6H), 1.42 (s, 6H), 1.31-1.27 (m, 2H), 0.76 (d, J=7.2 Hz, 3H).

Example 2: Synthetic Method 2

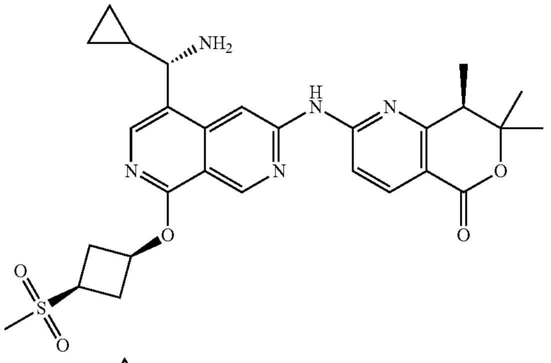

or

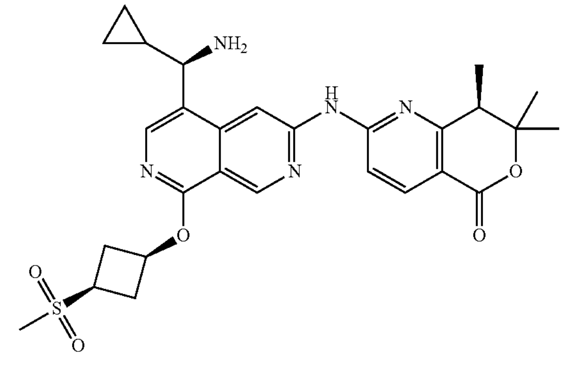

(R)-2-((5-((S or R)-Amino(cyclopropyl)methyl)-8-(cis-3-(methylsulfonyl)cyclobutoxy)-2,7-naphthyridin-3-yl)amino)-7,7,8-trimethyl-7,8-dihydro-5H-pyrano[4,3-b]pyridin-5-one (Compound 62)

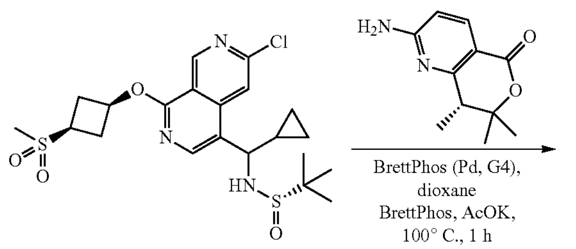

Precursor of Compound 62, which is represented by one of the structures below

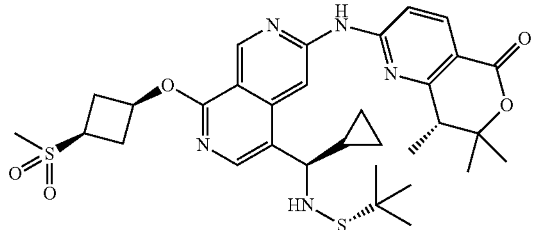

or

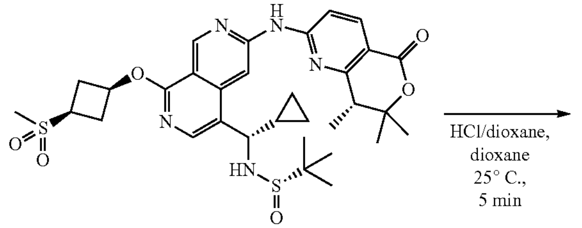

Compound 62, which is represented by one of the structures below

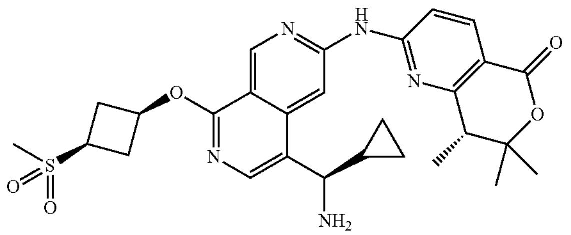

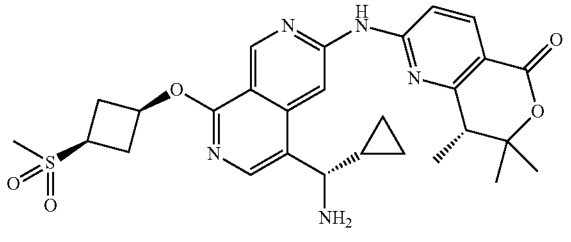

Step 1: (S)—N—((R or S)-Cyclopropyl(1-(cis-3-(methylsulfonyl)cyclobutoxy)-6-(((R)-7,7,8-trimethyl-5-oxo-7,8-dihydro-5H-pyrano[4,3-b]pyridin-2-yl)amino)-2,7-naphthyridin-4-yl)methyl)-2-methylpropane-2-sulfinamide A mixture of (R)-2-amino-7,7,8-trimethyl-7,8-dihydro-5H-pyrano[4,3-b]pyridin-5-one (Intermediate 3, 44.6 mg, 216 umol), (S)—N-((6-chloro-1-(cis-3-(methylsulfonyl)cyclobutoxy)-2,7-naphthyridin-4-yl)(cyclopropyl)methyl)-2-methylpropane-2-sulfinamide (Intermediate 58, 100 mg, 206 umol), BrettPhos (22.1 mg, 41.2 umol), BrettPhos G4 pre-catalyst (18.9 mg, 20.6 umol), and KOAc (60.6 mg, 617 umol) in dioxane (3 mL) was degassed and purged with nitrogen 3 times, and then the mixture was stirred at 100° C. for 1 h. The reaction mixture was then filtered and concentrated to give a residue. The residue was purified by prep-TLC (PE/EA=0:1) to give the title compound (one of two isomers, stereochemistry at the cyclopropyl position undetermined) as the second eluting isomer (20 mg, 15% yield, white solid). MS (ES+) $C_{32}H_{41}N_5O_6S_2$ requires: 655, found: 656[M+H]$^+$.

Step 2: (R)-2-((5-((S or R)-Amino(cyclopropyl)methyl)-8-(cis-3-(methylsulfonyl)cyclobutoxy)-2,7-naphthyridin-3-yl)amino)-7,7,8-trimethyl-7,8-dihydro-5H-pyrano[4,3-b]pyridin-5-one To a solution of (S)—N—((R or S)-cyclopropyl(1-(cis-3-(methylsulfonyl)cyclobutoxy)-6-(((R)-7,7,8-trimethyl-5-oxo-7,8-dihydro-5H-pyrano[4,3-b]pyridin-2-yl)amino)-2,7-naphthyridin-4-yl)methyl)-2-methylpropane-2-sulfinamide (20 mg, 30.5 umol) in dioxane (2 mL) was added 4 M HCl in dioxane (1 mL). The reaction mixture was stirred at 25° C. for 5 min, then was concentrated to give a residue was purified by prep-HPLC (column: Waters Xbridge 150x25 mmx5 m; mobile phase: [water (0.05% ammonia hydroxide v/v)-ACN]; B %: 25%-55%, 10 min) to give the title compound (16 mg, 93% yield) as a yellow solid. MS (ES+) $C_{28}H_{33}N_5O_5S$ requires: 551, found: 552[M+H]$^+$. $^1$H NMR (400 MHz, $CD_3OD$): δ ppm 9.39-9.23 (m, 1H), 8.97-8.83 (m, 1H), 8.20 (s, 1H), 8.15-8.07 (m, 1H), 7.19 (d, J=8.8 Hz, 1H), 5.61-5.27 (m, 2H), 3.83 (d, J=6.4 Hz, 2H), 3.67-3.56 (m, 1H), 3.22-3.11 (m, 1H), 2.93 (s, 4H), 2.68 (d, J=5.2 Hz, 2H), 1.54-1.43 (m, 9H), 0.73-0.34 (m, 4H).

Example 3: Inhibition of MAP4K1 Biochemical Enzymatic Activity

MAP4K1 (HPK1) and relevant off-target enzymatic activity was monitored using the Perkin Elmer electrophoretic mobility shift technology platform—the EZReader 2. Fluorescent labeled substrate peptide was incubated in the presence of kinase and ATP, and in the presence of dosed compound, such that each dose of compound resulted in a reflective proportion of the peptide to be phosphorylated. Within the linear, steady-state phase of the kinase enzymatic reaction, the mixed pool of phosphorylated (product) and non-phosphorylated (substrate) peptides was passed through the microfluidic system of the PerkinElmer EZ Reader 2, under an applied electric potential difference. The presence of the phosphate group on the product peptide provided a difference in mass and charge between that of the substrate peptide, resulting in a separation of the substrate and product pools in the sample (Perrin et al. 2010). As the product and substrate peptide mixture passes the lasers within the instrument, these pools are detected ($\lambda_{ex}$=488 nm, $\lambda_{em}$=568 nm) and resolved as separate peaks. The ratio between these peaks reflects the activity of the compound at that concentration, in that well, under those conditions.

Enzyme Activity Inhibition Assay Protocol:

Inhibitors were dissolved in 100% DMSO at a stock concentration of 10 mM. A 100x, 10-point, 4-fold serial dilution of each inhibitor was created in 100% DMSO either manually or on a Hamilton STAR liquid handler, starting at a relevant concentration, usually 1 mM. A volume of 0.130 μL of each concentration was transferred to the relevant wells of a 384-well plate (Greiner 781 201) in duplicate using a TTPLabtech Mosquito nano-litre dispenser. Using a Multidrop Combi, the remaining constituents of the kinase reaction were added to the 130 nL of dosed compound as follows (see table below for final reaction details):

Enzyme activity assays at the $^{APP}$KM for ATP or 1 mM ATP: In each well of a 384-well plate, 0.1-15 nM of untreated enzyme was incubated in a total of 13 μL of buffer (100 mM HEPES pH 7.5, 0.015% Brij 35, 10 mM $MgCl_2$, 1 mM DTT) with 1.5 μM fluorescent peptid and 20-1000 μM ATP, at 25° C., for 60-180 minutes in the presence or absence of a dosed concentration series of compound (1% DMSO final concentration). The kinase reactions were stopped by the addition of 70 μl of Stop buffer (100 mM HEPES pH 7.5, 0.015% Brij 35, 35 mM EDTA and 0.2% of Coating Reagent 3 (Caliper Lifesciences)). The plates were read on a Caliper EZReader 2 as described above.

TABLE 2

Kinase Reaction Conditions

| Enzyme (Source) | Enzyme Concentration | ATP Concentration | Substrate Peptide & Concentration | Kinase Reaction Time |
|---|---|---|---|---|
| HPK1 (Invitrogen) | 0.5 nM | 26 μM | S6K2tide, 1.5 μM | 120 min. |
| HPK1 (Invitrogen) | 0.25 nM | 1000 μM | S6K2tide, 1.5 μM | 120 min. |
| LCK (Invitrogen) | 12 nM | 26 μM | FLAtide, 1.5 μM | 60 min. |
| HGK (Invitrogen) | 0.1 nM | 50 μM | FL25tide, 1.5 μM | 60 min. |
| GLK (SignalChem) | 15 nM | 20 μM | PKAtide, 2 μM | 180 min. |

S6K2tide; Carna Biosciences (5-FAM-Proprietary Sequence-CONH2)
FLAtide; Perkin Elmer (5-FAM-EGIYGVLFKKK (SEQ ID NO: 1)-$CONH_2$)
FL25tide; Perkin Elmer (5-FAM-VDGKEIYNTIRRK (SEQ ID NO: 2)-$CONH_2$)
PKAtide; Anaspec Peptide Co. (5-FAM-GRTGRRNSI (SEQ ID NO: 3)-$CONH_2$)

Perrin D, Frémaux C, Shutes A. Capillary microfluidic electrophoretic mobility shift assays: application to enzymatic assays in drug discovery. Expert Opin Drug Discov. 2010, 5(1):51-63.

The results obtained in these experiments for compounds prepared according to the examples are summarized in Table 3 below.

TABLE 3

| Compound # | MAP4K1 IC50 (nM) | IL-2 Primary T Cell EC50 (nM) |
|---|---|---|
| 1 | 0.26 | |
| 2 | 0.89 | |
| 3 | 0.12 | 39 |
| 4 | 1.85 | |
| 5 | 1.77 | |
| 6 | 0.18 | 7 |
| 7 | 0.28 | 11 |
| 8 | 0.31 | |
| 9 | 0.92 | |
| 10 | 0.12 | |
| 11 | 0.29 | 39 |
| 12 | 0.56 | |
| 13 | 0.12 | 15 |
| 14 | 0.28 | |
| 15 | 0.10 | 13 |
| 16 | 0.31 | 44 |
| 17 | 0.15 | |
| 18 | 0.33 | 43 |
| 19 | 0.90 | |
| 20 | 0.13 | |
| 21 | 0.18 | |
| 22 | 0.30 | |
| 23 | 0.30 | |
| 24 | 0.15 | |
| 25 | 1.53 | |
| 26 | 0.26 | 17 |
| 27 | 0.08 | 15 |
| 28 | 0.14 | 250 |
| 29 | 0.29 | 24 |
| 30 | 0.79 | |
| 31 | 0.20 | |
| 32 | 0.18 | |
| 33 | 0.21 | |
| 34 | 0.56 | |
| 35 | 0.48 | |
| 36 | 0.54 | |
| 37 | 0.44 | |
| 38 | 0.12 | 5 |
| 39 | 0.13 | 11 |
| 40 | 0.86 | |
| 41 | 0.68 | |
| 42 | 0.09 | 9 |
| 43 | 0.12 | |
| 44 | 0.19 | |
| 45 | 0.20 | |
| 46 | 0.71 | |
| 47 | 0.38 | 53 |
| 48 | 0.59 | 55 |
| 49 | 0.31 | |
| 50 | 0.56 | |
| 51 | 0.15 | 25 |
| 52 | 0.13 | 9 |
| 53 | 0.11 | 21 |

TABLE 3-continued

| Compound # | MAP4K1 IC50 (nM) | IL-2 Primary T Cell EC50 (nM) |
|---|---|---|
| 54 | 0.82 | |
| 55 | 0.36 | 34 |
| 56 | 0.21 | |
| 57 | 0.53 | |
| 58 | 0.10 | |
| 59 | 0.15 | |
| 60 | 0.19 | 10 |
| 61 | 0.15 | |
| 62 | 0.33 | 76 |
| 63 | 0.09 | 14 |
| 64 | 0.21 | 105 |
| 65 | 0.20 | 11 |
| 66 | 0.24 | 21 |
| 67 | 0.77 | 40 |
| 68 | 0.51 | |
| 69 | 0.10 | 15 |
| 70 | 0.23 | |
| 71 | 0.28 | |
| 72 | 0.10 | |
| 73 | 0.24 | |
| 74 | 0.33 | 51 |
| 75 | 0.07 | 28 |
| 76 | 0.07 | 25 |
| 77 | 0.06 | 3 |
| 78 | 0.14 | 7 |
| 79 | 0.34 | 94 |
| 80 | 0.08 | 9 |
| 81 | 0.10 | 18 |
| 82 | 0.35 | |
| 83 | 0.92 | |
| 84 | 0.74 | |
| 85 | 0.37 | 85 |
| 86 | 0.20 | 26 |
| 87 | 0.13 | 29 |
| 88 | 0.21 | 23 |
| 89 | 0.24 | |
| 90 | 0.11 | 3 |
| 91 | 0.22 | 24 |
| 92 | 0.14 | 15 |
| 93 | 0.19 | 9 |
| 94 | 0.14 | 26 |
| 95 | 0.08 | 52 |
| 96 | 0.77 | |
| 97 | 2.11 | |
| 98 | 0.23 | 67 |
| 99 | 0.39 | 72 |
| 100 | 0.15 | |
| 101 | 0.48 | |
| 102 | 0.14 | 15 |
| 103 | 0.55 | |
| 104 | 0.17 | 10 |
| 105 | 0.37 | 41 |
| 106 | 0.22 | |
| 107 | 0.26 | |
| 108 | 0.22 | |
| 109 | 0.15 | |
| 110 | 0.22 | 36 |
| 111 | 0.12 | |
| 112 | 0.13 | 25 |
| 113 | 0.14 | |
| 114 | 0.17 | |
| 115 | 0.33 | 59 |
| 116 | 0.09 | |
| 117 | 0.05 | 6 |
| 118 | 0.11 | 27 |
| 119 | 0.22 | |
| 120 | 0.52 | |
| 121 | 0.59 | |
| 122 | 0.10 | 27 |
| 123 | 0.16 | 34 |
| 124 | 0.26 | |
| 125 | 0.18 | |
| 126 | 0.17 | 21 |
| 127 | 0.12 | 10 |
| 128 | 0.16 | 36 |
| 129 | 0.16 | 7 |

TABLE 3-continued

| Compound # | MAP4K1 IC50 (nM) | IL-2 Primary T Cell EC50 (nM) |
|---|---|---|
| 130 | 0.22 | |
| 131 | 1.94 | |
| 132 | 0.19 | 66 |
| 133 | 0.20 | 23 |
| 134 | 0.48 | |
| 135 | 0.45 | |
| 136 | 0.28 | 10 |
| 137 | 0.21 | |
| 138 | 0.30 | 38 |
| 139 | 0.36 | 74 |
| 140 | 0.33 | 33 |
| 141 | 0.15 | 15 |
| 142 | 0.20 | |
| 143 | 0.15 | 16 |
| 144 | 0.23 | 39 |
| 145 | 0.21 | 32 |
| 146 | 1.41 | |
| 147 | 0.46 | |
| 148 | 0.57 | 26 |
| 149 | 0.25 | |
| 150 | 0.32 | 14 |
| 151 | 0.16 | 9 |
| 152 | 0.29 | 11 |
| 153 | 0.27 | 25 |
| 154 | 0.62 | |
| 155 | 0.37 | 17 |
| 156 | 2.38 | |
| 157 | 1.57 | |
| 158 | 0.86 | |
| 159 | 0.42 | |
| 160 | 1.61 | |
| 161 | 0.94 | |
| 162 | 0.30 | 32 |
| 163 | 0.22 | |
| 164 | 1.48 | |
| 165 | 1.15 | |
| 166 | 0.20 | |
| 167 | 0.19 | |
| 168 | 0.26 | 35 |
| 169 | 0.60 | |
| 170 | | |
| 171 | | |
| 172 | 1.86 | |
| 173 | 9.80 | |
| 174 | 5.35 | |
| 175 | 23.30 | |
| 176 | 0.23 | 69 |
| 177 | 1.10 | |
| 178 | 0.55 | |
| 179 | 0.49 | |
| 180 | 3.03 | |
| 181 | 0.18 | 85 |
| 182 | 0.16 | 21 |
| 183 | 0.16 | 43 |
| 184 | 0.83 | |
| 185 | 0.22 | |
| 186 | 0.15 | 15 |
| 187 | 2.20 | |
| 188 | 0.96 | |
| 189 | 1.05 | |
| 190 | 5.10 | |
| 191 | 3.67 | |
| 192 | 0.94 | |

Example 4: T Cell Enhancement of Cytokines

Isolation and Expansion of T Cells from Whole Blood

T cells are isolated from whole blood of healthy donors by immunomagnetic negative selection following manufacture's protocol (StemCell Technologies, human T cell isolation kit). Purity of isolated cells is assessed by flow cytometry and yields 95-98% $CD3^+$ T cells. For expansion of T cells, $1\times10^6$ cells/well are plated in serum free cell expansion media (ThermoFisher) containing 30 U of recombinant human IL2 (R&D) and stimulated with 25 ul of CD3/CD28 beads (Invitrogen) in 24 well plates for 3-4 days. T cells are then expanded in 175 cm flasks and maintained at a cell density of 1 to $2.5\times10^6$ cells/ml days by addition of ⅔ of fresh media every 2-3 days. After 10-14 days, cells are frozen in BamBanker freezing media (Thermo) and stored in liquid nitrogen. Phenotypic analysis of expanded T cells by flow cytometry, routinely shows 60% cells are $CD8^+$ T cells upon freezing.

Cytokine Measurement

For IL2 measurement, expanded $CD3^+$ T cells are dispensed at 100K cells/well (cultured in X-VIVO 10 Serum-free media) and are stimulated with plate-bound anti-CD3 and soluble anti-CD28 in the presence of vehicle or compound of the disclosure at various concentrations for 24 h. As outlined in the manufacturer's protocol (Cisbio), 16 μL of conditioned media is transferred to a white 384-well low volume plate. Following a 24 h incubation with the anti-IL2 antibodies, the homogenous time resolved fluorescence (HTRF) is measured.

Example 5: Inhibition of Anti-Tumor Activity in a Syngeneic Mouse Model

Generation of the MCA205 Syngeneic xenograft anti-tumor efficacy study

Six to eight-week-old female, C57BL/6 mice (Jackson Labs, Bar Harbor, ME) are implanted subcutaneously on the left flank with $1\times10^6$ MCA205 cells/mouse. After tumors reach an average volume of 50 $mm^3$, mice are randomized into treatment groups, 10 mice per group, with tumors in the size range of 30-70 $mm^3$. Compounds of the disclosure 10-30 mg/kg, anti-mouse PD-L1 mAb (B7H1, clone #10F.9G2 Bio-X-cell, Lebanon, NH) and vehicle either alone or in different combinations are administered to tumor bearing mice. Reduction in tumor volume is measured [$mm^3$] over time.

EQUIVALENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

Those skilled in the art will recognize or be able to ascertain using no more than routine experimentation, many equivalents to the specific embodiments of the disclosure described and claimed herein. Such equivalents are intended to be encompassed by the following claims.

SEQUENCE LISTING

```
Sequence total quantity: 3
SEQ ID NO: 1           moltype = AA  length = 11
FEATURE                Location/Qualifiers
REGION                 1..11
                       note = Synthetic peptide
source                 1..11
                       mol_type = protein
                       organism = synthetic construct
SEQUENCE: 1
EGIYGVLFKK K                                                      11

SEQ ID NO: 2           moltype = AA  length = 13
FEATURE                Location/Qualifiers
REGION                 1..13
                       note = Synthetic peptide
source                 1..13
                       mol_type = protein
                       organism = synthetic construct
SEQUENCE: 2
VDGKEIYNTI RRK                                                    13

SEQ ID NO: 3           moltype = AA  length = 9
FEATURE                Location/Qualifiers
REGION                 1..9
```

-continued

```
                         note = Synthetic peptide
source                   1..9
                         mol_type = protein
                         organism = synthetic construct

SEQUENCE: 3
GRTGRRNSI                                                    9
```

What is claimed is:

1. A compound of Formula I:

I

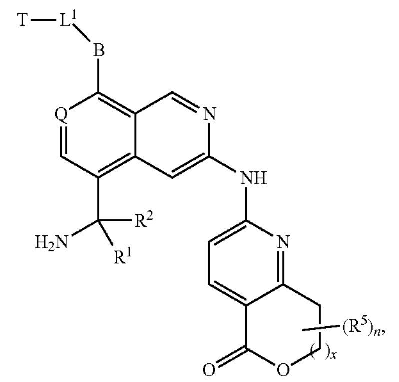

or a pharmaceutically acceptable salt thereof, wherein:

T is selected from

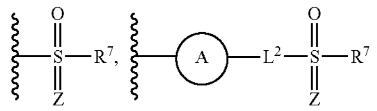

and 4-5 membered heterocycle containing

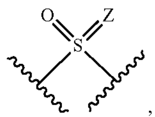

, wherein said heterocycle of T is optionally substituted with 1-2 $R^6$;

Z is absent, O or NH;

Ring A is $C_{4-6}$ cycloalkyl or 4-6 membered heterocycle containing nitrogen, wherein said cycloalkyl or heterocycle of Ring A is optionally substituted with 1-2 $R^6$;

$L^1$ is selected from bond and $C_1$-$C_3$ alkylene, wherein said alkylene of $L^1$ is optionally substituted with 1-2 $R^{11}$;

$L^2$ is selected from bond and $C_1$-$C_3$ alkylene;

B is O or NH;

Q is N or CH;

x is 0, 1, or 2;

n is 0, 1, 2, 3, or 4;

$R^1$ and $R^2$ are each independently selected from hydrogen, $C_{1-6}$ alkyl, $C_{3-6}$ cycloalkyl, and 4 to 6-membered heterocycle, wherein said alkyl of $R^1$ and $R^2$ is optionally substituted with 1-2 $R^3$;

each $R^3$ is independently selected from halogen, hydroxyl and $OR^4$;

each $R^4$ is independently selected from $C_{1-3}$ alkyl, $CF_3$, $CH_2F$, and $CHF_2$;

each $R^5$ is independently selected from $C_{1-2}$ alkyl, $CF_3$, $CH_2F$, and $CHF_2$, or two $R^5$ attached to the same carbon atom taken together with the carbon atom to which they attach form $C_{3-5}$ cycloalkyl; or two $R^5$ attached to two adjacent carbon atoms taken together with the two adjacent carbon atoms to which they attach form $C_{4-6}$ cycloalkyl;

each $R^6$ is independently selected from $CH_3$, methoxy, $CF_3$, $CH_2F$, and $CHF_2$;

$R^7$ is selected from $C_{1-3}$ alkyl, $C_{3-6}$ cycloalkyl, $OC_{1-4}$ alkyl, $NR^9R^{10}$, and 3-5 membered heterocycle containing nitrogen or oxygen, wherein said alkyl, cycloalkyl, or heterocycle of $R^7$ is optionally substituted with 1-3 $R^8$;

each $R^8$ is independently selected from halogen, $C_{1-3}$ alkyl, hydroxyl and $OC_{1-3}$ alkyl, wherein said alkyl of $R^8$ is optionally substituted with 1-3 $R^{12}$;

$R^9$ is selected from $C_{1-2}$ alkyl;

$R^{10}$ is selected from $C_{1-2}$ alkyl;

each $R^{11}$ is independently selected from halogen, methoxy, $C_{1-2}$ alkyl, $CH_2F$, $CHF_2$ and $CF_3$, or two $R^{11}$ taken together with the two adjacent carbon atoms to which they attach form cyclopropyl; and each $R^{12}$ is halogen.

2. The compound of claim 1, wherein the compound is represented by Formula IV:

IV

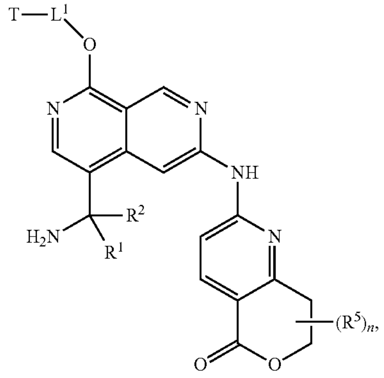

or a pharmaceutically acceptable salt thereof.

3. The compound of claim 1, wherein the compound is represented by Formula VII:

VII

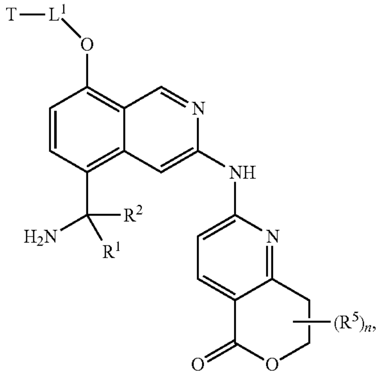

or a pharmaceutically acceptable salt thereof.

4. The compound of claim 2, or a pharmaceutically acceptable salt thereof, wherein:

$L^1$ is bond;

T is

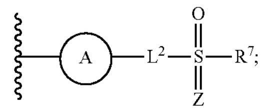

and $L^2$ is a bond or methylene.

5. The compound of claim 4, or a pharmaceutically acceptable salt thereof, wherein Ring A is selected from azetidinylene, cyclobutylene, cyclopentylene and pyrrolidinylene, wherein said azetidinylene, cyclobutylene, cyclopentylene and pyrrolidinylene is optionally substituted with 1-2 $R^6$.

6. The compound of claim 2, or a pharmaceutically acceptable salt thereof, wherein:

$L^1$ is $C_1$-$C_3$ alkylene optionally substituted with 1-2 $R^{11}$; and

T is Z

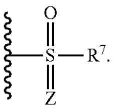

7. The compound of claim 6, or a pharmaceutically acceptable salt thereof, wherein $L^1$ is selected from Formula L-1, L-2, L-3, L-4, L-5, L-6 and L-7:

L-1

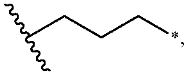

L-2

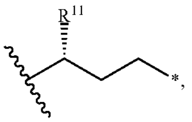

-continued

L-3

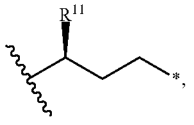

L-4

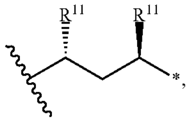

L-5

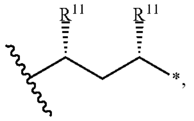

L-6

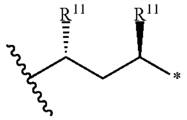

and

L-7

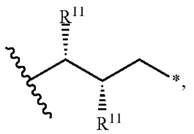

wherein:

 represents a bond to B; and

—* represents a bond to T.

8. The compound of claim 7, or a pharmaceutically acceptable salt thereof, wherein Z is O.

9. The compound of claim 2, or a pharmaceutically acceptable salt thereof, wherein:

T is 4-5 membered heterocycle containing sulfone, wherein said heterocycle is optionally substituted with 1-2 $R^6$; and $L^1$ is selected from bond, methylene and ethylene.

10. The compound of claim 8, or a pharmaceutically acceptable salt thereof, wherein:

$R^1$ and $R^2$ are each independently selected from hydrogen, $C_{1-6}$ alkyl, and $C_{3-6}$ cycloalkyl, wherein said alkyl is optionally substituted with $R^3$;

each $R^3$ is independently selected from halogen, hydroxyl and $OR^4$; and each $R^4$ is $C_{1-3}$ alkyl.

11. The compound of claim 10, or a pharmaceutically acceptable salt thereof, wherein $R^1$ and $R^2$ are each independently selected from hydrogen, $CH_3$, $CH_2CH_3$, $CH_2CH_2CH_3$, $CH_2$—$OCH_3$ and cyclopropyl.

12. The compound of claim 11, or a pharmaceutically acceptable salt thereof, wherein:

$R^5$ is $CH_3$, or two $R^5$ attached to the same carbon atom taken together with the carbon atom to which they attach form cyclopropyl;

n is 1, 2, 3 or 4;

$R^7$ is selected from $C_{1-3}$ alkyl, $CH_2F$, $CHF_2$, $CF_3$, $C_{3-6}$ cycloalkyl and $NR^9R^{10}$;

$R^9$ is selected from $C_{1-2}$ alkyl; and $R^{10}$ is selected from $C_{1-2}$ alkyl.

13. The compound of claim 12, or a pharmaceutically acceptable salt thereof, wherein $R^7$ is selected from $CH_3$, $CF_3$, $CH_2CH_3$, $CH(CH_3)_2$, cyclopropyl and $N(CH_3)_2$; and each $R^{11}$ is independently $CH_3$, $CF_3$ or $CH_2CH_3$.
14. The compound of claim 13, or a pharmaceutically acceptable salt thereof, wherein each $R^{11}$ is $CH_3$.
15. A compound, or pharmaceutically acceptable salt thereof, selected from:
| Compound No. | Structure |
|---|---|
| 1 | 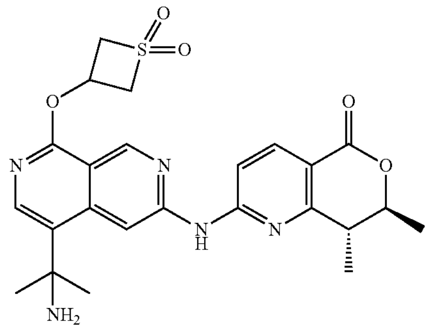 [SMILES: C[C@@H]1OC(=O)c2ccc(Nc3cc4c(C(C)(C)N)cnc(OC5CS(=O)(=O)C5)c4cn3)nc2[C@H]1C] |
| 2 | 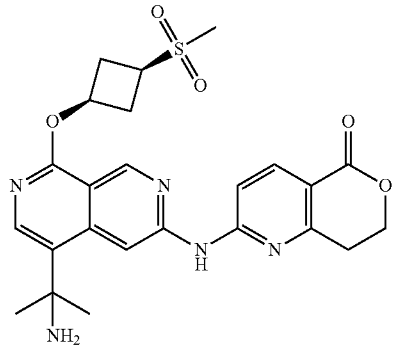 [SMILES: CC(C)(N)c1cnc(O[C@H]2C[C@@H](S(C)(=O)=O)C2)c2cnc(Nc3ccc4c(n3)CCOC4=O)cc12] |
| 3 | 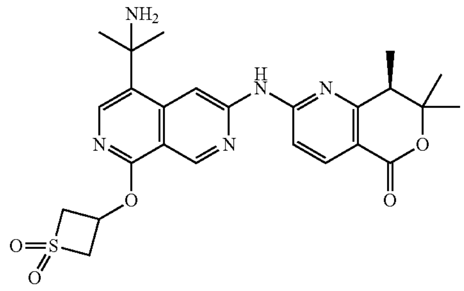 [SMILES: C[C@@H]1c2nc(Nc3cc4c(C(C)(C)N)cnc(OC5CS(=O)(=O)C5)c4cn3)ccc2C(=O)OC1(C)C] |
| 4 | 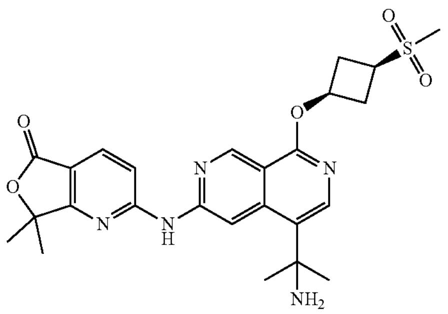 |
-continued
| Compound No. | Structure |
|---|---|
| 5 | 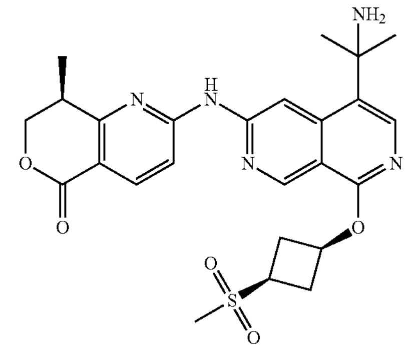 [SMILES: C[C@@H]1COC(=O)c2ccc(Nc3cc4c(C(C)(C)N)cnc(O[C@H]5C[C@@H](S(C)(=O)=O)C5)c4cn3)nc21] |
| | 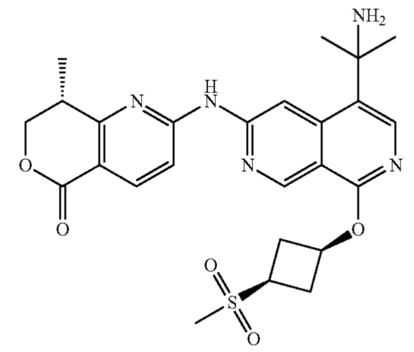 [SMILES: C[C@H]1COC(=O)c2ccc(Nc3cc4c(C(C)(C)N)cnc(O[C@H]5C[C@@H](S(C)(=O)=O)C5)c4cn3)nc21] |
| 6 | 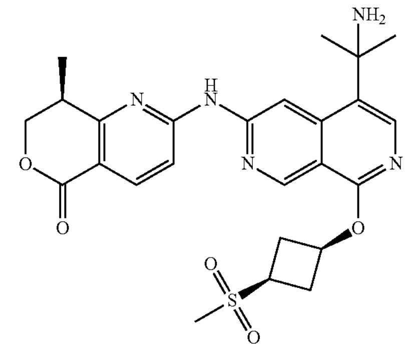 [SMILES: C[C@@H]1COC(=O)c2ccc(Nc3cc4c(C(C)(C)N)cnc(O[C@H]5C[C@@H](S(C)(=O)=O)C5)c4cn3)nc21] |
| | 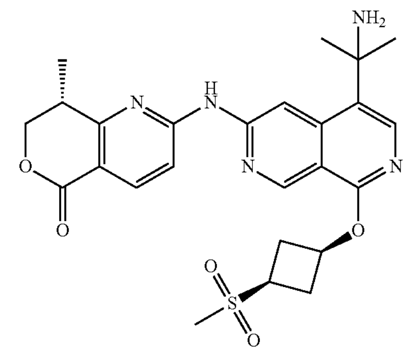 [SMILES: C[C@H]1COC(=O)c2ccc(Nc3cc4c(C(C)(C)N)cnc(O[C@H]5C[C@@H](S(C)(=O)=O)C5)c4cn3)nc21] |

-continued
| Compound No. | Structure |
| --- | --- |
| 7 | 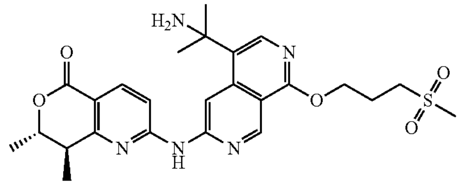 |
| 8 | 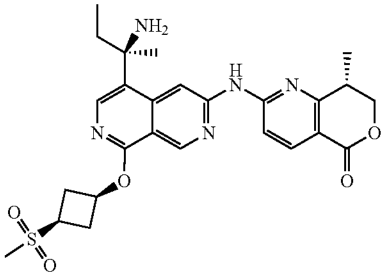 [SMILES: CC[C@@](C)(N)c1cnc(O[C@H]2C[C@@H](S(C)(=O)=O)C2)c2cnc(Nc3ccc4c(n3)[C@H](C)COC4=O)cc12] |
| | 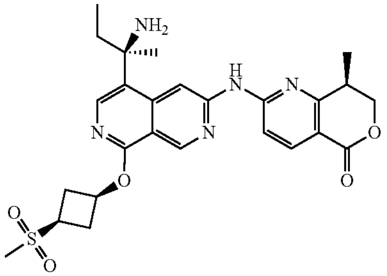 [SMILES: CC[C@@](C)(N)c1cnc(O[C@H]2C[C@@H](S(C)(=O)=O)C2)c2cnc(Nc3ccc4c(n3)[C@@H](C)COC4=O)cc12] |
| 9 | 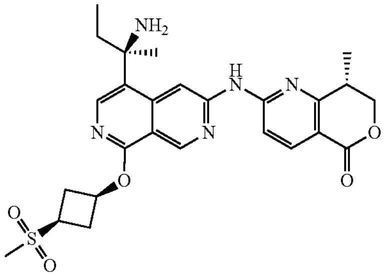 [SMILES: CC[C@@](C)(N)c1cnc(O[C@H]2C[C@@H](S(C)(=O)=O)C2)c2cnc(Nc3ccc4c(n3)[C@H](C)COC4=O)cc12] |
| | 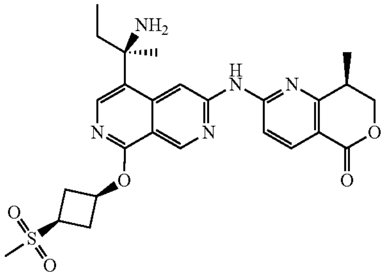 [SMILES: CC[C@@](C)(N)c1cnc(O[C@H]2C[C@@H](S(C)(=O)=O)C2)c2cnc(Nc3ccc4c(n3)[C@@H](C)COC4=O)cc12] |
-continued
| Compound No. | Structure |
| --- | --- |
| 10 | 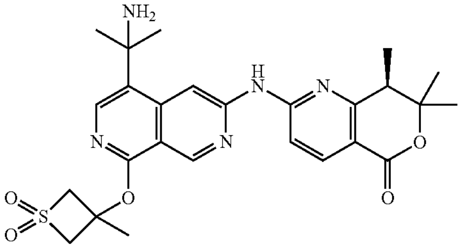 [SMILES: C[C@@H]1c2nc(Nc3cc4c(C(C)(C)N)cnc(OC5(C)CS(=O)(=O)C5)c4cn3)ccc2C(=O)OC1(C)C] |
| 11 | 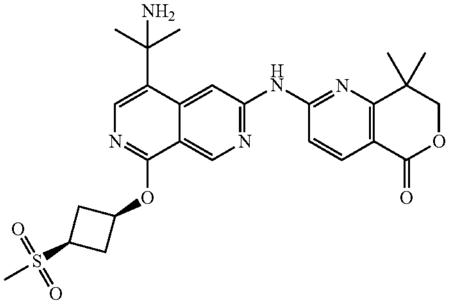 [SMILES: CC(C)(N)c1cnc(O[C@H]2C[C@@H](S(C)(=O)=O)C2)c2cnc(Nc3ccc4c(n3)C(C)(C)COC4=O)cc12] |
| 12 | 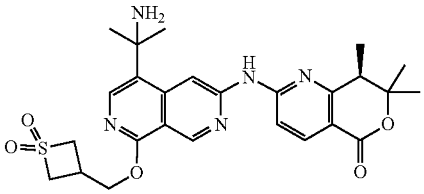 [SMILES: C[C@@H]1c2nc(Nc3cc4c(C(C)(C)N)cnc(OCC5CS(=O)(=O)C5)c4cn3)ccc2C(=O)OC1(C)C] |
| 13 | 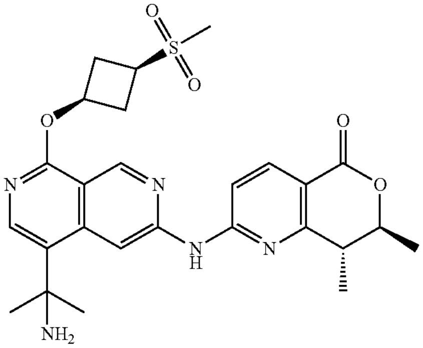 [SMILES: C[C@@H]1OC(=O)c2ccc(Nc3cc4c(C(C)(C)N)cnc(O[C@H]5C[C@@H](S(C)(=O)=O)C5)c4cn3)nc2[C@H]1C] |
| 14 | 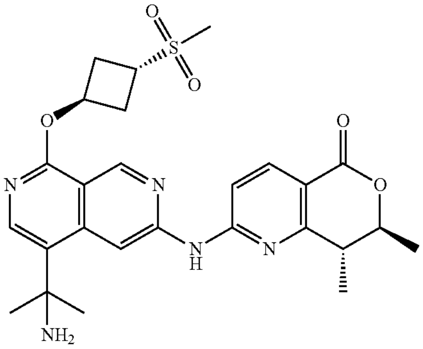 [SMILES: C[C@@H]1OC(=O)c2ccc(Nc3cc4c(C(C)(C)N)cnc(O[C@H]5C[C@H](S(C)(=O)=O)C5)c4cn3)nc2[C@H]1C] |

-continued
| Compound No. | Structure |
|---|---|
| 15 | 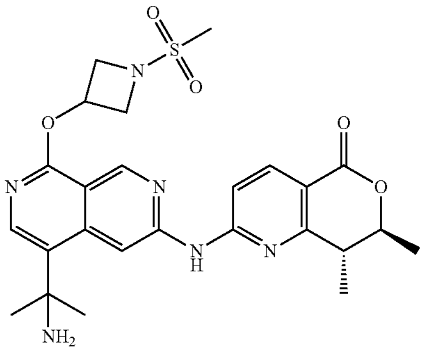 [SMILES: C[C@@H]1OC(=O)c2ccc(Nc3cc4c(C(C)(C)N)cnc(OC5CN(S(C)(=O)=O)C5)c4cn3)nc2[C@H]1C] |
| 16 | 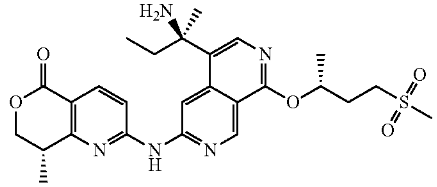 [SMILES: CC[C@@](C)(N)c1cnc(O[C@H](C)CCS(C)(=O)=O)c2cnc(Nc3ccc4c(n3)[C@H](C)COC4=O)cc12] |
| | 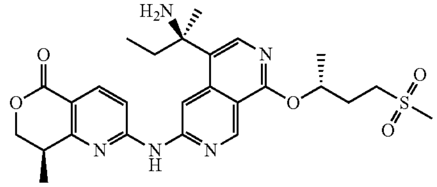 [SMILES: CC[C@@](C)(N)c1cnc(O[C@H](C)CCS(C)(=O)=O)c2cnc(Nc3ccc4c(n3)[C@@H](C)COC4=O)cc12] |
| 17 | 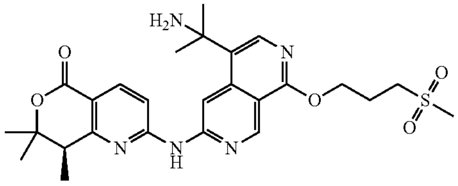 |
| 18 | 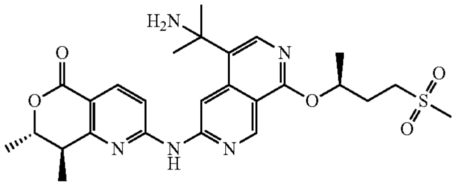 |
| | 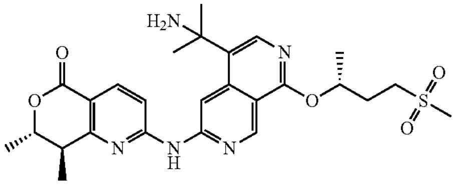 |
| 19 | 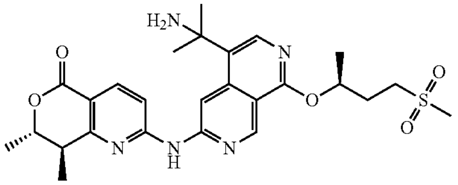 |
-continued
| Compound No. | Structure |
|---|---|
| | 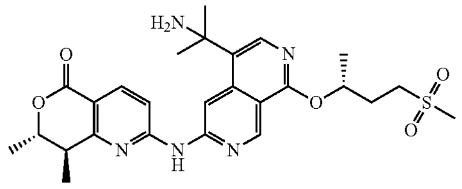 |
| 20 | 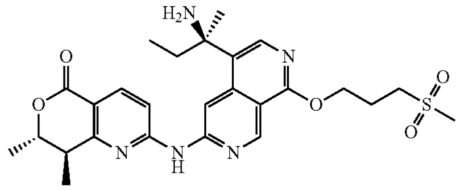 |
| 21 | 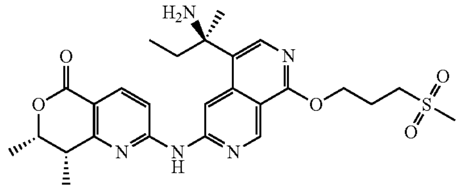 |
| | 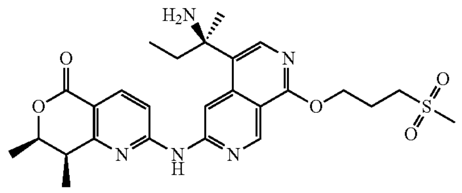 |
| 22 | 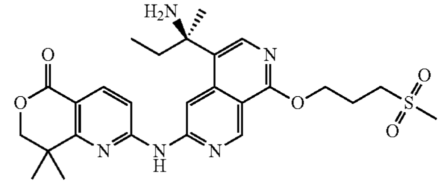 [SMILES: CC[C@@](C)(N)c1cnc(OCCCS(C)(=O)=O)c2cnc(Nc3ccc4c(n3)C(C)(C)COC4=O)cc12] |
| 23 | 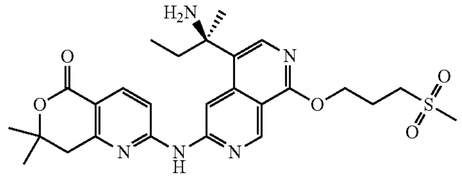 |
| 24 | 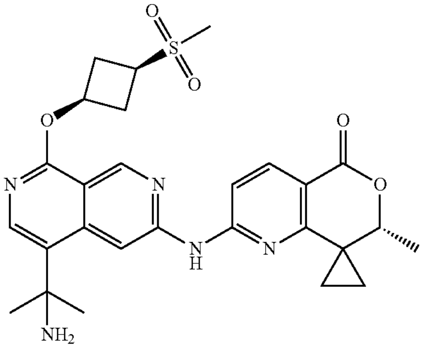 [SMILES: C[C@H]1OC(=O)c2ccc(Nc3cc4c(C(C)(C)N)cnc(O[C@H]5C[C@@H](S(C)(=O)=O)C5)c4cn3)nc2C12CC2] |

-continued
| Compound No. | Structure |
|---|---|
| | 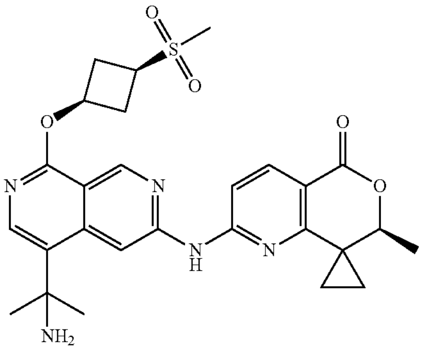 [SMILES: C[C@@H]1OC(=O)c2ccc(Nc3cc4c(C(C)(C)N)cnc(O[C@H]5C[C@@H](S(C)(=O)=O)C5)c4cn3)nc2C12CC2] |
| 25 | 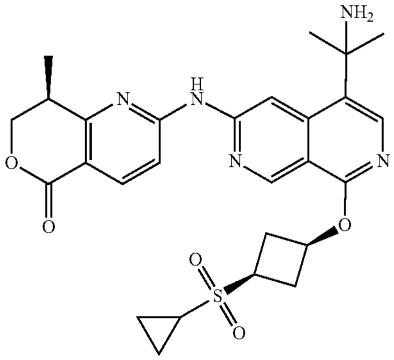 [SMILES: C[C@@H]1COC(=O)c2ccc(Nc3cc4c(C(C)(C)N)cnc(O[C@H]5C[C@@H](S(=O)(=O)C6CC6)C5)c4cn3)nc21] |
| | 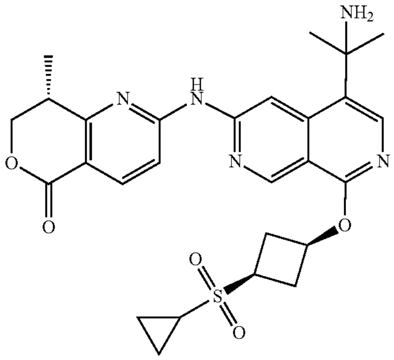 [SMILES: C[C@H]1COC(=O)c2ccc(Nc3cc4c(C(C)(C)N)cnc(O[C@H]5C[C@@H](S(=O)(=O)C6CC6)C5)c4cn3)nc21] |
| 26 | 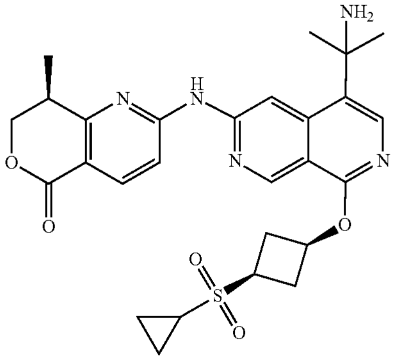 [SMILES: C[C@@H]1COC(=O)c2ccc(Nc3cc4c(C(C)(C)N)cnc(O[C@H]5C[C@@H](S(=O)(=O)C6CC6)C5)c4cn3)nc21] |
-continued
| Compound No. | Structure |
|---|---|
| | 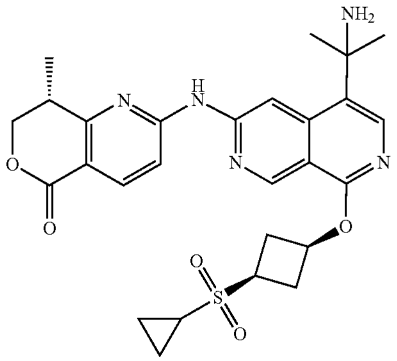 [SMILES: C[C@H]1COC(=O)c2ccc(Nc3cc4c(C(C)(C)N)cnc(O[C@H]5C[C@@H](S(=O)(=O)C6CC6)C5)c4cn3)nc21] |
| 27 | 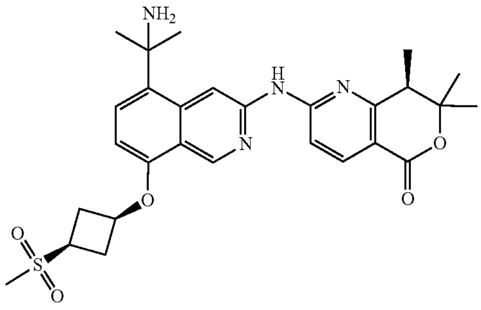 |
| 28 | 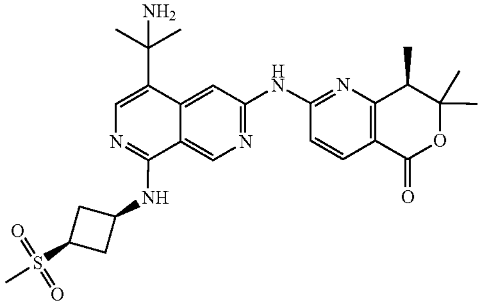 |
| 29 | 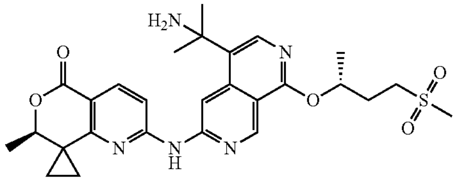 |
| | 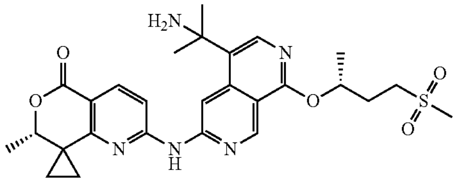 |

-continued
| Compound No. | Structure |
| --- | --- |
| 30 | 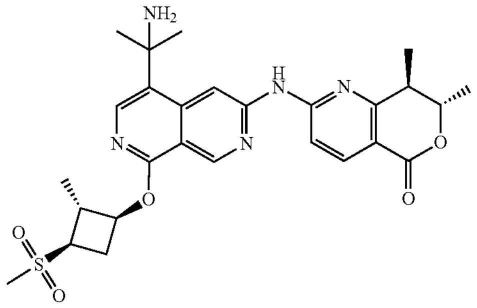 |
| | 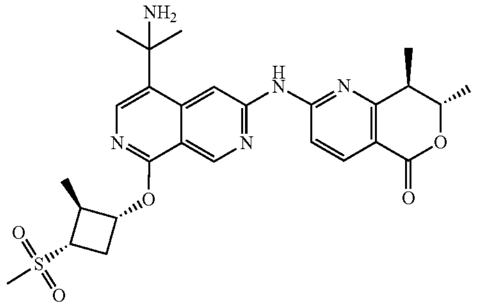 |
| 31 | 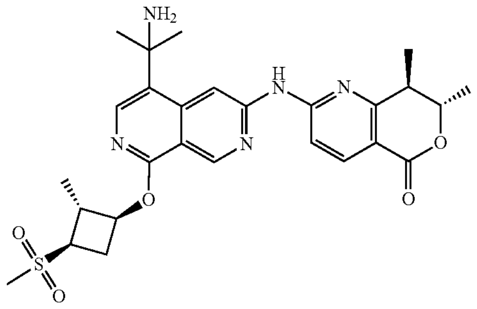 |
| | 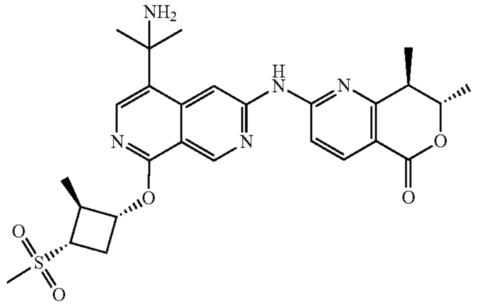 |
-continued
| Compound No. | Structure |
| --- | --- |
| 32 | 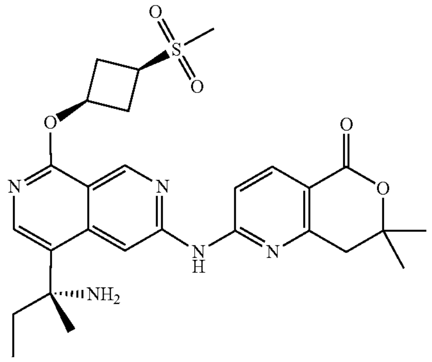 [SMILES: CC[C@@](C)(N)c1cnc(O[C@H]2C[C@@H](S(C)(=O)=O)C2)c2cnc(Nc3ccc4c(n3)CC(C)(C)OC4=O)cc12] |
| 33 | 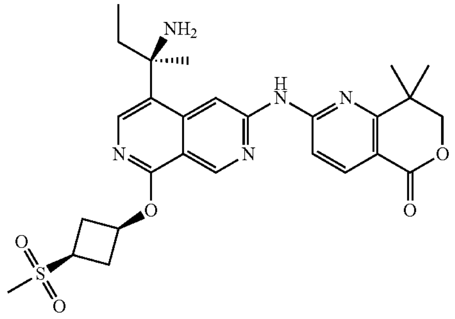 [SMILES: CC[C@@](C)(N)c1cnc(O[C@H]2C[C@@H](S(C)(=O)=O)C2)c2cnc(Nc3ccc4c(n3)C(C)(C)COC4=O)cc12] |
| 34 | 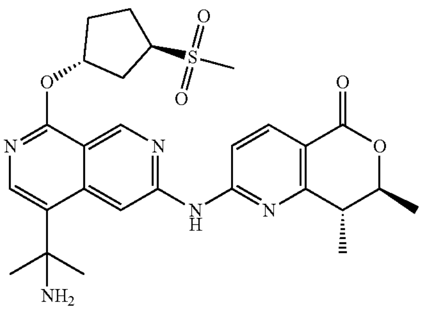 [SMILES: C[C@@H]1OC(=O)c2ccc(Nc3cc4c(C(C)(C)N)cnc(O[C@@H]5CC[C@@H](S(C)(=O)=O)C5)c4cn3)nc2[C@H]1C] |
| | 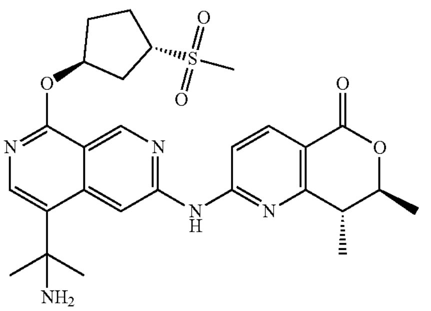 [SMILES: C[C@@H]1OC(=O)c2ccc(Nc3cc4c(C(C)(C)N)cnc(O[C@H]5CC[C@H](S(C)(=O)=O)C5)c4cn3)nc2[C@H]1C] |

-continued
| Compound No. | Structure |
|---|---|
| 35 | 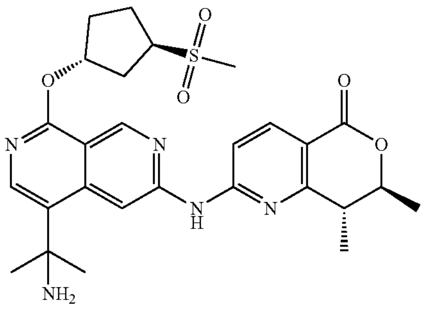 [SMILES: C[C@@H]1OC(=O)c2ccc(Nc3cc4c(C(C)(C)N)cnc(O[C@@H]5CC[C@@H](S(C)(=O)=O)C5)c4cn3)nc2[C@H]1C] |
| | 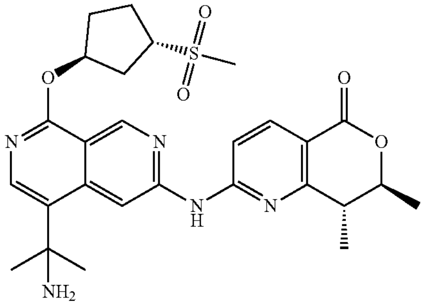 [SMILES: C[C@@H]1OC(=O)c2ccc(Nc3cc4c(C(C)(C)N)cnc(O[C@H]5CC[C@H](S(C)(=O)=O)C5)c4cn3)nc2[C@H]1C] |
| 36 | 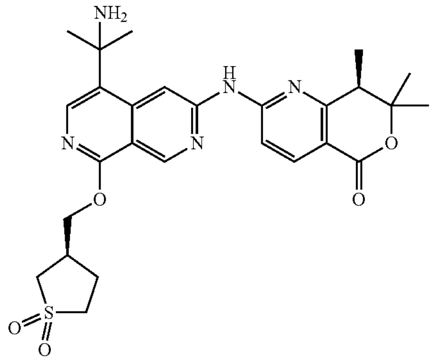 [SMILES: C[C@@H]1c2nc(Nc3cc4c(C(C)(C)N)cnc(OC[C@H]5CCS(=O)(=O)C5)c4cn3)ccc2C(=O)OC1(C)C] |
| | 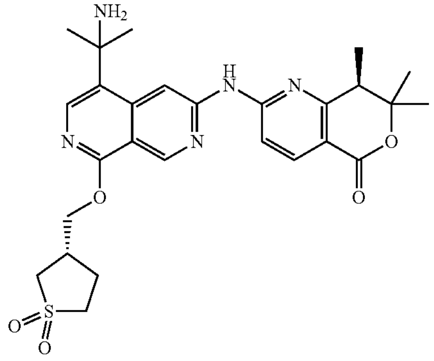 [SMILES: C[C@@H]1c2nc(Nc3cc4c(C(C)(C)N)cnc(OC[C@@H]5CCS(=O)(=O)C5)c4cn3)ccc2C(=O)OC1(C)C] |
-continued
| Compound No. | Structure |
|---|---|
| 37 | 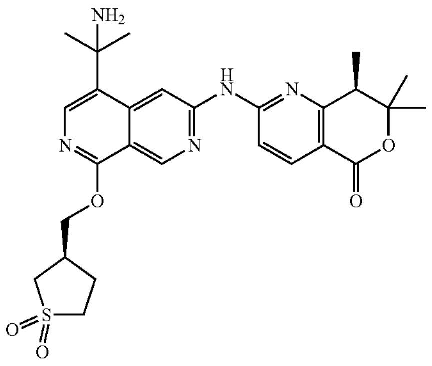 [SMILES: C[C@@H]1c2nc(Nc3cc4c(C(C)(C)N)cnc(OC[C@H]5CCS(=O)(=O)C5)c4cn3)ccc2C(=O)OC1(C)C] |
| | 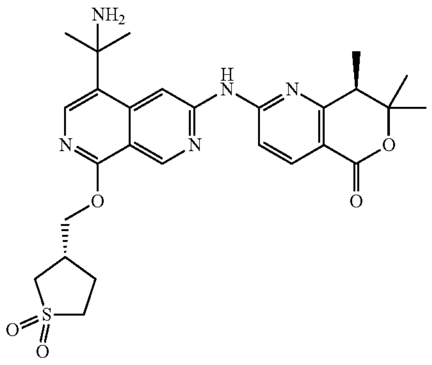 [SMILES: C[C@@H]1c2nc(Nc3cc4c(C(C)(C)N)cnc(OC[C@@H]5CCS(=O)(=O)C5)c4cn3)ccc2C(=O)OC1(C)C] |
| 38 | 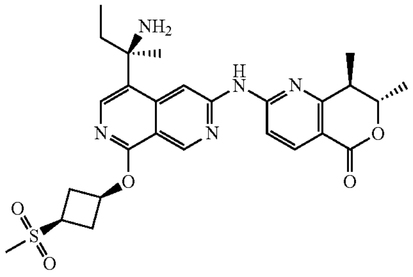 |
| 39 | 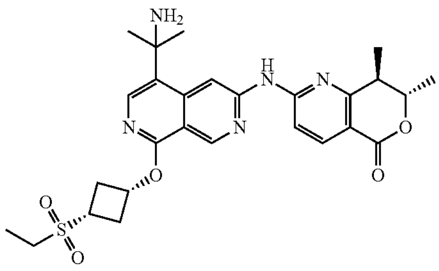 [SMILES: CCS(=O)(=O)[C@H]1C[C@@H](Oc2ncc(C(C)(C)N)c3cc(Nc4ccc5c(n4)[C@@H](C)[C@H](C)OC5=O)ncc23)C1] |

-continued
| Compound No. | Structure |
|---|---|
| 40 | 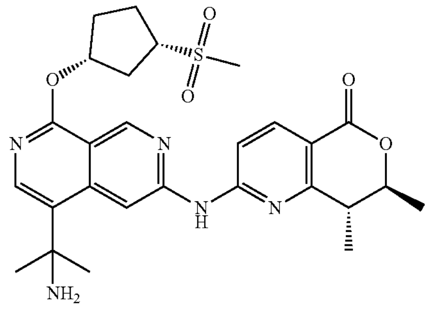 [SMILES: C[C@@H]1OC(=O)c2ccc(Nc3cc4c(C(C)(C)N)cnc(O[C@@H]5CC[C@H](S(C)(=O)=O)C5)c4cn3)nc2[C@H]1C] |
| | 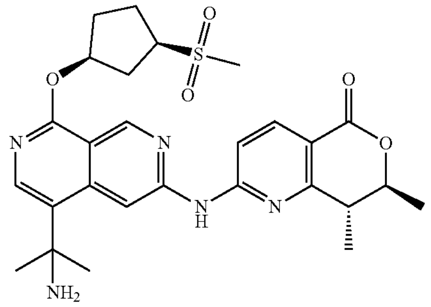 [SMILES: C[C@@H]1OC(=O)c2ccc(Nc3cc4c(C(C)(C)N)cnc(O[C@H]5CC[C@@H](S(C)(=O)=O)C5)c4cn3)nc2[C@H]1C] |
| 41 | 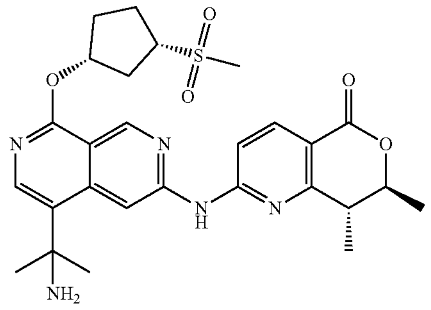 [SMILES: C[C@@H]1OC(=O)c2ccc(Nc3cc4c(C(C)(C)N)cnc(O[C@@H]5CC[C@H](S(C)(=O)=O)C5)c4cn3)nc2[C@H]1C] |
| | 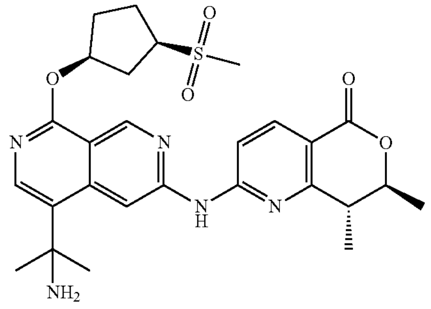 |
| 42 | 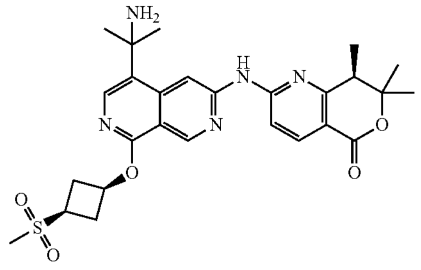 |
-continued
| Compound No. | Structure |
|---|---|
| 43 | 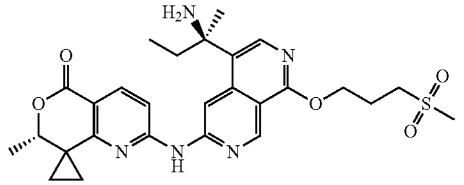 |
| | 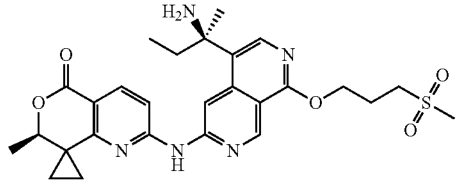 |
| 44 | 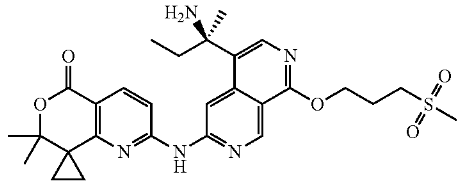 |
| 45 | 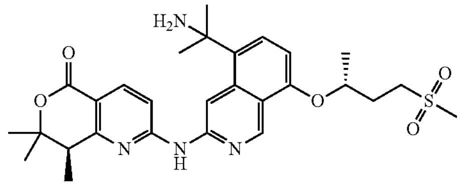 |
| | 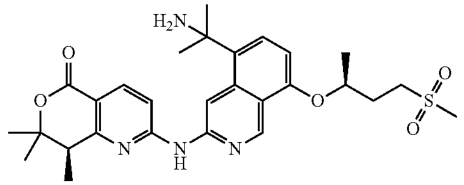 |
| 46 | 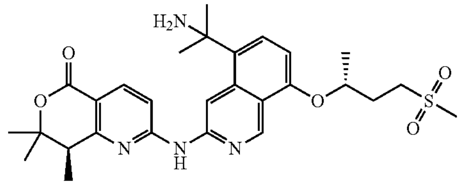 |
| | 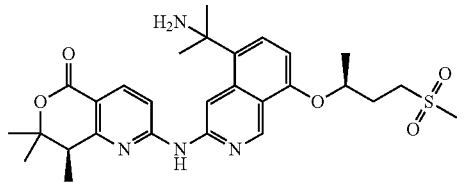 |
| 47 | 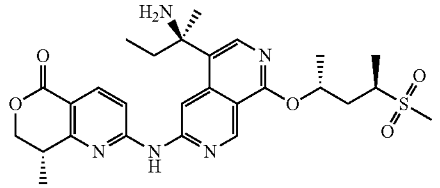 [SMILES: CC[C@@](C)(N)c1cnc(O[C@H](C)C[C@@H](C)S(C)(=O)=O)c2cnc(Nc3ccc4c(n3)[C@H](C)COC4=O)cc12] |

-continued
| Compound No. | Structure |
|---|---|
| | 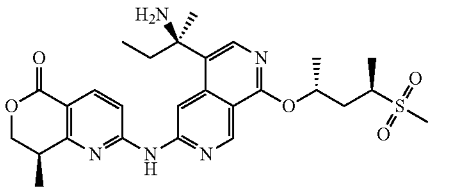 [SMILES: CC[C@@](C)(N)c1cnc(O[C@H](C)C[C@@H](C)S(C)(=O)=O)c2cnc(Nc3ccc4c(n3)[C@@H](C)COC4=O)cc12] |
| 48 | 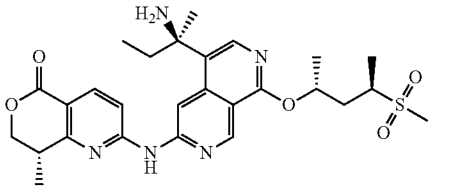 [SMILES: CC[C@@](C)(N)c1cnc(O[C@H](C)C[C@@H](C)S(C)(=O)=O)c2cnc(Nc3ccc4c(n3)[C@H](C)COC4=O)cc12] |
| | 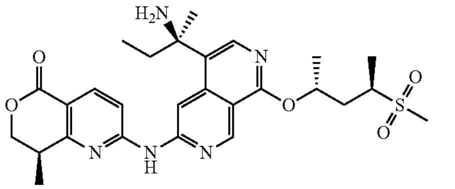 [SMILES: CC[C@@](C)(N)c1cnc(O[C@H](C)C[C@@H](C)S(C)(=O)=O)c2cnc(Nc3ccc4c(n3)[C@@H](C)COC4=O)cc12] |
| 49 | 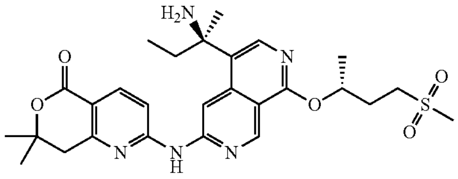 |
| 50 | 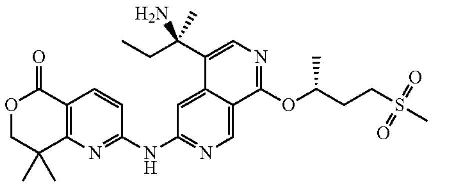 [SMILES: CC[C@@](C)(N)c1cnc(O[C@H](C)CCS(C)(=O)=O)c2cnc(Nc3ccc4c(n3)C(C)(C)COC4=O)cc12] |
| 51 | 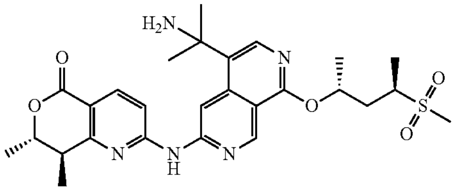 |
| 52 | 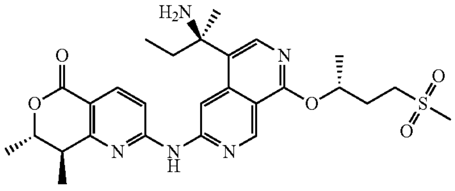 |
-continued
| Compound No. | Structure |
|---|---|
| 53 | 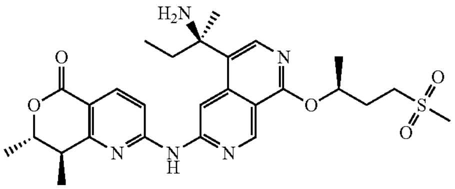 |
| 54 | 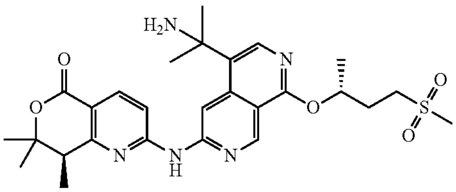 |
| | 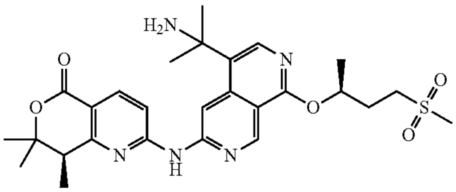 |
| 55 | 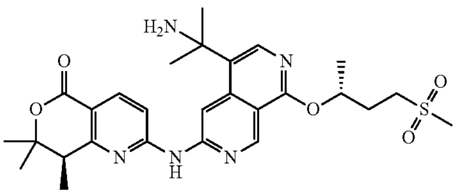 |
| | 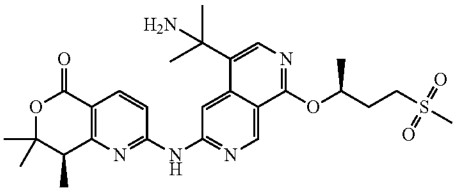 |
| 56 | 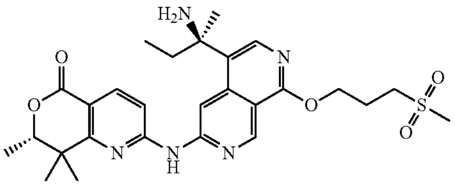 |
| | 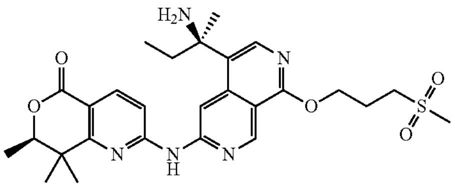 |

-continued
| Compound No. | Structure |
|---|---|
| 57 | 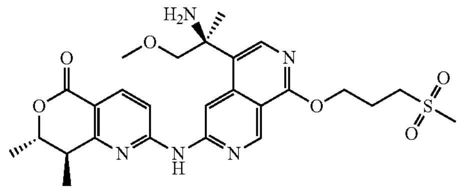 |
| 58 | 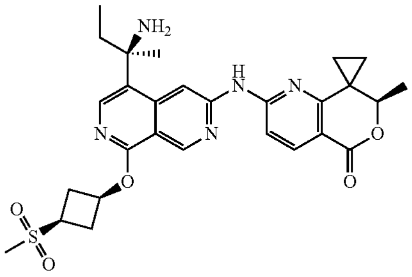 |
| | 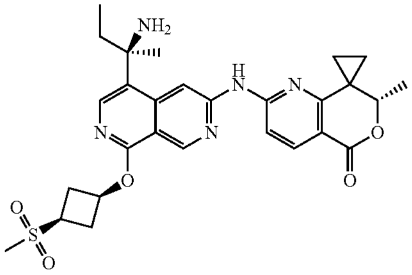 |
| 59 | 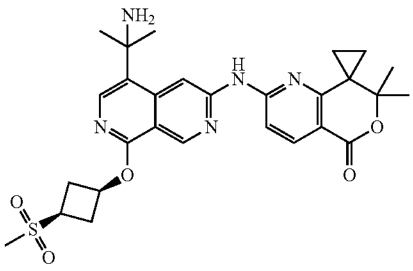 |
| 60 | 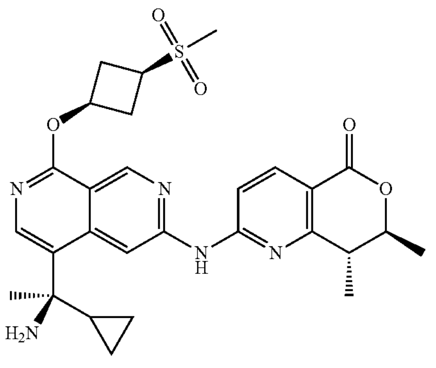 [SMILES: C[C@@H]1OC(=O)c2ccc(Nc3cc4c([C@](C)(N)C5CC5)cnc(O[C@H]5C[C@@H](S(C)(=O)=O)C5)c4cn3)nc2[C@H]1C] |
-continued
| Compound No. | Structure |
|---|---|
| | 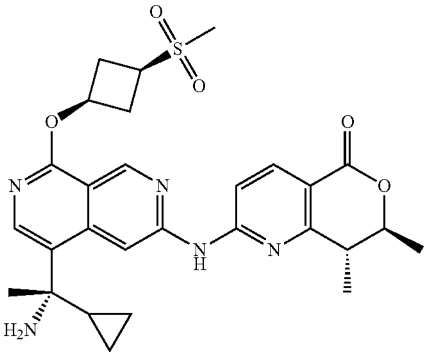 [SMILES: C[C@@H]1OC(=O)c2ccc(Nc3cc4c([C@@](C)(N)C5CC5)cnc(O[C@H]5C[C@@H](S(C)(=O)=O)C5)c4cn3)nc2[C@H]1C] |
| 61 | 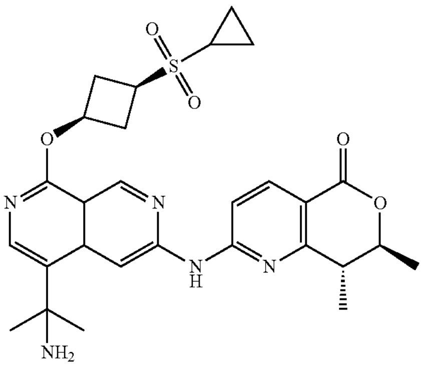 [SMILES: C[C@@H]1OC(=O)c2ccc(NC3=CC4C(C(C)(C)N)=CN=C(O[C@H]5C[C@@H](S(=O)(=O)C6CC6)C5)C4C=N3)nc2[C@H]1C] |
| 62 | 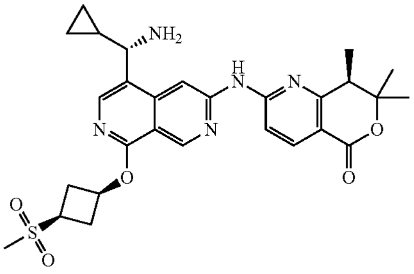 |
| | 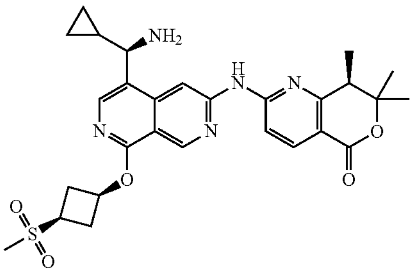 |
| 63 | 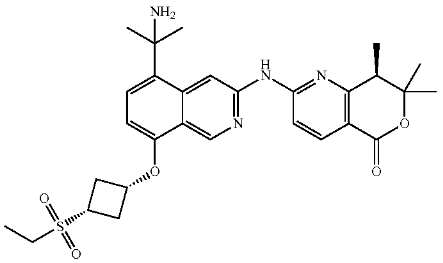 |

-continued
| Compound No. | Structure |
|---|---|
| 64 | 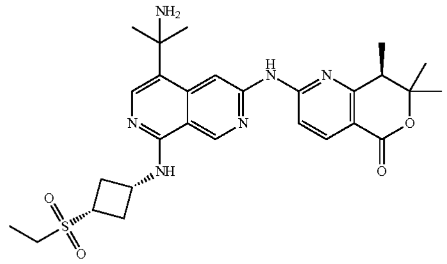 |
| 65 | 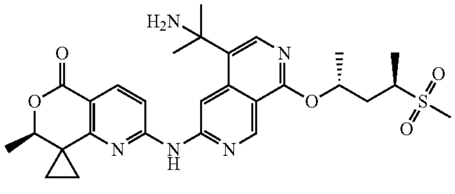 |
| | 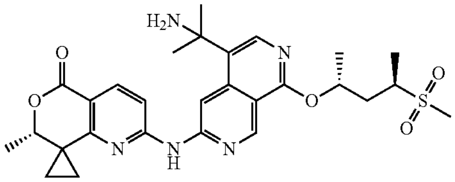 |
| 66 | 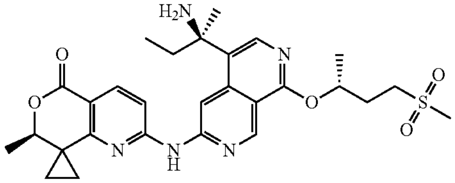 |
| | 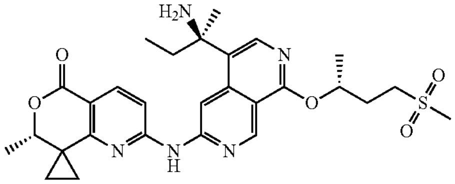 |
| 67 | 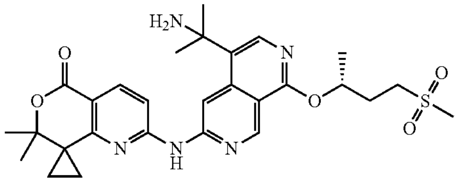 |
| 68 | 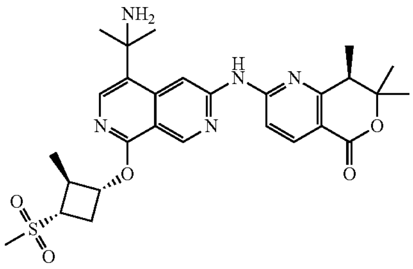 |
-continued
| Compound No. | Structure |
|---|---|
| | 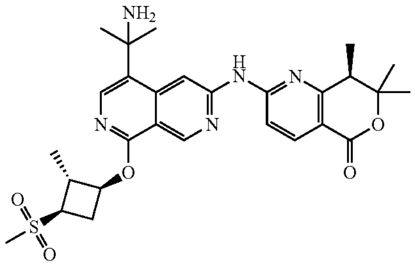 |
| 69 | 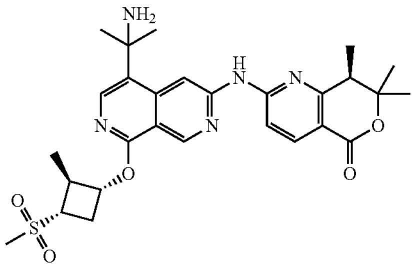 |
| | 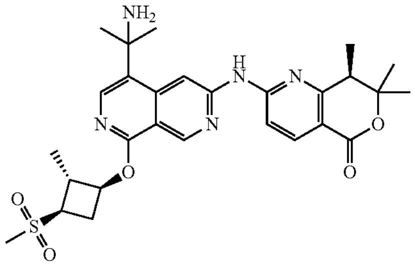 |
| 70 | 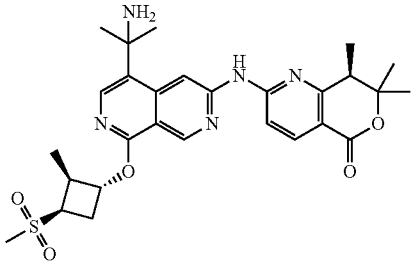 |
| | 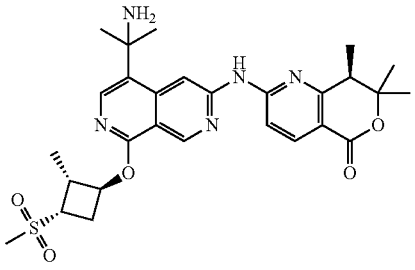 |

-continued
| Compound No. | Structure |
|---|---|
| 71 | 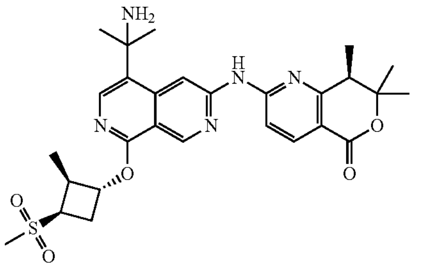 |
| | 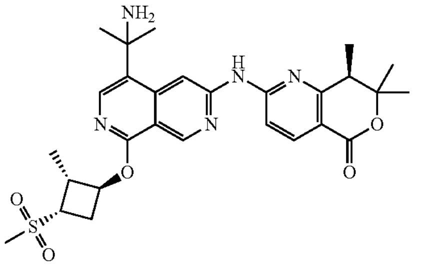 |
| 72 | 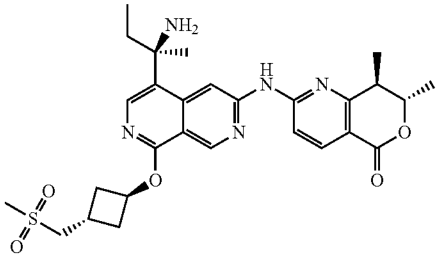 |
| 73 | 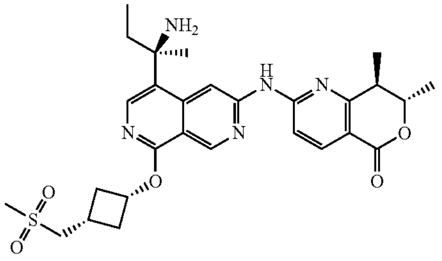 |
| 74 | 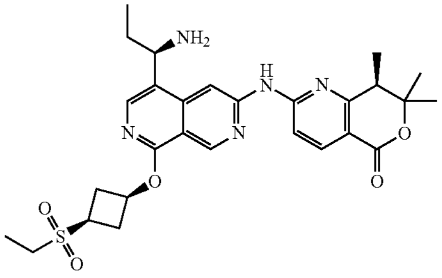 [SMILES: CC[C@@H](N)c1cnc(O[C@H]2C[C@@H](S(=O)(=O)CC)C2)c2cnc(Nc3ccc4c(n3)[C@@H](C)C(C)(C)OC4=O)cc12] |
-continued
| Compound No. | Structure |
|---|---|
| | 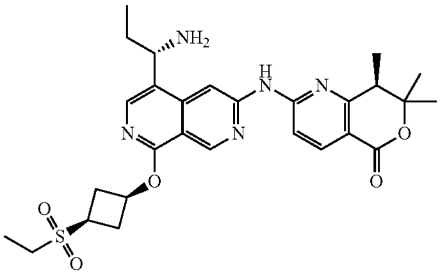 [SMILES: CC[C@H](N)c1cnc(O[C@H]2C[C@@H](S(=O)(=O)CC)C2)c2cnc(Nc3ccc4c(n3)[C@@H](C)C(C)(C)OC4=O)cc12] |
| 75 | 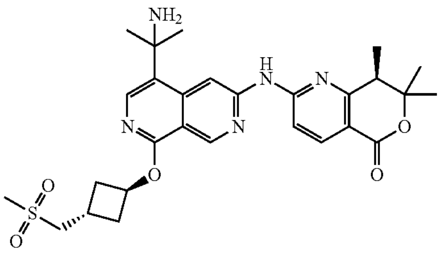 |
| 76 | 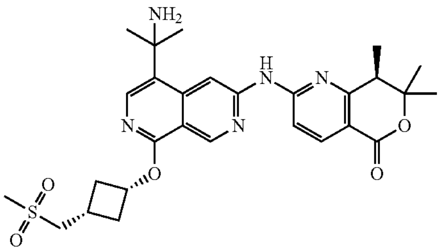 |
| 77 | 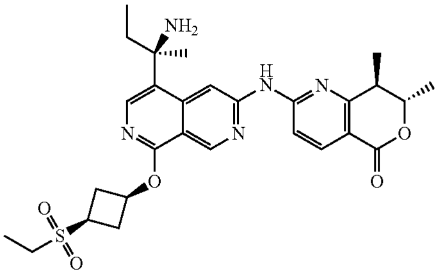 [SMILES: CC[C@@](C)(N)c1cnc(O[C@H]2C[C@@H](S(=O)(=O)CC)C2)c2cnc(Nc3ccc4c(n3)[C@@H](C)[C@H](C)OC4=O)cc12] |
| 78 | 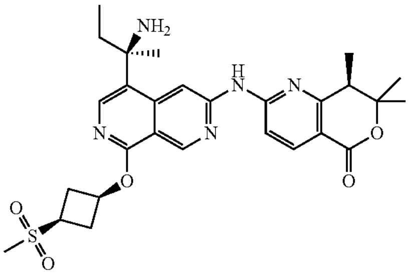 |

-continued
| Compound No. | Structure |
| --- | --- |
| 79 | 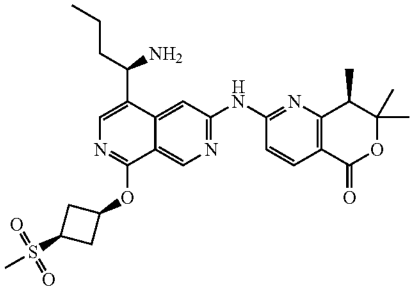 |
| | 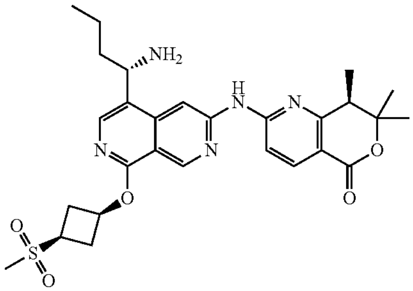 |
| 80 | 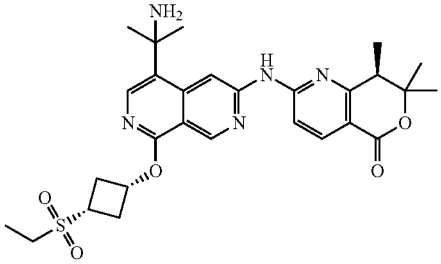 [SMILES: CCS(=O)(=O)[C@H]1C[C@@H](Oc2ncc(C(C)(C)N)c3cc(Nc4ccc5c(n4)[C@@H](C)C(C)(C)OC5=O)ncc23)C1] |
| 81 | 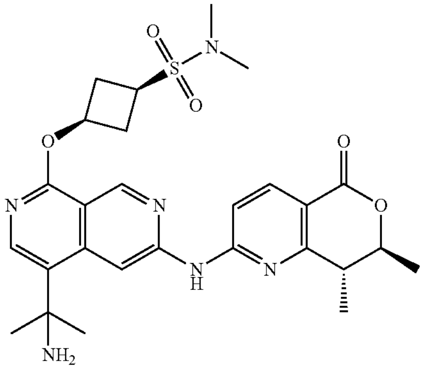 [SMILES: C[C@@H]1OC(=O)c2ccc(Nc3cc4c(C(C)(C)N)cnc(O[C@H]5C[C@@H](S(=O)(=O)N(C)C)C5)c4cn3)nc2[C@H]1C] |
| 82 | 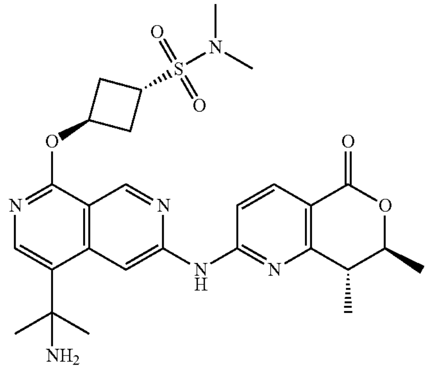 [SMILES: C[C@@H]1OC(=O)c2ccc(Nc3cc4c(C(C)(C)N)cnc(O[C@H]5C[C@H](S(=O)(=O)N(C)C)C5)c4cn3)nc2[C@H]1C] |
| 83 | 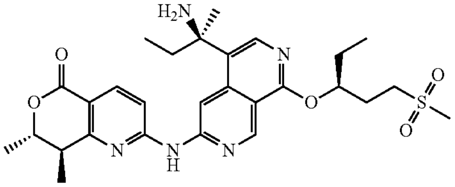 |
| | 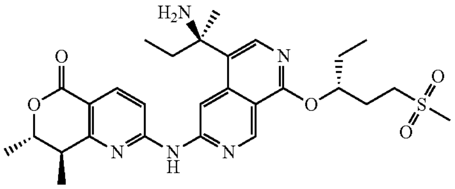 |
| 84 | 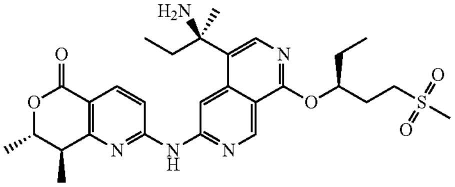 |
| | 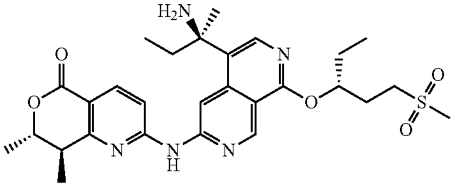 |
| 85 | 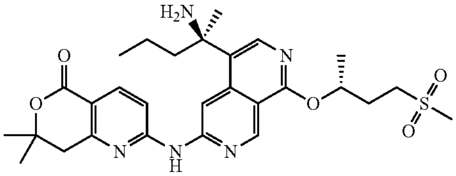 |
| | 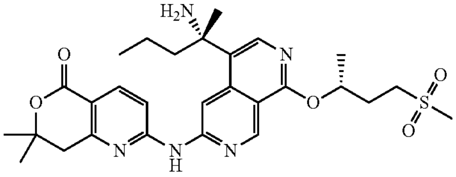 |

-continued
| Compound No. | Structure |
|---|---|
| 86 | 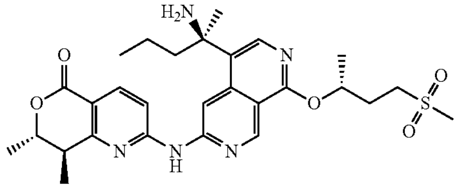 |
| | 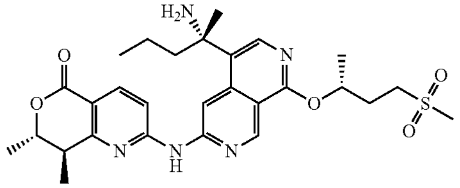 |
| 87 | 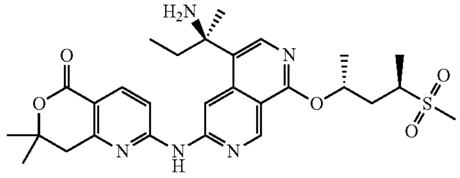 |
| 88 | 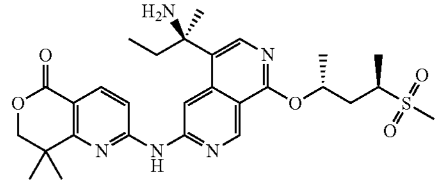 [SMILES: CC[C@@](C)(N)c1cnc(O[C@H](C)C[C@@H](C)S(C)(=O)=O)c2cnc(Nc3ccc4c(n3)C(C)(C)COC4=O)cc12] |
| 89 | 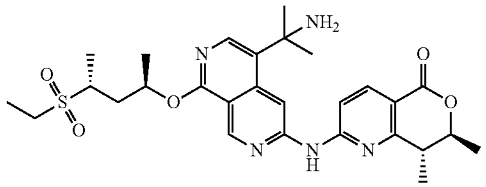 [SMILES: CCS(=O)(=O)[C@H](C)C[C@@H](C)Oc1ncc(C(C)(C)N)c2cc(Nc3ccc4c(n3)[C@@H](C)[C@H](C)OC4=O)ncc12] |
| 90 | 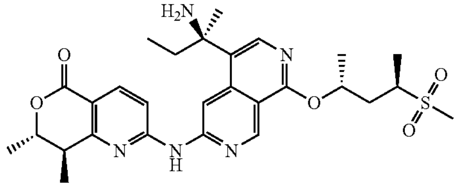 |
| 91 | 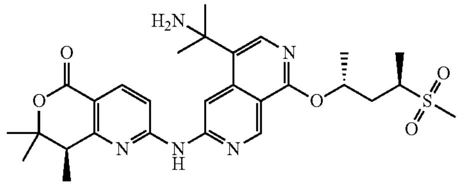 |
| 92 | 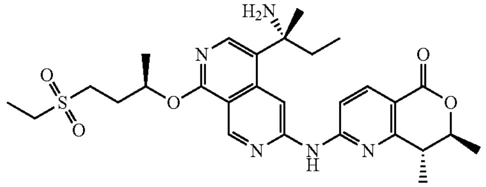 [SMILES: CC[C@@](C)(N)c1cnc(O[C@H](C)CCS(=O)(=O)CC)c2cnc(Nc3ccc4c(n3)[C@@H](C)[C@H](C)OC4=O)cc12] |
-continued
| Compound No. | Structure |
|---|---|
| | 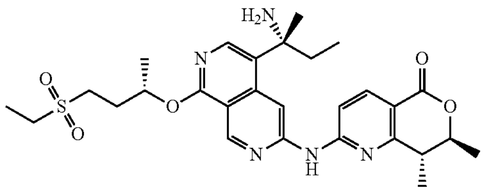 [SMILES: CC[C@@](C)(N)c1cnc(O[C@@H](C)CCS(=O)(=O)CC)c2cnc(Nc3ccc4c(n3)[C@@H](C)[C@H](C)OC4=O)cc12] |
| 93 | 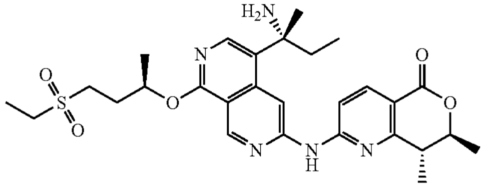 [SMILES: CC[C@@](C)(N)c1cnc(O[C@H](C)CCS(=O)(=O)CC)c2cnc(Nc3ccc4c(n3)[C@@H](C)[C@H](C)OC4=O)cc12] |
| | 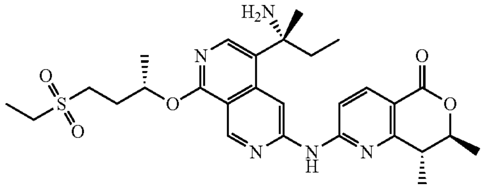 [SMILES: CC[C@@](C)(N)c1cnc(O[C@@H](C)CCS(=O)(=O)CC)c2cnc(Nc3ccc4c(n3)[C@@H](C)[C@H](C)OC4=O)cc12] |
| 94 | 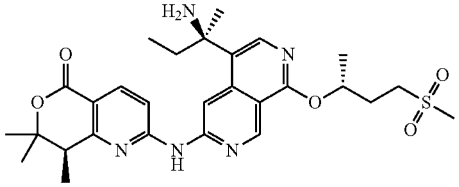 |
| 95 | 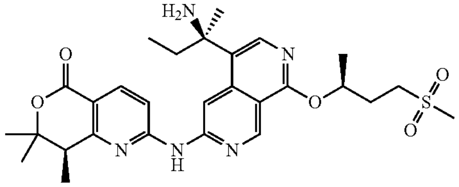 |
| 96 | 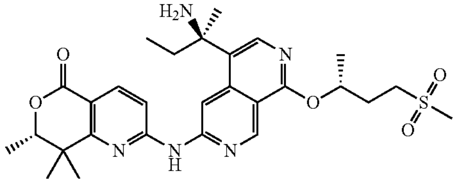 |
| | 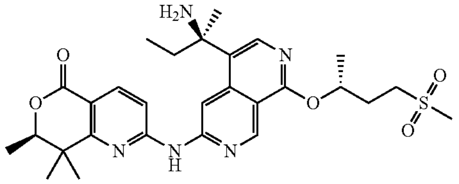 |

-continued
| Compound No. | Structure |
| --- | --- |
| 97 | 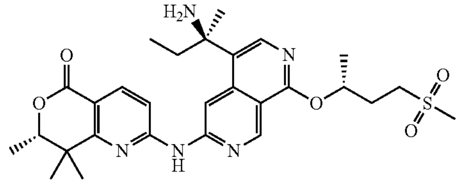 |
| | 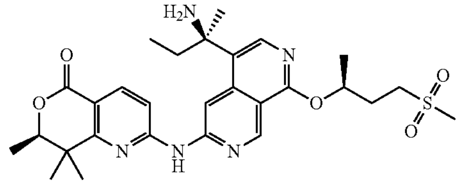 |
| 98 | 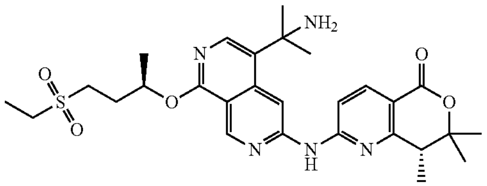 [SMILES: CCS(=O)(=O)CC[C@@H](C)Oc1ncc(C(C)(C)N)c2cc(Nc3ccc4c(n3)[C@@H](C)C(C)(C)OC4=O)ncc12] |
| | 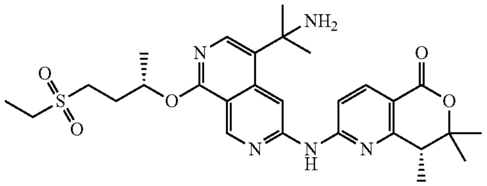 [SMILES: CCS(=O)(=O)CC[C@H](C)Oc1ncc(C(C)(C)N)c2cc(Nc3ccc4c(n3)[C@@H](C)C(C)(C)OC4=O)ncc12] |
| 99 | 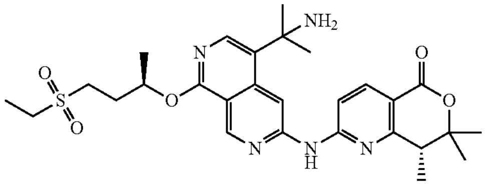 [SMILES: CCS(=O)(=O)CC[C@@H](C)Oc1ncc(C(C)(C)N)c2cc(Nc3ccc4c(n3)[C@@H](C)C(C)(C)OC4=O)ncc12] |
| | 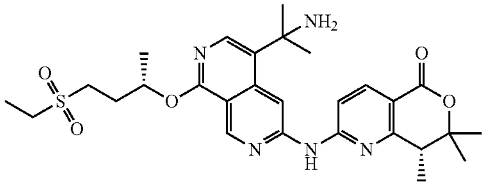 |
| 100 | 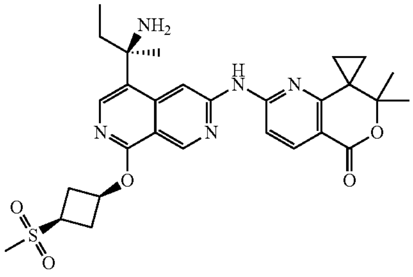 |
| 101 | 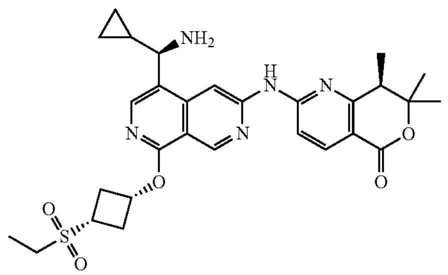 [SMILES: CCS(=O)(=O)[C@H]1C[C@@H](Oc2ncc([C@H](N)C3CC3)c3cc(Nc4ccc5c(n4)[C@@H](C)C(C)(C)OC5=O)ncc23)C1] |
| | 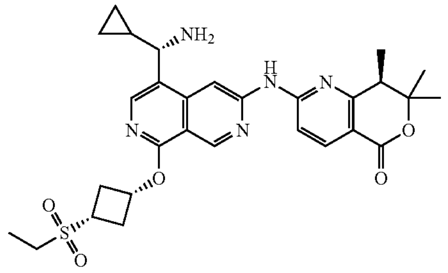 [SMILES: CCS(=O)(=O)[C@H]1C[C@@H](Oc2ncc([C@@H](N)C3CC3)c3cc(Nc4ccc5c(n4)[C@@H](C)C(C)(C)OC5=O)ncc23)C1] |
| 102 | 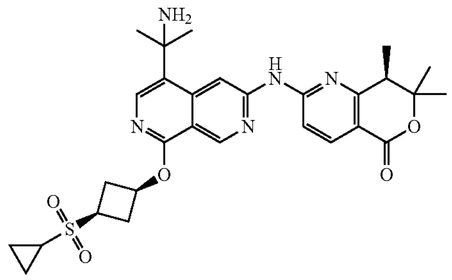 [SMILES: C[C@@H]1c2nc(Nc3cc4c(C(C)(C)N)cnc(O[C@H]5C[C@@H](S(=O)(=O)C6CC6)C5)c4cn3)ccc2C(=O)OC1(C)C] |
| 103 | 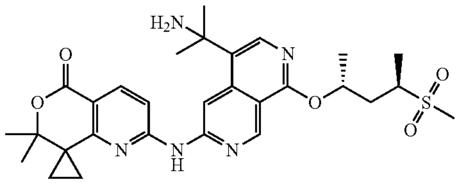 |
| 104 | 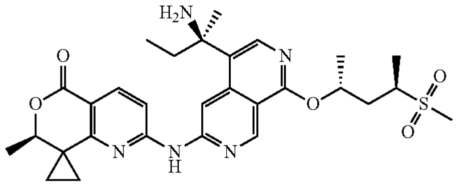 |
| | 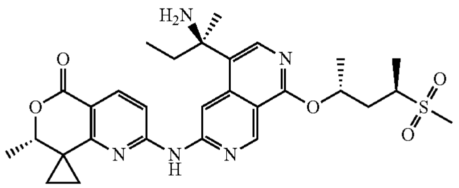 |

-continued
| Compound No. | Structure |
|---|---|
| 105 | 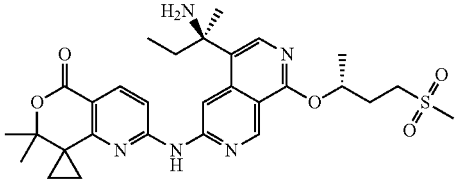 |
| 106 | 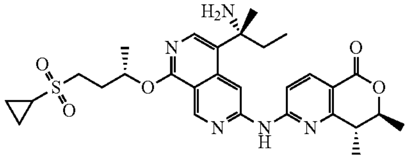 [SMILES: CC[C@@](C)(N)c1cnc(O[C@@H](C)CCS(=O)(=O)C2CC2)c2cnc(Nc3ccc4c(n3)[C@@H](C)[C@H](C)OC4=O)cc12] |
| | 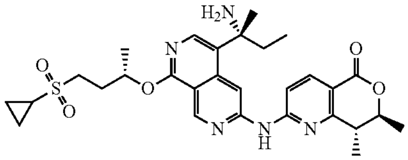 [SMILES: CC[C@@](C)(N)c1cnc(O[C@@H](C)CCS(=O)(=O)C2CC2)c2cnc(Nc3ccc4c(n3)[C@@H](C)[C@H](C)OC4=O)cc12] |
| 107 | 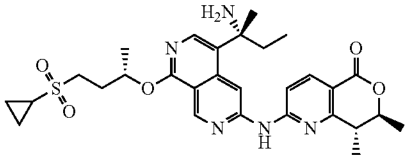 [SMILES: CC[C@@](C)(N)c1cnc(O[C@@H](C)CCS(=O)(=O)C2CC2)c2cnc(Nc3ccc4c(n3)[C@@H](C)[C@H](C)OC4=O)cc12] |
| | 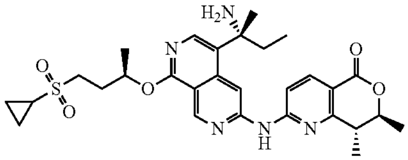 [SMILES: CC[C@@](C)(N)c1cnc(O[C@H](C)CCS(=O)(=O)C2CC2)c2cnc(Nc3ccc4c(n3)[C@@H](C)[C@H](C)OC4=O)cc12] |
| 108 | 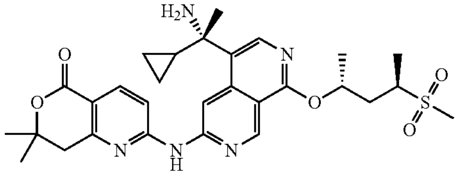 |
| | 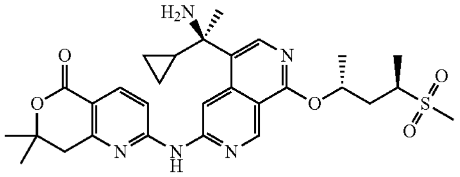 |
| 109 | 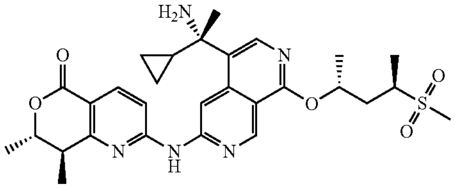 |
-continued
| Compound No. | Structure |
|---|---|
| | 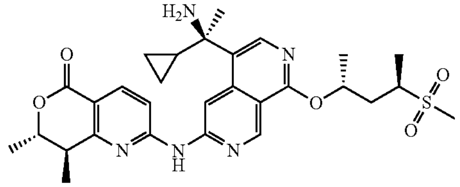 |
| 110 | 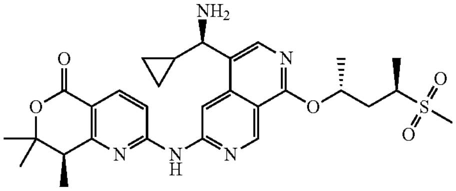 |
| | 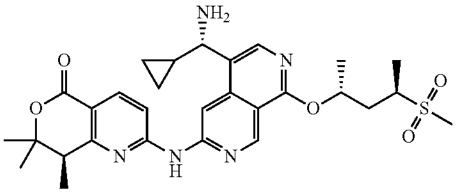 |
| 111 | 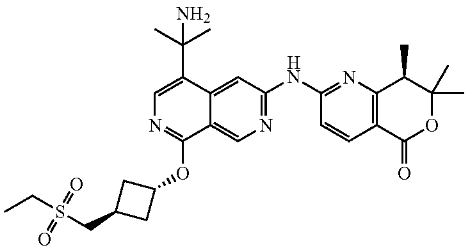 [SMILES: CCS(=O)(=O)C[C@H]1C[C@H](Oc2ncc(C(C)(C)N)c3cc(Nc4ccc5c(n4)[C@@H](C)C(C)(C)OC5=O)ncc23)C1] |
| 112 | 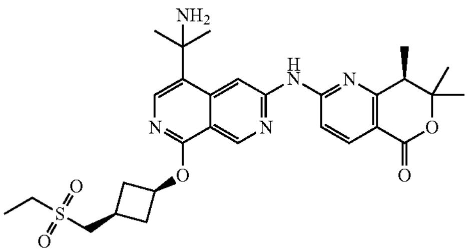 [SMILES: CCS(=O)(=O)C[C@H]1C[C@@H](Oc2ncc(C(C)(C)N)c3cc(Nc4ccc5c(n4)[C@@H](C)C(C)(C)OC5=O)ncc23)C1] |
| 113 | 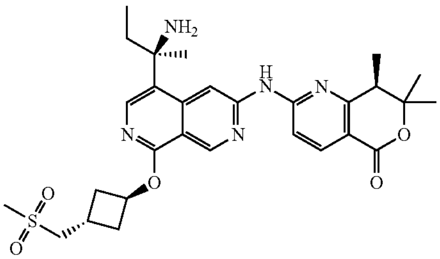 |

-continued
| Compound No. | Structure |
|---|---|
| 114 | 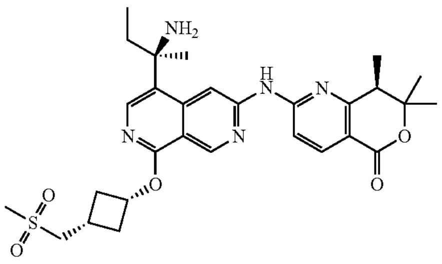 |
| 115 | 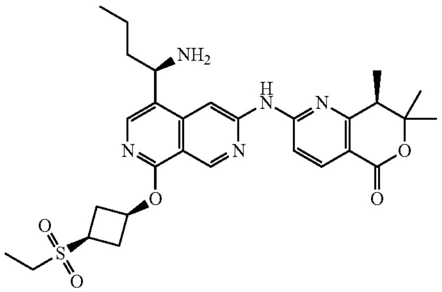 [SMILES: CCC[C@@H](N)c1cnc(O[C@H]2C[C@@H](S(=O)(=O)CC)C2)c2cnc(Nc3ccc4c(n3)[C@@H](C)C(C)(C)OC4=O)cc12] |
| | 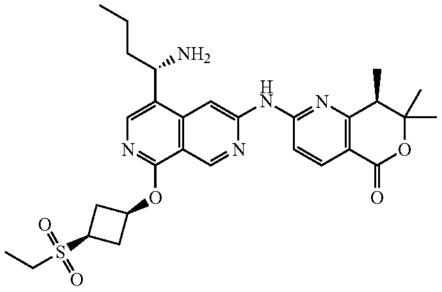 [SMILES: CCC[C@H](N)c1cnc(O[C@H]2C[C@@H](S(=O)(=O)CC)C2)c2cnc(Nc3ccc4c(n3)[C@@H](C)C(C)(C)OC4=O)cc12] |
| 116 | 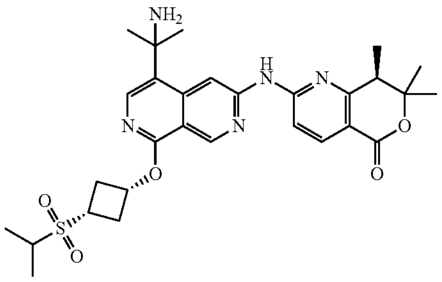 [SMILES: CC(C)S(=O)(=O)[C@H]1C[C@@H](Oc2ncc(C(C)(C)N)c3cc(Nc4ccc5c(n4)[C@@H](C)C(C)(C)OC5=O)ncc23)C1] |
| 117 | 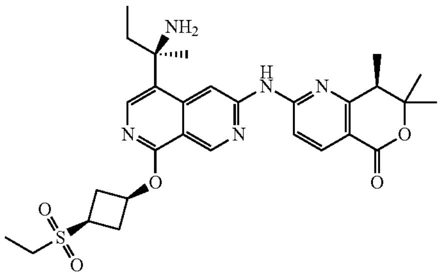 [SMILES: CC[C@@](C)(N)c1cnc(O[C@H]2C[C@@H](S(=O)(=O)CC)C2)c2cnc(Nc3ccc4c(n3)[C@@H](C)C(C)(C)OC4=O)cc12] |
-continued
| Compound No. | Structure |
|---|---|
| 118 | 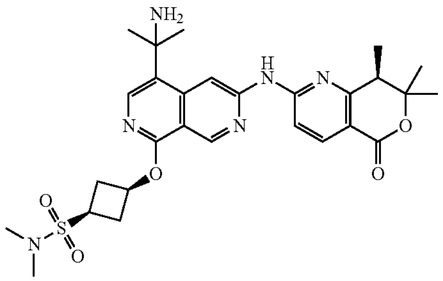 |
| 119 | 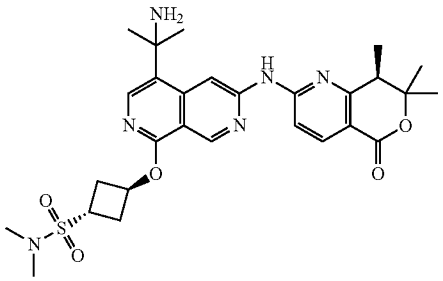 |
| 120 | 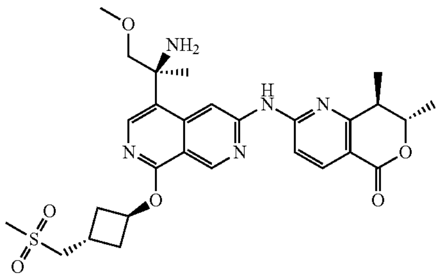 |
| 121 | 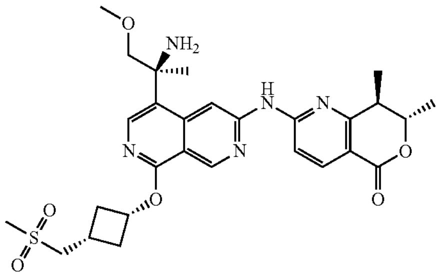 |
| 122 | 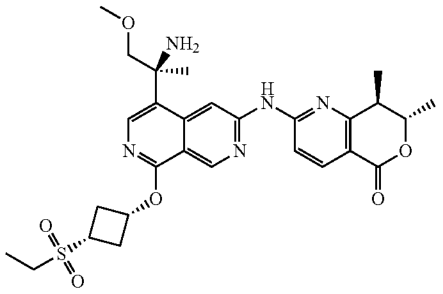 [SMILES: CCS(=O)(=O)[C@H]1C[C@@H](Oc2ncc([C@](C)(N)COC)c3cc(Nc4ccc5c(n4)[C@@H](C)[C@H](C)OC5=O)ncc23)C1] |

-continued
| Compound No. | Structure |
| --- | --- |
| 123 | 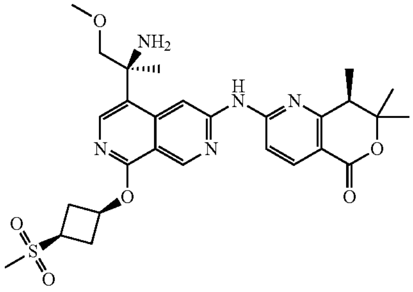 |
| 124 | 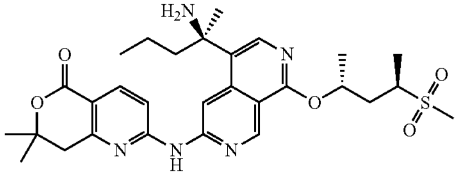 |
| | 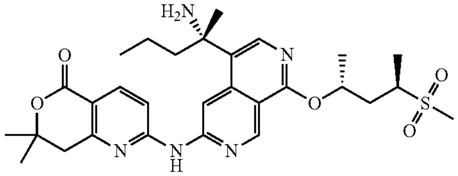 |
| 125 | 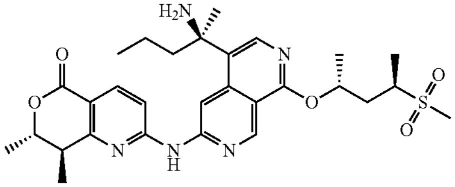 |
| | 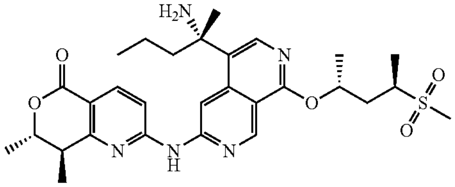 |
| 126 | 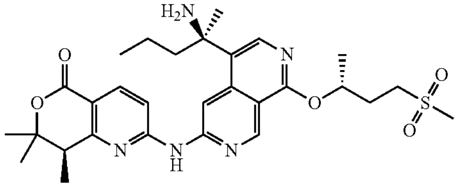 |
| | 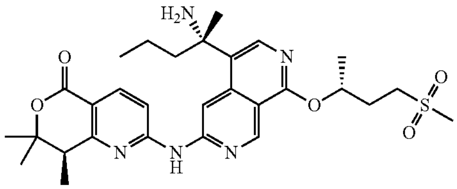 |
-continued
| Compound No. | Structure |
| --- | --- |
| 127 | 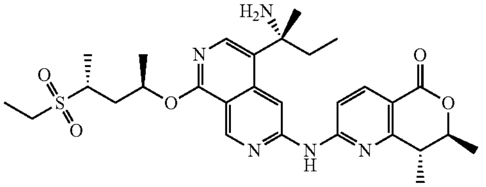 [SMILES: CC[C@@](C)(N)c1cnc(O[C@H](C)C[C@@H](C)S(=O)(=O)CC)c2cnc(Nc3ccc4c(n3)[C@@H](C)[C@H](C)OC4=O)cc12] |
| 128 | 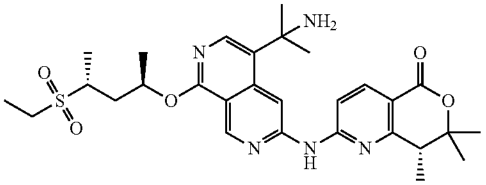 [SMILES: CCS(=O)(=O)[C@H](C)C[C@@H](C)Oc1ncc(C(C)(C)N)c2cc(Nc3ccc4c(n3)[C@@H](C)C(C)(C)OC4=O)ncc12] |
| 129 | 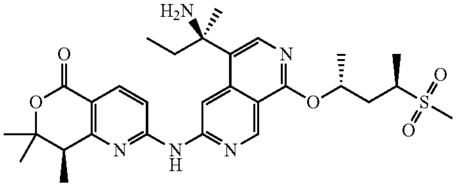 |
| 130 | 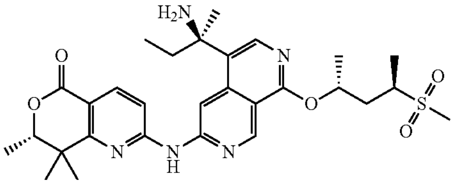 |
| | 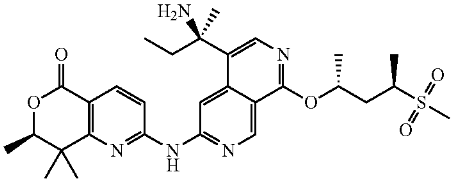 |
| 131 | 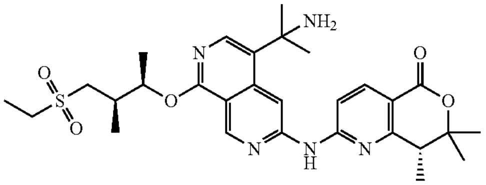 [SMILES: CCS(=O)(=O)C[C@H](C)[C@@H](C)Oc1ncc(C(C)(C)N)c2cc(Nc3ccc4c(n3)[C@@H](C)C(C)(C)OC4=O)ncc12] |
| | 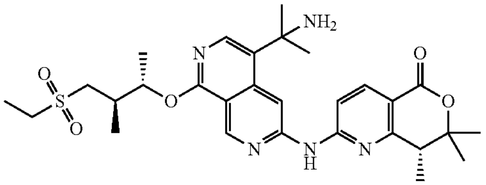 [SMILES: CCS(=O)(=O)C[C@H](C)[C@H](C)Oc1ncc(C(C)(C)N)c2cc(Nc3ccc4c(n3)[C@@H](C)C(C)(C)OC4=O)ncc12] |
| | 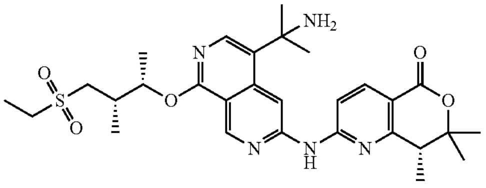 |

-continued
| Compound No. | Structure |
|---|---|
| | 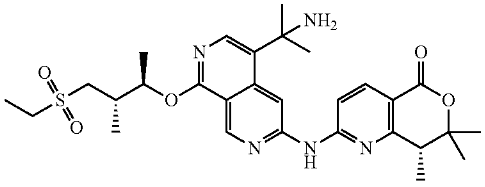 |
| 132 | 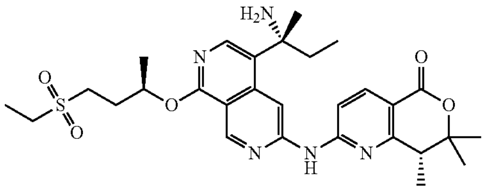 [SMILES: CC[C@@](C)(N)c1cnc(O[C@H](C)CCS(=O)(=O)CC)c2cnc(Nc3ccc4c(n3)[C@@H](C)C(C)(C)OC4=O)cc12] |
| | 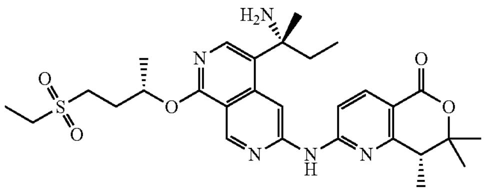 [SMILES: CC[C@@](C)(N)c1cnc(O[C@@H](C)CCS(=O)(=O)CC)c2cnc(Nc3ccc4c(n3)[C@@H](C)C(C)(C)OC4=O)cc12] |
| 133 | 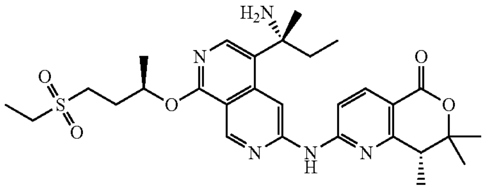 [SMILES: CC[C@@](C)(N)c1cnc(O[C@H](C)CCS(=O)(=O)CC)c2cnc(Nc3ccc4c(n3)[C@@H](C)C(C)(C)OC4=O)cc12] |
| | 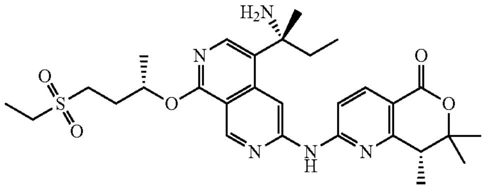 [SMILES: CC[C@@](C)(N)c1cnc(O[C@@H](C)CCS(=O)(=O)CC)c2cnc(Nc3ccc4c(n3)[C@@H](C)C(C)(C)OC4=O)cc12] |
| 134 | 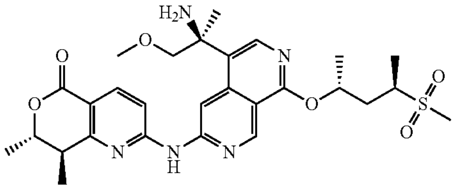 |
| 135 | 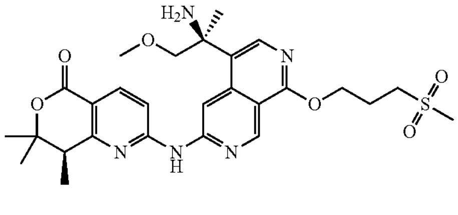 |
-continued
| Compound No. | Structure |
|---|---|
| 136 | 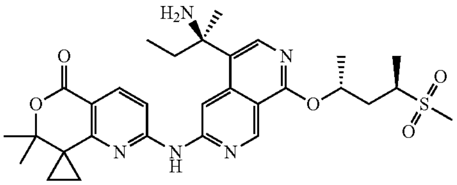 |
| 137 | 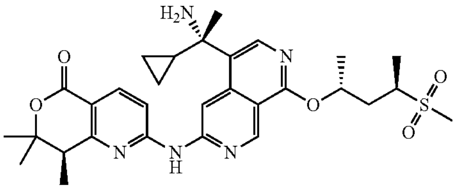 |
| | 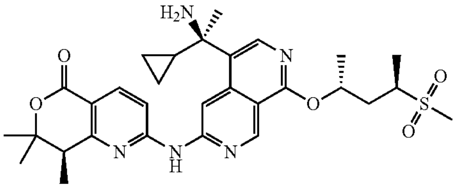 |
| 138 | 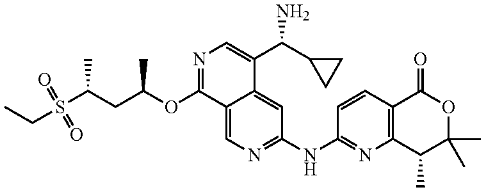 [SMILES: CCS(=O)(=O)[C@H](C)C[C@@H](C)Oc1ncc([C@H](N)C2CC2)c2cc(Nc3ccc4c(n3)[C@@H](C)C(C)(C)OC4=O)ncc12] |
| | 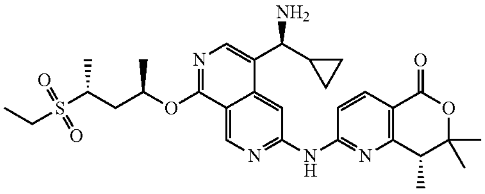 [SMILES: CCS(=O)(=O)[C@H](C)C[C@@H](C)Oc1ncc([C@@H](N)C2CC2)c2cc(Nc3ccc4c(n3)[C@@H](C)C(C)(C)OC4=O)ncc12] |
| 139 | 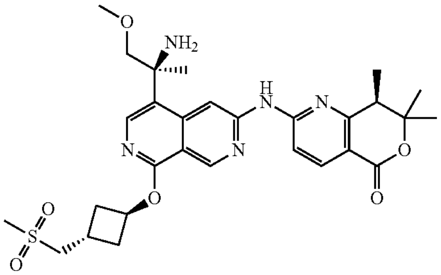 |
| 140 | 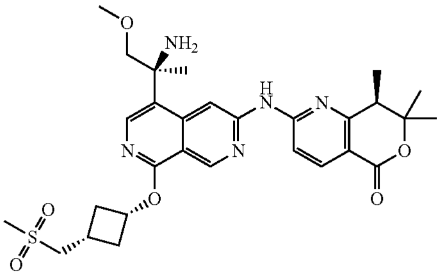 |

-continued
| Compound No. | Structure |
|---|---|
| 141 | 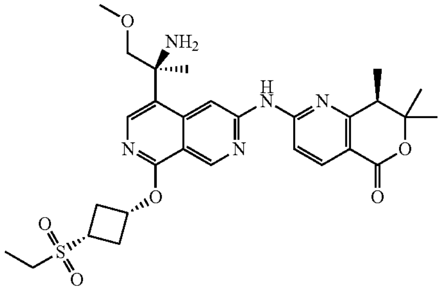 [SMILES: CCS(=O)(=O)[C@H]1C[C@@H](Oc2ncc([C@](C)(N)COC)c3cc(Nc4ccc5c(n4)[C@@H](C)C(C)(C)OC5=O)ncc23)C1] |
| 142 | 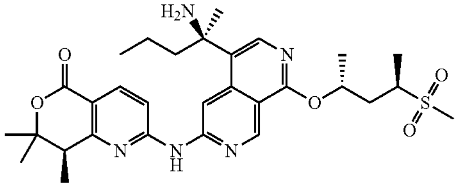 |
| | 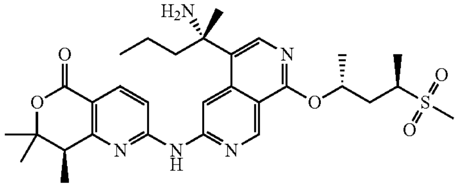 |
| 143 | 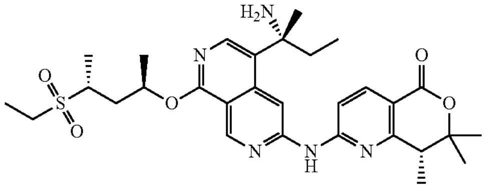 [SMILES: CC[C@@](C)(N)c1cnc(O[C@H](C)C[C@@H](C)S(=O)(=O)CC)c2cnc(Nc3ccc4c(n3)[C@@H](C)C(C)(C)OC4=O)cc12] |
| 144 | 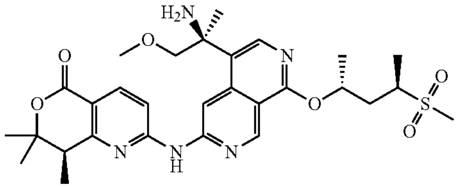 |
| 145 | 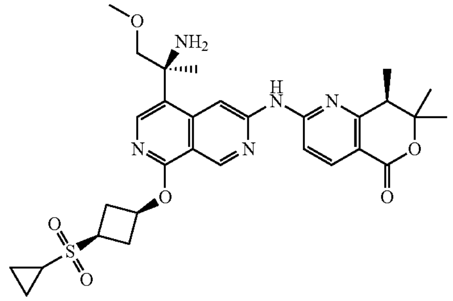 [SMILES: COC[C@@](C)(N)c1cnc(O[C@H]2C[C@@H](S(=O)(=O)C3CC3)C2)c2cnc(Nc3ccc4c(n3)[C@@H](C)C(C)(C)OC4=O)cc12] |
-continued
| Compound No. | Structure |
|---|---|
| 146 | 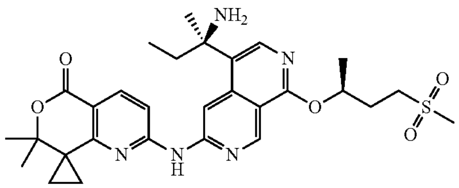 |
| 147 | 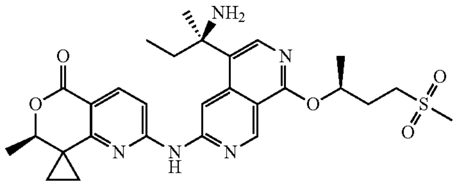 |
| | 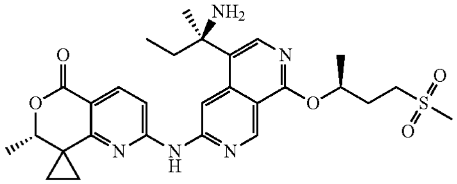 |
| 148 | 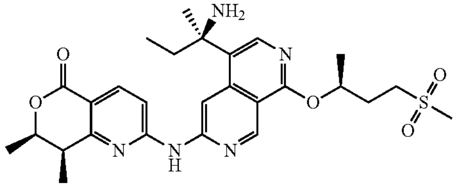 |
| | 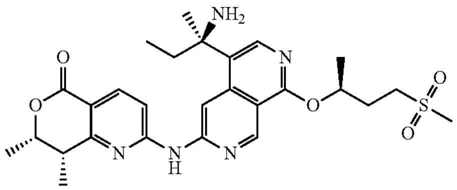 |
| 149 | 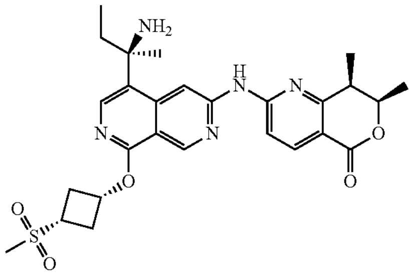 |
| | 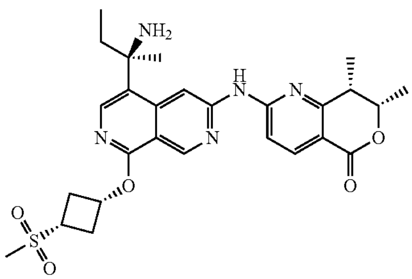 |

-continued
| Compound No. | Structure |
|---|---|
| 150 | 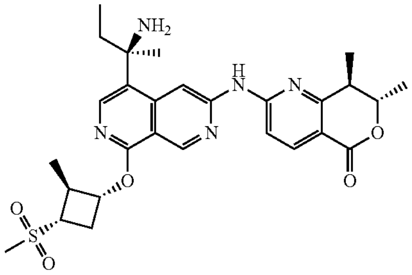 |
| | 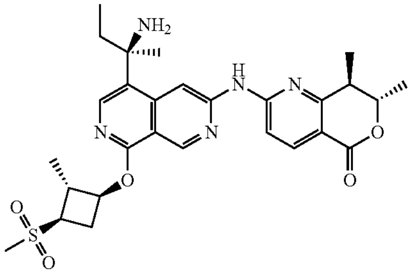 |
| 151 | 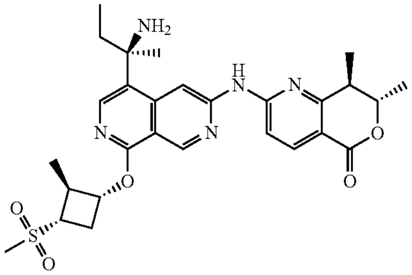 |
| | 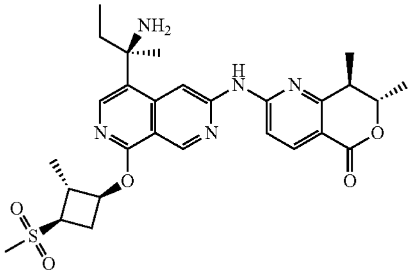 |
| 152 | 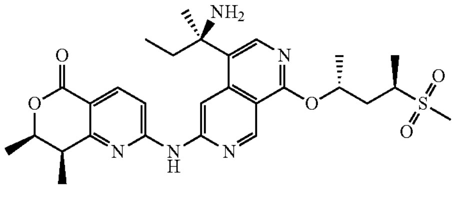 |
| | 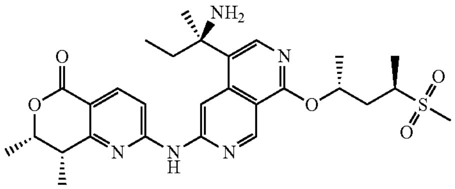 |
-continued
| Compound No. | Structure |
|---|---|
| 153 | 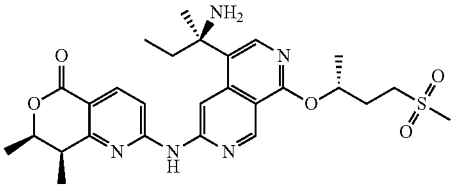 |
| | 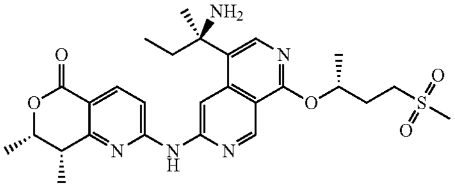 |
| 154 | 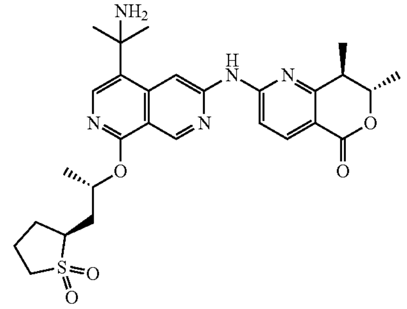 [SMILES: C[C@@H]1OC(=O)c2ccc(Nc3cc4c(C(C)(C)N)cnc(O[C@@H](C)C[C@@H]5CCCS5(=O)=O)c4cn3)nc2[C@H]1C] |
| | 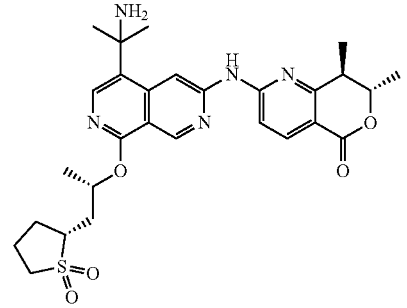 [SMILES: C[C@@H]1OC(=O)c2ccc(Nc3cc4c(C(C)(C)N)cnc(O[C@@H](C)C[C@H]5CCCS5(=O)=O)c4cn3)nc2[C@H]1C] |
| | 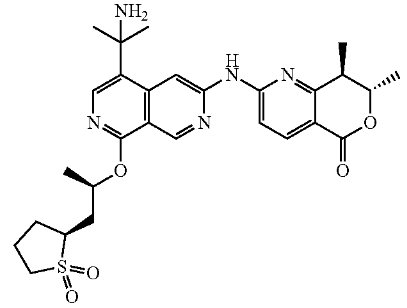 [SMILES: C[C@H](C[C@@H]1CCCS1(=O)=O)Oc1ncc(C(C)(C)N)c2cc(Nc3ccc4c(n3)[C@@H](C)[C@H](C)OC4=O)ncc12] |

-continued
| Compound No. | Structure |
|---|---|
| | 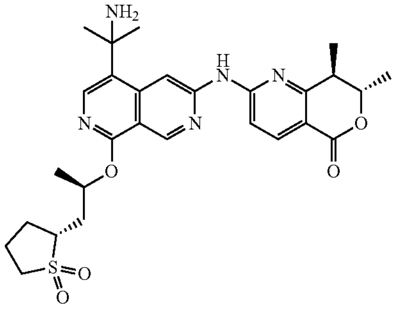 [SMILES: C[C@H](C[C@H]1CCCS1(=O)=O)Oc1ncc(C(C)(C)N)c2cc(Nc3ccc4c(n3)[C@@H](C)[C@H](C)OC4=O)ncc12] |
| 155 | 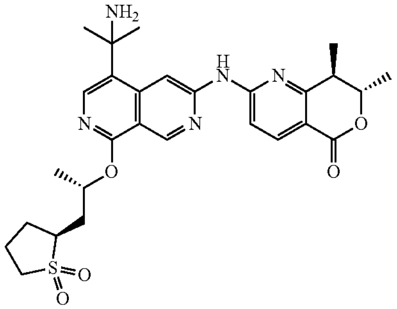 [SMILES: C[C@@H]1OC(=O)c2ccc(Nc3cc4c(C(C)(C)N)cnc(O[C@@H](C)C[C@@H]5CCCS5(=O)=O)c4cn3)nc2[C@H]1C] |
| | 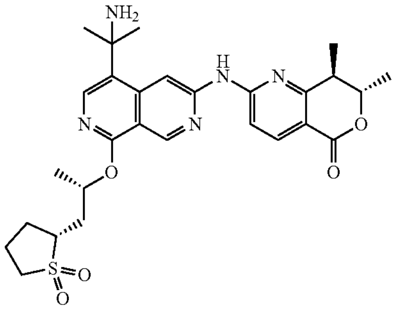 [SMILES: C[C@@H]1OC(=O)c2ccc(Nc3cc4c(C(C)(C)N)cnc(O[C@@H](C)C[C@H]5CCCS5(=O)=O)c4cn3)nc2[C@H]1C] |
| | 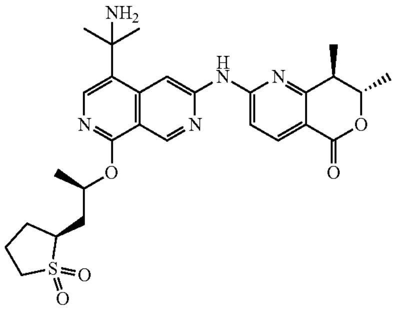 [SMILES: C[C@H](C[C@@H]1CCCS1(=O)=O)Oc1ncc(C(C)(C)N)c2cc(Nc3ccc4c(n3)[C@@H](C)[C@H](C)OC4=O)ncc12] |
| | 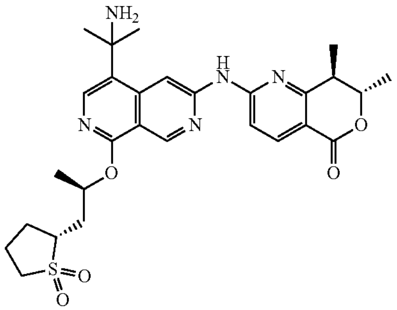 [SMILES: C[C@H](C[C@H]1CCCS1(=O)=O)Oc1ncc(C(C)(C)N)c2cc(Nc3ccc4c(n3)[C@@H](C)[C@H](C)OC4=O)ncc12] |
-continued
| Compound No. | Structure |
|---|---|
| 156 | 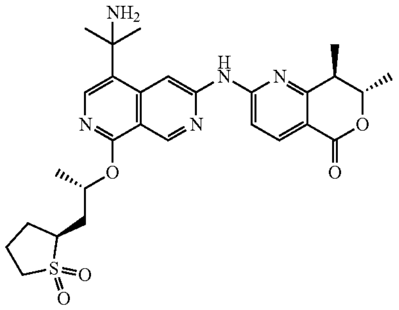 [SMILES: C[C@@H]1OC(=O)c2ccc(Nc3cc4c(C(C)(C)N)cnc(O[C@@H](C)C[C@@H]5CCCS5(=O)=O)c4cn3)nc2[C@H]1C] |
| | 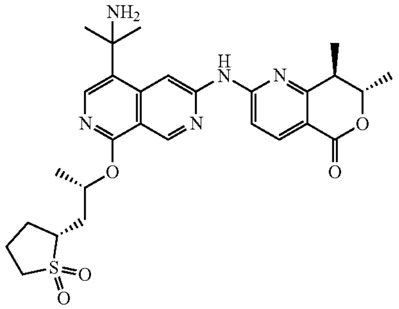 [SMILES: C[C@@H]1OC(=O)c2ccc(Nc3cc4c(C(C)(C)N)cnc(O[C@@H](C)C[C@H]5CCCS5(=O)=O)c4cn3)nc2[C@H]1C] |
| | 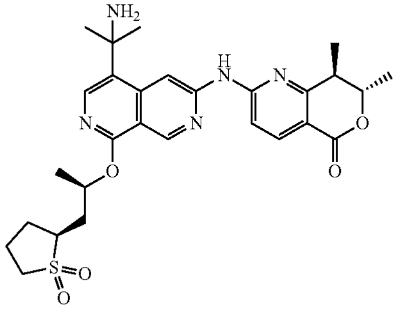 [SMILES: C[C@H](C[C@@H]1CCCS1(=O)=O)Oc1ncc(C(C)(C)N)c2cc(Nc3ccc4c(n3)[C@@H](C)[C@H](C)OC4=O)ncc12] |
| | 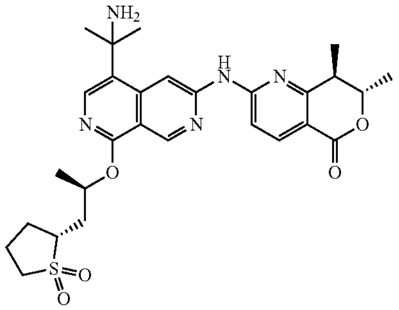 [SMILES: C[C@H](C[C@H]1CCCS1(=O)=O)Oc1ncc(C(C)(C)N)c2cc(Nc3ccc4c(n3)[C@@H](C)[C@H](C)OC4=O)ncc12] |

-continued
| Compound No. | Structure |
|---|---|
| 157 | 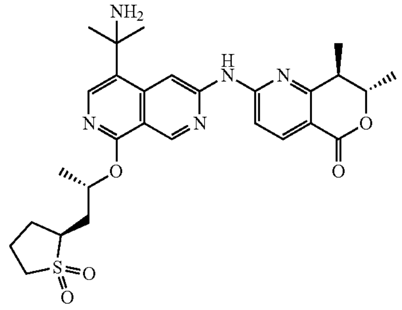 [SMILES: C[C@@H]1OC(=O)c2ccc(Nc3cc4c(C(C)(C)N)cnc(O[C@@H](C)C[C@@H]5CCCS5(=O)=O)c4cn3)nc2[C@H]1C] |
| | 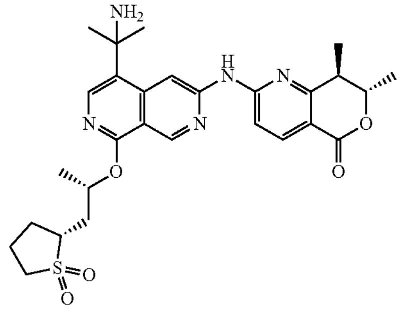 [SMILES: C[C@@H]1OC(=O)c2ccc(Nc3cc4c(C(C)(C)N)cnc(O[C@@H](C)C[C@H]5CCCS5(=O)=O)c4cn3)nc2[C@H]1C] |
| | 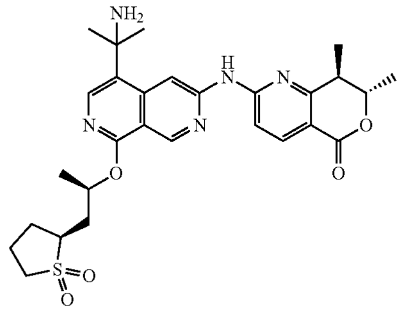 [SMILES: C[C@H](C[C@@H]1CCCS1(=O)=O)Oc1ncc(C(C)(C)N)c2cc(Nc3ccc4c(n3)[C@@H](C)[C@H](C)OC4=O)ncc12] |
| | 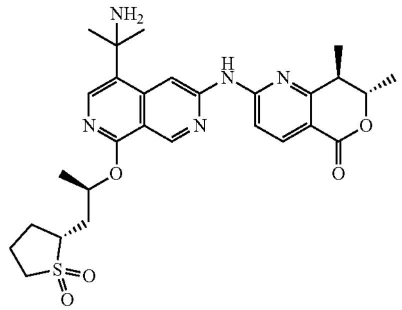 [SMILES: C[C@H](C[C@H]1CCCS1(=O)=O)Oc1ncc(C(C)(C)N)c2cc(Nc3ccc4c(n3)[C@@H](C)[C@H](C)OC4=O)ncc12] |
| 158 | 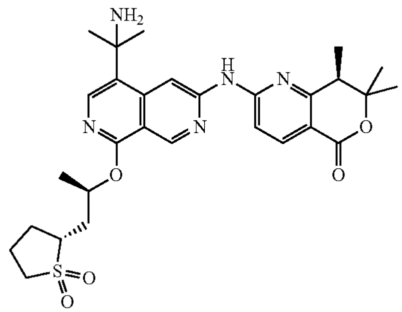 [SMILES: C[C@H](C[C@H]1CCCS1(=O)=O)Oc1ncc(C(C)(C)N)c2cc(Nc3ccc4c(n3)[C@@H](C)C(C)(C)OC4=O)ncc12] |
-continued
| Compound No. | Structure |
|---|---|
| | 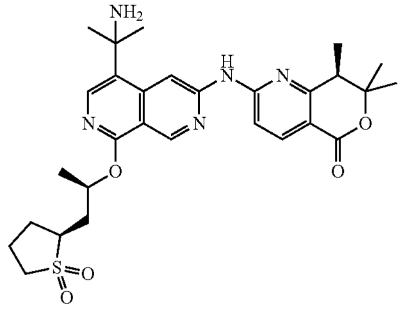 [SMILES: C[C@H](C[C@@H]1CCCS1(=O)=O)Oc1ncc(C(C)(C)N)c2cc(Nc3ccc4c(n3)[C@@H](C)C(C)(C)OC4=O)ncc12] |
| | 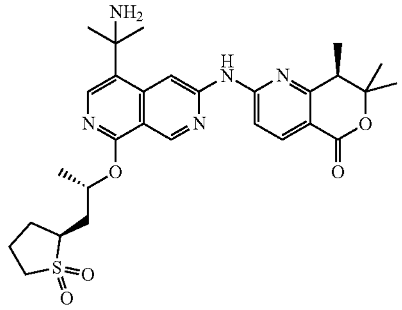 [SMILES: C[C@@H]1c2nc(Nc3cc4c(C(C)(C)N)cnc(O[C@@H](C)C[C@@H]5CCCS5(=O)=O)c4cn3)ccc2C(=O)OC1(C)C] |
| | 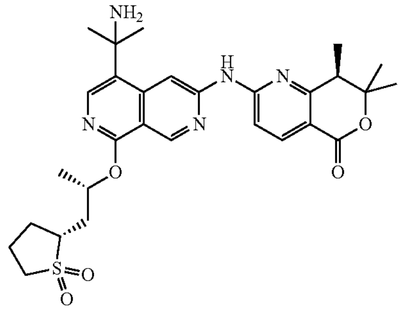 [SMILES: C[C@@H]1c2nc(Nc3cc4c(C(C)(C)N)cnc(O[C@@H](C)C[C@H]5CCCS5(=O)=O)c4cn3)ccc2C(=O)OC1(C)C] |
| 159 | 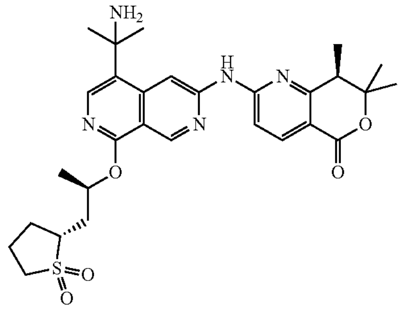 [SMILES: C[C@H](C[C@H]1CCCS1(=O)=O)Oc1ncc(C(C)(C)N)c2cc(Nc3ccc4c(n3)[C@@H](C)C(C)(C)OC4=O)ncc12] |

-continued
| Compound No. | Structure |
|---|---|
| | 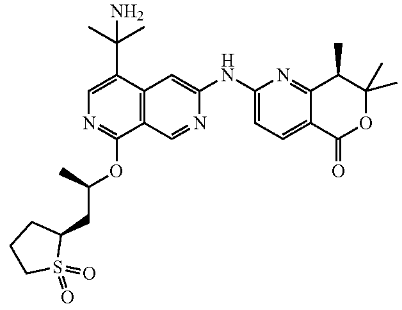 [SMILES: C[C@H](C[C@@H]1CCCS1(=O)=O)Oc1ncc(C(C)(C)N)c2cc(Nc3ccc4c(n3)[C@@H](C)C(C)(C)OC4=O)ncc12] |
| | 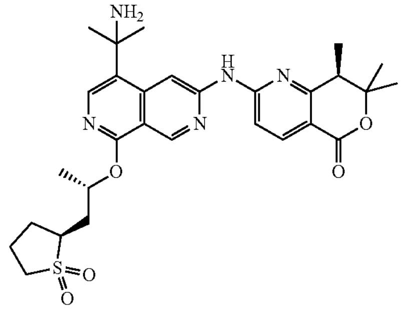 [SMILES: C[C@@H]1c2nc(Nc3cc4c(C(C)(C)N)cnc(O[C@@H](C)C[C@@H]5CCCS5(=O)=O)c4cn3)ccc2C(=O)OC1(C)C] |
| | 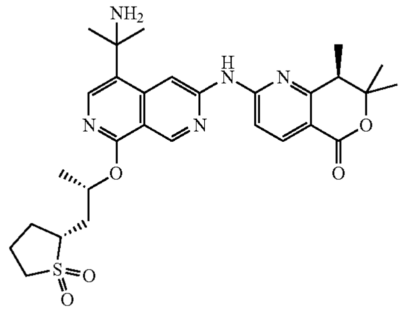 [SMILES: C[C@@H]1c2nc(Nc3cc4c(C(C)(C)N)cnc(O[C@@H](C)C[C@H]5CCCS5(=O)=O)c4cn3)ccc2C(=O)OC1(C)C] |
| 160 | 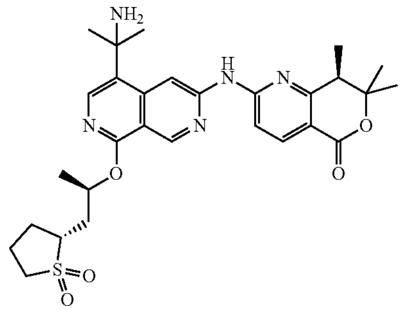 [SMILES: C[C@H](C[C@H]1CCCS1(=O)=O)Oc1ncc(C(C)(C)N)c2cc(Nc3ccc4c(n3)[C@@H](C)C(C)(C)OC4=O)ncc12] |
| | 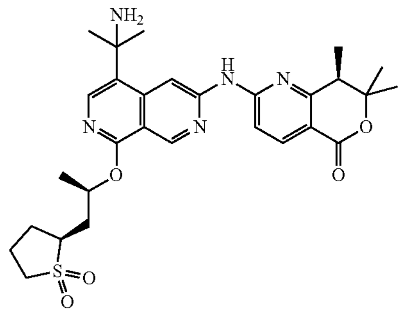 [SMILES: C[C@H](C[C@@H]1CCCS1(=O)=O)Oc1ncc(C(C)(C)N)c2cc(Nc3ccc4c(n3)[C@@H](C)C(C)(C)OC4=O)ncc12] |
-continued
| Compound No. | Structure |
|---|---|
| | 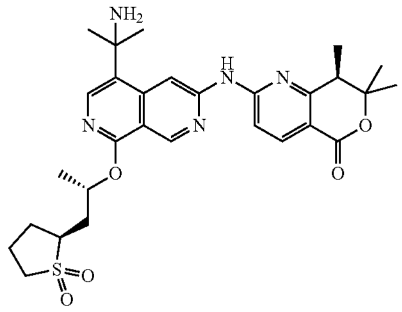 [SMILES: C[C@@H]1c2nc(Nc3cc4c(C(C)(C)N)cnc(O[C@@H](C)C[C@@H]5CCCS5(=O)=O)c4cn3)ccc2C(=O)OC1(C)C] |
| | 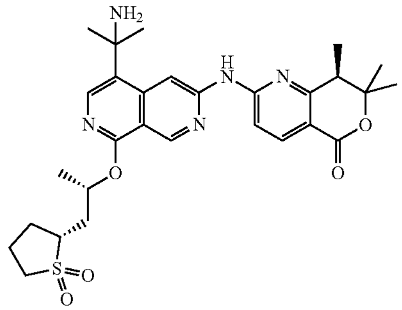 [SMILES: C[C@@H]1c2nc(Nc3cc4c(C(C)(C)N)cnc(O[C@@H](C)C[C@H]5CCCS5(=O)=O)c4cn3)ccc2C(=O)OC1(C)C] |
| 161 | 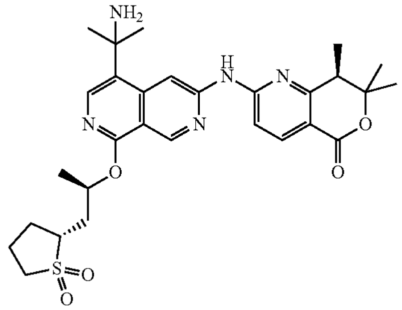 [SMILES: C[C@H](C[C@H]1CCCS1(=O)=O)Oc1ncc(C(C)(C)N)c2cc(Nc3ccc4c(n3)[C@@H](C)C(C)(C)OC4=O)ncc12] |
| | 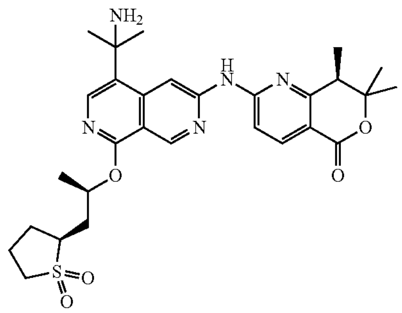 [SMILES: C[C@H](C[C@@H]1CCCS1(=O)=O)Oc1ncc(C(C)(C)N)c2cc(Nc3ccc4c(n3)[C@@H](C)C(C)(C)OC4=O)ncc12] |

-continued
| Compound No. | Structure |
| --- | --- |
| | 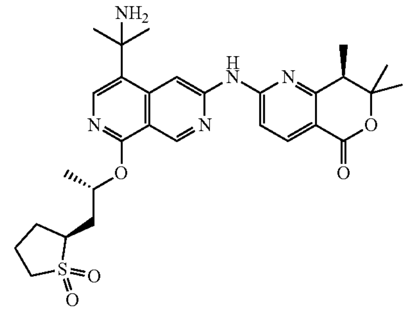 [SMILES: C[C@@H]1c2nc(Nc3cc4c(C(C)(C)N)cnc(O[C@@H](C)C[C@@H]5CCCS5(=O)=O)c4cn3)ccc2C(=O)OC1(C)C] |
| | 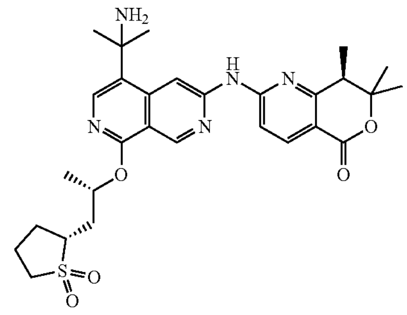 [SMILES: C[C@@H]1c2nc(Nc3cc4c(C(C)(C)N)cnc(O[C@@H](C)C[C@H]5CCCS5(=O)=O)c4cn3)ccc2C(=O)OC1(C)C] |
| 162 | 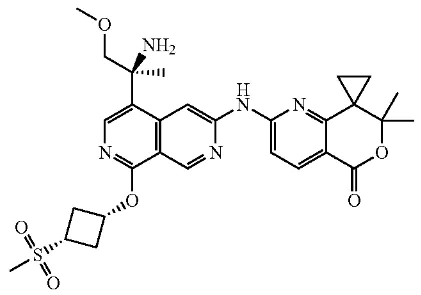 |
| 163 | 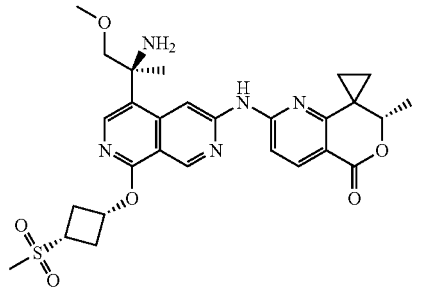 |
| | 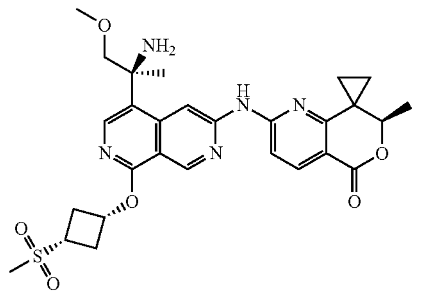 |
-continued
| Compound No. | Structure |
| --- | --- |
| 164 | 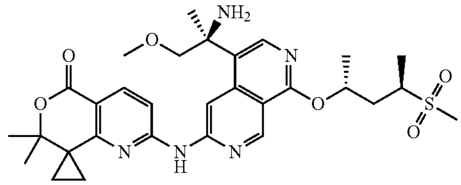 |
| 165 | 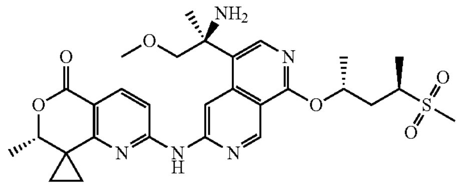 |
| | 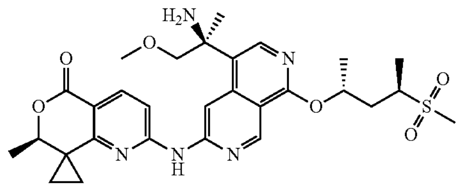 |
| 166 | 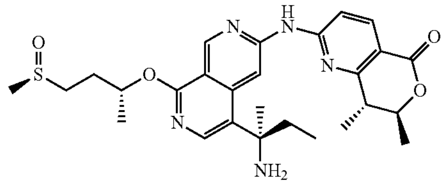 |
| | 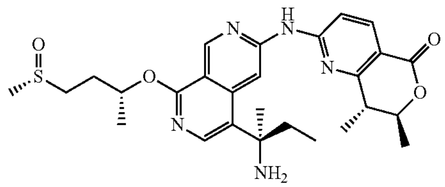 [SMILES: CC[C@@](C)(N)c1cnc(O[C@H](C)CC[S@](C)=O)c2cnc(Nc3ccc4c(n3)[C@@H](C)[C@H](C)OC4=O)cc12] |
| 167 | 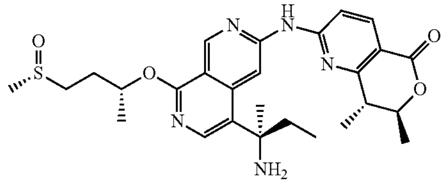 [SMILES: CC[C@@](C)(N)c1cnc(O[C@H](C)CC[S@](C)=O)c2cnc(Nc3ccc4c(n3)[C@@H](C)[C@H](C)OC4=O)cc12] |
| | 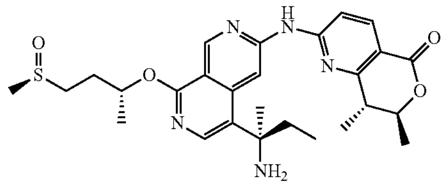 [SMILES: CC[C@@](C)(N)c1cnc(O[C@H](C)CC[S@@](C)=O)c2cnc(Nc3ccc4c(n3)[C@@H](C)[C@H](C)OC4=O)cc12] |
| 168 | 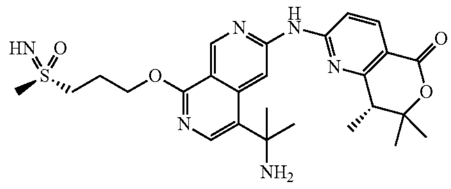 [SMILES: C[C@@H]1c2nc(Nc3cc4c(C(C)(C)N)cnc(OCCC[S@](C)(=N)=O)c4cn3)ccc2C(=O)OC1(C)C] |

-continued
| Compound No. | Structure |
|---|---|
| | 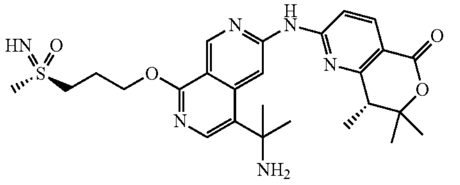 [SMILES: C[C@@H]1c2nc(Nc3cc4c(C(C)(C)N)cnc(OCCC[S@@](C)(=N)=O)c4cn3)ccc2C(=O)OC1(C)C] |
| 169 | 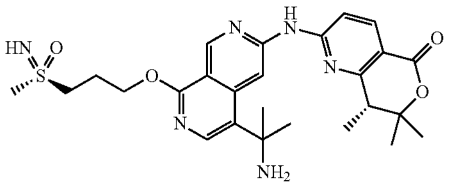 [SMILES: C[C@@H]1c2nc(Nc3cc4c(C(C)(C)N)cnc(OCCC[S@@](C)(=N)=O)c4cn3)ccc2C(=O)OC1(C)C] |
| | 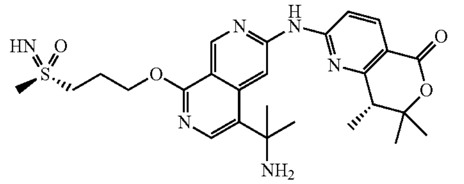 [SMILES: C[C@@H]1c2nc(Nc3cc4c(C(C)(C)N)cnc(OCCC[S@](C)(=N)=O)c4cn3)ccc2C(=O)OC1(C)C] |
| 170 | 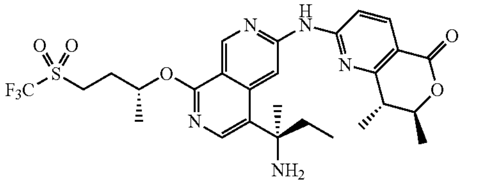 [SMILES: CC[C@@](C)(N)c1cnc(O[C@H](C)CCS(=O)(=O)C(F)(F)F)c2cnc(Nc3ccc4c(n3)[C@@H](C)[C@H](C)OC4=O)cc12] |
| | 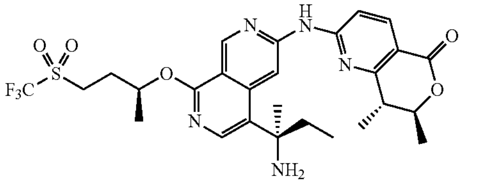 [SMILES: CC[C@@](C)(N)c1cnc(O[C@@H](C)CCS(=O)(=O)C(F)(F)F)c2cnc(Nc3ccc4c(n3)[C@@H](C)[C@H](C)OC4=O)cc12] |
| 171 | 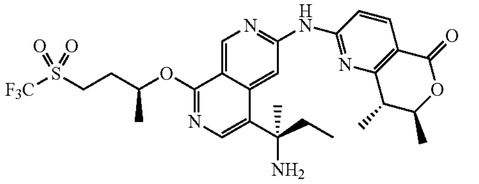 [SMILES: CC[C@@](C)(N)c1cnc(O[C@@H](C)CCS(=O)(=O)C(F)(F)F)c2cnc(Nc3ccc4c(n3)[C@@H](C)[C@H](C)OC4=O)cc12] |
| | 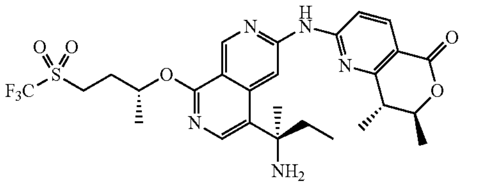 [SMILES: CC[C@@](C)(N)c1cnc(O[C@H](C)CCS(=O)(=O)C(F)(F)F)c2cnc(Nc3ccc4c(n3)[C@@H](C)[C@H](C)OC4=O)cc12] |
-continued
| Compound No. | Structure |
|---|---|
| 172 | 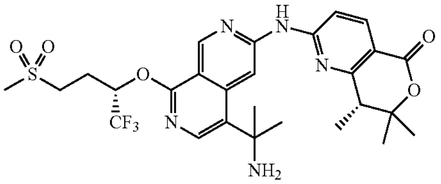 [SMILES: C[C@@H]1c2nc(Nc3cc4c(C(C)(C)N)cnc(O[C@@H](CCS(C)(=O)=O)C(F)(F)F)c4cn3)ccc2C(=O)OC1(C)C] |
| | 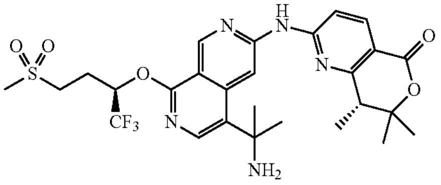 |
| 173 | 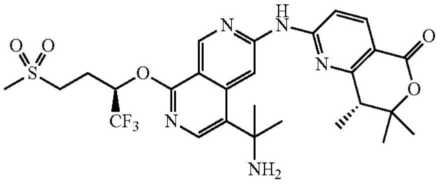 [SMILES: C[C@@H]1c2nc(Nc3cc4c(C(C)(C)N)cnc(O[C@H](CCS(C)(=O)=O)C(F)(F)F)c4cn3)ccc2C(=O)OC1(C)C] |
| | 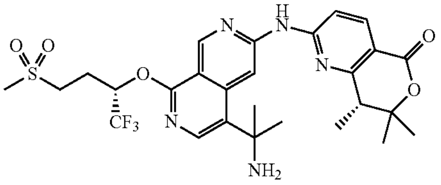 |
| 174 | 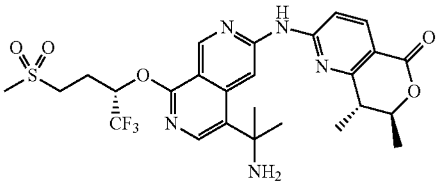 |
| | 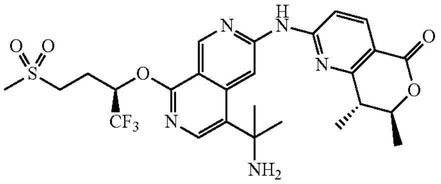 [SMILES: C[C@@H]1OC(=O)c2ccc(Nc3cc4c(C(C)(C)N)cnc(O[C@H](CCS(C)(=O)=O)C(F)(F)F)c4cn3)nc2[C@H]1C] |
| 175 | 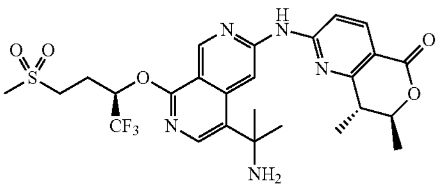 [SMILES: C[C@@H]1OC(=O)c2ccc(Nc3cc4c(C(C)(C)N)cnc(O[C@H](CCS(C)(=O)=O)C(F)(F)F)c4cn3)nc2[C@H]1C] |

-continued
| Compound No. | Structure |
| --- | --- |
| | 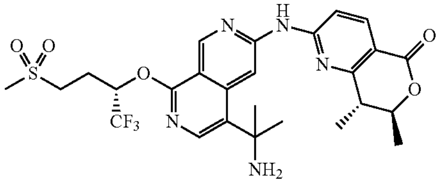 [SMILES: C[C@@H]1OC(=O)c2ccc(Nc3cc4c(C(C)(C)N)cnc(O[C@@H](CCS(C)(=O)=O)C(F)(F)F)c4cn3)nc2[C@H]1C] |
| 176 | 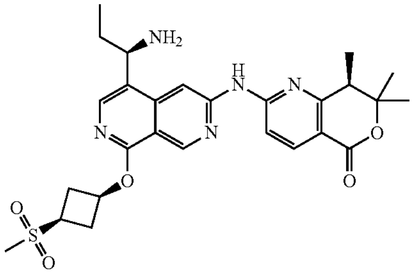 |
| | 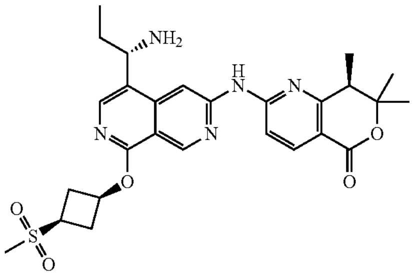 |
| 177 | 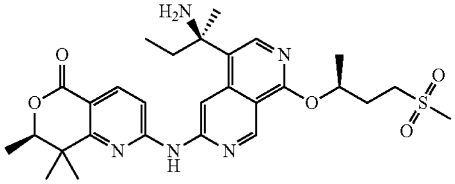 |
| 178 | 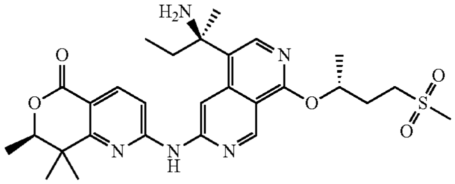 |
| 179 | 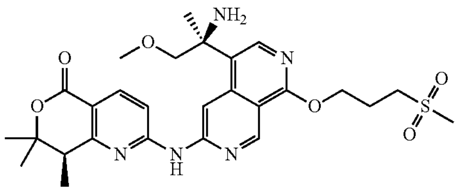 |
| | 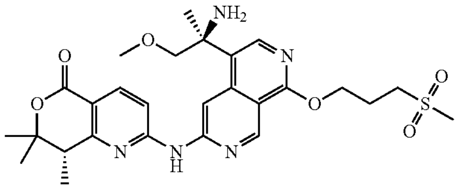 |
-continued
| Compound No. | Structure |
| --- | --- |
| 180 | 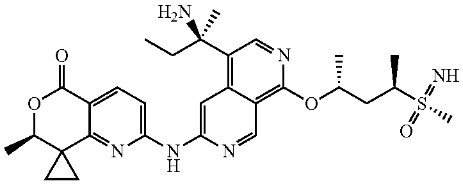 |
| | 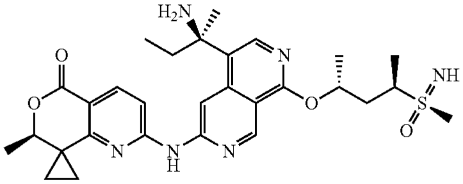 |
| | 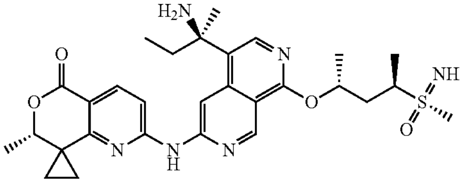 |
| | 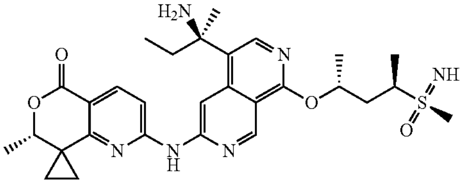 |
| 181 | 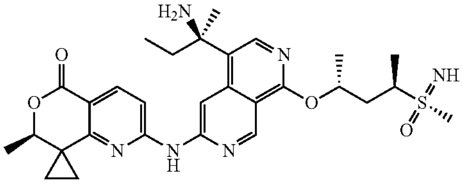 |
| | 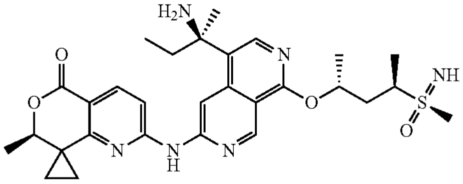 |
| | 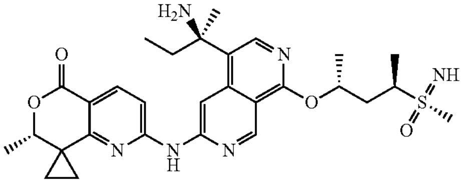 |
| | 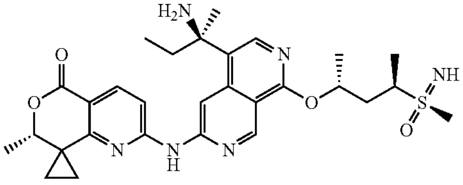 |

-continued
| Compound No. | Structure |
|---|---|
| 182 | 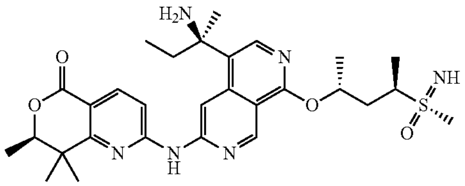 |
| | 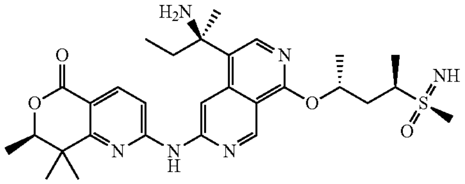 |
| | 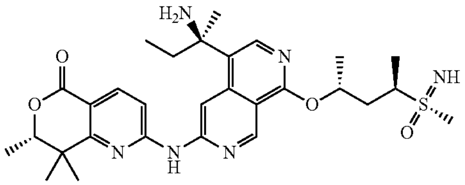 |
| | 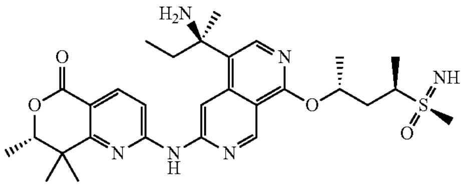 |
| 183 | 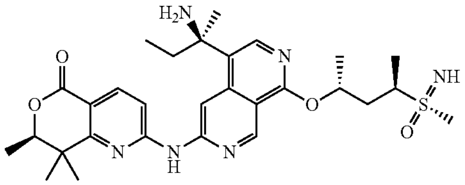 |
| | 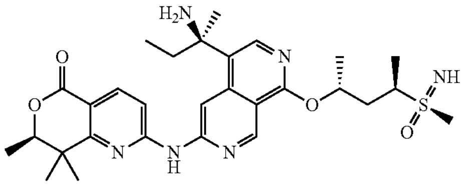 |
| | 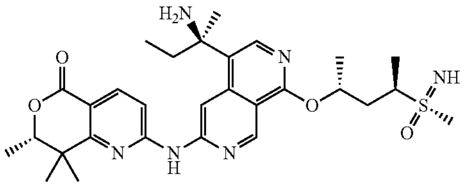 |
-continued
| Compound No. | Structure |
|---|---|
| | 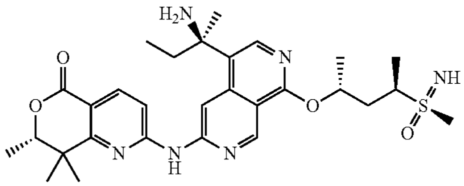 |
| 184 | 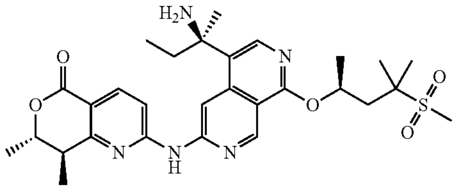 |
| | 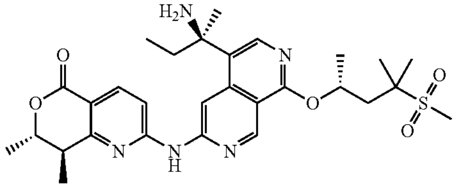 |
| 185 | 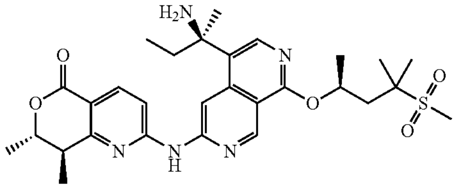 |
| | 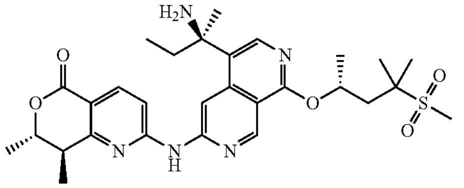 |
| 186 | 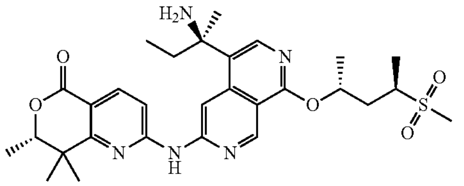 |
| | 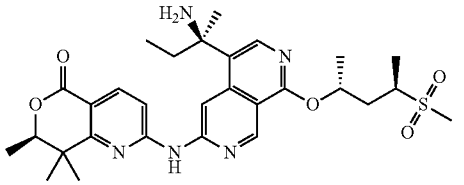 |
| 187 | 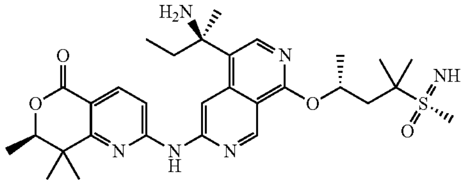 |

-continued
| Compound No. | Structure |
|---|---|
| | 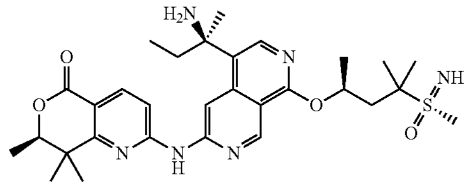 |
| | 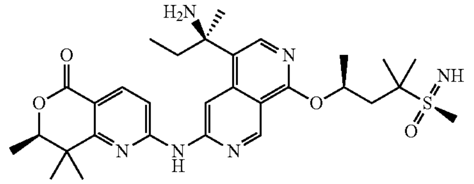 |
| | 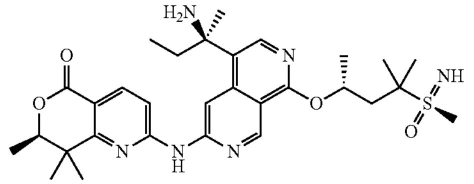 |
| | 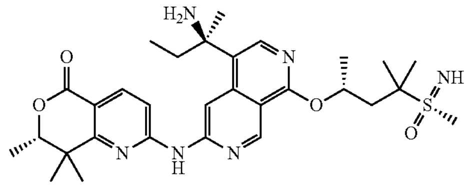 |
| | 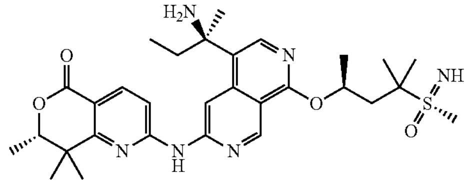 |
| | 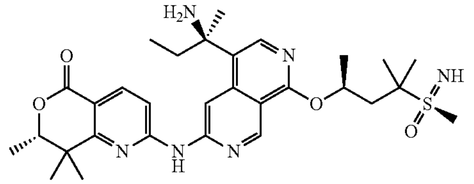 |
| | 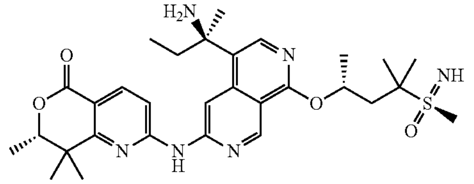 |
-continued
| Compound No. | Structure |
|---|---|
| 188 | 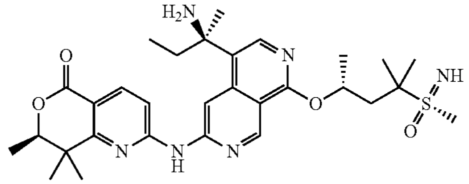 |
| | 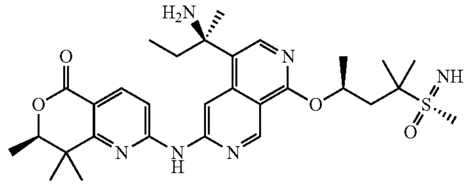 |
| | 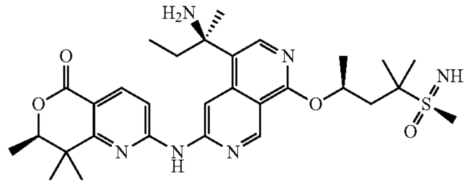 |
| | 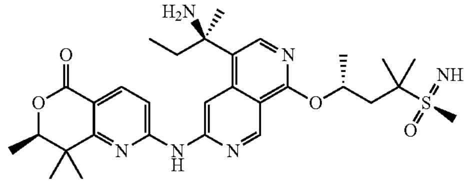 |
| | 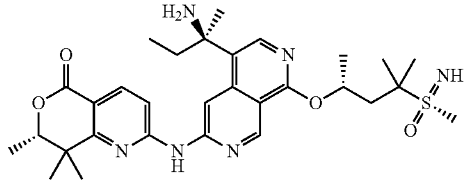 |
| | 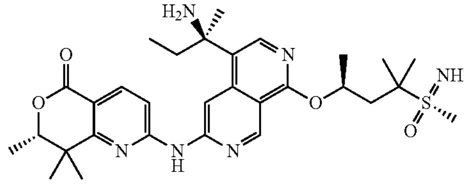 |
| | 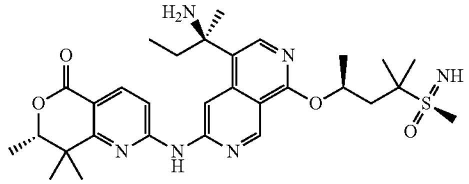 |
| | 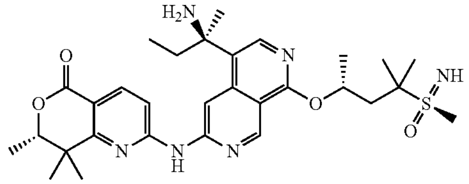 |

-continued
| Compound No. | Structure |
| --- | --- |
| 189 | 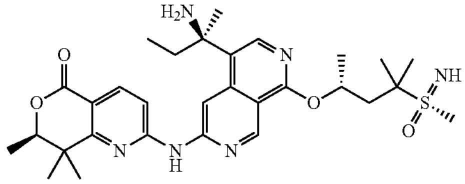 |
| | 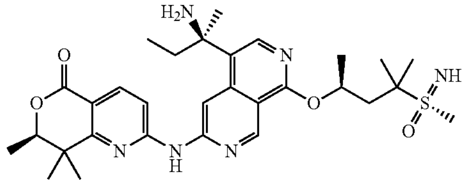 |
| | 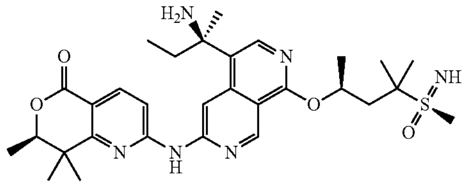 |
| | 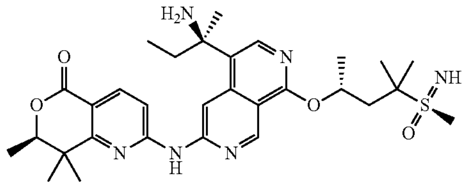 |
| | 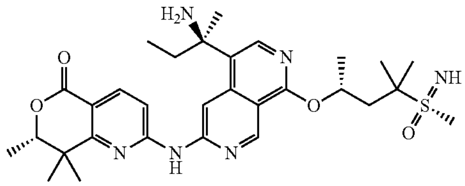 |
| | 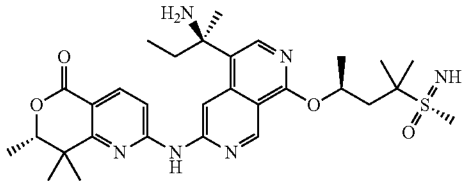 |
| | 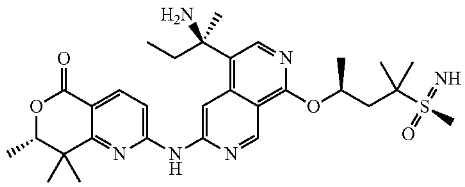 |
-continued
| Compound No. | Structure |
| --- | --- |
| | 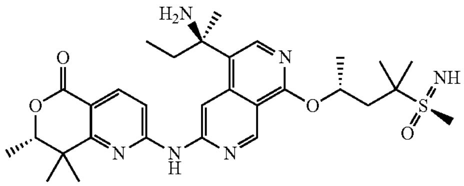 |
| 190 | 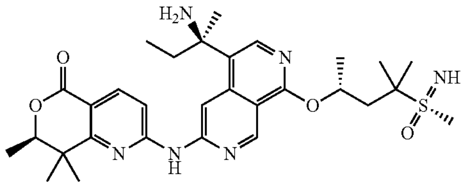 |
| | 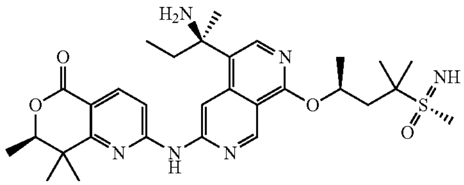 |
| | 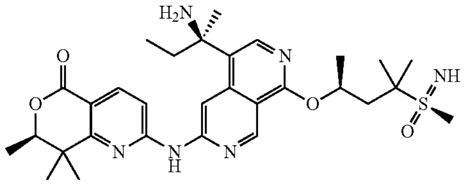 |
| | 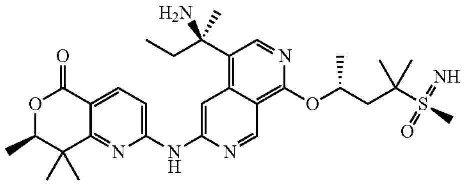 |
| | 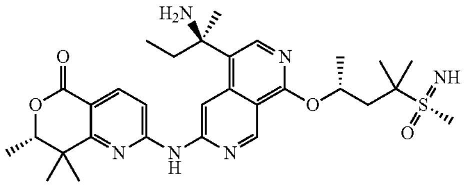 |
| | 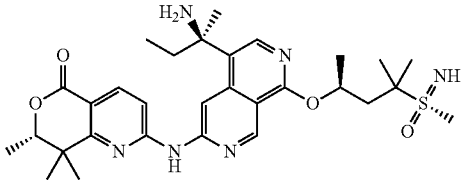 |
| | 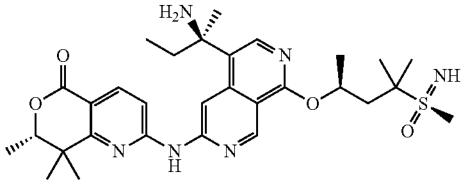 |

-continued

| Compound No. | Structure |
|---|---|
| | 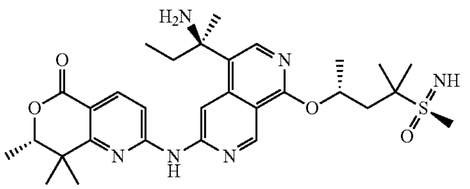 |
| 191 | 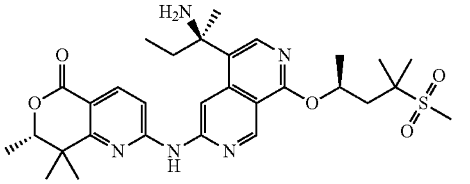 |
| | 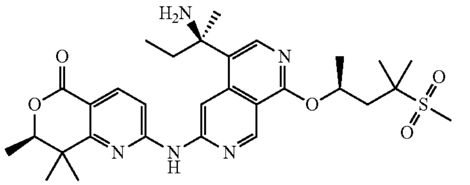 |
| | 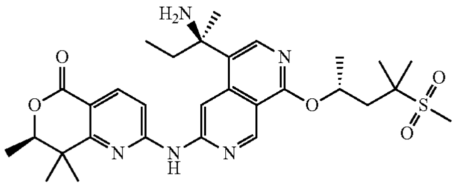 |
| | 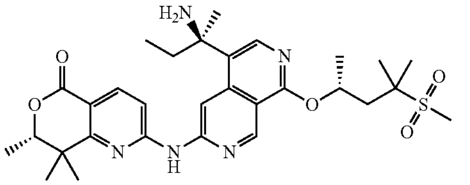 |
| 192 | 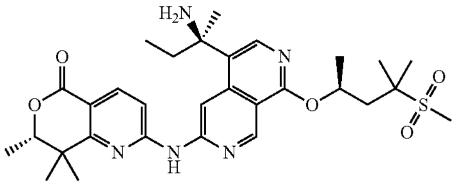 |
| | 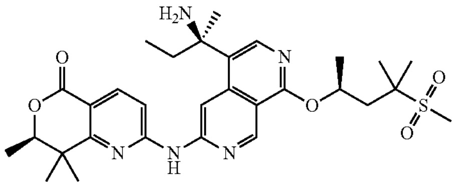 |

-continued

| Compound No. | Structure |
|---|---|
| | 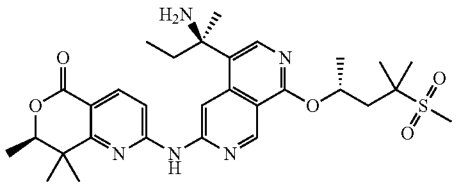 |
| | and |
| | 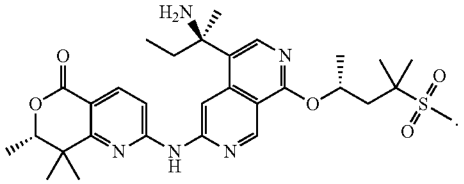 |

16. A pharmaceutical composition comprising the compound of claim 1, or a pharmaceutically acceptable salt thereof, and a pharmaceutically acceptable carrier or excipient.

17. A method of inhibiting MAP4K1 in a subject in need thereof, comprising contacting MAP4K1 with an effective amount of the compound of claim 1 or a pharmaceutically acceptable salt thereof.

18. A method for T-cell activation in a subject in need thereof, comprising administering to said subject an effective amount of the compound of claim 1 or a pharmaceutically acceptable salt thereof, wherein the T-cell activation is characterized by enhanced levels of IL-2 and enhanced levels of T-cell proliferation.

19. The compound of claim 1, or a pharmaceutically acceptable salt thereof, wherein the compound is

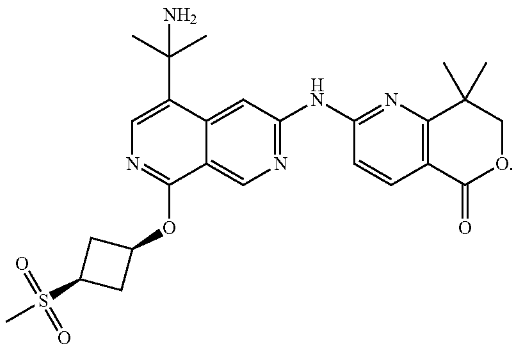 [SMILES: CC(C)(N)c1cnc(O[C@H]2C[C@@H](S(C)(=O)=O)C2)c2cnc(Nc3ccc4c(n3)C(C)(C)COC4=O)cc12]

20. The compound of claim 1, or a pharmaceutically acceptable salt thereof, wherein the compound is selected from

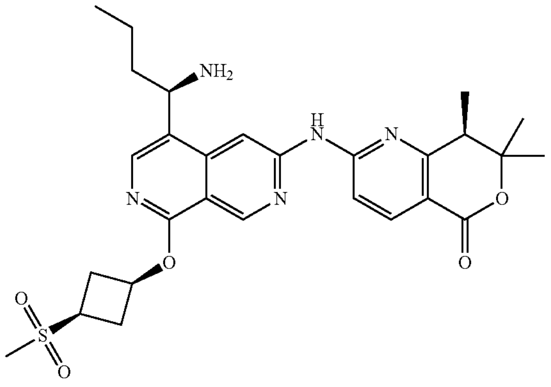

and

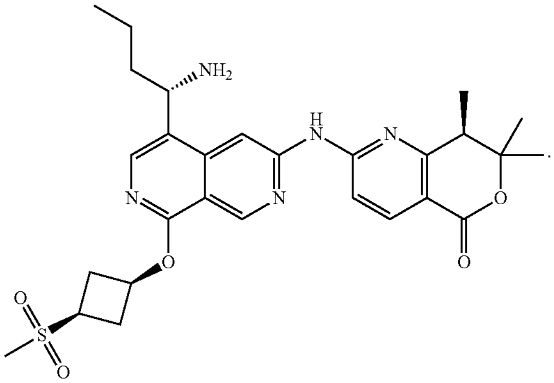

21. The compound of claim 1, or a pharmaceutically acceptable salt thereof, wherein the compound is selected from

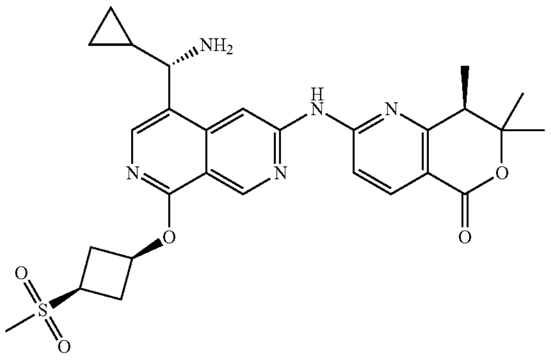

and

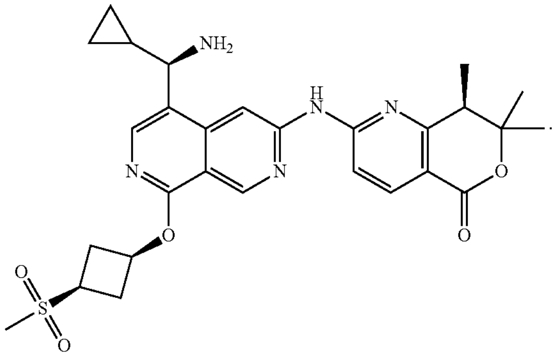

22. The compound of claim 1, or a pharmaceutically acceptable salt thereof, wherein the compound is

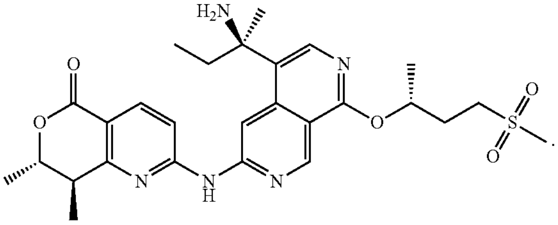

23. The compound of claim 1, or a pharmaceutically acceptable salt thereof, wherein the compound is

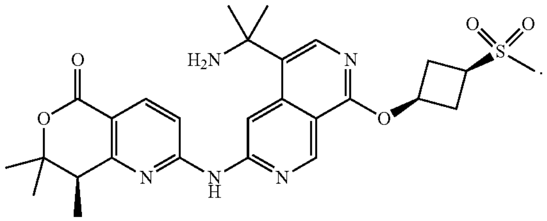

24. The compound of claim 1, or a pharmaceutically acceptable salt thereof, wherein the compound is selected from

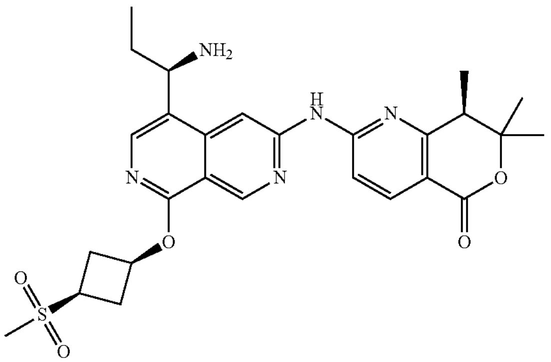

and

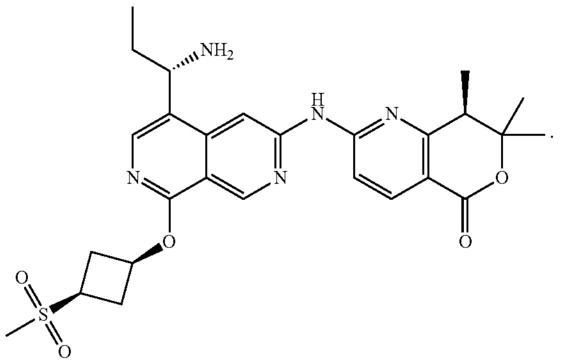

25. The compound of claim 1, or a pharmaceutically acceptable salt thereof, wherein the compound is

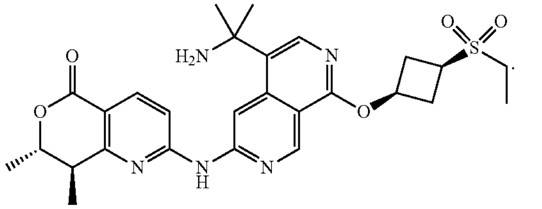 [SMILES: CCS(=O)(=O)[C@H]1C[C@@H](Oc2ncc(C(C)(C)N)c3cc(Nc4ccc5c(n4)[C@@H](C)[C@H](C)OC5=O)ncc23)C1]

26. The compound of claim 1, or a pharmaceutically acceptable salt thereof, wherein the compound is

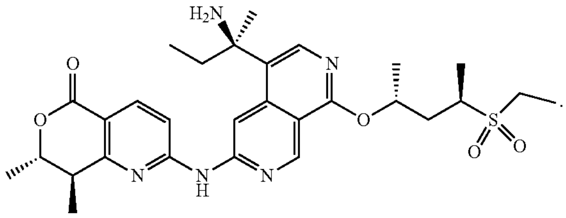 [SMILES: CC[C@@](C)(N)c1cnc(O[C@H](C)C[C@@H](C)S(=O)(=O)CC)c2cnc(Nc3ccc4c(n3)[C@@H](C)[C@H](C)OC4=O)cc12]

27. The compound of claim 1, or a pharmaceutically acceptable salt thereof, wherein the compound is

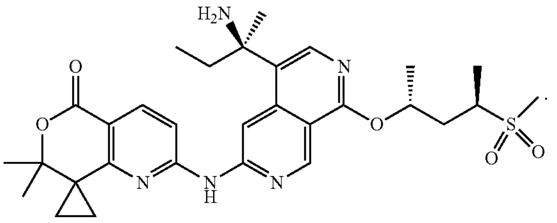 [SMILES: CC[C@@](C)(N)c1cnc(O[C@H](C)C[C@@H](C)S(C)(=O)=O)c2cnc(Nc3ccc4c(n3)C3(CC3)C(C)(C)OC4=O)cc12]

28. The compound of claim 1, or a pharmaceutically acceptable salt thereof, wherein the compound is selected from

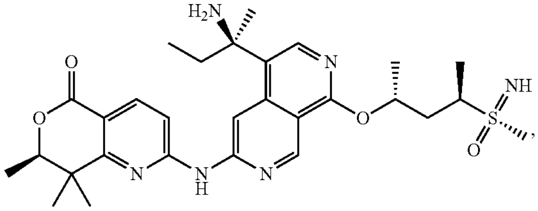

,

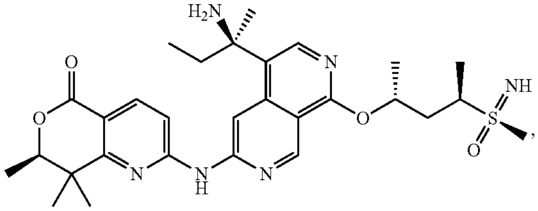

,

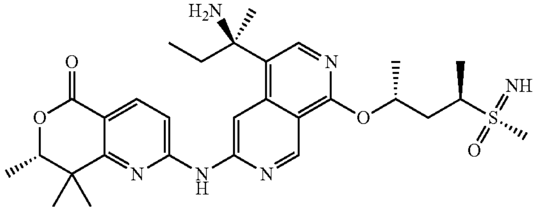

and

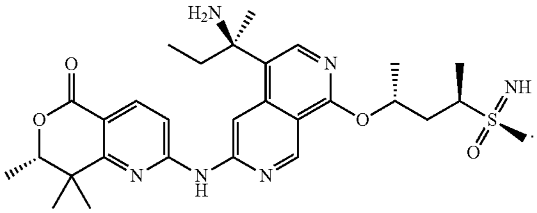

29. The compound of claim 1, or a pharmaceutically acceptable salt thereof, wherein the compound is selected from

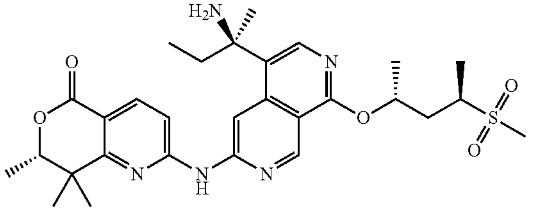

and

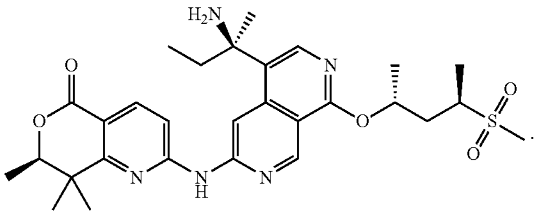

30. The compound of claim 1, or a pharmaceutically acceptable salt thereof, wherein the compound is selected from

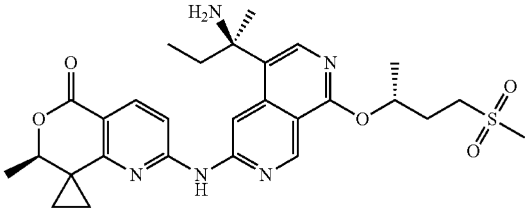
and
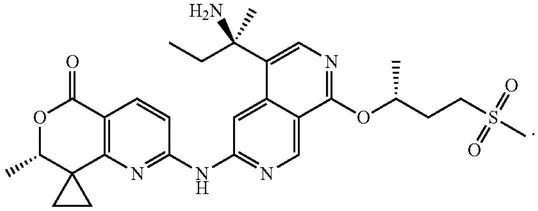
.
* * * * *